(12) United States Patent
Kick et al.

(10) Patent No.: US 9,751,869 B2
(45) Date of Patent: Sep. 5, 2017

(54) LXR MODULATORS

(71) Applicants: BRISTOL-MYERS SQUIBB COMPANY, Princeton, NJ (US); Exelixis Patent Company LLC, South San Francisco, CA (US)

(72) Inventors: Ellen K. Kick, Pennington, NJ (US); Mandar Bodas, Bangalore (IN); Raju Mohan, Encinitas, CA (US); Brett B. Busch, San Diego, CA (US); Claudia Averbuj, San Diego, CA (US); Meriah Valente, Pennington, NJ (US); Nicholas Wurtz, Pennington, NJ (US); Prasanna Savanor Maddu Rao, Karnataka (IN); Jeevanprakash Shetty, Karnataka (IN); Alla Venu, Karnataka (IN)

(73) Assignees: Bristol-Myers Squibb Company, Princeton, NJ (US); Exelixis Patent Company LLC, South San Francisco, CA (US)

( * ) Notice: Subject to any disclaimer, the term of this patent is extended or adjusted under 35 U.S.C. 154(b) by 0 days.

(21) Appl. No.: 14/774,839

(22) PCT Filed: Mar. 14, 2014

(86) PCT No.: PCT/US2014/027679
§ 371 (c)(1),
(2) Date: Sep. 11, 2015

(87) PCT Pub. No.: WO2014/152738
PCT Pub. Date: Sep. 25, 2014

(65) Prior Publication Data
US 2016/0289222 A1    Oct. 6, 2016

Related U.S. Application Data

(60) Provisional application No. 61/787,422, filed on Mar. 15, 2013.

(51) Int. Cl.
*C07D 413/14* (2006.01)
*C07D 405/14* (2006.01)
*C07D 413/10* (2006.01)
*C07D 403/10* (2006.01)

(52) U.S. Cl.
CPC ......... *C07D 413/14* (2013.01); *C07D 403/10* (2013.01); *C07D 405/14* (2013.01); *C07D 413/10* (2013.01)

(58) Field of Classification Search
None
See application file for complete search history.

(56) References Cited

U.S. PATENT DOCUMENTS

| | | |
|---|---|---|
| 5,017,607 A | 5/1991 | Chiesi |
| 5,908,852 A | 6/1999 | Talley et al. |
| 7,482,366 B2 | 1/2009 | Bayne et al. |
| 7,998,986 B2 | 8/2011 | Bayne et al. |
| 7,998,995 B2 | 8/2011 | Boren et al. |
| 8,569,352 B2 | 10/2013 | Busch et al. |
| 8,618,154 B2 | 12/2013 | Busch et al. |
| 8,703,805 B2 | 4/2014 | Busch et al. |

(Continued)

FOREIGN PATENT DOCUMENTS

| | | |
|---|---|---|
| WO | 2004052280 A2 | 6/2004 |
| WO | 2004083189 A1 | 9/2004 |
| WO | 2004094395 A2 | 11/2004 |

OTHER PUBLICATIONS

Cancer [online], [retrieved on Jul. 6, 2007] Retrieved from the Internet, URL: http://www.nlm.nih.gov/medlineplus/cancer.html.*

(Continued)

*Primary Examiner* — Kristin Vajda
(74) *Attorney, Agent, or Firm* — Fox Rothschild LLP

(57) ABSTRACT

The present invention provides compounds of Formula I and Formula II: or pharmaceutically acceptable salts or solvates thereof, as modulators of liver X receptors (LXRs), and compositions comprising any of such novel compounds and methods of use thereof. These compounds are useful as medicaments for treatment and/or prophylaxis for diseases or conditions related to activity of LXRs.

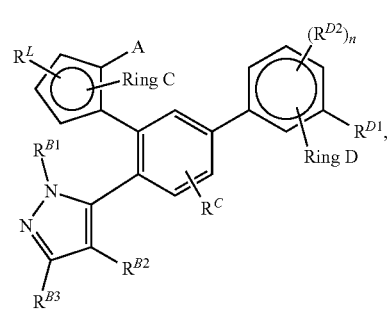

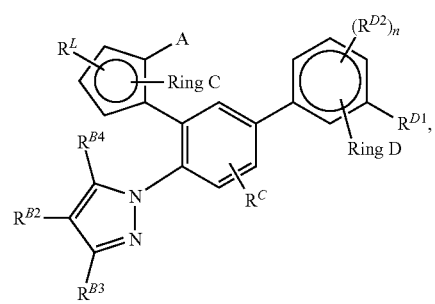

19 Claims, No Drawings

(56) References Cited

U.S. PATENT DOCUMENTS

| | | |
|---|---|---|
| 9,000,022 B2 | 4/2015 | Busch et al. |
| 2005/0179032 A1 | 8/2005 | Halik et al. |
| 2014/0163081 A1 | 6/2014 | Busch et al. |
| 2015/0299136 A1 | 10/2015 | Busch et al. |
| 2016/0280661 A1 | 9/2016 | Busch |
| 2016/0304499 A1 | 10/2016 | Kick et al. |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Compound Summary for: CID 70837251, Create Date: Oct. 26, 2006 http://pubchem.ncbi.nlm.nih.gov/summary/summary.cgi?cid=70837251&loc=ec_rcs.
Compound Summary for: CID 44156382, Create Date: Oct. 26, 2006 http://pubchem.ncbi.nlm.nih.gov/summary/summary.cgi?cid=44156382&loc=ec_rcs.
Compound Summary for: CID 11093423, Create Date: Oct. 26, 2006 http://pubchem.ncbi.nlm.nih.gov/summary/summary.cgi?cid=11093423&loc=ec_rcs.
Loren et al., "Liver X receptor modulators: a review of recently patented compounds (2009-2012)," Expert Opinion on Therapeutic Patents (Jul. 5, 2013); 23(10):1317-1335.
Li et al., "Liver X receptor modulators: a review of recently patented compounds (2007-2009)," Expert Opinion on Therapeutic Patents (Mar. 20, 2010); 20(4):535-562.

* cited by examiner

LXR MODULATORS

CROSS-REFERENCE TO RELATED APPLICATIONS

This application is a U.S. National Phase of International Application No. PCT/US2014/027679, filed Mar. 14, 2014, which claims priority of U.S. Provisional Application No. 61/787,422, filed Mar. 15, 2013, the contents of which are incorporated herein by reference in their entirety.

FIELD OF THE INVENTION

This invention relates to compounds that modulate the activity of liver X receptors (LXRs). The invention also provides pharmaceutical compositions comprising the compounds of the invention and methods of using those compositions, for example, for the treatment and/or prophylaxis of coronary heart disease, atherosclerosis, heart failure, and related cardiovascular diseases. In particular, pyrazole isomers and derivatives are provided for modulating the activity of LXRs.

BACKGROUND OF THE INVENTION

Blood cholesterol is a major risk factor for coronary heart disease (CHD) due to the central role that cholesterol metabolism plays in the disease. Circulating low density lipoprotein (LDL) is modified through oxidation in vascular tissue. Macrophages in the subendothelial space take up these cholesterol-rich particles and accumulate large quantities of cholesteryl esters and pro-inflammatory lipids, thereby becoming foam cells. This sets up a chronic inflammatory process in the arterial wall involving macrophages, other inflammatory cells, cytokines, and smooth muscle cells, followed by disruption of the arterial endothelial surface, vessel narrowing, and ultimately thrombosis and vessel occlusion resulting in myocardial infarction (MI). Lowering circulating LDL decreases the uptake of oxidized LDL by macrophages, thereby limiting this pathological process. Statins decrease risk for CHD by lowering LDL. In addition to cholesterol delivery mechanisms mediated by LDL, there is a cholesterol removal process termed reverse cholesterol transport (RCT) in which excess cholesterol in peripheral tissues is trafficked back to the liver where it is secreted via the bile into the intestine, and excreted in feces (Cuchel, M., Rader, D. J. (2006). *Circulation* 113(21): 2548-2555). The transfer of cholesterol to the liver takes place, in part, on high density lipoprotein (HDL) and this key role in RCT is one of the main reasons why HDL cholesterol (HDL-C) is often the lipid risk factor most closely correlated with CHD in epidemiologic studies. i.e. HDL-C has a strong inverse correlation with disease risk (Gordon, D. J. et al., (1989). *Circulation* 79(1):8-15; Duffy D. & Rader D. J. (2009). *Nat Rev Cardiol* 6 (7):455-63). In addition, HDL has anti-oxidant activity that inhibits the generation of pro-inflammatory oxidized LDL.

The removal of cholesterol from atherosclerotic lesions is thought to attenuate the disease process and, thus, stimulating RCT is likely to be a beneficial therapeutic modality. This is a major rationale for developing LXR agonists for the treatment of atherosclerosis. LXRs (α and β isoforms) are master regulators of cellular and whole-body RCT controlling the transcription of genes involved in all major phases of movement of peripheral cellular cholesterol to the liver and out of the body.

LXRs are able to sense excess intracellular cholesterol by binding to and being transactivated by specific oxysterol cholesterol metabolites. Upon activation, LXRs induce the expression of a variety of cholesterol efflux transporters, apolipoproteins, and lipoprotein modification pathways in multiple tissues that facilitate the removal of excess cellular and whole-body cholesterol (Fiévet C, Staels B. (2009). *Biochem Pharmacol.* 77(8): 1316-27). It is anticipated that such an integrated stimulus of foam cell macrophage cholesterol efflux, trafficking in the circulation, uptake and metabolism in the liver, and excretion in feces will have a robust anti-atherosclerosis effect.

Two important target genes that are induced by LXR agonists in a variety of tissues, including foam cell macrophages, are the ABC transporters ABCA1 and ABCG1. These are lipid efflux transporters that pump cholesterol out of the cell onto HDL acceptors, generating HDL-C. They play a critical role in helping macrophage foam cells efflux excess sterol (Jessup, W., I. C. Gelissen, et al. (2006). *Curr Opin Lipidol* 17(3): 247-57). LXR agonists also induce apolipoprotein E in macrophages (Laffitte, B. A., J. J. Repa, et al. (2001). *Proc Natl Acad Sci USA*. 98(2): 507-12.) which also helps to promote cholesterol efflux from these cells. HDL-C can be taken up directly by the liver or the cholesterol can be first transferred to LDL via the cholesteryl ester transfer protein (CETP) and be delivered to the liver through the LDL receptor. LXRs also induce CETP expression in liver and adipose tissue (Luo, Y. and A. R. Tall (2000). *J Clin Invest.* 105(4): 513-20.), which could facilitate RCT flux via the LDL pathway. Excess hepatic cholesterol can be converted to bile acids or secreted directly into the bile for subsequent excretion. The liver secretion and intestinal excretion steps are also stimulated by LXR agonists through the induction of two additional ABC transporters, ABCG5 and ABCG8 (Repa, J. J., K. E. Berge, et al. (2002). *J Biol Chem.* 277(21): 18793-800). These transporters pump cholesterol out of the hepatocyte into bile and also limit absorption of cholesterol by transporting enterocyte cholesterol into the lumen of the gut.

LXRs also inhibit the NF-κB-dependent induction in macrophages of a variety of inflammatory genes such as iNOS, COX-2 and IL-6 among others (Joseph, S. B., A. Castrillo, et al. (2003). *Nat Med.* 9(2): 213-9), and LXR agonists inhibit inflammatory processes in vitro and in vivo. Recent studies also suggest that synthetic LXR agonists could affect acquired immunity by limiting T-cell proliferative responses to activating signals (Bensinger, S. J., M. N. Bradley, et al. (2008). *Cell* 134(1), 97-111). These effects on innate and acquired immunity are additional potential anti-atherosclerotic mechanisms of LXR agonists.

LXRs also have favorable effects on glucose homeostasis. Treatment of diabetic mouse models with LXR agonists results in the inhibition of hepatic PGC-1, PEPCK, and glucose-6 phosphatase (G6Pase) and the stimulation of hepatic glucokinase, resulting in marked inhibition of hepatic glucose output (HGO) (Laffitte, B. A., L. C. Chao, et al. (2003). *Proc Natl Acad Sci USA*. 100(9): 5419-24). In addition, GLUT4 expression in adipose tissue is upregulated by LXR agonism, thereby increasing peripheral glucose disposal. Consistent with this, LXR agonist treatment of cultured adipocytes increased glucose uptake. Finally, LXR agonism appears to downregulate glucocorticoid action in liver. LXR agonists inhibit hepatic 11β-HSD1 expression (Stulnig, T. M., U. Oppermann, et al. (2002). *Diabetes.* 51(8): 2426-33), an enzyme that converts inactive cortisone to active corticosterone, thus likely lowering liver glucocorticoid. This downregulation of hepatic glucocorticoid activity is likely the mechanism for LXR regulation of PEPCK, G-6-Pase, and glucokinase. Thus, by both inhibiting hepatic glucose output and stimulating peripheral glucose disposal, LXR treatment markedly lowers plasma glucose in diabetic rodent models.

Recently LXRs have also been shown to be important regulators of prostate cancer cell survival. Disruption of lipid rafts in response to LXR-dependent cholesterol efflux (Dufour J. et al. (2012). *Curr Opin Pharmacol.* 2012 Jul. 19). Lowering membrane cholesterol results in a suppression of the AKT survival pathway and consequently apoptosis. Thus, stimulating the LXR-AKT pathway may be beneficial for prostate cancer. Similarly, LXR activation has been suggested to have utility in treating a variety of other cancers including those of the breast (Vedin, L-L. et al., (2009) *Carcinogenesis.* 30 (4): 575-79) and pancreas (Rasheed et al., (2012) *Cancer Research.* 72 (8), Supplement 1, Abstract 3494).

LXR agonists have also been suggested to be useful for the prevention and treatment of photo and chronological skin aging, through their positive effects on keratinocyte and fibroblast gene expression (Chang, K. C. et al., (2008) *Mol Endocrinol.* 22(11): 2407-19).

In addition to the positive effects on cholesterol metabolism, LXRs stimulate fatty acid and triglyceride (TG) synthesis in the liver, primarily through inducing the transcription factor SREBP-1c. Consequently, most LXR agonists cause at least some degree of undesirable accumulation of lipids within hepatocytes and elevated plasma TG and LDL (Groot, P. H., et al. (2005). *J Lipid Res.* 46(10): 2182-91), a property primarily attributed to LXRα specific activity (Peet, D. J., et al. (1998). *Cell.* 93(5): 693-704; Lund, E. G., et al. (2006). *Biochem Pharmacol.* 71(4): 453-63). This is the major mechanism-based adverse effect of the target class and is most pronounced in full pan agonists. Strategies to minimize the undesirable lipid effects include identifying LXRβ selective compounds that are also partial agonists. Partial agonists can display tissue-specific activation or repression of nuclear receptors (Albers, M., et al. (2006). *J Biol Chem.* 281(8): 4920-30), as was demonstrated for the anti-estrogen tamoxifen, which functions as an antagonist of estrogen signaling in breast tissue and an agonist in the uterus (Delmas, P. D., et al. (1997). *N Engl J Med* 337(23): 1641-1647). Characterization of LXR isoform-specific null mice indicates that LXRα is the predominant mediator of LXR activity in the liver Peet, D. J., et al. (1998). *Cell.* 93(5): 693-704; Lund, E. G., et al. (2006). *Biochem Pharmacol.* 71(4): 453-63). In macrophages, however, LXRβ alone is sufficient to mediate the effects of LXR ligands on target gene expression. Therefore, compounds with limited LXRα activity should have anti-atherogenic activity while limiting unwanted hepatic effects.

Liver X Receptors

LXRs are adopted orphan members of the nuclear receptor superfamily. There are two LXR isoforms, LXRα and LXRβ, and both heterodimerize with the Retinoid X Receptor (RXR) (Song, C., et al. (1994). *Proc Natl Acad Sci USA.* 91(23): 10809-13; Apfel, R., et al. (1994). *Mol Cell Biol.* 14(10): 7025-35; Willy, P. J., et al. (1995). *Genes Dev.* 9(9): 1033-45). Both LXRs, when complexed with RXR, bind to distinct regions of DNA called LXR response elements (LXREs) present in the promoters of LXR target genes. The LXR response elements take the form of two degenerate hexad direct repeat sequences, the consensus being AGGTCA, separated by 4 nucleotides, collectively termed a DR4 repeat (Willy, P. J. and D. J. Mangelsdorf (1997). *Genes Dev.* 11(3): 289-98). LXR$_α$ is found predominantly in the liver, with lower levels found in kidney, intestine, spleen and adrenal tissue (see, e.g., Willy, et al. (1995) *Genes Dev.* 9(9):1033-1045). LXR$_β$ is ubiquitous in mammals and was found in nearly all tissues examined.

SUMMARY OF THE INVENTION

In one embodiment, the present invention comprises compounds or an individual isomer or mixture of isomers, an isotope or a pharmaceutically acceptable salt thereof, which are useful as modulators of the activity of liver X receptors (LXRs).

In one aspect, the invention provides compounds according to one of the following formulae,

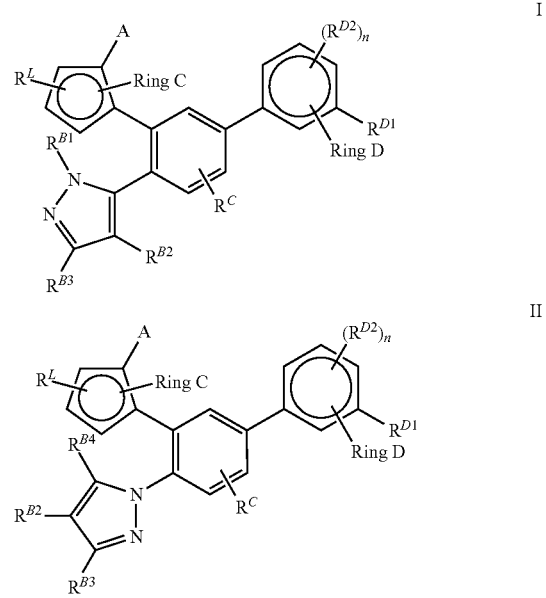

or a pharmaceutically acceptable salt thereof, wherein the variables for each formula are defined herein.

The present invention also provides processes and intermediates for making the compounds of the present invention.

Another aspect of this invention is directed to a composition comprising a compound of the invention together with a pharmaceutically acceptable carrier, diluent, or excipient. When water is a carrier or diluent, the composition optionally further comprises another pharmaceutically acceptable carrier or diluent and/or a pharmaceutically acceptable excipient. Within this aspect are such compositions for pharmaceutical use.

Another aspect of this invention is directed to methods of treating, inhibiting, or ameliorating the symptoms of a disease or disorder that is modulated or otherwise affected by LXR activity or in which LXR activity is implicated, comprising administering to a subject in need thereof a therapeutically effective amount of a compound of the present invention or an individual isomer or mixture of isomers or a pharmaceutically acceptable salt thereof.

Another aspect of this invention is directed to methods of modulating cholesterol metabolism to a subject in need thereof, comprising administering an effective cholesterol metabolism-modulating amount of a compound of the present invention or an individual isomer or mixture of isomers or a pharmaceutically acceptable salt thereof.

Another aspect of this invention is directed to methods of preventing or treating atherosclerosis in a subject in need thereof, comprising administering an effective cholesterol metabolism-modulating amount of a compound of the present invention or an individual isomer or mixture of isomers or a pharmaceutically acceptable salt thereof.

Another aspect of this invention is directed to methods of modulating LXR activity to a subject in need thereof, comprising contacting the nuclear receptor with a compound of the present invention or an individual isomer or mixture of isomers or a pharmaceutically acceptable salt thereof.

Another aspect of this invention is directed to methods of increasing cholesterol efflux from cells of a subject in need thereof, comprising administering an effective cholesterol efflux-increasing amount of a compound of the present invention or an individual isomer or mixture of isomers or a pharmaceutically acceptable salt thereof.

Another aspect of this invention is directed to methods of increasing the expression of ATP-Binding Cassette A1 (ABCA1) and ATP-Binding Cassette G1 (ABCG1) in the cells of a subject in need thereof, comprising administering an effective ABCA1 and ABCG1 expression-increasing amount of a compound of the present invention or an individual isomer or mixture of isomers or a pharmaceutically acceptable salt thereof.

Another aspect of this invention is directed to methods of treating, inhibiting, or ameliorating one or more symptoms of a disease or disorder which is affected by cholesterol, comprising administering to a subject in need thereof a therapeutically effective amount of a compound of the present invention or an individual isomer or mixture of isomers or a pharmaceutically acceptable salt thereof.

Another aspect of this invention is directed to pharmaceutical compositions comprising a compound of the present invention or an individual isomer or mixture of isomers or a pharmaceutically acceptable salt thereof and at least one pharmaceutically acceptable carrier or excipient.

Another aspect of this invention is directed to regulation of reverse cholesterol transport and inflammatory signaling pathways that are implicated in human disease pathology including atherosclerosis and associated diseases such as myocardial infarction, peripheral arterial disease, and ischemic stroke in a subject in need thereof, comprising administering an effective reverse cholesterol transport and inflammatory signaling pathways regulating amount of a compound of the present invention or an individual isomer or mixture of isomers or a pharmaceutically acceptable salt thereof.

Another aspect of this invention is directed to treatment of the metabolic syndrome which comprises a constellation of disorders of metabolism including obesity, hypertension, insulin resistance, and diabetes including treatment of diseases resulting from compromised metabolism and immunity including atherosclerosis and diabetes as well as autoimmune disorders and diseases in a subject in need thereof, comprising administering a therapeutically effective amount of a compound of the present invention or an individual isomer or mixture of isomers or a pharmaceutically acceptable salt thereof.

Another aspect of this invention is directed to treatment of atherosclerosis, insulin resistance, osteoarthritis, stroke, hyperglycemia, dyslipidemia, psoriasis, aged and UV skin wrinkling, diabetes, cancer, Alzheimer's disease, inflammation, immunological disorders, lipid disorders, obesity, diabetic kidney disease, conditions characterized by a perturbed epidermal barrier function, conditions of disturbed differentiation or excess proliferation of the epidermis or mucous membrane, or cardiovascular disorders in a subject in need thereof, comprising administering a therapeutically effective amount of a compound of the present invention or an individual isomer or mixture of isomers or a pharmaceutically acceptable salt thereof.

Another aspect of this invention is directed to treatment of atherosclerosis, comprising administering a therapeutically effective amount of a compound of the present invention or an individual isomer or mixture of isomers or a pharmaceutically acceptable salt thereof.

The compounds of the invention may be useful in therapy.

The compounds of the invention may be used for the manufacture of a medicament for the treatment and/or prophylaxis of diseases or disorders associated with modulation of LXR activity.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

In embodiment (1) of the first aspect, the present invention comprises compound of formula I or II,

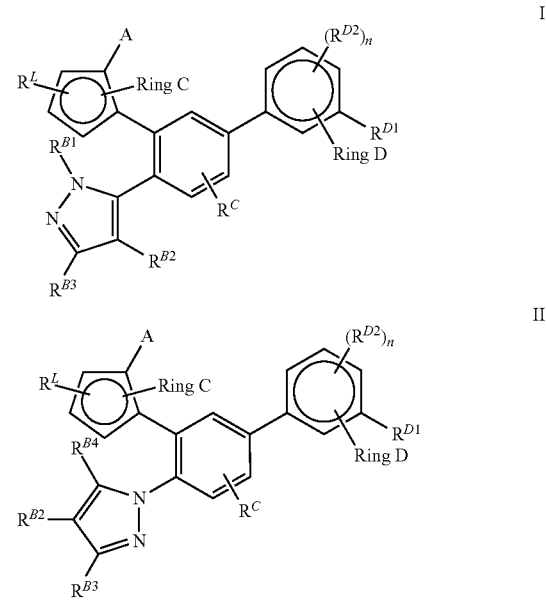

or a pharmaceutically acceptable salt or prodrug thereof, wherein

Ring C is selected from oxazolyl and triazolyl;
Ring D is selected from phenyl and pyridyl;
A is phenyl or a 5 or 6 membered heteroaryl, wherein the phenyl is optionally fused to a 5 or 6 membered heterocyclyl or 5 or 6 membered heteroaryl,
wherein A is optionally substituted with 1 to 5, preferably 1, 2, or 3, $R^A$ groups,
wherein
each $R^A$ is independently $R^{A1}$, —$C_1$-$C_6$alkyl-$R^{A1}$, $C_1$-$C_6$alkyl, $C_1$-$C_6$haloalkyl, $C_2$-$C_6$alkenyl, $C_2$-$C_6$alkynyl, $C_3$-$C_8$cycloalkyl, pyrrolidinone, or pyrrolidinyl, wherein the cycloalkyl is optionally substituted with 1, 2, 3, or 4 groups that are independently $R^{A1}$, $C_1$-$C_6$alkyl, or —$C_1$-$C_6$alkyl-$R^{A1}$, wherein
   each $R^{A1}$ is independently halogen, cyano, nitro, —OR, —$NR_2$, —SR, —C(O)R, or —C(O)OR;
alternatively, $2R^A$ on adjacent carbons can join to form a —O—$CH_2$—O—, —O—$CH_2$—$CH_2$—, —O—$CH_2$—$CH_2$—O—, —$CH_2$—$CH_2$—$CH_2$—, or —O—$CF_2$—O—;
$R^{B1}$ is hydrogen, $C_{1-3}$alkyl, halo, cyclopropyl, or $C_{1-3}$haloalkyl;
$R^{B2}$ is hydrogen, halo, —CN, or $C_{1-3}$alkyl;
$R^{B3}$ is hydrogen, $C_{1-6}$alkyl, $C_{1-6}$haloalkyl, $C_{3-6}$cycloalkyl, any of which can be substituted with 0-1 $R^{B5}$, cyano, —C(O)—R, —C(O)$NR_2$, —NHC(O)R, —$NHSO_2$R, or a 5-membered ring heteroaryl, wherein the heteroaryl consists of carbon atoms and 1, 2, or 3 heteroatoms selected from the group consisting of N, S, and O;
$R^{B4}$ is H, halogen, —$C_{1-3}$alkyl, —$C_{1-3}$haloalkyl, —$C_3$-$C_6$-cycloalkyl, or —O—$C_{1-3}$alkyl;
$R^{B5}$ is cyano, —O—R, —C(O)$NR_2$, —C(O)OR, —$NR_2$, —OC(O)—$NH_2$, or a 5-membered ring heteroaryl, wherein the heteroaryl consists of carbon atoms and 1, 2, or 3 heteroatoms selected from the group consisting of N, S, and O;
$R^C$ is hydrogen, halogen, cyano, or nitro;
n is 0, 1, 2, 3, or 4; and
each $R^{D1}$ and $R^{D2}$ are independently $R^{D3}$, $C_1$-$C_6$alkyl, —$C_1$-$C_6$alkyl-$R^{D3}$, $C_1$-$C_6$haloalkyl, $C_2$-$C_6$alkenyl, $C_2$-$C_6$alkynyl, or $C_3$-$C_8$cycloalkyl, wherein the cycloalkyl is each optionally substituted with 1, 2, 3, or 4 groups that are independently $R^{D3}$, $C_1$-$C_6$alkyl, $C_3$-$C_6$cycloalkyl, or —$C_1$-$C_6$alkyl-$R^{D3}$, wherein
each $R^{D3}$ is independently halogen, cyano, —OR, —$NR_2$, —SR, —C(O)R, —C(O)OR, —C(O)$NR_2$, —S(O)R, —$S(O)_2$R, —S(O)$NR_2$, —$S(O)_2NR_2$, —OC(O)R, —OC(O)OR, —OC(O)$NR_2$, —N(R)C(O)R, —N(R)C(O)OR, —N(R)C(O)$NR_2$, —N(R)$S(O)_2$R, —N(R)S$(O)_2$OR, —N(R)$S(O)_2NR_2$, or —$S(O)_2$N(R)C(O)$NR_2$; and
$R^L$ is hydrogen, $C_1$-$C_6$alkyl, $C_3$-$C_6$-cyclopropyl, $C_1$-$C_6$haloalkyl, —C(O)R, —C(O)OR, —C(O)$NR_2$, —S(O)R, —$S(O)_2$R, —S(O)OR, —$S(O)_2$OR, —S(O)$NR_2$, or —$S(O)_2NR_2$;
wherein
each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl, or —$C_1$-$C_6$alkyl-$C_3$-$C_6$cycloalkyl; wherein
each $R^2$ is independently cyano, —$OR^3$, —C(O)$NH_2$, —$N(R^3)_2$, —$N(R^3)S(O)_2R^3$, —$N(R^3)S(O)_2OR^3$, or —$N(R^3)S(O)_2N(R^3)_2$, wherein each $R^3$ is independently hydrogen, $C_1$-$C_6$alkyl, $C_{3-6}$cycloalkyl, or $C_1$-$C_6$haloalkyl.
A compound of formula I or II,

I

II or a pharmaceutically acceptable salt thereof, wherein
Ring C is selected from oxazolyl and triazolyl;
Ring D is selected from phenyl and pyridyl;
A is phenyl, pyridinyl or pyrimidinyl, wherein A is optionally substituted with 1 to 5, preferably 1, 2, or 3, $R^A$ groups, wherein
   each $R^A$ is independently halogen, —CN, —$C_{1-6}$alkyl, —$C_{1-6}$haloalkyl, $C_3$-$C_6$cycloalkyl, —O—$C_{1-6}$haloalkyl, —O—$C_{1-6}$alkyl, —CO—$C_{1-6}$alkyl, —O—$C_{3-6}$cycloalkyl, pyrrolidinone, pyrrolidinyl, —C(O)O—$C_{1-6}$alkyl, or —$NR_2$; or
   alternatively, two adjacent $R^A$ join to form —O—$CH_2$—O— or —O—$CF_2$—O—;
$R^{B1}$ is —$C_{1-3}$alkyl, —$C_{1-3}$haloalkyl, or cyclopropyl;
$R^{B2}$ is H, halogen, —CN, or —$C_{1-3}$-alkyl;
$R^{B3}$ is H, $C_{1-6}$alkyl, $C_{1-6}$haloalkyl, $C_{3-6}$cycloalkyl, any of which can be substituted with 0-1 $R^{B5}$, cyano, —C(O)—R, —C(O)$NR_2$, —NHC(O)R, —$NHSO_2$R, or a 5-membered ring heteroaryl, wherein the heteroaryl consists of carbon atoms and 1, 2, or 3 heteroatoms selected from the group consisting of N, S, and O and is substituted with 0-1 R;
$R^{B4}$ is H, halogen, —$C_{1-3}$alkyl, —$C_{1-3}$haloalkyl, cyclopropyl, or —O—$C_{1-3}$alkyl;
$R^{B5}$ is cyano, —O—R, —C(O)$NR_2$, —C(O)OR, —$NR_2$, —OC(O)—$NH_2$, or a 5-membered ring heteroaryl, wherein the heteroaryl consists of carbon atoms and 1, 2, or 3 heteroatoms selected from the group consisting of N, S, and O;
each R is independently hydrogen, $C_1$-$C_6$alkyl, —$C_1$-$C_6$alkyl-$R^2$, —$C_1$-$C_6$haloalkyl, —$C_1$-$C_6$haloalkyl-$R^2$, —$C_3$-$C_6$cycloalkyl or —$C_1$-$C_6$alkyl-$C_{3-6}$cycloalkyl; alternatively, two Rs along with the N to which they attach form morpholinyl, pyrrolidinyl, or piperdinyl;
each $R^2$ is independently —OH, —C(O)$NH_2$, or cyano,
n is 0, 1, 2, 3, or 4; and
$R^{D1}$ is —$S(O)_2$—$C_{1-3}$alkyl, —$S(O)_2N(R^3)_2$, —$C(CH_3)_2$—C(O)$NH_2$, —$C(CH_3)_2$—CN, or -cyclopropyl-C(O)$NH_2$;
each $R^{D2}$ is independently halogen or —$CH_2$OH;
$R^3$ is H, $C_{1-3}$alkyl, cyclopropyl, $C_{1-3}$haloalkyl;
$R^C$ is hydrogen or halogen; and
$R^L$ is absent, hydrogen, $C_1$-$C_6$alkyl, $C_3$-$C_6$-cyclopropyl or $C_1$-$C_6$haloalkyl.
In another aspect, the present invention provides compound of formula (Ia) or (IIa), wherein

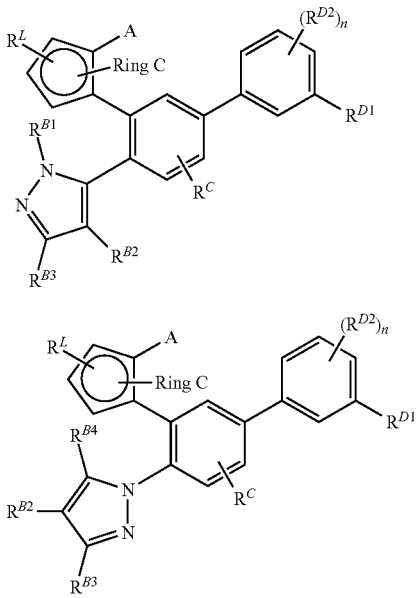

In another aspect, the present invention provides compounds of formula (I), (II), (Ia), or (IIa), wherein
$R^{B1}$ is $C_{1-3}$alkyl, $C_{1-3}$haloalkyl, or cyclopropyl;
$R^{B2}$ is H, halogen, —CN, or methyl;
$R^{B3}$ is $C_{1-6}$alkyl, $C_{1-6}$haloalkyl, $C_{3-8}$cycloalkyl, any of which can be substituted with 0-1 $R^{B5}$; cyano, —C(O)NR$_2$, —NHC(O)R, or —NHSO$_2$R; and
$R^{B4}$ is H, halogen, methyl, —CF$_3$, cyclopropyl, or —O—C$_{1-3}$alkyl.

In another aspect, the present invention provides compound of formula (I), (II), (Ia), or (IIa), wherein
$R^{B5}$ is cyano, —O—R, —C(O)NR$_2$, —C(O)OR, or —OC(O)—NH$_2$; and
each R is independently hydrogen, $C_1$-$C_6$alkyl, —$C_1$-$C_6$alkyl-R$^2$, $C_1$-$C_6$haloalkyl, —$C_1$-$C_6$haloalkyl-R$^2$, $C_3$-$C_6$cycloalkyl, or $C_1$-$C_6$alkyl-$C_{3-6}$cycloalkyl, or alternatively, two Rs along with the N to which they attach form morpholinyl, pyrrolidinyl, or piperdinyl.

In another aspect, the present invention provides compound of formula (I), (II), (Ia), or (IIa), wherein
A is phenyl optionally substituted with 1 to 5, preferably 1 to 3, $R^A$ groups, or pyridinyl optionally substituted with 1 to 4, preferably 1, 2, or 3 $R^A$ groups.

In another aspect, the present invention provides compound of formula (I), (II), (Ia), or (IIa), wherein
A is phenyl optionally substituted with 1 to 5, preferably 1, 2, or 3, $R^A$ groups.

In another aspect, the present invention provides compound of formula (I), (II), (Ia), or (IIa), wherein
each $R^A$ is independently halogen, —CN, $C_{1-4}$alkyl, $C_{1-2}$haloalkyl, cyclopropyl, cyclohexyl, —O—$C_{1-3}$haloalkyl, —O—$C_{1-3}$alkyl, —CO—$C_{1-3}$alkyl, —O—$C_{3-6}$cycloalkyl, —C(O)O—$C_{1-3}$alkyl, or —NR$_2$; or
alternatively, two adjacent $R^A$ join to form —O—CH$_2$—O— or —O—CF$_2$—O—.

In another aspect, the present invention provides compound of formula (I), (II), (Ia), or (IIa), wherein
each $R^A$ is independently halogen, —CN, methyl, ethyl, propyl, i-propyl, —CF$_3$, CHF$_2$, cyclopropyl, cyclohexyl, —O—CF$_3$, —O—CHF$_2$, —O—CH$_3$, —CO—C$_{1-3}$alkyl, —O—$C_{3-6}$cycloalkyl, —C(O)O—$C_{1-3}$alkyl, or —NR$_2$; or
alternatively, two adjacent $R^A$ join to form —O—CH$_2$—O— or —O—CF$_2$—O—.

In another aspect, the present invention provides compound of formula (I), (II), (Ia), or (IIa), wherein
each R is independently hydrogen, $C_1$-$C_3$alkyl, —$C_1$-$C_3$alkyl-R$^2$, $C_1$-$C_3$haloalkyl, —$C_1$-$C_3$haloalkyl-R$^2$, cyclopropyl, or —$C_1$-$C_3$alkyl-$C_{3-6}$cycloalkyl; or alternatively, two Rs along with the N to which they attach form morpholinyl, pyrrolidinyl, or piperdinyl.

In another aspect, the present invention provides compound of formula (I), (II), (Ia), or (IIa), wherein
Ring C is selected from oxazolyl, and
$R^L$ is hydrogen or methyl.

In another aspect, the present invention provides compound of formula (I), (II), (Ia), or (IIa), wherein
Ring C is selected from triazolyl, and
$R^L$ is hydrogen.

In another aspect, the present invention provides compound of formula (I), (II), (Ia), or (IIa), wherein
Ring D is selected from phenyl.

In another aspect, the present invention provides compound of formula (I), (II), (Ia), or (IIa), wherein
each $R^{D1}$ is —S(O)$_2$-methyl, —S(O)$_2$N(R$^3$)$_2$, —C(CH$_3$)$_2$—C(O)NH$_2$, -cyclopropyl-C(O)NH$_2$; and
$R^3$ is H or $C_{1-3}$-alkyl.

In another aspect, the present invention comprises compound of formula (I), (II), (Ia), or (IIa), wherein
$R^{D1}$ is —SO$_2$-alkyl, —SO$_2$NR$_2$, —C(Me)$_2$-CONH$_2$, or

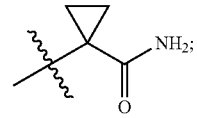 [SMILES: *C1(C(N)=O)CC1]

and
$R^{D2}$ is —$C_{1-6}$alkyl-OH or halo.

In another aspect, the present invention comprises compound of formula (I), (II), (Ia), or (IIa), wherein
$R^{D1}$ is —SO$_2$—CH$_3$ or —SO$_2$NR$_2$.

In another aspect, the present invention comprises compound of formula (I), (II), (Ia), or (IIa), wherein
$R^{D1}$ is —SO$_2$—CH$_3$.

In another aspect, the present invention comprises compound of formula (I), (II), (Ia), or (IIa), wherein $R^{D2}$ is —$C_{1-6}$alkyl-OH or halo.

A compound listed in any one of the examples.

In another aspect, the present invention provides compounds of formula (I), (II), (Ia), or (IIa), wherein
Ring C is

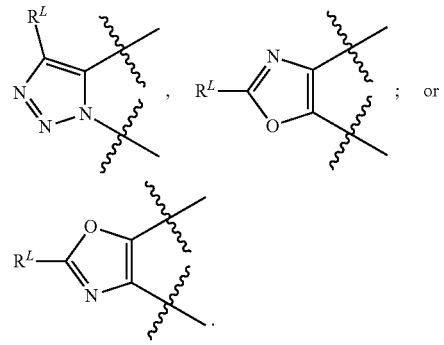

In another aspect, the present invention provides compounds of formula (Ia), or (IIa), wherein the compound is formula (Ia).

In another aspect, the present invention provides compounds of formula (Ia).

In another aspect, the present invention provides compounds of formula (IIa).

In another aspect, the present invention provides compounds of formula (I), (II), (Ia), or (IIa), wherein $R^C$ is hydrogen.

In another aspect, the present invention provides compounds of formula (I), (II), (Ia), or (IIa), wherein Ring D is

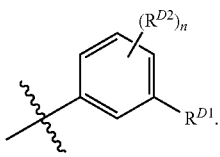

In another aspect, the present invention provides compounds of formula (I), (II), (Ia), or (IIa), wherein Ring D is

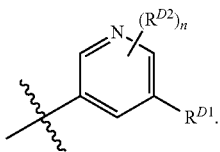

In another embodiment, the present invention provides a compound of formula I or formula II:

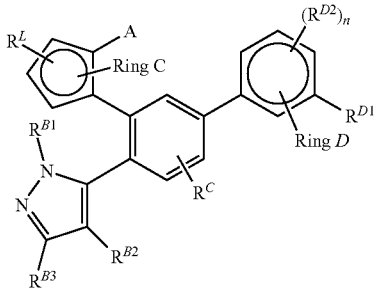

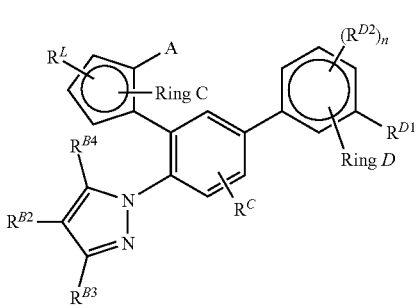

or a pharmaceutically acceptable salt or solvate thereof, wherein
Ring C is selected from oxazolyl and triazolyl;
Ring D is selected from phenyl and pyridyl;

A is phenyl or a 5 or 6 membered heteroaryl, wherein the phenyl is optionally fused to a 5 or 6 membered heterocyclyl or 5 or 6 membered heteroaryl, wherein A is optionally substituted with 1 to 5, preferably 1, 2, or 3, $R^A$ groups, wherein
each $R^A$ is independently $R^{A1}$, —$C_1$-$C_6$alkyl-$R^{A1}$, $C_1$-$C_6$alkyl, $C_1$-$C_6$haloalkyl, $C_2$-$C_6$alkenyl, $C_2$-$C_6$alkynyl, $C_3$-$C_8$cycloalkyl, pyrrolidinone, or pyrrolidinyl, wherein the cycloalkyl is optionally substituted with 1, 2, 3, or 4 groups that are independently $R^{A1}$, $C_1$-$C_6$alkyl, or —$C_1$-$C_6$alkyl-$R^{A1}$, wherein
each $R^{A1}$ is independently halogen, cyano, nitro, —OR, —$NR_2$, —SR, —C(O)R, or —C(O)OR;
alternatively, $2R^A$ on adjacent carbons can join to form a —O—$CH_2$—O—, —O—$CH_2$—$CH_2$—, —O—$CH_2$—$CH_2$—O—, —$CH_2$—$CH_2$—$CH_2$—, or —O—$CF_2$—O—;

$R^{B1}$ is hydrogen, $C_{1-3}$alkyl, halo, cyclopropyl, or $C_{1-3}$haloalkyl;

$R^{B2}$ is hydrogen, halo, —CN, —C(O)$NR_2$, or $C_{1-3}$alkyl;

$R^{B3}$ is $C_{1-6}$alkyl, $C_{1-6}$haloalkyl, or $C_{3-6}$cycloalkyl, each of which is substituted with 0-1 $R^{B5}$; hydrogen, cyano, —C(O)—R, —C(O)$NR_2$, —NHC(O)R, —NHSO$_2$R, or a 5-membered ring heteroaryl, wherein the heteroaryl ring consists of carbon atoms and 1, 2, or 3 heteroatoms independently selected from the group consisting of N, S, and O and is substituted with 0-1 R;

$R^{B4}$ is H, halogen, —$C_{1-3}$alkyl, —$C_{1-3}$haloalkyl, —$C_{3-6}$cycloalkyl, or —O—$C_{1-3}$alkyl;

$R^{B5}$ is cyano, —O—R, —C(O)$NR_2$, —C(O)OR, —$NR_2$, —OC(O)—$NH_2$, —S(O)$_2NR_2$, or a 5-membered ring heteroaryl, wherein the heteroaryl ring consists of carbon atoms and 1, 2, or 3 heteroatoms independently selected from the group consisting of N, S, and O;

$R^C$ is hydrogen, halogen, cyano, or nitro;

n is 0, 1, 2, 3, or 4; and each $R^{D1}$ and $R^{D2}$ are independently $R^{D3}$, $C_1$-$C_6$alkyl, —$C_1$-$C_6$alkyl-$R^{D3}$, $C_1$-$C_6$haloalkyl, $C_2$-$C_6$alkenyl, $C_2$-$C_6$alkynyl, or $C_3$-$C_8$cycloalkyl, wherein the cycloalkyl is each optionally substituted with 1, 2, 3, or 4 groups that are independently $R^{D3}$, $C_1$-$C_6$alkyl, $C_3$-$C_6$cycloalkyl, or —$C_1$-$C_6$alkyl-$R^{D3}$, wherein
each $R^{D3}$ is independently halogen, cyano, —OR, —$NR_2$, —SR, —C(O)R, —C(O)OR, —C(O)$NR_2$, —S(O)R, —S(O)$_2$R, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)$_2$R, —N(R)S(O)$_2$OR, —N(R)S(O)$_2NR_2$, or —S(O)$_2$N(R)C(O)$NR_2$; and $R^L$ is hydrogen, $C_1$-$C_6$alkyl, $C_3$-$C_6$cycloalkyl, $C_1$-$C_6$haloalkyl, —C(O)R, —C(O)OR, —C(O)$NR_2$, —S(O)R, —S(O)$_2$R, —S(O)OR, —S(O)$_2$OR, —S(O)$NR_2$, or —S(O)$_2NR_2$;
wherein
each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl, or —$C_1$-$C_6$alkyl-$C_3$-$C_6$cycloalkyl; or
for any —C(O)$NR_2$ or —$NR_2$,
alternatively, the two Rs along with the N to which they attach may form morpholinyl, pyrrolidinyl, or piperdinyl; and
wherein
each $R^2$ is independently cyano, —$OR^3$, —C(O)$NH_2$, —$N(R^3)_2$, —$N(R^3)S(O)_2R^3$, —$N(R^3)S(O)_2OR^3$, or —N(R³)S(O)₂N(R³)₂, wherein each R³ is independently hydrogen, $C_1$-$C_6$alkyl, $C_{3-6}$cycloalkyl, or $C_1$-$C_6$haloalkyl.

In another embodiment, the present invention provides a compound of formula I or formula II:

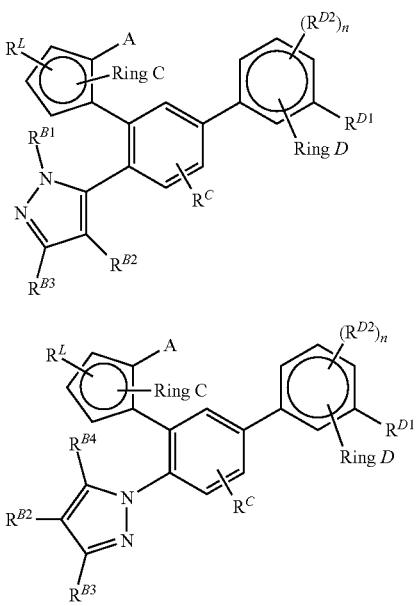

or a pharmaceutically acceptable salt or solvate thereof, wherein

Ring C is selected from oxazolyl and triazolyl;
Ring D is selected from phenyl and pyridyl;
A is phenyl, pyridinyl or pyrimidinyl, wherein A is optionally substituted with 1 to 5, preferably 1, 2, or 3, $R^A$ groups, wherein
  each $R^A$ is independently halogen, —CN, —$C_{1-6}$alkyl, —$C_{1-6}$haloalkyl, $C_3$-$C_6$cycloalkyl, —O—$C_{1-6}$haloalkyl, —O—$C_{1-6}$alkyl, —CO—$C_{1-6}$alkyl, —O—$C_{3-6}$cycloalkyl, pyrrolidinone, pyrrolidinyl, —C(O)O—$C_{1-6}$alkyl, or —NR₂; or
  alternatively, two adjacent $R^A$'s join to form —O—CH₂—O— or —O—CF₂—O—;
$R^{B1}$ is —$C_{1-3}$alkyl, —$C_{1-3}$haloalkyl, or cyclopropyl;
$R^{B2}$ is hydrogen, halogen, —CN, —C(O)NH₂, or —$C_{1-3}$-alkyl;
$R^{B3}$ is $C_{1-6}$alkyl, $C_{1-6}$haloalkyl, or $C_{3-6}$cycloalkyl, each of which is substituted with 0-1 $R^{B5}$; hydrogen cyano, —C(O)—R, —C(O)NR₂, —NHC(O)R, —NHSO₂R, or a 5-membered ring heteroaryl, wherein the heteroaryl ring consists of carbon atoms and 1, 2, or 3 heteroatoms independently selected from the group consisting of N, S, and O and is substituted with 0-1 R;
$R^{B4}$ is hydrogen, halogen, —$C_{1-3}$alkyl, —$C_{1-3}$haloalkyl, cyclopropyl, or —O—$C_{1-3}$alkyl;
$R^{B5}$ is cyano, —O—R, —C(O)NR₂, —C(O)OR, —NR₂, —OC(O)—NH₂, or a 5-membered ring heteroaryl, wherein the heteroaryl ring consists of carbon atoms and 1, 2, or 3 heteroatoms independently selected from the group consisting of N, S, and O;
each R is independently hydrogen, $C_1$-$C_6$alkyl, —$C_1$-$C_6$alkyl-$R^2$, —$C_1$-$C_6$haloalkyl, —$C_1$-$C_6$haloalkyl-$R^2$, —$C_3$-$C_6$cycloalkyl or —$C_1$-$C_6$alkyl-$C_{3-6}$cycloalkyl; or for any —C(O)NR₂ or —NR₂, alternatively, two Rs along with the N to which they attach may form morpholinyl, pyrrolidinyl, or piperdinyl;
each $R^2$ is independently —OH, —C(O)NH₂, or cyano,
n is 0, 1, 2, 3, or 4; and
$R^{D1}$ is —S(O)₂—$C_{1-3}$alkyl, —S(O)₂N(R³)₂, —C(CH₃)₂—C(O)NH₂, —C(CH₃)₂—CN, or -cyclopropyl-C(O)NH₂;
each $R^{D2}$ is independently halogen or —CH₂OH;
$R^3$ is H, $C_{1-3}$alkyl, cyclopropyl, $C_{1-3}$haloalkyl;
$R^C$ is hydrogen or halogen; and
$R^L$ is absent, hydrogen, $C_1$-$C_6$alkyl, $C_3$-$C_6$cycloalkyl or $C_1$-$C_6$haloalkyl.

In another embodiment, the present invention provides a compound of formula (Ia) or (IIa), or a pharmaceutically acceptable salt or solvate thereof, wherein

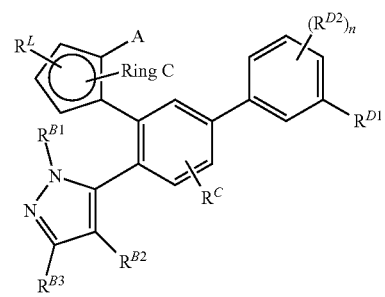

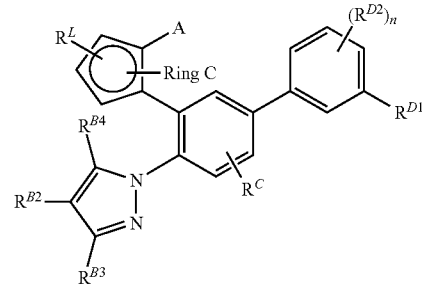

In another embodiment, the present invention provides a compound of formula (I), (II), (Ia), or (IIa), or a pharmaceutically acceptable salt or solvate thereof, wherein
$R^{B1}$ is $C_{1-3}$alkyl, $C_{1-3}$haloalkyl, or cyclopropyl;
$R^{B2}$ is H, halogen, —CN, or methyl;
$R^{B3}$ is $C_{1-6}$alkyl, $C_{1-6}$haloalkyl, or $C_{3-8}$cycloalkyl, each of which is substituted with 0-1 $R^{B5}$; cyano, —C(O)NR₂, —NHC(O)R, or —NHSO₂R; and
$R^{B4}$ is H, halogen, methyl, —CF₃, cyclopropyl, or —O—$C_{1-3}$alkyl.

In another embodiment, the present invention provides a compound of formula (I), (II), (Ia), or (IIa), or a pharmaceutically acceptable salt or solvate thereof, wherein
$R^{B5}$ is cyano, —O—R, —C(O)NR₂, —C(O)OR, or —OC(O)—NH₂; and
each R is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_3$-$C_6$cycloalkyl, or $C_1$-$C_6$alkyl-$C_{3-6}$cycloalkyl; or for —C(O)NR₂, alternatively, two Rs along with the N to which they attach may form morpholinyl, pyrrolidinyl, or piperdinyl.

In another embodiment, the present invention provides a compound of formula (I), (II), (Ia), or (IIa), or a pharmaceutically acceptable salt or solvate thereof, wherein A is phenyl optionally substituted with 1 to 5, preferably 1 to 3, $R^A$ groups, or pyridinyl optionally substituted with 1 to 4, preferably 1, 2, or 3, $R^A$ groups.

In another embodiment, the present invention provides a compound of formula (I), (II), (Ia), or (IIa), or a pharmaceutically acceptable salt or solvate thereof, wherein A is phenyl optionally substituted with 1 to 5, preferably 1, 2, or 3, $R^A$ groups.

In another embodiment, the present invention provides a compound of formula (I), (II), (Ia), or (IIa), or a pharmaceutically acceptable salt or solvate thereof, wherein each $R^A$ is independently halogen, —CN, $C_{1-4}$alkyl, $C_{1-2}$haloalkyl, cyclopropyl, cyclohexyl, —O—$C_{1-3}$haloalkyl, —O—$C_{1-3}$alkyl, —CO—$C_{1-3}$alkyl, —O—$C_{3-6}$cycloalkyl, —C(O)O—$C_{1-3}$alkyl, or —$NR_2$; or alternatively, two adjacent $R^A$'s join to form —O—$CH_2$—O— or —O—$CF_2$—O—.

In another embodiment, the present invention provides a compound of formula (I), (II), (Ia), or (IIa), or a pharmaceutically acceptable salt or solvate thereof, wherein each $R^A$ is independently halogen, —CN, methyl, ethyl, propyl, isopropyl, —$CF_3$, $CHF_2$, cyclopropyl, cyclohexyl, —O—$CF_3$, —O—$CHF_2$, —O—$CH_3$, —CO—$C_{1-3}$alkyl, —O—$C_{3-6}$cycloalkyl, —C(O)O—$C_{1-3}$alkyl, or —$NR_2$; or alternatively, two adjacent $R^A$'s join to form —O—$CH_2$—O— or —O—$CF_2$—O—.

In another embodiment, the present invention provides a compound of formula (I), (II), (Ia), or (IIa), or a pharmaceutically acceptable salt or solvate thereof, wherein each R is independently hydrogen, $C_1$-$C_3$alkyl, $C_1$-$C_3$alkyl-$R^2$, $C_1$-$C_3$haloalkyl, —$C_1$-$C_3$haloalkyl-$R^2$, cyclopropyl, or —$C_1$-$C_3$alkyl-$C_{3-6}$cycloalkyl; or for any —C(O)$NR_2$ or —$NR_2$, alternatively, two Rs along with the N to which they attach may form morpholinyl, pyrrolidinyl, or piperdinyl.

In another embodiment, the present invention provides a compound of formula (I), (II), (Ia), or (IIa), or a pharmaceutically acceptable salt or solvate thereof, wherein Ring C is oxazolyl, and
$R^L$ is hydrogen or methyl.

In another embodiment, the present invention provides a compound of formula (I), (II), (Ia), or (IIa), or a pharmaceutically acceptable salt or solvate thereof, wherein Ring C is triazolyl, and
$R^L$ is hydrogen.

In another embodiment, the present invention provides a compound of formula (I), (II), (Ia), or (IIa), or a pharmaceutically acceptable salt or solvate thereof, wherein Ring D is phenyl.

In another embodiment, the present invention provides a compound of formula (I), (II), (Ia), or (IIa), or a pharmaceutically acceptable salt or solvate thereof, wherein each $R^{D1}$ is —S(O)$_2$-methyl, —S(O)$_2$N($R^3$)$_2$, —C(CH$_3$)$_2$—C(O)NH$_2$, -cyclopropyl-C(O)NH$_2$; and
$R^3$ is H or $C_{1-3}$-alkyl.

In another embodiment, the present invention provides a compound of formula (I), (II), (Ia), or (IIa), or a pharmaceutically acceptable salt or solvate thereof, wherein $R^{D1}$ is —SO$_2$-alkyl, —SO$_2$NR$_2$, —C(Me)$_2$-CONH$_2$, or

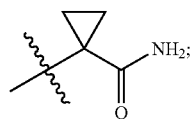 [SMILES: *C1(C(N)=O)CC1]

and
$R^{D2}$ is —$C_{1-6}$alkyl-OH or halo.

In another embodiment, the present invention provides a compound of formula (I), (II), (Ia), or (IIa), or a pharmaceutically acceptable salt or solvate thereof, wherein $R^{D1}$ is —SO$_2$—CH$_3$ or —SO$_2$NR$_2$.

In another embodiment, the present invention provides a compound of formula (I), (II), (Ia), or (IIa), or a pharmaceutically acceptable salt or solvate thereof, wherein $R^{D1}$ is —SO$_2$—CH$_3$.

In another embodiment, the present invention provides a compound of formula (I), (II), (Ia), or (IIa), or a pharmaceutically acceptable salt or solvate thereof, wherein $R^{D2}$ is —$C_{1-6}$alkyl-OH or halo.

In another embodiment, the present invention provides a compound selected from Examples 1-448, or a pharmaceutically acceptable salt or solvate thereof.

The various compounds described herein, or their pharmaceutically acceptable salts, may contain one or more asymmetric centers and may thus give rise to isomers, such as enantiomers, diastereomers, and other stereoisomeric forms. Such forms may be defined, in terms of absolute stereochemistry, as (R)- or (S)-, or as (D)- or (L)- for amino acids. The present invention is meant to include all such possible individual stereoisomers and mixtures thereof, including their racemic and optically pure enantiomeric or diastereomeric forms. The compounds are normally prepared as racemates and can conveniently be used as such, or optically active (+) and (−), (R)- and (S)-, or (D)- and (L)-isomers or corresponding diastereomers may be prepared using chiral synthons or chiral reagents, or they may be resolved from racemic mixtures using conventional techniques, such as chiral chromatography or reverse phase HPLC. When the compounds described herein contain olefinic double bonds or other centers of geometric asymmetry, and unless specified otherwise, it is intended that the compounds include both E and Z geometric isomers.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H or D and $^3$H or T, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H or D, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The present invention may be embodied in other specific forms without parting from the spirit or essential attributes thereof. This invention encompasses all combinations of aspects and/or embodiments of the invention noted herein. It is understood that any and all aspects or embodiments of the present invention may be taken in conjunction with any other aspect or embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)—O—$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon, or 1 to 8 carbon atoms, 1 to 6 carbon atoms, 1 to 4 carbon atoms, or 1 to 3 carbon atoms, atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkyloxycarbonyl" as used herein means an —C(O)OR° group, where R° is an alkyl group as defined herein.

The term "alkylcarbonyloxy" as used herein means an —OC(O)R° group, where R° is an alkyl group as defined herein.

The term "alkylthio" as used herein, means an —SR° group, where R° is an alkyl group as defined herein.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein, means a —$NH_2$ group.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3 (4H)-on-7-yl, 2H-benzo[b][1,4]oxazin3 (4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2 (3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carboxy" as used herein, means a —$CO_2H$ group.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein.

Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Nuclear receptor" refers to a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound. A nuclear receptor is a member of a superfamily of regulatory proteins that are receptors for various endogenous small molecules, e.g., steroids, retinoids, vitamin D and thyroid hormones. These proteins bind to cis-acting elements in the promoters of their target genes and modulate gene expression in response to a ligand therefore. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin D$_3$, fatty acids/peroxisome proliferators and ecdysone, that bind to HREs as heterodimers with a common partner, the retinoid X receptor (RXR). Among the latter receptors is LXR.

"Liver X receptor" or "LXR" refers to a nuclear receptor implicated in cholesterol biosynthesis. As used herein, the term LXR refers to both LXR$_\alpha$ and LXR$_\beta$, two forms of the protein found in mammals. Liver X receptor-α or LXR$_\alpha$ refers to the receptor described in U.S. Pat. Nos. 5,571,696, 5,696,233 and 5,710,004, and Willy et al. (1995) *Genes Dev.* 9(9): 1033-1045. Liver X receptor-β or LXR$_\beta$ refers to the receptor described in Peet et al. (1998) *Curr. Opin. Genet. Dev.* 8(5):571-575; Song et al. (1995) *Ann. N.Y. Acad. Sci.* 761:38-49; Alberti et al. (2000) *Gene* 243(1-2):93-103; and references cited therein; and in U.S. Pat. Nos. 5,571,696, 5,696,233 and 5,710,004.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

Compounds described herein may form salts or solvates, which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety and an acidic moiety, zwitterions ("inner salts") may be formed and are included within the term "salt(s)" as used herein. In one embodiment, the salts are pharmaceutically acceptable (i.e., non-toxic, physiologically acceptable), although other salts are also useful, e.g., in isolation or purification steps which may be employed during preparation. Salts of the compounds described herein may be formed, for example, by reacting a compound with an amount of acid or base, such as an equivalent amount, in a medium such as one in which the salt precipitates or in an aqueous medium followed by lyophilization.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Base addition salt" refers to those salts which retain the biological effectiveness and properties of the free acids, which are not biologically or otherwise undesirable. These salts are prepared from addition of an inorganic base or an organic base to the free acid.

Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Acid addition salts" and "base addition salts" which are not pharmaceutically acceptable may be useful in the preparation and/or purification of the compounds.

The present invention is intended to cover the compounds in their neutral state, salts of those compounds, or mixtures of the compounds in their neutral state with one or more salt forms, or mixtures of salt forms.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment, prophylaxis treatment, and/or reducing the risk of a disease or disorder described herein, in a subject, preferably a human, and includes:

i. inhibiting a disease or disorder, i.e., arresting its development; or
ii. relieving a disease or disorder, i.e., causing regression of the disorder.

"Subject" refers to a warm blooded animal such as a mammal, such as a human, or a human child, which is afflicted with, or has the potential to be afflicted with one or more diseases and disorders described herein.

"Atherosclerosis" refers to a process whereby atherosclerotic plaques form within the inner lining of the artery wall leading to atherosclerotic cardiovascular diseases.

Atherosclerotic cardiovascular diseases can be recognized and understood by physicians practicing in the relevant fields of medicine, and include without limitation, restenosis, coronary heart disease (also known as coronary artery disease or ischemic heart disease), cerebrovascular disease including ischemic stroke, multi-infarct dementia, and peripheral vessel disease, including intermittent claudication, and erectile dysfunction.

"Dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL).

"$EC_{50}$" refers to a dosage, concentration or amount of a particular test compound that elicits a dose-dependent response at 50% of maximal expression of a particular response that is induced, provoked or potentiated by the particular test compound.

"Cholesterol" refers to a steroid alcohol that is an essential component of cell membranes and myelin sheaths and, as used herein, incorporates its common usage. Cholesterol also serves as a precursor for steroid hormones and bile acids.

"Triglyceride(s)" or "TGs" refers to three fatty acid molecules esterified to a glycerol molecule and serve to store fatty acids which are used by muscle cells for energy production or are taken up and stored in adipose tissue.

"$IC_{50}$" refers to an amount, concentration or dosage of a particular test compound that achieves a 50% inhibition of a maximal response, such as modulation of nuclear receptor, including the $LXR_\alpha$ or $LXR_\beta$ activity, in an assay that measures such response.

"LXR" or "LXRs" refers to both $LXR_\alpha$ and $LXR_\beta$.

"$LXR_\alpha$" (LXR alpha) refers to all mammalian forms of such receptor including, for example, alternative splice isoforms and naturally occurring isoforms. Representative $LXR_\alpha$ species include, without limitation the rat (Genbank Accession NM_031627), mouse (Genbank Accession BC012646), and human (GenBank Accession No. U22662) forms of the receptor.

"$LXR_\beta$" (LXR beta) refers to all mammalian forms of such receptor including, for example, alternative splice isoforms and naturally occurring isoforms. Representative $LXR_\beta$ species include, without limitation the rat (GenBank Accession NM_031626), mouse (Genbank Accession NM_009473), and human (GenBank Accession No. U07132) forms of the receptor.

"Obese" and "obesity" refer to a Body Mass Index (BMI) greater than 27.8 $kg/m^2$ for men and 27.3 $kg/m^2$ for women (BMI equals weight $(kg)/(height)^2(m^2)$.

"Stable compound" and "stable structure" are meant to indicate a compound that is sufficiently robust to survive isolation to a useful degree of purity from a reaction mixture, and formulation into an efficacious therapeutic agent. The present invention is intended to cover stable compounds.

Utility

The compounds of the invention exhibit valuable pharmacological properties and are particularly useful as LXR agonists, antagonists, inverse agonists, partial agonists and antagonists, or are selective to $LXR_\alpha$ or to $LXR_\beta$. The compounds of the invention are useful for the treatment of diseases or disorders described herein, such as those associated with, or having symptoms arising from the complications of, altered cholesterol transport, reverse cholesterol transport, fatty acid metabolism, cholesterol absorption, cholesterol re-absorption, cholesterol secretion, cholesterol excretion, or cholesterol metabolism.

These diseases include, for example, atherosclerosis, atherosclerotic cardiovascular diseases, (see, e.g., International Patent Application Publication Nos. WO 00/57915 and WO 00/37077), dyslipidemia, hyperglycemia, insulin resistance, diabetes, obesity, syndrome X (US Patent Application Publication No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retintis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), or Alzheimer's disease (see, e.g., International Patent Application Publication No. WO 00/17334; *Trends in Neurosci-*

*ences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J. Lipid Res.* (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a subject with atherosclerosis or atherosclerotic cardiovascular disease manifest by clinical signs of such disease, wherein the methods comprise administering to the subject a therapeutically effective amount of a compound or composition of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a subject at risk for such an event.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a subject in need of such treatment. Additionally, the instant invention also provides a method for preventing or reducing the risk of developing hyperglycemia, insulin resistance, diabetes or syndrome X in a subject, comprising the administration of a prophylactically effective amount of a compound or composition of the present invention to a subject at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). Uncontrolled hyperglycemia is associated with increased and premature mortality due to an increased risk for macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM). Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese subjects and lipid oxidation is increased.

Premature development of atherosclerosis and an increased rate of cardiovascular and peripheral vascular diseases are characteristic features of subjects with diabetes. Hyperlipidemia is an important precipitating factor for these diseases. Hyperlipidemia is a disorder generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. *Ann. Chim. Med.* (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., *Diabetes* (1974), Vol. 23, pp. 105-11 (1974); and Laakso, M. and Lehto, S., *Diabetes Reviews* (1997), Vol. 5, No. 4, pp. 294-315). Several lipoprotein abnormalities have been described among diabetic subjects (Howard B., et al., *Arteriosclerosis* (1978), Vol. 30, pp. 153-162).

Further provided by this invention are methods of using the compounds of the invention to treat obesity, as well as the complications of obesity. Obesity is linked to a variety of medical disorders including diabetes and hyperlipidemia. Obesity is also a known risk factor for the development of type 2 diabetes (See, e.g., Barrett-Conner, E., *Epidemol. Rev.* (1989), Vol. 11, pp. 172-181; and Knowler, et al., *Am. J Clin. Nutr.* (1991), Vol. 53, pp. 1543-1551).

Administration and Formulation

A compound of the invention can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

A compound of the invention can be administered in any acceptable solid, semi-solid, liquid or gaseous dosage form. Acceptable dosage forms include, but are not limited to, aerosols, capsules, creams, emulsions, gases, gels, grains, liniments, lotions, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories.

A dosage form of the invention may be comprised solely of a compound of the invention or the compound of the invention may be formulated along with conventional excipients, pharmaceutical carriers, adjuvants, and/or other medicinal or pharmaceutical agents. Acceptable excipients include, but are not limited to, (a) antiadherents, such as croscarmellose sodium, crosprovidone, sodium starch glycolate, microcrystalline cellulose, starch and talc; (b) binders, such as cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac, zein and enteric agents; (d) disintegrants, such as cellulose, crosslinked polyvinyl pyrrolidone, sodium carboxymethyl cellulose, methylcellulose, microcrystalline cellulose, sodium starch glycolate and starch; (e) filling agents, such as calcium carbonate, cellulose, dibasic calcium phosphate, glucose, lactose, mannitol, sorbitol and sucrose; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Capsules may contain any of the afore listed excipients, and may additionally contain a semi-solid or liquid carrier, such as a polyethylene glycol or vegetable-based oils. Pharmaceutical carriers include soluble polymers, microparticles made of insoluble or biodegradable natural and synthetic polymers, microcapsules or microspheres, lipoproteins, liposomes and micelles.

The pharmaceutical composition may be in the form of a liquid, e.g., an elixir, syrup, solution, emulsion, suspension, or other like forms or may be presented as a dry product for reconstitution with water or other suitable vehicle before use. Liquid preparations may contain conventional additives such as (a) liquid diluents, such as water, saline, Ringer's solution, fixed oils such as synthetic mono or diglycerides, or polyethylene glycols, glycerin, propylene glycol or other solvents; (b) surfactants, suspending agents, or emulsifying agents, such as polyoxyethylene sorbitan fatty acid esters, saturated polyglycolized glycerides, monoglycerides, fatty acid esters, block copolymers of ethylene oxide and propylene oxide, polyoxyl stearates, ethoxylated castor oils, and ethoxylated hydroxystearic acids; (c) buffers, such as acetates, citrates or phosphates; (d) chelating agents, such as ethylenediaminetetraacetic acid; (e) antibacterial agents, such as benzyl alcohol or methyl paraben; (f) antioxidants, such as ascorbic acid or sodium bisulfite; (g) isotonic agents, sodium chloride or dextrose; as well as sweetening and flavoring agents, dyes and preservatives.

A pharmaceutical composition of the invention will contain a therapeutically effective amount of a compound of the invention, as an individual stereoisomer or mixture of stereoisomers, or a pharmaceutically acceptable salt thereof, with the remainder of the pharmaceutical composition comprised of one or more pharmaceutically acceptable excipients. Generally, for oral administration, a compound of the invention, as an individual stereoisomer or mixture of stereoisomers, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, as an individual stereoisomer or mixture of stereoisomers, or a pharmaceutically acceptable salt thereof will comprise from 5% to 75% by weight of a pharmaceutically acceptable composition, with the remainder of the composition comprised of one or more pharmaceutically acceptable excipients. For parenteral administration, a compound of the invention, as an individual stereoisomer or mixture of stereoisomers, or a pharmaceutically acceptable salt thereof will comprise from 0.01% to 1% by weight of a pharmaceutically acceptable composition. Methods for preparing the dosage forms of the invention are known, or will be apparent, to those skilled in this art; for example, see Remington's Pharmaceutical Sciences, 18th Ed., (Mack Publishing Company, Easton, Pa., 1990).

A therapeutically effective amount of a compound of the invention will vary depending upon a sundry of factors including the activity, metabolic stability, rate of excretion and duration of action of the compound, the age, weight, general health, sex, diet and species of the subject, the mode and time of administration of the compound, the presence of adjuvants or additional therapeutically active ingredients in a composition, and the severity of the disease for which the therapeutic effect is sought.

The compounds of the invention can be administered to human subjects at dosage levels in the range of about 0.1 to about 10,000 mg per day. A normal human adult having a body weight of about 70 kilograms can be administered a dosage in the range of from about 0.15 µg to about 150 mg per kilogram of body weight per day. Typically, a normal adult human will be administered from about 0.1 mg to about 25 mg, or 0.5 mg to about 10 mg per kilogram of body weight per day. The compounds of the invention may be administered in one or more unit dose forms. The unit doses may be administered one to four times a day, or two times a day, or once a day. In an alternate method of describing an effective dose, an oral unit dose is one that is necessary to achieve a blood serum level of about 0.05 to 20 µg/ml or about 1 to 20 µg/ml in a subject. The optimum dose of a compound of the invention for a particular subject can be determined by one of ordinary skill in the art.

Compounds of the invention, or an individual isomer or mixture of isomers or a pharmaceutically acceptable salt thereof, may also be administered simultaneously with, prior to, or after administration of one or more of the therapeutic agents described below. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the subject together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In one embodiment, the compounds of the invention are used in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A: cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, the compounds of the invention are used in combination with one or more of the following therapeutic agents in treating cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulae of these and additional HMG-CoA reductase inhibitors that can be used in combination with the compounds of the invention are described at page 87 of M. Yalpani, "Cholesterol Lowering Drugs," Chemistry & Industry, pp. 85-89 (5 Feb. 1996). In presently preferred embodiments, the HMG-CoA reductase inhibitor is selected from lovastatin and simvastatin.

In an additional embodiment, the compounds of the invention are used in combination with one or more of the following therapeutic agents in treating with one or more additional active diabetes agents depending on the desired target therapy (see, e.g., Turner, N. et al., Prog. Drug Res. (1998), Vol. 51, pp. 33-94; Haffner, S., Diabetes Care (1998), Vol. 21, pp. 160-178; and DeFronzo, R. et al. (eds.), Diabetes Reviews (1997), Vol. 5, No. 4). A number of studies have investigated the benefits of combination therapies with oral agents (see, e.g., Mahler, R., J. Clin. Endocrinol. Metab. (1999), Vol. 84, pp. 1165-71; United Kingdom Prospective Diabetes Study Group: UKPDS 28, Diabetes Care (1998), Vol. 21, pp. 87-92; Bardin, C. W. (ed.), Current Therapy In Endocrinology And Metabolism, 6th Edition (Mosby—Year Book, Inc., St. Louis, Mo. 1997); Chiasson, J. et al., Ann. Intern. Med. (1994), Vol. 121, pp. 928-935; Coniff, R. et al., Clin. Ther. (1997), Vol. 19, pp. 16-26; Coniff, R. et al., Am. J. Med. (1995), Vol. 98, pp. 443-451; Iwamoto, Y. et al., Diabet. Med. (1996), Vol. 13, pp. 365-370; Kwiterovich, P., Am. J. Cardiol (1998), Vol. 82 (12A), pp. 3U-17U). These studies indicate that diabetes and hyperlipidemia modulation can be further improved by the addition of a second agent to the therapeutic regimen.

In a further embodiment, the compounds of the invention are used in combination with one or more of the following therapeutic agents in treating in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the therapeutic agents discussed above for treating atherosclerosis.

In yet another embodiment, the compounds of the invention are used in combination with one or more of the following therapeutic agents in treating obesity or obesity-related disorders. Such agents, include, but are not limited to, phenylpropanolamine, phentermine, diethylpropion, mazindol, fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

Example A

Scintillation Proximity Assay (SPA)

The SPA assay measures the radioactive signal generated by the binding of $^3$H-24,25-epoxycholesterol to LXR$_α$-RXR$_α$ or LXR$_β$-RXR$_α$ heterodimers The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

Required Materials:
1. Label: 24(S),25-[26,27-(3H)]-epoxy-cholesterol (Perkin Elmer)
2. $LXR_\alpha$ lysate: Baculovirus expressed $LXR_\alpha$/RXR heterodimer both with a 6-HIS tag produced as a crude lysate
3. $LXR_\beta$ lysate: Baculovirus expressed $LXR_\beta$/RXR heterodimer both with a 6-HIS tag produced as a crude lysate
4. SPA beads: YSi copper His-tag SPA beads (Perkin Elmer)
5. Plates: Optiplate, Opaque, 384-well plate (Perkin Elmer)
6. Protein lysate dilution buffer: (20 mM Tris-HCl pH 7.9, 500 mM NaCl, 5 mM Imidazole).
7. 2×SPA Buffer: (40 mM $K_2HPO_4$/$KH_2PO_4$ pH7.3, 100 mM NaCl, 0.05% Tween 20, 20% Glycerol, 4 mM EDTA)
8. 2×SPA Buffer w/o EDTA: (40 mM $K_2HPO_4$/$KH_2PO_4$ pH7.3, 100 mM NaCl, 0.05% Tween 20, 20% Glycerol)

Stock Solutions
0.5 M $K_2HPO_4$/$KH_2PO_4$ pH 7.3
0.5 M EDTA pH 8.0
5 M NaCl
10% Tween-20
Glycerol Preparation of Protein Lysates Baculovirus expression plasmids for human RXR α (accession No NM_002957), $LXR_\alpha$ (accession No U22662), and $LXR_\beta$ (accession No U07132) were made by cloning the appropriate full-length cDNAs into the pBacPakhis2 vector (Clontech, CA) following standard procedures. Insertion of the cDNAs into the pBAcPakhis2 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately $2.0 \times 10^6$/ml at 27° C., in a total volume of 1 L per 3 L sized shake flasks, cultured under standard conditions. To prepare the $LXR_\alpha$ lysate, insect cells were co-infected with the recombinant viruses containing $LXR_\alpha$ and $RXR_\alpha$ in a ratio of 2:1. To prepare the $LXR_\beta$ lysate, insect cells were co-infected with the recombinant viruses containing $LXR_\beta$ and $RXR_\alpha$ in a ratio of 2:1. In both cases cells were incubated for 68 hours at 27° C. with constant shaking prior to harvesting.

After incubation, cells were harvested by centrifugation and pelleted. Cell pellets were resuspended in 40 ml of freshly prepared ice-cold extraction buffer (20 mM Tris pH 8.0, 10 mM Imidazole, 400 mM NaCl, 10% glycerol, 0.1 mM DTT and EDTA free protease inhibitor tablet (Sigma Catalog No:S8830)), per 1 L culture.

Cells were homogenized slowly on ice using a Dounce homogenizer to achieve 80-90% cell lysis. The homogenate was centrifuged in a pre-chilled rotor (Ti50 or Ti70, or equivalent) at 45,000 rpm for 40 minutes at 4° C. Aliquots of the supernatant were frozen on dry ice and stored frozen at −80° C. until quantification and quality control.

Preparation of Screening Reagents

[$^3$H]24,25 Epoxycholesterol (EC) solution: For a single 384-well plate, 52.26 µL of [$^3$H] EC (specific activity 76 Ci/mmol, concentration 1 mCi/mL) was added to 4.5 mL of 2×SPA buffer to provide for a final concentration of 76.25 nM. For each additional 384-well plate, an additional 52.27 µL of [$^3$H] EC was added to 4.5 mL of additional 2×SPA buffer. The final concentration of [$^3$H] EC in the well was 25 nM.

$LXR_\alpha$ lysate (prepared as above) was diluted with protein lysate dilution buffer. 9000 µL of diluted $LXR_\alpha$ lysate was prepared per 384-well plate and 9000 µL of diluted $LXR_\alpha$ lysate was prepared for each additional 384-well plate.

$LXR_\beta$ lysate (prepared as above) was diluted with protein lysate dilution buffer. 9000 µL of diluted $LXR_\beta$ lysate was prepared per 384-well plate and 9000 µL of diluted LXRβ lysate was prepared for each additional 384-well plate.

SPA bead solution: 4.5 mL of 2×SPA buffer w/o EDTA, 3.6 mL of $H_2O$, and 0.9 mL of Ysi His-tag SPA beads (vortex well before taking) were mixed together to prepare 10% SPA bead solution for a 384-well plate involving LXR lysate. 4.5 mL of 2×SPA buffer w/o EDTA, 2.7 mL of $H_2O$, and 1.8 mL of Ysi His-tag SPA beads (vortex well before taking) were mixed together to prepare 20% SPA bead solution for a 384-well plate involving $LXR_\beta$ lysate.

Procedure:

Appropriate dilutions of each compound were prepared in a 384-well plate and pipetted into the appropriate wells of two 384 well plate at 1 µL per well.

20 µL of [$^3$H] EC was added to each well of both 384 well plates.

20 µl of diluted $LXR_\alpha$ lysate was added to each well of the first 384 well plate.

20 µL of diluted $LXR_\beta$ lysate was added to each well of the second 384 well plate.

20 µL of 10% SPA bead solution was added to each well of first 384 well plate. 20 µL of 20% SPA bead solution was added to each well of second 384 well plate The plates were covered with clear sealer, placed on a shaker (300 RPM) for 10 minutes then incubated at ambient temperature for 10 minutes and then spinned at 1000 RPM for 10 minutes at ambient temperature.

The Plates were analyzed using a luminescent plate reader (MicroBeta, Wallac) using the program projectAD 3H_384CPM. The setting for n projectAD 3H_384CPM was:

Counting Mode: CPM;
Sample Type: Top-read;
Count time: 1 minute.

Assays for $LXR_\alpha$ and $LXR_\beta$ were performed in the identical manner. The determined Ki represents the average of at least three independent dose response experiments. The binding affinity for each compound may be determined by non-linear regression analysis using the one site competition formula to determine the $IC_{50}$ where:

$$Y = Bottom + (Top - Bottom)/(1 + 10^{X-\log IC50}).$$

The Ki is than calculated using the Cheng and Prusoff equation where:

$$Ki = IC_{50}/(1 + [Concentration\ of\ Ligand]/Kd\ of\ Ligand).$$

For this assay, typically the Concentration of Ligand=25 nM and the Kd of EC for the receptor is 200 nM as determined by saturation binding.

The compounds of the invention demonstrated the ability to bind to $LXR_\beta$ and/or $LXR_\alpha$, when tested in this assay.

Example B

Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay, expression plasmids for LXRα and LXRβ are introduced separately via transient transfection into mammalian cells along with a luciferase reporter plasmid that contains one copy of a DNA sequence that is bound by LXR-RXR heterodimers (LXRE; Willy, P. et. al. 1995). LXRs heterodimerize with the endogenous RXR. Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials

CV-1 African Green Monkey Kidney Cells

Co-transfection expression plasmids, comprising full-length LXR$_\alpha$ (pCMX-h LXR$_\alpha$ or LXR$_\beta$ (pCMX-hLXR$_\beta$), reporter plasmid (LXREx1-Tk-Luciferase), and control (pCMX-Galactosidase expression vector) (Willey et al. Genes & Development 9 1033-1045 (1995)).

Transfection reagent such as FuGENE6 (Roche) or Transit 2020 (Mirus Bio)

1× cell lysis buffer:
22.4 mM Tricine pH 8.0
0.56 mM EGTA pH 8.0
5.6 mM MgSO$_4$
0.6% Triton X-100
5.6% glycerol
10× luciferase substrate solution:
10 mM HEPES pH 6.5
2.75 mM D-Luciferin
0.75 mM Coenzyme-A
3.7 mM ATP
96 mM DTT Preparation of Screening Reagents CV-1 cells were prepared 24 hours prior to the experiment by plating them into T-175 flasks or 500 cm$^2$ dishes in order to achieve 70-80% confluency on the day of the transfection. The number of cells to be transfected was determined by the number of plates to be screened. Each well of a 384 well plate requires 1.5×10$^4$ cells. DNA Transfection Reagent was prepared by mixing the required plasmid DNAs with a cationic lipid transfection reagent Transit 2020 (Mirus Bio) for CV1 by following the instructions provided with the reagents. Optimal DNA amounts were determined empirically per cell line and size of vessel to be transfected. For each T175 cm$^2$ flask a total of 44.4 ug for CV1 of DNA, 133 ul Transit2020 and 4.5 ml DMEM for CV1 was mixed and added. Cells were then incubated at least 5 hours at 37° C. to prepare screening cells.

Luciferase assay reagent was prepared by combining before use:
1 part of 10× Luciferase substrate solution
9 parts of 1× cell lysis buffer.

Procedure

Assay plates were prepared by dispensing 5 μL of compound per well of a 384 well plate to achieve final compound concentration of 10 μM and no more than 0.5% DMSO. Media was removed from the screening cells, the cells trypsinized, harvested cells by centrifugation, counted, and plated at a density of approximately 1.5×10$^4$ cells in the 384 well assay plate prepared above in a volume of about 95 uL. Assay plates containing both compounds and screening cells (100 μL in total volume) were incubated for 20 hours at 37° C.

After incubation with compounds, media was removed from the cells and luciferase assay reagent (30 μL/well) added. After ~2 minutes at ambient temperature, the assay plates were read on a luminometer (PE Biosystems Northstar reader with on-board injectors, or Envision (Perkin Elmer) or equivalent).

The LXR/LXRE co-transfection assay can be used to establish the EC$_{50}$/IC$_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethylpropionamide)) or a low control (DMSO/vehicle). The dose response curves are generated from a 10 point curve with concentrations differing by ½ LOG units. Each point represents the average of 4 wells of data from a 384 well plate.

The data from this assay is fitted to the following equation, from which the EC$_{50}$ value may be solved:

$$Y = \text{Bottom} + (\text{Top} - \text{Bottom})/(1 + 10^{((\log EC50 - X)*HillSlope)}).$$

The EC$_{50}$/IC$_{50}$ is therefore defined as the concentration at which an agonist or antagonist elicits a response that is halfway between the Top (maximum) and Bottom (baseline) values. The EC$_{50}$/IC$_{50}$ values represented are the averages of at least 2 and normally 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethylpropionamide) that is measured individually in each dose response experiment.

Table 1 lists LXRβ EC$_{50}$ values and % efficacy measurements in the cotransfection assay for examples of this invention.

| Example # | LXRbeta agonism EC50 (uM) | LXRbeta % EFFICACY |
| --- | --- | --- |
| 1 | 0.783 | 68 |
| 2 | 0.026 | 89 |
| 3 | 0.245 | 73 |
| 4 | 1.580 | 82 |
| 5 | 0.012 | 109 |
| 6 | 0.252 | 84 |
| 7 | 0.377 | 66 |
| 8 | 2.317 | 79 |
| 9 | 0.070 | 82 |
| 10 | 0.031 | 104 |
| 11 | 0.015 | 104 |
| 12 | 0.074 | 81 |
| 13 | 0.045 | 83 |
| 14 | 0.032 | 99 |
| 15 | 0.011 | 95 |
| 16 | 0.163 | 89 |
| 17 | 0.061 | 96 |
| 18 | 0.057 | 87 |
| 19 | 0.091 | 79 |
| 20 | 0.038 | 86 |
| 21 | 0.022 | 82 |
| 22 | 0.126 | 80 |
| 23 | 0.042 | 79 |
| 24 | 1.381 | 48 |
| 25 | 1.024 | 78 |
| 26 | 0.903 | 81 |
| 27 | 1.566 | 111 |
| 28 | 0.501 | 107 |
| 29 | 1.228 | 80 |
| 30 | 1.094 | 15 |
| 31 | 0.568 | 50 |
| 32 | 1.759 | 43 |
| 33 | 1.426 | 66 |
| 34 | 0.878 | 63 |

| Example # | LXRbeta agonism EC50 (uM) | LXRbeta % EFFICACY |
|---|---|---|
| 35 | 2.230 | 87 |
| 36 | 2.731 | 91 |
| 37 | 1.562 | 47 |
| 38 | 1.130 | 60 |
| 39 | 0.776 | 79 |
| 40 | 0.695 | 76 |
| 41 | 0.321 | 45 |
| 42 | 0.196 | 67 |
| 43 | 0.412 | 65 |
| 44 | 1.346 | 57 |
| 45 | 0.297 | 45 |
| 46 | 0.025 | 45 |
| 47 | 0.663 | 72 |
| 48 | 0.046 | 27 |
| 49 | 0.086 | 69 |
| 50 | 0.122 | 61 |
| 51 | 0.007 | 73 |
| 52 | 2.520 | 30 |
| 53 | 0.046 | 94 |
| 54 | 0.297 | 53 |
| 55 | 0.761 | 24 |
| 56 | 1.098 | 35 |
| 57 | 0.158 | 18 |
| 58 | 0.018 | 94 |
| 59 | 0.006 | 76 |
| 60 | 0.007 | 85 |
| 61 | 0.592 | 40 |
| 62 | 0.030 | 72 |
| 63 | 0.055 | 33 |
| 64 | 0.024 | 42 |
| 65 | 0.067 | 55 |
| 66 | 0.027 | 27 |
| 67 | 0.024 | 79 |
| 68 | 0.029 | 51 |
| 69 | 0.160 | 24 |
| 70 | 0.317 | 42 |
| 71 | 0.047 | 52 |
| 72 | 0.073 | 60 |
| 73 | 0.042 | 55 |
| 74 | 0.092 | 60 |
| 75 | 7.668 | 52 |
| 76 | 0.084 | 88 |
| 77 | 0.030 | 86 |
| 78 | 0.072 | 79 |
| 79 | 0.017 | 87 |
| 80 | 0.131 | 58 |
| 81 | 0.184 | 43 |
| 82 | 0.059 | 33 |
| 83 | 0.497 | 62 |
| 84 | 0.061 | 26 |
| 85 | 0.588 | 55 |
| 86 | 0.715 | 37 |
| 87 | 0.134 | 33 |
| 88 | 0.085 | 49 |
| 89 | 4.779 | 37 |
| 90 | 0.058 | 34 |
| 91 | 0.135 | 45 |
| 92 | 0.105 | 38 |
| 93 | 0.016 | 93 |
| 94 | 0.032 | 87 |
| 95 | 0.019 | 65 |
| 96 | 0.126 | 61 |
| 97 | 0.048 | 82 |
| 98 | 0.258 | 57 |
| 99 | 0.279 | 26 |
| 100 | 0.193 | 52 |
| 101 | 0.079 | 50 |
| 102 | 0.227 | 96 |
| 103 | 0.148 | 47 |
| 104 | 0.054 | 56 |
| 105 | 0.074 | 66 |
| 106 | 0.071 | 64 |
| 107 | 1.247 | 37 |
| 108 | 0.529 | 30 |
| 109 | 0.356 | 52 |
| 110 | 0.244 | 55 |
| 111 | 0.284 | 51 |
| 112 | 0.257 | 33 |
| 113 | 0.344 | 37 |
| 114 | 0.273 | 28 |
| 115 | 0.019 | 62 |
| 116 | 0.026 | 99 |
| 117 | 0.049 | 70 |
| 118 | 0.007 | 86 |
| 119 | 1.082 | 60 |
| 120 | 0.046 | 32 |
| 121 | 0.175 | 40 |
| 122 | 0.063 | 22 |
| 123 | 0.094 | 35 |
| 124 | 0.769 | 24 |
| 125 | 0.179 | 88 |
| 126 | 0.299 | 85 |
| 127 | 0.059 | 99 |
| 128 | 0.159 | 44 |
| 129 | 0.087 | 48 |
| 130 | 0.113 | 56 |
| 131 | 0.178 | 47 |
| 132 | 0.157 | 49 |
| 133 | 0.012 | 66 |
| 300 | 0.153 | 99 |
| 301 | 0.032 | 101 |
| 302 | 0.227 | 93 |
| 303 | 0.825 | 102 |
| 304 | 2.855 | 26 |
| 305 | 2.044 | 45 |
| 306 | 0.203 | 71 |
| 307 | 0.091 | 98 |
| 308 | 1.654 | 29 |
| 309 | 0.120 | 68 |
| 310 | 0.027 | 75 |
| 311 | 0.798 | 37 |
| 312 | 0.798 | 34 |
| 313 | 0.020 | 59 |
| 314 | 0.011 | 68 |
| 315 | 0.070 | 48 |
| 316 | 0.293 | 24 |
| 317 | 0.092 | 27 |
| 318 | 0.246 | 84 |
| 319 | 0.071 | 80 |
| 320 | 0.472 | 58 |
| 321 | 1.445 | 40 |
| 322 | 1.111 | 58 |
| 323 | 0.948 | 48 |
| 324 | 1.228 | 44 |
| 325 | 0.012 | 78 |
| 326 | 0.015 | 77 |
| 327 | 0.027 | 78 |
| 328 | 0.024 | 112 |
| 329 | 0.003 | 92 |
| 330 | 0.005 | 64 |
| 331 | 0.061 | 82 |
| 332 | 0.035 | 70 |
| 333 | 0.035 | 69 |
| 334 | 0.305 | 80 |
| 335 | 0.029 | 71 |
| 336 | 0.033 | 75 |
| 337 | 0.178 | 77 |
| 338 | 0.186 | 58 |
| 339 | 0.060 | 64 |
| 340 | 0.279 | 72 |
| 341 | 0.058 | 76 |
| 342 | 0.432 | 46 |
| 343 | 0.149 | 74 |
| 344 | 0.116 | 72 |
| 345 | 0.073 | 75 |
| 346 | 0.037 | 90 |
| 347 | 0.035 | 92 |
| 348 | 0.059 | 57 |
| 349 | 0.008 | 72 |
| 350 | 0.066 | 91 |

| Example # | LXRbeta agonism EC50 (uM) | LXRbeta % EFFICACY |
|---|---|---|
| 351 | 0.062 | 77 |
| 352 | 0.014 | 76 |
| 353 | 0.023 | 93 |
| 354 | 0.010 | 101 |
| 355 | 0.196 | 65 |
| 356 | 0.071 | 63 |
| 357 | 0.392 | 41 |
| 358 | 0.105 | 30 |
| 359 | 0.316 | 14 |
| 360 | 0.263 | 12 |
| 361 | 0.652 | 12 |
| 362 | 0.064 | 22 |
| 363 | 1.524 | 22 |
| 364 | 0.950 | 18 |
| 365 | 0.424 | 76 |
| 366 | 0.293 | 28 |
| 367 | 0.264 | 55 |
| 368 | 0.890 | 50 |
| 369 | 0.226 | 99 |
| 370 | 0.125 | 86 |
| 371 | 0.119 | 33 |
| 372 | 0.123 | 38 |
| 373 | 0.092 | 22 |
| 374 | 0.421 | 47 |
| 375 | 0.198 | 62 |
| 376 | 1.296 | 53 |
| 377 | 0.028 | 23 |
| 378 | 0.015 | 29 |
| 379 | 0.027 | 86 |
| 380 | 0.465 | 29 |
| 381 | 1.082 | 61 |
| 382 | 0.629 | 50 |
| 383 | 0.018 | 76 |
| 384 | 0.015 | 73 |
| 385 | 0.042 | 71 |
| 386 | 0.034 | 86 |
| 387 | 0.082 | 79 |
| 388 | 0.009 | 78 |
| 389 | 0.007 | 84 |
| 390 | 0.010 | 72 |
| 391 | 0.165 | 56 |
| 392 | 0.012 | 71 |
| 393 | 0.744 | 40 |
| 394 | 0.016 | 97 |
| 395 | 0.011 | 83 |
| 396 | 0.090 | 67 |
| 397 | 0.194 | 68 |
| 398 | 0.038 | 63 |
| 399 | 0.200 | 60 |
| 400 | 0.038 | 53 |
| 401 | 0.131 | 76 |
| 402 | 0.014 | 67 |
| 403 | 0.082 | 62 |
| 404 | 0.185 | 67 |
| 405 | 0.100 | 63 |
| 406 | 0.143 | 63 |
| 407 | 0.067 | 91 |
| 408 | 0.018 | 73 |
| 409 | 0.045 | 69 |
| 410 | 0.020 | 82 |
| 411 | 0.019 | 90 |
| 412 | 0.029 | 93 |
| 413 | 0.052 | 73 |
| 414 | 0.092 | 80 |
| 415 | 0.458 | 37 |
| 416 | 3.048 | 27 |
| 417 | 1.011 | 16 |
| 418 | 0.728 | 74 |
| 419 | 0.004 | 71 |
| 420 | 0.007 | 74 |
| 421 | 0.021 | 76 |
| 422 | 0.004 | 98 |
| 423 | 0.060 | 78 |
| 424 | 0.013 | 60 |
| 425 | 0.024 | 99 |
| 426 | 0.008 | 72 |
| 427 | 0.094 | 58 |
| 428 | 0.093 | 83 |
| 429 | 0.348 | 60 |
| 430 | 0.041 | 80 |
| 431 | 0.037 | 69 |
| 432 | 0.019 | 79 |
| 433 | 0.050 | 83 |
| 434 | 0.013 | 78 |
| 435 | 0.030 | 53 |
| 436 | 0.006 | 61 |
| 437 | 0.321 | 49 |
| 438 | 0.128 | 70 |
| 439 | 0.038 | 64 |
| 440 | 0.051 | 62 |
| 441 | 0.176 | 31 |
| 442 | 0.052 | 60 |
| 443 | 0.022 | 35 |
| 444 | 0.076 | 63 |
| 445 | 0.170 | 63 |
| 446 | 0.030 | 28 |
| 447 | 0.116 | 28 |
| 448 | 0.279 | 30 |

Abbreviations

Ac: acetic (AcOH: acetic acid, EtOAc: ethyl acetate, KOAc: potassium acetate, Ac$_2$O: acetic anhydride, AcCl: acetyl chloride)
AIBN: azobisisobutyronitrile
aq: aqueous
CAN: ceric ammonium nitrate
Cp*Ru(COD)Cl: 1,5-cyclooctadiene(pentamethylcyclopentadienyl)ruthenium(II) chloride
DCE: 1,2-dichloroethane
DCM: dichloromethane
Dess-Martin periodinane: 1,1,1-Tris(acetyloxy)-1,1-dihydro-1,2-benziodoxol-3-(1H)-one
DME: 1,2-dimethoxyethane
DMF: dimethylformamide
DMS: dimethyl sulfide
DMSO: dimethyl sulfoxide
dppf (e.g: PdCl$_2$(dppf)): 1,1'-bis(diphenylphosphino)ferrocene
EDCI: 1-ethyl-3-(3-dimethylaminopropyl) carbodiimide
ESI: electrospray ionization
Et: ethyl (EtOH: ethanol, EtOAc: ethyl acetate, NaOEt: sodium ethoxide, Et$_3$N: triethylamine)
GCMS: gas chromatography-mass spectrometry
HOBt: 1-hydroxybenzotriazole
HPLC: high-performance liquid chromatography
hrs: hours
Hx: hexanes
IR: infrared spectroscopy
LCMS: liquid chromatography-mass spectrometry
LDA: lithium diisopropylamide
LHMDS: lithium hexamethyldisilazide
m-CPBA: meta-chloroperoxybenzoic acid
Me: methyl (MeOH: methanol, MeCN: acetonitrile, MeMgBr: methyl magnesium bromide, MeTHF: 2-methyltetrahydrofuran, NaOMe: sodium methoxide)
min: minutes
MS: mass spectrometry
MW (or wave): microwave NBS: N-bromosuccinimide
NCS: N-chlorosuccinimide
NIS: N-iodosuccinimide
NMR: nuclear magnetic resonance
ppm: part per million
pTSA (or pTsOH): para-toluenesulfonic acid
RAP: relative area percent
rt: room temperature
RT: retention time
Sat.: saturated
TFA: trifluoroacetic acid
THF: tetrahydrofuran
TLC: thin layer chromatography
TMSCN: trimethylsilyl cyanide
TosMIC: Toluenesulfonylmethyl isocyanide General Methods LCMS Method A:
Column: PUROSPHER@Star RP-18 (4.0×55 mm), 3 μm
Mobile phase A: 20 mM NH$_4$OAc in 90% H$_2$O, 10% MeCN
Mobile phase B: 20 mM NH$_4$OAc in 10% H$_2$O, 90% MeCN
Flow: 2.5 mL/min LCMS Method B:
Column: ZORBOX SB C18 (4.6×50 mm), 5 μm (positive mode)
Mobile phase A: 10% MeOH; 90% H$_2$O; 0.1% TFA
Mobile phase B: 90% MeOH; 10% H$_2$O; 0.1% TFA
Flow: 5 mL/min HPLC Method A:
Column: SUNFIRE C18 (4.6×150 mm), 3.5 micron BBRC/LC/011
0.05% TFA in Water pH adjusted to 2.5 using diluted ammonia
Mobile phase A: Buffer:MeCN (95:5)
Mobile Phase B: MeCN:Buffer (95:5)

| Flow: 1 mL/min | |
|---|---|
| Time | % B |
| 0 | 10 |
| 12 | 100 |
| 15 | 100 |

Synthesis

The compounds of the present invention may be prepared in a number of methods well known to those skilled in the art, including, but not limited to those described below, or through modifications of these methods by applying standard techniques known to those skilled in the art of organic synthesis. The compounds were named using ChemBioDraw Ultra 12.0 (CambridgeSoft). The reagents and starting materials are commercially available, or readily synthesized by well-known techniques by one of ordinary skill in the arts. It is understood that in the following description, combinations of substituents and/or variables of the depicted formulae are permissible only if such contributions result in stable compounds. Unless otherwise indicated, all compounds associated with NMR and/or mass spectra data were prepared and the NMR and mass spectra measured.

INTERMEDIATES

Intermediate Scheme 1

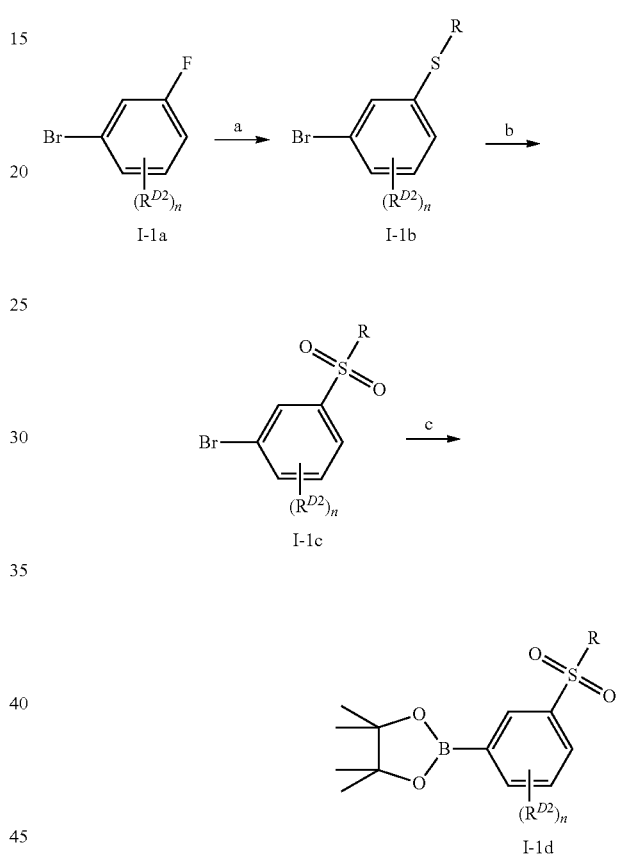

a) i. 1.0M LHMDS in THF; ii. R'SNa, reflux; b) mCPBA, CH$_2$Cl$_2$; c) PdCl$_2$(dppf), bis(pinacolato)diboron, KOAc, DMSO, 80° C.

Intermediates of the type I-1d can be prepared by treating an appropriately substituted 1-bromo-3-fluorobenzene (I-1a) with an appropriate base such as LHMDS followed by addition of a thiol reagent (RSNa) to afford I-1b. Oxidation to the sulfone can be achieved with m-CPBA affording I-1c. Subsequent treatment of the bromide with palladium boronylation conditions such as PdCl$_2$(dppf), bis(pinacoloato)diboron and KOAc affords Intermediate I-1d. Modifications of this route known to one skilled in the art can be achieved to obtain various substituents at R$^D$. For instance, reduction of a carboxylic acid with reagents such as BH$_3$ in THF provides a methylalcohol. As well similar chemistry can be employed on pyridine systems to provide intermediates that are used to make compounds of the invention.

Intermediate 1

(2-fluoro-6-(methylsulfonyl)-4-(4,4,5,5-tetramethyl-1,3,2-dioxaborolan-2-yl)phenyl)methanol

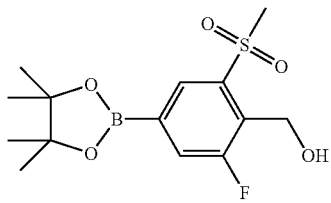 [SMILES: CC1(C)OB(c2cc(F)c(CO)c(S(C)(=O)=O)c2)OC1(C)C]

Intermediate 1a

Preparation of
4-bromo-2-fluoro-6-(methylthio)benzoic acid

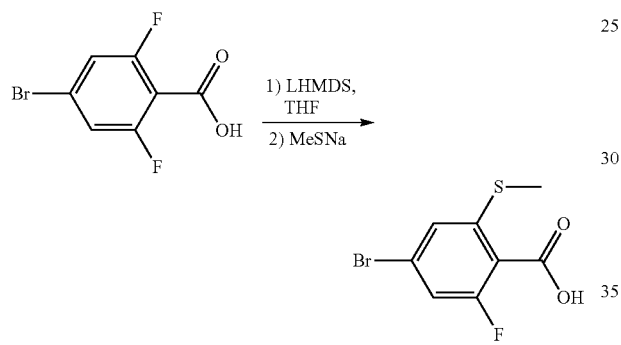

To a 500 mL round bottom flask attached with condenser was added 4-bromo-2,6-difluorobenzoic acid (16.0 g, 67.5 mmol) and anhydrous THF (110 mL). The reaction flask was cooled in an ice bath prior to dropwise addition of 1.0 M LHMDS (74.0 mL, 1.1 equiv). The reaction suspension was stirred at rt for 20 min prior to addition of sodium thiomethoxide (5.21 g, 74.2 mmol). The reaction solution was allowed to stir at reflux for 3 hr. The reaction was determined to be complete after quenching a reaction aliquot in dilute aq. HCl and running GCMS: found m/z=265, 267 parent ions. The cooled reaction mixture was quenched with $H_2O$ and diluted with EtOAc (200 mL). The reaction mixture was transferred to a separatory funnel, and 1.0 N aq. HCl was added to give a pH=2-3 solution. The EtOAc layer was separated, washed with brine, dried over $Na_2SO_4$, and concentrated in vacuo to afford 14.6 g (81% yield) of the intermediate 6-fluoro-4-bromo-2-methylsulfanyl-benzoic acid as a waxy white solid. $^1$H NMR (400 MHz, $CDCl_3$) δ 7.18 (s, 1H), 7.12 (dd, J=8 Hz, 1H), 2.49 (s, 3H); GCMS m/z=265, 267 [M]$^+$. Alternatively, the intermediate 6-fluoro-4-bromo-2-methylsulfanyl-benzoic acid was prepared as follows:

To a 20 L flask was charged dimethyl formamide (14.5 L, 10.0 vol), followed by sodium hydroxide (294 g, 1.2 eq) and the reaction mass cooled to −15 to −10° C. 4-bromo-2,6-difluororbenzoic acid (1450 g, 1.0 equiv) was added over a period of 10-15 min at −15 to −10° C. and stirred for an additional 10-15 min. Sodium thiomethoxide (515 g, 1.2 equiv) was added over a period of 5-10 min at −10 to −5° C. On completion of the addition, the temperature of the reaction was raised to 25-28° C. over a period of 45 to 60 min and maintained at that temperature 1.5-2 h. The temperature of the reaction was then raised to 60-65° C. over a period of 30-60 min and maintained at 60-65° C. for 5 hrs until the reaction was deemed complete. The reaction mixture was then cooled to 20-25° C. and quenched with a cooled (5-10° C.) solution of 2N HCl (5.05 L of 12N HCl in 30.3 L water). Following the quench, EtOAc (14.5 L, 10 vol) was added and the mixture stirred for 10-15 min. The phases were separated and the aqueous layer was extracted with EtOAc (7.25 L, 5 vol). The two phases were separated and the combined organic layer was washed with a brine solution (725 g of NaCl in 3.63 L of water). The phases were separated and the organic layer was washed with water (7.25 L, 5 vol). The phases were separated and the organic layer was dried over sodium sulfate (1450 g). The organic layer was filtered to remove the sodium sulfate, which was then washed with EtOAc (2.90 L, 2 vol). The organic layer was concentrated under reduced pressure at 45-50° C./30-40 mm Hg to ~1 to 1.2 volumes and petroleum ether (7.25 L, 5 vol) was added at 40-45° C. over a period of 15-20 min. The solution was cooled to 20-25° C. over a period of 20-25 min. The solid was filtered and washed with petroleum ether (2.90 L, 2 vol) and the product dried under vacuum at 25-28° C., 0.4 to 0.7 mbar to afford 1410 g (87% yield, 99.4 Area %) of the intermediate 6-fluoro-4-bromo-2-methylsulfanyl-benzoic acid.

Intermediate 1b

Preparation of
(4-bromo-2-fluoro-6-(methylthio)phenyl)methanol

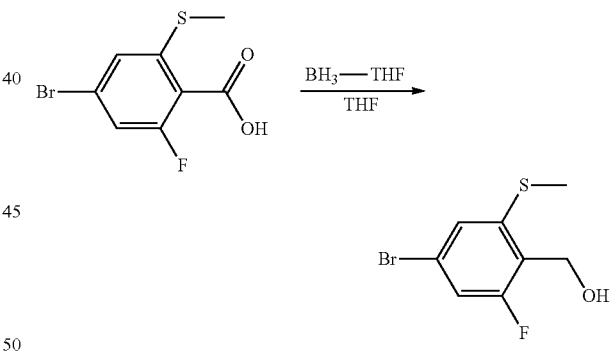

Into a $N_2$ purged 500 mL round bottom flask attached with condenser was added 6-fluoro-4-bromo-2-methylsulfanyl-benzoic acid (14.6 g, 55.0 mmol) and anhydrous THF (70.0 mL). The reaction solution was allowed to cool to 0° C. prior to dropwise addition of a 1.0 M $BH_3$-THF (83.0 mL, 1.5 equiv) solution in THF. The reaction solution was stirred at rt then at reflux for an additional 2 hr. The reaction solution was cooled prior to quenching with a 1:1 $H_2O$/THF solution. The reaction solution was transferred to a separatory funnel with EtOAc (100 mL) and an aqueous solution of $K_2CO_3$ was added. The EtOAc phase was separated, washed with brine, dried over $Na_2SO_4$, and concentrated in vacuo. The crude product was purified by chromatography through a 110 g $SiO_2$ column using a solvent gradient of 100% Hx to 55% EtOAc. The purified title product was obtained as a solid white wax (13.7 g, 99% yield). $^1$H NMR (400 MHz, CDCl$_3$) δ 7.13 (s, 1H), 7.06 (dd, J$_1$=8 Hz, J$_2$=2 Hz, 1H), 4.77 (s, 2H), 2.51 (s, 3H), 2.20-2.05 (br s, 1H); GCMS m/z=251, 253 [M]$^+$.

Alternatively, the intermediate (4-bromo-2-fluoro-6-(methylthio)phenyl)methanol was prepared as follows:

To a 20 L flask was charged 4-bromo-2-fluoro-6-(methylthio)benzoic acid (1400 g, 1.0 eq) followed by THF (14 L, 10 vol) under nitrogen. To this solution was added borane-dimethyl sulfide complex (800 g, 1000 mL) at 25-28° C. over a period of 30-45 min. The reaction temperature was raised to 60-65° C. over a period of 30-45 min and the temperature maintained until HPLC showed <1% of 4-bromo-2-fluoro-6-(methylthio)benzoic acid (~3-4 hrs). On completion of the reaction the mixture was cooled to 10-15° C. over a period of 30-40 min. The reaction was then quenched with MeOH (2.1 L, 1.5 vol) over a period of 1 to 1½ hrs at 10-15° C. The reaction mass was then concentrated under vacuum at 40-50° C./0.4 to 0.7 mbar to 1 to 1.5 volumes. The resultant mixture was dissolved in DCM (8.4 L, 6 vol). The organic layer was washed with an ammonium chloride solution (560 g NH$_4$Cl in 2.8 L water, 2 vol). The phases were separated and the organic layer was washed with 10% NaHCO$_3$ solution (2.8 L, 2 vol), saturated brine solution (2.1 L, 1.5 vol) and water (4.2 L, 3 vol). The organic layer was separated and dried over sodium sulfate (700 g). The sodium sulfate was removed by filtration and washed with DCM (2.8 L, 2 vol). The organic layer was concentrated under vacuum at 40-45° C./0.4 to 0.7 mbar to 1 to 1.2 vol to afford the product which was dried under vacuum at 45-50° C./0.4 to 0.7 mbar. The title product was obtained in 90% yield (1200 g) with 90.1 Area %.

Intermediate 1c

Preparation of (4-bromo-2-fluoro-6-(methanesulfonyl)phenyl)-methanol

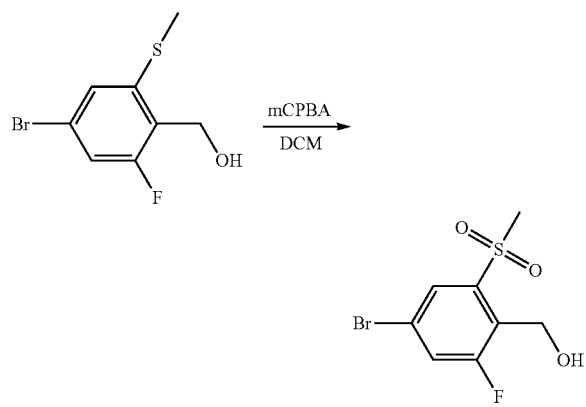

To a 500 mL flask was added (4-bromo-2-fluoro-6-(methylthio)phenyl)methanol (13.7 g, 54.6 mmol) and anhydrous DCM (125 mL). The solution was cooled to 0-3° C. in an ice bath prior to portion wise addition of 3-chloroperbenzoic acid (77% max., Aldrich) (18.8 g, 2 equiv). The reaction solution was then allowed to warm to rt where it remained for 18 hrs. The reaction was then concentrated in vacuo to remove DCM and the residue was washed into a separatory funnel with EtOAc and 1 M aq. NaOH. The EtOAc layer was separated, washed with 1 M aq NaOH, dried over Na$_2$SO$_4$, and concentrated in vacuo. The residue was purified by flash chromatography (Biotage, 65×200 mm SiO$_2$ column, gradient elution from 100% Hx to 90% EtOAc/Hx). Appropriate fractions were combined and concentrated in vacuo to afford the title compound as a colorless, semi-crystalline solid, yield: 8.10 g (52%). $^1$H NMR (400 MHz, DMSO-d$_6$) δ 7.98 (dd, J=8 Hz, 1H), 7.91 (s, 1H), 5.45 (t, J=8 Hz, 1H), 4.88 (dd, J$_1$=8 Hz, J$_2$=2 Hz, 2H), 3.42 (s, 3H); $^{19}$F NMR (400 MHz, DMSO-d$_6$) δ -111.8 ppm; GCMS m/z=283, 285 [M]$^+$.

Intermediate 1

Preparation of (2-fluoro-6-(methylsulfonyl)-4-(4,4,5,5-tetramethyl-1,3,2-dioxaborolan-2-yl)phenyl)methanol

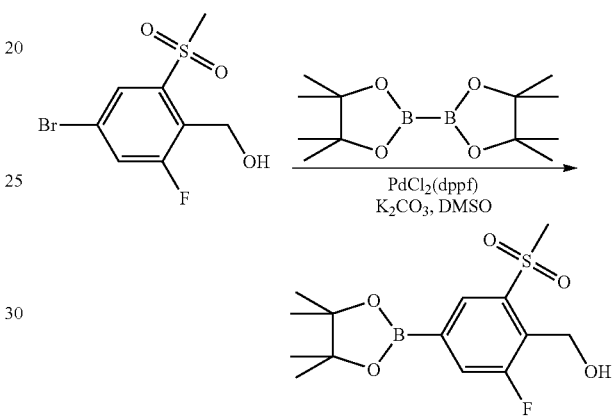

To a 100 mL round bottom flask, purged with dry N$_2$, was weighed (4-bromo-2-fluoro-6-(methanesulfonyl)phenyl)-methanol (1.98 g, 6.99 mmol), bis(pinacolato)diboron (2.13 g 1.2 equiv), dichloro[1,1'-bis(diphenylphosphino) ferrocene]palladium (II) DCM adduct (560 mg, 10 mol %), potassium carbonate (2.06 g, 3 equiv), and DMSO (25.0 mL). The resulting suspension was allowed to stir at 90° C. for 3 hrs. An aliquot of reaction solution was found to contain no more starting bromide as determined by LCMS analysis. The cooled reaction suspension was diluted with EtOAc (50 mL) and water (50 mL) and filtered through a Celite padded Buchner Funnel. The resulting filtrate was transferred to a separatory funnel, and the organic phase was separated. The aqueous phase was extracted with EtOAc, and the combined EtOAc phases were washed with brine, dried over Na$_2$SO$_4$, and concentrated in vacuo. The residue was purified by silica gel flash chromatography (Biotage SP-1, 40 g SiO$_2$ column, gradient elution from 100% Hx to 60% EtOAc/Hx) to afford a clear viscous oil. The product was isolated as an amorphous white powder by dissolving in DCM and reprecipitation resulted upon addition of Hx. The title compound was isolated as a solid white powder, yield: 1.90 g (82% yield). $^1$H NMR (400 MHz, CDCl$_3$) δ 8.28 (s, 1H), 7.79 (d, J=8 Hz, 1H), 5.03 (d, J=8 Hz, 2H), 3.23 (s, 3H) 3.05 (t, J=8 Hz, 1H), 1.35 (s, 6H); $^{19}$F NMR (400 MHz, CDCl$_3$) δ -116.3 ppm.

Alternatively, the intermediate (2-fluoro-6-(methylsulfonyl)-4-(4,4,5,5-tetramethyl-1,3,2-dioxaborolan-2-yl)phenyl)methanol was prepared as follows: To a 500 mL jacketed reactor equipped with a stir bar, temperature probe, reflux condenser and a nitrogen inlet was charged methyl tetrahydrofuran (MeTHF) (75 mL, 5 volumes) followed by potassium acetate (5.2 g, 53 mmol, 1 equiv.) and (oxydi-2,1- phenylene)bis(diphenylphosphine) (320 mg; 600 μmoles, 0.011 equiv.) and bis(pinacolato)diboron (18 g, 69 mmol, 1.3 equiv.). The reaction flask was evacuated to less than 150 Torr, and then back filled with nitrogen. This degassing procedure was repeated 3 times. Pd(OAc)$_2$ (94 mg; 420 μmoles, 0.0075 equiv.) was charged to the reactor and the reaction flask was evacuated to less than 150 Torr, and then back filled with nitrogen and the sequence repeated 3 times. The resulting slurry was allowed to age at 20-25° C. for 15 min. Upon completion of the 15 min age, the slurry was heated to an internal temperature of 80° C. As the mixture in the reactor was heating to temperature, in a separate flask was charged (4-bromo-2-fluoro-6-(methanesulfonyl)phenyl)-methanol (15 g, 53 mmol, 1 equiv.) followed by MeTHF (75 mL, 5 volumes). The resulting solution was degassed by bubbling nitrogen subsurface for not less than 15 min. prior to use. Once the catalyst mixture had reached reflux, the degassed solution of (4-bromo-2-fluoro-6-(methanesulfonyl)phenyl)-methanol in MeTHF was added to the reaction in a single portion and allowed to react. The reaction typically takes ~20 hrs to complete after the addition of substrate. Upon completion (typically <0.75 RAP of starting material the reaction was cooled to 20-25° C. Once at rt the reaction was diluted with MeTHF (75 mL, 5 volumes) and washed with a 5 wt % NaCl solution (7.5 volumes, 110 mL) for at least 15 min. The phases were separated and the upper product rich MeTHF stream was filtered through Celite to remove insoluble palladium residues. The Celite cake was washed with MeTHF (75 mL, 5 volumes). The reaction was treated with functionalized silica (30 equiv) to remove palladium and color. The slurry was agitated for at least 60 min and then filtered to remove the silica. The used silica was washed with MeTHF (5 volumes, 75 mL). The combined organic phase was washed with water (5 volumes, 75 mL). The organic was distilled to 5 volumes (75 mL) under vacuum (60-70 Torr, bath temp of 30° C.). When the 75 mL landmark was reached the distillation was stopped and heptane (75 mL, 5 volumes) was added dropwise to the reaction solution. After ~35 mL of heptanes had been added the product began to crystallize from the solution. On completion of the addition the product was isolated by filtration and the wet cake washed with MeTHF-heptanes (1:9) solution (2×75 mL) and dried at 50° C. The title product was obtained a white solid, 14 g, (78% yield) with 99.6 Area %.

Intermediate 2

Preparation of (2-chloro-6-(methylsulfonyl)-4-(4,4,5,5-tetramethyl-1,3,2-dioxaborolan-2-yl)phenyl)methanol

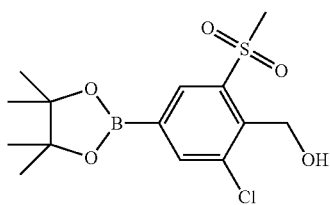 [SMILES: CC1(C)OB(c2cc(Cl)c(CO)c(S(C)(=O)=O)c2)OC1(C)C]

Intermediate 2 can be prepared by similar chemistry described above from commercially available 2-chloro-6-fluorobenzaldehyde; however iridium borylation using [Ir(OMe)(COD)]$_2$ can be used to install the boronate para to the hydroxymethyl substituent.

Intermediate 3

4,4,5,5-tetramethyl-2-(4-methyl-3-(methylsulfonyl)phenyl)-1,3,2-dioxaborolane

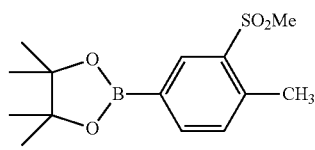

Intermediate 3 was prepared from 4-bromo-1-methyl-2-(methylsulfonyl)benzene in a similar procedure as Intermediate 1. MS (ESI) 297.2 [M+H]$^+$. $^1$H NMR (400 MHz, CDCl$_3$) δ ppm 8.46 (s, 1H), 7.92 (d, 1H, J=7.4 Hz), 7.35 (d, 1H, J=7.4 Hz), 3.08 (s, 3H), 2.74 (s, 3H), 1.31 (s, 12H).

Intermediate 4

N,N-dimethyl-3-(4,4,5,5-tetramethyl-1,3,2-dioxaborolan-2-yl)benzamide

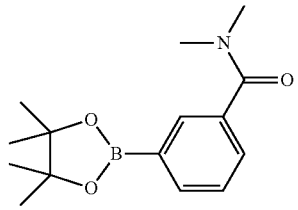 [SMILES: CN(C)C(=O)c1cccc(B2OC(C)(C)C(C)(C)O2)c1]

Intermediate 4a

Preparation of 3-bromo-N,N-dimethylbenzamide

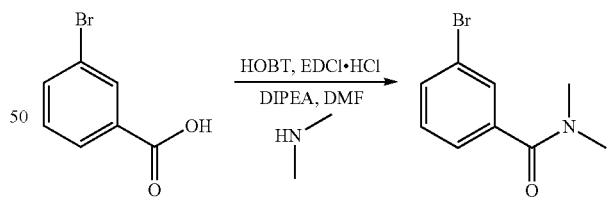

To a mixture of 3-bromobenzoic acid (2.7 g, 14 mmol), 1-hydroxybenzotriazole (3.6 g, 27 mmol), EDC (5.1 g, 27 mmol) and diisopropylethylamine (8.7 mL, 47 mmol) in DMF (50 mL) was added dimethylamine (1.2 g, 14 mL, 27 mmol) at 0° C. and the reaction mixture was stirred overnight at rt under a nitrogen atmosphere. The reaction mixture was diluted with water (40 mL) and extracted with EtOAc (2×50 mL). The combined organic extracts were washed with water, brine, dried over Na$_2$SO$_4$ and concentrated to give crude product. The crude was triturated with pet ether and filtered, and the solid was dried under vacuum to yield the title compound (2.9 g, 95% yield). MS (ESI) 229.1 [M+H]$^+$.

Intermediate 4 was prepared from Intermediate 4a in a similar procedure as Intermediate 1d. MS (ESI) 276.2 [M+H]+.

Intermediate 5

1-(3-(4,4,5,5-tetramethyl-1,3,2-dioxaborolan-2-yl)phenyl)cyclopropanecarboxamide

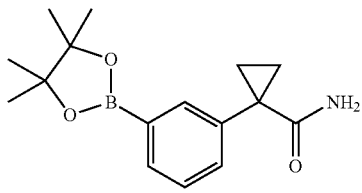 [SMILES: CC1(C)OB(c2cccc(C3(C(N)=O)CC3)c2)OC1(C)C]

Intermediate 5a

Preparation of 1-(3-bromophenyl)cyclopropanecarboxamide

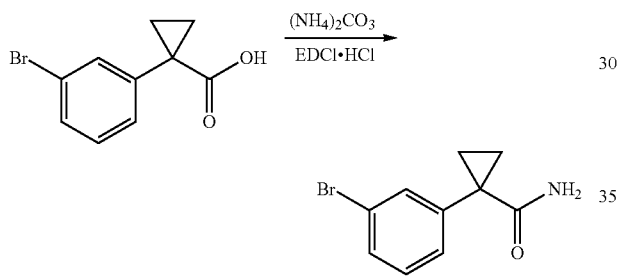

To a mixture of 1-(3-bromophenyl)cyclopropanecarboxylic acid (0.5 g, 2.074 mmol), 1-hydroxybenzotriazole (0.364 g, 2.70 mmol), EDC (0.517 g, 2.70 mmol) and triethylamine (0.867 mL, 6.22 mmol) in DMF (8 mL) was added ammonium carbonate (0.239 g, 2.489 mmol) at 0° C. The reaction mixture was stirred overnight at rt under a nitrogen atmosphere. The reaction mixture was diluted with water (40 mL) and extracted with EtOAc (2×50 mL). Combined organic extracts were washed with water, brine, dried over Na$_2$SO$_4$ and concentrated to give crude product. Crude material was triturated with pet ether and filtered. The solid was dried under vacuum to give the title compound (0.4 g, 1.666 mmol, 80% yield) as a off white solid. MS (ESI) [M+H]+: 241.0

Intermediate 5

Preparation of 1-(3-(4,4,5,5-tetramethyl-1,3,2-dioxaborolan-2-yl)phenyl)cyclopropanecarboxamide

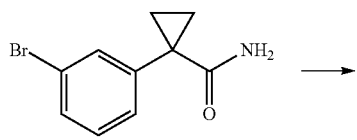

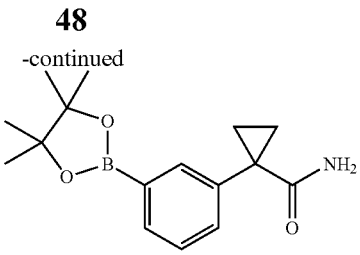

To a mixture of Intermediate 5a (200 mg, 0.833 mmol), bis(pinacolato)diboron (275 mg, 1.083 mmol) and potassium acetate (245 mg, 2.50 mmol) in dioxane (5 mL) was added dppf (23.09 mg, 0.042 mmol) and PdCl$_2$(dppf) (30.5 mg, 0.042 mmol). The reaction mixture was stirred at 85° C. for 12 h under nitrogen atmosphere. The reaction mixture was cooled to rt, diluted with water (30 mL) and extracted with EtOAc (2×25 mL). The combined organic extracts were washed with water, brine, dried over Na$_2$SO$_4$ and concentrated to give crude product. Crude solid was washed with 10% EtOAc in hexane (20 mL), filtered, and dried under vacuum to give 1-(3-(4,4,5,5-tetramethyl-1,3,2-dioxaborolan-2-yl)phenyl)cyclopropanecarboxamide (150 mg, 0.522 mmol, 62.7% yield) as a off white solid. MS (ESI) [M+H]+: 288.1

Intermediate 6

2-(3-(cyclopropylsulfonyl)phenyl)-4,4,5,5-tetramethyl-1,3,2-dioxaborolane

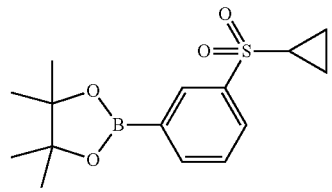 [SMILES: CC1(C)OB(c2cccc(S(=O)(=O)C3CC3)c2)OC1(C)C]

Intermediate 6a

Preparation of (3-bromophenyl)(cyclopropyl)sulfane

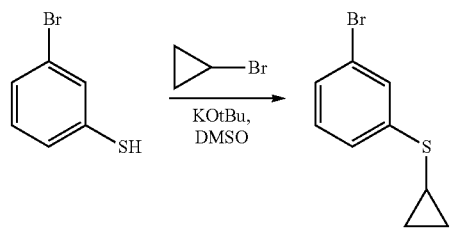

To a cooled (0° C.) solution of potassium tert butoxide (0.36 g, 2.9 mmol) in DMSO (12 mL) was added 3-bromothiophenol (0.50 g, 2.6 mmol) under a nitrogen atmosphere and the reaction mixture was stirred for 15 min. A solution of cyclopropylbromide (0.96 g, 7.8 mmol) in DMSO (1.0 mL) was added dropwise. The reaction mixture was allowed to warm to rt, and followed by heating to 80° C. for 48 hrs. The reaction mixture was cooled to rt and diluted with cold water (10 mL) and EtOAc (10 mL). The layers were separated and the aqueous layer was extracted EtOAc (20 mL×2). The combined organic extracts were washed with water, brine, dried over Na₂SO₄ and concentrated in vacuo to give the title compound (0.40 g, 66% yield). MS (ESI) 230.1 [M+H]⁺.

Intermediate 6 was prepared from Intermediate 6a using procedures similar to Intermediate 1c and Intermediate 1. MS (ESI) 309.1 [M+H]⁺.

Intermediate 7

2-(3-((difluoromethyl)sulfonyl)phenyl)-4,4,5,5-tetramethyl-1,3,2-dioxaborolane

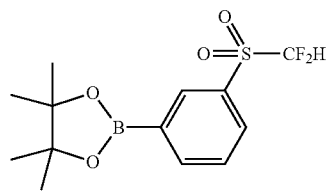 [SMILES: CC1(C)OB(c2cccc(S(=O)(=O)C(F)F)c2)OC1(C)C]

Intermediate 7a

Preparation of (3-bromophenyl)(difluoromethyl)sulfane

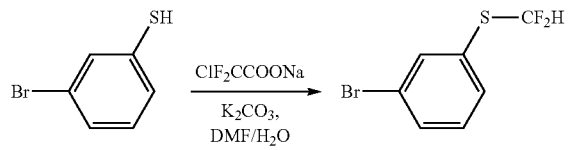

A solution of 3-bromothiophenol (0.50 g, 2.6 mmol), K₂CO₃ (0.73 g, 5.3 mmol) and sodium chlorodifluoroacetate (0.81 g, 5.3 mmol) in DMF (4.5 mL) and water (0.50 mL) was heated to 130° C. for 1 hr. The reaction mixture was cooled to rt and diluted with diethyl ether (25 mL). The organic solution was washed with a citric acid solution, brine, dried over Na₂SO₄ and concentrated in vacuo to give the crude product. The crude product was purified by silica gel column chromatography using EtOAc: Hx (2:8) as an eluent to afford the title compound (0.60 g, 95% yield). MS (ESI) 239.8 [M+H]⁺.

Intermediate 7 was prepared from Intermediate 7a using procedures similar to Intermediate 1c and Intermediate 1. MS (ESI) 319.1 [M+H]⁺.

Intermediate 8

2-methyl-2-(3-(4,4,5,5-tetramethyl-1,3,2-dioxaborolan-2-yl)phenyl)propanamide

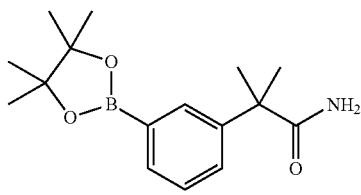 [SMILES: CC(C)(C(N)=O)c1cccc(B2OC(C)(C)C(C)(C)O2)c1]

Intermediate 8a

Preparation of 2-(3-bromophenyl)-2-methylpropanenitrile

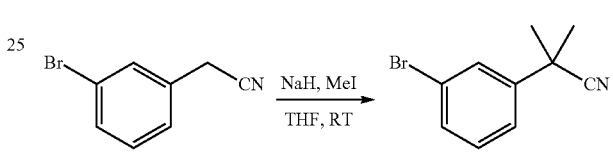

To a dried 1 L double neck round bottom flask fitted with a U tube (for nitrogen atmosphere) and septum was added 2-(3-bromophenyl)acetonitrile (25 g, 128 mmol). THF (350 mL) was added and the reaction solution was cooled to 0° C. Then NaH (18.36 g, 383 mmol) was added to the reaction mixture portion-wise (5 g each time). The reaction mixture was stirred at 0° C. for 2 h. MeI (39.9 mL, 638 mmol) was added at 0° C. dropwise through an addition funnel and the mixture was stirred for 0.5 h at 0° C. and then warmed to rt. After 3 h at rt the starting material was consumed completely based on TLC. The reaction mixture was quenched with ice cold water (400 mL) at −10° C. The aqueous was extracted with EtOAc (3×250 mL). The organic layers were washed with brine (1×200 mL), dried over Na₂SO₄, filtered and concentrated to get crude brown product. The material was purified by combiflash using 120 g silica column and eluting with up to 10% EtOAc in pet ether as eluent to get 2-(3-bromophenyl)-2-methylpropanenitrile (16.1 g, 71.8 mmol, 56.3% yield) as clear liquid.

¹H NMR (400 MHz, CDCl₃) δ ppm 7.60 (m, 1H) 7.44 (m, 2H) 7.24-7.29 (m, 1H) 1.72 (s, 6H).

Intermediate 8b

Preparation of 2-(3-bromophenyl)-2-methylpropanamide

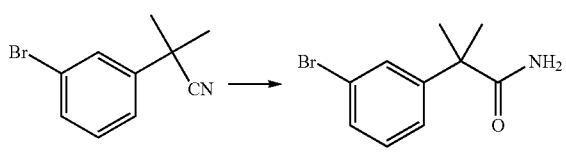

To 2-(3-bromophenyl)-2-methylpropanenitrile (870 mg, 3.88 mmol) was added $H_2SO_4$ (2.1 mL, 39.4 mmol) dropwise at rt and the reaction mixture was stirred at rt overnight. Ice cold water (15 mL) was added to the reaction mixture dropwise, and the mixture was stirred for 5 min. The reaction mixture was filtered, and washed with cold water until washings become neutral. The solids were also washed with pet.ether (3×20 mL), and dried under high vacuum to obtain 2-(3-bromophenyl)-2-methylpropanamide (500 mg, 2.065 mmol, 53.2% yield) as white amorphous solid. $^1$H NMR (400 MHz, DMSO-$d_6$) δ ppm 7.46-7.49 (m, 1H) 7.43 (dt, J=7.53, 1.51 Hz, 1H) 7.28-7.36 (m, 2H) 6.92-7.02 (m, 2H) 1.43 (s, 6H).

Intermediate 8

Preparation of 2-methyl-2-(3-(4,4,5,5-tetramethyl-1,3,2-dioxaborolan-2-yl)phenyl)propanamide

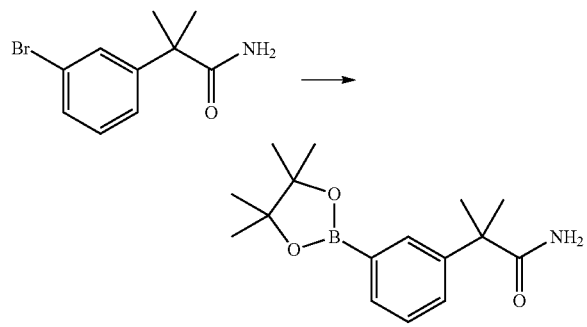

A suspension of 2-(3-bromophenyl)-2-methylpropanamide (5 g, 20.65 mmol), bis(pinacolato)diboron (6.29 g, 24.78 mmol) and potassium acetate (6.08 g, 62.0 mmol) in DME (95 mL) was purged with nitrogen for 20 minutes at rt, followed by addition of $PdCl_2$(dppf) (0.453 g, 0.620 mmol) and purging with nitrogen for 10 min. The reaction mixture was heated at 100° C. for 1 h, and the starting material was consumed by TLC. The reaction mixture was cooled to rt, filtered through a celite bed, and washed with EtOAc (3×50 mL). The filtrate was concentrated to afford brown gummy solid, which was purified by combiflash using 120 g silica column eluting with 60% of EtOAc in pet ether as eluent to get Intermediate 8 (2.2 g, 7.61 mmol, 36.8% yield) as white crystalline solid.

$^1$H NMR (400 MHz, DMSO-$d_6$) δ ppm 7.64 (s, 1H), 7.53 (dt, J=7.22, 1.04 Hz, 1H), 7.49 (ddd, J=7.84, 2.07, 1.38 Hz, 1H), 7.32-7.37 (m, 1H), 6.90 (d, J=17.32 Hz, 2H), 1.43 (s, 6H), 1.31 (s, 12H).

Intermediate 9

5-chloro-3-(trifluoromethyl)-1H-pyrazole

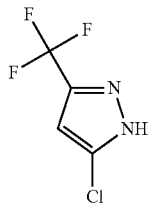

Intermediate 9 could be purchased, or it could be prepared by the following procedure:

Intermediate 9a

Preparation of N,N-dimethyl-3-(trifluoromethyl)-1H-pyrazole-1-sulfonamide

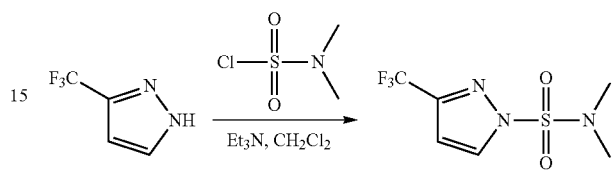

To a solution of 3-(trifluoromethyl)-1H-pyrazole (7.5 g, 55 mmol) in DCM (70 mL) was added $Et_3N$ (11 mL, 77 mmol) and dimethylsulfamoyl chloride (11 g, 77 mmol). The reaction mixture was heated to a reflux for 2 days. The reaction mixture was diluted with water (60 mL) and extracted with diethyl ether (3×60 mL). The combined organic extracts were dried over $Na_2SO_4$, filtered into a round bottom flask and concentrated under reduced pressure to afford the title compound (7.5 g, 31 mmol, 56% yield). $^1$H NMR (400 MHz, DMSO-$d_6$) δ ppm 8.55 (d, 1H, J=1.51 Hz), 7.11 (d, 1H, J=2.51 Hz), 2.90-3.11 (m, 6H), 2.81 (s, 1H).

Intermediate 9b

Preparation of N 5-chloro-N,N-dimethyl-3-(trifluoromethyl)-1H-pyrazole-1-sulfonamide

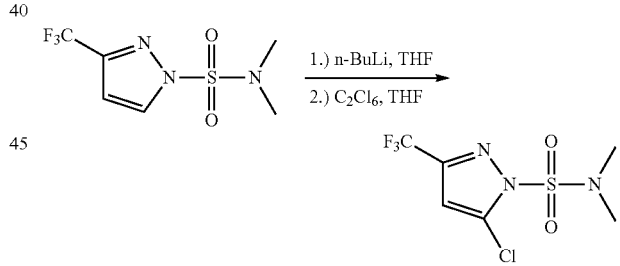

To a solution of N,N-dimethyl-3-(trifluoromethyl)-1H-pyrazole-1-sulfonamide (7.5 g, 31 mmol) in THF (50 mL) at −78° C. was added n-butyllithium (12 mL, 31 mmol) dropwise The reaction was allowed to stir for 30 min before a solution of hexachloroethane (8.0 g, 34 mmol) in THF (10 mL) was added to the reaction mixture dropwise. After 4 hrs, the reaction mixture was quenched with saturated ammonium chloride solution (20 mL) and extracted with EtOAc (3×100 mL). The combined organic extracts were dried over $Na_2SO_4$, filtered into a round bottom flask and concentrated under reduced pressure to afford the title compound (7.0 g, 25 mmol, 82% yield). $^1$H NMR (400 MHz, DMSO-$d_6$) δ ppm 6.97 (s, 1H), 2.9 (s, 6H).

Intermediate 9

Preparation of
5-chloro-3-(trifluoromethyl)-1H-pyrazole

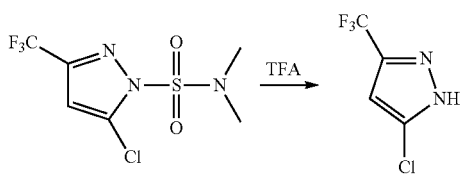 [SMILES: CN(C)S(=O)(=O)n1nc(C(F)(F)F)cc1Cl ; FC(F)(F)c1cc(Cl)[nH]n1]

5-chloro-N,N-dimethyl-3-(trifluoromethyl)-1H-pyrazole-1-sulfonamide (8.0 g, 29 mmol) was brought up in solution with TFA (11 mL, 140 mmol) at 0° C., and the mixture was allowed to stir at rt overnight. The reaction mixture was concentrated under reduced pressure, diluted with EtOAc (50 mL) and then washed with water (50 mL). The aqueous layer was extracted with EtOAc (2×50 mL). The combined organics were dried over $Na_2SO_4$, filtered into a round bottom flask and concentrated under reduced pressure to afford the title compound (5.0 g, 29 mmol, 100% yield). $^1$H NMR (400 MHz, DMSO-$d_6$) δ ppm 6.97 (s, 1H).

Intermediate 10

Preparation of
4-chloro-3-(trifluoromethyl)-1H-pyrazole

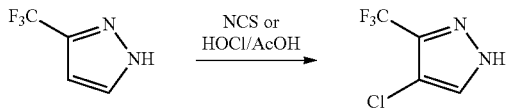 [SMILES: FC(F)(F)c1cc[nH]n1 ; FC(F)(F)c1n[nH]cc1Cl]

To a solution of 3-(trifluoromethyl)-1H-pyrazole (10.0 g, 73.5 mmol) in MECN (250 mL) was added NCS (13.7 g, 103 mmol). The reaction mixture was heated the reaction mixture at 60° C. for 3 h. The MECN was evaporated to afford a white solid. To the residue was added $CCl_4$ (80 mL) and the mixture was stirred vigorously for 20 minutes. The solids were filtered and washed with CCl4 (2×10 mL). The combined filtrates were concentrated to afford a white solid (12.5 gm) $^1$H NMR (400 MHz, $CD_3OD$) δ ppm 7.89 (s, 1H). MS (ESI) 168.7 [M–H].

Alternatively, the pyrazole can be chlorinated in acetic acid using an excess of 10% sodium hypochlorite in water.

Intermediate 11

Preparation of
4-methyl-3-(trifluoromethyl)-1H-pyrazole

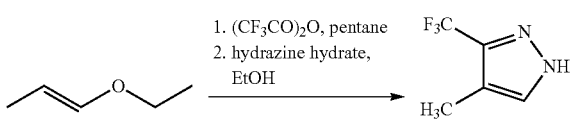

To a mixture of isomers of (E)-1-ethoxyprop-1-ene (5.0 g, 58 mmol) in dry pentane (40 mL) at 0° C. was added drop wise trifluoroacetic anhydride (8.2 mL, 58 mmol). The reaction mixture was stirred at 0° C. for 2 h, allowed to warm to rt with continued stirring for 24 h. The solution was cooled to 0° C. and hydrazine monohydrate (3.15 mL, 65.0 mmol) diluted in EtOH (35 mL) was added drop wise. The mixture was stirred for 30 min. The solution was concentrated to dryness, and the residue was dispersed in water (30 mL). The white precipitate was filtered, washed with water and dried in open air to afford the title compound (4.10 g, 25.9 mmol). $^1$H NMR (400 MHz, $CDCl_3$) δ ppm 7.42 (s, 1H), 2.20 (s, 3H). (Guillou, S, et al. (2011) Tetrahedron. 67: 8451-8457).

Intermediate 12

Preparation of ethyl
3-cyclopropyl-1H-pyrazole-4-carboxylate

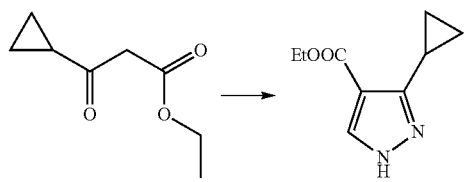

In a 100 mL round-bottomed flask was added ethyl 3-cyclopropyl-3-oxopropanoate (1.0 g, 6.4 mmol), triethyl orthoformate (1.27 mL, 7.68 mmol), and $Ac_2O$ (1.81 mL, 19.2 mmol) to give a yellow solution. The reaction mixture was stirred for 2 h at 120° C. followed by heating at 140° C. for 5 h. The mixture was concentrated under vacuum, and the residue was dissolved in EtOH (10 mL). Hydrazine (0.308 g, 9.60 mmol) was added, and then the reaction mixture was heated to reflux for 3 h. Some of the MeOH was removed under reduced pressure, and the remaining mixture was diluted with EtOAc (70 mL). The organics were washed with $H_2O$ and brine. The organics were dried over $Na_2SO_4$, filtered and concentrated at reduced pressure to afford the title compound as a colorless solid, which was used without further purification. $^1$H NMR (300 MHz, $CDCl_3$) δ ppm 7.93 (s, 1H), 4.32 (q, J=4.2 Hz, 2H), 2.58 (m, 1H), 1.37 (t, J=4.2 Hz, 3H), 1.07 (m, 2H), 0.89 (m, 2H).

Intermediate 12

Preparation of
(5-bromo-3-(methylsulfonyl)pyridin-2-yl)methanol

Intermediate 12a

Preparation of methyl
5-bromo-3-(methylthio)picolinate

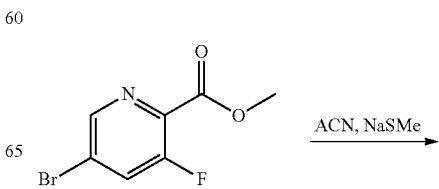

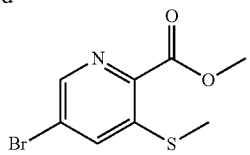

Methyl 5-bromo-3-fluoropicolinate was prepared from the commercially available 5-bromo-3-fluoropicolinic acid with thionyl chloride in MeOH, as known to one skilled in the art.

To a solution of methyl 5-bromo-3-fluoropicolinate (1.9 g, 8.1 mmol) in ACN (50 mL) was added NaSMe (0.569 g, 8.12 mmol), and the reaction mixture was stirred at rt overnight. The solvent was removed under vacuum. The residue was diluted with water (50 mL), which was extracted with EtOAc (3×50 mL). The combined organic layers were washed with water (1×35 mL) and brine (1×35 mL), dried with $Na_2SO_4$, filtered and concentrated to obtain the crude material, which was purified by silica gel column chromatography (EtOAc:Hexane:40:60) to afford the title compound as a white solid (1.4 g, 5.3 mmol). MS (ESI) 235 [M+H]; $^1$H NMR (400 MHz, $CD_3OD$) δ ppm 8.38 (d, J=2 Hz, 1H), 7.86 (d, J=2 Hz, 1H), 4.67 (s, 2H), 2.55 (s, 3H).

Intermediate 12b

Preparation of (5-bromo-3-(methylthio)pyridin-2-yl)methanol

To the solution of methyl 5-bromo-3-(methylthio)picolinate (1.4 g, 5.3 mmol) in MeOH (50 mL) was added $NaBH_4$ (1.01 g, 26.7 mmol) at 0° C. Then the mixture was allowed to warm to rt and was stirred for 3 h. The solvent was removed under vacuum. The residue was dissolved in EtOAc (50 mL) and water (20 mL), and the layers were separated. The aqueous material was washed with EtOAc (2×30 mL), and the combined organic solution was washed with brine (1×30 mL), dried by $Na_2SO_4$, filtered and concentrated to the title compound as a off white solid (1.15 g), which was used in the next step without purification. MS (ESI) 261.6 [M+H]; $^1$H NMR (400 MHz, $CDCl_3$) δ ppm 8.47 (d, J=2 Hz, 1H), 7.75 (d, J=2 Hz, 1H), 4.00 (s, 3H), 2.46 (s, 3H).

Intermediate 12

To the solution of (5-bromo-3-(methylthio)pyridin-2-yl)methanol (1.15 g, 4.91 mmol) in DCM (100 mL) was added m-CPBA (1.69 g, 9.82 mmol) at 0° C. After 10 min. the mixture was allowed to warm to rt, and the mixture was stirred overnight. The solvents were removed under vacuum. The residue was dissolved in EtOAc (80 mL), washed with 1 N NaOH (2×25 mL) and brine solution (1×25 mL), dried with $Na_2SO_4$, filtered and concentrated to obtain the crude product. The crude product was purified by silica gel column chromatography (EtOAc:Hexane; 70:30) to afford the title compound as a white solid (235 mg, 0.859 mmol). $^1$H NMR (400 MHz, $CD_3OD$) δ ppm 8.93 (d, J=2.4 Hz, 1H), 8.53 (d, J=2.4, 1H), 5.05 (s, 2H), 3.3 (s, 3H).

EXAMPLES

Preparation of Compounds of the Invention

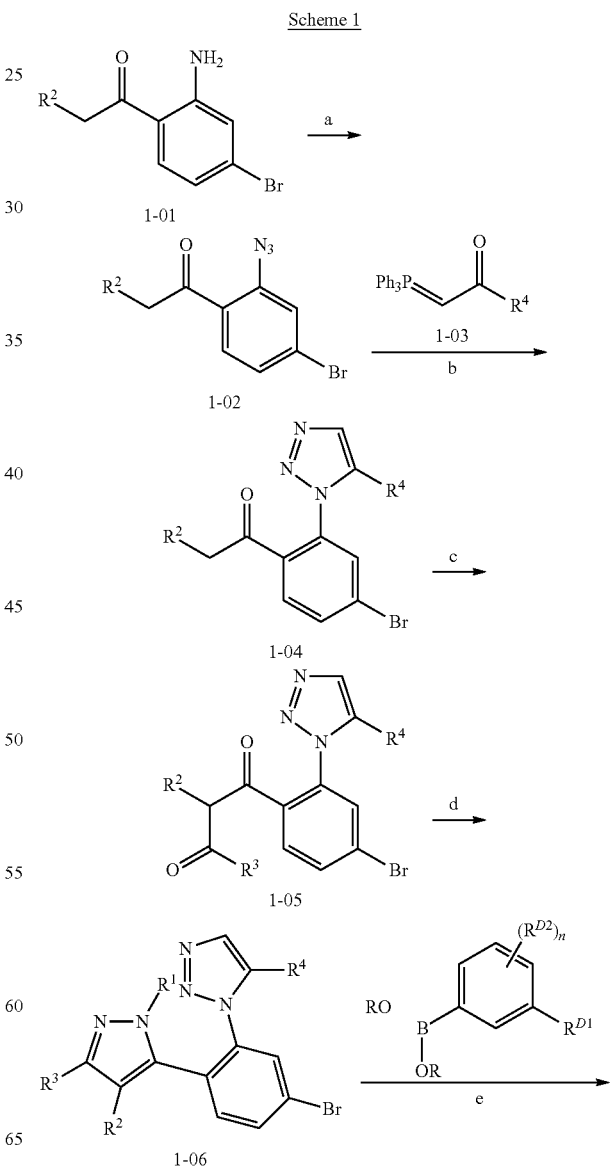

Scheme 1

57
-continued

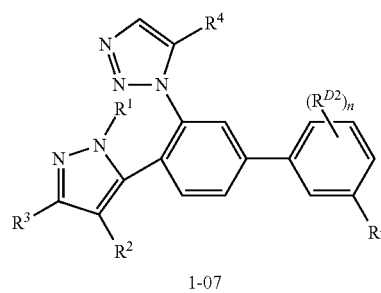

1-07

(a) NaNO₂, NaN₃, HCl, THF; (b) toluene, 110° C.; (c) R³COOEt, NaOEt, EtOH;
(d) methylhydrazine sulfate, H₂SO₄, EtOH; (e) PdCl₂(dppf), K₂CO₃, DME, H₂O;

Particular embodiments of the invention include compounds exemplified by general structure 1-07 in Scheme 1. In general, pyrazole compounds of formula 1-07 can be synthesized following the methodology shown in Scheme 1. The aniline (1-01), which is purchased or prepared by methods known to one skilled in the art, is converted to the azide (1-02) using sodium nitrite and sodium azide under acidic conditions. The azide (1-02) reacts with the phosphorane (1-03) to yield the triazole (1-04). After formation of the enolate, the alkyl ketone (1-05) is alkylated with an appropriately substituted ester (R³COOEt) to give the 1,3-diketone (1-05). Reaction of the diketone (1-05) with an alkyl hydrazine sulfate under acidic conditions gives exclusively (or in some cases mainly) the desired regioisomer of the pyrazole (1-06). The minor isomer can be removed by silica gel column chromatography if necessary. Palladium mediated coupling between the aryl bromide (1-06) with the aryl boronic acid or ester derivatives produces 1-07.

Additional chemistry known to one skilled in the art can be carried out at the R³ position including reductions, grignard additions, alkylations, fluorinations, acylations, amidations, and heterocycle forming reactions to prepare compounds of the invention. For example, when R³ contains an ester (e.g. CF₂COOEt or COOEt) additional functionalization can be carried out by one skilled in the art to make amides, as well as, primary, secondary and tertiary alcohols.

Example 1

1,1-difluoro-1-(1-methyl-5-(3'-(methylsulfonyl)-3-(5-(4-(trifluoromethoxy)phenyl)-1H-1,2,3-triazol-1-yl)biphenyl-4-yl)-1H-pyrazol-3-yl)propan-2-ol

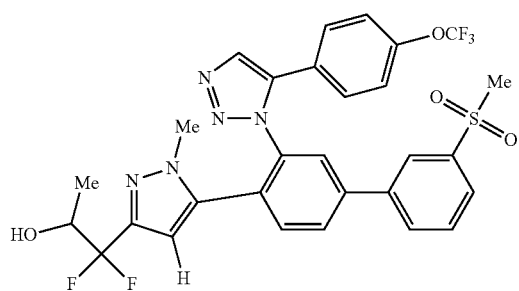 [SMILES: CC(O)C(F)(F)c1cc(-c2ccc(-c3cccc(S(C)(=O)=O)c3)cc2-n2nncc2-c2ccc(OC(F)(F)F)cc2)n(C)n1]

58

Example 1a

Preparation of 1-(2-amino-4-bromophenyl)ethanone

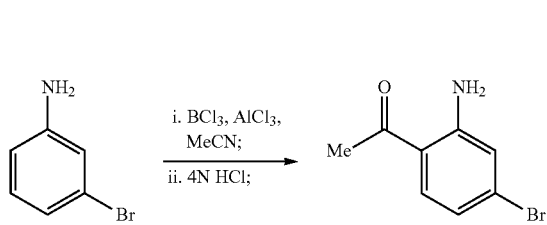 [SMILES: Nc1cccc(Br)c1 ; CC(=O)c1ccc(Br)cc1N]

In a 100 mL round bottom flask, boron trichloride in DCM (32.0 mL, 32.0 mmol) was brought to 0° C., and 3-bromoaniline (5.00 g, 29.1 mmol) in MeCN (36.0 mL) was added dropwise over 20 min. Aluminum chloride (1.86 g, 14.0 mmol) was added portion-wise and the reaction mixture was heated to reflux for 18 hrs. The reaction mixture was cooled to rt, HCl (4 N, 20.0 mL) was added slowly, and the mixture was heated to reflux for 2 hrs. After being cooled to rt, the acidic solution was extracted with DCM (25 mL). The aqueous layer was brought to pH 8 with 6 N NaOH and extracted with DCM (25 mL×2). The combined organics were washed with brine, dried over Na₂SO₄ and concentrated in vacuo to give the crude product. The crude residue was purified by chromatography thru a 40 g SiO₂ column using a mobile phase gradient of 0% to 100% EtOAc/Hx over 30 min to afford the title compound (2.90 g, 13.6 mmol, 47% yield). MS (ESI) 214.0 [M+H]+. ¹H NMR (500 MHz, CDCl₃) δ ppm 7.56 (d, J=8.80 Hz, 1H) 6.84 (s, 1H) 6.77 (d, J=8.80 Hz, 1H) 6.34 (br. s., 2H) 2.55 (s, 3H).

Example 1b

Preparation of 1-(2-azido-4-bromophenyl)ethanone

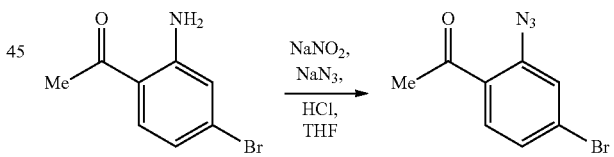

Example 1a (180 mg, 0.84 mmol) was dissolved in THF (5.0 mL) and 0.50 mL of concentrated HCL and cooled to −10° C. Sodium nitrite (70 mg, 1.0 mmol) dissolved in 0.50 mL of water was added dropwise and stirred for 30 min. Afterwards, sodium azide (160 mg, 2.5 mmol) dissolved in 0.50 mL of water was added dropwise. The reaction mixture was allowed to warm to rt and stir for 18 hrs. The reaction mixture was diluted with EtOAc (10 mL) and washed with saturated aq NaHCO₃ (10 mL). The aqueous layer was extracted with EtOAc (10 mL×2), and the combined organics were washed with aq NaCl (20 mL), dried over Na₂SO₄, filtered into a round bottom flask and concentrated in vacuo to give the title compound as a brown solid (190 mg, 0.78 mmol, 92% yield). ¹H NMR (500 MHz, CDCl₃) δ ppm 7.61 (d, J=8.25 Hz, 1H) 7.38 (s, 1H) 7.34 (d, J=8.25 Hz, 1H) 2.63 (s, 3H). IR 2348, 2112 cm⁻¹.

Example 1c

Preparation of Phosphorane

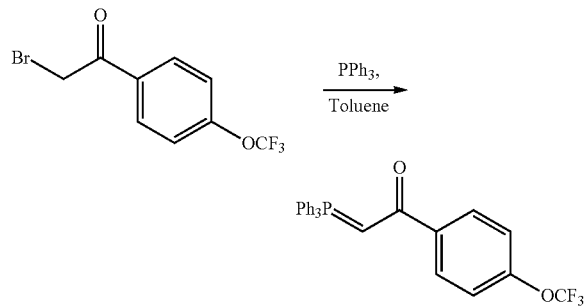

Example 1b (3.00 g, 10.6 mmol) and triphenylphosphine (3.43 g, 13.1 mmol) in toluene (106 mL) were refluxed for 2 hrs. The reaction mixture was cooled to 0° C. and the solids were filtered off and washed with toluene. The solids were triturated in THF and filtered. The solid filter cake was treated with 50.0 mL of 2 N NaOH solution, and stirred at rt overnight. The solids filtered, washed with water and dried under vacuum to afford the title compound as a white solid, (4.00 g, 8.62 mmol, 81% yield). MS (ESI) 465.2 [M+H]+. $^1$H NMR (500 MHz, CDCl$_3$) δ ppm 8.00 (d, J=8.25 Hz, 2H) 7.72 (dd, J=12.65, 7.15 Hz, 6H) 7.55-7.62 (m, 3H) 7.44-7.53 (m, 6H) 7.19 (d, J=8.25 Hz, 2H) 4.34-4.44 (m, 1H). $^{19}$F NMR (500 MHz, CDCl$_3$) δ ppm −57.42 (s, 3F).

Example 1d

Preparation of 1-(4-bromo-2-(5-(4-(trifluoromethoxy)phenyl)-1H-1,2,3-triazol-1-yl)phenyl)ethanone

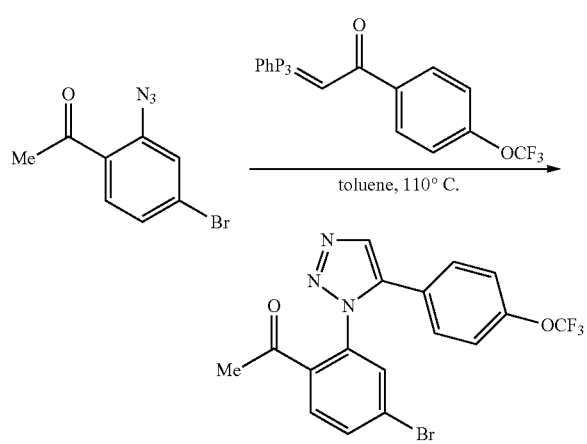

In a sealed tube, Example 1c (1.08 g, 2.33 mmol) and Example 1b (700 mg, 2.33 mmol) were brought up in toluene (20 mL) and heated to 110° C. for 18 hrs. The solvent was removed from the reaction in vacuo and the crude residue was purified by chromatography thru a 40 g SiO$_2$ column using a mobile phase gradient of 0% to 65% EtOAc/Hx over 25 min to afford the title compound as a red brown oil, (928 mg, 1.96 mmol, 84% yield). MS (ESI) 426.0 [M+H]+. $^1$H NMR (500 MHz, CDCl$_3$) δ ppm 7.90 (s, 1H) 7.77 (d, J=8.25 Hz, 1H) 7.65 (d, J=8.25 Hz, 1H) 7.54 (s, 1H) 7.26 (d, J=7.15 Hz, 2H) 7.18-7.23 (m, 2H) 2.17 (s, 3H). $^{19}$F NMR (500 MHz, CDCl$_3$) δ ppm −57.53 (s, 3F).

Example 1e

Preparation of ethyl 5-(4-bromo-2-(5-(4-(trifluoromethoxy)phenyl)-1H-1,2,3-triazol-1-yl)phenyl)-2,2-difluoro-3,5-dioxopentanoate

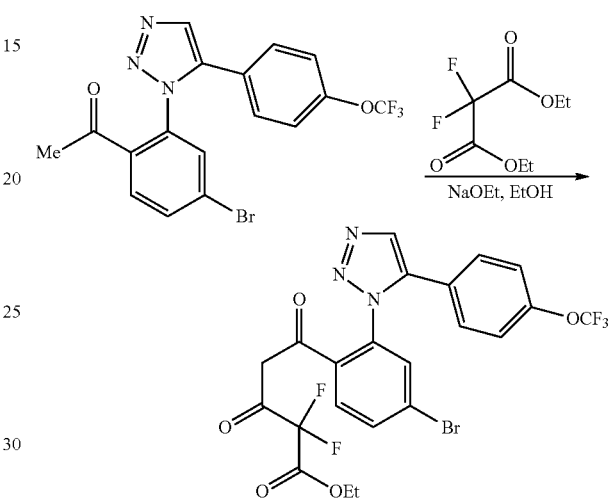

In a dry 25 mL round bottom flask under an Ar atmosphere, NaOEt (9.71 mL, 26.0 mmol) in EtOH (21% weight) and diethyl-2,2-difluoromalonate (2.55 g, 13.0 mmol) were stirred at rt for 10 min. A solution of Example 1d (554 mg, 1.30 mmol) in EtOH (6.00 mL) was added dropwise and the reaction was stirred at rt over 18 hrs. The EtOH was removed in vacuo and the crude oil was dissolved in 1 M HCl (10 mL). The aqueous solution was extracted with EtOAc (20 mL×3), and the combined organics were washed with aq NaCl (20 mL), dried over Na$_2$SO$_4$, filtered into a round bottom flask and concentrated in vacuo to give the title compound as a crude brown oil (749 mg, 1.30 mmol). MS (ESI) 576.0 [M+H]+.

Example 1f

Preparation of ethyl 2-(5-(4-bromo-2-(5-(4-(trifluoromethoxy)phenyl)-1H-1,2,3-triazol-1-yl)phenyl)-1-methyl-1H-pyrazol-3-yl)-2,2-difluoroacetate

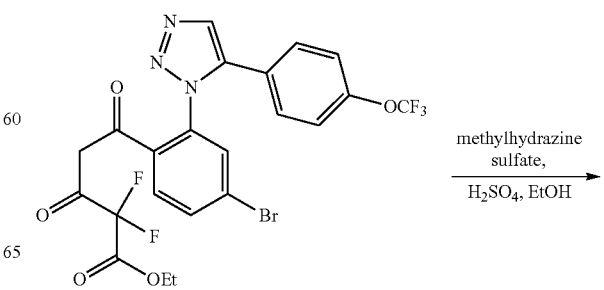

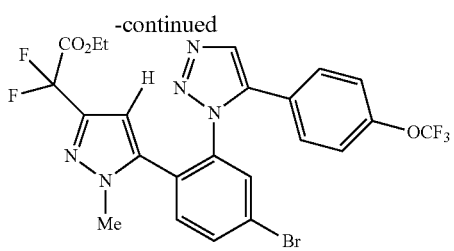

Example 1e (749 mg, 1.30 mmol) was brought up in EtOH (1.00 mL) and to it was added methylhydrazine sulfate (206 mg, 1.43 mmol) and H$_2$SO$_4$ (0.500 mL, 9.38 mmol). The reaction mixture was stirred at rt for 18 hrs. The reaction was diluted with EtOAc (10 mL) and washed with saturated aq NaHCO$_3$ (20 mL). The aqueous layer was extracted with EtOAc (10 mL×2), and the combined organics were washed with aq NaCl (20 mL), dried over Na$_2$SO$_4$, filtered into a round bottom flask and concentrated in vacuo to give the crude product. The crude residue was purified by chromatography thru a 12 g SiO$_2$ column using a mobile phase gradient of 0% to 100% EtOAc/Hx over 16 min to afford the title compound as an orange solid, (494 mg, 0.842 mmol, 65% yield). MS (ESI) 586.1 [M+H]+. $^1$H NMR (500 MHz, CDCl$_3$) δ ppm 8.09 (s, 1H) 7.80 (d, J=8.25 Hz, 1H) 7.70 (s, 1H) 7.23 (d, J=8.25 Hz, 1H) 7.14 (d, J=8.25 Hz, 2H) 6.85 (d, J=8.80 Hz, 2H) 5.55 (s, 1H) 4.39 (q, J=7.15 Hz, 2H) 3.08 (s, 3H) 1.38 (t, J=7.15 Hz, 3H).

Example 1g

Preparation of 2-(5-(4-bromo-2-(5-(4-(trifluoromethoxy)phenyl)-1H-1,2,3-triazol-1-yl)phenyl)-1-methyl-1H-pyrazol-3-yl)-2,2-difluoroacetic acid

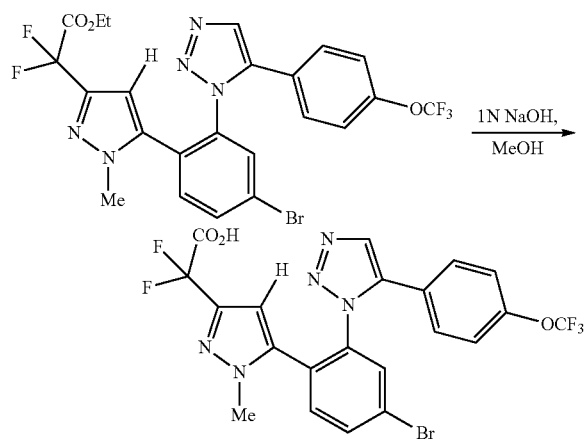

Example 1f (84.8 mg, 0.145 mmol) was brought up in MeOH (1.00 mL) and to it was added 1 M NaOH (0.723 mL, 0.723 mmol). The reaction mixture was stirred at rt for 18 hrs. The reaction was diluted with water and EtOAc (10 mL), and the layers were separated. The aqueous layer was acidified to pH 3 with 1 N HCl, and then extracted with EtOAc (10 mL×2). The combined organics were washed with aq NaCl (10 mL), dried over Na$_2$SO$_4$ and concentrated to give the title compound as a pale yellow powder (75.9 mg, 0.136 mmol, 94% yield). MS (ESI) 558.1 [M+H]+. $^1$H NMR (500 MHz, CDCl$_3$) δ ppm 8.10 (s, 1H) 7.84 (d, J=8.25 Hz, 1H) 7.82 (s, 1H) 7.25-7.29 (m, 1H) 7.17 (d, J=8.25 Hz, 2H) 6.91 (d, J=8.80 Hz, 2H) 5.62 (s, 1H) 3.10 (s, 3H). $^{19}$F NMR (500 MHz, CDCl$_3$) δ ppm −57.51 (s, 3F) −100.16 (s, 2F).

Example 1h

Preparation of 2-(5-(4-bromo-2-(5-(4-(trifluoromethoxy)phenyl)-1H-1,2,3-triazol-1-yl)phenyl)-1-methyl-1H-pyrazol-3-yl)-2,2-difluoro-N-methoxy-N-methylacetamide

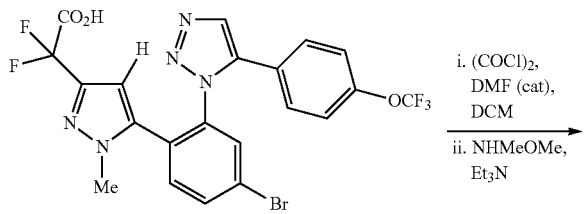

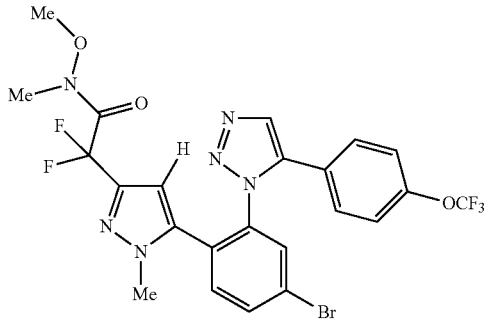

Example 1g (97.8 mg, 0.175 mmol) was brought up in DCM (3.00 mL), and DMF (1.36 μL, 0.0180 mmol) was added. Oxalyl chloride (0.109 mL, 0.219 mmol) in DCM was added dropwise. The reaction was stirred at rt for 30 min. N,O-dimethylhydroxylamine hydrochloride (20.5 mg, 0.210 mmol) was added in one portion followed by Et$_3$N (0.0980 mL, 0.701 mmol). The reaction mixture was stirred for 2 hrs. The reaction mixture was diluted with EtOAc (20 mL) and water (20 mL). The layers were separated and the aqueous layer was extracted EtOAc (10 mL×3). The combined organic extracts were washed with aq NaCl (20 mL), dried over Na$_2$SO$_4$, filtered into a round bottom flask and concentrated in vacuo to give the crude product. The crude residue was purified by chromatography thru a 4 g SiO$_2$ column using a mobile phase gradient of 0% to 100% EtOAc/Hx over 16 min to afford the title compound as an white solid, (105 mg, 0.175 mmol, 100% yield). MS (ESI) 601.2 [M+H]+.

Example 1i

Preparation of 1-(5-(4-bromo-2-(5-(4-(trifluoromethoxy)phenyl)-1H-1,2,3-triazol-1-yl)phenyl)-1-methyl-1H-pyrazol-3-yl)-1,1-difluoropropan-2-one

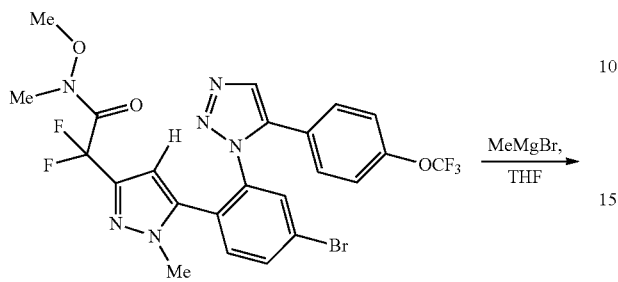

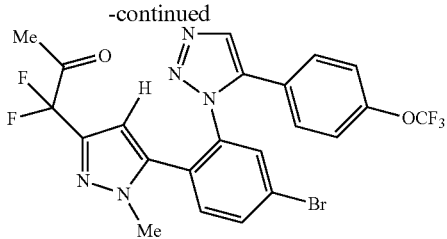

Example 1h (137 mg, 0.227 mmol) was brought up in THF (2.00 mL) and cooled to −78° C. Methylmagnesium bromide (325 μL, 0.455 mmol, 1.4 M in toluene/THF) was added dropwise, and the reaction mixture was allowed to warm to rt and stirred for 3 hrs. The reaction mixture was quenched with saturated aq NH₄Cl (5 mL). The layers were separated and the aqueous layer was extracted with EtOAc (10 mL×3). The combined organic extracts were washed with aq NaCl (20 mL), dried over Na₂SO₄, filtered into a round bottom flask and concentrated in vacuo to afford the title compound as a clear oil (107 mg, 0.193 mmol, 85% yield). MS (ESI) 556.2 [M+H]+. ¹H NMR (500 MHz, CDCl₃) δ ppm 8.09 (s, 1H) 7.80 (s, 1H) 7.72 (s, 1H) 7.23 (d, J=8.25 Hz, 1H) 7.14 (d, J=8.25 Hz, 2H) 6.87 (d, J=8.25 Hz, 2H) 5.54 (s, 1H) 3.10 (s, 3H) 2.43 (s, 3H).

Example 1j

Preparation of 1,1-difluoro-1-(1-methyl-5-(3'-(methylsulfonyl)-3-(5-(4-(trifluoromethoxy)phenyl)-1H-1,2,3-triazol-1-yl)biphenyl-4-yl)-1H-pyrazol-3-yl)propan-2-one

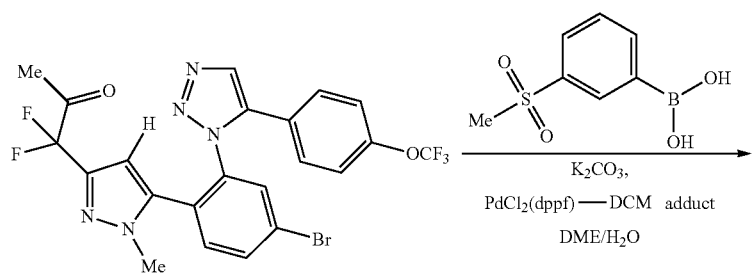

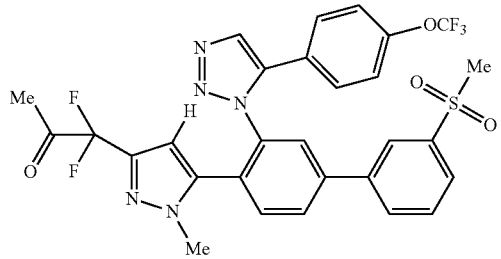

In a 0.5-2 mL sized conical microwave vial, Example 1i (54 mg, 0.10 mmol), 3-(methylsulfonyl)phenylboronic acid (39 mg, 0.19 mmol), K₂CO₃ (40 mg, 0.29 mmol) and PdCl₂(dppf)-DCM adduct (8.0 mg, 10 mol) were brought up in DME (1.0 mL) and water (0.10 mL). The vial was sealed and heated in the microwave at 120° C. for 20 min. The reaction mixture was diluted with EtOAc (10 mL) and water (10 mL) and the layers separated. The aqueous layer was extracted with EtOAc (10 mL×2), and the combined organic extracts were washed with aq NaCl (10 mL), dried over Na₂SO₄, filtered into a round bottom flask and concentrated in vacuo to give the crude product. The crude residue was purified by chromatography thru a 4 g SiO₂ column using a mobile phase gradient of 0% to 100% EtOAc/Hx over 15 min to afford the title compound as a clear oil, (59 mg, 0.090 mmol, 98% yield). MS (ESI) 632.3 [M+H]+.

Example 1

Preparation of 1,1-difluoro-1-(1-methyl-5-(3'-(methylsulfonyl)-3-(5-(4-(trifluoromethoxy)phenyl)-1H-1,2,3-triazol-1-yl)biphenyl-4-yl)-1H-pyrazol-3-yl)propan-2-ol

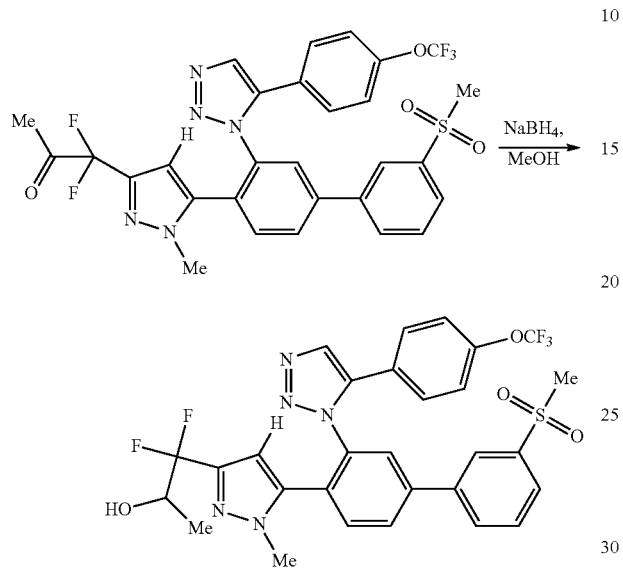

Example 1j (30 mg, 0.048 mmol) was brought up in MeOH (1.0 mL) and cooled to −78° C. NaBH$_4$ (2.7 mg, 0.071 mmol) was added, and the reaction mixture was allowed to warm to rt and stirred for 3 hrs. The reaction mixture was diluted with EtOAc (10 mL) and water (10 mL). The layers were separated and the aqueous layer was acidified to pH 1 with concentrated HCl, and then extracted EtOAc (10 mL×3). The combined organic extracts were washed with aq NaCl (20 mL), dried over Na$_2$SO$_4$, filtered into a round bottom flask and concentrated in vacuo to give the crude product. The crude material was purified by prep HPLC with the following conditions: Column: Phenomenex Luna AXIA C18, 21.2×100 mm, 5-μm particles; Mobile Phase A: 10% MeOH—90% H$_2$O—0.1% TFA; Mobile Phase B: 90% MeOH—10% H$_2$O—0.1% TFA; Gradient: 40-100% B over 10 min, then a 4-minute hold at 100% B; Flow: 20 mL/min. The fractions containing the product were filtered over a NaHCO$_3$ resin frit (StratoSpheres™ SPE, 0.36 mmol) and concentrated in vacuo to give the title compound as a clear oil (8.5 mg, 0.013 mmol, 28% yield). MS (ESI) 634.3 [M+H]+. $^1$H NMR (400 MHz, CDCl$_3$) δ ppm 8.32 (s, 1H) 8.17 (d, J=2.20 Hz, 1H) 8.12 (d, J=7.14 Hz, 1H) 8.05 (t, J=9.34 Hz, 1H) 7.91-7.97 (m, 1H) 7.74-7.81 (m, 1H) 7.59-7.65 (m, 1H) 7.47-7.53 (m, 2H) 7.14 (d, J=7.70 Hz, 2H) 6.91 (d, J=8.79 Hz, 2H) 5.58 (s, 1H) 4.21-4.32 (m, 1H) 3.14-3.17 (m, 6H) 1.33 (d, J=6.60 Hz, 3H). $^{19}$F NMR (400 MHz, CDCl$_3$) δ ppm −57.67 (s, 3F) −101.98 (d, 1F) −110.29 (d, 1F).

Example 2

(4'-(3-(1,1-difluoropropyl)-1-methyl-1H-pyrazol-5-yl)-3-fluoro-5-(methylsulfonyl)-3'-(5-(4-(trifluoromethoxy)phenyl)-1H-1,2,3-triazol-1-yl)biphenyl-4-yl)methanol

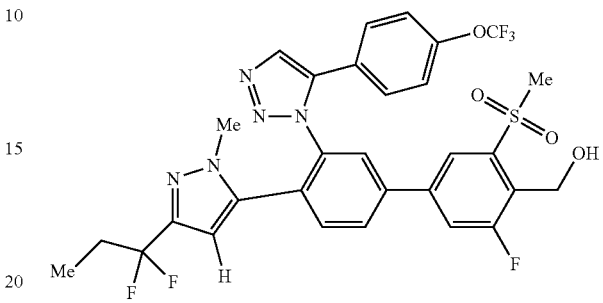

Example 2a

Preparation of 1-(4-bromo-2-(5-(4-(trifluoromethoxy)phenyl)-1H-1,2,3-triazol-1-yl)phenyl)-4,4-difluorohexane-1,3-dione

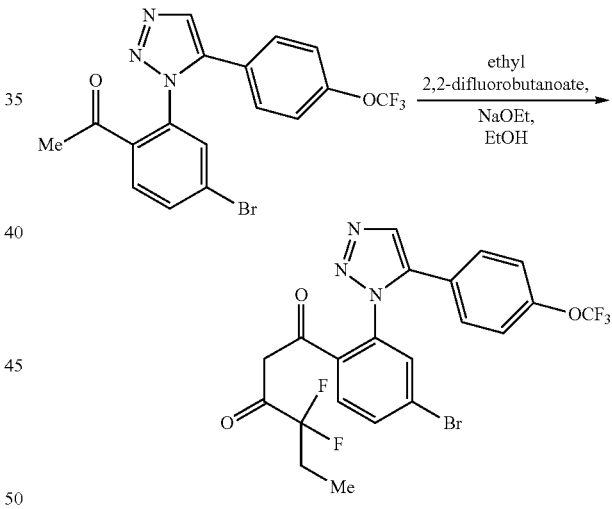

In a dry 25 mL round bottom flask under an Ar atmosphere, NaOEt (3.33 mL, 9.24 mmol) in EtOH (21% weight) and ethyl 2,2-difluorobutanoate (352 mg, 2.31 mmol) were stirred at rt for 10 min. A solution of Example 1e (197 mg, 0.462 mmol) in EtOH (2.00 mL) was added dropwise and the reaction was stirred at rt over 18 hrs. The EtOH was removed in vacuo and the crude oil was dissolved in 1 M HCl (10 mL). The aqueous solution was extracted with EtOAc (20 mL×3), and the combined organics were washed with aq NaCl (20 mL), dried over Na$_2$SO$_4$, filtered into a round bottom flask and concentrated in vacuo to give the title compound as a crude brown oil (246 mg, 0.462 mmol). MS (ESI) 532.0 [M+H]+.

Example 2 was prepared from Example 2a using procedures similar to that described in Example 1f and Example 1j. MS (ESI) 666.3 [M+H]+. $^1$H NMR (500 MHz, CDCl$_3$)

δ ppm 8.27 (s, 1H) 8.15 (s, 1H) 7.91 (d, J=8.25 Hz, 1H) 7.79 (d, J=9.90 Hz, 1H) 7.75 (s, 1H) 7.50 (d, J=8.25 Hz, 1H) 7.14 (d, J=8.25 Hz, 2H) 6.87 (d, J=8.80 Hz, 2H) 5.51 (s, 1H) 5.13 (d, J=6.60 Hz, 2H) 3.34 (s, 3H) 2.99 (t, J=6.87 Hz, 1H) 2.18 (td, J=16.22, 7.70 Hz, 2H) 1.02 (t, J=7.42 Hz, 3H). $^{19}$F NMR (500 MHz, CDCl$_3$) δ ppm −57.65 (s, 3F) −94.42 (s, 2F) −112.47 (s, 1F).

Example 3

1,1-difluoro-1-(5-(3'-fluoro-4'-(hydroxymethyl)-5'-(methylsulfonyl)-3-(5-(4-(trifluoromethoxy)phenyl)-1H-1,2,3-triazol-1-yl)biphenyl-4-yl)-1-methyl-1H-pyrazol-3-yl)-2-methylpropan-2-ol

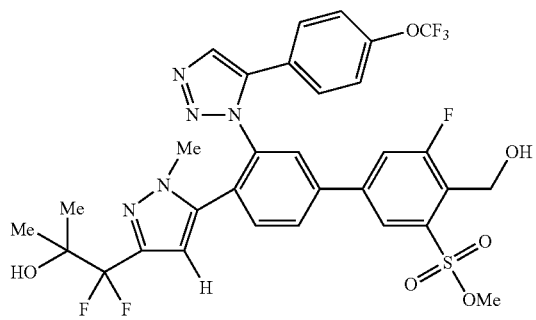 [SMILES: COS(=O)(=O)c1cc(-c2ccc(-c3cc(C(F)(F)C(C)(C)O)nn3C)c(-n3nncc3-c3ccc(OC(F)(F)F)cc3)c2)cc(F)c1CO]

Example 3a

Preparation of 1-(5-(4-bromo-2-(5-(4-(trifluoromethoxy)phenyl)-1H-1,2,3-triazol-1-yl)phenyl)-1-methyl-1H-pyrazol-3-yl)-1,1-difluoro-2-methylpropan-2-ol

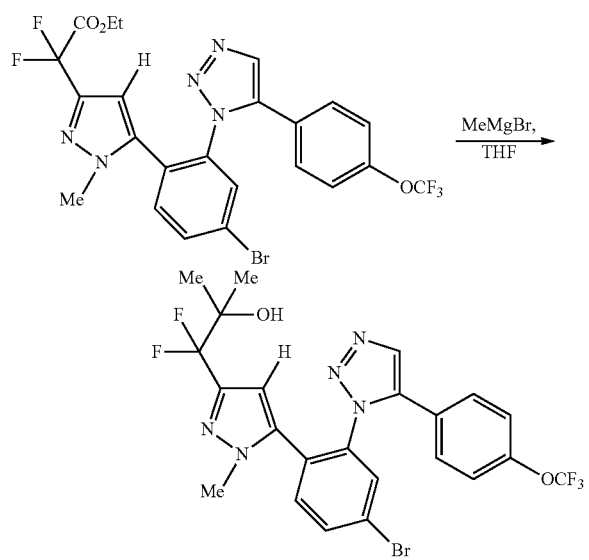

Example 1f (108 mg, 0.184 mmol) was brought up in THF (2.00 mL) and cooled to −78° C. Methylmagnesium bromide (461 μL, 0.645 mmol) in THF was added dropwise. The reaction mixture was warmed to rt and stirred for 3 hrs. The reaction mixture was quenched with saturated aq NH$_4$Cl (5 mL). The layers were separated and the aqueous layer was extracted EtOAc (10 mL×3). The combined organic extracts were washed with aq NaCl (20 mL), dried over Na$_2$SO$_4$, filtered into a round bottom flask and concentrated in vacuo to afford the title compound as a yellow oil (105 mg, 0.184 mmol, 100% yield). MS (ESI) 572.2 [M+H]+. $^1$H NMR (500 MHz, CDCl$_3$) δ ppm 8.08 (s, 1H) 7.81 (dd, J=8.25, 2.20 Hz, 1H) 7.71 (s, 1H) 7.24 (d, J=8.25 Hz, 1H) 7.14 (d, J=8.25 Hz, 2H) 6.90 (d, J=8.80 Hz, 2H) 5.54 (s, 1H) 3.11 (s, 3H) 1.31 (s, 6H).

Example 3 was prepared from Example 3a and Intermediate 1 using procedures similar to that described in Example 1j. MS (ESI) 696.3 [M+H]+. $^1$H NMR (400 MHz, CDCl$_3$) δ ppm 8.27 (s, 1H) 8.15 (s, 1H) 7.89-7.98 (m, 1H) 7.71-7.84 (m, 2H) 7.51 (d, J=8.25 Hz, 1H) 7.14 (d, J=8.25 Hz, 2H) 6.91 (d, J=8.79 Hz, 2H) 5.59 (s, 1H) 5.13 (s, 2H) 3.34 (s, 3H) 3.16 (s, 3H) 1.31 (s, 6H). $^{19}$F NMR (400 MHz, CDCl$_3$) δ ppm −57.6 (s, 3H) −106.5 (s, 2H) −112.4 (s, 1H).

Example 4

2,2-difluoro-2-(1-methyl-5-(3'-(methylsulfonyl)-3-(5-(4-(trifluoromethoxy)phenyl)-1H-1,2,3-triazol-1-yl)biphenyl-4-yl)-1H-pyrazol-3-yl)acetamide

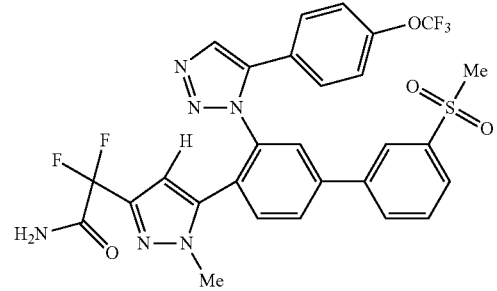 [SMILES: Cn1nc(C(F)(F)C(N)=O)cc1-c1ccc(-c2cccc(S(C)(=O)=O)c2)cc1-n1nncc1-c1ccc(OC(F)(F)F)cc1]

Example 4a

Preparation of 2-(5-(4-bromo-2-(5-(4-(trifluoromethoxy)phenyl)-1H-1,2,3-triazol-1-yl)phenyl)-1-methyl-1H-pyrazol-3-yl)-2,2-difluoroacetamide

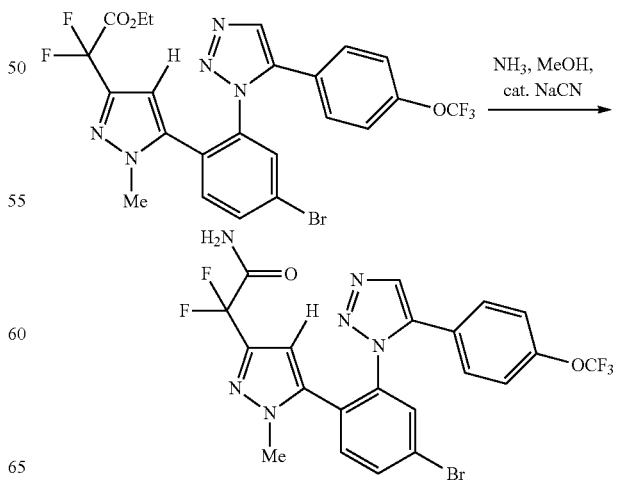

In a sealed tube, Example 1f (100 mg, 0.171 mmol) was brought up in ammonia (609 µL, 4.26 mmol) in MeOH and NaCN (0.836 mg, 0.0170 mmol) was added. The reaction mixture was heated to 45° C. for 18 hrs. The solvent was removed in vacuo, and the residue was brought up with EtOAc (10 mL) and water (10 mL). The layers were separated, and the aqueous layer was extracted with EtOAc (10 mL×2). The combined organics were washed with brine, dried over Na$_2$SO$_4$ and concentrated in vacuo to give the title compound (95.0 mg, 0.171 mmol, 100% yield). MS (ESI) 557.2 [M+H]+. $^1$H NMR (400 MHz, CDCl$_3$) δ ppm 8.10 (s, 1H), 7.81 (dd, J=8.25, 2.20 Hz, 1H), 7.72 (s, 1H), 7.23 (d, J=8.24 Hz, 1H), 7.15 (d, J=8.79 Hz, 2H), 6.88 (d, J=8.79 Hz, 2H), 6.49 (br. s., 1H), 5.68 (br. s., 1H), 5.57 (s, 1H), 3.10 (s, 3H).

Example 4 was prepared from Example 4a and 3-(methylsulfonyl)phenylboronic acid using procedures similar to that described in Example 1j. MS (ESI) 632.94 [M+H]+. $^1$H NMR (400 MHz, MeOD) δ ppm 8.41 (t, J=1.65 Hz, 1H) 8.36 (d, J=1.98 Hz, 1H) 8.18-8.22 (m, 1H) 8.13 (dd, J=8.14, 1.98 Hz, 1H) 8.05-8.09 (m, 1H) 7.89 (s, 2H) 7.83 (t, J=7.81 Hz, 1H) 7.70 (d, J=8.14 Hz, 1H) 7.23 (d, J=7.92 Hz, 2H) 7.05-7.09 (m, 2H) 5.58 (s, 1H) 3.23 (s, 3H) 3.17 (s, 3H).

Example 5

((4'-(3-(1,1-difluoroethyl)-1,4-dimethyl-1H-pyrazol-5-yl)-3-fluoro-5-(methylsulfonyl)-3'-(5-(4-(trifluoromethoxy)phenyl)-1H-1,2,3-triazol-1-yl)biphenyl-4-yl)methanol

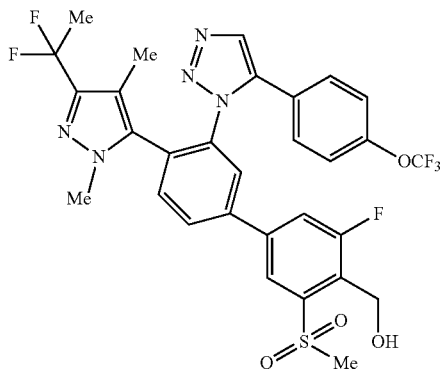 [SMILES: Cc1c(C(C)(F)F)nn(C)c1-c1ccc(-c2cc(F)c(CO)c(S(C)(=O)=O)c2)cc1-n1nncc1-c1ccc(OC(F)(F)F)cc1]

Example 5a

Preparation of 1-(2-azido-4-bromophenyl)ethanone

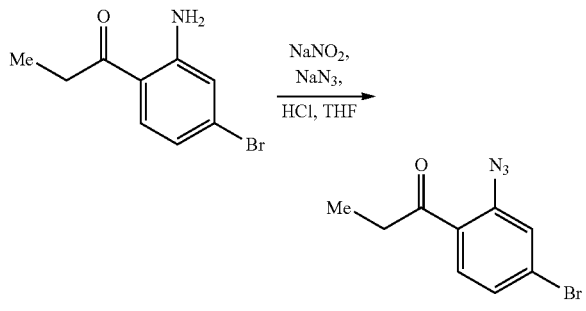

1-(2-amino-4-bromophenyl)propan-1-one (1.00 g, 4.38 mmol) was dissolved in THF (20 mL) and 4.0 mL of concentrated HCl and then cooled to 0° C. Sodium nitrite (0.605 g, 8.77 mmol) dissolved in 2.0 mL of water was added dropwise and stirred for 30 min. Afterwards, sodium azide (0.855 g, 13.2 mmol) dissolved in 2.0 mL of water was added dropwise. The reaction mixture was allowed to warm to rt and was stirred for 18 hrs. The reaction mixture was diluted with EtOAc (30 mL) and washed with saturated aq NaHCO$_3$ (30 mL). The aqueous layer was extracted with EtOAc (30 mL×2), and the combined organics were washed with aq NaCl (30 mL), dried over Na$_2$SO$_4$, filtered into a round bottom flask and concentrated in vacuo to give the crude product. The crude residue was purified by chromatography thru a 12 g SiO$_2$ column using a mobile phase gradient of 0% to 100% EtOAc/Hx over 15 min to afford the title compound as a yellow solid (1.08 g, 4.26 mmol, 97% yield). $^1$H NMR (500 MHz, CDCl$_3$) δ ppm 7.54 (d, J=8.25 Hz, 1H) 7.37 (s, 1H) 7.34 (d, J=8.25 Hz, 1H) 2.98 (q, J=7.15 Hz, 2H) 1.18 (t, J=7.42 Hz, 3H). Compound did not ionize for MS.

Example 5b

Preparation of 1 1-(4-bromo-2-(5-(4-(trifluoromethoxy)phenyl)-1H-1,2,3-triazol-1-yl)phenyl)propan-1-one

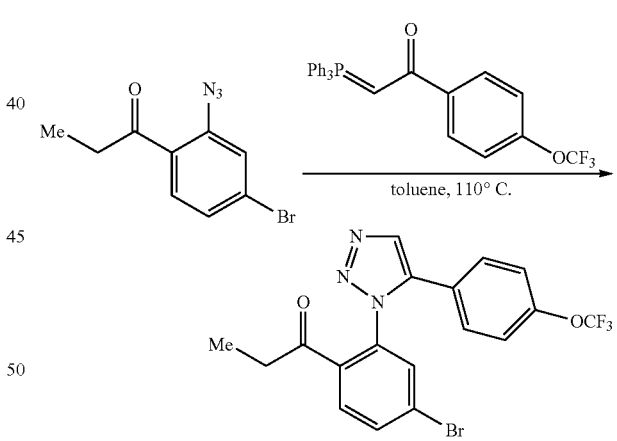

In a sealed tube, Example 1c (0.914 g, 1.97 mmol) and Example 5a (500 mg, 1.97 mmol) were brought up in toluene (18.0 mL) and heated to 110° C. for 18 hrs. The solvent was removed from the reaction in vacuo and the crude residue was purified by chromatography thru a 40 g SiO$_2$ column using a mobile phase gradient of 0% to 50% EtOAc/Hx over 25 min to afford the title compound as a yellow solid, (546 mg, 1.19 mmol, 61% yield). MS (ESI) 442.0 [M+H]+. $^1$H NMR (500 MHz, CDCl$_3$) δ 8 ppm 7.88 (s, 1H) 7.75 (d, J=8.25 Hz, 1H) 7.60 (d, J=8.25 Hz, 1H) 7.50 (s, 1H) 7.26-7.30 (m, 2H) 7.18-7.22 (m, 2H) 2.52 (q, J=7.15 Hz, 2H) 0.98 (t, J=7.15 Hz, 3H). $^{19}$F NMR (500 MHz, CDCl$_3$) δ ppm −57.6 (s, 3F).

Example 5c

Preparation of 1-(4-bromo-2-(5-(4-(trifluoromethoxy)phenyl)-1H-1,2,3-triazol-1-yl)phenyl)-4,4-difluoro-2-methylpentane-1,3-dione

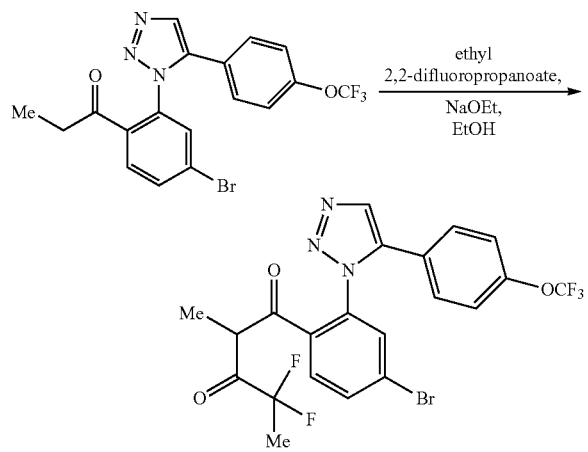

In a dry 25 mL round bottom flask under an Ar atmosphere, NaOEt (3.21 mL, 8.93 mmol) in EtOH (21% weight) and ethyl 2,2-difluoropropanoate (616 mg, 4.46 mmol) were stirred at rt for 10 min. A solution of Example 5b (393 mg, 0.893 mmol) in EtOH (2.0 mL) was added dropwise and the reaction mixture was stirred at rt over 18 hrs. The reaction was monitored by LCMS and was found to have 40% conversion to product. Another portion of NaOEt (3.21 mL, 8.93 mmol) in EtOH (21% weight) and ethyl 2,2-difluoropropanoate (616 mg, 4.46 mmol) were added, and the reaction mixture was stirred over 3 days. The EtOH was removed in vacuo and the crude oil was dissolved in 1 M HCl (10 mL). The aqueous solution was extracted with EtOAc (20 mL×3), and the combined organics were washed with aq NaCl (20 mL), dried over $Na_2SO_4$, filtered into a round bottom flask and concentrated in vacuo to give the crude product. The crude residue was purified by chromatography thru a 12 g $SiO_2$ column using a mobile phase gradient of 0% to 100% EtOAc/Hx over 20 min to afford the title compound as a brown oil (215 mg, 0.403 mmol, 45% yield). MS (ESI) 532.1 [M+H]+.

Example 5 was prepared from Example 5c using procedures similar to that described in Example 1f and Example 1j. MS (ESI) 666.3 [M+H]+. $^1$H NMR (500 MHz, CDCl$_3$) δ ppm 8.28 (s, 1H) 8.20 (s, 1H) 7.86-7.96 (m, 1H) 7.81 (d, J=9.90 Hz, 1H) 7.72 (s, 1H) 7.43 (d, J=8.25 Hz, 1H) 7.14 (d, J=8.80 Hz, 2H) 6.88 (d, J=8.80 Hz, 2H) 5.14 (d, J=7.15 Hz, 2H) 3.34 (s, 3H) 3.04 (s, 3H) 1.97 (t, J=18.42 Hz, 3H) 1.34 (s, 3H). $^{19}$F NMR (500 MHz, CDCl$_3$) δ ppm −57.63 (s, 3F) −84.98 (q, 2F) −112.48 (s, 1F).

The following compounds were prepared in a manner similar to that described in the previous experimental procedures:

| Ex # | Structure | Name | Molecular Ion |
|---|---|---|---|
| 6 | 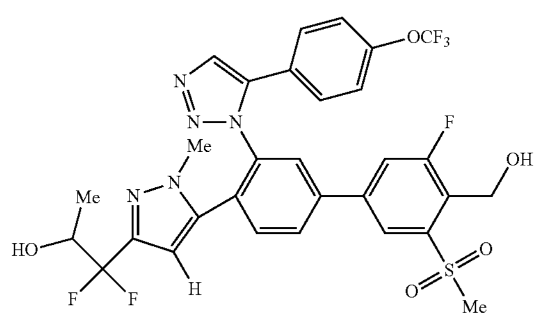 [SMILES: CC(O)C(F)(F)c1cc(-c2ccc(-c3cc(F)c(CO)c(S(C)(=O)=O)c3)cc2-n2nncc2-c2ccc(OC(F)(F)F)cc2)n(C)n1] | 1,1-difluoro-1-(5-(3'-fluoro-4'-(hydroxymethyl)-5'-(methylsulfonyl)-3-(5-(4-(trifluoromethoxy)phenyl)-1H-1,2,3-triazol-1-yl)biphenyl-4-yl)-1-methyl-1H-pyrazol-3-yl)propan-2-ol | MS (ESI) 682 [M + H]+ |
| 7 | 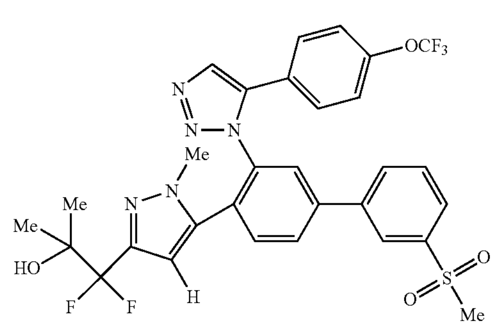 [SMILES: Cn1nc(C(F)(F)C(C)(C)O)cc1-c1ccc(-c2cccc(S(C)(=O)=O)c2)cc1-n1nncc1-c1ccc(OC(F)(F)F)cc1] | 1,1-difluoro-2-methyl-1-(1-methyl-5-(3'-(methylsulfonyl)-3-(5-(4-(trifluoromethoxy)phenyl)-1H-1,2,3-triazol-1-yl)biphenyl-4-yl)-1H-pyrazol-3-yl)propan-2-ol | MS (ESI) 648 [M + H]+ |

| Ex # | Structure | Name | Molecular Ion |
|---|---|---|---|
| 8 | 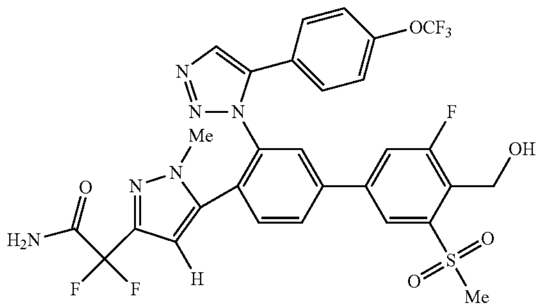 [SMILES: Cn1nc(C(F)(F)C(N)=O)cc1-c1ccc(-c2cc(F)c(CO)c(S(C)(=O)=O)c2)cc1-n1nncc1-c1ccc(OC(F)(F)F)cc1] | 2,2-difluoro-2-(5-(3'-fluoro-4'-(hydroxymethyl)-5'-(methylsulfonyl)-3-(5-(4-(trifluoromethoxy)phenyl)-1H-1,2,3-triazol-1-yl)biphenyl-4-yl)-1-methyl-1H-pyrazol-3-yl)acetamide | MS (ESI) 681 [M + H]+ |
| 9 | 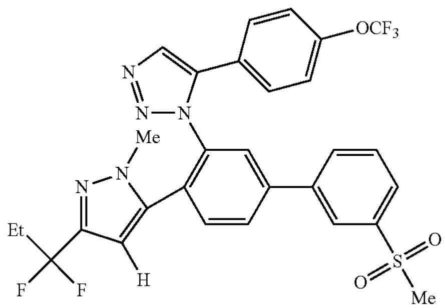 [SMILES: CCC(F)(F)c1cc(-c2ccc(-c3cccc(S(C)(=O)=O)c3)cc2-n2nncc2-c2ccc(OC(F)(F)F)cc2)n(C)n1] | 1-(4-(3-(1,1-difluoropropyl)-1-methyl-1H-pyrazol-5-yl)-3'-(methylsulfonyl)biphenyl-3-yl)-5-(4-(trifluoromethoxy)phenyl)-1H-1,2,3-triazole | MS (ESI) 618 [M + H]+ |
| 10 | 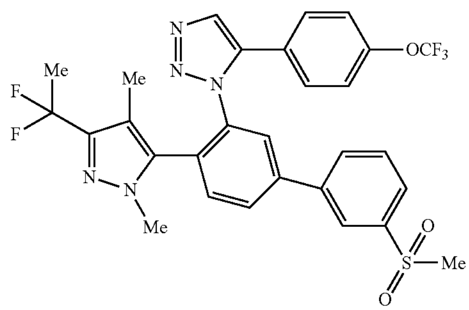 [SMILES: Cc1c(C(C)(F)F)nn(C)c1-c1ccc(-c2cccc(S(C)(=O)=O)c2)cc1-n1nncc1-c1ccc(OC(F)(F)F)cc1] | 1-(4-(3-(1,1-difluoroethyl)-1,4-dimethyl-1H-pyrazol-5-yl)-3'-(methylsulfonyl)biphenyl-3-yl)-5-(4-(trifluoromethoxy)phenyl)-1H-1,2,3-triazole | MS (ESI) 618 [M + H]+ |
| 11 | 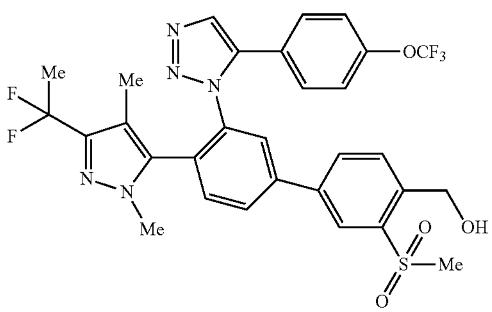 [SMILES: Cc1c(C(C)(F)F)nn(C)c1-c1ccc(-c2ccc(CO)c(S(C)(=O)=O)c2)cc1-n1nncc1-c1ccc(OC(F)(F)F)cc1] | (4'-(3-(1,1-difluoroethyl)-1,4-dimethyl-1H-pyrazol-5-yl)-3-(methylsulfonyl)-3'-(5-(4-(trifluoromethoxy)phenyl)-1H-1,2,3-triazol-1-yl)biphenyl-4-yl)methanol | MS (ESI) 648 [M + H]+ |
| 12 | 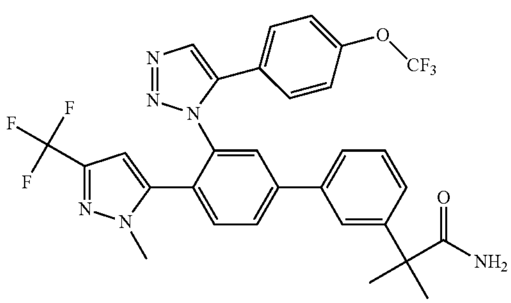 [SMILES: Cn1nc(C(F)(F)F)cc1-c1ccc(-c2cccc(C(C)(C)C(N)=O)c2)cc1-n1nncc1-c1ccc(OC(F)(F)F)cc1] | 2-methyl-2-{4'-[1-methyl-3-(trifluoromethyl)-1H-pyrazol-5-yl]-3'-(5-{4-[(trifluoromethyl)oxy]phenyl}-1H-1,2,3-triazol-1-yl)bipheny)-3-yl}propanamide | MS (ESI) 615 [M + H]+ |

| Ex # | Structure | Name | Molecular Ion |
|---|---|---|---|
| 13 | 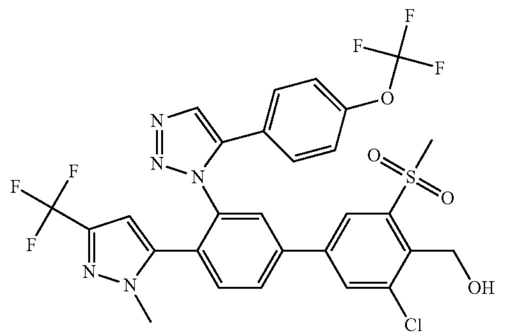 | [3-chloro-5-(methylsulfonyl)-4'-[1-methyl-3-(trifluoromethyl)-1H-pyrazol-5-yl]-3'-5-{4-[(trifluoromethyl)oxy]phenyl}-1H-1,2,3-triazol-1-yl)biphenyl-4-yl]methanol | MS (ESI) 672 [M + H]+ |
| 14 | 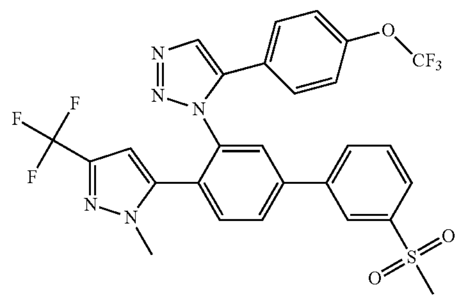 | 1-{3'-(methylsulfonyl)-4-[1-methyl-3-(trifluoromethyl)-1H-pyrazol-5-yl]biphenyl-3-yl}-5-{4-[(trifluoromethyl)oxy]phenyl}-1H-1,2,3-triazole | MS (ESI) 608 [M + H]+ |
| 15 | 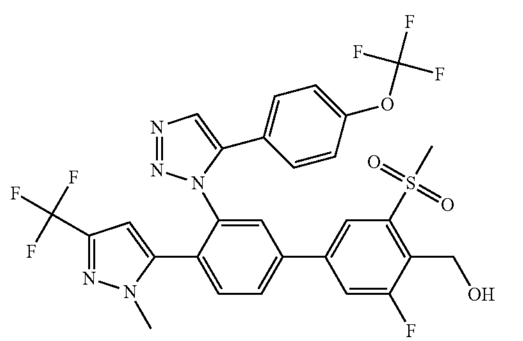 | (3-fluoro-4'-(1-methyl-3-(trifluoromethyl)-1H-pyrazol-5-yl)-5-(methylsulfonyl)-3'-(5-(4-(trifluoromethoxy)phenyl)-1H-1,2,3-triazol-1-yl)biphenyl-4-yl)methanol | |
| 16 | 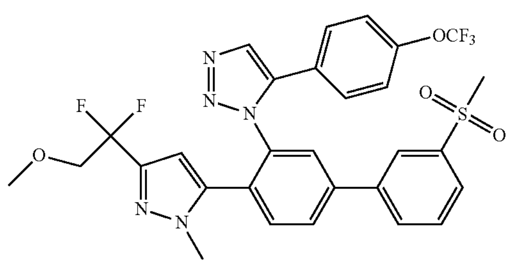 [SMILES: COCC(F)(F)c1cc(-c2ccc(-c3cccc(S(C)(=O)=O)c3)cc2-n2nncc2-c2ccc(OC(F)(F)F)cc2)n(C)n1] | 1-[4-{3-[1,1-difluoro-2-(methyloxy)ethyl]-1-methyl-1H-pyrazol-5-yl}-3'-(methylsulfonyl)biphenyl-3-yl]-5-{4-[(trifluoromethyl)oxy]phenyl}-1H-1,2,3-triazole | MS (ESI) 634.1 [M + H]+. |
| 17 | 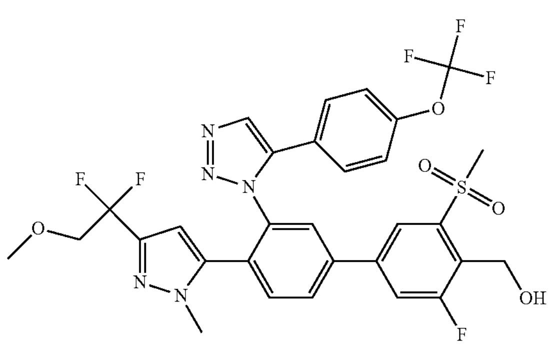 [SMILES: COCC(F)(F)c1cc(-c2ccc(-c3cc(F)c(CO)c(S(C)(=O)=O)c3)cc2-n2nncc2-c2ccc(OC(F)(F)F)cc2)n(C)n1] | [4'-{3-[1,1-difluoro-2-(methyloxy)ethyl]-1-methyl-1H-pyrazol-5-yl}-3-fluoro-5-(methylsulfonyl)-3'-(5-{4-[(trifluoromethyl)oxy]phenyl}-1H-1,2,3-triazol-1-yl)biphenyl-4-yl]methanol | MS (ESI) 682.1 [M + H]+. |

-continued

| Ex # | Structure | Name | Molecular Ion |
|---|---|---|---|
| 18 | 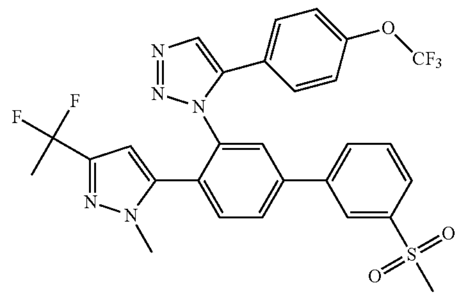 [SMILES: Cn1nc(C(C)(F)F)cc1-c1ccc(-c2cccc(S(C)(=O)=O)c2)cc1-n1nncc1-c1ccc(OC(F)(F)F)cc1] | 1-{4-[3-(1,1-difluoroethyl)-1-methyl-1H-pyrazol-5-yl]-3'-(methylsulfonyl)biphenyl-3-yl}-5-{4-[(trifluoromethyl)oxy]phenyl}-1H-1,2,3-triazole | MS (ESI) 604.1 [M + H]+. |
| 19 | 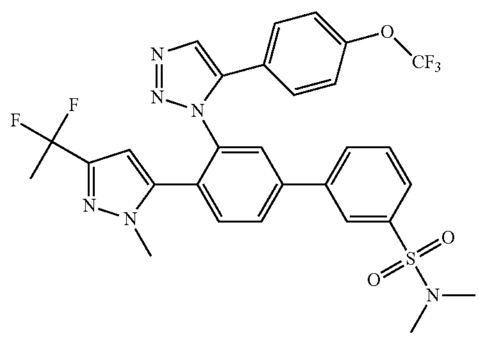 [SMILES: CN(C)S(=O)(=O)c1cccc(-c2ccc(-c3cc(C(C)(F)F)nn3C)c(-n3nncc3-c3ccc(OC(F)(F)F)cc3)c2)c1] | 4'-[3-(1,1-difluoroethyl)-1-methyl-1H-pyrazol-5-yl]-N,N-dimethyl-3'-(5-{4-[(trifluoromethyl)oxy]phenyl}-1H-1,2,3-triazol-1-yl)biphenyl-3-sulfonamide | MS (ESI) 633.2 [M + H]+. |
| 20 | 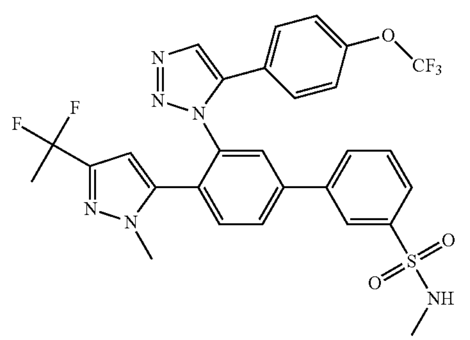 [SMILES: CNS(=O)(=O)c1cccc(-c2ccc(-c3cc(C(C)(F)F)nn3C)c(-n3nncc3-c3ccc(OC(F)(F)F)cc3)c2)c1] | 4'-[3-(1,1-difluoroethyl)-1-methyl-1H-pyrazol-5-yl]-N-methyl-3'-(5-{4-[(trifluoromethyl)oxy]phenyl}-1H-1,2,3-triazol-1-yl)biphenyl-3-sulfonamide | MS (ESI) 619.1 [M + H]+. |
| 21 | 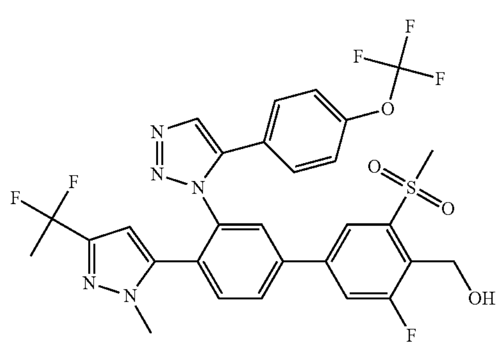 [SMILES: Cn1nc(C(C)(F)F)cc1-c1ccc(-c2cc(F)c(CO)c(S(C)(=O)=O)c2)cc1-n1nncc1-c1ccc(OC(F)(F)F)cc1] | {4'-[3-(1,1-difluoroethyl)-1-methyl-1H-pyrazol-5-yl]-3-fluoro-5-(methylsulfonyl)-3'-(5-{4-[(trifluoromethyl)oxy]phenyl}-1H-1,2,3-triazol-1-yl)biphenyl-4-yl}methanol | MS (ESI) 652.1 [M + H]+. |

-continued

| Ex # | Structure | Name | Molecular Ion |
|---|---|---|---|
| 22 | 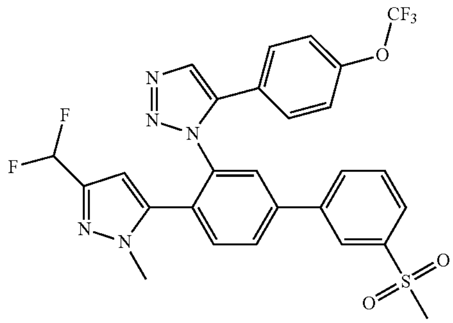 [SMILES: Cn1nc(C(F)F)cc1-c1ccc(-c2cccc(S(C)(=O)=O)c2)cc1-n1nncc1-c1ccc(OC(F)(F)F)cc1] | 1-{4-[3-(difluoromethyl)-1-methyl-1H-pyrazol-5-yl]-3'-(methylsulfonyl)biphenyl-3-yl}-5-{4-[(trifluoromethyl)oxy]phenyl}-1H-1,2,3-triazole | MS (ESI) 590.1 [M + H]+. |
| 23 | 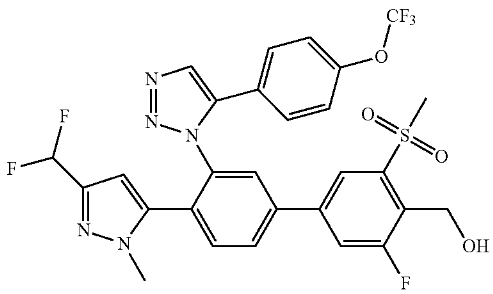 [SMILES: Cn1nc(C(F)F)cc1-c1ccc(-c2cc(F)c(CO)c(S(C)(=O)=O)c2)cc1-n1nncc1-c1ccc(OC(F)(F)F)cc1] | {4'-[3-(difluoromethyl)-1-methyl-1H-pyrazol-5-yl]-3-fluoro-5-(methylsulfonyl)-3'-(5-{4-[(trifluoromethyl)oxy]phenyl}-1H-1,2,3-triazol-1-yl)biphenyl-4-yl}methanol | MS (ESI) 638.1 [M + H]+. |
| 24 | 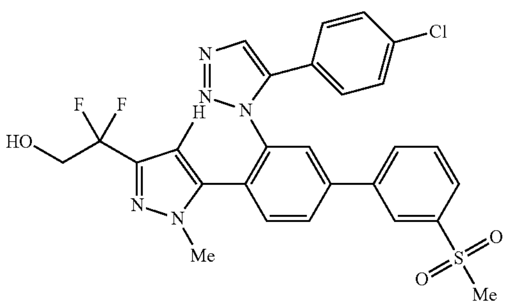 [SMILES: Cn1nc(C(F)(F)CO)cc1-c1ccc(-c2cccc(S(C)(=O)=O)c2)cc1-n1nncc1-c1ccc(Cl)cc1] | 2-(5-(3-(5-(4-chlorophenyl)-1H-1,2,3-triazol-1-yl)-3'-(methylsulfonyl)-[1,1'-biphenyl]-4-yl)-1-methyl-1H-pyrazol-3-yl)-2,2-difluoroethanol | MS (ESI) 569.9 [M + H]+. |
| 25 | 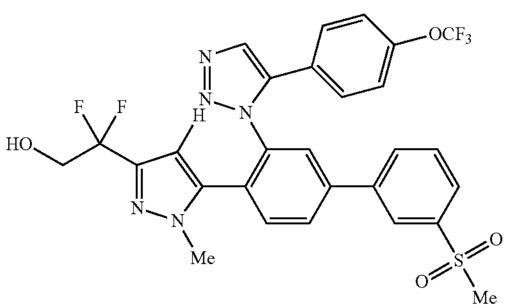 | 2,2-difluoro-2-(1-methyl-5-(3'-(methylsulfonyl)-3-(5-(4-(trifluoromethoxy)phenyl)-1H-1,2,3-triazol-1-yl)-[1,1'-biphenyl]-4-yl)-1H-pyrazol-3-yl)ethanol | MS (ESI) 620.1 [M + H]+. |
| 26 | 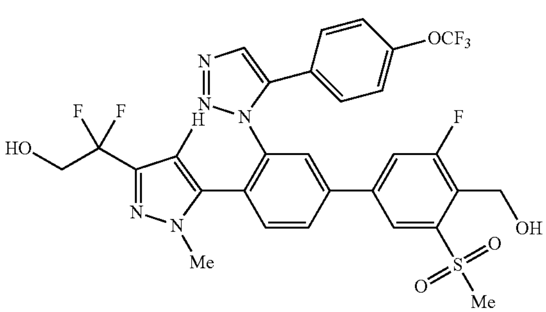 [SMILES: Cn1nc(C(F)(F)CO)cc1-c1ccc(-c2cc(F)c(CO)c(S(C)(=O)=O)c2)cc1-n1nncc1-c1ccc(OC(F)(F)F)cc1] | 2,2-difluoro-2-(5-(3'-fluoro-4'-(hydroxymethyl)-5'-(methylsulfonyl)-3-(5-(4-(trifluoromethoxy)phenyl)-1H-1,2,3-triazol-1-yl)-[1,1'-biphenyl]-4-yl)-1-methyl-1H-pyrazol-3-yl)ethanol | MS (ESI) 668.0 [M + H]+. |

-continued

| Ex # | Structure | Name | Molecular Ion |
|---|---|---|---|
| 27 | 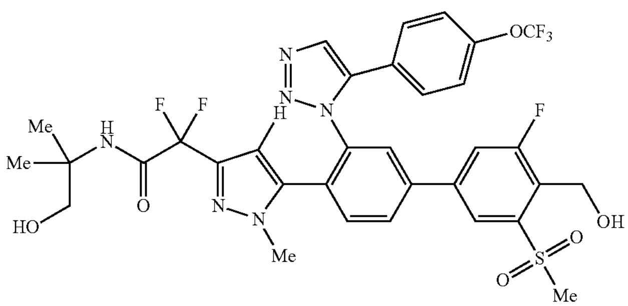 [SMILES: Cn1nc(C(F)(F)C(=O)NC(C)(C)CO)cc1-c1ccc(-c2cc(F)c(CO)c(S(C)(=O)=O)c2)cc1-n1nncc1-c1ccc(OC(F)(F)F)cc1] | 2,2-difluoro-2-(5-(3'-fluoro-4'-(hydroxymethyl)-5'-(methylsulfonyl)-3-(5-(4-(trifluoromethoxy)phenyl)-1H-1,2,3-triazol-1-yl)-[1,1'-biphenyl]-4-yl)-1-methyl-1H-pyrazol-3-yl)-N-(1-hydroxy-2-methylpropan-2-yl)acetamide | MS (ESI) 753.2 [M + H]+. |
| 28 | 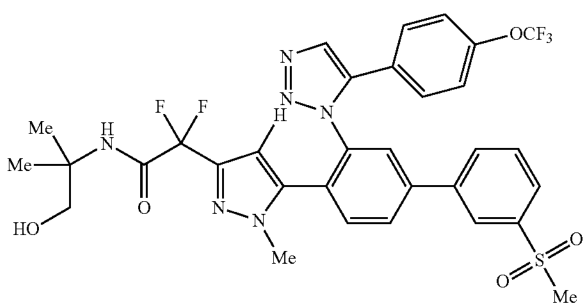 [SMILES: Cn1nc(C(F)(F)C(=O)NC(C)(C)CO)cc1-c1ccc(-c2cccc(S(C)(=O)=O)c2)cc1-n1nncc1-c1ccc(OC(F)(F)F)cc1] | 2,2-difluoro-N-(1-hydroxy-2-methylpropan-2-yl)-2-(1-methyl-5-(3'-(methylsulfonyl)-3-(5-(4-(trifluoromethoxy)phenyl)-1H-1,2,3-triazol-1-yl)-[1,1'-biphenyl]-4-yl)-1H-pyrazol-3-yl)acetamide | MS (ESI) 705.2 [M + H]+. |
| 29 | 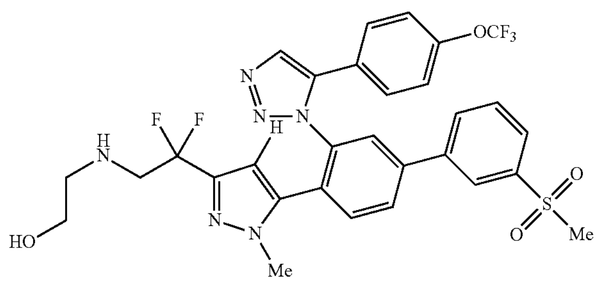 [SMILES: Cn1nc(C(F)(F)CNCCO)cc1-c1ccc(-c2cccc(S(C)(=O)=O)c2)cc1-n1nncc1-c1ccc(OC(F)(F)F)cc1] | 2-((2,2-difluoro-2-(1-methyl-5-(3'-(methylsulfonyl)-3-(5-(4-(trifluoromethoxy)phenyl)-1H-1,2,3-triazol-1-yl)-[1,1'-biphenyl]-4-yl)-1H-pyrazol-3-yl)ethyl)amino)ethanol | MS (ESI) 663.1 [M + H]+. |
| 30 | 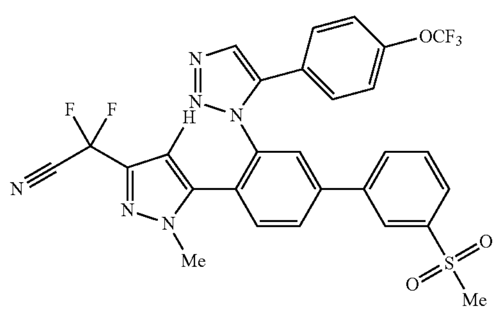 [SMILES: Cn1nc(C(F)(F)C#N)cc1-c1ccc(-c2cccc(S(C)(=O)=O)c2)cc1-n1nncc1-c1ccc(OC(F)(F)F)cc1] | 2,2-difluoro-2-(1-methyl-5-(3'-(methylsulfonyl)-3-(5-(4-(trifluoromethoxy)phenyl)-1H-1,2,3-triazol-1-yl)-[1,1'-biphenyl]-4-yl)-1H-pyrazol-3-yl)acetonitrile | MS (ESI) 614.9 [M + H]+. |
| 31 | 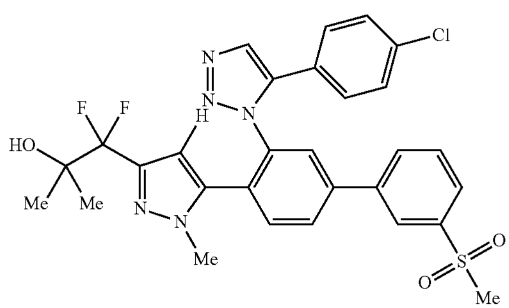 [SMILES: Cn1nc(C(F)(F)C(C)(C)O)cc1-c1ccc(-c2cccc(S(C)(=O)=O)c2)cc1-n1nncc1-c1ccc(Cl)cc1] | 1-(5-(3-(5-(4-chlorophenyl)-1H-1,2,3-triazol-1-yl)-3'-(methylsulfonyl)-[1,1'-biphenyl]-4-yl)-1-methyl-1H-pyrazol-3-yl)-1,1-difluoro-2-methylpropan-2-ol | MS (ESI) 598 [M + H]+. |

| Ex # | Structure | Name | Molecular Ion |
|---|---|---|---|
| 32 | 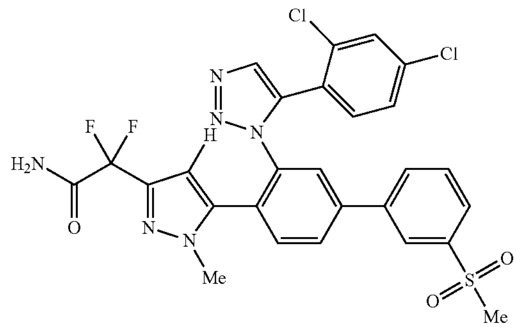 [SMILES: Cn1nc(C(F)(F)C(N)=O)cc1-c1ccc(-c2cccc(S(C)(=O)=O)c2)cc1-n1nncc1-c1ccc(Cl)cc1Cl] | 2-(5-(3-(5-(2,4-dichlorophenyl)-1H-1,2,3-triazol-1-yl)-3'-(methylsulfonyl)-[1,1'-biphenyl]-4-yl)-1-methyl-1H-pyrazol-3-yl)-2,2-difluoroacetamide | |
| 33 | 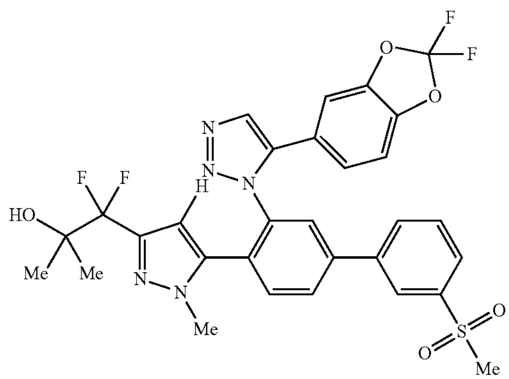 [SMILES: Cn1nc(C(F)(F)C(C)(C)O)cc1-c1ccc(-c2cccc(S(C)(=O)=O)c2)cc1-n1nncc1-c1ccc2c(c1)OC(F)(F)O2] | 1-(5-(3-(5-(2,2-difluorobenzo[d][1,3]dioxol-5-yl)-1H-1,2,3-triazol-1-yl)-3'-(methylsulfonyl)-[1,1'-biphenyl]-4-yl)-1-methyl-1H-pyrazol-3-yl)-1,1-difluoro-2-methylpropan-2-ol | |
| 34 | 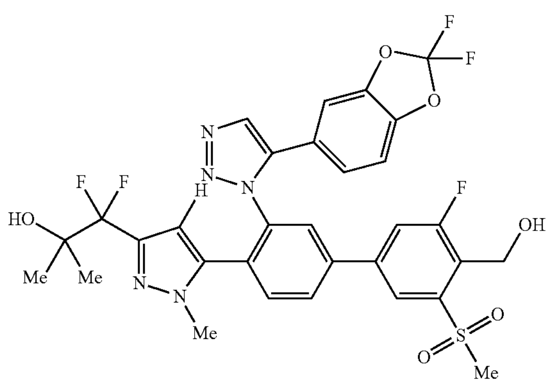 [SMILES: Cn1nc(C(F)(F)C(C)(C)O)cc1-c1ccc(-c2cc(F)c(CO)c(S(C)(=O)=O)c2)cc1-n1nncc1-c1ccc2c(c1)OC(F)(F)O2] | 1-(5-(3-(5-(2,2-difluorobenzo[d][1,3]dioxol-5-yl)-1H-1,2,3-triazol-1-yl)-3'-fluoro-4'-(hydroxymethyl)-5'-(methylsulfonyl)-[1,1'-biphenyl]-4-yl)-1-methyl-1H-pyrazol-3-yl)-1,1-difluoro-2-methylpropan-2-ol | |
| 35 | 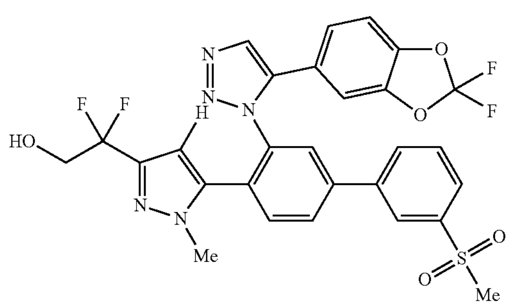 [SMILES: Cn1nc(C(F)(F)CO)cc1-c1ccc(-c2cccc(S(C)(=O)=O)c2)cc1-n1nncc1-c1ccc2c(c1)OC(F)(F)O2] | 2-(5-(3-(5-(2,2-difluorobenzo[d][1,3]dioxol-5-yl)-1H-1,2,3-triazol-1-yl)-3'-(methylsulfonyl)-[1,1'-biphenyl]-4-yl)-1-methyl-1H-pyrazol-3-yl)-2,2-difluoroethanol | |

| Ex # | Structure | Name | Molecular Ion |
|---|---|---|---|
| 36 | 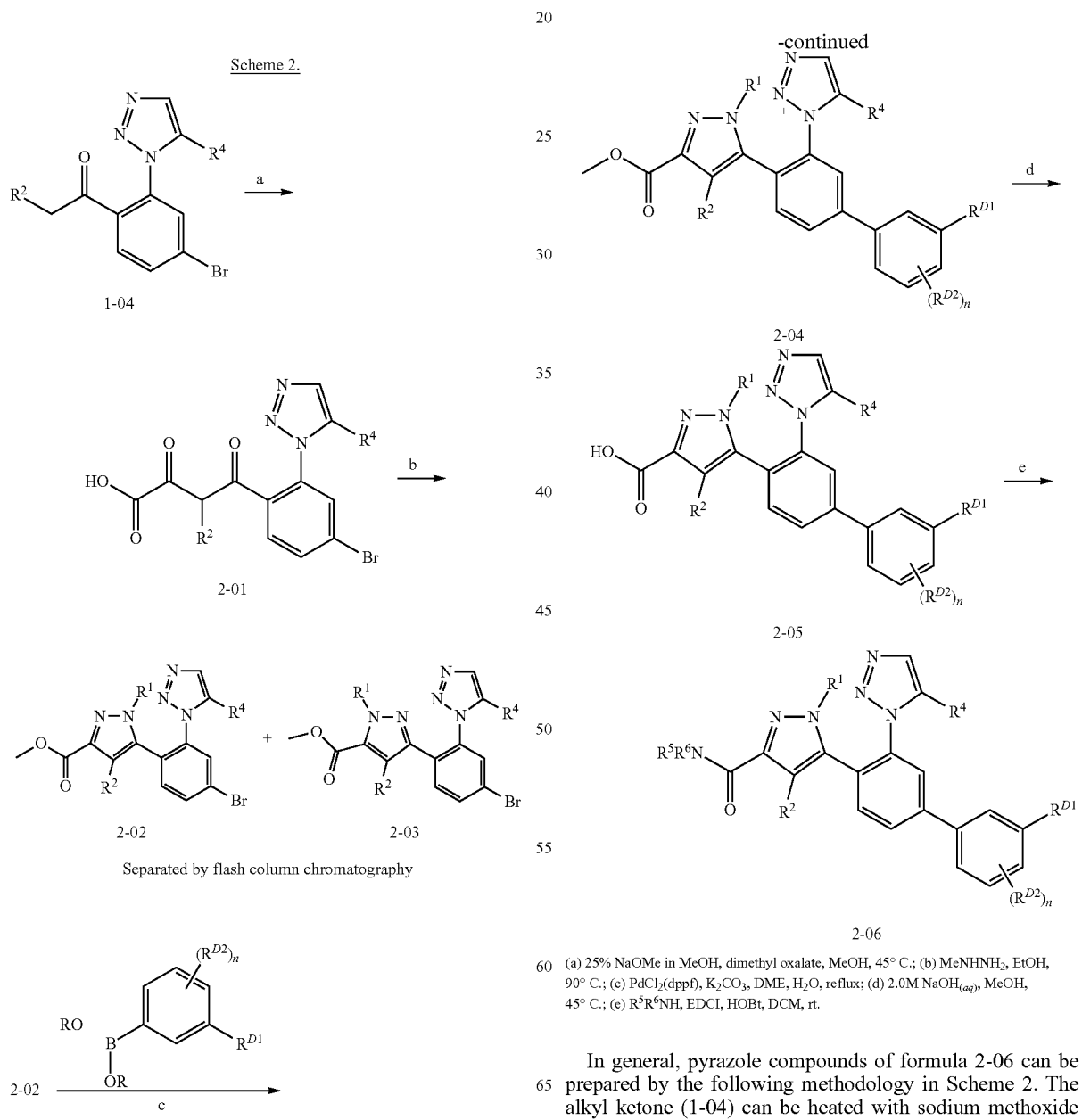 | 2-(5-(3-(5-(2,2-difluorobenzo[d][1,3]dioxol-5-yl)-1H-1,2,3-triazol-1-yl)-3'-fluoro-4'-(hydroxymethyl)-5'-(methylsulfonyl)-[1,1'-biphenyl]-4-yl)-1-methyl-1H-pyrazol-3-yl)-2,2-difluoroethanol | |

Scheme 2.

(a) 25% NaOMe in MeOH, dimethyl oxalate, MeOH, 45° C.; (b) MeNHNH$_2$, EtOH, 90° C.; (c) PdCl$_2$(dppf), K$_2$CO$_3$, DME, H$_2$O, reflux; (d) 2.0M NaOH$_{(aq)}$, MeOH, 45° C.; (e) R$^5$R$^6$NH, EDCI, HOBt, DCM, rt.

In general, pyrazole compounds of formula 2-06 can be prepared by the following methodology in Scheme 2. The alkyl ketone (1-04) can be heated with sodium methoxide and dimethyl oxalate to give the diketoester (2-01). Reaction of the diketone (2-01) with methyl hydrazine gives a majority of the desired pyrazole isomer (2-02) and a minor pyrazole isomer (2-03), and the isomers can be separated by column chromatography if necessary. A palladium mediate coupling with 2-02 and an appropriate boronic acid or boronate affords 2-04, which is hydrolyzed to the acid 2-05. Coupling of 2-05 to an appropriate amine provides compounds of formula 2-06.

Example 37

N-(1-cyano-1-methylethyl)-1-methyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide

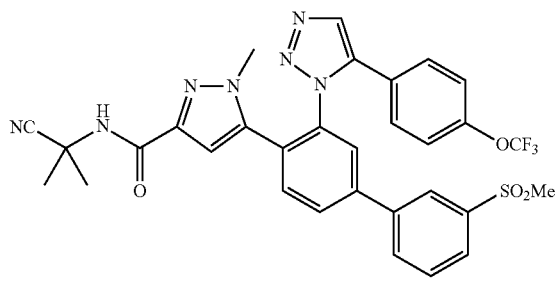 [SMILES: Cn1nc(C(=O)NC(C)(C)C#N)cc1-c1ccc(-c2cccc(S(C)(=O)=O)c2)cc1-n1nncc1-c1ccc(OC(F)(F)F)cc1]

Example 37a

Preparation of methyl 2-azido-4-bromobenzoate

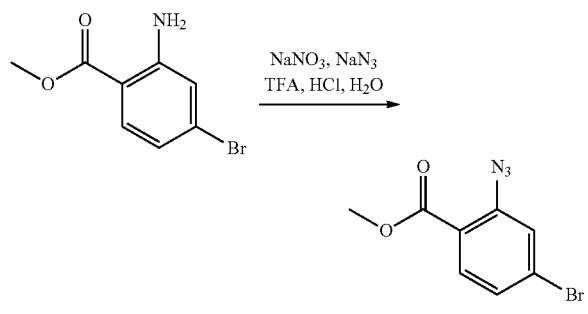

Methyl 2-amino-4-bromobenzoate (15 g, 65 mmol) in trifluoroacetic acid (75 mL) and concentrated HCl (15 mL) was cooled in an ice water bath. To it sodium nitrite (9.0 g, 130 mmol) in water (15 mL) was added via addition funnel over 15 min. The reaction stirred at 0° C. for 30 min. Then sodium azide (13 g, 196 mmol) was slowly added portionwise. The reaction was stirred at 0° C. to rt for 1.5 hrs. The solvents were removed and H$_2$O and EtOAc were added. The layers were separated and the organic layer was washed with saturated NaHCO$_3$ three times and dried over Na$_2$SO$_4$. The solvent was removed and the crude material was purified by chromatography thru a SiO$_2$ using a solvent gradient of 100% Hx to 20% EtOAc/Hx to afford the title compound (16 g, 61 mmol, 95%). $^1$H NMR (400 MHz, CDCl$_3$) δ ppm 7.74 (d, J=8.4 Hz, 1H), 7.38 (d, J=1.8 Hz, 1H), 7.34-7.29 (m, 1H), 3.90 (s, 3H).

Example 37b

Preparation of methyl 4-bromo-2-(5-(4-(trifluoromethoxy)phenyl)-1H-1,2,3-triazol-1-yl)benzoate

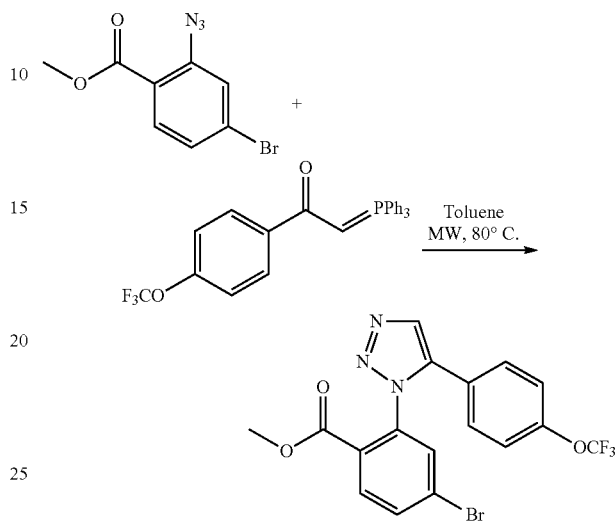

Example 37a (16 g, 62 mmol) and Example 1c (29 g, 62 mmol) in anhydrous toluene (100 mL). The mixture was heated at 80° C. by microwave for 1 hour. The solvent was removed and the crude mixture was purified by chromatography thru a SiO$_2$ column using a solvent gradient of 100% Hx to 20% EtOAc/Hx to afford the title compound (26 g, 59 mmol 95%). MS (ESI) 442, 444 [M+H]+. $^1$H NMR (400 MHz, CDCl$_3$) δ ppm 7.93-7.85 (m, 2H), 7.76 (dd, J=8.4, 1.9 Hz, 1H), 7.58 (d, J=1.9 Hz, 1H), 7.27-7.23 (m, 3H), 7.21-7.14 (m, 2H), 3.62 (s, 3H).

Example 37c

Preparation of 1-(4-bromo-2-(5-(4-(trifluoromethoxy)phenyl)-1H-1,2,3-triazol-1-yl)phenyl)ethanone

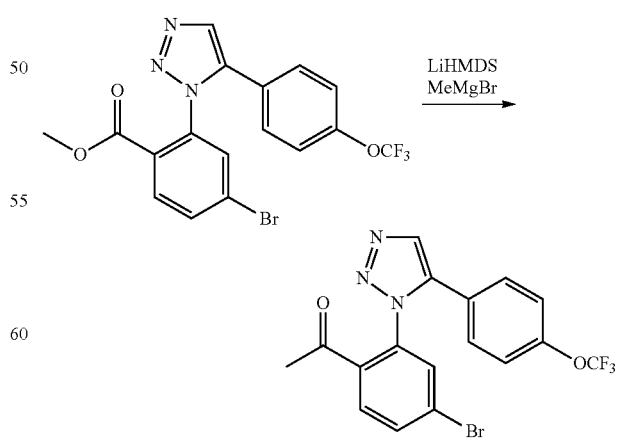

Example 37b (13 g, 28 mmol) in anhydrous THF (100 mL) was cooled to −78° C. To this a solution of lithium bis(trimethylsilyl)amide (140 mL of 1.0 M solution in THF, 140 mmol) was added dropwise via addition funnel. After the addition, methyl magnesium bromide (28 mL of 3.0 M solution in ether, 85 mmol) was added. The reaction mixture was stirred at −78° C. to 0° C. over 4 hrs and then quenched with 3.0 M HCl$_{(aq)}$ solution and extracted with EtOAc. The organic layer dried over Na$_2$SO$_4$ and the solvent removed. The crude material was purified by chromatography thru a SiO$_2$ column using a solvent gradient of 100% Hx to 30% EtOAc/Hx to afford the title compound (10 g, 24 mmol, 86%). MS (ESI) 426, 428 [M+H]+. $^1$H NMR (400 MHz, CDCl$_3$) δ ppm 7.89 (s, 1H), 7.76 (dd, J=8.3, 1.9 Hz, 1H), 7.64 (d, J=8.3 Hz, 1H), 7.53 (d, J=1.9 Hz, 1H), 7.28-7.24 (m, 2H), 7.20 (d, J=9.0 Hz, 2H), 2.17 (s, 3H).

Example 37d

Preparation of methyl 4-(4-bromo-2-(5-(4-(trifluoromethoxy)phenyl)-1H-1,2,3-triazol-1-yl)phenyl)-2,4-dioxobutanoate

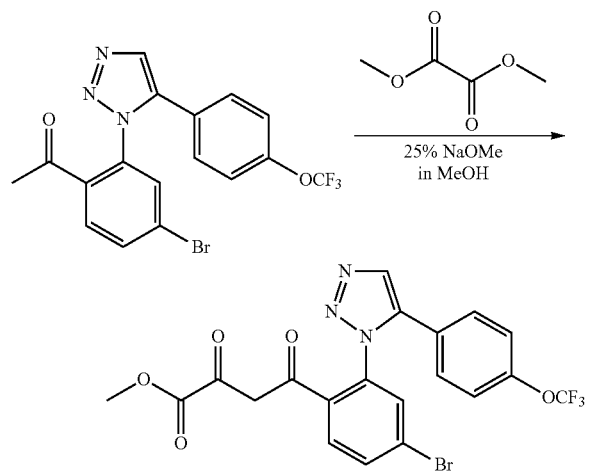

Example 37c (10 g, 24 mmol) and dimethyl oxalate (3.1 g, 26 mmol) was sonicated in MeOH (200 mL). To this mixture 25% NaOMe in MeOH (25 mL) was added via syringe over 10 min and heated at 45° C. for 16 hrs. The solution was acidified to pH 3 with 3.0 M HCl$_{(aq)}$ solution and the MeOH was removed in vacou. The aqueous solution was extracted with EtOAc and the organic layer was dried over Na$_2$SO$_4$. The solvent removed and the crude material was purified by chromatography thru a SiO$_2$ column using a solvent gradient of 100% Hx to 100% EtOAc to afford the title compound (6.7 g, 13 mmol, 55%). MS (ESI) 512 [M+H]+. $^1$H NMR (400 MHz, CDCl$_3$) δ ppm 13.88 (s, 1H), 7.87 (s, 1H), 7.80 (dd, J=8.3, 1.8 Hz, 1H), 7.76 (d, J=1.8 Hz, 1H), 7.61 (d, J=8.3 Hz, 1H), 7.17 (s, 4H), 6.13 (s, 1H), 3.88 (d, J=5.2 Hz, 3H).

Example 37e

Preparation of methyl 5-(4-bromo-2-(5-(4-(trifluoromethoxy)phenyl)-1H-1,2,3-triazol-1-yl)phenyl)-1-methyl-1H-pyrazole-3-carboxylate

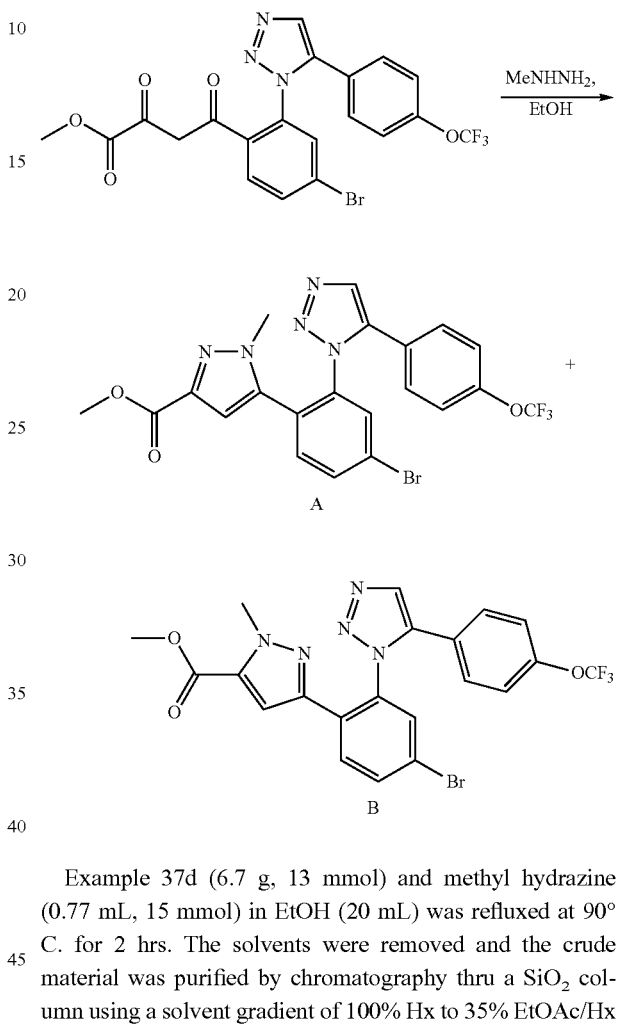

Example 37d (6.7 g, 13 mmol) and methyl hydrazine (0.77 mL, 15 mmol) in EtOH (20 mL) was refluxed at 90° C. for 2 hrs. The solvents were removed and the crude material was purified by chromatography thru a SiO$_2$ column using a solvent gradient of 100% Hx to 35% EtOAc/Hx to separate the two isomers. Then it was repurified by chromatography thru a SiO$_2$ column using a solvent gradient of 100% Hx to 40% EtOAc/Hx to afford isomer A, the title compound (2.4 g, 4.7 mmol, 36%). MS (ESI) 522, 524 [M+H]+. $^1$H NMR (400 MHz, CDCl$_3$) δ ppm 7.75 (s, 1H), 7.73-7.65 (m, 2H), 7.34 (d, J=8.7 Hz, 2H), 7.27 (s, 1H), 7.19 (d, J=8.4 Hz, 2H), 4.80 (s, 1H), 3.71 (s, 3H), 2.99 (s, 3H). The other isomer B was repurified by chromatography thru a SiO$_2$ column using a solvent gradient of 100% Hx to 20% EtOAc/Hx to afford methyl 3-(4-bromo-2-(5-(4-(trifluoromethoxy)phenyl)-1H-1,2,3-triazol-1-yl)phenyl)-1-methyl-1H-pyrazole-5-carboxylate (0.82 g, 1.6 mmol, 12%). MS (ESI) 522, 524 [M+H]+. $^1$H NMR (400 MHz, CDCl$_3$) δ 7.87 (s, 1H), 7.73 (d, J=2.0 Hz, 2H), 7.66 (d, J=1.6 Hz, 1H), 7.07 (d, J=8.3 Hz, 2H), 7.01 (d, J=8.8 Hz, 2H), 5.94 (s, 1H), 4.01 (s, J=4.2 Hz, 3H), 3.82 (s, 3H).

Example 37f

Preparation of methyl 1-methyl-5-(3'-(methylsulfonyl)-3-(5-(4-(trifluoromethoxy)phenyl)-1H-1,2,3-triazol-1-yl)biphenyl-4-yl)-1H-pyrazole-3-carboxylate

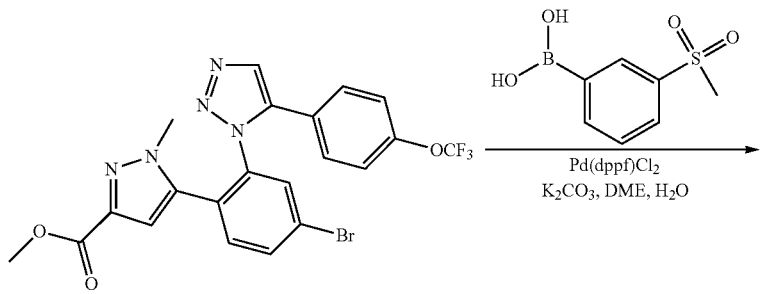

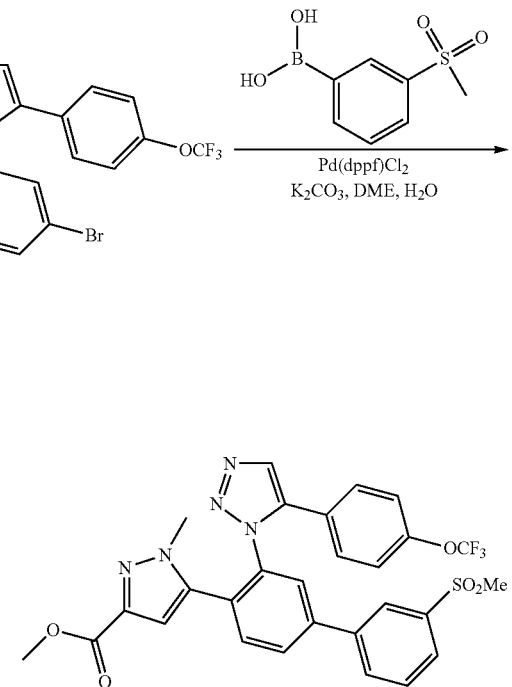

Example 37e (1.7 g, 3.3 mmol), 3-methylsulfonylphenyl boronic acid (0.75 g, 3.7 mmol), and Pd(dppf)Cl$_2$ (0.19 g, 0.33 mmol) were brought up in DME (10 mL). A 3.5 M K$_2$CO$_{3(aq)}$ solution (3.0 mL, 1.4 g, 11 mmol) was added to the reaction solution and the mixture was refluxed for 2 hrs, then cooled to rt. Charcoal was added and the mixture was stirred at rt, filtered through a pad of celite and the layers separated. The organic layer was dried over Na$_2$SO$_4$ and the solvent removed. The crude material was purified by chromatography thru a SiO$_2$ column using a solvent gradient of 100% DCM to 35% EtOAc/Hx to afford the title compound (0.96 g, 1.6 mmol, 51%). MS (ESI) 598 [M+H]+. $^1$H NMR (400 MHz, CDCl$_3$) δ ppm 8.31 (s, 1H), 8.14 (d, J=1.8 Hz, 1H), 8.08-8.00 (m, 2H), 7.96-7.91 (m, 1H), 7.80-7.73 (m, 2H), 7.49 (d, J=8.0 Hz, 1H), 7.12 (d, J=8.7 Hz, 2H), 6.89 (d, J=8.7 Hz, 2H), 5.93 (d, J=0.9 Hz, 1H), 3.89 (s, 3H), 3.20 (s, 3H), 3.16 (s, 3H).

Example 37g

Preparation of 1-methyl-5-(3'-(methylsulfonyl)-3-(5-(4-(trifluoromethoxy)phenyl)-1H-1,2,3-triazol-1-yl)biphenyl-4-yl)-1H-pyrazole-3-carboxylic acid

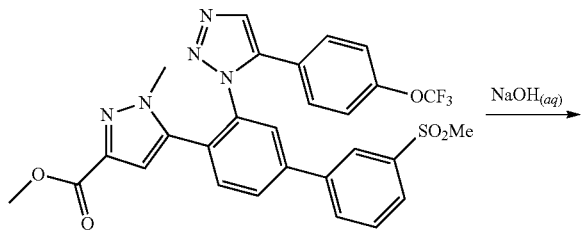

-continued

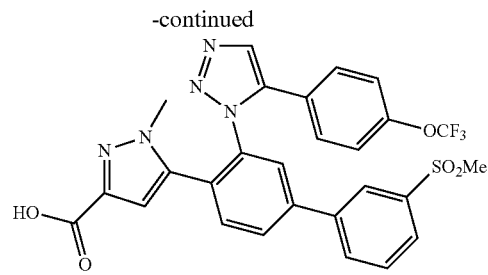

To Example 37f (960 mg, 1.6 mmol) in MeOH (10 mL) was added a 2.0 M NaOH$_{(aq)}$ solution (3.0 mL) and the mixture was heated at 45° C. for 4 hrs. The solvent was removed and the crude was acidified with 3.0 M HCl$_{(aq)}$ solution and extracted with DCM. The organic layer was dried over Na$_2$SO$_4$ and concentrated to afford the title compound (870 mg, 1.5 mmol, 93%). MS (ESI) 584 [M+H]+. $^1$H NMR (400 MHz, CDCl$_3$) δ ppm 8.31 (s, 1H), 8.15 (s, 1H), 8.05 (dd, J=13.7, 7.8 Hz, 2H), 7.95 (d, J=8.1 Hz, 1H), 7.82-7.74 (m, 2H), 7.51 (d, J=8.0 Hz, 1H), 7.15 (d, J=8.2 Hz, 2H), 6.92 (d, J=8.3 Hz, 2H), 6.00 (s, 1H), 3.24 (s, 3H), 3.16 (s, 3H).

Example 37

Preparation of N-(1-cyano-1-methylethyl)-1-methyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide

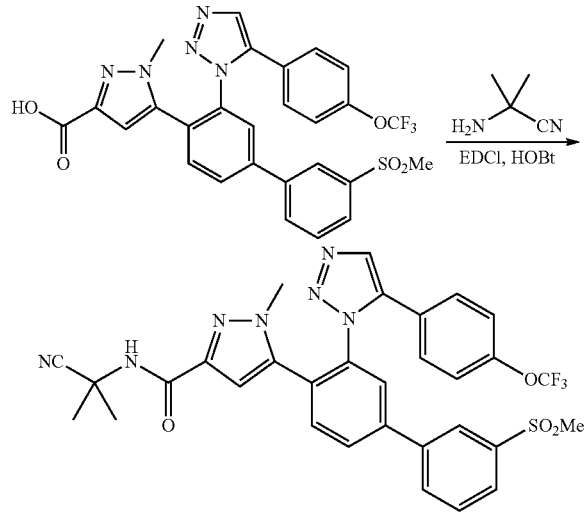

To a vial was added Example 37g (340 mg, 0.58 mmol), EDCI (170 mg, 0.87 mmol), HOBt hydrate (120 mg, 0.87 mmol), and DCM (2.0 mL). The mixture was stirred at rt for 1 hr and 2-amino-2-methyl propionitrile (98 mg, 1.2 mmol) was added. The reaction mixture was stirred at rt overnight. The next day the mixture was washed with $H_2O$ and dried over $Na_2SO_4$. The solvent was removed and the crude material was purified by chromatography thru a $SiO_2$ column using a solvent gradient of 100% Hx to 75% EtOAc/Hx to afford the title compound (164 mg, 25 mmol, 43%). MS (ESI) 650 [M+H]+. $^1$H NMR (400 MHz, CDCl$_3$) δ ppm 8.26 (s, 1H), 8.03 (dd, J=11.5, 4.9 Hz, 2H), 8.00-7.89 (m, 2H), 7.76 (dd, J=12.7, 4.7 Hz, 2H), 7.49 (d, J=8.0 Hz, 1H), 7.15 (d, J=8.1 Hz, 2H), 6.96 (d, J=8.8 Hz, 2H), 6.77 (s, 1H), 6.03 (s, 1H), 3.28 (s, 3H), 3.14 (s, 3H), 1.81 (s, 6H).

The following compounds were prepared in a manner similar to that described in the previous experimental procedures:

| Ex # | Structure | Name | Molecular Ion |
|---|---|---|---|
| 38 | 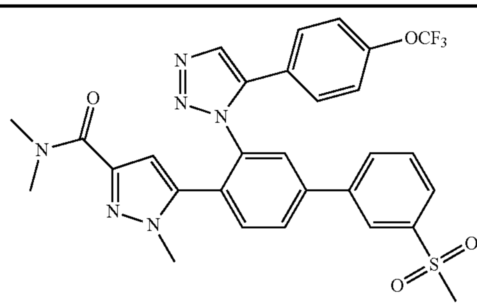 | N,N,1-trimethyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide | MS (ESI) 611 [M + H]+ |
| 39 | 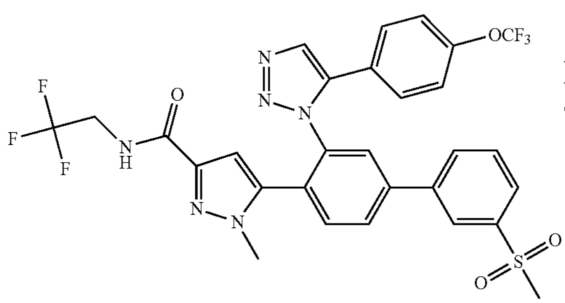 [SMILES: Cn1nc(C(=O)NCC(F)(F)F)cc1-c1ccc(-c2cccc(S(C)(=O)=O)c2)cc1-n1nncc1-c1ccc(OC(F)(F)F)cc1] | 1-methyl-5-[3'-(methylsulfonyl)-3-(5-{4-[(trifluoromethyl)oxy]phenyl}-1H-1,2,3-triazol-1-yl)biphenyl-4-yl]-N-(2,2,2-trifluoroethyl)-1H-pyrazole-3-carboxamide | MS (ESI) 665 [M + H]+ |
| 40 | 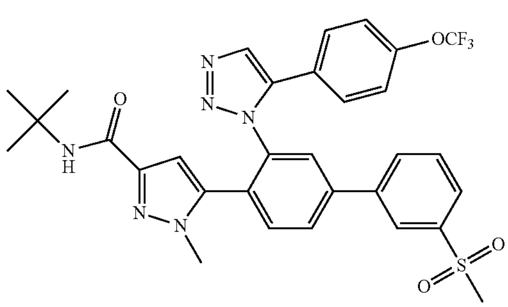 [SMILES: Cn1nc(C(=O)NC(C)(C)C)cc1-c1ccc(-c2cccc(S(C)(=O)=O)c2)cc1-n1nncc1-c1ccc(OC(F)(F)F)cc1] | N-(1,1-dimethylethyl)-1-methyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide | MS(ESI) 639 [M + H]+ |

Scheme 3.

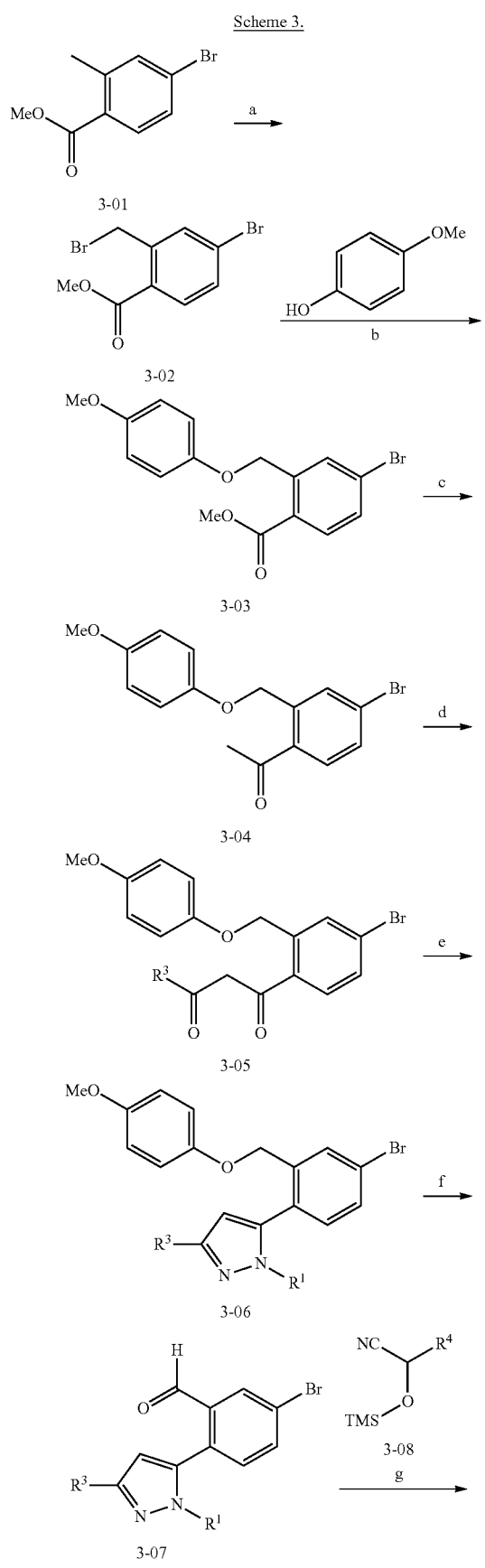

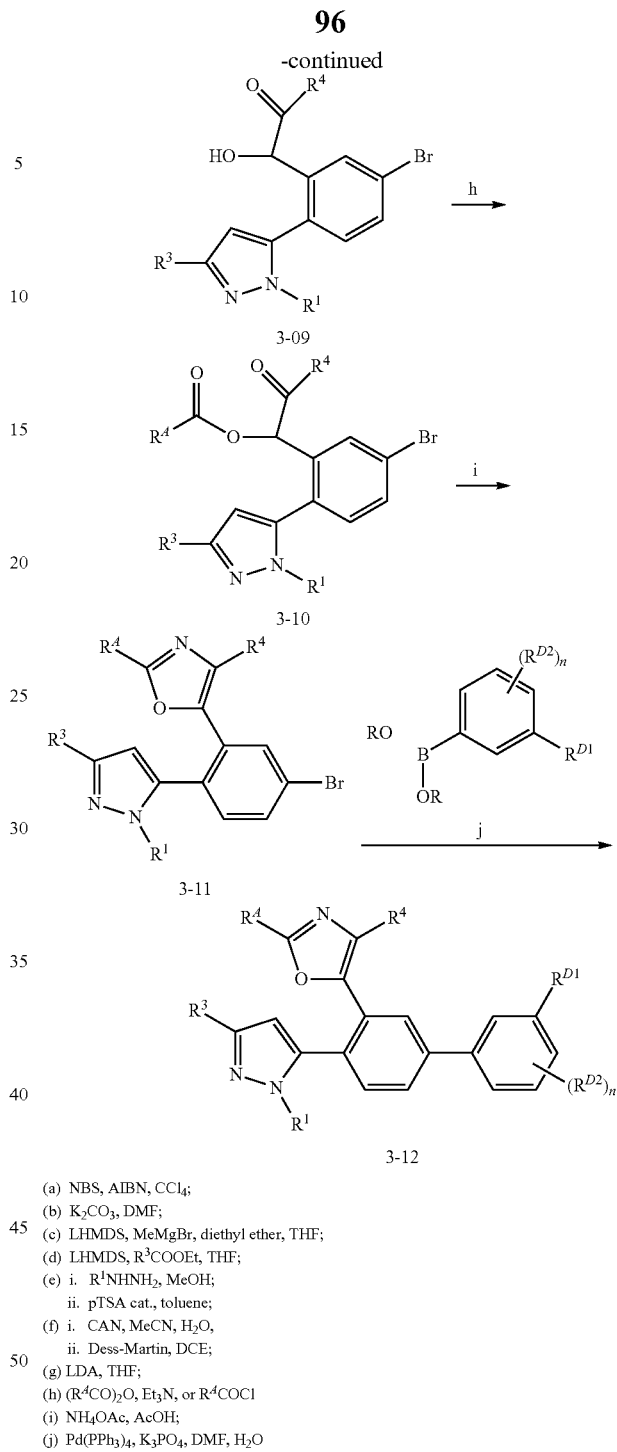

(a) NBS, AIBN, CCl₄;
(b) K₂CO₃, DMF;
(c) LHMDS, MeMgBr, diethyl ether, THF;
(d) LHMDS, R³COOEt, THF;
(e) i. R¹NHNH₂, MeOH;
   ii. pTSA cat., toluene;
(f) i. CAN, MeCN, H₂O,
   ii. Dess-Martin, DCE;
(g) LDA, THF;
(h) (R⁴CO)₂O, Et₃N, or R⁴COCl
(i) NH₄OAc, AcOH;
(j) Pd(PPh₃)₄, K₃PO₄, DMF, H₂O Specific compounds in the invention contain an oxazole as represented by general structure 3-12. In general, the oxazole compounds of formula 3-12 can be synthesized following the methodology shown in Scheme 3. The methyl 4-bromo-2-methylbenzoate (3-01) is converted to the benzylic bromide (3-02) by reaction with NBS and AIBN in CCl₄. The benzylic bromide (3-02) is displaced by 4-methoxyphenol under basic conditions to yield the biaryl ether compound, (3-03). The methyl ester (3-03) is transformed to the methyl ketone (3-04) by reaction with LHMDS and MeMgBr. Other alkyl functionality can be incorporated at this position by introduction of an appropriate Grignard reagent such as EtMgBr. The ketone (3-04) is reacted with a substituted ester (R³COOR) to provide the diketone (3-05). The diketone undergoes cyclization with a hydrazine to form the pyrazole (3-06). The alcohol protecting group is removed upon treatment with CAN, and the resulting alcohol is oxidized to the aldehyde (3-07) with Dess-Martin periodinane. The aldehyde (3-07) is reacted with the substituted aryl-2-(trimethylsilyloxy)acetonitrile (3-08) after deprotonation with LDA to afford the α-hydroxyketone (3-09). The substituted phenyl-2-(trimethylsilyloxy)acetonitrile (3-08) can be prepared by reacting an appropriate aldehyde with trimethylsilyl cyanide in the presence of catalytic zinc iodide. Acylation of 3-09 with an appropriate acyl chloride or anhydride in the presence of triethylamine provides the ester (3-10). Cyclization of 3-10 is then accomplished with ammonium acetate in acetic acid to afford the oxazole (3-11). The final compounds represented by the structure 3-12 are then obtained by subjecting 3-11 to a palladium-mediated coupling reaction with the appropriate phenyl boronate, and an example set of conditions is given in Scheme 3.

Additional chemistry known to one skilled in the art can be carried out at the R³ position including reductions, Grignard additions, alkylations, fluorinations, acylations, amidations, and heterocycle forming reactions to prepare compounds of the invention. For example, when R³ contains an ester (e.g. CF₂COOEt or COOEt) additional functionalization can be carried out by one skilled in the art to make amides as well as primary, secondary and tertiary alcohols. Several examples of these transformations are described in the Examples below.

Example 45

2-(5-(3-(4-(2,2-difluorobenzo[d][1,3]dioxol-5-yl)-2-methyloxazol-5-yl)-3'-fluoro-5'-(methylsulfonyl)biphenyl-4-yl)-1-methyl-1H-pyrazol-3-yl)-2,2-difluoroacetamide

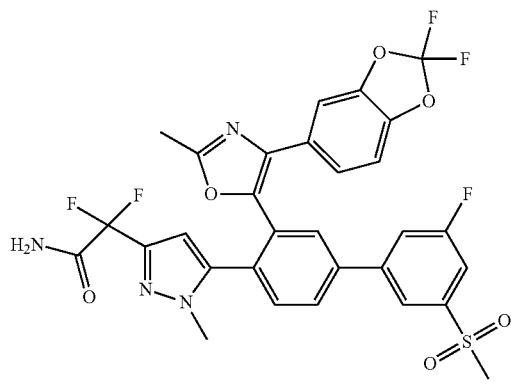 [SMILES: Cc1nc(-c2ccc3c(c2)OC(F)(F)O3)c(-c2cc(-c3cc(F)cc(S(C)(=O)=O)c3)ccc2-c2cc(C(F)(F)C(N)=O)nn2C)o1]

Example 45a

Preparation of 2-(2,2-difluorobenzo[d][1,3]dioxol-5-yl)-2-(trimethylsilyloxy)acetonitrile

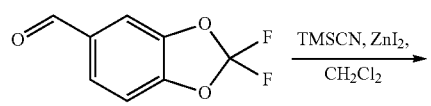

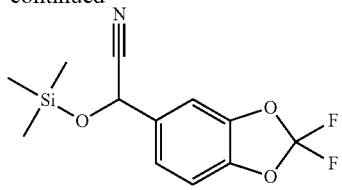

2,2-difluorobenzo[d][1,3]dioxole-5-carbaldehyde (1.0 g, 5.4 mmol) in anhydrous DCM (25 mL) was cooled to 10-15° C., and then ZnI₂ (0.051 g, 0.16 mmol) was added and the reaction mixture was stirred for 2-3 min. TMSCN (0.64 g, 6.5 mmol) was added to the reaction solution and the mixture was stirred at rt for 1 hour. The reaction solution was diluted with DCM (50 mL) and water (50 mL) and the layers were separated. The organic extracts were washed with aq NaCl (50 mL), dried over Na₂SO₄, filtered and concentrated in vacuo to give the title compound as an pale brown liquid, (2.3 g, 8.1 mmol, 75% yield). ¹HNMR (400 MHz, CDCl₃): δ ppm 7.25 (d, 1H, J=11.2 Hz), 7.20 (d, 1H, J=8.4 Hz), 7.10 (d, 1H, J=8.4 Hz) 5.46 (s, 1H), 0.26 (s, 9H).

Example 45b

Preparation of methyl 2-(5-(4-bromo-2-formylphenyl)-1-methyl-1H-pyrazol-3-yl)-2,2-difluoroacetate

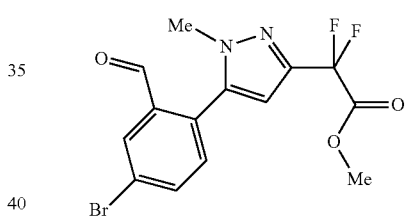

Example 45b was prepared from Example 53c and dimethyl 2,2-difluoromalonate using procedures similar to that described in Example 54a-b, and Example 53f. ¹H NMR (400 MHz, CDCl₃) δ ppm 9.81 (s, 1H), 8.16 (s, 1H), 7.83 (m, 1H), 7.30 (d, 1H, J=8 Hz), 6.60 (s, 1H), 3.94 (s, 3H), 3.71 (s, 3H).

Example 45c

Preparation of methyl 2-(5-(4-bromo-2-(2-(2,2-difluorobenzo[d][1,3]dioxol-5-yl)-1-hydroxy-2-oxoethyl)phenyl)-1-methyl-1H-pyrazol-3-yl)-2,2-difluoroacetate

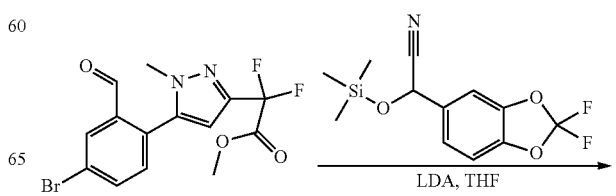

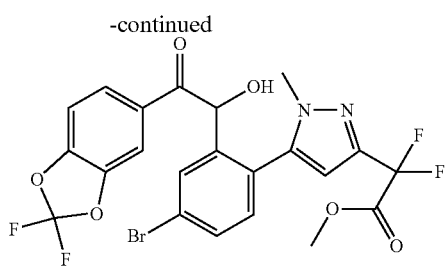

A solution of Example 45a (2.3 g, 8.1 mmol) in anhydrous THF (25 mL) was cooled to −78° C., and then lithium diisopropylamide (0.86 g, 8.1 mmol) was added dropwise over 3 min. The reaction mixture was stirred for 20 min, then a solution of Example 45b (3.2 g, 8.5 mmol) in dry THF (10 mL) was added dropwise at −78° C. The reaction was maintained at −78° C. for 5-10 min and then allowed warm to rt over 1 hr. The reaction mixture was quenched with a saturated ammonium chloride solution, and then most of the THF was removed under reduced pressure. Water (50 mL) was added to the crude slurry and the solution was brought to pH 6-7, then extracted with EtOAc (2×50 mL). The organic extracts were washed with aq NaCl (50 mL), dried over Na$_2$SO$_4$, filtered and concentrated in vacuo to give the crude compound as a brown solid, which was taken forward without purification (4.5 g, 8.1 mmol). MS (ESI) 559.0 [M+H]+.

Example 45d

Preparation of methyl 2-(5-(2-(1-acetoxy-2-(2,2-difluorobenzo[d][1,3]dioxol-5-yl)-2-oxoethyl)-4-bromophenyl)-1-methyl-1H-pyrazol-3-yl)-2,2-difluoroacetate

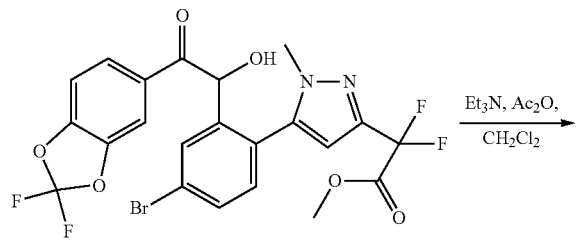

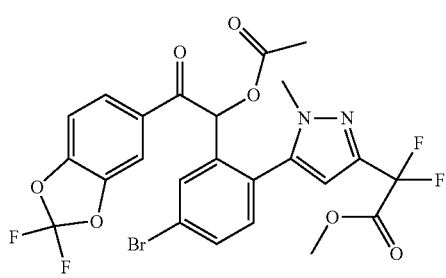

Ac$_2$O (1.1 g, 11 mmol) was added to a cooled (10° C.) solution of Example 45c (4.5 g, 8.1 mmol) and Et$_3$N (2.0 g, 20 mmol) in DCM (35 mL). The reaction mixture was allowed to stir at rt for 18 hrs. The solvents were removed in vacuo to give the crude compound as a brown solid, which was taken forward without purification (5.0 g, 8.3 mmol). MS (ESI) 601.0 [M+H]+.

Example 45e

Preparation of 2-(5-(4-bromo-2-(4-(2,2-difluorobenzo[d][1,3]dioxol-5-yl)-2-methyloxazol-5-yl)phenyl)-1-methyl-1H-pyrazol-3-yl)-2,2-difluoroacetic acid

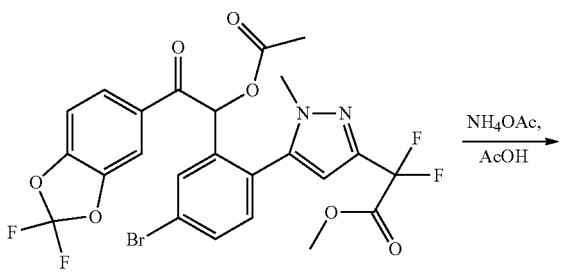

Ammonium acetate (0.30 g, 3.8 mmol) was added to a solution of Example 45d (5.0 g, 8.3 mmol) in glacial AcOH (40 mL) and the reaction mixture was heated at 115° C. for 18 hrs. After being cooled to rt, the solvents were removed in vacuo to give the crude product. The crude residue was purified by chromatography thru a SiO$_2$ column using the mobile phase of 10% MeOH in chloroform to afford the title compound as a brown solid, (6.0 g, 7.1 mmol, 85% yield over 3 steps). MS (ESI) 568.0 [M+H]+.

Example 45f

Preparation of 2-(5-(3-(4-(2,2-difluorobenzo[d][1,3]dioxol-5-yl)-2-methyloxazol-5-yl)-3'-fluoro-5'-(methylsulfonyl)biphenyl-4-yl)-1-methyl-1H-pyrazol-3-yl)-2,2-difluoroacetic acid

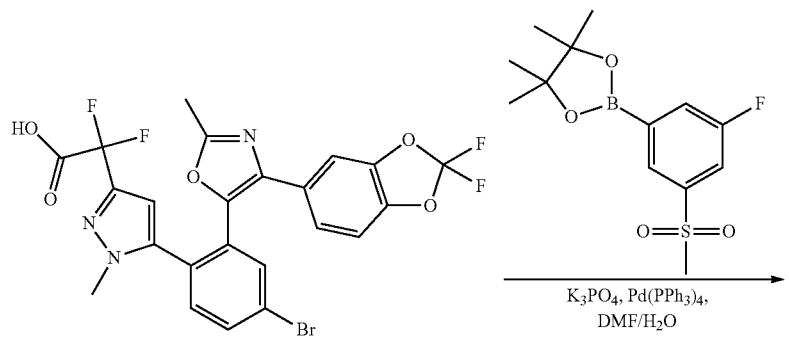

In a dry two neck round bottom flask, Example 45e (0.20 g, 0.35 mmol), 2-2-(3-fluoro-5-(methylsulfonyl)phenyl)-4,4,5,5-tetramethyl-1,3,2-dioxaborolane (0.11 g, 0.35 mmol), and K$_3$PO$_4$ (0.075 g, 0.35 mmol) were brought into solution with DMF (5.0 mL) and water (1.0 mL). The reaction flask was purged with nitrogen for 5-10 min before Pd(PPh$_3$)$_4$ (0.41 g, 0.35 mmol) was added, and then the mixture was heated at 80° C. for 18 hrs. The reaction mixture was cooled to rt and concentrated under reduced pressure. The crude mixture was diluted with DCM (50 mL) and washed with water (2×20 mL). The organic extracts were washed with aq NaCl (20 mL), dried over Na$_2$SO$_4$, filtered into a flask and concentrated in vacuo to afford the crude compound as a brown solid, which was taken forward without purification (0.20 g, 0.076 mmol, 21% yield). MS (ESI) 661.8 [M+H]+.

Example 45

Preparation of 2-(5-(3-(4-(2,2-difluorobenzo[d][1,3]dioxol-5-yl)-2-methyloxazol-5-yl)-3'-fluoro-5'-(methylsulfonyl)biphenyl-4-yl)-1-methyl-1H-pyrazol-3-yl)-2,2-difluoroacetamide

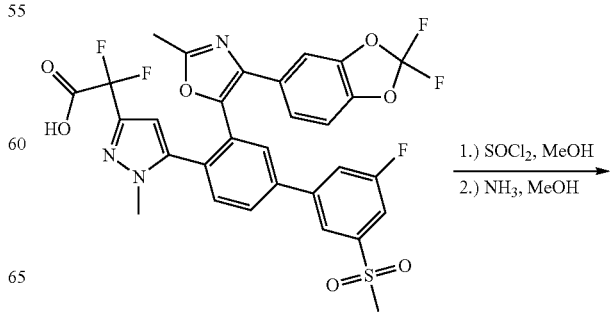

-continued

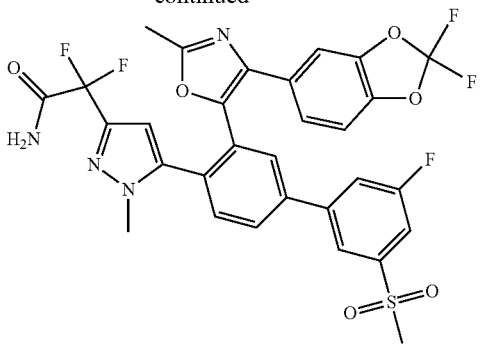

Sulfurous dichloride (0.020 g, 0.17 mmol) was added dropwise to a cooled solution (0-10° C.) of Example 45f (0.10 g, 0.15 mmol) in MeOH (3.5 mL). The reaction solution was stirred for 2 hr at rt. The solvents were removed in vacuo to afford the crude methyl 2-(5-(3-(4-(2,2-difluorobenzo[d][1,3]dioxol-5-yl)-2-methyloxazol-5-yl)-3'-fluoro-5'-(methylsulfonyl)-[1,1'-biphenyl]-4-yl)-1-methyl-1H-pyrazol-3-yl)-2,2-difluoroacetate (0.10 g, 0.15 mmol), which was dissolved in methanolic ammonia (30%, 3.0 mL) and heated at 55° C. for 3 hrs. The reaction mixture was cooled to rt and concentrated under reduced pressure. The crude mixture was diluted with EtOAc (20 mL) and washed with H$_2$O (20 mL), then 1N HCl (10 mL). The organic extracts were washed with aq NaCl (20 mL), dried over Na$_2$SO$_4$, filtered into a flask and concentrated in vacuo to give the crude product. The crude product was purified by preparative HPLC purification (Xbridge phenyl (150×19 m), 5 t; Mobile phase A: 0.05% TFA in water; Mobile phase B: 100% CH$_3$CN; Flow: 14.0 mL/min (0-100%), RT=12.18 min) to afford the title compound as an off-white solid, (18 mg, 0.025 mmol, 17% yield). MS (ESI) 660.8 [M+H]+. $^1$HNMR (400 MHz, CD$_3$OD): δ ppm 8.02-8.12 (m, 2H), 8.01 (dd, 1H, J=4 Hz, J=9.2 Hz), 7.90 (dt, 1H, J=4 Hz, J=8.4 Hz), 7.81 (dt, 1H, J=3.6 Hz, J=7.6 Hz), 7.67 (d, 1H, J=4 Hz), 7.04-7.13 (m, 3H), 6.15 (s, 1H), 3.49 (s, 3H), 3.25 (s, 3H), 2.53 (s, 3H).

Example 46

2-(5-(3-(2-cyclopropyl-4-(2,2-difluorobenzo[d][1,3]dioxol-5-yl)oxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide

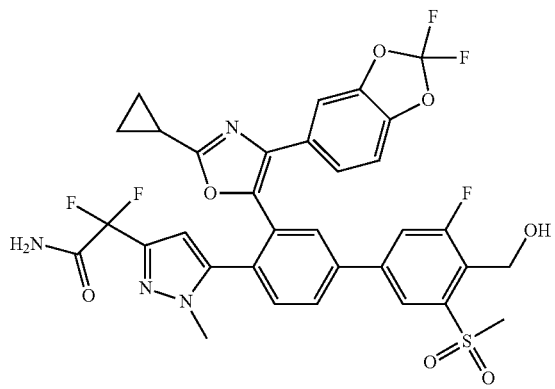 [SMILES: Cn1nc(C(F)(F)C(N)=O)cc1-c1ccc(-c2cc(F)c(CO)c(S(C)(=O)=O)c2)cc1-c1oc(C2CC2)nc1-c1ccc2c(c1)OC(F)(F)O2]

Example 46a

Preparation of 1-(5-bromo-2-(3-(1,1-difluoro-2-methoxy-2-oxoethyl)-1-methyl-1H-pyrazol-5-yl)phenyl)-2-(2,2-difluorobenzo[d][1,3]dioxol-5-yl)-2-oxoethyl cyclopropanecarboxylate

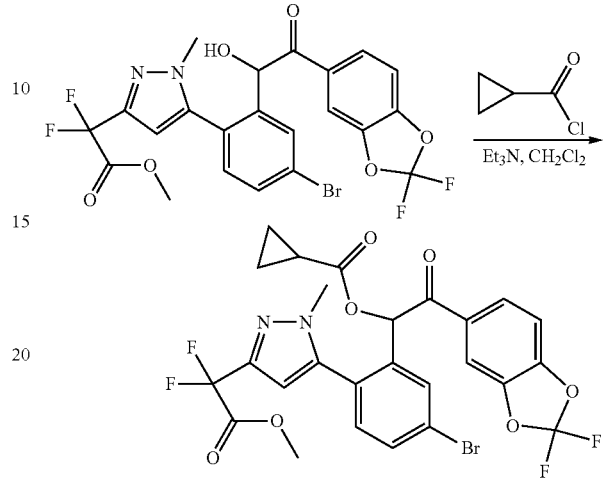

Cyclopropanecarbonyl chloride (0.34 g, 3.2 mmol) was added to a cooled (10° C.) solution of Example 45c (1.8 g, 3.2 mmol) and Et$_3$N (0.45 mL, 3.2 mmol) in DCM (15 mL). The reaction mixture was stirred at rt for 18 hrs. The solvents were removed in vacuo. The crude residue was diluted with EtOAc (20 mL) and washed with water (20 mL), and aq NaCl (20 mL). The organics layer was dried over Na$_2$SO$_4$, filtered into a flask, and concentrated in vacuo to give the crude compound as a brown solid, which was taken forward without purification (2.0 g, 0.83 mmol). MS (ESI) 628.6 [M+H]+.

Example 46 was prepared from Example 46a using procedures similar to that described in Example 45. MS (ESI) 717.2 [M+H]$^+$. 1H NMR (400 MHz, MeOH-d$_4$) δ ppm 8.14 (s, 1H), 8.01 (d, 1H, J=2.01 Hz), 7.97 (dd, 1H, J=8.16, 1.88 Hz), 7.88 (dd, 1H, J=10.54, 2.01 Hz), 7.67 (d, 1H, J=8.03 Hz), 7.20 (s, 1H), 7.15-7.17 (m, 2H), 6.25 (s, 1H), 5.14 (s, 2H), 3.54 (s, 3H), 3.39 (s, 3H), 2.09-2.17 (m, 1H), 1.08-1.15 (m, 2H), 0.98-1.03 (m, 2H).

Example 47

2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetonitrile

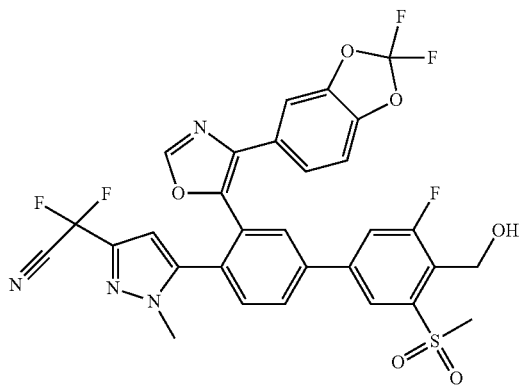 [SMILES: Cn1nc(C(F)(F)C#N)cc1-c1ccc(-c2cc(F)c(CO)c(S(C)(=O)=O)c2)cc1-c1ocnc1-c1ccc2c(c1)OC(F)(F)O2]

Example 47

Preparation of 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetonitrile

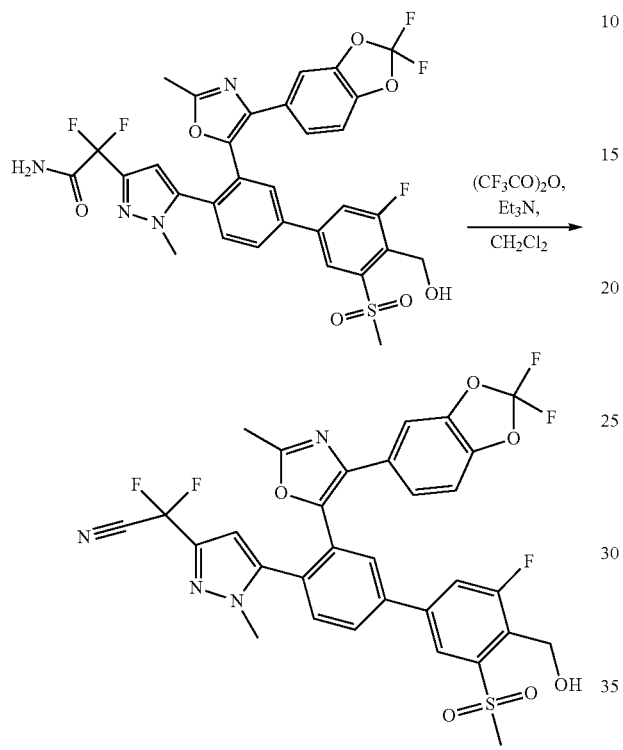

2,2,2-trifluoroacetic anhydride (67 mg, 0.32 mmol) was added to a cooled (0° C.) solution of 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoroacetamide (55 mg, 0.080 mmol, prepared by methods described in previous Examples) in dry DCM (3.5 mL). After the reaction mixture was stirred for 2 min, Et$_3$N (0.050 mL, 0.36 mmol) was added and the reaction mixture was stirred at rt for 4 hrs. The reaction mixture was concentrated in vacuo. The crude mixture was diluted with EtOAc (20 mL) and washed with water (20 mL), then aq NaCl (20 mL), dried over Na$_2$SO$_4$, filtered into a round bottom flask and concentrated in vacuo to give crude product. The crude product was purified by preparative HPLC purification (Symmetry shield (250×19 m), 5 t; Mobile phase A: 10 mM NH$_4$OAc; Mobile phase B: 100% CH$_3$CN; Flow: 17.0 mL/min (0-100%), RT=11.057 min) to afford the title compound as a white solid, (9.5 mg, 0.013 mmol, 17% yield). MS (ESI) 673.0 [M+H]$^+$. $^1$HNMR (400 MHz, CD$_3$OD): δ ppm 8.22 (s, 1H), 8.13 (d, 1H, J=2 Hz), 8.03 (dd, 1H, J=2 Hz, J=8 Hz), 7.95 (dd, 1H, J=1.6 Hz, J=10.4 Hz), 7.67 (d, 1H, J=8 Hz), 7.01-7.12 (m, 3H), 6.23 (s, 1H), 5.15 (d, 2H, J=1.6 Hz), 3.51 (s, 3H), 3.40 (s, 3H), 2.55 (s, 3H).

Example 48

1,1-difluoro-2-methyl-1-(1-methyl-5-(3-(2-methyl-4-(4-(trifluoromethoxy)phenyl)oxazol-5-yl)-3'-(methylsulfonyl)biphenyl-4-yl)-1H-pyrazol-3-yl)propan-2-ol

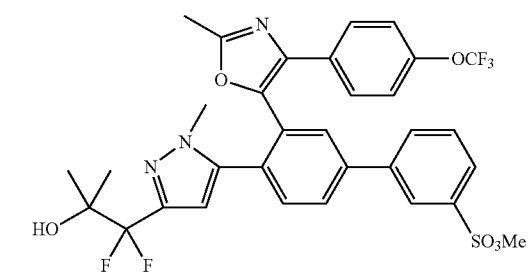

Example 48a

Preparation of methyl 2,2-difluoro-2-(1-methyl-5-(3-(2-methyl-4-(4-(trifluoromethoxy)phenyl)oxazol-5-yl)-3'-(methylsulfonyl)biphenyl-4-yl)-1H-pyrazol-3-yl)acetate

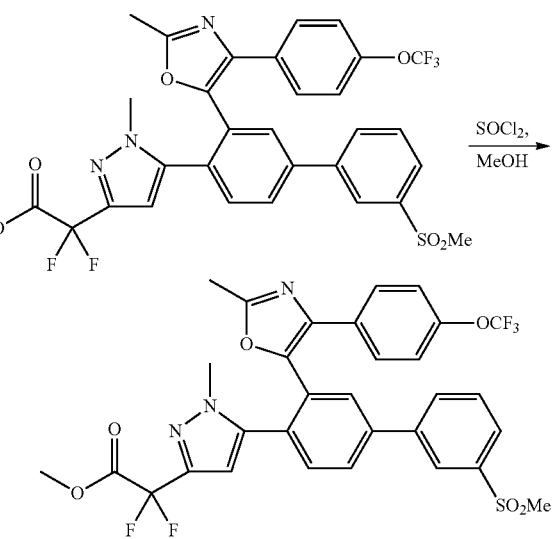

To a solution of 2,2-difluoro-2-(1-methyl-5-(3-(2-methyl-4-(4-(trifluoromethoxy)phenyl)oxazol-5-yl)-3'-(methylsulfonyl)biphenyl-4-yl)-1H-pyrazol-3-yl)acetic acid (0.050 g, 0.077 mmol, prepared by methods described in previous Examples) in MeOH (0.30 mL) was added thionyl chloride (0.010 mL, 0.15 mmol) at 0° C. After the reaction mixture was stirred for 1 hr, it was quenched with saturated aq. NaHCO$_3$ and the MeOH was removed in vacuo. The aqueous phase was extracted with EtOAc (10 mL×2). The combined organic extracts were washed with brine, dried over Na$_2$SO$_4$, filtered, and concentrated to afford the title compound (0.050 g, 0.076 mmol, 98% yield) MS (ESI) 662 [M+H]$^+$.

Example 48

Preparation of 1,1-difluoro-2-methyl-1-(1-methyl-5-(3-(2-methyl-4-(4-(trifluoromethoxy)phenyl)oxazol-5-yl)-3'-(methylsulfonyl)biphenyl-4-yl)-1H-pyrazol-3-yl)propan-2-ol

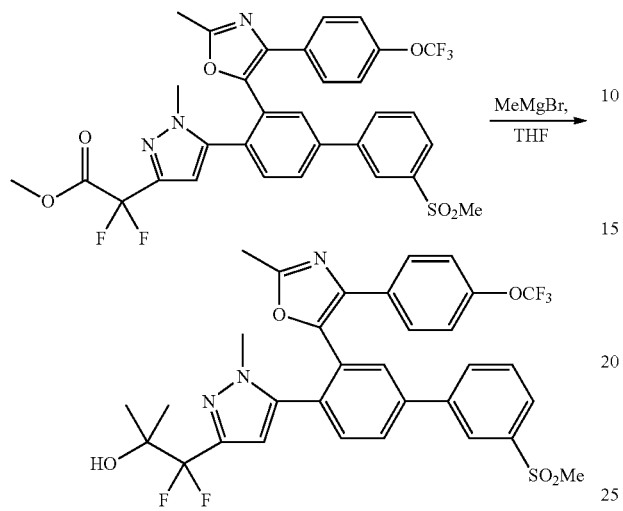

To a solution of Example 48a (0.030 g, 0.045 mmol) in THF (0.10 mL) was added MeMgBr (0.045 mL, 0.13 mmol, 3M in ether) at 0° C. After the reaction mixture was stirred for 4 hrs, it was quenched with saturated aq. NH₄Cl. The organic phase was separated and the aqueous phase was extracted with EtOAc (10 mL×2). The combined organic extracts were washed with brine, dried over Na₂SO₄, filtered and concentrated to afford the crude product which was purified by preparative HPLC (Atlantis dC18 (150×19 m), 5μ; Mobile phase A: CH₃CO₂H:CH₃CN (10:90); Mobile phase B: 100% CH₃CN; Flow: 16.0 mL/min (0-100%), RT=10.28 min) to yield the title compound (8.0 mg, 0.012 mmol, 26% yield). MS (ESI) 662 [M+H]⁺. ¹HNMR (400 MHz, CD₃OD): δ ppm 8.29 (t, 1H, J=1.6 Hz), 8.01-8.08 (m, 4H), 7.79 (t, 1H, J=8 Hz), 7.7 (d, 1H, J=8 Hz), 7.41-7.44 (m, 2H), 7.21-7.23 (m, 2H), 6.08 (s, 1H), 3.52 (s, 3H), 3.22 (s, 3H), 2.52 (s, 3H), 1.24 (s, 6H).

Example 49

2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2,2-difluoroethanol

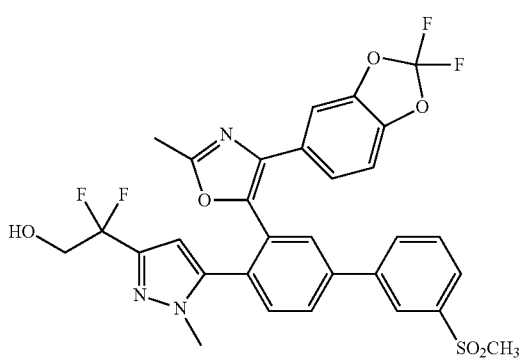 [SMILES: Cc1nc(-c2ccc3c(c2)OC(F)(F)O3)c(-c2cc(-c3cccc(S(C)(=O)=O)c3)ccc2-c2cc(C(F)(F)CO)nn2C)o1]

Example 49

Preparation of 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2,2-difluoroethanol

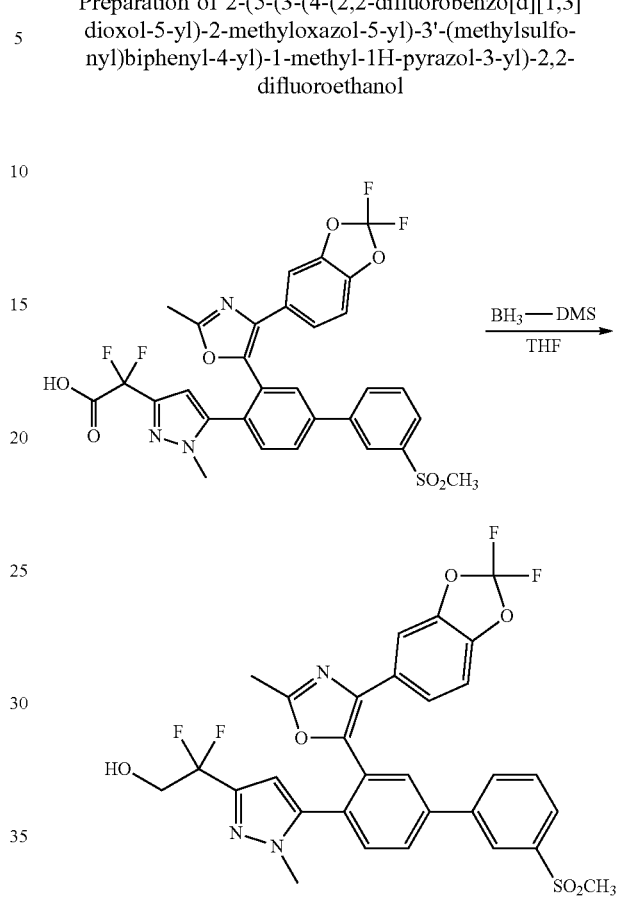

To a solution of 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)-2,2-difluoroacetic acid (210 mg, 0.32 mmol, prepared by methods described in previous Examples) in dry THF (8 mL) was added BH₃-DMS (0.50 mL, 2 M solution in THF) at 0° C. The mixture was stirred at rt for 18 hrs. The reaction mixture was quenched by adding MeOH (2 mL) dropwise. The reaction mixture was concentrated in vacuo. The crude residue was diluted with EtOAc (20 mL) and washed with water (20 mL), then brine (20 mL), dried over Na₂SO₄, filtered into a flask and concentrated in vacuo to give the crude alcohol. The crude product was purified by preparative HPLC (Symmetry C18 (250×4.6 m), 5μ; Mobile phase A: CH₃CO₂H: CH₃CN (10:90); Mobile phase B: 100% CH₃CN; Flow: 1.0 mL/min (0-100%), RT=9.23 min) to afford the title compound as a white solid, (17 mg, 0.025 mmol, 6% yield). MS (ESI) 630.2 [M+H]+. ¹H-NMR (400 MHz, MeOD): δ 8.28 (t, J=1.6 Hz, 1H), 8.10 (dd, J₁=1.6 Hz, J₂=6.4, 2H), 8.03-8.08 (m, 2H), 7.99 (dd, J₁=2 Hz, J₂=8 Hz, 1H), 7.80 (t, J=8 Hz, 1H), 7.65 (d, J=8 Hz, 1H), 7.03-7.11 (m, 3H), 6.06 (s, 1H), 3.95 (t, J=13.6 Hz, 2H), 3.47 (s, 3H), 3.31 (bs, 3H), 2.53 (s, 3H).

Example 50

2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide

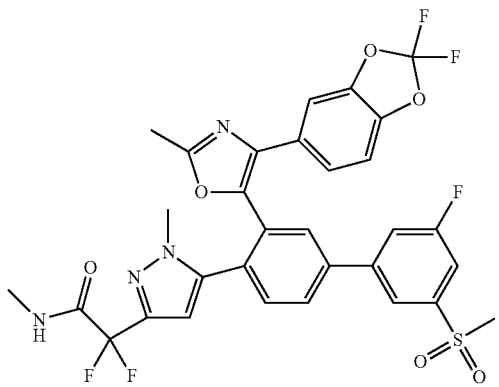

Example 50

Preparation of 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide

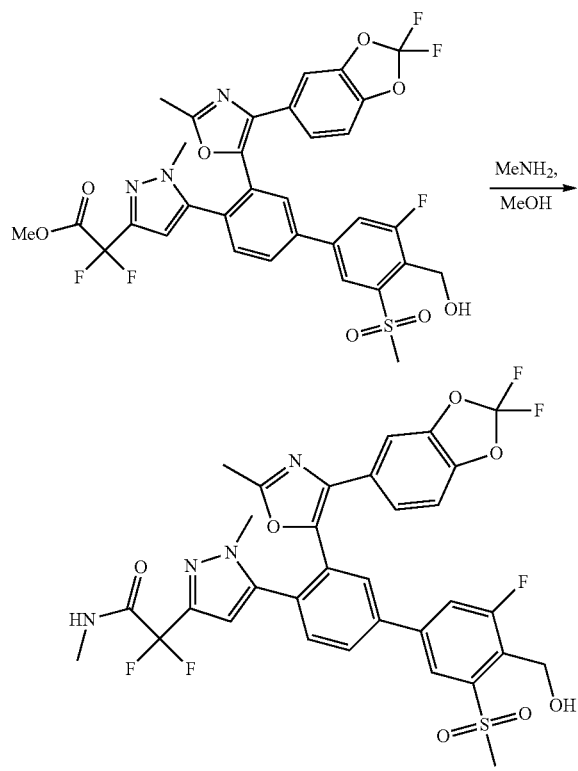

Methyl 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoroacetate (50 mg, 0.071 mmol, prepared by methods described in previous Examples) was dissolved in dry MeOH (3.0 mL) and to it was added a solution of methyl amine (4.4 mg, 0.14 mmol) in MeOH (0.050 mL). The reaction mixture was heated in a high pressure sealed tube at 55° C. for 5 hrs. The reaction mixture was concentrated in vacuo and the crude product was purified by preparative TLC (Silica gel, 75% EtOAc in pet. ether) to afford the title compound as an off-white solid, (13 mg, 0.018 mmol, 26% yield). MS (ESI) 705.3 [M+H]+. $^1$HNMR (400 MHz, CD$_3$OD): δ ppm 8.20 (d, 1H, J=1.2 Hz), 8.08 (d, 1H, J=1.6 Hz), 7.99 (dd, 1H, J=2 Hz, J=8 Hz), 7.93 (dd, 1H, J=2 Hz, J=10.4 Hz), 7.66 (d, 1H, J=8.4 Hz), 7.03-7.12 (m, 3H), 6.13 (s, 1H), 5.14 (d, 2H, J=1.6 Hz), 3.48 (s, 3H), 3.40 (s, 3H), 2.85 (s, 3H), 2.52 (s, 3H).

Example 51

(4'-(3-(difluoro(1,3,4-oxadiazol-2-yl)methyl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol

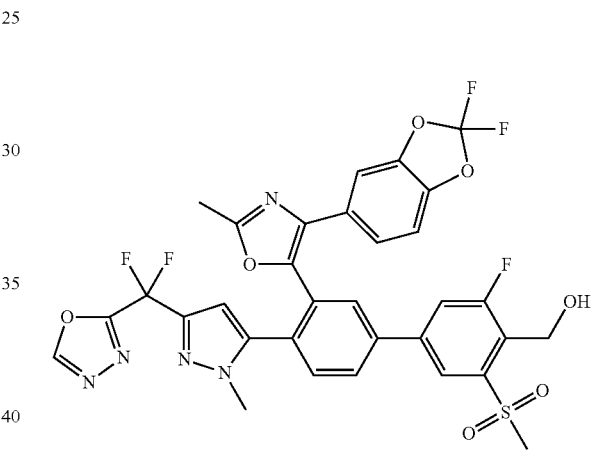

Example 51

Preparation of (4'-(3-(difluoro(1,3,4-oxadiazol-2-yl)methyl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol

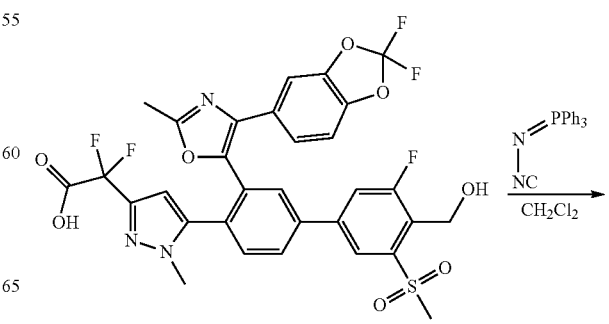

111

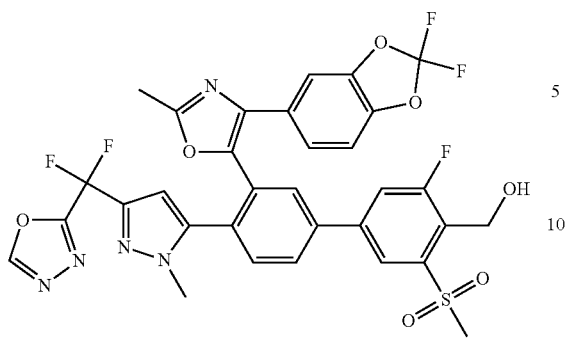

A solution of 2-(5-(3-(4-(2,2-difluorobenzo[d][1,3]di-oxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoroacetic acid (35 mg, 0.051 mmol, prepared by methods described in previous Examples) in DCM (10 mL) was added dropwise over 15 min to a solution of (isocyanoimino)triphenylphosphorane (15 mg, 0.051 mmol) in DCM (10 mL). The reaction mixture was stirred for 12 hrs at rt. The reaction mixture was concentrated in vacuo and the crude product was purified by preparative TLC (Silica gel, 1.2% MeOH in DCM) twice to afford the title compound as a white solid, (1.5 mg, 2.0 µmol, 4% yield). MS (ESI) 716.1 [M+H]+. $^1$HNMR (400 MHz, CD$_3$OD): δ ppm 9.21 (s, 1H), 8.22 (s, 1H), 8.12 (d, 1H, J=2 Hz), 8.01 (dd, 1H, J=2 Hz, J=8.4 Hz), 7.93 (dd, 1H, J=2 Hz, J=10.4 Hz), 7.69 (d, 1H, J=8.4 Hz), 7.03-7.12 (m, 3H), 6.28 (s, 1H), 5.15 (d, 2H, J=1.6 Hz), 3.46 (s, 3H), 3.41 (s, 3H), 2.55 (s, 3H).

Example 52

(4'-(3-(difluoro(4H-1,2,4-triazol-3-yl)methyl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol

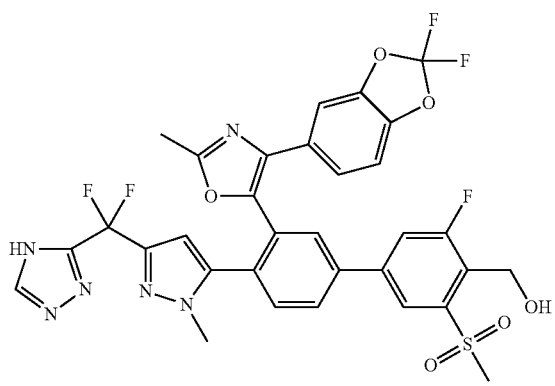 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)c3nnc[nH]3)nn2C)o1]

112

Example 52

Preparation of (4'-(3-(difluoro(4H-1,2,4-triazol-3-yl)methyl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl) biphenyl-4-yl) methanol

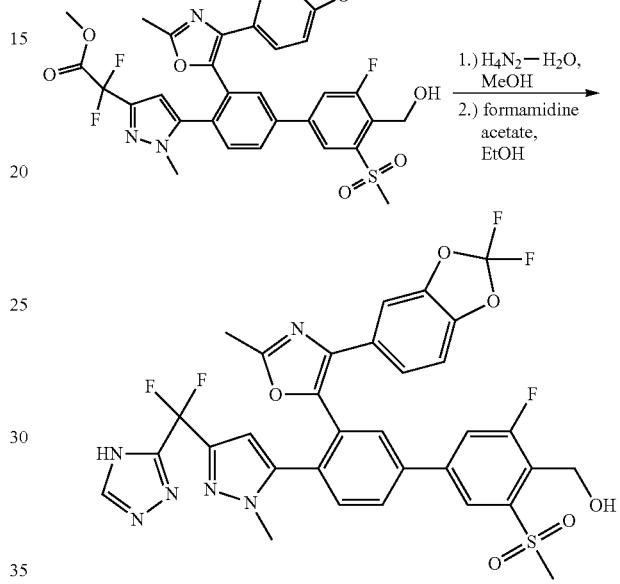

To a solution of methyl 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoroacetate (500 mg, 0.71 mmol) in MeOH (25 mL) was added hydrazine monohydrate (28 mg, 0.86 mmol) and the reaction mixture was heated to 55° C. for 4 hrs. The reaction mixture was concentrated in vacuo. The crude product was recrystallized from 50% DCM: petroleum ether to afford crude intermediate, 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetohydrazide (MS (ESI) 706.0 [M+H]+). The intermediate was then added to a solution of formamidine acetate (89 mg, 0.85 mmol) in EtOH (10 mL). The reaction mixture was heated to 80° C. for 6 hrs. The reaction mixture was concentrated in vacuo. The crude product was purified by column chromatography using CHCl$_3$: MeOH (1:9) as an eluent to afford the crude product (33% HPLC pure). The crude product was purified by preparative HPLC (Atlantis dC18 (250×19 m), 5 t; Mobile phase A: 10 mM NH$_4$OAc, Mobile phase B: MeOH; Flow: 17.0 mL/min (0-100%), RT=12.85 min) to afford the title compound as a white solid, (2.0 mg, 2.6 µmol, 0.6% yield). MS (ESI) 715.0 [M+H]+.
$^1$H-NMR (400 MHz, CDCl$_3$): δ ppm 8.26 (s, 1H), 8.14 (s, 1H), 7.88-7.89 (d, 1H, J=2.0 Hz), 7.76-7.78 (dd, 1H, J=1.6 Hz, J=6.2 Hz), 7.64-7.67 (dd, 1H, J=2.0 Hz, J=9.8 Hz), 7.51-7.55 (m, 2H), 6.99-7.05 (m, 2H), 6.91-6.93 (d, 1H, J=8 Hz), 6.20 (s, 1H), 5.09 (d, 2H, J=4.8 Hz), 3.48 (s, 3H), 3.29 (s, 3H), 2.88 (t, 1H, J=5.25 Hz), 2.49 (s, 3H), 2.19 (t, 1H).

Example 53

2-methyl-5-(4-(1-methyl-3-(trifluoromethyl)-1H-pyrazol-5-yl)-3'-(methylsulfonyl)biphenyl-3-yl)-4-(4-(trifluoromethoxy)phenyl)Oxazole

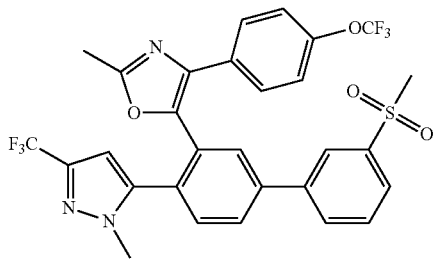 [SMILES: Cc1nc(-c2ccc(OC(F)(F)F)cc2)c(-c2cc(-c3cccc(S(C)(=O)=O)c3)ccc2-c2cc(C(F)(F)F)nn2C)o1]

Example 53a

Preparation of methyl 4-bromo-2-(bromomethyl)benzoate

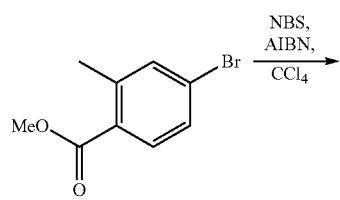

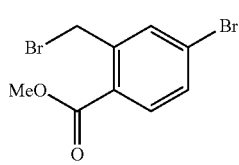

Methyl 4-bromo-2-methylbenzoate (10 g, 45 mmol) was brought up in anhydrous CCl$_4$ (70 mL) and to the solution was added NBS (7.9 g, 45 mmol), and AIBN (370 mg, 2.2 mmol). The reaction mixture was heated to 90° C. for 30 min. After being cooled to rt, the reaction solution was poured into water (100 mL). The layers were separated and the aqueous layer was extracted with DCM (100 mL). The combined organics were dried over Na$_2$SO$_4$, filtered into a flask and concentrated in vacuo to give the title compound as pale yellow oil with white crystals, 16 g of crude product, which was taken forward without purification. MS (ESI) 308 [M+H]$^+$. $^1$H NMR (400 MHz, CDCl$_3$) δ ppm 7.84 (d, J=8.4 Hz, 1H), 7.63 (d, J=2.0 Hz, 1H), 7.50 (dd, J=8.4, 2.0 Hz, 1H), 4.89 (s, 2H), 3.94 (s, 3H).

Example 53b

Preparation of methyl 4-bromo-2-((4-methoxyphenoxy)methyl)benzoate

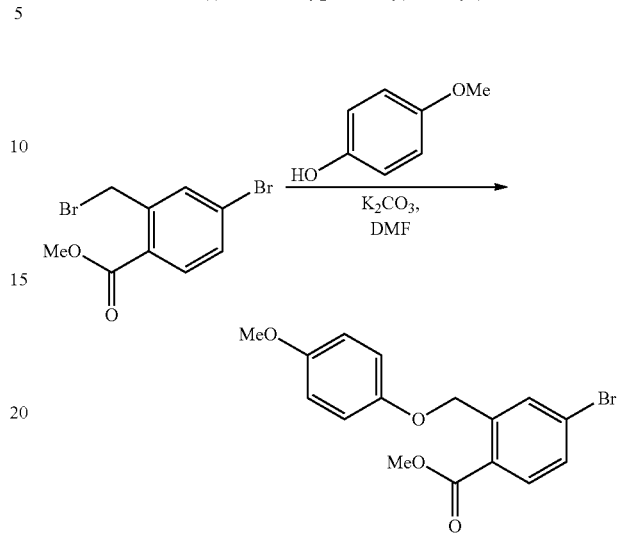

Example 53a (13 g, 43 mmol) was brought up in DMF (100 mL) and to the solution was added 4-methoxyphenol (4.6 g, 37 mmol), and K$_2$CO$_3$ (15 g, 110 mmol). The reaction mixture was heated to a reflux for 30 min. After being cooled to rt, the reaction solution was poured into water (100 mL). The layers were separated and the aqueous layer was extracted with DCM (80 mL). The combined organics were dried over Na$_2$SO$_4$, filtered into a round bottom flask and concentrated in vacuo. The crude material was purified by column chromatography thru a 300 g SiO$_2$ column using a mobile phase gradient of 0-25% EtOAc/Hx to afford the title compound as a white fluffy solid (15 g, 42 mmol, 97% yield). MS (ESI) 352 [M+H]$^+$.

Example 53c

Preparation of 1-(4-bromo-2-((4-methoxyphenoxy)methyl)phenyl)ethanone

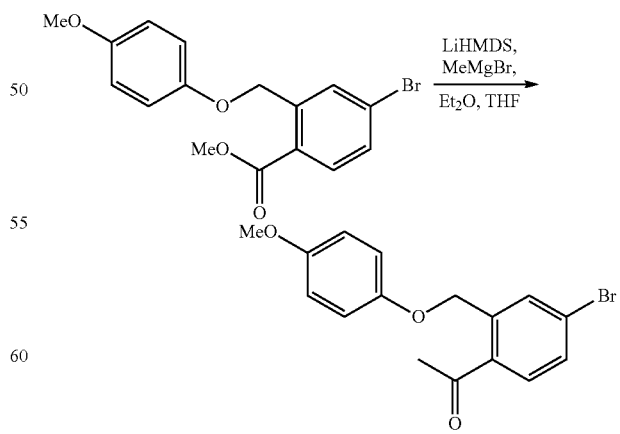

In a dry N$_2$ purged three-neck round bottom flask, LHMDS in THF (67 mL, 67 mmol) was cooled to −10° C. A solution of methyl magnesium bromide in diethyl ether (13 mL, 40 mmol) was added dropwise via an addition funnel, and the reaction temperature was kept between −10° C. to 0° C. Example 53b (4.7 g, 13 mmol) in anhydrous THF (30 mL) was added dropwise. The solution was allowed to warm to rt and was stirred for 18 hrs. The reaction solution was poured into ice-cold saturated aq NH$_4$Cl (50 mL). The solution was extracted with DCM (50 mL×2). The combined organics were dried over Na$_2$SO$_4$, filtered into a round bottom flask and concentrated in vacuo to give the crude compound as yellow-orange oil, which was taken forward without purification (5.0 g, 15 mmol). MS (ESI) 335, 337 [M+H]$^+$.

Example 53d

Preparation of 1-(4-bromo-2-((4-methoxyphenoxy) methyl)phenyl)-4,4,4-trifluorobutane-1,3-dione

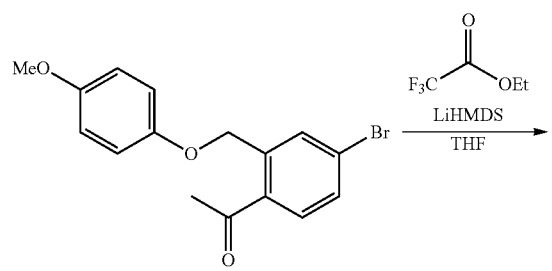

Example 53c (9.4 g, 28 mmol) was dissolved in anhydrous THF (60 mL) and cooled to −78° C. LHMDS in THF (28 mL, 28 mmol) was added dropwise, and the reaction mixture was maintained at −20° C. for 1 hr. The reaction solution was cooled to −50° C. and ethyl trifluoroacetate (10 mL, 84 mmol) was added dropwise. The reaction solution was allowed to gradually warm to rt, and then was quenched with ice-cold 1 M HCl (80 mL). The aqueous was extracted with DCM (80 mL×2). The combined organics were dried over Na$_2$SO$_4$, filtered into a round bottom flask and concentrated in vacuo to give the crude compound as brown-orange oil, which was taken forward without purification (12 g, 27 mmol). MS (ESI) 432, 434 [M+H]$^+$.

Example 53e

Preparation of 5-(4-bromo-2-((4-methoxyphenoxy) methyl)phenyl)-1-methyl-3-(trifluoromethyl)-1H-pyrazole

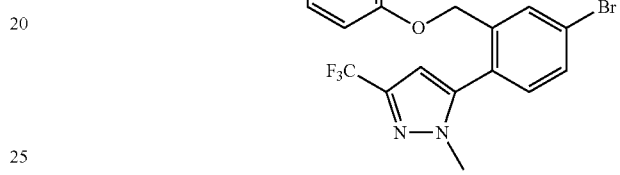

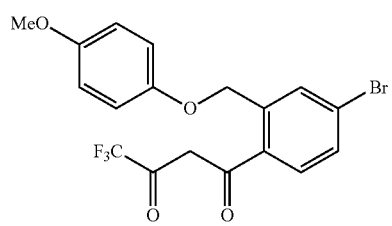

Example 53d (12 g, 27 mmol) was brought up in MeOH (20 mL) and cooled to −10° C. Methylhydrazine (1.6 mL, 30 mmol) dissolved in MeOH (10 mL) was added dropwise. The reaction mixture was stirred for 1 hr, and MeOH was removed under vacuo. The product was extracted in DCM (100 mL) and was washed with H$_2$O (100 mL×2). The two pyrazole isomers were separated from each other by chromatography thru a 300 g SiO$_2$ column using a mobile phase gradient of 0-30% EtOAc/Hx. The desired isomer was the last to elute as the open form hydrazone. This isomer was dissolved in toluene (70 mL) and catalytic pTSA (100 mg) was added. The reaction mixture was heated to a reflux for 2 hrs. The reaction solution was poured into water (100 mL) and the product was extracted with DCM (80 mL×2). The combined organics were dried over Na$_2$SO$_4$, filtered into a flask and concentrated in vacuo to give the title compound as dark oil (4.3 g, 9.8 mmol, 36% yield). MS (ESI) 442, 444 [M+H]$^+$. 1H NMR (400 MHz, CDCl$_3$) δ ppm 7.94-7.85 (m, 1H), 7.44 (dd, J=8.3, 2.1 Hz, 1H), 7.10 (d, J=8.3 Hz, 1H), 6.94-6.87 (m, 2H), 6.87-6.80 (m, 3H), 5.26 (d, J=15.0 Hz, 2H), 3.76 (s, 3H), 3.05 (s, 3H).

Example 53f

Preparation of 5-(4-bromo-2-((4-methoxyphenoxy) methyl)phenyl)-1-methyl-3-(trifluoromethyl)-1H-pyrazole

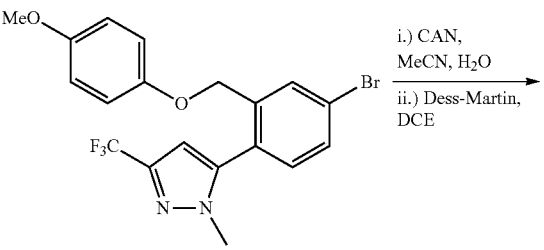

-continued

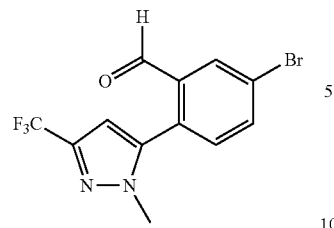

Example 53e (11 g, 24 mmol) was dissolved in 80 mL CH₃CN and 20 mL water, and cooled to 0° C. After portion-wise addition of CAN (27 g, 49 mmol), the reaction mixture was stirred for 30 min. The mixture was extracted in EtOAc (100 mL), and the organics were washed with water (100 mL×2). The combined organics were dried over Na₂SO₄, filtered into a flask and concentrated in vacuo. The product was taken to the oxidation without further purification.

The crude residue was dissolved in 50 mL of DCE and Dess-Martin Periodinane (21 g, 48 mmol) was added, and the mixture was stirred for 30 min. The mixture was poured into water and extracted with DCM (80 mL). The organic phase was dried over Na₂SO₄, filtered into a flask and concentrated in vacuo to give the title compound (5.3 g, 16 mmol, 66% yield). MS (ESI) 332, 334 [M+H]+. $^1$H NMR (400 MHz, CDCl₃) δ 10.36 (s, 1H), 8.13 (d, J=2.2 Hz, 1H), 7.75 (dd, J=8.3, 2.2 Hz, 1H), 7.48 (d, J=7.9 Hz, 1H), 6.85 (dd, J=14.9, 6.1 Hz, 1H), 4.08 (d, J=0.6 Hz, 3H).

Example 53 was prepared from Example 53f and 4-(trifluoromethoxy)benzaldehyde using procedures similar to those described in Example 45. MS (ESI) 622 [M+H]⁺. $^1$H NMR (400 MHz, CDCl₃) δ ppm 8.22 (t, J=1.7 Hz, 1H), 8.00-7.85 (m, 3H), 7.86-7.74 (m, 2H), 7.68 (t, J=7.8 Hz, 1H), 7.43-7.34 (m, 2H), 7.03 (m, 2H), 6.20 (s, 1H), 3.81 (d, J=26.5 Hz, 3H), 3.12 (d, J=6.4 Hz, 3H), 2.59 (s, 3H).

Example 54

2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)propan-2-ol

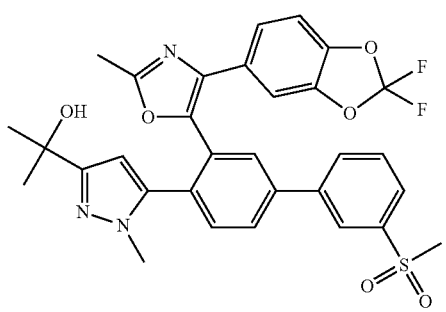 [SMILES: Cc1nc(-c2ccc3c(c2)OC(F)(F)O3)c(-c2cc(-c3cccc(S(C)(=O)=O)c3)ccc2-c2cc(C(C)(C)O)nn2C)o1]

Example 54a

Preparation of methyl 4-(4-bromo-2-((4-methoxyphenoxymethyl)phenyl)-2,4-dioxobutanoate

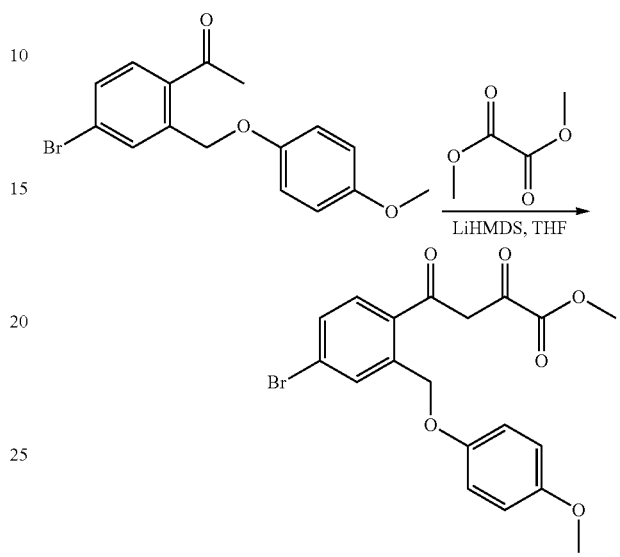

To a solution of Example 53c (4.0 g, 12 mmol) in dry THF (25 mL) at −50° C. was added LHMDS (2.0 g, 12 mmol) and the mixture was stirred for 20 min. Dimethyl oxalate (1.4 g, 12 mmol) was added to the reaction mixture. The mixture was stirred at −50° C. for 15 min and then at rt overnight. The reaction mixture was concentrated in vacuo and the crude residue was diluted with EtOAc (50 mL). The solution was washed with water (50 mL), then with aq NaCl (50 mL), dried over Na₂SO₄, filtered into a round bottom flask and concentrated in vacuo to give the title compound as a yellow solid, (4.4 g, 10 mmol, 87% yield). MS (ESI) 421.0 [M+H]+.

Example 54b

Preparation of methyl 5-(4-bromo-2-((4-methoxyphenoxy)methyl)phenyl)-1-methyl-1H-pyrazole-3-carboxylate

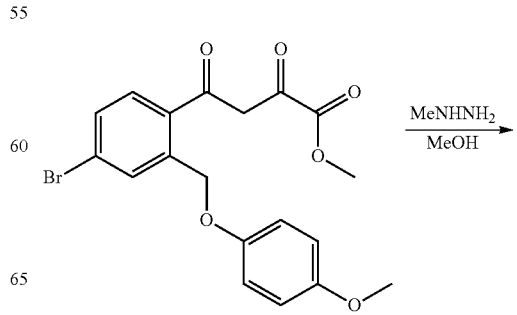

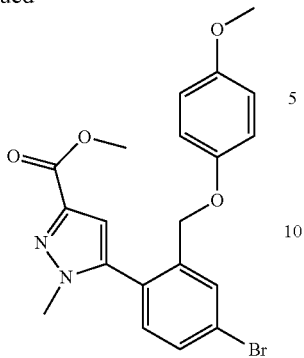

Methylhydrazine sulfate (0.48 g, 10 mmol) was added to a stirred solution of Example 54a (4.4 g, 10 mmol) in MeOH (50 mL) at 0-10° C. The reaction mixture was stirred at rt overnight. The solvents were removed under reduced pressure. The residue was dissolved in EtOAc (50 mL). The solution was washed with water (50 mL), then with aq NaCl (50 mL), dried over Na$_2$SO$_4$, filtered into a flask and concentrated under reduced pressure. The crude residue was purified by chromatography thru a SiO$_2$ column using the mobile phase of 25% EtOAc in petroleum ether to afford the title compound as a yellow solid, (3.5 g, 7.3 mmol, 71% yield). MS (ESI) 431.0 [M+H]+.

Example 54c

Preparation of methyl 5-(4-bromo-2-formylphenyl)-1-methyl-1H-pyrazole-3-carboxylate

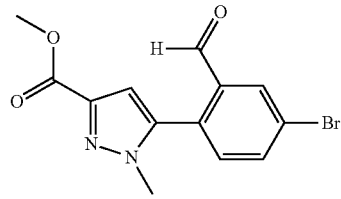 [SMILES: COC(=O)c1cc(-c2ccc(Br)cc2C=O)n(C)n1]

Example 54c was prepared from Example 54b using a procedure similar to that described in Example 53f. MS (ESI) 324.0 [M+H]+. $^1$H NMR (400 MHz, CDCl$_3$) δ ppm 9.82 (s, 1H), 8.18 (d, 1H, J=2.0 Hz), 7.84 (dd, 1H, J=8.1, 2.1 Hz), 7.30 (d, 1H, J=8.2 Hz), 6.87 (s, 1H), 3.95 (s, 3H), 3.77 (s, 3H).

Example 54d

Preparation of 2-(5-(4-bromo-2-(4-(2,2-difluorobenzo[d][1,3]dioxol-5-yl)-2-methyloxazol-5-yl)phenyl)-1-methyl-1H-pyrazol-3-yl)propan-2-ol

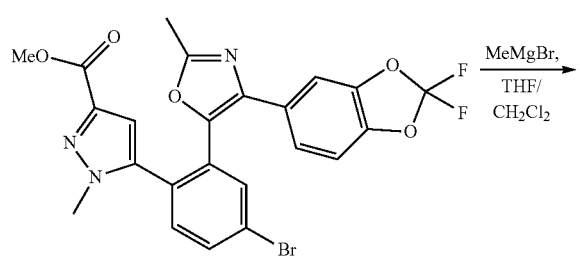

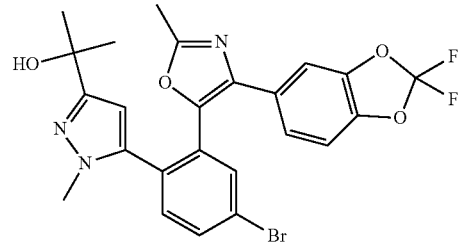

Methyl 5-(4-bromo-2-(4-(2,2-difluorobenzo[d][1,3]dioxol-5-yl)-2-methyloxazol-5-yl)phenyl)-1-methyl-1H-pyrazole-3-carboxylate was prepared from Example 54c and Example 45a using procedures similar to that described in Example 45. Methyl 5-(4-bromo-2-(4-(2,2-difluorobenzo[d][1,3]dioxol-5-yl)-2-methyloxazol-5-yl)phenyl)-1-methyl-1H-pyrazole-3-carboxylate (0.20 g, 0.38 mmol) was brought up in THF (1.5 mL) and DCM (1.5 mL) and cooled to −78° C. MeMgBr (0.045 g, 0.38 mmol) in THF was added dropwise. The reaction mixture was warmed to rt and was stirred for 2 hrs. The reaction mixture was quenched with saturated aq NH$_4$Cl (5 mL). The layers were separated and the aqueous layer was extracted EtOAc (10 mL×3). The combined organics were washed with aq NaCl (20 mL), dried over Na$_2$SO$_4$, filtered into a round bottom flask and concentrated in vacuo to afford the crude compound as a brown solid (200 mg, 0.18 mmol). MS (ESI) 532.0 [M+H]+.

Example 54 was prepared from Example 54d and 3-(methylsulfonyl)phenylboronic acid using a procedure similar to that described in Example 45f. MS (ESI) 608.2 [M+H]$^+$. 1H NMR (400 MHz, MeOH-d$_4$) δ ppm 8.27-8.29 (m, 1H), 8.09-8.12 (m, 1H), 8.06-8.07 (m, 1H), 8.02-8.06 (m, 1H), 7.98-8.01 (m, 1H), 7.91-7.93 (m, 1H), 7.78-7.83 (m, 1H), 7.63-7.66 (m, 1H), 7.13-7.16 (m, 1H), 7.10-7.12 (m, 1H), 5.90-5.91 (m, 1H), 3.45 (s, 3H), 3.22 (s, 3H), 2.54 (s, 3H), 1.43 (s, 6H).

Example 55

N-(2-cyanopropan-2-yl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazole-3-carboxamide

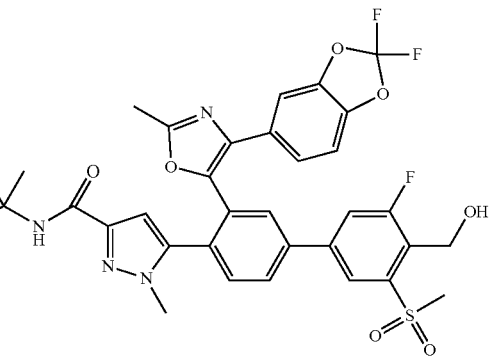

Example 55a

Preparation of 5-(4-bromo-2-(4-(2,2-difluorobenzo[d][1,3]dioxol-5-yl)-2-methyloxazol-5-yl)phenyl)-1-methyl-1H-pyrazole-3-carboxylic acid

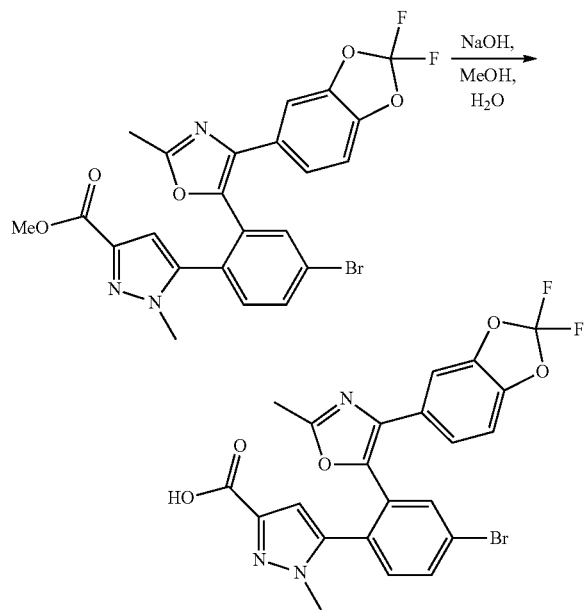

Methyl 5-(4-bromo-2-(4-(2,2-difluorobenzo[d][1,3]dioxol-5-yl)-2-methyloxazol-5-yl)phenyl)-1-methyl-1H-pyrazole-3-carboxylate was prepared from Example 54c and Example 45a using procedures similar to that described in Examples 45.

To a solution of methyl 5-(4-bromo-2-(4-(2,2-difluorobenzo[d][1,3]dioxol-5-yl)-2-methyloxazol-5-yl)phenyl)-1-methyl-1H-pyrazole-3-carboxylate (200 mg, 0.38 mmol) in MeOH (5 mL) and water (5 mL) was added NaOH (15 mg, 0.38 mmol) and the mixture was stirred overnight at rt. The reaction mixture was concentrated under reduced pressure, acidified with 1N HCl and then extracted with the EtOAc (15 mL×2). The combined organics were washed with aq NaCl (20 mL), dried over Na$_2$SO$_4$, filtered into a flask and concentrated in vacuo to afford the title compound as a yellow solid (180 mg, 0.31 mmol, 81% yield). MS (ESI) 518.0 [M+H]+.

Example 55b

Preparation of N-(2-cyanopropan-2-yl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazole-3-carboxamide

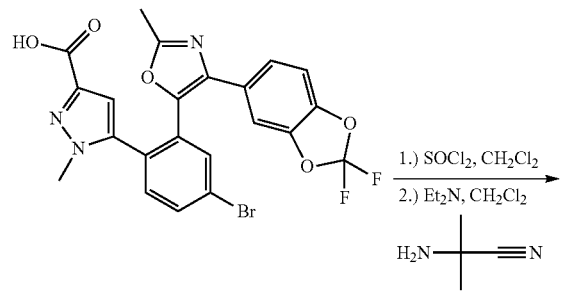

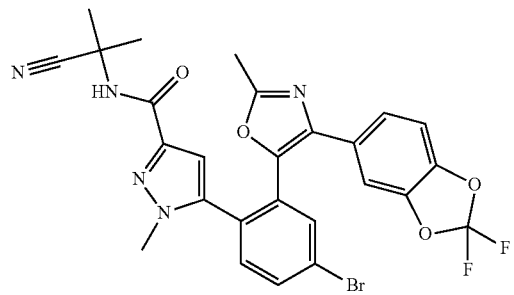

Sulfurous dichloride (29 mg, 0.24 mmol) was added dropwise to a cooled solution (0-10° C.) of Example 55a (130 mg, 0.24 mmol) in anhydrous DCM (10 mL). The solution was stirred for 2 hrs at 0-10° C. The reaction mixture was added to a cooled (0-10° C.) solution of 2-amino-2-methylpropanenitrile (20 mg, 0.24 mmol) and Et$_3$N (0.034 mL, 0.24 mmol). The mixture was stirred overnight at rt. The crude mixture was diluted with EtOAc (30 mL) and washed with water (20 mL), then with aq NaCl (20 mL), dried over Na$_2$SO$_4$, filtered into a flask and concentrated in vacuo to give the crude product. The crude residue was purified by chromatography thru a SiO$_2$ column using the mobile phase of 60% EtOAc in petroleum ether to afford the title compound as brown solid, (100 mg, 0.087 mmol, 51% yield). MS (ESI) 584.0 [M+H]+.

Example 55 was prepared from Example 55b and Intermediate 1 using a similar procedure to that described in Example 45f. MS (ESI) 708.0 [M+H]+. 1H NMR (400 MHz, MeOH-d$_4$) δ ppm 8.22 (s, 1H), 8.10 (d, 1H, J=2.01 Hz), 7.98-8.03 (m, 1H), 7.94 (dd, 1H, J=10.42, 1.88 Hz), 7.66 (d, 1H, J=8.03 Hz), 7.01-7.13 (m, 3H), 6.35 (s, 1H), 5.15 (d, 2H, J=1.76 Hz), 3.53 (s, 3H), 3.40 (s, 3H), 2.54 (s, 3H), 1.78 (s, 6H).

Example 56

5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazole-3-carboxamide

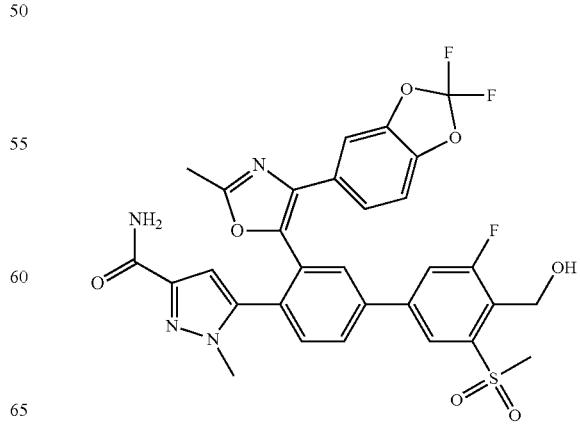

Example 56a

Preparation of 5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazole-3-carboxamide

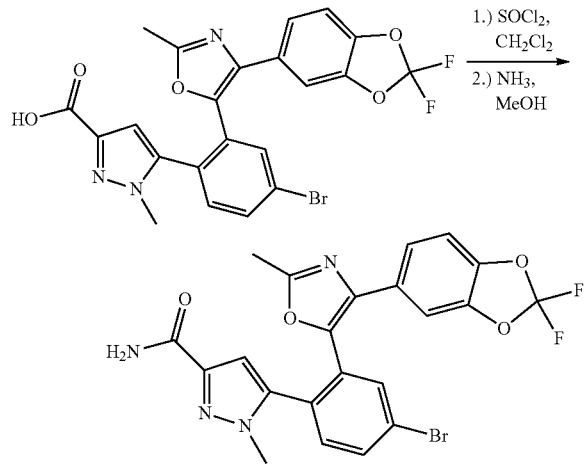

Sulfurous dichloride (0.013 mL, 0.17 mmol) was added dropwise to a cooled solution (0-10° C.) of Example 55a (90 mg, 0.17 mmol) in anhydrous DCM (5.0 mL). The reaction solution was stirred for 2 hrs at 0-10° C. Methanolic ammonia (5.0 mL, 30%) was added to the mixture, and the reaction mixture was allowed to warm to rt and was stirred overnight. The crude mixture was diluted with EtOAc (20 mL) and washed with water (20 mL), then with aq NaCl (20 mL), dried over $Na_2SO_4$, filtered into a round bottom flask and concentrated in vacuo to give the crude product. The crude residue was purified by chromatography thru a $SiO_2$ column using the mobile phase of 60% EtOAc in petroleum ether to afford the title compound as pale yellow solid, (80 mg, 0.088 mmol, 51% yield). MS (ESI) 517.0 [M+H]+.

Example 56 was prepared from Example 56a and Intermediate 1 using a similar procedure to that described in Example 45f. MS (ESI) 641.0 [M+H]+. $^1$H NMR (400 MHz, MeOH-$d_4$) δ ppm 8.23 (s, 1H), 8.11 (d, 1H, J=2.01 Hz), 8.01 (dd, 1H, J=8.03, 2.01 Hz), 7.95 (dd, 1H, J=10.42, 1.88 Hz), 7.67 (d, 1H, J=8.03 Hz), 7.03-7.14 (m, 3H), 6.33 (s, 1H), 5.15 (s, 2H), 3.52 (s, 3H), 3.41 (s, 3H), 2.55 (s, 3H).

Example 57

(3'-(4-(2,2-difluorobenzo[d][1,3]dioxol-5-yl)-2-methyloxazol-5-yl)-3-fluoro-4'-(1-methyl-3-(oxazol-5-yl)-1H-pyrazol-5-yl)-5-(methylsulfonyl)-[1,1'-biphenyl]-4-yl)methanol

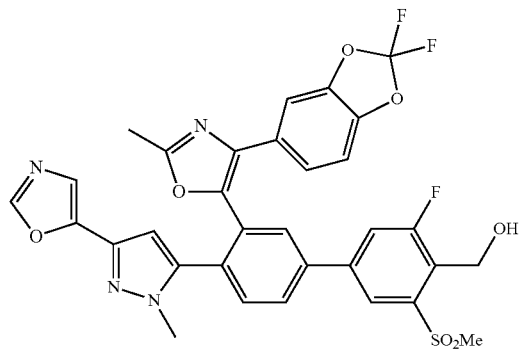 [SMILES: Cc1nc(-c2ccc3c(c2)OC(F)(F)O3)c(-c2cc(-c3cc(F)c(CO)c(S(C)(=O)=O)c3)ccc2-c2cc(-c3cnco3)nn2C)o1]

Example 57a

Preparation of (5-(4-bromo-2-(4-(2,2-difluorobenzo[d][1,3]dioxol-5-yl)-2-methyloxazol-5-yl)phenyl)-1-methyl-1H-pyrazol-3-yl)methanol

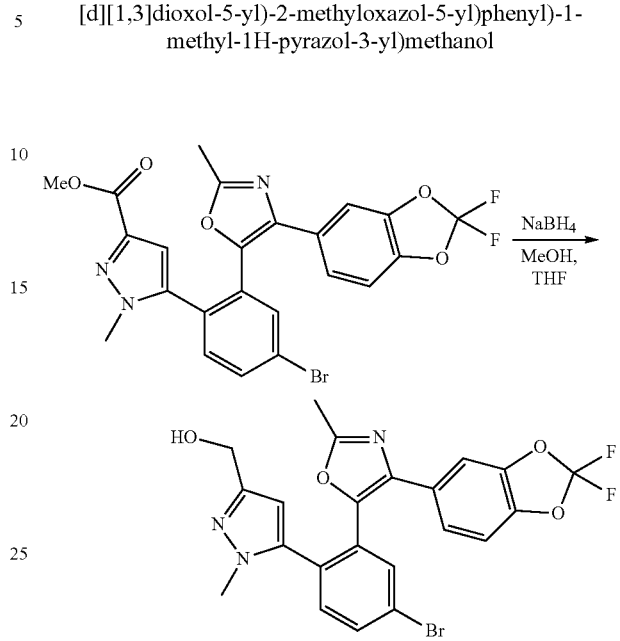

$NaBH_4$ (194 mg, 5.13 mmol) was added to a cooled solution (0° C.) of methyl 5-(4-bromo-2-(4-(2,2-difluorobenzo[d][1,3]dioxol-5-yl)-2-methyloxazol-5-yl)phenyl)-1-methyl-1H-pyrazole-3-carboxylate (800 mg, 1.46 mmol) in THF (25 mL). After 5 min, MeOH (6.3 mL) was added to the reaction mixture in a dropwise manner. The reaction mixture was stirred for 18 hrs at rt. The mixture was quenched with $H_2O$ (10 mL), and extracted with EtOAc (2×30 mL). The combined organic layers were washed with $H_2O$ (20 mL), and brine (20 mL), dried over $Na_2SO_4$, filtered into a flask and concentrated in vacuo to give the crude product. The crude residue was purified by chromatography thru a $SiO_2$ column using the mobile phase of 60% EtOAc in petroleum ether to afford the title compound as a light yellow semi-solid (450 mg, 0.073 mmol, 60% yield). MS (ESI) 506.0 [M+H]+.

Example 57b

Preparation of 5-(4-bromo-2-(4-(2,2-difluorobenzo[d][1,3]dioxol-5-yl)-2-methyloxazol-5-yl)phenyl)-1-methyl-1H-pyrazole-3-carbaldehyde

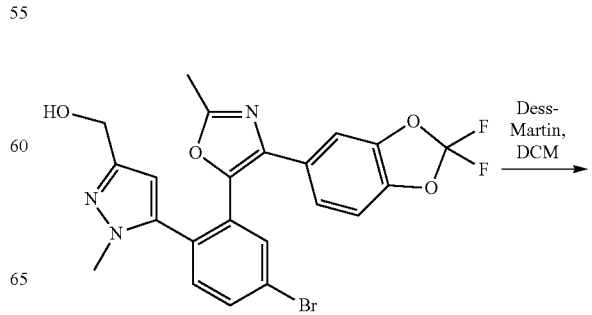

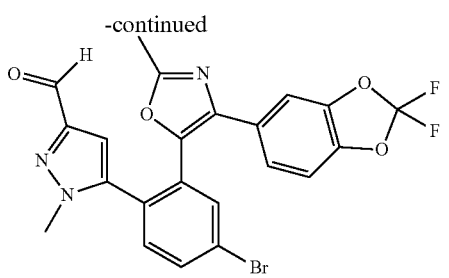

To a solution of 5-(4-bromo-2-(4-(2,2-difluorobenzo[d][1,3]dioxol-5-yl)-2-methyloxazol-5-yl)phenyl)-1-methyl-1H-pyrazol-3-yl)methanol (425 mg, 0.843 mmol) in dry DCM (150 mL) was added Dess-Martin Periodinane (536 mg, 1.26 mmol) at 0° C. The mixture was stirred for 2 hrs. The precipitate was filtered through a celite pad, and the filtrate was concentrated. The resulting residue was dissolved in a minimum amount of Et$_2$O (10 mL) and cooled to 0° C. (to precipitate more benzoic acid) and decanted. The solution was concentrated in vacuo. The crude residue was purified by chromatography thru a SiO$_2$ column using the mobile phase of 40% EtOAc in petroleum ether to afford the title compound as a colorless oil (380 mg, 90% yield). MS (ESI) 504.0 [M+H]+. $^1$HNMR (400 MHz, CDCl$_3$): δ ppm 9.79 (s, 1H), 7.81 (d, 1H, J=2 Hz) 7.07 (dd, 1H, J=8 Hz, 2 Hz), 7.24-7.25 (m, 1H), 6.99-7.02 (m, 2H), 6.92 (d, 1H, J=8 Hz), 6.34 (s, 1H), 3.52 (s, 3H), 2.44 (s, 3H).

Example 57c

Preparation of 5-(5-bromo-2-(1-methyl-3-(oxazol-5-yl)-1H-pyrazol-5-yl)phenyl)-4-(2,2-difluorobenzo[d][1,3]dioxol-5-yl)-2-methyloxazole

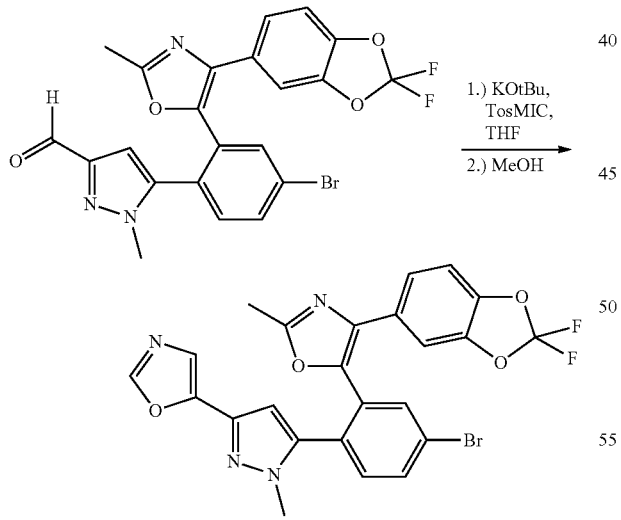

To a suspension of KOtBu (8.4 mg, 0.075 mmol) in THF (5.0 mL) was added a solution of TosMIC (11 mg, 0.055 mmol) in THF (5.0 mL) at −78° C., and the reaction mixture was stirred for 15 min before being treated dropwise with a solution of 5-(4-bromo-2-(4-(2,2-difluorobenzo[d][1,3]dioxol-5-yl)-2-methyloxazol-5-yl)phenyl)-1-methyl-1H-pyrazole-3-carbaldehyde (25 mg, 0.050 mmol) in THF (50 mL). The reaction mixture was stirred for 1.5 hrs at −78° C. before MeOH (50 mL) was added to the solution. The mixture was heated to a reflux for 2 hrs, and then the solvent was removed under reduced pressure. The residue was poured into ice water and extracted with DCM. The organic layer was washed with 2% HCl followed by water, dried over Na$_2$SO$_4$, and then concentrated under reduced pressure to afford the title compound as off-white solid, (10 mg, 0.018 mmol, 36% yield). MS (ESI) 542.0 [M+H]+.

Example 57 was prepared from Example 57c and Intermediate 1 using a similar procedure to that described in Example 45f, except with using PdCl$_2$(dppf) as a catalyst. MS (ESI) 665.2 [M+H]+. $^1$H NMR (400 MHz, CDCl$_3$) δ ppm 8.17 (1H, s) 7.90 (1H, d, J=1.6 Hz) 7.85 (1H, s) 7.83-7.87 (1H, m) 7.76-7.81 (1H, m) 7.64-7.71 (1H, m) 7.54 (1H, d, J=8.00 Hz) 7.03 (1H, s) 6.98 (1H, d, J=1.50 Hz) 6.87 (1H, d, J=8.25 Hz) 6.03 (1H, s) 5.11 (2H, d, J=5.50 Hz) 3.48 (3H, s) 3.30 (3H, s) 2.87 (1H, t, J=6.8 Hz) 2.50 (3H, s).

Example 58

2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)acetonitrile

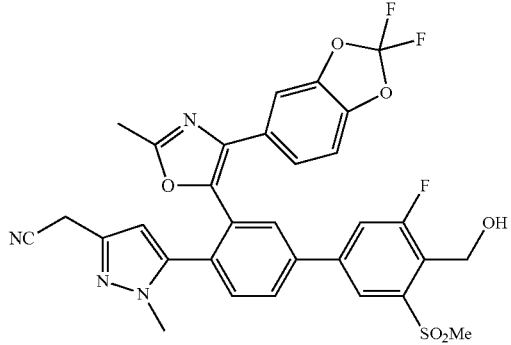 [SMILES: Cc1nc(-c2ccc3c(c2)OC(F)(F)O3)c(-c2cc(-c3cc(F)c(CO)c(S(C)(=O)=O)c3)ccc2-c2cc(CC#N)nn2C)o1]

Example 58a

Preparation of 5-(5-bromo-2-(3-(chloromethyl)-1-methyl-1H-pyrazol-5-yl)phenyl)-4-(2,2-difluorobenzo[d][1,3]dioxol-5-yl)-2-methyloxazole

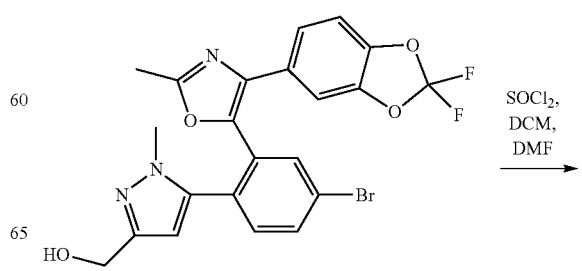

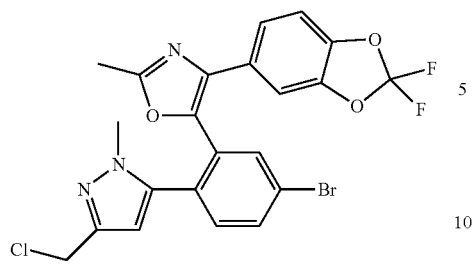

(5-(4-bromo-2-(4-(2,2-difluorobenzo[d][1,3]dioxol-5-yl)-2-methyloxazol-5-yl)phenyl)-1-methyl-1H-pyrazol-3-yl)methanol was prepared from ethyl 5-(4-bromo-2-(4-(2,2-difluorobenzo[d][1,3]dioxol-5-yl)-2-methyloxazol-5-yl)phenyl)-1-methyl-1H-pyrazole-3-carboxylate (see Example 54d starting material) using standard reduction procedures similar to that described in Examples 62k.

To a cold 0° C. solution of (5-(4-bromo-2-(4-(2,2-difluorobenzo[d][1,3]dioxol-5-yl)-2-methyloxazol-5-yl)phenyl)-1-methyl-1H-pyrazol-3-yl)methanol (1.8 g, 3.6 mmol) in DCM (20 mL) and DMF (0.020 mL), SOCl₂ (0.85 g, 7.1 mmol) was added dropwise. The reaction mixture was stirred at rt for 2 hrs. The reaction mixture was quenched slowly at 0° C. with a saturated solution of NaHCO₃. The mixture was extracted with DCM (15 mL×2). The combined organic extracts were washed with aq NaCl (20 mL), dried over Na₂SO₄, filtered into a round bottom flask and concentrated in vacuo to afford the crude product. The crude residue was purified by chromatography thru a SiO₂ column using the mobile phase gradient of 0-30% EtOAc/Hx to afford title compound as a brown solid (1.3 g, 2.4 mmol, 68% yield). MS (ESI) 522.0 [M+H]+.

Example 58b

Preparation of 2-(5-(4-bromo-2-(4-(2,2-difluorobenzo[d][1,3]dioxol-5-yl)-2-methyloxazol-5-yl)phenyl)-1-methyl-1H-pyrazol-3-yl)acetonitrile

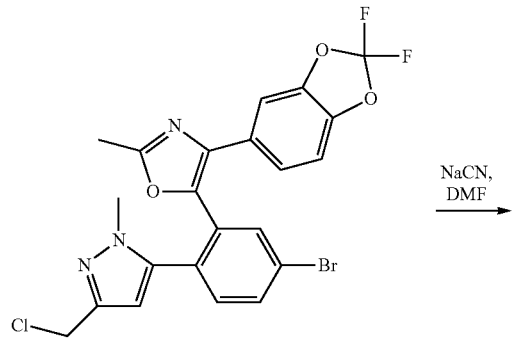

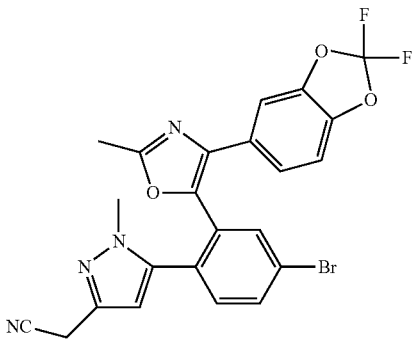

To a stirred solution of Example 58a (1.0 g, 1.9 mmol) in DMF (10 mL), was added NaCN (0.19 g, 3.8 mmol). The mixture was stirred overnight at 50° C. The reaction mixture was quenched with ice cold water and concentrated in vacou to remove DMF. The crude mixture was diluted with DCM (50 mL), washed with aq NaCl (20 mL), dried over Na₂SO₄, filtered into a flask and concentrated in vacuo to give the crude product. The crude residue was purified by chromatography thru a SiO₂ column using the mobile phase gradient of 0-30% EtOAc/Hx to afford the title compound as pale yellow solid, (0.92 g, 1.8 mmol, 94% yield). MS (ESI) 513.1 [M+H]+.

Example 58 was prepared from Example 58b and Intermediate 1 using a similar procedure to that described in Example 45f, except with using PdCl₂(dppf) as a catalyst. MS (ESI) 637.2 [M+H]+. ¹H NMR (400 MHz, CDCl₃) δ ppm 8.14 (1H, s) 7.86 (1H, d, J=1.75 Hz) 7.77 (1H, dd, J=8.00, 2.00 Hz) 7.62-7.68 (1H, m) 7.51 (1H, d, J=8.25 Hz) 7.09 (1H, dd, J=8.38, 1.63 Hz) 7.03 (1H, d, J=1.50 Hz) 6.96 (1H, d, J=8.25 Hz) 5.88 (1H, s) 5.10 (2H, d, J=5.50 Hz) 3.56 (2H, s), 3.45 (3H, s) 3.29 (3H, s) 2.87 (1H, t, J=7.13 Hz) 2.51 (3H, s).

Example 59

(S)-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)propanenitrile

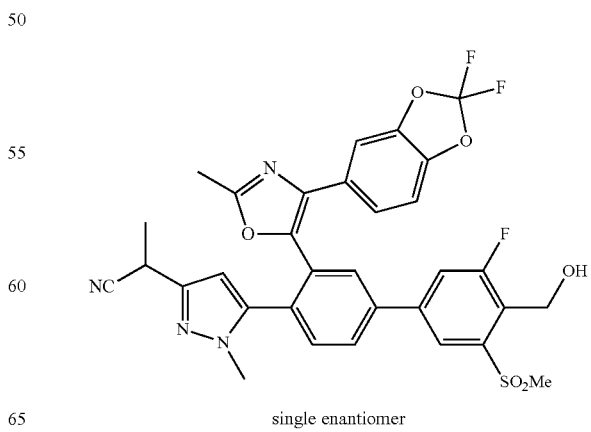

single enantiomer

Example 59a

Preparation of 2-(5-(4-bromo-2-(4-(2,2-difluorobenzo[d][1,3]dioxol-5-yl)-2-methyloxazol-5-yl)phenyl)-1-methyl-1H-pyrazol-3-yl)propanenitrile

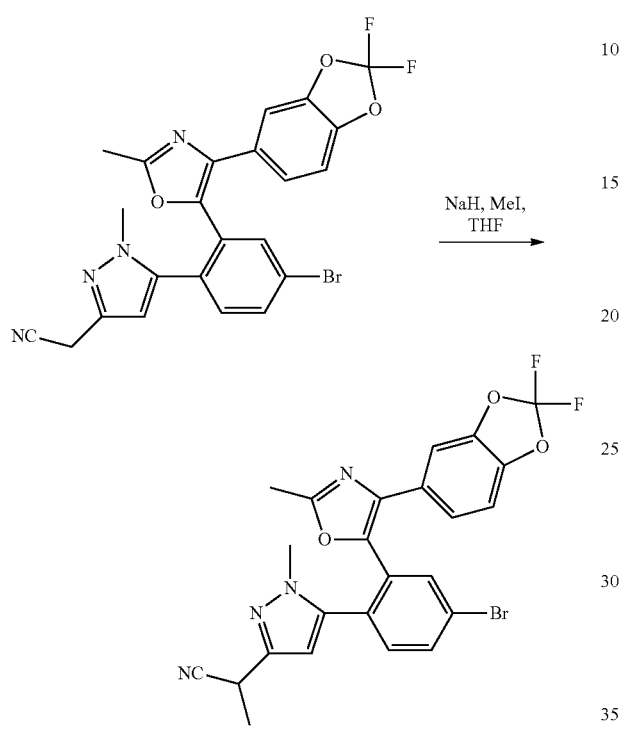

To a cold 0° C. solution of Example 58b (150 mg, 0.29 mmol) in THF (10 mL) was added NaH (14 mg, 0.58 mmol). The reaction mixture was stirred for 30 min. Iodomethane (0.037 mL, 0.58 mmol) was added at 0° C. Then the reaction mixture was bought slowly to rt and stirred for 2 hrs. The reaction mixture was quenched slowly at 0° C. with a saturated aq solution of NH$_4$Cl. The mixture was extracted with EtOAc (15 mL×2). The combined organic extracts were washed with aq NaCl (20 mL), dried over Na$_2$SO$_4$, filtered into a flask and concentrated in vacuo to afford the crude product. The crude residue was purified by chromatography thru a SiO$_2$ column using the mobile phase gradient of 0-30% EtOAc/Hx to afford title compound as a pale yellow solid (60 mg, 0.11 mmol, 39% yield). MS (ESI) 527.2 [M+H]+.

Example 59 was prepared from Example 59a and Intermediate 1 using a similar procedure to that described in Example 45f, except with using K$_2$CO$_3$ as a base. The racemic mixture was separated by chiral preparative HPLC [Chiral pak-IC (250×10) mm JH, 70% CO$_2$, 30% (0.5% DEA method), Flow rate (10 mL/min)]) to afford chirally pure product. Chiral HPLC: 97.39% Pure; RT=9.11 mins, [column: Chiralpak-I A, (4.6×250 mm), 5 micron); Co-solvent: EtOH; CO$_2$ Flow Rate: 2.55/mins, Co-solvent flow rate: 0.45/min]; Specific optical rotation: [α]$_{25}$D=+60 (c 0.1, MeOH). MS (ESI) 651.2 [M+H]+. $^1$H NMR (400 MHz, DMSO-d$_6$) δ ppm 8.06-8.13 (3H, m), 8.04 (1H, dd, J=8.03, 2.01 Hz), 7.69 (1H, d, J=8.03 Hz), 7.28 (1H, d, J=8.53 Hz), 7.19 (1H, d, J=1.51 Hz), 7.01 (1H, dd, J=8.28, 1.76 Hz), 5.84 (1H, s), 5.54 (1H, t, J=5.25 Hz), 4.94 (2H, dd, J=5.27, 1.51 Hz), 4.06 (1H, q, J=14.8 Hz), 3.43 (3H, s), 3.38 (3H, s), 2.46 (3H, s), 1.36 (3H, d, J=7.2 Hz).

Example 60

1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)cyclopropanecarbonitrile

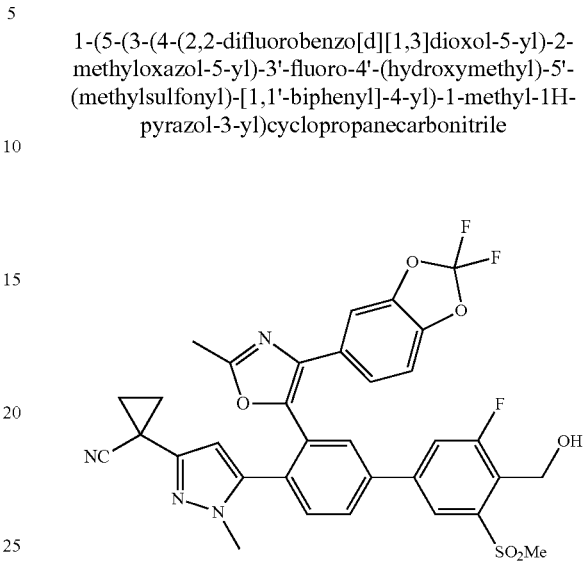

Example 60a

Preparation of 1-(5-(4-bromo-2-(4-(2,2-difluorobenzo[d][1,3]dioxol-5-yl)-2-methyloxazol-5-yl)phenyl)-1-methyl-1H-pyrazol-3-yl)cyclopropanecarbonitrile

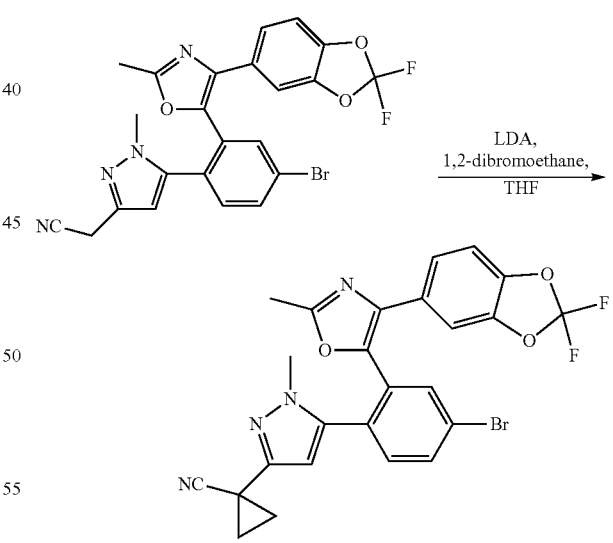

To a cold −78° C. solution of Example 58b (100 mg, 0.20 mmol) in THF (10 mL) was added LDA (0.39 mL, 0.78 mmol). The reaction mixture was stirred for 30 min. 1,2-Dibromoethane (0.10 mL, 1.2 mmol) was added, and the mixture was slowly brought to rt and stirred for 2 hrs. The reaction mixture was quenched slowly at 0° C. with a saturated aq solution of NH$_4$Cl. The mixture was extracted with EtOAc (15 mL×2). The combined organic extracts were washed with aq NaCl (20 mL), dried over Na$_2$SO$_4$, filtered into a round bottom flask and concentrated in vacuo to afford the crude product. The crude residue was purified by chromatography thru a SiO$_2$ column using the mobile phase gradient of 0-30% EtOAc/Hx to afford title compound as a pale yellow solid (64 mg, 0.12 mmol, 61% yield). MS (ESI) 539.2 [M+H]+.

Example 60 was prepared from Example 60a and Intermediate 1 using a similar procedure to that described in Example 45f, except with using K$_2$CO$_3$ as a base. MS (ESI) 663.2 [M+H]+. $^1$H NMR (300 MHz, DMSO-d$_6$) δ ppm 7.96-8.18 (4H, m), 7.67 (1H, d, J=8.03 Hz), 7.30 (1H, d, J=8.40 Hz), 7.16 (1H, s), 6.97 (1H, dd, J=8.45, 1.65 Hz), 5.74 (1H, s), 5.51-5.64 (1H, m), 4.96 (2H, d, J=3.78 Hz), 3.45 (3H, s), 3.31 (3H, s), 2.49 (3H, s), 1.52-1.67 (2H, m), 1.10-1.31 (2H, m).

Example 61

2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)acetamide

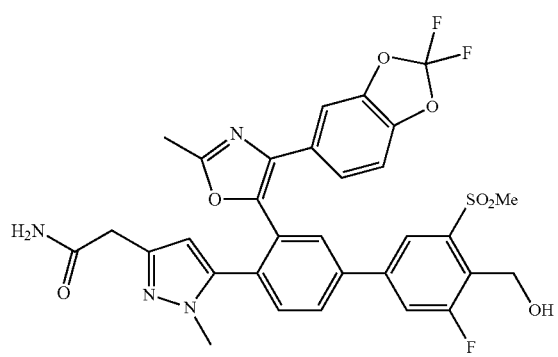 [SMILES: Cc1nc(-c2ccc3c(c2)OC(F)(F)O3)c(-c2cc(-c3cc(F)c(CO)c(S(C)(=O)=O)c3)ccc2-c2cc(CC(N)=O)nn2C)o1]

Example 61a

Preparation of 2-(5-(4-bromo-2-(4-(2,2-difluorobenzo[d][1,3]dioxol-5-yl)-2-methyloxazol-5-yl)phenyl)-1-methyl-1H-pyrazol-3-yl)acetamide

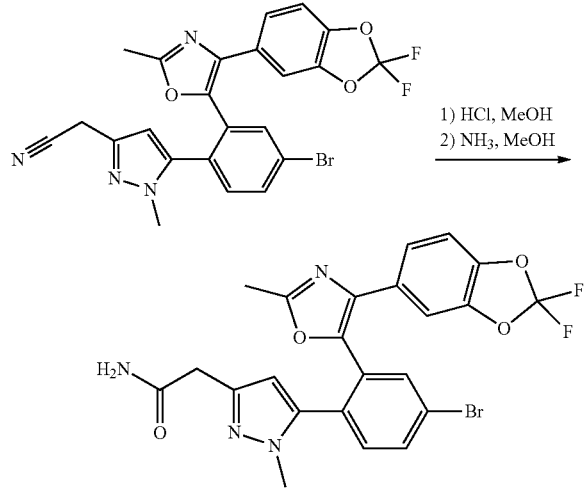

A solution of Example 58b (300 mg, 0.58 mmol) in methanolic HCl (4 N, 20 mL, 0.58 mmol) was heated to 55° C. for 4 hrs. The reaction solution was concentrated under reduced pressure, and diluted with a saturated NaHCO$_3$ solution. The aqueous solution was extracted with DCM (15 mL×2). The combined organic extracts were washed with aq NaCl (20 mL), dried over Na$_2$SO$_4$, filtered into a flask and concentrated in vacuo to afford the crude ester intermediate, which was used without purification (MS (ESI) 546.6 [M+H]+). The intermediate methyl ester (100 mg, 0.18 mmol) was dissolved in MeOH (3.5 mL) and methanolic ammonia (1M, 5.0 mL, 5.0 mmol). The reaction mixture was heated to 70° C. overnight. The solution was concentrated under reduced pressure, and the crude compound was taken to the next step without purification. MS (ESI) 531.9 [M+H]+.

Example 61 was prepared from Example 61a and Intermediate 1 using a similar procedure to that described in Example 45f, except with using PdCl$_2$(dppf) as a catalyst. MS (ESI) 655.2 [M+H]+. $^1$H NMR (400 MHz, CDCl$_3$) δ ppm 8.15 (1H, d, J=1.25 Hz), 7.86 (1H, s), 7.77 (1H, dd, J=8.25, 2.00 Hz), 7.66 (1H, dd, J=10.01, 1.75 Hz), 7.49-7.54 (1H, m), 7.07 (1H, dd, J=8.25, 1.50 Hz), 7.02 (1H, d, J=1.25 Hz), 6.93 (1H, d, J=8.25 Hz), 6.31 (1H, br. s.), 5.78 (1H, s), 5.27 (1H, br. s.) 5.10 (2H, d, J=5.25 Hz), 3.46 (3H, s), 3.42 (2H, s), 3.29 (3H, s), 2.87 (1H, t, J=6.8 Hz) 2.50 (3H, s).

Scheme 4

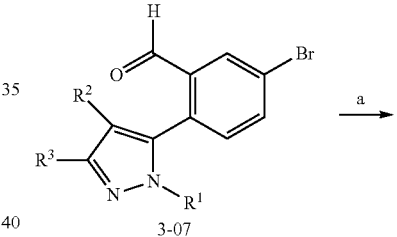

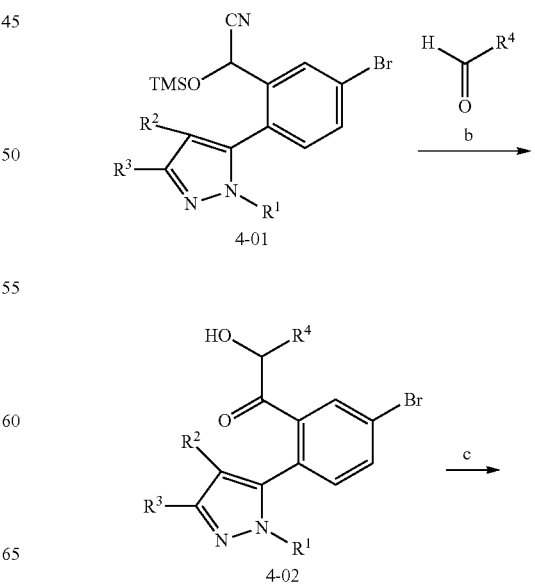

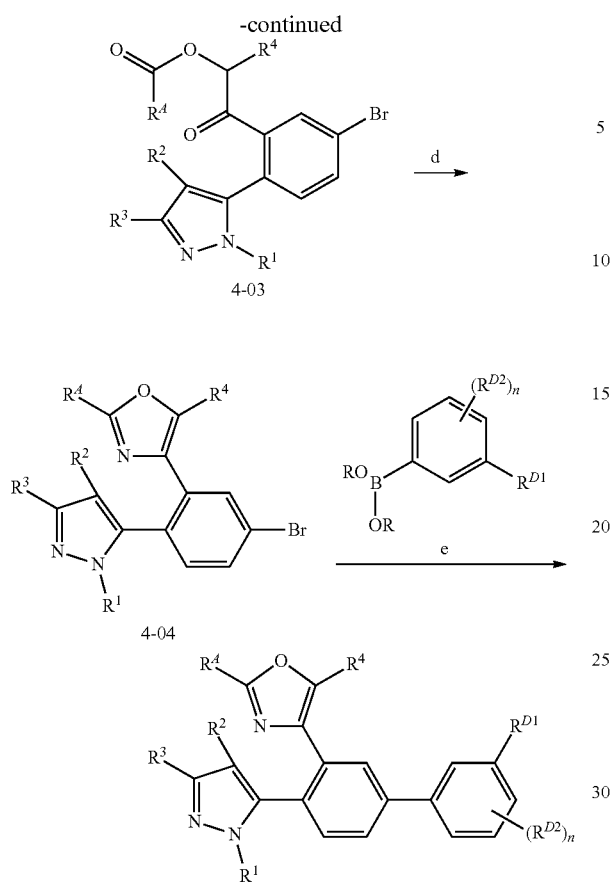

(a) TMSCN, ZnI₂, CH₂Cl₂; (b) LDA, THF; (c) R⁴COCl, Et₃N, CH₂Cl₂ or (R⁴CO)₂O, Et₃N, CH₂Cl₂; (d) NH₄OAc, AcOH; (e) PdCl₂(dppf), NaHCO₃, DMF, H₂O Specific compounds in the invention contain an oxazole as represented by general structure 4-05. In general, the oxazole compounds of formula 4-05 can be synthesized following the methodology shown in Scheme 4. The aldehyde (3-07) is converted to an aryl-2-(trimethylsilyloxy) acetonitrile (4-01) by treatment with TMSCN in the presence of zinc iodide. Treatment of 4-01 with LDA followed by addition of an appropriately substituted aldehyde affords the α-hydroxyketone (4-02). Acylation of 4-02 with an appropriate acyl chloride or anhydride in the presence of triethylamine provides the ester (4-03). Cyclization is then accomplished with ammonium acetate in acetic acid to afford the oxazole (4-04). Compounds represented by the structure 4-05 are then obtained by subjecting 4-04 to a palladium-mediated coupling reaction with the appropriate aryl boronate, and an example set of conditions is given in Scheme 4.

Additional chemistry known to one skilled in the art can be carried out at the R³ position including reductions, Grignard additions, alkylations, fluorinations, acylations, amidations, and heterocycle forming reactions to prepare compounds of the invention. For example, when R³ contains an ester (e.g. CF₂COOEt or COOEt) additional functionalization can be carried out by one skilled in the art to make amides as well as primary, secondary and tertiary alcohols. Several examples of these transformations are described in the Examples below.

Example 62

2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2-methylpropan-1-ol

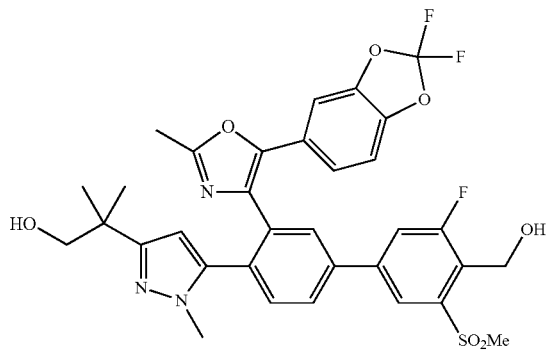 [SMILES: Cc1nc(-c2cc(-c3cc(F)c(CO)c(S(C)(=O)=O)c3)ccc2-c2cc(C(C)(C)CO)nn2C)c(-c2ccc3c(c2)OC(F)(F)O3)o1]

Example 62a

Preparation of methyl 2,2-dimethyl-3-oxopropanoate

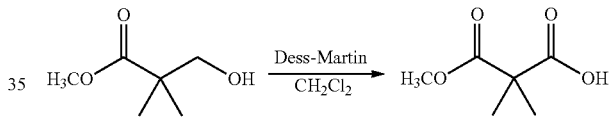

To a solution of methyl 3-hydroxy-2,2-dimethylpropanoate (8.0 g, 61 mmol) in dry DCM (150 mL) was added Dess-Martin Periodinane (39 g, 91 mmol) at 0° C. and the mixture was stirred at rt for 18 hrs. The precipitate was filtered through a celite pad, and the filtrate was concentrated. The resulting residue was dissolved in a minimum amount of Et₂O (10 mL) and cooled to 0° C. (to precipitate more benzoic acid) and decanted. The solution was concentrated in vacuo. The crude residue was purified by chromatography thru a SiO₂ column using the mobile phase of 11% EtOAc in petroleum ether to afford the title compound as a colorless oil (6.5 g, 50 mmol, 83% yield). ¹HNMR (400 MHz, CDCl₃): δ ppm 9.66 (s, 1H), 3.75 (s, 3H), 1.35 (s, 6H).

Example 62b

Preparation of methyl 5-(4-bromo-2-((4-methoxyphenoxy)methyl)phenyl)-3-hydroxy-2,2-dimethyl-5-oxopentanoate

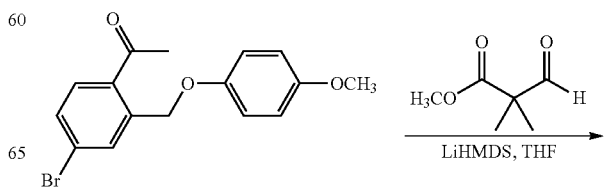

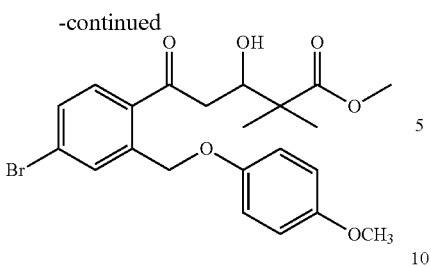

LHMDS (15 mL, 15 mmol) was added dropwise to a solution of Example 53c (2.5 g, 7.5 mmol) in dry THF (35 mL) at −78° C. and the mixture was stirred at −78° C. for 0.5 hr. Example 62a (1.9 g, 15 mmol) in dry THF (10 mL) was then added dropwise, and the mixture was stirred at −78° C. for 5 hrs. The reaction mixture was quenched with 1N HCl (5 mL) and extracted with EtOAc (2×20 mL). The combined organic layers were washed with water (10 mL), then aq NaCl (20 mL), dried over $Na_2SO_4$, filtered into a round bottom flask and concentrated under reduced pressure. The crude residue was purified by chromatography thru a $SiO_2$ column using the mobile phase of 30% EtOAc in petroleum ether to afford the title compound as a light yellow oil (3.4 g, 7.3 mmol, 98% yield). $^1$HNMR (400 MHz, $CDCl_3$): δ ppm 8.00 (d, 1H, J=2 Hz), 7.66, (d, 1H, J=8.4 Hz), 7.55 (dd, 1H, J=2.0 Hz, J=8.0 Hz), 6.93 (dd, 2H, J=2.4 Hz, J=6.8 Hz), 6.84 (dd, 2H, J=2.4 Hz, J=6.8 Hz), 5.29 (s, 2H), 4.33-4.37 (m, 1H), 3.78 (s, 3H), 3.72 (s, 3H), 3.13 (d, 1H, J=4.8 Hz), 3.02-3.06 (m, 2H), 1.25 (s, 6H).

Example 62c

Preparation of methyl 5-(4-bromo-2-((4-methoxy-phenoxy)methyl)phenyl)-2,2-dimethyl-3,5-dioxo-pentanoate

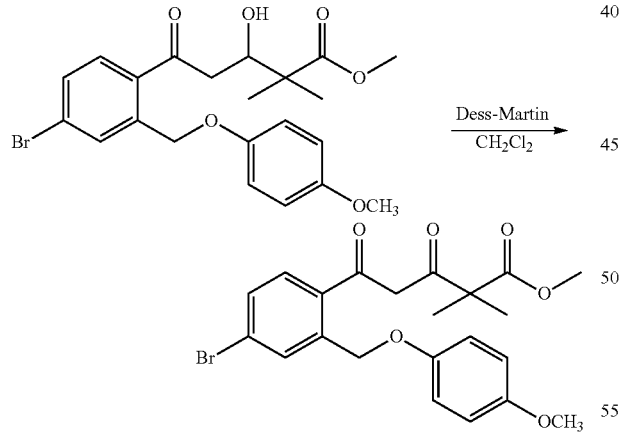

To a solution of Example 62b (8.8 g, 19 mmol) in DCM (200 mL) at 0° C. was added Dess-Martin Periodinane (12 g, 28 mmol). The reaction mixture was stirred at rt for 3 hrs, then cooled to 0° C. and 10% $NaHCO_3$ was added. The mixture was stirred for 30 min and the layers separated. The aqueous layer was extracted with DCM (2×250 mL) and the combined organic layers were washed with water (150 mL), then aq NaCl (150 mL), dried over $Na_2SO_4$, filtered into a round bottom flask and concentrated under reduced pressure. The crude residue was purified by chromatography thru a $SiO_2$ column using the mobile phase of 20% EtOAc in petroleum ether to afford the title compound as a brown oil (5.5 g, 12 mmol, 63% yield). $^1$HNMR (400 MHz, $CDCl_3$): δ ppm 7.88 (t, 1H, J=1.6 Hz), 7.50, (dd, 1H, J=2 Hz, J=8 Hz), 7.35 (dd, 1H, J=2 Hz, J=8 Hz), 6.90 (dd, 2H, J=2.8 Hz, J=6.8 Hz), 6.83 (dd, 2H, J=2.4 Hz, J=6.8 Hz), 5.99 (s, 1H), 5.20 (s, 2H), 3.73 (s, 3H), 3.71 (s, 3H), 1.42 (s, 6H).

Example 62d

Preparation of methyl 2-(5-(4-bromo-2-((4-methoxyphenoxy)methyl)phenyl)-1-methyl-1H-pyrazol-3-yl)-2-methylpropanoate

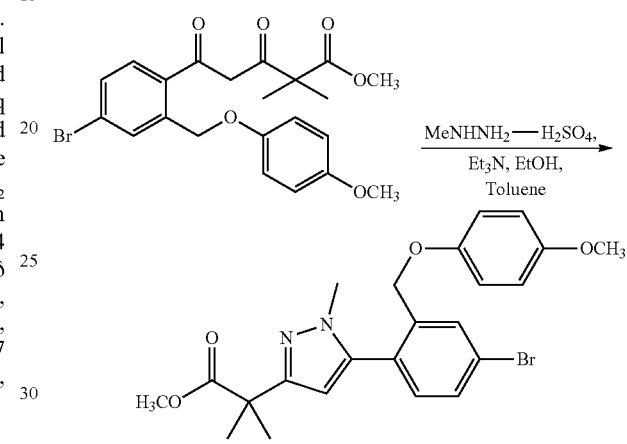

Methylhydrazine sulfate (2.1 g, 14 mmol) and $Et_3N$ (2.0 mL, 14 mmol) were added to a stirred solution of Example 62c (3.3 g, 7.1 mmol) in EtOH (30 mL) and toluene (10 mL). The reaction mixture was heated to 70° C. for 6 hrs. The solvents were removed under reduced pressure. The residue was dissolved in EtOAc (200 mL). The organic solution was washed with water (100 mL), then saturated aq. $NaHCO_3$ (3×100 mL), dried over $Na_2SO_4$, filtered into a flask and concentrated under reduced pressure. The crude residue was purified by chromatography thru a $SiO_2$ column using the mobile phase of 18% EtOAc in petroleum ether to afford the title compound as a brown liquid (3.0 g, 6.2 mmol, 87% yield). $^1$HNMR (400 MHz, $CDCl_3$): δ ppm 7.81 (d, 1H, J=2.4 Hz), 7.54, (dd, 1H, J=2.4 Hz, J=8.0 Hz), 7.17 (d, 1H, J=8.0 Hz), 6.79 (dd, 2H, J=2.8 Hz, J=6.8 Hz), 6.74 (dd, 2H, J=2.4 Hz, J=6.8 Hz), 6.15 (s, 1H), 4.74 (s, 2H), 3.75 (s, 3H), 3.63 (s, 3H), 3.61 (s, 3H), 1.56 (s, 6H).

Example 62e

Preparation of methyl 2-(5-(4-bromo-2-(hydroxymethyl)phenyl)-1-methyl-1H-pyrazol-3-yl)-2-methyl-propanoate

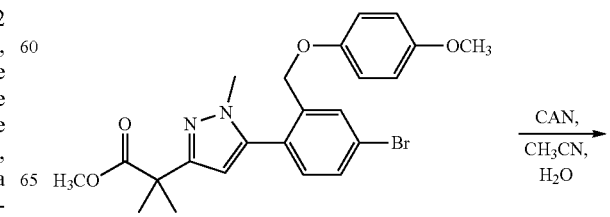

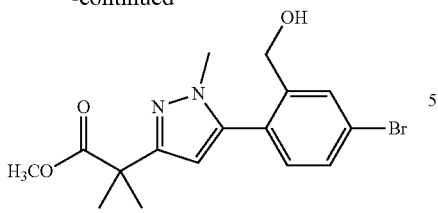

CAN (7.0 g, 13 mmol) was added to a cooled solution (0° C.) of Example 62d (3.0 g, 6.3 mmol) in MeCN (30 mL) and water (25 mL). The mixture was stirred for 2 hrs. The MeCN was removed under reduced pressure, and the aqueous layer was extracted with DCM (2×100 mL). The combined organic layers were washed with water (50 mL), then brine (100 mL), dried over $Na_2SO_4$, filtered into a flask and concentrated under reduced pressure. The crude residue was purified by chromatography thru a $SiO_2$ column using the mobile phase of 30% EtOAc in petroleum ether to afford the title compound as a brown liquid (1.8 g, 4.9 mmol, 77% yield). $^1$HNMR (400 MHz, $CDCl_3$): δ ppm 7.77 (d, 1H, J=2 Hz), 7.50, (dd, 1H, J=2 Hz, J=8 Hz), 7.12 (dd, 1H, J=2 Hz, J=8 Hz), 6.14 (s, 1H), 4.50 (s, 2H), 3.70 (s, 3H), 3.61 (s, 3H), 1.61 (brs, 1H), 1.56 (s, 6H).

Example 62f

Preparation of methyl 2-(5-(4-bromo-2-formylphenyl)-1-methyl-1H-pyrazol-3-yl)-2-methylpropanoate

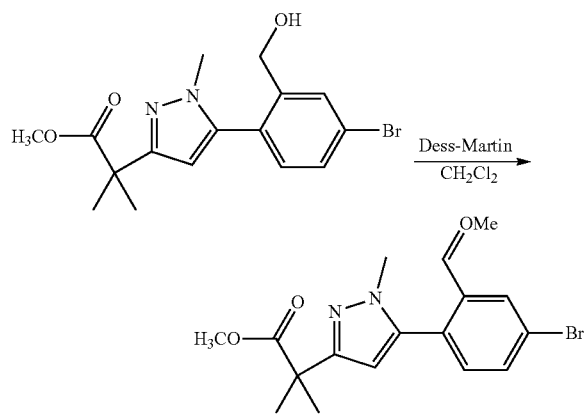

To a solution of Example 62e (3.0 g, 8.2 mmol) in DCM (100 mL) at 0° C. was added Dess-Martin Periodinane (6.9 g, 16 mmol). The mixture was stirred at rt for 2 hrs, then cooled to 0° C. and 10% $NaHCO_3$ was added. The reaction mixture was stirred for 30 min, and the layers separated. The aqueous layer was extracted with DCM (2×100 mL). The combined organic layers were washed with water (100 mL), then brine (100 mL), dried over $Na_2SO_4$, filtered into a round bottom flask and concentrated under reduced pressure. The crude residue was purified by chromatography thru a $SiO_2$ column using the mobile phase of 33% EtOAc in petroleum ether to afford the title compound as a yellow oil, (2.4 g, 6.5 mmol, 80% yield). $^1$HNMR (400 MHz, $CDCl_3$): δ ppm 9.83 (s, 1H), 8.17 (d, 1H, J=2.4 Hz), 7.80, (dd, 1H, J=2.4 Hz, J=8.4 Hz), 7.31 (d, 1H, J=8.4 Hz), 6.25 (s, 1H), 3.70 (s, 3H), 3.68 (s, 3H), 1.62 (s, 6H).

Example 62g

Preparation of methyl 2-(5-(4-bromo-2-(cyano(trimethylsilyloxy)methyl)phenyl)-1-methyl-1H-pyrazol-3-yl)-2-methylpropanoate

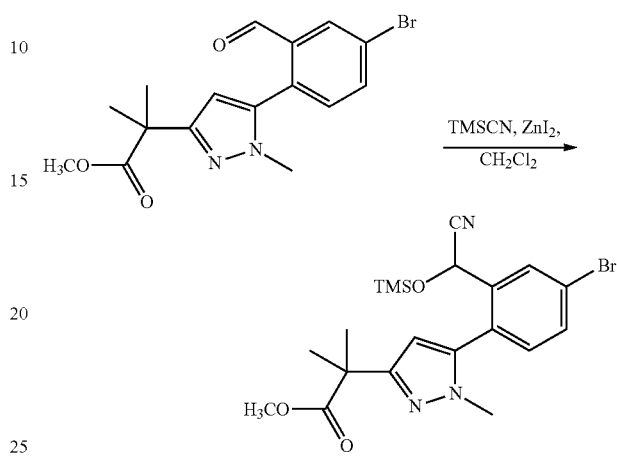

Zinc iodide (0.25 g, 0.77 mmol) was added to a cooled solution (0° C.) of Example 62f (2.8 g, 7.7 mmol) in DCM (70 mL). The mixture was stirred for 10 min before TMSCN (2.1 mL, 15 mmol) was added. The reaction mixture was stirred at rt for 18 hrs. The mixture was diluted with $H_2O$, and the layers separated. The aqueous layer was extracted with DCM (2×30 mL). The combined organic layers were washed with $H_2O$ (35 mL), then brine (20 mL), dried over $Na_2SO_4$, filtered into a round bottom flask and concentrated in vacuo to give the title compound as a light yellow solid (3.0 g, 6.5 mmol). MS (ESI) 464.0 [M+H]+.

Example 62h

Preparation of methyl 2-(5-(4-bromo-2-(2-(2,2-difluorobenzo[d][1,3]dioxol-5-yl)-2-hydroxyacetyl)phenyl)-1-methyl-1H-pyrazol-3-yl)-2-methylpropanoate

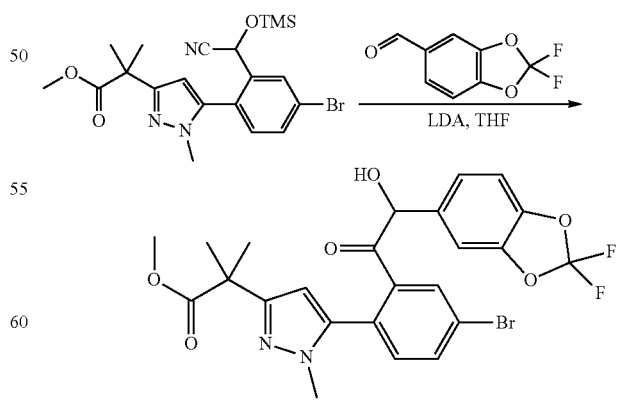

To a cooled solution (−78° C.) of Example 62g (500 mg, 1.1 mmol) in THF (15 mL) was added a 2.0 M solution of LDA (0.59 mL, 1.2 mmol) in THF. After stirring for 45 min, a solution of 2,2-difluorobenzo[d][1,3]dioxole-5-carbaldehyde (240 mg, 1.3 mmol) in THF (3.0 mL) was added dropwise. The reaction was stirred for 1 hr. The reaction mixture was quenched with 10 mL of 10% HCl. The layers were separated, and the aqueous layer was extracted with EtOAc (2×20 mL). The combined organic layers were washed with H₂O (10 mL), and brine (20 mL), dried over Na₂SO₄, filtered into a round bottom flask and concentrated in vacuo to give the crude compound as a light yellow oil (600 mg, 1.1 mmol). MS (ESI) 551.0 [M+H]+.

Example 62i

Preparation of methyl 2-(5-(2-(2-acetoxy-2-(2,2-difluorobenzo[d][1,3]dioxol-5-yl)acetyl)-4-bromophenyl)-1-methyl-1H-pyrazol-3-yl)-2-methylpropanoate

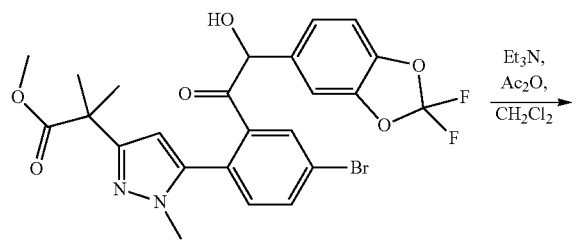

Ac₂O (0.15 mL, 1.6 mmol) was added to a cooled solution (0° C.) of Example 62h (600 mg, 1.1 mmol) and Et₃N (0.46 mL, 3.3 mmol) in DCM (25 mL). The mixture was allowed to stir at rt for 18 hrs. The mixture was diluted with H₂O, and the layers were separated. The aqueous layer was extracted with DCM (2×25 mL). The combined organic layers were washed with brine (50 mL), dried over Na₂SO₄, filtered into a round bottom flask and concentrated in vacuo to give the crude compound as a light brown oil (600 mg, 1.0 mmol). MS (ESI) 593.0 [M+H]+.

Example 62j

Preparation of methyl 2-(5-(4-bromo-2-(5-(2,2-difluorobenzo[d][1,3]dioxol-5-yl)-2-methyloxazol-4-yl)phenyl)-1-methyl-1H-pyrazol-3-yl)-2-methylpropanoate

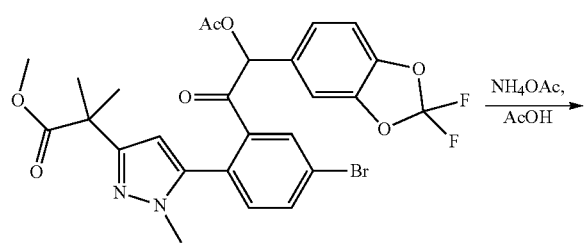

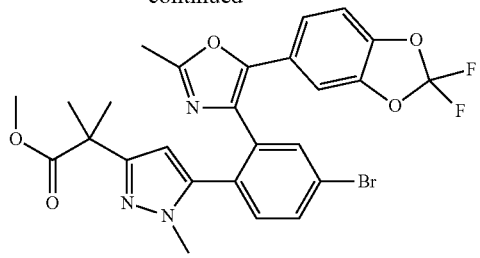

Ammonium acetate (780 mg, 10 mmol) was added to a solution of Example 62i (600 mg, 1.1 mmol) in AcOH (15 mL). The mixture was heated to 100° C. for 18 hrs. After being cooled to rt, the reaction mixture was concentrated in vacuo, neutralized with 10% NaOH and extracted with DCM (2×20 mL). The combined organic layers were washed with water (20 mL), and brine (20 mL), dried over Na₂SO₄, filtered into a round bottom flask and concentrated in vacuo to give the crude product. The crude residue was purified by chromatography thru a SiO₂ column using the mobile phase of 38% EtOAc in petroleum ether to afford the title compound as a light brown solid, (200 mg, 0.35 mmol, 34% yield). MS (ESI) 574.0 [M+H]+.

Example 62k

Preparation of 2-(5-(4-bromo-2-(5-(2,2-difluorobenzo[d][1,3]dioxol-5-yl)-2-methyloxazol-4-yl)phenyl)-1-methyl-1H-pyrazol-3-yl)-2-methylpropan-1-ol

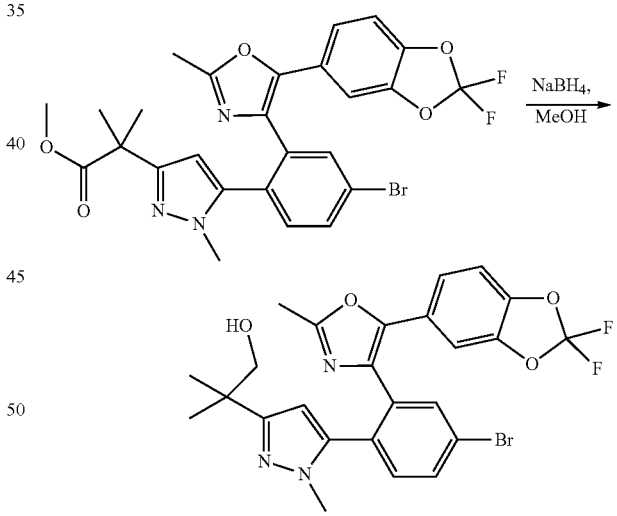

NaBH₄ (9.9 mg, 0.26 mmol) was added to a cooled solution (0° C.) of Example 62j (75 mg, 0.13 mmol) in MeOH (10 mL). The reaction mixture was stirred for 18 hrs at rt. The mixture was quenched with H₂O (10 mL), and extracted with EtOAc (2×30 mL). The combined organic layers were washed with H₂O (20 mL), and brine (20 mL), dried over Na₂SO₄, filtered into a flask and concentrated in vacuo to give the crude product. The crude residue was purified by chromatography thru a SiO₂ column using the mobile phase of 60% EtOAc in petroleum ether to afford the title compound as a light yellow semi-solid (40 mg, 0.073 mmol, 56% yield). MS (ESI) 546.0 [M+H]+.

Example 62

Preparation of 2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2-methylpropan-1-ol

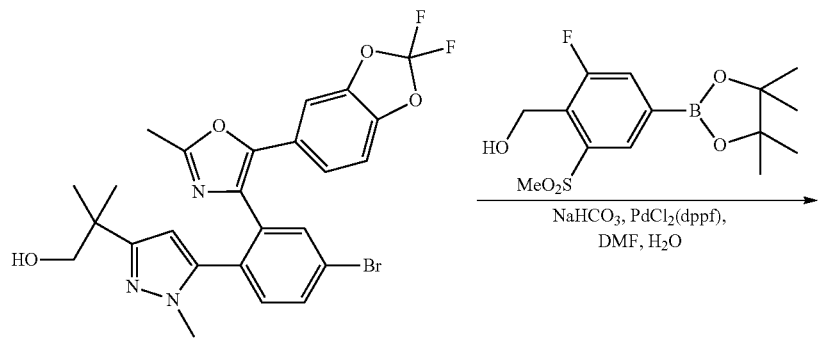

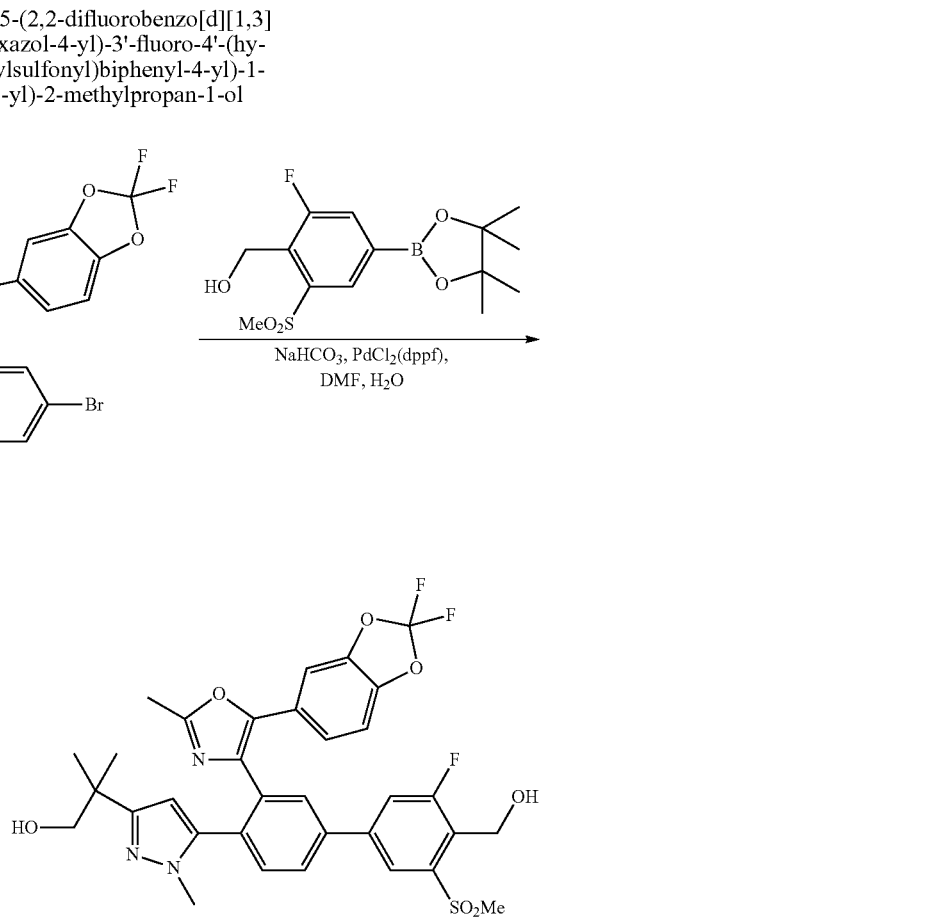

Example 62k (40 mg, 0.073 mmol), Intermediate 1 (36 mg, 0.11 mmol) and sodium bicarbonate (18 mg, 0.22 mmol) were dissolved in DMF (10 mL) and water (2 mL). The mixture was heated to 50° C. PdCl$_2$(dppf) (5.4 mg, 7.3 µmol) was added, and the temperature was raised to 80° C. for 45 min. The mixture was diluted with EtOAc (30 mL) and H$_2$O (10 mL), and the layers were separated. The aqueous layer was extracted with EtOAc (2×20 mL). The combined organic layers were washed with H$_2$O (10 mL), and brine (20 mL), dried over Na$_2$SO$_4$, filtered into a flask and concentrated in vacuo to give the crude product. The crude product was purified by preparative HPLC (Atlantis dC18 (250×19 m), 5µ; Mobile phase A: 10 mM NH$_4$OAc, Mobile phase B: MeOH; Flow: 15.0 mL/min (0-100%), RT=13.24) to afford the title compound as an off-white solid (6.8 mg, 0.099 mmol, 13% yield). MS (ESI) 670.2 [M+H]+. $^1$HNMR (400 MHz, CDCl$_3$): δ ppm 8.15 (d, 1H, J=1.2 Hz), 7.85 (d, 1H, J=1.6 Hz), 7.76, (dd, 1H, J=2 Hz, J=8 Hz), 7.66 (dd, 1H, J=2 Hz, J=8 Hz), 7.53 (dd, 1H, J=1.6 Hz, J=8 Hz), 7.09 (dd, 1H, J=1.6 Hz, J=8.4 Hz), 7.02 (d, 1H, J=1.6 Hz), 6.94 (d, 1H, J=8.4 Hz), 5.69 (s, 1H), 5.10 (d, 2H, J=1.6 Hz), 3.49 (s, 2H), 3.40 (s, 3H), 3.29 (s, 3H), 2.50 (s, 3H), 1.12 (s, 6H).

Example 63

2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2-methylpropanamide

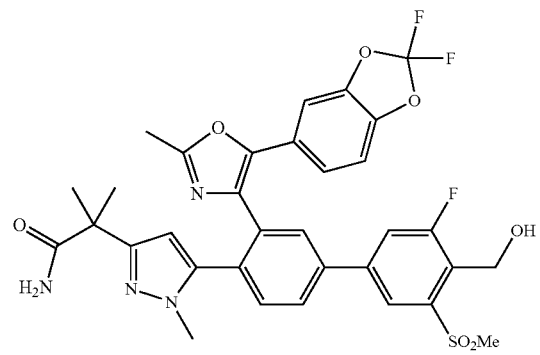 [SMILES: Cc1nc(-c2cc(-c3cc(F)c(CO)c(S(C)(=O)=O)c3)ccc2-c2cc(C(C)(C)C(N)=O)nn2C)c(-c2ccc3c(c2)OC(F)(F)O3)o1]

Example 63 was prepared from Example 62j using procedures similar to Example 55a, Example 56a and Example 62. MS (ESI) 683.2 [M+H]$^+$. 1H NMR (400 MHz, MeOH-d$_4$) δ ppm 8.22 (1H, s) 8.09 (1H, s) 8.00 (1H, dd, J=8.16, 2.13 Hz) 7.95 (1H, dd, J=10.54, 1.76 Hz) 7.67 (1H, d, J=8.03 Hz) 7.07-7.16 (3H, m) 5.86 (1H, s) 5.15 (2H, s) 3.45 (3H, s) 3.41 (3H, s) 2.55 (3H, s) 1.42 (6H, s).

Example 64

3-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2,3-dimethylbutan-2-ol

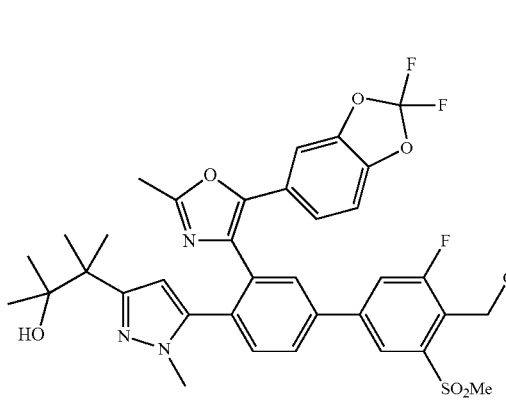

Example 64 was prepared from Example 62j using procedures similar to Example 54d and Example 62. MS (ESI) 698.2 [M+H]⁺. ¹H NMR (400 MHz, CDCl₃) δ ppm 8.14 (1H, s), 7.82 (1H, d, J=1.75 Hz), 7.78 (1H, dd, J=8.00, 2.00 Hz), 7.65 (1H, dd, J=10.01, 1.75 Hz), 7.51-7.58 (1H, m), 7.15 (1H, dd, J=8.25, 1.75 Hz), 7.10 (1H, d, J=1.50 Hz), 6.92-7.00 (1H, m), 5.76-5.80 (1H, m), 5.09 (2H, d, J=5.6), 3.46 (3H, s), 3.29 (3H, s), 2.88 (1H, t, J=6.8), 2.46 (3H, s), 1.18 (6H, s), 1.02 (6H, s).

Example 65

2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2-methylpropanamide

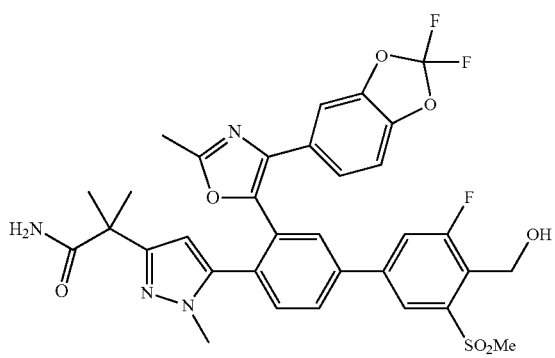 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C(N)=O)nn2C)o1]

Example 65a

Preparation of methyl 2-(5-(4-bromo-2-(4-(2,2-difluorobenzo[d][1,3]dioxol-5-yl)-2-methyloxazol-5-yl)phenyl)-1-methyl-1H-pyrazol-3-yl)-2-methylpropanoate

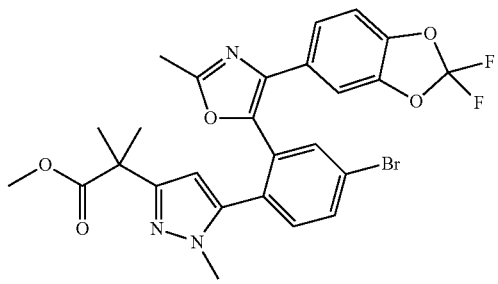 [SMILES: COC(=O)C(C)(C)c1cc(-c2ccc(Br)cc2-c2oc(C)nc2-c2ccc3c(c2)OC(F)(F)O3)n(C)n1]

Example 65a was prepared from Example 62f and Example 45a using procedures similar to that described in Examples 45c through Example 45e.

Example 65 was prepared from Example 65a using procedures similar to Example 55a, Example 56a and Example 62 (modified by using K₂CO₃ as a base rather than NaHCO₃). MS (ESI) 683.2 [M+H]⁺. ¹H NMR (400 MHz, CDCl₃) δ ppm 8.16 (s, 1H), 7.87 (d, 1H, J=1.75 Hz), 7.78 (dd, 1H, J=8.00, 2.00 Hz), 7.67 (dd, 1H, J=10.01, 1.75 Hz), 7.53 (d, 1H, J=8.00 Hz), 7.08 (dd, 1H, J=8.25, 1.50 Hz), 7.02 (d, 1H, J=1.50 Hz), 6.93 (d, 1H, J=8.51 Hz), 6.52 (br. s., 1H), 5.80 (s, 1H), 5.44-5.51 (m, 1H), 5.10 (d, 2H, J=1.50 Hz), 3.44 (s, 3H), 3.30 (s, 3H), 2.50 (s, 3H), 1.44 (s, 6H).

Example 66

3-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,3-dimethylbutan-2-ol

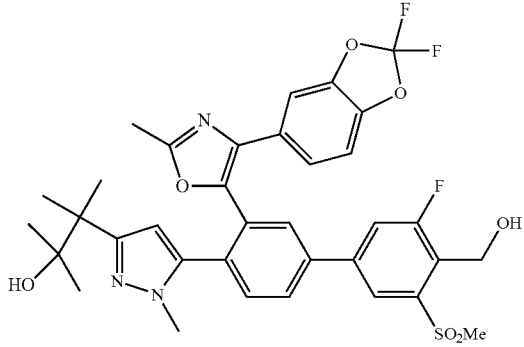 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C(C)(C)O)nn2C)o1]

Example 66 was prepared from Example 65a using procedures similar to Example 54d and Example 62 (modified by using K₂CO₃ as a base rather than NaHCO₃). MS (ESI) 698.2 [M+H]⁺. ¹H NMR (400 MHz, CDCl₃) δ ppm 8.14 (s, 1H), 7.82 (d, 1H, J=1.76 Hz), 7.78 (dd, 1H, J=8.03, 2.01 Hz), 7.65 (dd, 1H, J=10.04, 1.76 Hz), 7.56 (d, 1H, J=8.03 Hz), 7.16 (dd, 1H, J=8.41, 1.63 Hz), 7.11 (d, 1H, J=1.51 Hz), 6.94 (d, 1H, J=8.28 Hz), 5.78 (s, 1H), 5.10 (d, 2H, J=1.51 Hz), 3.47 (s, 3H), 3.29 (s, 3H), 2.47 (s, 3H), 1.19 (s, 6H), 1.02 (s, 6H).

Example 67

2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2-methylpropanenitrile

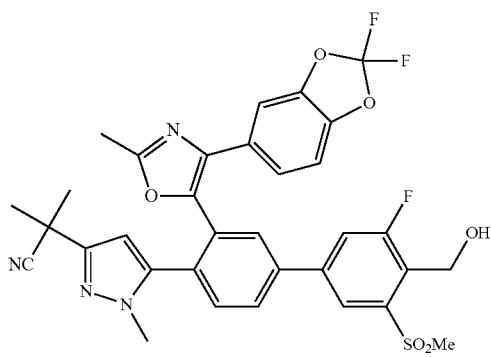 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C#N)nn2C)o1]

Example 67 was prepared from Example 65 using the procedure similar to Example 47. MS (ESI) 665.2 [M+H]⁺. ¹H NMR (400 MHz, MeOH-d₄) δ ppm 8.23 (s, 1H), 8.10 (d, 1H, J=1.76 Hz), 8.00 (d, 1H, J=8.03 Hz), 7.95 (d, 1H, J=10.29 Hz), 7.66 (d, 1H, J=8.03 Hz), 7.14 (s, 2H), 7.08 (s, 1H), 5.93 (s, 1H), 5.15 (s, 2H), 3.42 (d, 3H, J=13.05 Hz), 3.37 (s, 3H), 2.55 (s, 3H), 1.59 (s, 6H).

Example 68

(4'-(3-(2-(1,3,4-oxadiazol-2-yl)propan-2-yl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol

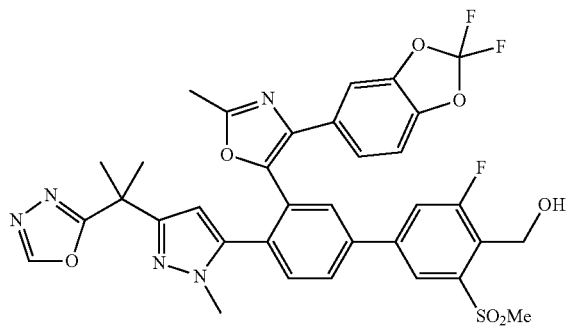 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)c3nnco3)nn2C)o1]

Example 68a

Preparation of 2-(5-(4-bromo-2-(4-(2,2-difluorobenzo[d][1,3]dioxol-5-yl)-2-methyloxazol-5-yl)phenyl)-1-methyl-1H-pyrazol-3-yl)-2-methylpropanehydrazide

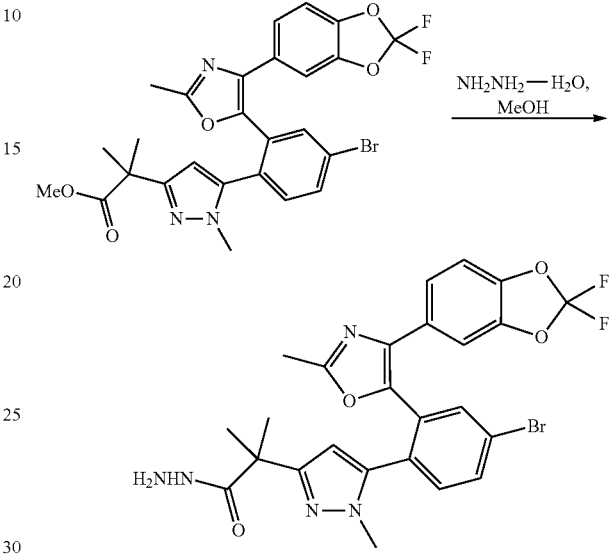

Example 65a (200 mg, 0.35 mmol) and hydrazine hydrate (0.035 mL, 0.67 mmol) were brought up in MeOH (5.0 mL) in a 25 mL sealed tube. The reaction mixture was stirred at 80° C. overnight and then concentrated under reduced pressure. The residue was dissolved in EtOAc (100 mL), washed with aq NaCl (100 mL), dried over Na₂SO₄, filtered into a round bottom flask and concentrated under reduced pressure to afford the title compound as a colorless solid (180 mg, 0.32 mmol, 90% yield). MS (ESI) 574.0 [M+H]⁺.

Example 68b

Preparation of 2-(2-(5-(4-bromo-2-(4-(2,2-difluorobenzo[d][1,3]dioxol-5-yl)-2-methyloxazol-5-yl)phenyl)-1-methyl-1H-pyrazol-3-yl)propan-2-yl)-1,3,4-oxadiazole

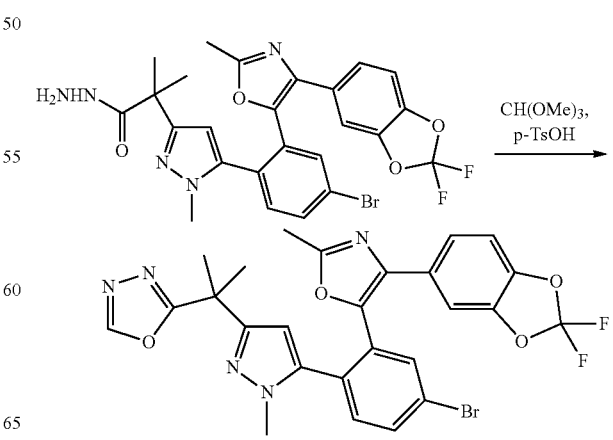

In a 25 mL round-bottomed flask equipped with a distillation apparatus, a mixture of Example 68a (100 mg, 0.17 mmol), trimethylorthoformate (19 μl, 0.17 mmol) and pTsOH (3.3 mg, 0.017 mmol) was heated to 80-120° C. removing MeOH by distillation. The reaction was cooled to rt, diluted with EtOAc (70 mL), washed with saturated aq NaHCO₃ (100 mL), and brine (100 mL), dried over Na₂SO₄, filtered into a flask and concentrated under reduced pressure to afford the title compound as a yellow solid, (90 mg, 0.11 mmol, 65% yield). MS (ESI) 584.0 [M+H]⁺.

Example 68 was prepared from Example 68b using a procedure similar to Example 62 (modified by using K₂CO₃ as a base rather than NaHCO₃). MS (ESI) 708.2 [M+H]⁺. ¹H NMR (400 MHz, MeOH-d₄) δ ppm 8.90 (s, 1H), 8.22 (s, 1H), 8.08 (d, 1H, J=1.76 Hz), 7.91-8.02 (m, 2H), 7.64 (d, 1H, J=8.03 Hz), 7.09-7.15 (m, 2H), 7.06 (d, 1H, J=1.76 Hz), 5.80 (s, 1H), 5.15 (s, 2H) 3.36 (s, 6H), 2.53 (s, 3H), 1.69 (s, 6H).

Example 69

1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-N,N-dimethylmethanesulfonamide

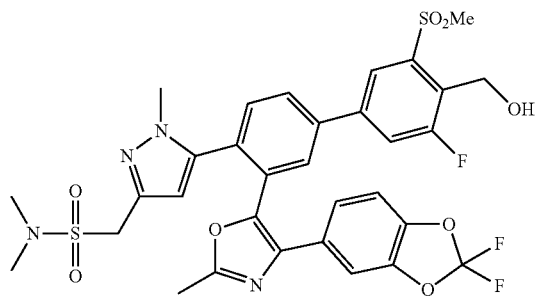 [SMILES: Cc1nc(-c2ccc3c(c2)OC(F)(F)O3)c(-c2cc(-c3cc(F)c(CO)c(S(C)(=O)=O)c3)ccc2-c2cc(CS(=O)(=O)N(C)C)nn2C)o1]

Example 69a

Preparation of sodium (5-(4-bromo-2-(4-(2,2-difluorobenzo[d][1,3]dioxol-5-yl)-2-methyloxazol-5-yl)phenyl)-1-methyl-1H-pyrazol-3-yl)methanesulfonate

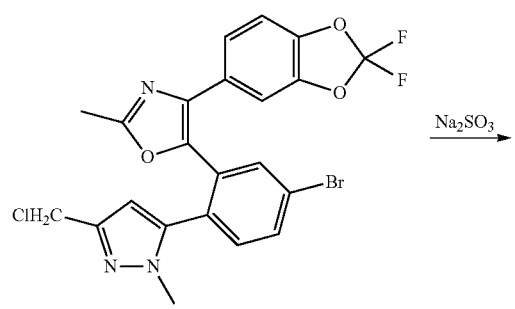

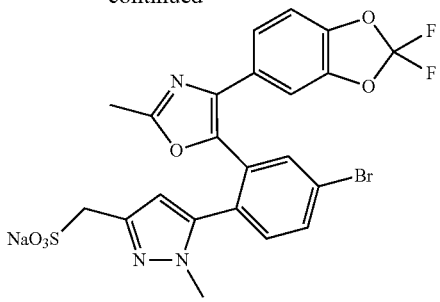

To a 100 mL round-bottomed flask was added Example 58a (500 mg, 0.960 mmol) in EtOH (20 mL). Then sodium sulfite (241 mg, 1.91 mmol) in water (20 mL) was added to the reaction mixture. The resulting mixture was heated to reflux for 5 h, and then cooled to rt. After removal of the solvents, the residue was dissolved in benzene which was then removed under vacuum (3×5 mL). The residue was dried under vacuum to give the title compound (560 mg, crude) as white colour solid, which was taken forward without further purification. MS (ESI) 570.1 [M+H]⁺.

Example 69b

Preparation of 1-(5-(4-bromo-2-(4-(2,2-difluorobenzo[d][1,3]dioxol-5-yl)-2-methyloxazol-5-yl)phenyl)-1-methyl-1H-pyrazol-3-yl)-N,N-dimethylmethanesulfonamide

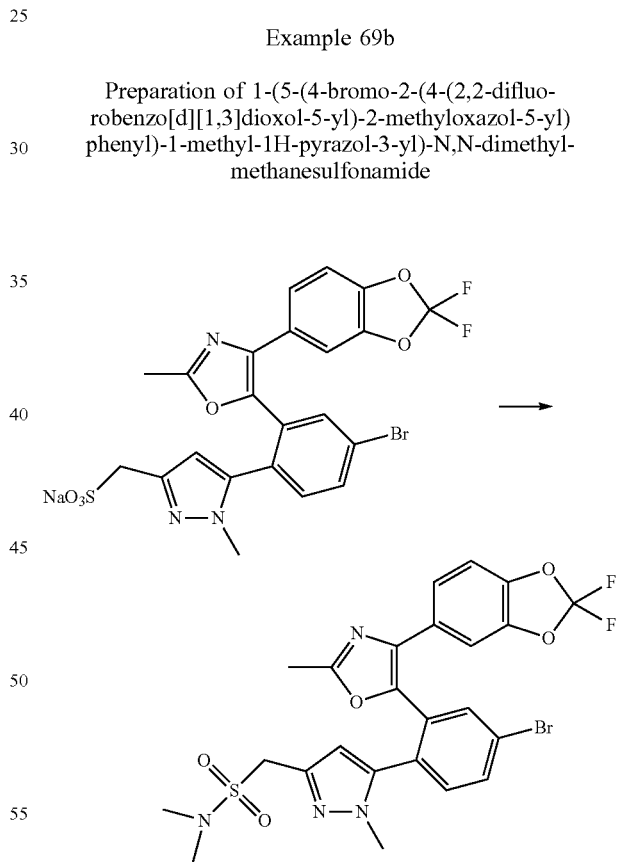

In a 50 mL round-bottomed flask Example 69a (100 mg, 0.17 mmol) was added to DCE (15 mL) to give a white suspension. Then SOCl₂ (0.025 mL, 0.34 mmol) was added drop wise at 0° C. and under a nitrogen atmosphere. The reaction mixture was stirred for 3 hrs at rt. Then dimethyl amine in THF (5 mL, 10 mmol of amine) was added drop wise to the above solution at 10° C. Then reaction mixture was stirred for 1 hr at rt. Then the reaction mixture was diluted with DCM (40 mL) and washed with H₂O, sat'd.

NH₄Cl, and brine. The organic layer was dried with Na₂SO₄, filtered and concentrated at reduced pressure to obtain a yellow colour crude product, which was taken forward without further purification. MS (ESI) 597.22 [M+H]⁺.

Example 69 was prepared from Example 69b and Intermediate 1 using a procedure similar to that described in Example 62, except that K₂CO₃ was used as a base and dioxane/water was the reaction solvent. MS (ESI) 719.2 [M+H]⁺. ¹H NMR (400 MHz, METHANOL-d₄) δ ppm 8.20 (1H, s), 8.00-8.06 (2H, m), 7.89-7.94 (2H, m), 7.69 (1H, d, J=8.03 Hz), 7.19 (1H, s), 7.13 (2H, app. s), 6.11 (1H, s), 5.14 (2H, d, J=1.76 Hz), 4.21 (2H, s), 3.55 (3H, s), 3.39 (3H, s), 2.75 (6H, s), 2.52 (3H, s).

The following compounds were prepared in a manner similar to that described in the experimental procedures:

| Ex # | Structure | Name | Characterization |
|---|---|---|---|
| 70 | 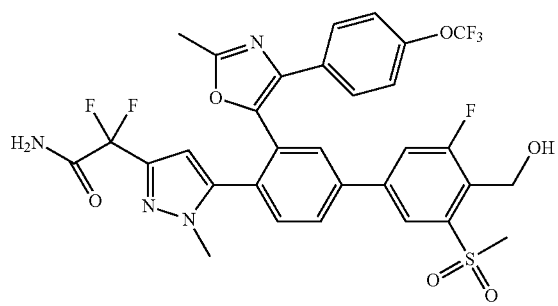 [SMILES: Cc1nc(-c2ccc(OC(F)(F)F)cc2)c(-c2cc(-c3cc(F)c(CO)c(S(C)(=O)=O)c3)ccc2-c2cc(C(F)(F)C(N)=O)nn2C)o1] | 2,2-difluoro-2-(5-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1-methyl-1H-pyrazol-3-yl)acetamide | MS (ESI) 696 [M + H]+ ¹H NMR (400 MHz, METHANOL-d₄) δ ppm 8.23 (1 H, s) 8.09 (1 H, d, J = 1.76 Hz) 8.00 (1 H, dd, J = 8.28, 2.01 Hz) 7.90 (1 H, dd, J = 10.42, 1.88 Hz) 7.67 (1 H, d, J = 8.03 Hz) 7.35-7.40 (2 H, m) 7.22 (2 H, d, J = 8.03 Hz) 6.14 (1 H, s) 5.15 (2 H, d, J = 1.76 Hz) 3.49 (3 H, s) 3.41 (3 H, s) 2.53 (3 H, s) |
| 71 | 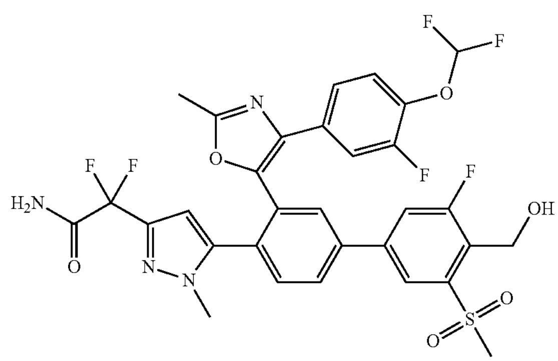 [SMILES: Cc1nc(-c2ccc(OC(F)F)c(F)c2)c(-c2cc(-c3cc(F)c(CO)c(S(C)(=O)=O)c3)ccc2-c2cc(C(F)(F)C(N)=O)nn2C)o1] | 2-(5-(3-(4-(4-(difluoromethoxy)-3-fluorophenyl)-2-methyloxazol-5-yl)-fluoro-4'-(hydroxymethyl)-5'-(methylsulfonyl)biphenyl-4-yl)-1-methyl-1H-pyrazol-3-yl)-2,2-difluoroacetamide | MS (ESI) 695 [M + H]+ ¹H NMR (400 MHz, CDCl₃-d) δ ppm 8.15 (1 H, s) 7.90 (1 H, s) 7.78 (1 H, d, J = 7.78 Hz) 7.67 (1 H, d, J = 9.79 Hz) 7.52 (1 H, d, J = 7.78 Hz) 7.01-7.18 (3 H, m) 6.39-6.81 (2 H, m) 6.18 (1 H, s) 5.59 (1 H, br. s.) 5.07-5.14 (2 H, m) 3.47 (3 H, s) 3.30 (3 H, s) 2.87 (1 H, br. s.) 2.51 (3 H, s) |
| 72 | 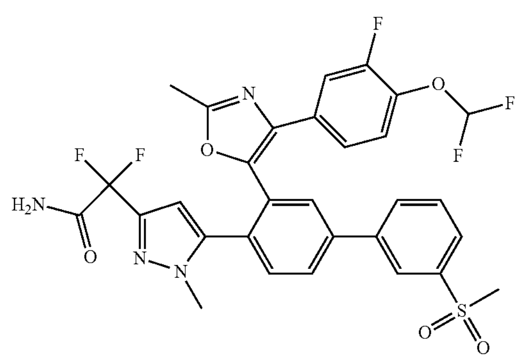 [SMILES: Cc1nc(-c2ccc(OC(F)F)c(F)c2)c(-c2cc(-c3cccc(S(C)(=O)=O)c3)ccc2-c2cc(C(F)(F)C(N)=O)nn2C)o1] | 2'-(5-(3-(4-(4-(difluoromethoxy)-3-fluorophenyl)-2-methyloxazol-5-yl)-3'-(methylsulfonyl)biphenyl-4-yl)-1-methyl-1H-pyrazol-3-yl)-2,2-difluoroacetamide | MS (ESI) 647 [M + H]+ ¹H NMR (400 MHz, CDCl₃-d) δ ppm 8.20 (1 H, t, J = 1.63 Hz) 7.98-8.03 (1 H, m) 7.89-7.94 (2 H, m) 7.80 (1 H, dd, J = 8.13, 1.88 Hz) 7.69-7.75(1 H, m) 7.49-7.54 (1 H, m) 7.03-7.18 (3 H, m) 6.38-6.81 (2 H, m) 6.16-6.20 (1 H, m) 5.60 (1 H, br. s.) 3.48 (3 H, s) 3.12 (3 H, s) 2.50 (3 H, s) |
| 73 | 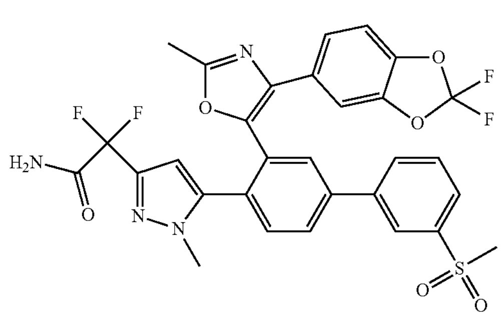 [SMILES: Cc1nc(-c2ccc3c(c2)OC(F)(F)O3)c(-c2cc(-c3cccc(S(C)(=O)=O)c3)ccc2-c2cc(C(F)(F)C(N)=O)nn2C)o1] | 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2,2-difluoroacetamide | MS (ESI) 644 [M + H]+ ¹H NMR (400 MHz, CDCl₃) δ ppm 8.21 (1 H, t, J = 1.76 Hz) 8.00 (1 H, d, J = 7.78 Hz) 7.92 (2 H, d, J = 2.01 Hz) 7.79 (1 H, dd, J = 8.03, 2.01 Hz) 7.69-7.76 (1 H, m) 7.51 (1 H, d, J = 8.03 Hz) 7.00-7.06 (2 H, m) 6.91-6.96 (1 H, m) 6.49 (1 H, br. s.) 6.15 (1 H, s) 5.63 (1 H, br. s.) 3.46 (3 H, s) 3.12 (3 H, s) 2.50 (3 H, s) |

-continued

| Ex # | Structure | Name | Characterization |
|---|---|---|---|
| 74 | 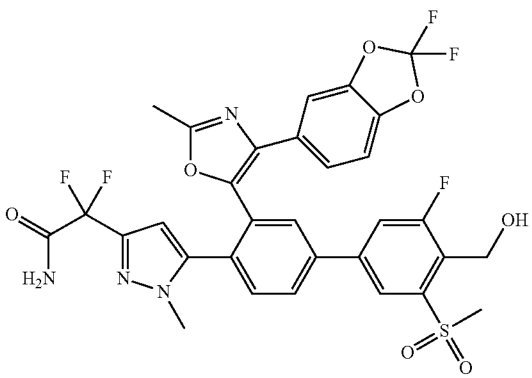 | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide | MS (ESI) 691 [M + H]+ $^1$H NMR (400 MHz, CDCl$_3$) δ ppm 8.16 (1 H, s) 7.90 (1 H, d, J = 1.76 Hz) 7.78 (1 H, dd, J = 8.03, 2.01 Hz) 7.63-7.71 (1 H, m) 7.52 (1 H, d, J = 8.03 Hz) 7.00-7.06 (2 H, m) 6.92-6.97 (1 H, m) 6.50 (1 H, br. s.) 6.17 (1 H, s) 5.65 (1 H, br. s.) 5.12 (2 H, s) 3.47 (3 H, s) 3.31 (3 H, s) 2.52 (3 H, s) |
| 75 | 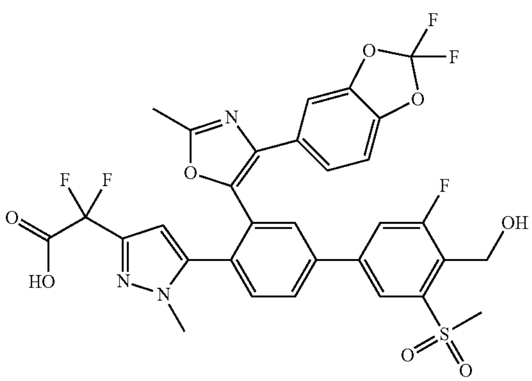 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)O)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetic acid | MS (ESI) 692.1 [M + H]+ |
| 76 | 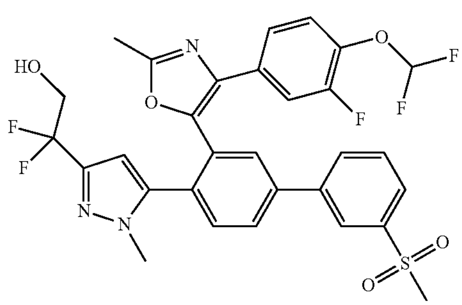 [SMILES: Cc1nc(-c2ccc(OC(F)F)c(F)c2)c(-c2cc(-c3cccc(S(C)(=O)=O)c3)ccc2-c2cc(C(F)(F)CO)nn2C)o1] | 2-(5-(3-(4-(4-(difluoromethoxy)-3-fluorophenyl)-2-methyloxazol-5-yl)-3'-(methylsulfonyl)biphenyl-4-yl)-1-methyl-1H-pyrazol-3-yl)-2,2-difluoroethanol | MS (ESI) 634 [M + H]+ |
| 77 | 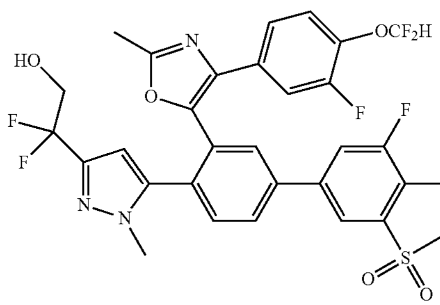 | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroethanol | MS (ESI) 682 [M + H]+ |

| Ex # | Structure | Name | Characterization |
|---|---|---|---|
| 78 | 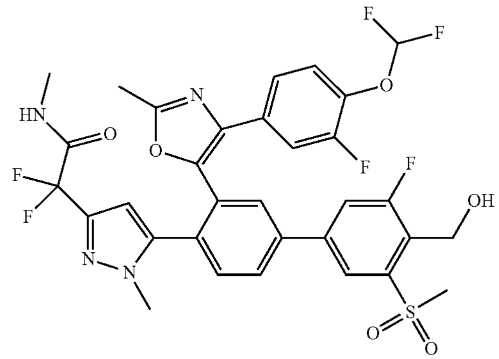 [SMILES: CNC(=O)C(F)(F)c1cc(-c2ccc(-c3cc(F)c(CO)c(S(C)(=O)=O)c3)cc2-c2oc(C)nc2-c2ccc(OC(F)F)c(F)c2)n(C)n1] | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide | MS (ESI) 709.2 [M + H]+ <br> 1H NMR (400 MHz, METHANOL-d4) δ ppm 8.21 (1 H, d, J = 1.26 Hz) 8.10 (1 H, d, J = 1.76 Hz) 8.02 (1 H, dd, J = 8.03, 2.01 Hz) 7.94 (1 H, dd, J = 10.54, 1.76 Hz) 7.69 (1 H, d, J = 8.03 Hz) 7.16-7.25 (2 H, m) 7.08-7.12 (1 H, m) 6.69-7.08 (1 H, m) 6.18 (1 H, s) 5.15 (2 H, d, J = 1.76 Hz) 3.52 (3 H, s) 3.41 (3 H, s) 2.86 (3 H, s) 2.53 (3 H, s) |
| 79 | 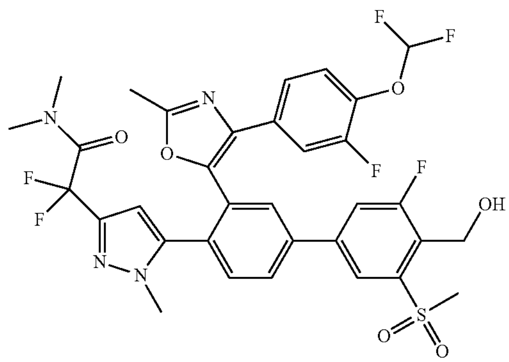 [SMILES: Cc1nc(-c2ccc(OC(F)F)c(F)c2)c(-c2cc(-c3cc(F)c(CO)c(S(C)(=O)=O)c3)ccc2-c2cc(C(F)(F)C(=O)N(C)C)nn2C)o1] | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N,N-dimethylacetamide | MS (ESI) 723.2 [M + H]+ <br> 1H NMR (400 MHz, METHANOL-d4) δ ppm 8.22 (1 H, d, J = 1.25 Hz) 8.11 (1 H, d, J = 1.76 Hz) 8.04 (1 H, dd, J = 8.03, 2.01 Hz) 7.95 (1 H, dd, J = 10.42, 1.88 Hz) 7.72 (1 H, d, J = 8.03 Hz) 7.18-7.26 (2 H, m) 7.09-7.14 (1 H, m) 6.68-7.08 (1 H, m) 6.20 (1 H, s) 5.15 (2 H, d, J = 1.76 Hz) 3.54 (3 H, s) 3.41 (3 H, s) 3.06 (3 H, s) 2.96 (3 H, s) 2.53 (3 H, s) |
| 80 | 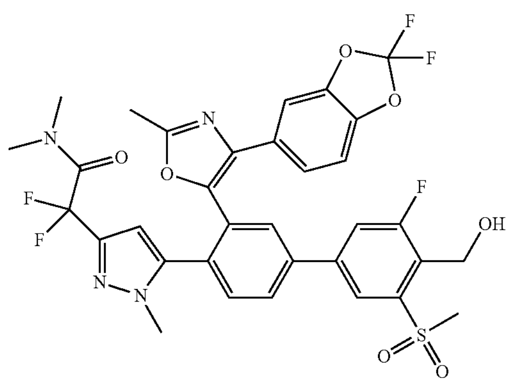 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)N(C)C)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N,N-dimethylacetamide | MS (ESI) 719.3 [M + H]+ <br> 1H NMR (400 MHz, METHANOL-d4) δ ppm 8.22 (1 H, d, J = 1.25 Hz) 8.10 (1 H, d, J = 1.76 Hz) 8.02 (1 H, dd, J = 8.03, 2.01 Hz) 7.94 (1 H, dd, J = 10.54, 2.01 Hz) 7.69 (1 H, d, J = 8.03 Hz) 7.03-7.16 (3 H, m) 6.17 (1 H, s) 5.15 (2 H, s) 3.50 (3 H, s) 3.40 (3 H, s) 3.05 (3 H, s) 2.98 (3 H, s) 2.53 (3 H, s) |
| 81 | 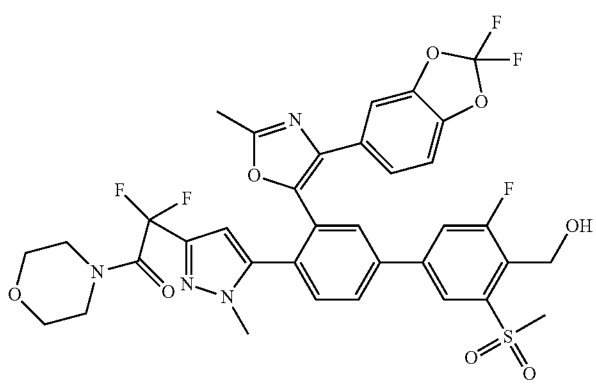 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)N3CCOCC3)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-1-morpholinoethanone | MS (ESI) 760.8 [M + H]+ |

| Ex # | Structure | Name | Characterization |
|---|---|---|---|
| 82 | 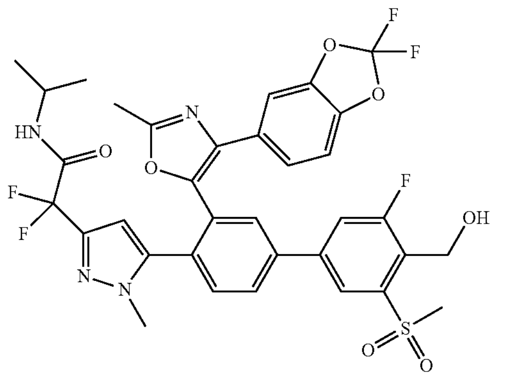 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NC(C)C)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-isopropylacetamide | MS (ESI) 732.8 [M + H]$^+$ |
| 83 | 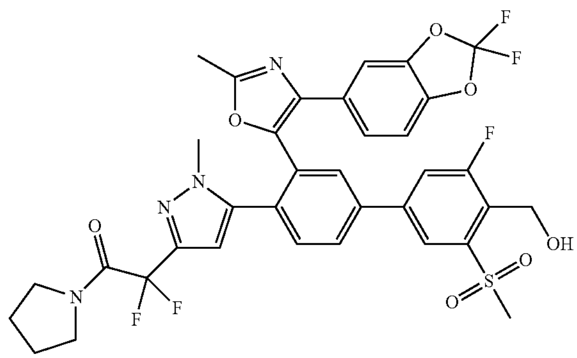 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)N3CCCC3)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoro-1-(pyrrolidin-1-yl)ethanone | MS (ESI) 745 [M + H]$^+$ |
| 84 | 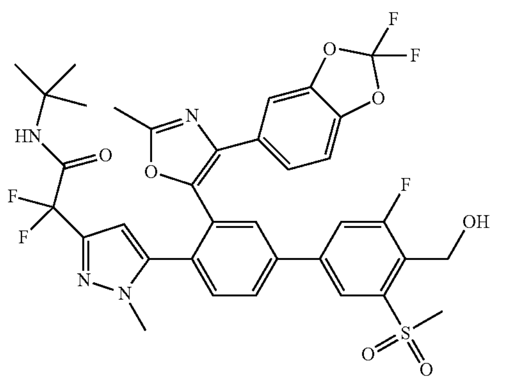 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NC(C)(C)C)nn2C)o1] | N-tert-butyl-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide | MS (ESI) 747.0 [M + H]$^+$ |
| 85 | 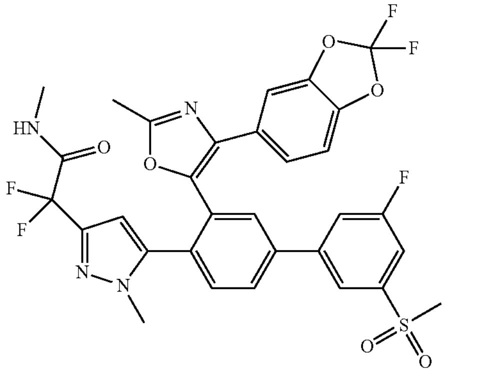 [SMILES: CNC(=O)C(F)(F)c1cc(-c2ccc(-c3cc(F)cc(S(C)(=O)=O)c3)cc2-c2oc(C)nc2-c2ccc3c(c2)OC(F)(F)O3)n(C)n1] | 2-(5-(3-(4-(2,2-difluorobenzo[d][1,3]dioxol-5-yl)-2-methyloxazol-5-yl)-3'-fluoro-5'-(methylsulfonyl)biphenyl-4-yl)-1-methyl-1H-pyrazol-3-yl)-2,2-difluoro-N-methylacetamide | MS (ESI) 675.0 [M + H]$^+$ |

| Ex # | Structure | Name | Characterization |
|---|---|---|---|
| 86 | 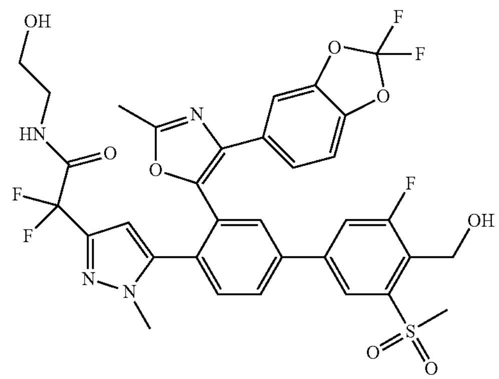 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCCO)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-(2-hydroxyethyl)acetamide | MS (ESI) 735.2 [M + H]$^+$ |
| 87 | 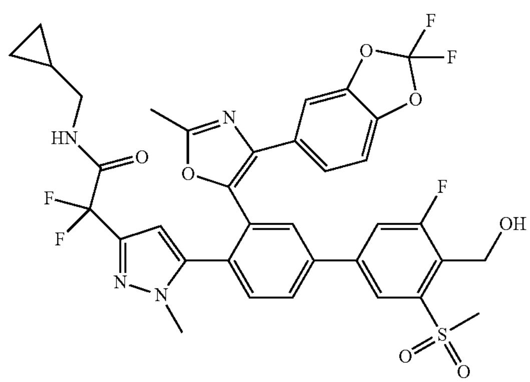 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCC3CC3)nn2C)o1] | N-(cyclopropylmethyl)-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide | MS (ESI) 745.0 [M + H]$^+$ |
| 88 | 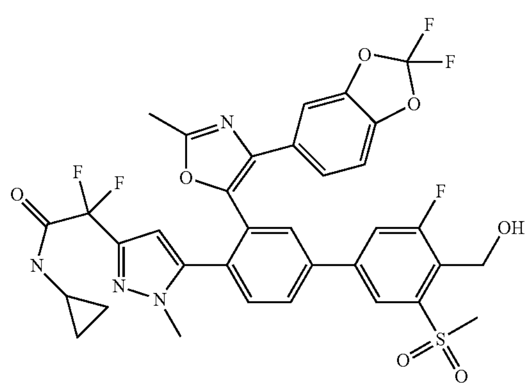 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NC3CC3)nn2C)o1] | N-cyclopropyl-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide | MS (ESI) 731.0 [M + H]$^+$ |
| 89 | 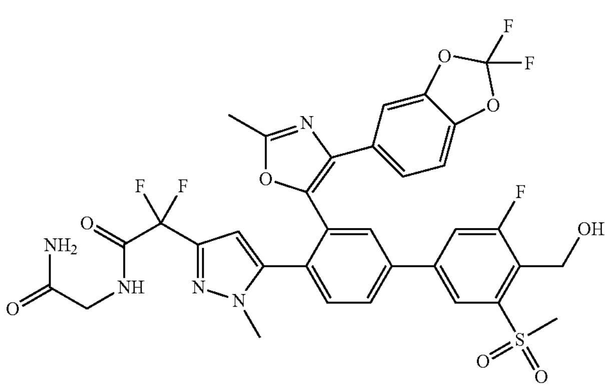 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCC(N)=O)nn2C)o1] | N-(2-amino-2-oxoethyl)-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide | MS (ESI) 748.0 [M + H]$^+$ |

| Ex # | Structure | Name | Characterization |
|---|---|---|---|
| 90 | 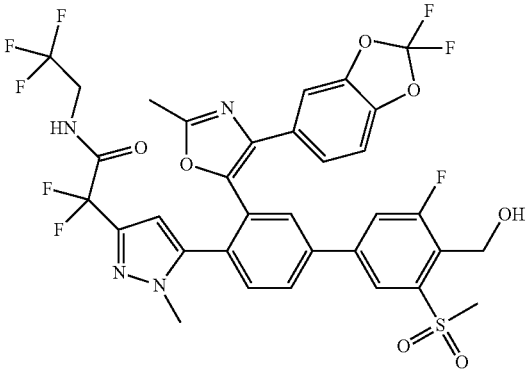 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCC(F)(F)F)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-(2,2,2-trifluoroethyl)acetamide | MS (ESI) 773.0 [M + H]+ |
| 91 | 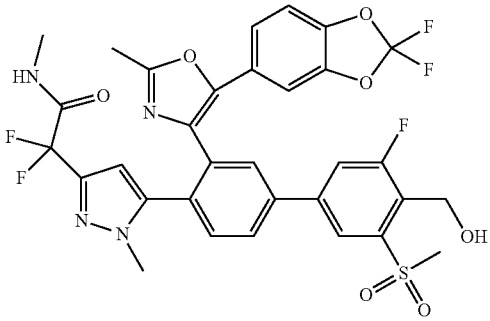 | 2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide | MS (ESI) 657.2 [M + H]+. 1H NMR (400 MHz, METHANOL-d4) δ ppm 8.20 (1 H, d, J = 1.25 Hz) 8.09 (1 H, d, J = 1.76 Hz) 8.00 (1 H, dd, J = 8.03, 2.01 Hz) 7.93 (1 H, dd, J = 10.54, 1.76 Hz) 7.66 (1 H, d, J = 8.03 Hz) 7.01-7.14 (3 H, m) 6.14 (1 H, s) 5.15 (2 H, s) 3.48 (3 H, s) 3.40 (3 H, s) 2.85 (3 H, s) 2.53 (3 H, s) |
| 92 | 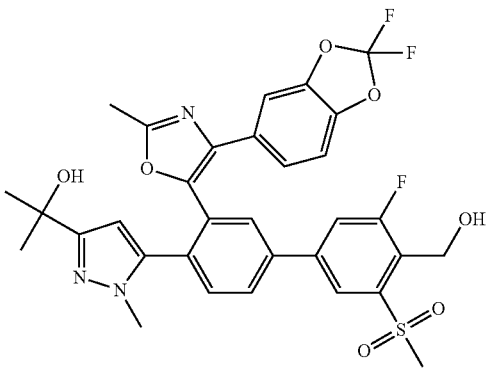 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)O)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)propan-2-ol | MS (ESI) 656.2 [M + H]+ |
| 93 | 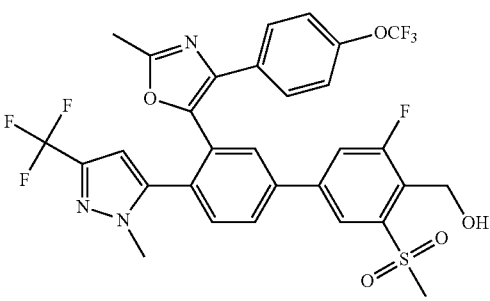 [SMILES: Cc1nc(-c2ccc(OC(F)(F)F)cc2)c(-c2cc(-c3cc(F)c(CO)c(S(C)(=O)=O)c3)ccc2-c2cc(C(F)(F)F)nn2C)o1] | (3-fluoro-4'-(1-methyl-3-(trifluoromethyl)-1H-pyrazol-5-yl)-3'-(2-methyl-4-(4-(trifluoromethoxy)phenyl)oxazol-5-yl)-5-(methylsulfonyl)biphenyl-4-yl)methanol | MS (ESI) 670 [M + H]+ |

| Ex # | Structure | Name | Characterization |
|---|---|---|---|
| 94 | 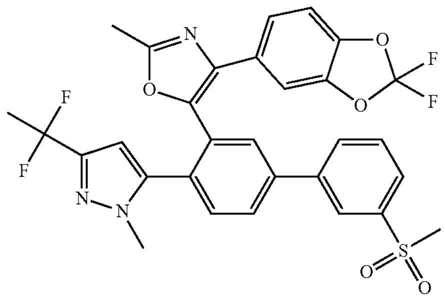 [SMILES: Cc1nc(-c2ccc3c(c2)OC(F)(F)O3)c(-c2cc(-c3cccc(S(C)(=O)=O)c3)ccc2-c2cc(C(C)(F)F)nn2C)o1] | 4-(2,2-difluorobenzo[d][1,3]dioxol-5-yl)-5-(4-(3-(1,1-difluoroethyl)-1-methyl-1H-pyrazol-5-yl)-3'-(methylsulfonyl)biphenyl-3-yl)-2-methyloxazole | MS (ESI) 614.2 [M + H]⁺ |
| 95 | 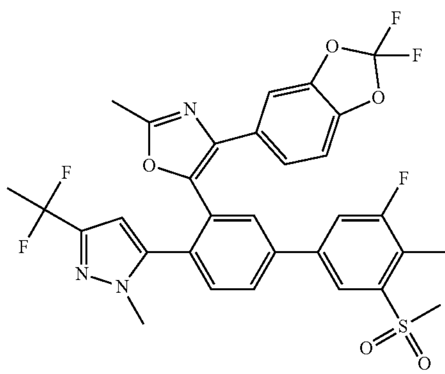 | (3'-(4-(2,2-difluorobenzo[d][1,3]dioxol-5-yl)-2-methyloxazol-5-yl)-4'-(3-(1,1-difluoroethyl)-1-methyl-1H-pyrazol-5-yl)-3-fluoro-5-(methylsulfonyl)biphenyl-4-yl)methanol | MS (ESI) 662.2 [M + H]⁺<br>¹H NMR (400 MHz, METHANOL-d₄) δ ppm 8.24 (1 H, d, J = 1.26 Hz) 8.12 (1 H, d, J = 1.76 Hz) 7.89-8.02 (2 H, m) 7.65 (1 H, d, J = 8.03 Hz) 6.99-7.13 (3 H, m) 6.00 (1 H, s) 5.16 (2 H, s) 3.44 (3 H, s) 3.41 (3 H, s) 2.56 (3 H, s) 1.82-1.94 (3 H, m) |
| 96 | 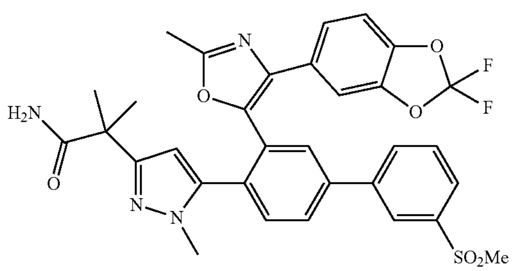 [SMILES: Cc1nc(-c2ccc3c(c2)OC(F)(F)O3)c(-c2cc(-c3cccc(S(C)(=O)=O)c3)ccc2-c2cc(C(C)(C)C(N)=O)nn2C)o1] | 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2-methylpropanamide | MS (ESI) 635.2 [M + H]⁺ |
| 97 | 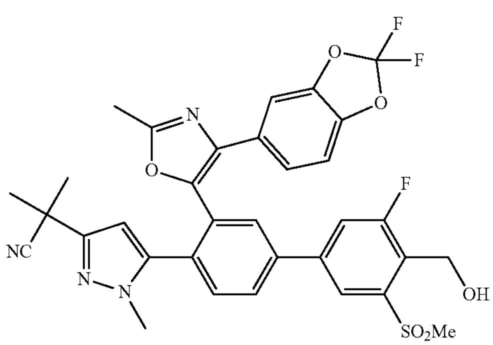 | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2-methylpropanenitrile | MS (ESI) 617.2 [M + H]⁺<br>¹H NMR (400 MHz, METHANOL-d₄) δ ppm 8.23 (1 H, s) 8.14 (1 H, d, J = 1.76 Hz) 8.01 (1 H, dd, J = 8.28, 2.01 Hz) 7.95 (1 H, dd, J = 10.42, 1.63 Hz) 7.67 (1 H, d, J = 8.03 Hz) 7.00-7.13 (3 H, m) 6.23 (1 H, s) 5.15 (2H, d, J = 1.76 Hz) 3.51 (3 H, s) 3.41 (3H, s) 2.55 (3 H, s) 1.65 (6 H, s) |

| Ex # | Structure | Name | Characterization |
|---|---|---|---|
| 98 | 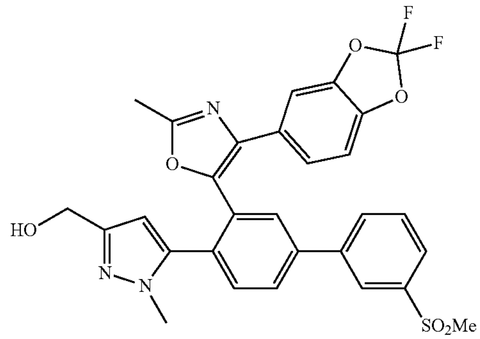 [SMILES: Cc1nc(-c2ccc3c(c2)OC(F)(F)O3)c(-c2cc(-c3cccc(S(C)(=O)=O)c3)ccc2-c2cc(CO)nn2C)o1] | (5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)methanol | MS (ESI) 580.2 [M + H]+ |
| 99 | 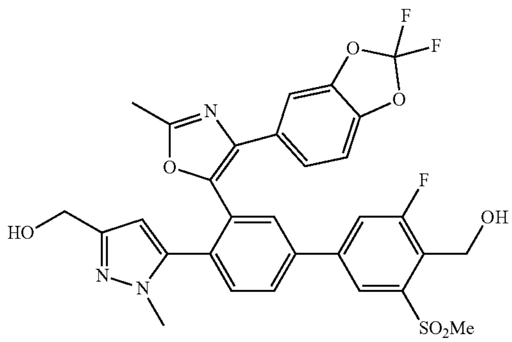 [SMILES: Cc1nc(-c2ccc3c(c2)OC(F)(F)O3)c(-c2cc(-c3cc(F)c(CO)c(S(C)(=O)=O)c3)ccc2-c2cc(CO)nn2C)o1] | (5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)methanol | MS (ESI) 628.0 [M + H]+ |
| 100 | 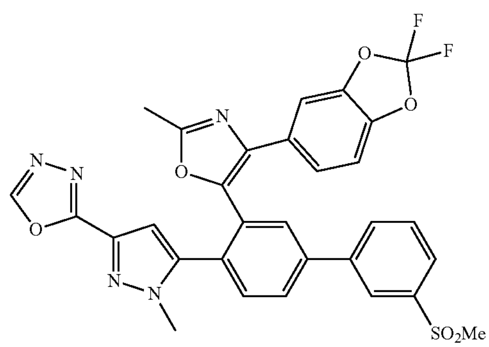 [SMILES: Cc1nc(-c2ccc3c(c2)OC(F)(F)O3)c(-c2cc(-c3cccc(S(C)(=O)=O)c3)ccc2-c2cc(-c3nnco3)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)-1,3,4-oxadiazole | MS (ESI) 618.2 [M + H]+ |
| 101 | 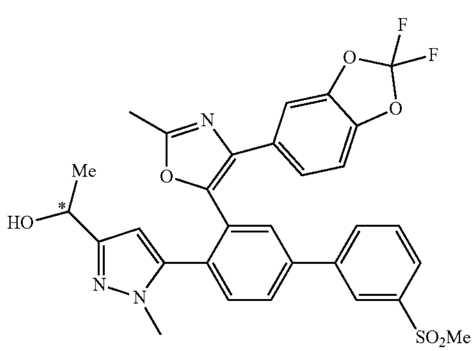 [SMILES: Cc1nc(-c2ccc3c(c2)OC(F)(F)O3)c(-c2cc(-c3cccc(S(C)(=O)=O)c3)ccc2-c2cc(C(C)O)nn2C)o1] | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethanol | MS (ESI) 594.2 [M + H]+ Specific optical rotation: [α]25D = +8.00 (c 0.1, MeOH) $^1$H NMR (400 MHz, METHANOL-d$_4$) δ ppm 8.28 (1 H, s) 7.97-8.13 (4 H, m) 7.77-7.84 (1 H, m) 7.64 (1 H, d, J = 7.78 Hz) 7.05-7.16 (3 H, m) 5.90 (1 H, s) 4.65-4.74 (1 H, m) 3.44 (3 H, s) 3.20-3.25 (3 H, s) 2.54 (3 H, s) 1.37 (3 H, d, J = 6.53 Hz) |

-continued

| Ex # | Structure | Name | Characterization |
|---|---|---|---|
| 102 | 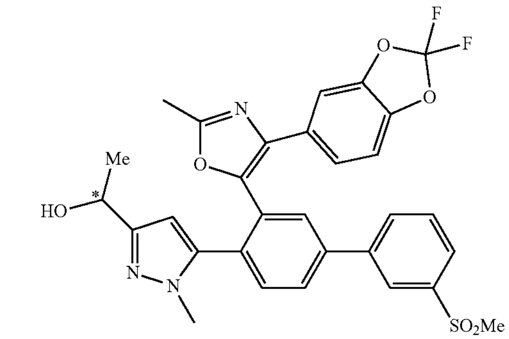 [SMILES: Cc1nc(-c2ccc3c(c2)OC(F)(F)O3)c(-c2cc(-c3cccc(S(C)(=O)=O)c3)ccc2-c2cc(C(C)O)nn2C)o1] | 1-(5-(3-(4-(2,2-difluorobezo[d][1,3]dioxol-5-yl)-2-methyloxazol-5-yl)-3'-(methylsulfonyl)[1,1']-biphenyl]-4-yl)-1-methyl-1H-pyrazol-3-yl)ethanol | MS (ESI) 594.2 [M + H]+ Specific optical rotation: [α]25D = −7.60 (c 0.1, MeOH) ¹H NMR (400 MHz, METHANOL-d₄) δ ppm 8.28 (1 H, s) 7.97-8.13 (4 H, m) 7.77-7.84 (1 H, m) 7.64 (1 H, d, J = 7.78 Hz) 7.05-7.16 (3 H, m) 5.90 (1 H, s) 4.65-4.74 (1 H, m) 3.44 (3 H, s) 3.20-3.25 (3 H, s) 2.54 (3 H, s) 1.37 (3 H, d, J = 6.53 Hz) |
| 103 | 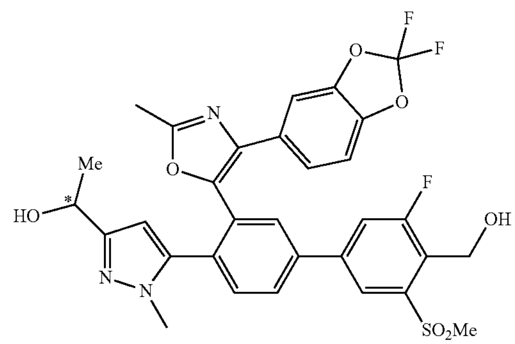 [SMILES: Cc1nc(-c2ccc3c(c2)OC(F)(F)O3)c(-c2cc(-c3cc(F)c(CO)c(S(C)(=O)=O)c3)ccc2-c2cc(C(C)O)nn2C)o1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethanol | MS (ESI) 642.2 [M + H]+ Specific optical relation: [α]25D = +7.60 (c 0.1, MeOH) ¹H NMR (400 MHz, METHANOL-d₄) δ ppm 8.21 (1 H, s) 8.07 (1 H, d, J = 1.76 Hz) 7.88-8.03 (2 H, m) 7.65 (1 H, d, J = 8.28 Hz) 7.02-7.17 (3 H, m) 5.90 (1 H, s) 5.15 (2 H, d, J = 2.01 Hz) 4.70 (1 H, d, J = 6.53 Hz) 3.44 (3 H, s) 3.42 (3 H, s) 2.54 (3 H, s) 1.36 (3 H, d, J = 6.53 Hz) |
| 104 | 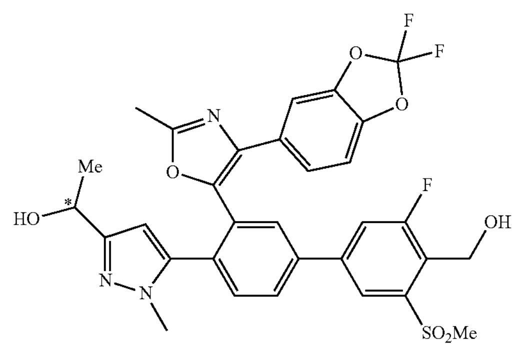 [SMILES: Cc1nc(-c2ccc3c(c2)OC(F)(F)O3)c(-c2cc(-c3cc(F)c(CO)c(S(C)(=O)=O)c3)ccc2-c2cc(C(C)O)nn2C)o1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethanol | MS (ESI) 642.2 [M + H]+ Specific optical rotation: [α]25D = −4.40 (c 0.1, MeOH) ¹H NMR (400 MHz, METHANOL-d₄) δ ppm 8.21 (1 H, s) 8.07 (1 H, d, J = 1.76 Hz) 7.88-8.03 (2 H, m) 7.65 (1 H, d, J = 8.28 Hz) 7.02-7.17 (3 H, m) 5.90 (1 H, s) 5.15 (2 H, d, J = 2.01 Hz) 4.70 (1 H, d, J = 6.53 Hz) 3.44 (3 H, s) 3.42 (3 H, s) 2.54 (3 H, s) 1.36 (3 H, d, J = 6.53 Hz) |
| 105 | 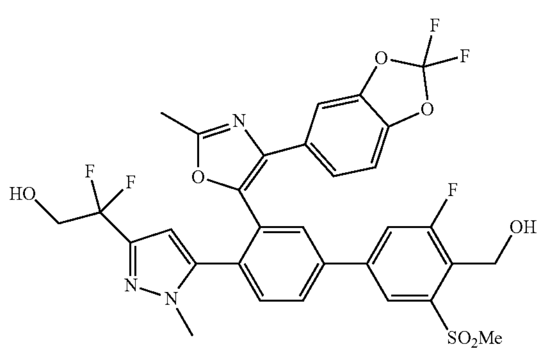 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)CO)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoroethanol | MS (ESI) 678.4 [M + H]+ ¹H NMR (400 MHz, CDCl₃) δ ppm 8.16 (1 H, s) 7.90 (1 H, d, J = 1.75 Hz) 7.78 (1 H, dd, J = 8.00, 2.00 Hz) 7.67 (1 H, dd, J = 9.88, 1.88 Hz) 7.46-7.54 (1 H, m) 6.89-7.05 (3 H, m) 6.07 (1 H, s) 5.11 (2 H, d, J = 1.75 Hz) 4.04 (2H, t, J = 12.4 Hz) 3.44 (3 H, s) 3.30 (3 H, s) 2.53 (3H, s) |

-continued

| Ex # | Structure | Name | Characterization |
|---|---|---|---|
| 106 | 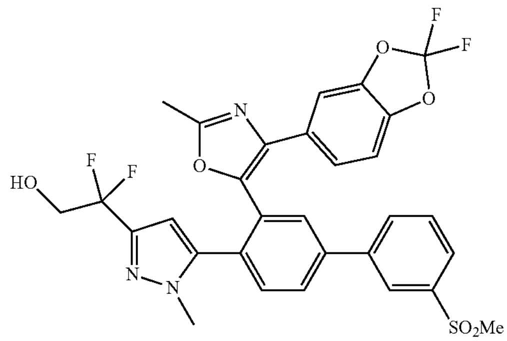 [SMILES: Cc1nc(-c2ccc3c(c2)OC(F)(F)O3)c(-c2cc(-c3cccc(S(C)(=O)=O)c3)ccc2-c2cc(C(F)(F)CO)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)-2,2-difluoroethanol | MS (ESI) 630.4 [M + H]+ |
| 107 | 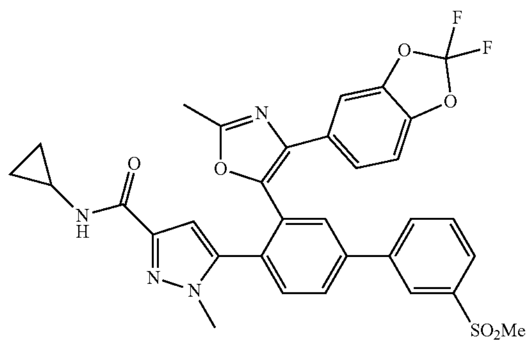 [SMILES: Cc1nc(-c2ccc3c(c2)OC(F)(F)O3)c(-c2cc(-c3cccc(S(C)(=O)=O)c3)ccc2-c2cc(C(=O)NC3CC3)nn2C)o1] | N-cyclopropyl-5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carboxamide | MS (ESI) 633.2 [M + H]+ |
| 108 | 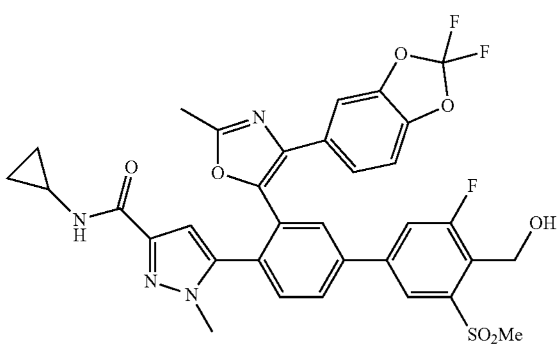 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NC3CC3)nn2C)o1] | N-cyclopropyl-5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carboxamide | MS (ESI) 681.2 [M + H]+ |
| 109 | 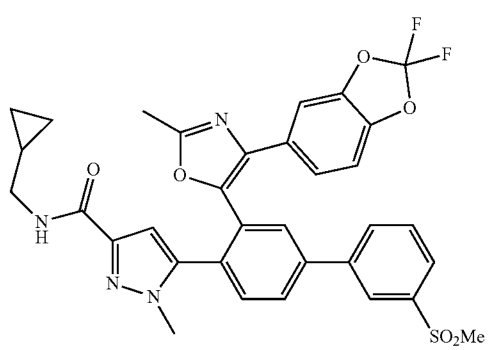 [SMILES: Cc1nc(-c2ccc3c(c2)OC(F)(F)O3)c(-c2cc(-c3cccc(S(C)(=O)=O)c3)ccc2-c2cc(C(=O)NCC3CC3)nn2C)o1] | N-(cyclopropylmethyl)-5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carboxamide | MS (ESI) 647.2 [M + H]+ |

| Ex # | Structure | Name | Characterization |
|---|---|---|---|
| 110 | 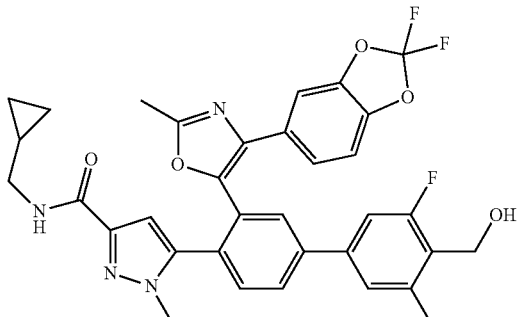 | N-(cyclopropylmethyl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carboxamide | MS (ESI) 695.2 [M + H]+ |
| 111 | 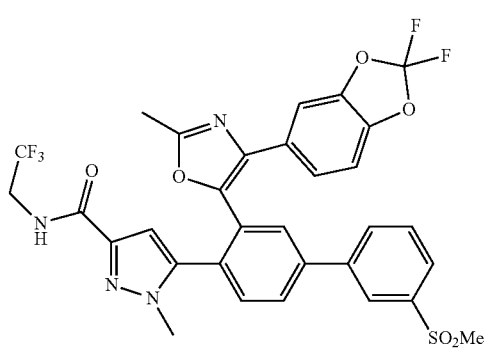 [SMILES: Cc1nc(-c2ccc3c(c2)OC(F)(F)O3)c(-c2cc(-c3cccc(S(C)(=O)=O)c3)ccc2-c2cc(C(=O)NCC(F)(F)F)nn2C)o1] | 5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-N-(2,2,2-trifluoroethyl)-1H-pyrazole-3-carboxamide | MS (ESI) 675.0 [M + H]+ |
| 112 | 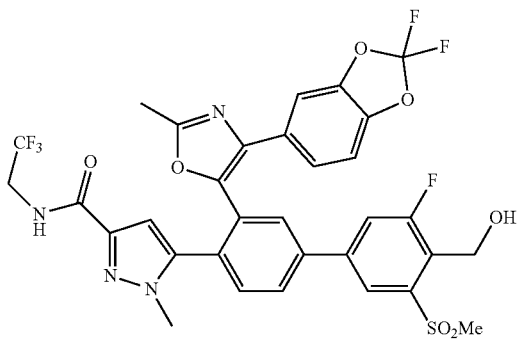 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NCC(F)(F)F)nn2C)o1] | 5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-N-(2,2,2-trifluoroethyl)-1H-pyrazole-3-carboxamide | MS (ESI) 723.0 [M + H]+ |
| 113 | 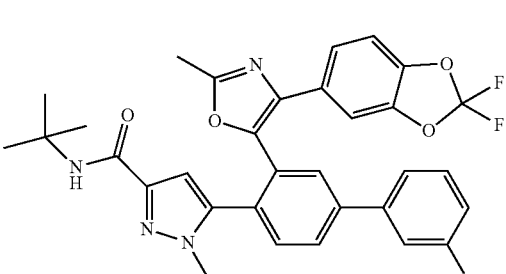 | N-(tert-butyl)-5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carboxamide | MS (ESI) 649.2 [M + H]+ |

| Ex # | Structure | Name | Characterization |
|---|---|---|---|
| 114 | 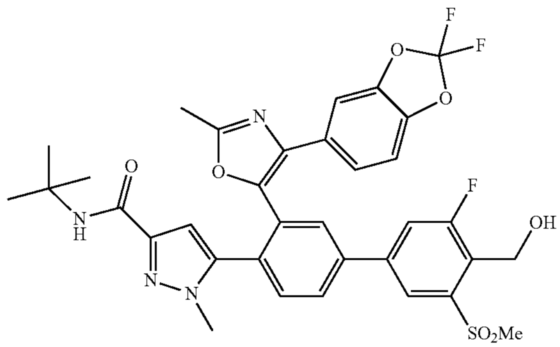 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NC(C)(C)C)nn2C)o1] | N-(tert-butyl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carboxamide | MS (ESI) 697.2 [M + H]$^+$ |
| 115 | 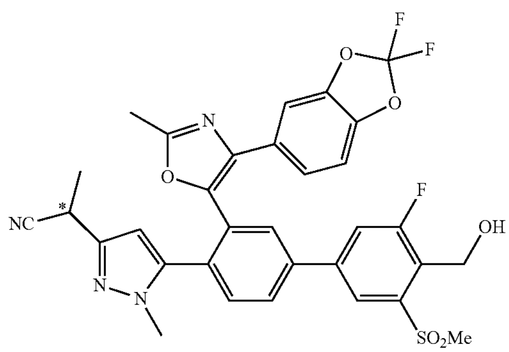 [SMILES: Cc1nc(-c2ccc3c(c2)OC(F)(F)O3)c(-c2cc(-c3cc(F)c(CO)c(S(C)(=O)=O)c3)ccc2-c2cc(C(C)C#N)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)propanenitrile | MS (ESI) 651.2 [M + H]$^+$<br>Specific optical rotation: [α]25D = −2 (c 0.1, MeOH)<br>1H NMR (400 MHz, DMSO-d6) d ppm 8.06-8.13 (3 H, m) 8.04 (1 H, dd, J = 8.03, 2.01 Hz) 7.69 (1 H, d, J = 8.03 Hz) 7.28 (1 H, d, J = 8.53 Hz) 7.19 (1 H, d, J = 1.51 Hz) 7.01 (1 H, dd, J = 8.28, 1.76 Hz) 5.84 (1 H, s) 5.54 (1 H, t, J = 5.2 Hz) 4.94 (2 H, dd, J = 5.27, 1.51 Hz) 4.06 (1H, q, J = 14.8 Hz), 3.43 (3 H, s) 3.38 (3 H, s), 2.46 (3 H, s) 1.36 (3 H, d, J = 7.2 Hz) |
| 116 | 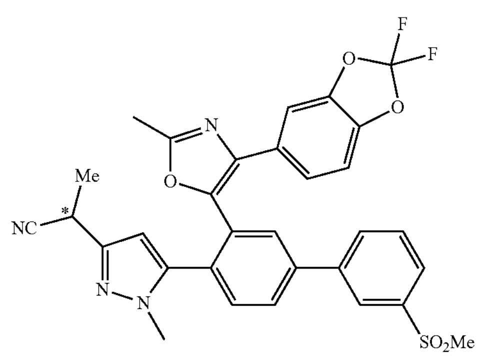 [SMILES: Cc1nc(-c2ccc3c(c2)OC(F)(F)O3)c(-c2cc(-c3cccc(S(C)(=O)=O)c3)ccc2-c2cc(C(C)C#N)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)propanenitrile | MS (ESI) 603.2 [M + H]$^+$<br>Specific optical rotation: [α]25D = +2 (c 0.1, MeOH)<br>$^1$H NMR (400 MHz, DMSO-d$_6$) δ ppm 8.29 (1 H, t, J = 1.63 Hz) 8.13-8.22 (2 H, m) 8.07 (1 H, dd, J = 8.03, 2.01 Hz) 7.95-8.02 (1 H, m) 7.76-7.85 (1 H, m) 7.71 (1 H, d, J = 8.03 Hz) 7.31 (1 H, d, J = 8.53 Hz) 7.21 (1 H, d, J = 1.51 Hz) 7.03 (1 H, dd, J = 8.28, 1.76 Hz) 5.85 (1 H, s) 4.09 (1 H, q, J = 7.28 Hz) 2.46 (3 H, s) 3.41 (3 H, s) 3.32 (3 H, s) 2.50 (3 H, s) 1.40 (3 H, d, J = 6.53 Hz) |
| 117 | 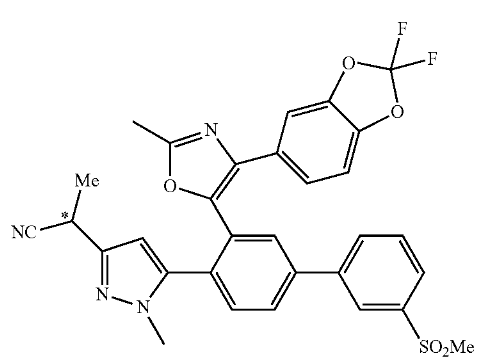 [SMILES: Cc1nc(-c2ccc3c(c2)OC(F)(F)O3)c(-c2cc(-c3cccc(S(C)(=O)=O)c3)ccc2-c2cc(C(C)C#N)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)propanenitrile | MS (ESI) 603.2 [M + H]$^+$<br>Specific optical relation: [α]25D = −2 (c 0.1, MeOH)<br>$^1$H NMR (400 MHz, DMSO-d$_6$) δ ppm 8.29 (1 H, t, J = 1.63 Hz) 8.13-8.22 (2 H, m) 8.05 (1 H, dd, J = 8.03, 2.01 Hz) 7.95-8.02 (1 H, m) 7.75-7.85 (1 H, m) 7.69 (1 H, d, J = 8.03 Hz) 7.31 (1 H, d, J = 8.53 Hz) 7.21 (1 H, d, J = 1.51 Hz) 7.03 (1 H, dd, J = 8.28, 1.76 Hz) 5.85 (1 H, s) 4.08 (1 H, q, J = 7.28 Hz) 2.46 (3 H, s) 3.41 (3 H, s) 3.32 (3 H, s) 2.50 (3 H, s) 1.40 (3 H, d, J = 6.53 Hz) |

-continued

| Ex # | Structure | Name | Characterization |
|---|---|---|---|
| 118 | 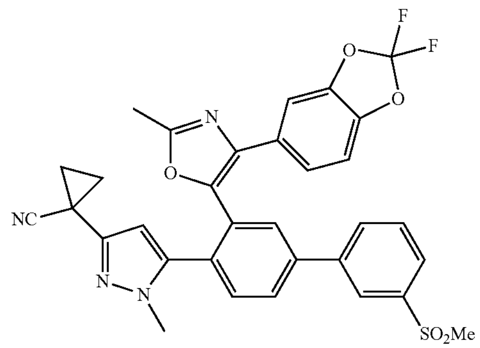 [SMILES: Cc1nc(-c2ccc3c(c2)OC(F)(F)O3)c(-c2cc(-c3cccc(S(C)(=O)=O)c3)ccc2-c2cc(C3(C#N)CC3)nn2C)o1] | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)cyclopropanecarbonitrile | MS (ESI) 615.2 [M + H]$^+$ |
| 119 | 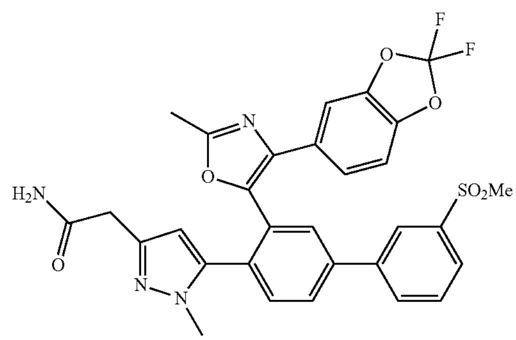 [SMILES: Cc1nc(-c2ccc3c(c2)OC(F)(F)O3)c(-c2cc(-c3cccc(S(C)(=O)=O)c3)ccc2-c2cc(CC(N)=O)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)acetamide | MS (ESI) 607.2 [M + H]$^+$ |
| 120 | 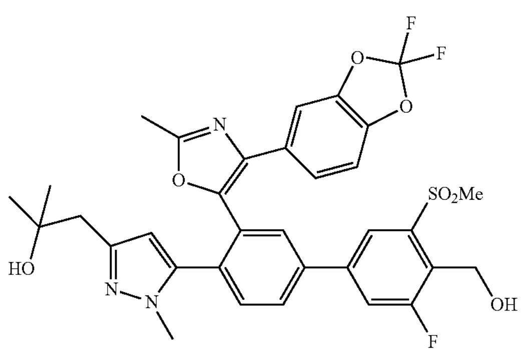 [SMILES: Cc1nc(-c2ccc3c(c2)OC(F)(F)O3)c(-c2cc(-c3cc(F)c(CO)c(S(C)(=O)=O)c3)ccc2-c2cc(CC(C)(C)O)nn2C)o1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2-methylpropan-2-ol | MS (ESI) 670.2 [M + H]$^+$ |
| 121 | 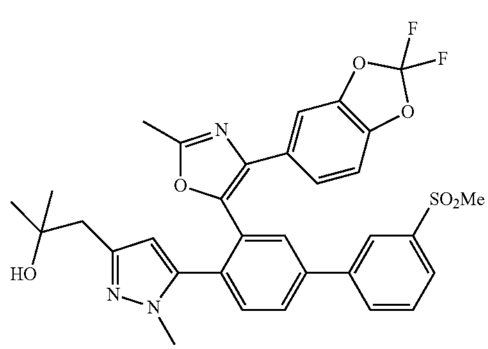 [SMILES: Cc1nc(-c2ccc3c(c2)OC(F)(F)O3)c(-c2cc(-c3cccc(S(C)(=O)=O)c3)ccc2-c2cc(CC(C)(C)O)nn2C)o1] | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)-2-methylpropan-2-ol | MS (ESI) 622.2 [M + H]$^+$ |

| Ex # | Name | Characterization |
|---|---|---|
| 122 | 5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carbonitrile | MS (ESI) 623.4 [M + H]+ <br> 1H NMR (400 MHz, CDCl3) δ ppm 8.13 (1 H, d, J = 1.25 Hz) 7.88 (1 H, d, J = 1.75 Hz) 7.80 (1 H, dd, J = 8.13, 1.88 Hz) 7.64 (1 H, dd, J = 9.88, 1.88 Hz) 7.48-7.55 (1 H, m) 7.05-7.13 (1 H, m) 6.93-7.04 (2 H, m) 6.27 (1 H, s) 5.10 (2 H, s) 3.53-3.61 (3 H, s) 3.29 (3 H, s) 2.50 (3 H, s) |
| 123 | 5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carbonitrile | MS (ESI) 575.2 [M + H]+ |
| 124 | N-(2-hydroxy-2-methylpropyl)-1-methyl-5-(3-(2-methyl-4-(4-(trifluoromethoxy)phenyl)oxazol-5-yl)-3'-methylsulfonyl)-[1,1'-biphenyl]-4-yl)-1H-pyrazole-3-carboxamide | |
| 125 | (3-chloro-4'-(1-methyl-3-(trifluoromethyl)-1H-pyrazol-5-yl)-3'-(2-methyl-4-(4-(trifluoromethoxy)phenyl)oxazol-5-yl)-5-(methylsulfonyl)-[1,1'-biphenyl]-4-yl)methanol | MS (ESI) 686.1 [M + H]+ |
| 126 | 4'-(1-methyl-3-(trifluoromethyl)-1H-pyrazol-5-yl)-3'-(2-methyl-4-(4-(trifluoromethoxy)phenyl)oxazol-5-yl)-[1,1'-biphenyl]-3-sulfonamide | |

| Ex # | Structure | Name | Characterization |
|------|-----------|------|------------------|
| 127 | 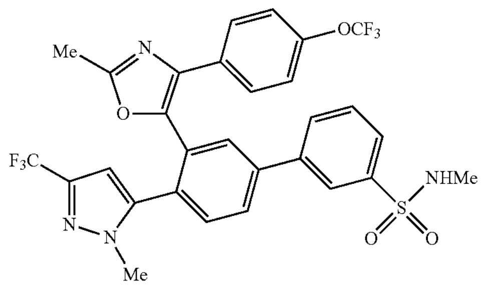 [SMILES: CNS(=O)(=O)c1cccc(-c2ccc(-c3cc(C(F)(F)F)nn3C)c(-c3oc(C)nc3-c3ccc(OC(F)(F)F)cc3)c2)c1] | N-methyl-4'-(1-methyl-3-(trifluoromethyl)-1H-pyrazol-5-yl)-3'-(2-methyl-4-(trifluoromethoxy)phenyl)oxazol-5-yl)-[1,1'-biphenyl]-3-sulfonamide | MS (ESI) 637.2 [M + H]+ |
| 128 | 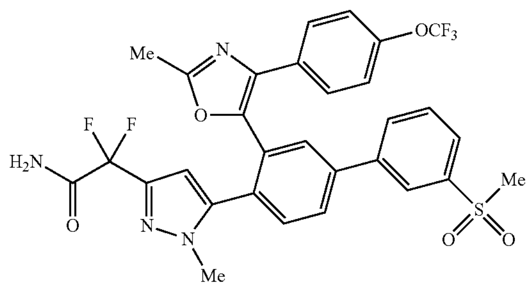 [SMILES: Cc1nc(-c2ccc(OC(F)(F)F)cc2)c(-c2cc(-c3cccc(S(C)(=O)=O)c3)ccc2-c2cc(C(F)(F)C(N)=O)nn2C)o1] | 2,2-difluoro-2-(1-methyl-5-(3-(2-methyl-4-(4-(trifluoromethoxy(phenyl)oxazol-5-yl)-3'-(methylsulfonyl)-[1,1'-biphenyl]-4-yl)-1H-pyrazol-3-yl)acetamide | MS (ESI) 646.9 [M + H]+ |
| 129 | 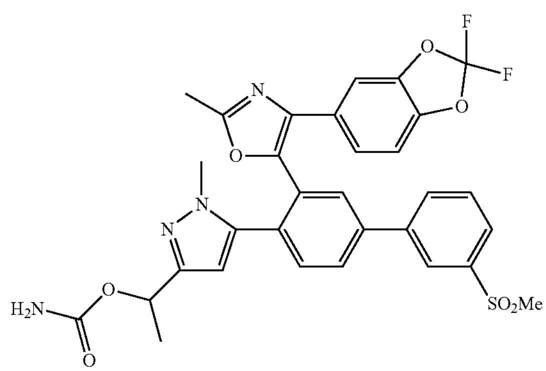 | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethyl carbamate | MS (ESI) 637 [M + 1] Specific optical rotation: [α]$^{25}$D = −24 (c 0.1, MeOH); $^1$H NMR (400 MHz, DMSO-d$_6$) δ ppm 8.28 (1H, s), 8.12-8.17 (2H, m), 8.05 (1H, dd, J = 8.00 Hz, 1.6 Hz), 7.98 (1H, d, J = 8.03 Hz), 7.80 (1H, t, J = 7.61 Hz), 7.68 (1H, d, J = 8.4 Hz), 7.30 (1H, d, J = 8.4 Hz), 7.21 (1H, d, J = 1.2 Hz), 7.03 (1H, dd, J = 8.41 Hz, 1.62 Hz), 6.41 (2H, brs), 5.76 (1H, s), 5.48 (1H, q, J = 6.5 Hz), 3.40 (3H, s), 3.30 (3H, s), 2.48 (3H, s), 1.30 (3H, d, J = 6.5 Hz). |
| 130 | 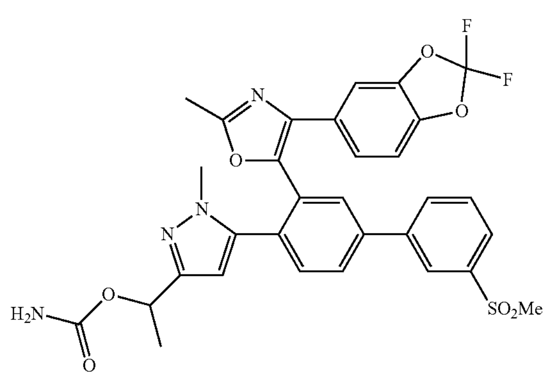 | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethyl carbamate | MS (ESI) 637 [M + 1] Specific optical relation: [α]$^{25}$D = 22 (c 0.1, MeOH) |

-continued

| Ex # | Structure | Name | Characterization |
|---|---|---|---|
| 131 | 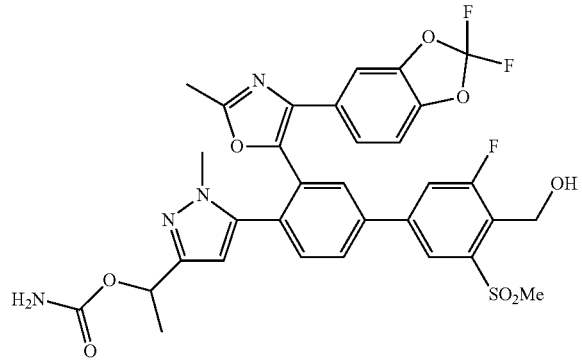 chiral | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethyl carbamate | MS (ESI) 686 [M + 1] Specific optical rotation: [α]$^{25}$D = 27.2 (c 0.1, MeOH) |
| 132 | 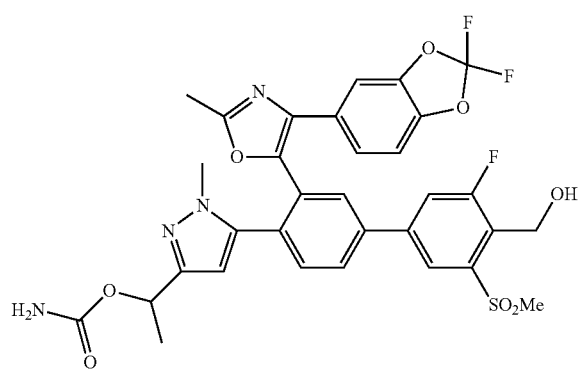 chiral | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethyl carbamate | MS (ESI) 686 [M + 1] Specific optical rotation: [α]$^{25}$D = −10 (c 0.1, MeOH) |
| 133 | 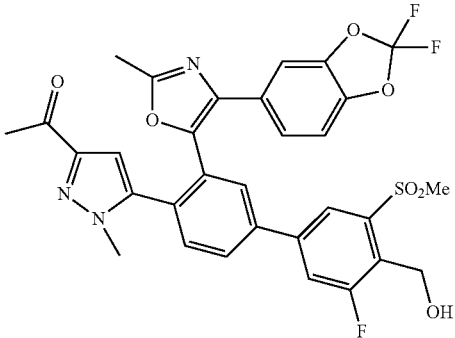 [SMILES: CC(=O)c1cc(-c2ccc(-c3cc(F)c(CO)c(S(C)(=O)=O)c3)cc2-c2oc(C)nc2-c2ccc3c(c2)OC(F)(F)O3)n(C)n1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethanone | MS (ESI) 640.51 [M + 1]. $^1$H NMR (400 MHz, METHANOL-d$_4$) δ ppm 8.24 (1 H, d, J = 1.0 Hz), 8.13 (1 H, m), 7.98-8.02 (2 H, m), 7.64 (1 H, d, J = 8.28 Hz), 7.08 (1 H, m), 6.96-7.03 (2 H, m), 6.29 (1 H, s), 5.16 (2 H, d, J = 2 Hz), 3.50 (3 H, s), 3.40 (3 H, s), 2.56 (3 H, s), 2.46 (3 H, s). |

Scheme 5

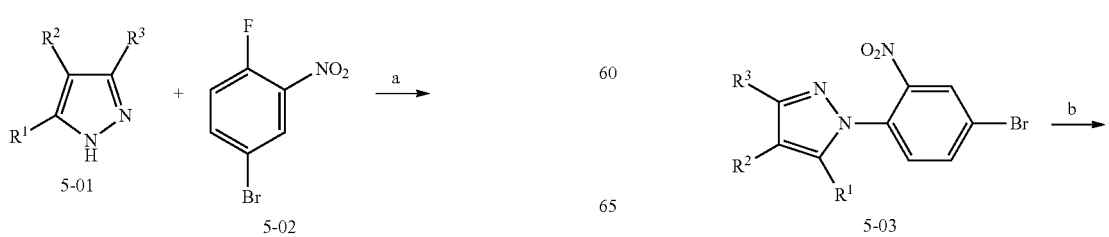

Example 300

1-{3'-(methylsulfonyl)-4-[5-methyl-3-(trifluoromethyl)-1H-pyrazol-1-yl]biphenyl-3-yl}-5-{4-[(trifluoromethyl)oxy]phenyl}-1H-1,2,3-triazole

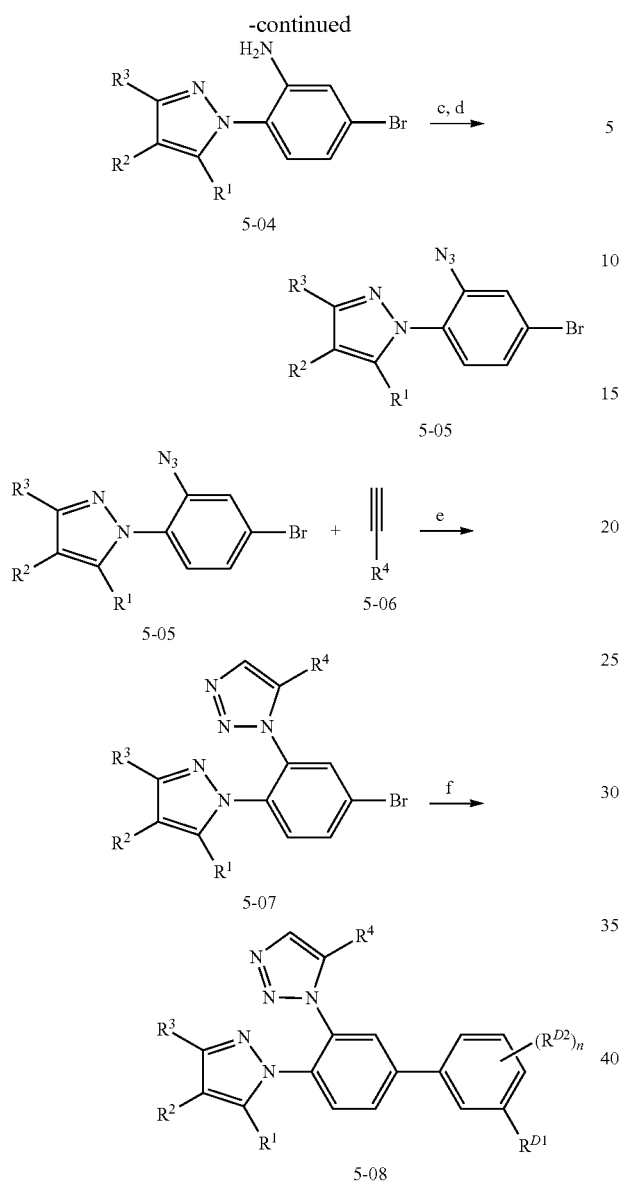

(a) K$_2$CO$_3$, DMF, 60° C.; (b) H$_2$, PtO$_2$, EtOAc; (c) aq NaNO$_2$, conc. HCl, 0° C.; (d) aq NaN$_3$, 0° C.; (e) Cp*Ru(cod)Cl, THF; (f) ArB(OR)$_2$, PdCl$_2$dppf, aq K$_2$CO$_3$, 65° C.;

In general, triazole compounds of formula 5-08 can be synthesized following the methodology shown in Scheme 5. The substituted pyrazole 5-01 undergoes a S$_N$Ar reaction with 4-bromo-1-fluoro-2-nitrobenzene (5-02) in the presence of K$_2$CO$_3$ in DMF to give the nitrophenyl pyrazole (5-03). Then 5-03 can be converted to the aniline (5-04) by hydrogenation in the presence of the platinum (IV) oxide catalyst. The aniline (5-04) is converted to the azide (5-05) using sodium nitrite and sodium azide under acidic conditions. Azide 5-05 reacts with the alkyne (5-06) in the presence of 1,5-cyclooctadiene(pentamethylcyclopentadienyl) ruthenium(II) chloride (Cp*Ru(COD)Cl) to yield the triazole (5-07). Suzuki coupling between the aryl bromide (5-07) and an appropriate aryl boronic acid or boronic ester produces the product (5-08).

Example 300a

Preparation of 1-(4-bromo-2-nitrophenyl)-5-methyl-3-(trifluoromethyl)-1H-pyrazole

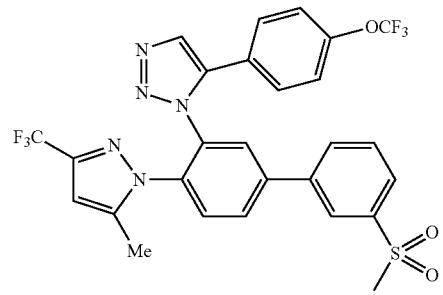 [SMILES: Cc1cc(C(F)(F)F)nn1-c1ccc(-c2cccc(S(C)(=O)=O)c2)cc1-n1nncc1-c1ccc(OC(F)(F)F)cc1]

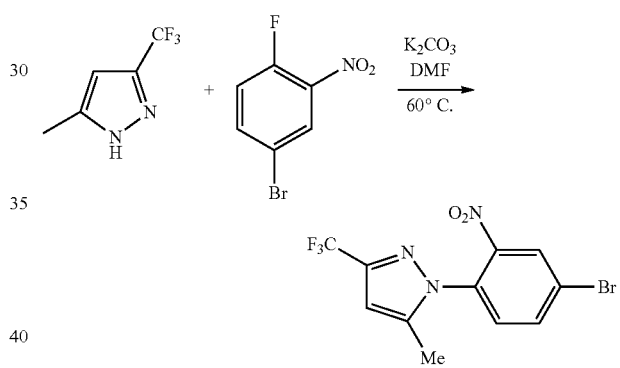

In a 500 mL round bottom flask, 5-methyl-3-(trifluoromethyl)-1H-pyrazole (150 g, 100 mmol), 4-bromo-1-fluoro-2-nitrobenzene (22 g, 100 mmol) and K$_2$CO$_3$ (35 g, 250 mmol) were brought up in DMF (200 mL) and the mixture was stirred at 60° C. for 6 hrs. The mixture was poured into H$_2$O (200 mL) and extracted with Et$_2$O (100 mL×3). The combined organic phase was concentrated in vacuo. The crude product was obtained in nearly quantitative yield (37 g) and was used for the next reaction without further purification. MS (ESI) 351.1 [M+H]+.

Example 300b

Preparation of 5-bromo-2[5-methyl-3-(trifluoromethyl)-1H-pyrazol-1-yl]aniline

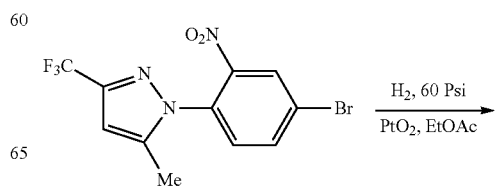

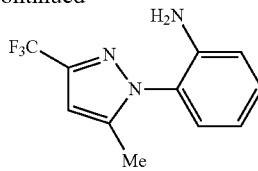

To an oven dried, N₂ purged Parr flask was added Example 300a (18 g, 51 mmol) and EtOAc (200 mL), followed by PtO₂ (540 mg, 3 wt %). The flask was attached to a Parr Shaker Hydrogenator, evacuated and then back-filled with 60 psi H₂ three times. The final H₂ pressure was set to 60 psi and the reaction mixture was shaken for 4 hrs. The inorganic solid was removed by filtration, and the filtrate was concentrated in vacuo. The crude product was purified by chromatography thru a SiO₂ column using a mobile phase gradient of 10-25% EtOAc/Hx to give the product aniline (16 g, 49 mmol, 95% yield). MS (ESI) 321.1 [M+H]+.

Example 300c

Preparation of 1-(2-azido-4-bromophenyl)-5-methyl-3-(trifluoromethyl)-1H-pyrazole

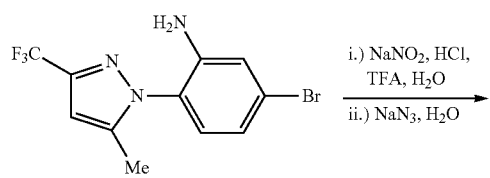

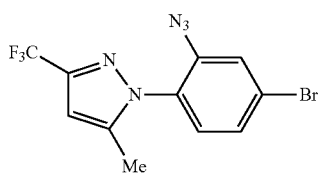

Example 300b (8.1 g, 25 mmol) was dissolved in concentrated HCl (36 mL), H₂O (27 mL) and TFA (18 mL) and the flask was cooled to 0° C. NaNO₂ (3.5 g, 51 mmol) dissolved in 18 mL of H₂O was added dropwise over 15 min. The mixture was stirred at 0° C. for 1 hr. Afterward, a solution of NaN₃ (5.0 g, 61 mmol) in 15 mL of H₂O was added dropwise over 20 min. The reaction mixture was stirred at 0° C. for 2.5 hrs. To this reaction mixture cooled with an ice water bath was added NaHCO₃ slowly and carefully until it was neutral or weakly basic. The aqueous layer was extracted with DCM (100 mL×3). The combined organics were washed with aq NaCl (100 mL), dried over Na₂SO₄, filtered into a round bottom flask and concentrated in vacuo to give the crude product (6.1 g, 70% yield). The crude product was used for the next reaction without further purification.

Example 300d

Preparation of 1-{5-bromo-2-[5-methyl-3-(trifluoromethyl)-1H-pyrazol-1]pheny}-5-[4-(trifluoromethoxy)phenyl]-1H-1,2,3-triazole

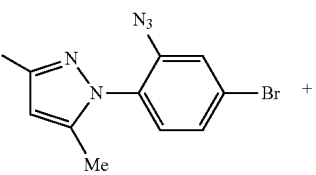

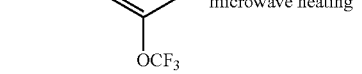

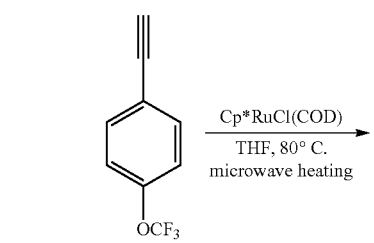

To a solution of Example 300c (0.70 g, 2.0 mmol) and 1-ethynyl-4-(trifluoromethoxy)benzene (0.75 g, 4.0 mmol) in anhydrous THF (8 mL) was added Cp*RuCl(COD) (77 mg, 0.20 mmol). The microwave reaction vial was purged with nitrogen gas and heated in microwave at 80° C. for 5 hrs. The reaction mixture was cooled to rt, and the solvent was removed. The crude product was purified by chromatography thru SiO₂ column using a mobile phase gradient of 10-25% EtOAc/Hx to give the title compound (0.31 g, 0.59 mmol, 29% yield). MS (ESI) 533 [M+H]+.

Example 300 was prepared from Example 300d and 3-(methylsulfonyl)phenylboronic acid using a similar procedure to that described in Example 37f. MS (ESI) 608.1 [M+H]+. ¹H NMR (400 MHz, CDCl₃) δ ppm 8.22 (m, 1H), 8.04 (m, 1H), 7.96-7.89 (m, 3H), 7.76-7.72 (m, 2H), 7.63 (m, 1H), 7.16 (m, 4H), 6.22 (s, 1H), 3.13 (s, 3H), 1.93 (s, 3H).

The following compounds were made in a manner similar to that described in the previous experimental procedures:

| Ex # | Structure | Name | Molecular Ion |
|---|---|---|---|
| 301 | 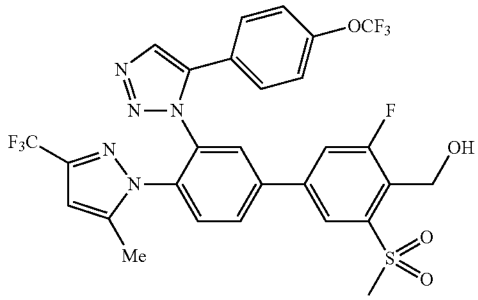 [SMILES: Cc1cc(C(F)(F)F)nn1-c1ccc(-c2cc(F)c(CO)c(S(C)(=O)=O)c2)cc1-n1nncc1-c1ccc(OC(F)(F)F)cc1] | [3-fluoro-5-(methylsulfonyl)-4'-[5-methyl-3-(trifluoromethyl)-1H-pyrazol-1-yl]-3'-(5-{4-[(trifluoromethyl)oxy]phenyl}-1H-1,2,3-triazol-1-yl)biphenyl-4-yl]methanol | MS (ESI) 656.1 [M + H]+. |
| 302 | 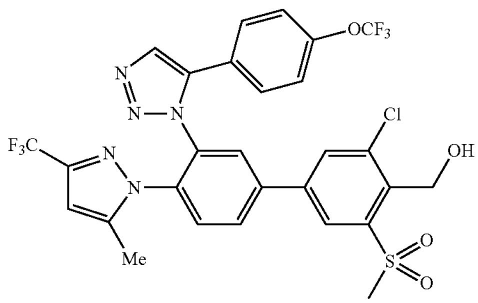 [SMILES: Cc1cc(C(F)(F)F)nn1-c1ccc(-c2cc(Cl)c(CO)c(S(C)(=O)=O)c2)cc1-n1nncc1-c1ccc(OC(F)(F)F)cc1] | [3-chloro-5-(methylsulfonyl)-4'-[5-methyl-3-(trifluoromethyl)-1H-pyrazol-1-yl]-3'-(5-{4-[(trifluoromethyl)oxy]phenyl}-1H-1,2,3-triazol-1-yl)biphenyl-4-yl]methanol | MS (ESI) 673.1 [M + H]+. |
| 303 | 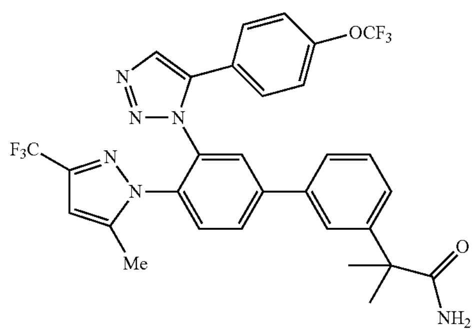 [SMILES: Cc1cc(C(F)(F)F)nn1-c1ccc(-c2cccc(C(C)(C)C(N)=O)c2)cc1-n1nncc1-c1ccc(OC(F)(F)F)cc1] | 2-methyl-2-{4'-[5-methyl-3-(trifluoromethyl)-1H-pyrazol-1-yl]-3'-(5-{4-[(trifluoromethyl)oxy]phenyl}-1H-1,2,3-triazol-1-yl)biphenyl-3-yl}propanamide | MS (ESI) 615.2 [M + H]+. |

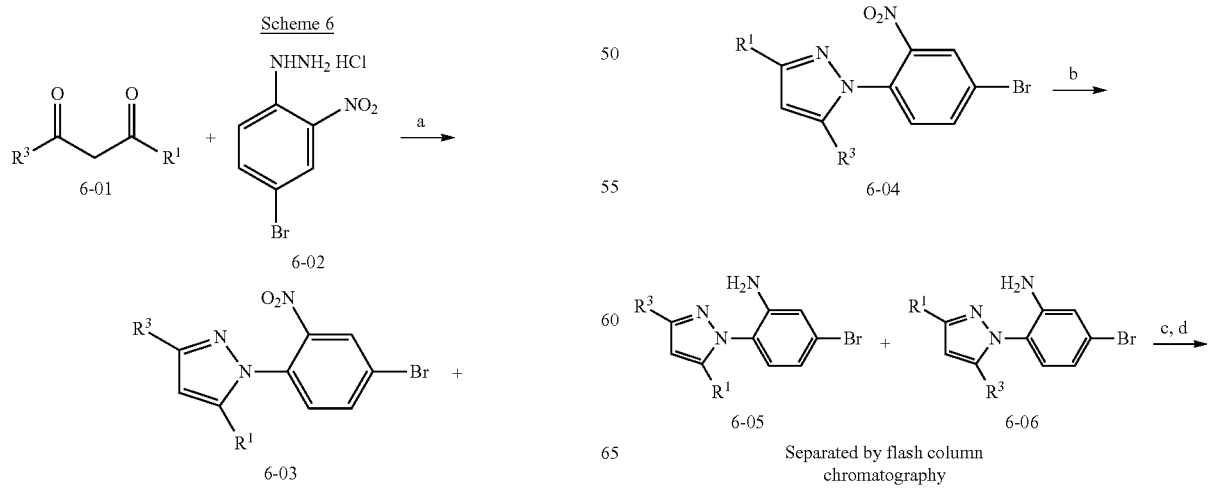

Scheme 6

187

-continued

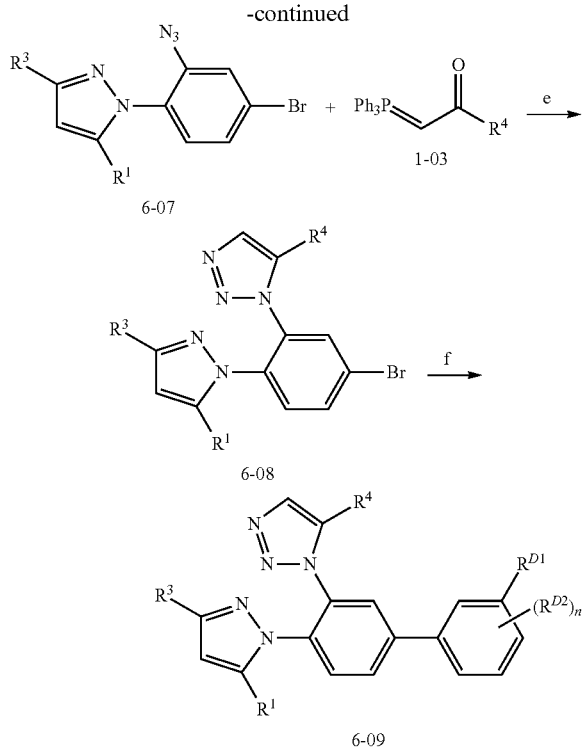

(a) EtOH, reflux; (b) H₂, 60 psi, V doped Pt/C; (c) aq NaNO₂, TFA, conc. HCl, 0° C.; (d) aq NaN₃, 0° C.; (e) toluene, reflux; (f) ArB(OR)₂, PdCl₂(dppf), aq K₂CO₃, 65° C.;

In general, triazole compounds of formula 6-09 can be synthesized following the methodology shown in Scheme 6. Dione 6-01 and a (4-bromo-2-nitrophenyl)hydrazine hydrochloride are heated to reflux in EtOH to give pyrazole regioisomers 6-03 and 6-04. The mixture of nitrophenyl pyrazoles (6-03) and (6-04) were converted to anilines (6-05) and (6-06) by hydrogenation in the presence of Pt/C doped with vanadium catalyst. The two isomers 6-05 and 6-06 are separated by flash silica gel column chromatography. The aniline 6-05 is converted to the azide 6-07 using sodium nitrite and sodium azide under acidic conditions. The azide (6-07) reacts with the phosphorane 1-03 in the presence of catalyst Cp*RuCl(COD) to yield the triazole 6-08. Palladium mediated coupling between the aryl bromide (6-08) with the aryl boronic acid or ester produces the product (6-09).

Example 304

1-{4-[3-(1,1-difluoroethyl)-5-methyl-1H-pyrazol-1-yl]-3'-(methylsulfonyl)biphenyl-3-yl}-5-{4-[(trifluoromethyl)oxy]phenyl}-1H-1,2,3-triazole

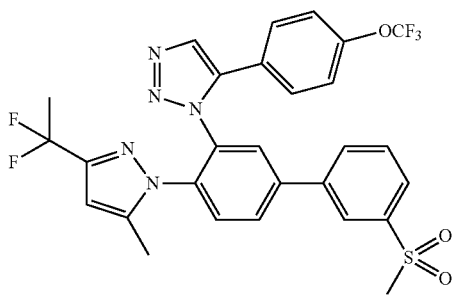 [SMILES: Cc1cc(C(C)(F)F)nn1-c1ccc(-c2cccc(S(C)(=O)=O)c2)cc1-n1nncc1-c1ccc(OC(F)(F)F)cc1]

188

Example 304a

Preparation of 1-(4-bromo-2-nitrophenyl)-3-(1,1-difluoroethyl)-5-methyl-1H-pyrazole

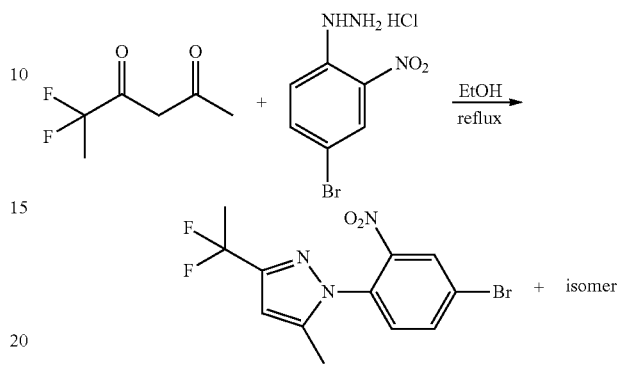

To a solution of 5,5-difluorohexane-2,4-dione (1.7 g, 11 mmol) in EtOH (60 mL) was added (4-bromo-2-nitrophenyl)hydrazine hydrochloride (3.0 g, 11 mmol). The reaction vessel was heated to reflux for 2 hrs. The reaction mixture was concentrated to give a mixture of the title compound and its pyrazole isomer. The crude product was used for the next reaction without purification.

Example 304b

Preparation of 5-bromo-2-[3-(1,1-difluoroethyl)-5-methyl-1H-pyrazol-1-yl]aniline

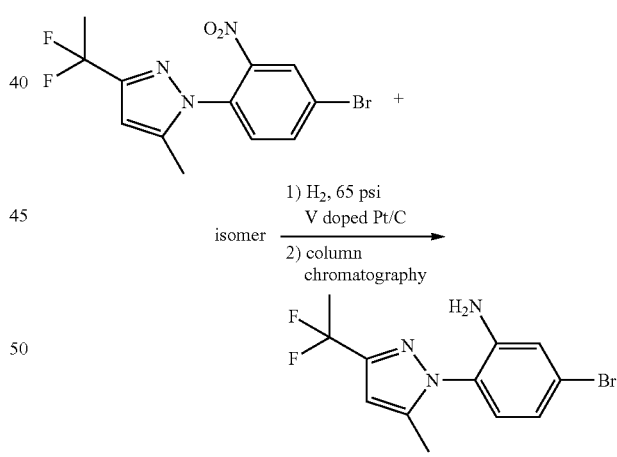

To an oven dried, N₂ purged Parr flask, was added the crude product mixture of Example 304a (1.7 g, 4.9 mmol) and DCM (25 mL), followed by vanadium doped Pt/C (1.0 g). The flask was attached to a Parr Shaker Hydrogenator, evacuated and backfilled with 65 psi H₂ three times. The final H₂ pressure was set to 65 psi and the reaction vessel was shaken for 4 hrs. The inorganic solid was removed by filtration, and the filtrate was concentrated in vacuo. The crude product was purified by chromatography thru a SiO₂ column using a mobile phase gradient of 10-20% EtOAc/Hx to give the desired isomer (0.42 g, 1.3 mmol, 28% yield). MS (ESI) 317.1 [M+H]+.

Example 304c

Preparation of 1-(2-azido-4-bromophenyl)-3-(1,1-difluoroethyl)-5-methyl-1H-pyrazole

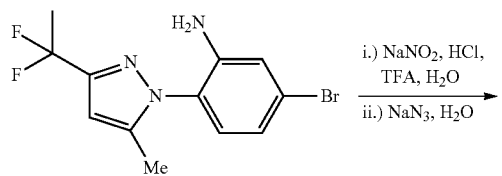

Example 304b 0.42 g, 1.3 mmol) was brought up in concentrated HCl (1.0 mL) and TFA (5.0 mL) and the reaction vessel was cooled to 0° C. NaNO$_2$ (0.19 g, 2.7 mmol) dissolved in 1.0 mL of water was added slowly over 15 min and the mixture was stirred at 0° C. for 1 hr. Afterwards, a solution of NaN$_3$ (0.26 g, 4.0 mmol) in water (1.0 mL) was added dropwise. The reaction mixture was stirred at 0° C. for 2.5 hrs. To the cooled reaction vessel, NaHCO$_3$ was slowly added until the mixture was neutral or weakly basic. The aqueous layer was extracted with DCM (15 mL×3), and the combined organics were washed with aq NaCl (20 mL), dried over Na$_2$SO$_4$, filtered into a flask and concentrated in vacuo to give the crude product (0.45 g, 1.2 mmol). The crude product was used for the next reaction without further purification.

Example 304d

Preparation of 1-{5-bromo-2-[3-(1,1-difluoroethyl)-5-methyl-1H-pyrazol-1-yl]phenyl}-5-[4-(trifluoromethoxy)pheny]-1H-1,2,3-triazole

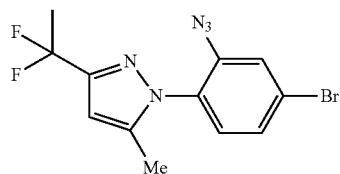

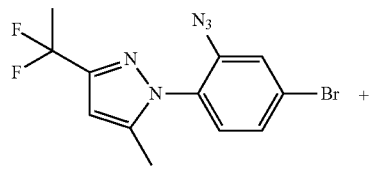

In a 50 mL round bottom flask, Example 1c (0.62 g, 1.3 mmol) and Example 304c (0.45 g, 1.3 mmol) were brought up in anhydrous toluene (10 mL) and heated to reflux for 5 hrs. The solvent was removed in vacuo. The crude residue was purified by chromatography thru a SiO$_2$ column using a mobile phase gradient of 10-20% EtOAc/Hx to afford the title compound (500 mg, 0.95 mmol, 71% yield). MS (ESI) 529.1 [M+H]+.

Example 304 was prepared from Example 304d and 3-(methylsulfonyl)phenylboronic acid using a similar procedure to that described in Example 1j. MS (ESI) 603.1 [M+H]+. $^1$H NMR (400 MHz, CDCl$_3$) δ ppm 8.06 (m, 1H), 7.97 (m, 1H), 7.83 (m, 2H), 7.75 (m, 1H), 7.67 (m, 1H), 7.50 (m, 1H), 7.45 (m, 2H), 7.20 (m, 2H), 6.26 (s, 1H), 3.09 (s, 3H), 2.04 (s, 3H), 1.86 (t, J$_{HF}$=18.49 Hz, 3H).

The following compounds were made in a similar manner to that described in the previous experimental procedures:

| Ex # | Structure | Name | Molecular Ion |
|---|---|---|---|
| 305 | 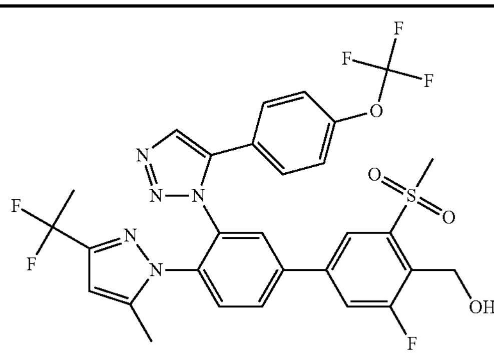 | {4'-[3-(1,1-difluoroethyl)-5-methyl-1H-pyrazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol | MS (ESI) 652.1 [M + H]+. |

| Ex # | Structure | Name | Molecular Ion |
|---|---|---|---|
| 306 | 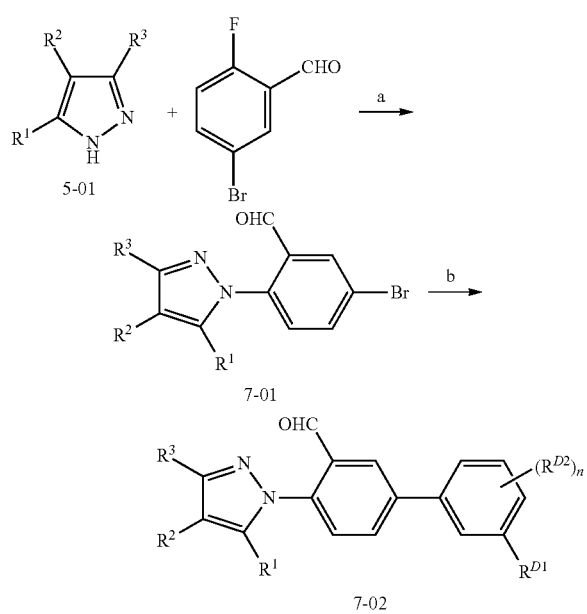 | 1-{4-[5-(1,1-difluoroethyl)-3-methyl-1H-pyrazol-1-yl]-3'-(methylsulfonyl)biphenyl-3-yl}-5-{4-[(trifluoromethyl)oxy]phenyl}-1H-1,2,3-triazole | MS (ESI) 604.1 [M + H]+. |

Scheme 7

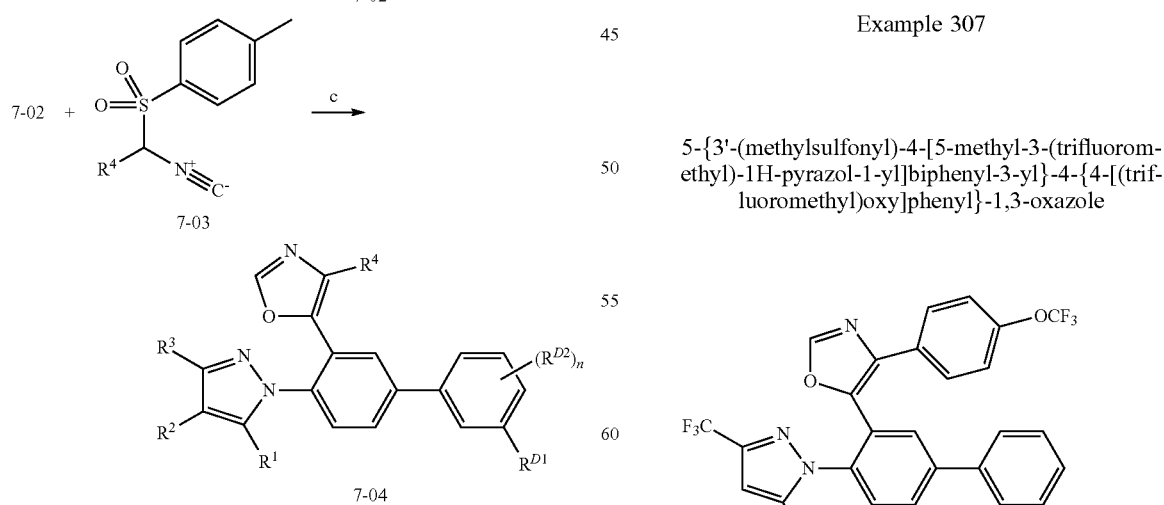

(a) $K_2CO_3$, DMF, 60° C.;
(b) ArB(OH)$_2$, PdCl$_2$(dppf), aq $K_2CO_3$, 65° C.;
(c) $K_2CO_3$, MeOH, DME, 50° C.

In general, the 4,5-di-aryloxazoles 7-04 can be synthesized following the methodology shown in Scheme 7. The pyrazole (5-01) undergoes a S$_N$Ar reaction with a 5-bromo-2-fluorobenzaldehyde in the presence of $K_2CO_3$ in DMF to give the 4-bromophenyl pyrazole (7-01), which undergoes palladium mediated coupling with an aryl boronic acid or ester to produce the product (7-02). The aldehyde (7-02) reacts with an appropriately substituted tosylmethylisocyanide (7-03) to give the 4,5-di-aryloxazole (7-04).

Compounds of the invention such as Example 308 and 309 were prepared from an appropriately substituted intermediate 7-01 (Scheme 7) and appropriately substituted intermediates 3-08 (Scheme 3), using the synthesis previously described in Scheme 3 (steps g-j). Alternatively, compounds of the invention such as Example 310 and 311 were prepared from an appropriately substituted intermediate 7-01 and the chemistry described in Scheme 4.

Example 307

5-{3'-(methylsulfonyl)-4-[5-methyl-3-(trifluoromethyl)-1H-pyrazol-1-yl]biphenyl-3-yl}-4-{4-[(trifluoromethyl)oxy]phenyl}-1,3-oxazole

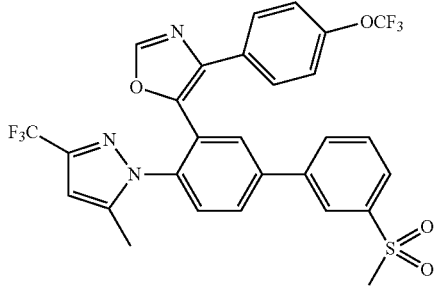 [SMILES: Cc1cc(C(F)(F)F)nn1-c1ccc(-c2cccc(S(C)(=O)=O)c2)cc1-c1ocnc1-c1ccc(OC(F)(F)F)cc1]

Example 307a

Preparation of 4-(5-methyl-3-(trifluoromethyl)-1H-pyrazol-1-yl)-3'-(methylsulfonyl)biphenyl-3-carbaldehyde

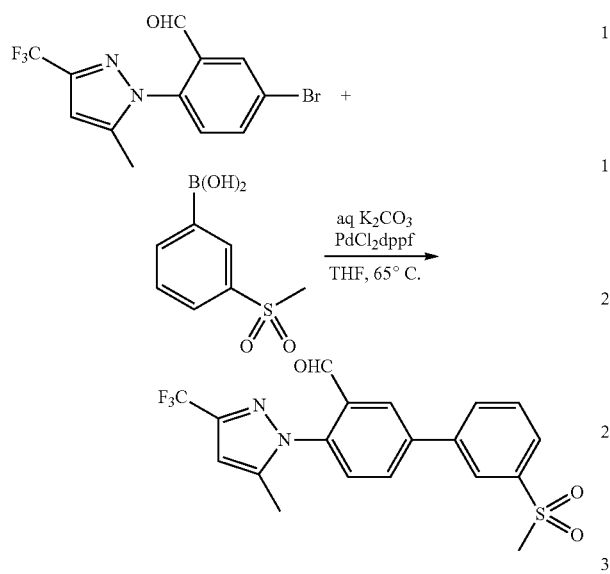

5-bromo-2-(5-methyl-3-(trifluoromethyl)-1H-pyrazol-1-yl)benzaldehyde was prepared from 5-methyl-3-(trifluoromethyl)-1H-pyrazole and 5-bromo-2-fluorobenzaldehyde using procedures similar to Example 128a.

In a 250 mL round-bottom flask, 5-bromo-2-(5-methyl-3-(trifluoromethyl)-1H-pyrazol-1-yl)benzaldehyde (11 g, 32 mmol), 3-(methylsulfonyl)phenylboronic acid (7.0 g, 35 mmol), K$_2$CO$_3$ (13 g, 96 mmol) and PdCl$_2$(dppf) (2.6 g, 3.2 mmol) were brought up in THF (110 mL) and water (10 mL). The reaction vessel was heated to 65° C. for 5 hrs. The cooled mixture was filtered through a celite pad, diluted with EtOAc (100 mL), dried over Na$_2$SO$_4$, filtered into a round bottom flask and concentrated in vacuo. The crude material was purified by chromatography thru a SiO$_2$ column using a mobile phase gradient of 30-60% EtOAc/Hx to afford the title compound (9.1 g, 24 mmol, 75% yield). MS (ESI) 409.1 [M+H]+.

Example 307b

Preparation of 5-{3'-(methylsulfonyl)-4-[5-methyl-3-(trifluoromethyl)-1H-pyrazol-1-yl]biphenyl-3-yl}-4-{4-[(trifluoromethyl)oxy]phenyl}-1,3-oxazole

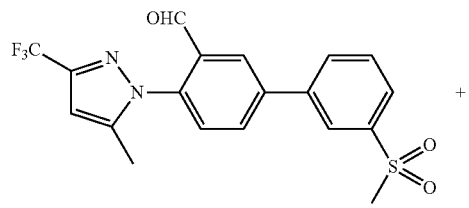

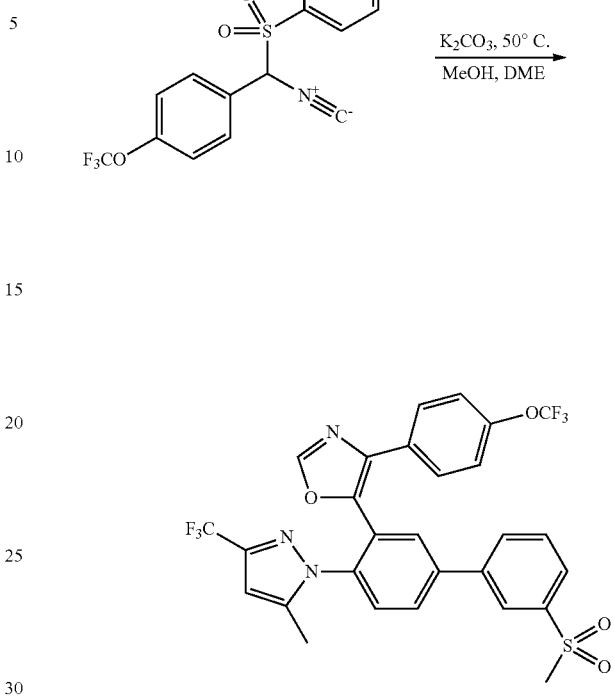

In a 25 mL round-bottom flask, Example 307a (150 mg, 0.37 mmol) and 1-(isocyano(4-(trifluoromethoxy)phenyl)methylsulfonyl)-4-methylbenzene (650 mg, 1.8 mmol) were brought up in MeOH (6 mL) and DME (2 mL). The reaction vessel was heated at 50° C. overnight. The cooled reaction mixture was concentrated and purified by HPLC to afford the title compound (32 mg, 0.052 mmol, 14% yield). MS (ESI) 608.1 [M+H]+. $^1$H NMR (400 MHz, CDCl$_3$) δ ppm 8.19 (m, 1H), 8.01 (m, 1H), 7.92 (m, 2H), 7.84 (m, 2H), 7.70 (m, 1H), 7.59 (m, 1H), 7.46 (m, 2H), 7.13 (m, 2H), 6.17 (s, 1H), 3.12 (s, 3H), 1.99 (s, 3H).

Example 308

1-(3-(2-methyl-4-(4-(trifluoromethoxy)phenyl)oxazol-5-yl)-3'-(methylsulfonyl)biphenyl-4-yl)-1H-pyrazole-3-carboxamide

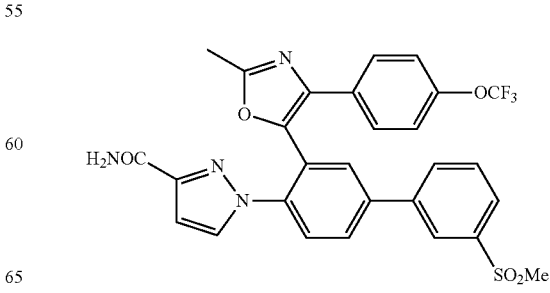

Example 308a

Preparation of ethyl 1-(4-bromo-2-(1-hydroxy-2-oxo-2-(4-(trifluoromethoxy)phenyl)ethyl)phenyl)-1H-pyrazole-3-carboxylate

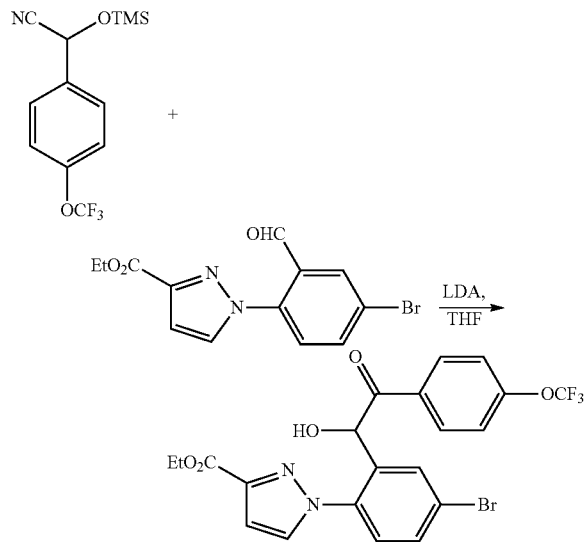

Ethyl 1-(4-bromo-2-formylphenyl)-1H-pyrazole-3-carboxylate was prepared from ethyl 1H-pyrazole-3-carboxylate and 5-bromo-2-fluorobenzaldehyde using procedures similar to Example 309a.

To a solution of 2-(4-(trifluoromethoxy)phenyl)-2-((trimethylsilyl)oxy)acetonitrile (prepared by a similar procedure to Example 45a) (0.50 g, 1.7 mmol) in THF (10 mL) under nitrogen atmosphere was added LDA (2.0 M solution in THF, 1.3 mL, 2.6 mmol) dropwise at −78° C. The reaction mixture was stirred at −78° C. for 30 min, and then a solution of ethyl 1-(4-bromo-2-formylphenyl)-1H-pyrazole-3-carboxylate (0.56 g, 1.7 mmol) in THF (20 mL) was added dropwise. The reaction mixture was stirred at −78° C. for 30 min, then allowed to warm to rt and stirred for 1 hr. The reaction mixture was quenched by addition of 1N HCl (20 mL) and was stirred for 30 min. The mixture was diluted with water (20 mL) and extracted with EtOAc (2×25 mL). The combined organic extracts were washed with water (20 mL), and brine (30 mL), dried over Na$_2$SO$_4$, filtered into a flask and concentrated under reduced pressure to afford the crude product, which was used without further purification (860 mg, 1.7 mmol). MS (ESI) 513.0 [M+H]$^+$.

Example 308b

Preparation of ethyl 1-(2-(1-acetoxy-2-oxo-2-(4-(trifluoromethoxy)phenyl)ethyl)-4-bromophenyl)-1H-pyrazole-3-carboxylate

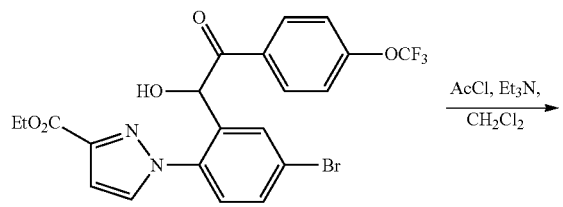

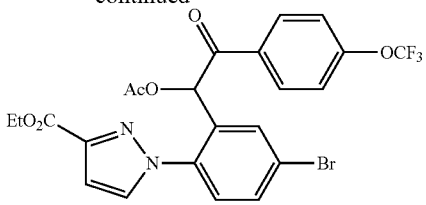

To a cooled solution (0° C.) of Example 308a (0.86 g, 1.7 mmol) and Et$_3$N (0.93 mL, 6.7 mmol) in DCM (25 mL) was added AcCl (0.24 mL, 3.4 mmol) dropwise and the reaction mixture was stirred at rt overnight. The reaction mixture was diluted with DCM (20 mL), washed with water (20 mL), and brine (30 mL), dried over Na$_2$SO$_4$, filtered into a round bottom flask and concentrated under reduced pressure to afford the crude product, which was used without further purification (880 mg, 1.6 mmol). MS (ESI) 555.0 [M+H]$^+$.

Example 308c

Preparation of ethyl 1-(4-bromo-2-(2-methyl-4-(4-(trifluoromethoxy)phenyl)oxazol-5-yl)phenyl)-1H-pyrazole-3-carboxylate

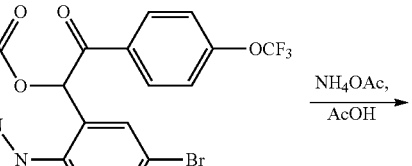

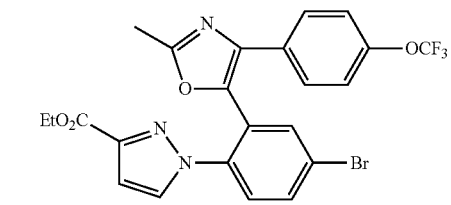

Ammonium acetate (1.2 g, 16 mmol) was added to a solution of Example 308b (0.88 g, 1.6 mmol) in AcOH (15 mL). The reaction mixture was heated to 125° C. for 3 hrs. After being cooled to rt, the reaction mixture was poured into ice (50 g), neutralized with 10% NaOH and extracted with DCM (2×50 mL). The combined organic layers were washed with water (30 mL), and brine (50 mL), dried over Na$_2$SO$_4$, filtered into a round bottom flask and concentrated in vacuo to give the crude product. The crude residue was purified by chromatography thru a SiO$_2$ column using the mobile phase of 20-25% EtOAc/Hx to afford the title compound (70 mg, 0.13 mmol, 8% yield). MS (ESI) 536.0 [M+H]+.

Example 308d

Preparation of ethyl 1-(3-(2-methyl-4-(4-(trifluoromethoxy)phenyl)oxazol-5-yl)-3'-(methylsulfonyl)biphenyl-4-yl)-1H-pyrazole-3-carboxylate

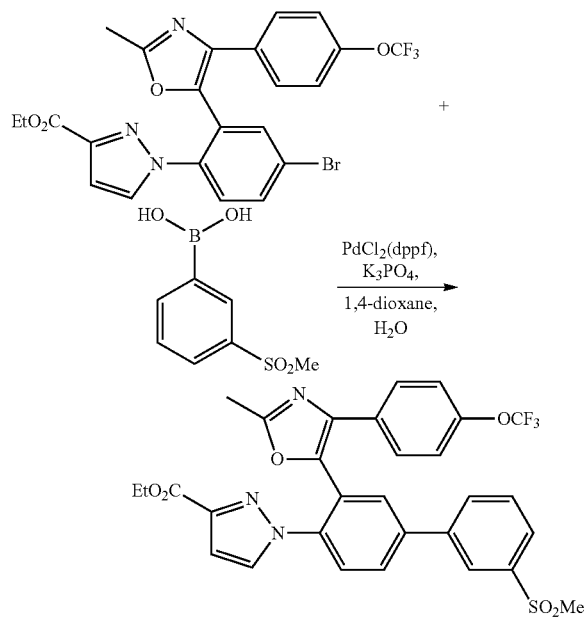

In a sealed tube, Example 308c (70 mg, 0.13 mmol), (3-(methylsulfonyl)phenyl)boronic acid (34 mg, 0.17 mmol) and $K_3PO_4$ (110 mg, 0.52 mmol) were brought to a solution in 1,4-dioxane (3.0 mL) and water (1.0 mL). The reaction mixture was purged with nitrogen for 5 min before $PdCl_2$(dppf) (7.6 mg, 10 μmol) was added, and the reaction mixture was heated to 100° C. for 2 hrs. The reaction mixture was cooled to rt, diluted with water (25 mL) and extracted with EtOAc (2×25 mL). The combined organic extracts were washed with water (30 mL), and brine (50 mL), dried over $Na_2SO_4$, filtered into a round bottom flask and concentrated in vacuo to give the crude product. The crude residue was purified by chromatography thru a 4 g $SiO_2$ column using the mobile phase gradient of 50-60% EtOAc/Hx to afford the title compound (40 mg, 0.065 mmol, 50% yield). MS (ESI) 612.0 [M+H]+.

Example 308

Preparation of 1-(3-(2-methyl-4-(4-(trifluoromethoxy)phenyl)oxazol-5-yl)-3'-(methylsulfonyl)biphenyl-4-yl)-1H-pyrazole-3-carboxamide

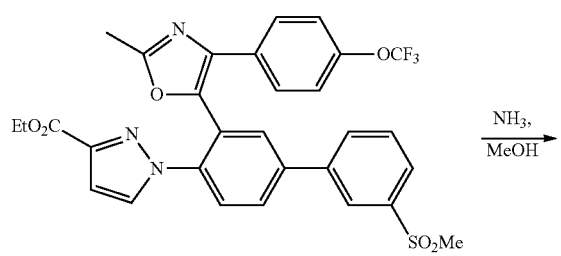

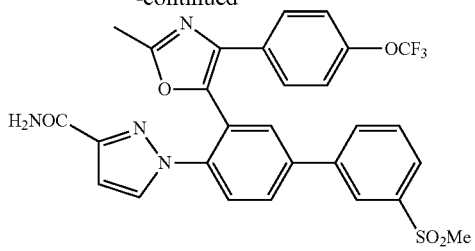

In a sealed tube, Example 308d (40 mg, 0.065 mmol) and methanolic ammonia (2.0 mL, 20 mmol, 10 M solution) were heated at 80° C. overnight. The reaction mixture was concentrated under reduced pressure to give crude product. The crude residue was purified by preparative HPLC [Column: SUNFIRE C18, 19×150 mm, 5 micron, Mobile Phase A: 10 mM NH4OAc in water: MeCN (90:10), Mobile phase B: MeCN] to give the title compound as a white solid (25 mg, 0.042 mmol, 65% yield). MS (ESI) 583.2 [M+H]+. $^1$H NMR (400 MHz, DMSO-$d_6$) δ ppm 8.29 (t, J=1.6 Hz, 1H), 8.14-8.18 (m, 3H), 7.91-7.97 (m, 2H), 7.74-7.82 (m, 2H), 7.44-7.47 (m, 2H), 7.24-7.28 (m, 3H), 7.12 (s, 1H), 6.58 (d, J=2.4 Hz, 1H), 3.31 (s, 3H), 2.49 (s, 3H).

Example 309

2-methyl-5-(3'-(methylsulfonyl)-4-(3-(trifluoromethyl)-1H-pyrazol-1-yl)-[1,1'-biphenyl]-3-yl)-4-(4-(trifluoromethoxy)phenyl)oxazole

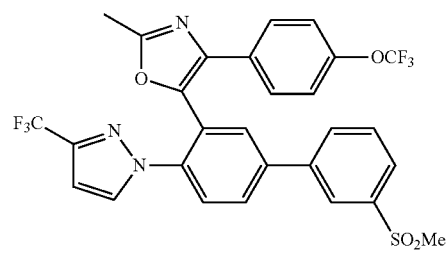 [SMILES: Cc1nc(-c2ccc(OC(F)(F)F)cc2)c(-c2cc(-c3cccc(S(C)(=O)=O)c3)ccc2-n2ccc(C(F)(F)F)n2)o1]

Example 309a

Preparation of 5-bromo-2-(3-(trifluoromethyl)-1H-pyrazol-1-yl)benzaldehyde

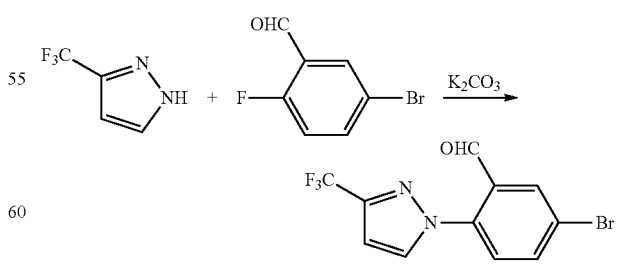

A mixture of 3-(trifluoromethyl)-1H-pyrazole (30 g, 220 mmol), 5-bromo-2-fluorobenzaldehyde (53.7 g, 265 mmol) and potassium carbonate (76 g, 551 mmol) in DMF (400 mL) was stirred at 70° C. for 3 hrs under nitrogen atmosphere. The solvents were evaporated under high vacuum to remove DMF, and the residue was poured into ice and extracted with EtOAc (2×250 mL). The combined organic extracts were washed with water, brine, dried over Na$_2$SO$_4$ and concentrated to give crude product. The crude was purified by column chromatography using Silica (230-400 mesh) with eluting 5% EtOAc/pet ether to get afford 45 g of the title compound. MS (ESI) 319/321 [M+H]+. $^1$H NMR (400 MHz, CDCl$_3$) δ ppm 9.94 (s, 1H), 8.17 (d, J=2.4 Hz, 1H), 7.84 (m, 2H), 7.42 (d, J=8.4 Hz, 1H), 6.82 (d, J=2.4 Hz, 1H).

Example 309b

Preparation of 2-(5-bromo-2-(3-(trifluoromethyl)-1H-pyrazol-1-yl)phenyl)-2-hydroxy-1-(4-(trifluoromethoxy)phenyl)ethanone

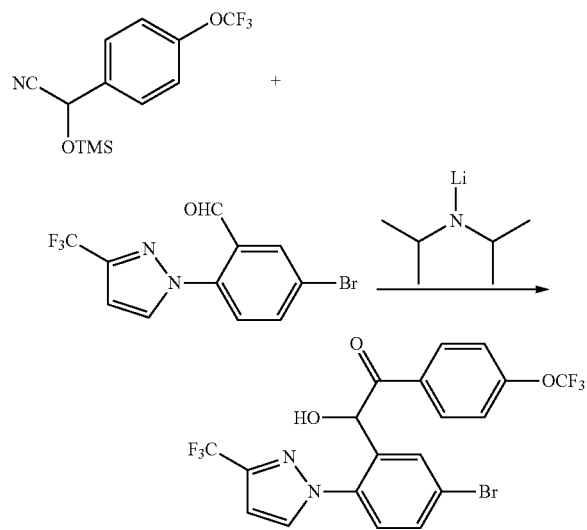

To a −78° C. cooled solution of 2-(4-(trifluoromethoxy) phenyl)-2-((trimethylsilyl)oxy)acetonitrile (1.0 g, 3.5 mmol) in THF (10 mL) was added lithium diisopropylamide (2.25 mL, 4.49 mmol) dropwise under N$_2$ atmosphere. The reaction mixture was stirred for 30 min at −78° C., and a solution of 5-bromo-2-(3-(trifluoromethyl)-1H-pyrazol-1-yl)benzaldehyde (1.16 g, 3.63 mmol) dissolved in THF (10 mL) was added dropwise. The reaction mixture was stirred at −78° C. for 30 min, and then allowed to warm to rt and stirred at rt for 1 hr. The reaction mixture was quenched by addition of 1N HCl (40 mL) and was stirred for 30 min. The reaction mixture was diluted with water (50 mL) and extracted with EtOAc (2×75 mL). The combined organic extracts were washed with water, brine, dried over Na$_2$SO$_4$ and concentrated to give 1.5 g of crude product as a pale brown oil. The material was taken forward without purification. MS (ESI) 509.0 [M+H]+.

Example 309c

Preparation of 5-(5-bromo-2-(3-(trifluoromethyl)-1H-pyrazol-1-yl)phenyl)-2-methyl-4-(4-(trifluoromethoxy)phenyl)oxazole

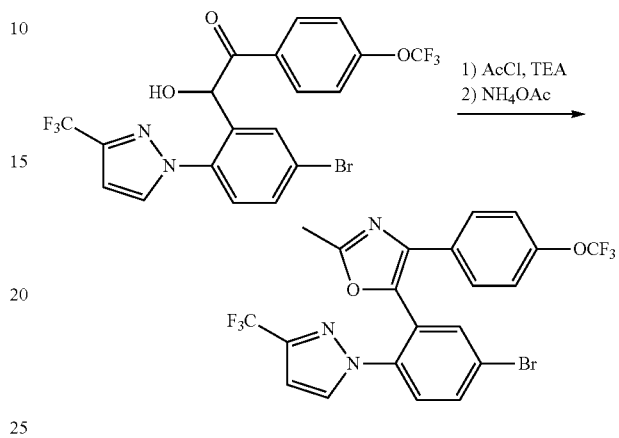

To a mixture of 2-(5-bromo-2-(3-(trifluoromethyl)-1H-pyrazol-1-yl)phenyl)-2-hydroxy-1-(4-(trifluoromethoxy) phenyl)ethanone (50 g, 98 mmol) and triethylamine (55 mL, 390 mmol) in DCM (1 L) was added acetyl chloride (14.0 mL, 196 mmol) dropwise at 0° C. The reaction mixture was stirred overnight at rt under a nitrogen atmosphere. The reaction mixture was diluted with DCM (150 mL), washed with water, brine, dried over Na$_2$SO$_4$ and concentrated to give crude product as a pale brown oil. The crude material was taken to the next step without further purification. MS (ESI) 551.0 [M+H]+.

A mixture of 1-(5-bromo-2-(3-(trifluoromethyl)-1H-pyrazol-1-yl)phenyl)-2-oxo-2-(4-(trifluoromethoxy)phenyl) ethyl acetate (35 g, 63.5 mmol) and ammonium acetate (48.9 g, 635 mmol) taken in acetic acid (630 mL) was stirred at 125° C. for 3 hr. The reaction mixture was cooled to rt. The reaction mass was concentrated under high vacuum to remove excess acetic acid, and was poured into ice with 10% NaOH (pH adjusted to 7-8). The mixture was extracted EtOAc (2×1 L). The combined organic extracts were washed with water, brine, dried over Na$_2$SO$_4$ and concentrated to give the crude product. The crude product was purified with column purification to afford 20 g of the title compound. MS (ESI) 532.0 [M+H]+. $^1$H NMR (400 MHz, CDCl$_3$) δ ppm 7.81 (d, J=2.0 Hz, 1H), 7.72 (d, J=2.0, 8.6 Hz, 1H), 7.69 (d, J=2.4 Hz, 1H), 7.36 (m, 2H), 7.23 (dd, J=1.2, 2.4 Hz, 1H), 7.07 (m, 2H), 6.34 (d, J=2.4 Hz, 1H), 2.49 (s, 1H).

Example 309 was prepared from Example 309c using procedures similar to Example 1j. MS (ESI) 608.0 [M+H]+. $^1$H NMR (400 MHz, CDCl$_3$) δ ppm 8.20 (t, J=1.2 Hz, 1H), 8.01-7.98 (m, 1H), 7.89-7.82 (m, 3H), 7.77-7.68 (m, 2H), 7.41-7.39 (m, 2H), 7.31 (d, J=3.2 Hz, 1H), 7.08-7.06 (d, J=8.0 Hz, 2H), 6.38 (d, J=2.4 Hz, 1H), 3.12 (s, 3H), 2.53 (s, 3H)

Example 310

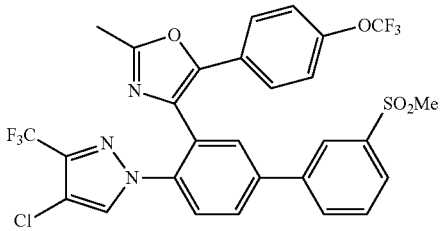 [SMILES: Cc1nc(-c2cc(-c3cccc(S(C)(=O)=O)c3)ccc2-n2cc(Cl)c(C(F)(F)F)n2)c(-c2ccc(OC(F)(F)F)cc2)o1]

4-(4-(4-chloro-3-(trifluoromethyl)-1H-pyrazol-1-yl)-3'-(methylsulfonyl)-[1,1'-biphenyl]-3-yl)-2-methyl-5-(4-(trifluoromethoxy)phenyl)oxazole

Example 310a

Preparation of 5-bromo-2-(4-chloro-3-(trifluoromethyl)-1H-pyrazol-1-yl)benzaldehyde

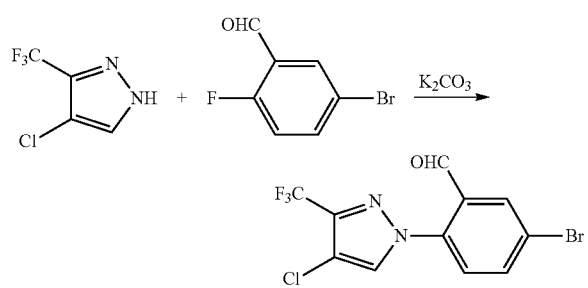

In a 250 mL round-bottomed flask was added 4-chloro-3-(trifluoromethyl)-1H-pyrazole (5.0 g, 29 mmol), 5-bromo-2-fluorobenzaldehyde (6.5 g, 32 mmol), and $K_2CO_3$ (8.1 g, 58 mmol) in MeCN (70 mL) to give a yellow suspension. The reaction mixture was stirred for 3 hrs at 80° C. under nitrogen atmosphere. The mixture was concentrated to a small volume on a rotary evaporator, and then 200 mL of EtOAc were added. The organics were washed with $H_2O$, and sat. NaCl. The organic solution was dried $Na_2SO_4$, filtered and concentrated at reduced pressure to give crude product. The crude product was added to a silica gel column and was eluted with 5%-15% of ethyl acetate-pet ether to afford 6.9 g of a yellow solid. $^1H$ NMR (300 MHz, $CDCl_3$) δ ppm 9.96 (s, 1H), 8.18 (d, J=2.4 Hz, 1H), 7.87 (m, 2H), 7.39 (d, J=8.7 Hz, 1H).

Example 310b

Preparation of 2-(5-bromo-2-(4-chloro-3-(trifluoromethyl)-1H-pyrazol-1-yl)phenyl)-2-((trimethylsilyl)oxy)acetonitrile

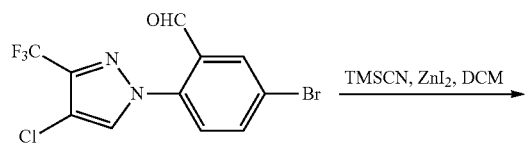

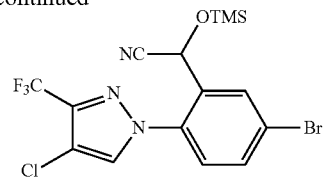

To stirred solution of Example 310a (1.0 g, 2.8 mmol) in DCM (16.6 mL) was added Zinc iodide (0.018 g, 0.057 mmol) and TMS-CN (0.425 mL, 3.39 mmol) at rt. The reaction mixture was stirred at rt for 2 h. The reaction mass was filter through a celite bed and washed with DCM (2×10 mL). The solvent was concentrated on rotary evaporator with a water bath temperature of 40° C., followed by drying under vacuum to afford the title compound (1.2 g, 2.6 mmol) as brown colour liquid. $^1H$ NMR (400 MHz, $CDCl_3$) δ ppm 8.02 (d, J=2 Hz, 1H), 7.78 (d, J=0.8 Hz, 1H), 7.66 (dd, J=8.4, 2 Hz, 1H), 7.21-7.26 (m, 1H), 6.01 (s, 9H).

Example 310c

Preparation of 4-(5-bromo-2-(4-chloro-3-(trifluoromethyl)-1H-pyrazol-1-yl)phenyl)-2-methyl-5-(4-(trifluoromethoxy)phenyl)oxazole Step 1.

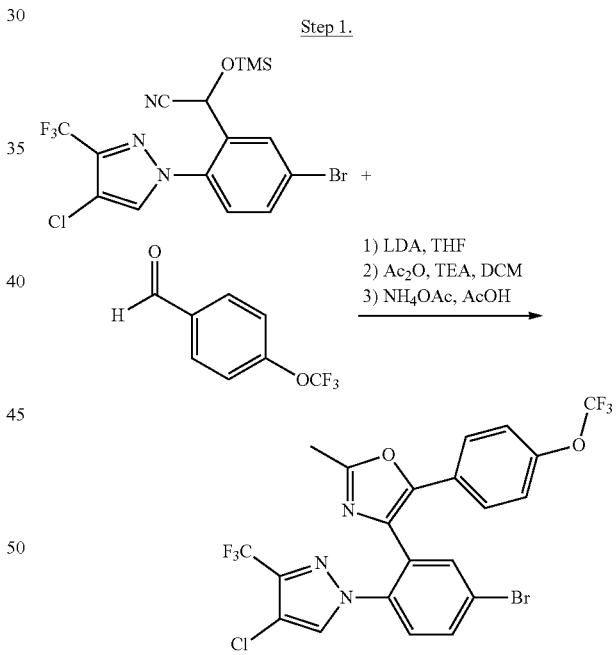

Example 310b (0.6 g, 1.3 mmol) in THF (15 mL) was cooled to −78° C. using a dry ice bath, and then LDA (0.93 mL, 1.8 mmol) was added over 5 min dropwise. After 30 min. of stirring at 78° C., 4-(trifluoromethoxy)benzaldehyde (0.302 g, 1.59 mmol) in 8 mL of THF was added dropwise via syringe over 5 min. Then the dry ice bath was removed, and the reaction mixture was allowed to warm to rt and was stirred for 1 h. A 50 mL aqueous solution of 10% HCl was added and the mixture was stirred for 1 hr at rt. EtOAc and $H_2O$ were added, the layers were separated and the organics were washed with brine. The organic layers were collected, dried over by $Na_2SO_4$, concentrated with a rotary evaporator. To the crude residue in a round bottom flask was added DCM (20 mL), and the flask was cooled to 0° C. TEA (0.308 mL, 2.21 mmol) was added to reaction mixture slowly. The mixture was stirred for 30 min, then Ac₂O (0.125 mL, 1.32 mmol) was added, and the reaction mixture was stirred for 6 h. The reaction mixture was charged with 45 mL of H₂O, and DCM. The layers were separated and the water was washed with DCM (2×40 mL). The organic layers were combined, dried over Na₂SO₄, and concentrated under reduced vacuum to afford the crude acetate MS (ESI) 585.2, 587.2 [M+H]+. The crude residue and ammonium acetate (0.790 g, 10.2 mmol) were charged to a reaction vessel in AcOH (10 mL), and the mixture was heated to reflux at 105° C. for 6 h. The reaction mixture was cooled to rt and then AcOH was removed under vacuum. The residue was diluted with EtOAc (50 mL), and the mixture was poured into a cooled 2M NaOH solution (30 mL). The layers were separated and the aqueous layer was washed with EtOAc (3×100 mL). The organic layers were combined, dried over Na₂SO₄, and concentrated under reduced vacuum to afford the crude product. The crude product was charged to a silica gel [230-400 nm] column and was eluted with 10%-60% of EtOAc-pet ether gradient to afford the title compound (0.16 g, 0.237 mmol) as a yellow oil. MS (ESI) 566.2, 568.2 [M+H]+.

Example 310 was prepared from Example 310c using procedures similar to Example 1j, except dioxane/water was used as solvent. MS (ESI) 642.2 [M+H]+. ¹H NMR (400 MHz, CD₃OD) δ ppm 8.30 (m, 1H), 8.02-8.14 (m, 4H) 7.90 (d, J=0.9 Hz, 1H), 7.76-7.84 (m, 2H), 7.37-7.40 (m, 2H), 7.18 (dd, J=8.9, 0.9 Hz, 2H), 3.23 (s, 3H), 2.58 (s, 3H).

Example 311

4-(4-(5-ethoxy-3-(trifluoromethyl)-1H-pyrazol-1-yl)-3'-(methylsulfonyl)biphenyl-3-yl)-2-methyl-5-(4-(trifluoromethoxy)phenyl)oxazole

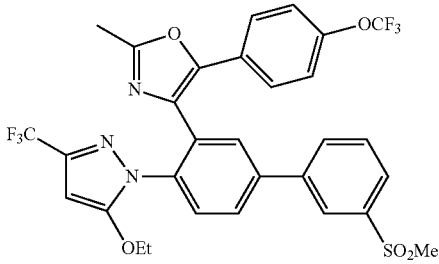 [SMILES: CCOc1cc(C(F)(F)F)nn1-c1ccc(-c2cccc(S(C)(=O)=O)c2)cc1-c1nc(C)oc1-c1ccc(OC(F)(F)F)cc1]

Example 311a

Preparation of (5-bromo-2-hydrazinylphenyl)methanol hydrochloride

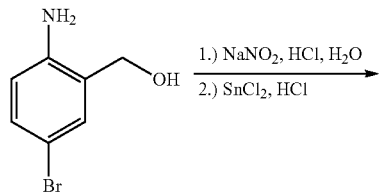

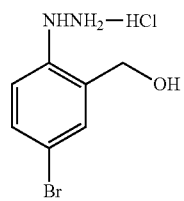

To a cooled solution (−10° C.) of (2-amino-5-bromophenyl)methanol (11 g, 54 mmol) in 6 N HCl (100 mL) was added a solution of sodium nitrite (4.1 g, 60 mmol) in water (15 mL) dropwise over 20 min, while maintaining the reaction temperature at −5 to 0° C. The reaction mixture was stirred at 0° C. for 30 min, and then was added dropwise to a solution of tin(II) chloride (21 g, 110 mmol) in HCl (37%, 250 mL) at −15° C. over 25 min. The reaction mixture was stirred at −10° C. for 15 min and then allowed to warm to rt and was stirred for 2 hrs. The mixture was filtered, the solids were washed with EtOAc and dried under vacuum to give the title compound as an off-white solid (11 g, 41 mmol, 76% yield). MS (ESI) 219.0 [M+H]+.

Example 311b

Preparation of (5-bromo-2-(5-ethoxy-3-(trifluoromethyl)-1H-pyrazol-1-yl)phenyl)methanol

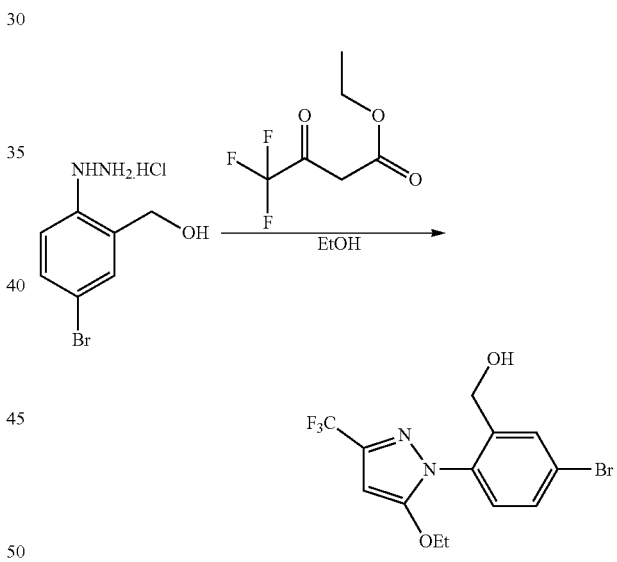

To a solution of Example 311a (3.0 g, 12 mmol) in EtOH (30 mL) was added ethyl 4,4,4-trifluoro-3-oxobutanoate (2.2 g, 12 mmol). The reaction mixture was stirred overnight at 80° C. The reaction mixture was diluted with water (60 mL) and extracted with EtOAc (4×60 mL). The combined organics were dried over Na₂SO₄, filtered into a round bottom flask and concentrated under reduced pressure to afford the crude product. The crude residue was purified by chromatography thru a SiO₂ column using the mobile phase of 20-40% EtOAc/Hx to afford the title compound, (2.2 g, 6.0 mmol, 51% yield) MS (ESI) 367.0 [M+H]+.

Example 311 was prepared from Example 311b using procedures similar to those in Example 62 and Example 310. MS (ESI) 652.0 [M+H]+. ¹H NMR (400 MHz, MeOH-d₄) δ ppm 8.26 (t, 1H, J=1.63 Hz), 7.98-8.08 (m, 4H), 7.78 (t, J=7.91 Hz, 1H), 7.71 (d, 1H, J=8.28 Hz), 7.42-7.49 (m, 2H), 7.19 (d, 2H, J=8.03 Hz), 5.88 (s, 1H), 3.96 (q, 2H, J=7.03 Hz), 3.21 (s, 3H), 2.52 (s, 3H), 1.20-1.27 (m, 3H).

Example 312

4-(4-(5-cyclopropyl-3-(trifluoromethyl)-1H-pyrazol-1-yl)-3'-(methylsulfonyl)biphenyl-3-yl)-2-methyl-5-(4-(trifluoromethoxy)phenyl)oxazole

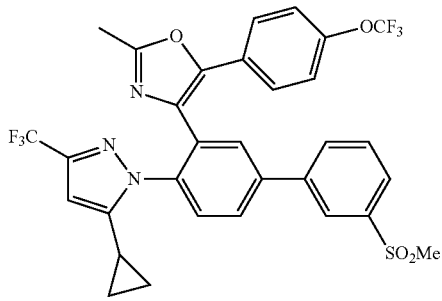 [SMILES: Cc1nc(-c2cc(-c3cccc(S(C)(=O)=O)c3)ccc2-n2nc(C(F)(F)F)cc2C2CC2)c(-c2ccc(OC(F)(F)F)cc2)o1]

Example 312a

Preparation of 1-cyclopropyl-4,4,4-trifluorobutane-1,3-dione

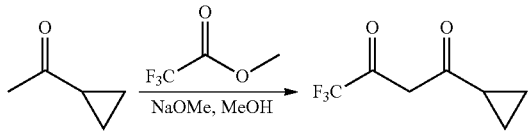

To a mixture of 1-cyclopropylethanone (15 g, 180 mmol) and methyl 2,2,2-trifluoroacetate (34 g, 270 mmol) in MeOH (180 mL) was added NaOMe (9.6 g, 180 mmol) in MeOH (180 mL) dropwise. The reaction mixture was stirred at rt for 16 hrs under N$_2$ atmosphere. The reaction mixture was acidified with 1N HCl (100 mL) and extracted with EtOAc (2×600 mL). The combined organic extracts were washed with water (200 mL), and brine (250 mL), dried over Na$_2$SO$_4$, filtered into a round bottom flask and concentrated under reduced pressure to afford the title compound as a pale brown oil (7.2 g, 40 mmol, 22% yield). GCMS 180.1.

Example 312b

Preparation of (5-bromo-2-(5-cyclopropyl-3-(trifluoromethyl)-1H-pyrazol-1-yl)phenyl)methanol

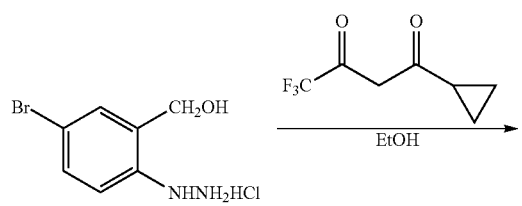

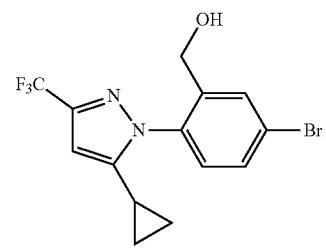

In a sealed tube, Example 312a (1.5 g, 5.9 mmol) and Example 311a (2.6 g, 15 mmol) were brought up in EtOH (150 mL) and the reaction mixture was stirred at 95° C. for 2 hrs. The reaction mixture was cooled to rt and concentrated in vacuo to give crude product as a pale brown oil. The crude residue was purified by chromatography thru a SiO$_2$ column using the mobile phase of 5% EtOAc/Hx to afford the title compound (1.3 g, 3.5 mmol, 59% yield). The regioisomer was confirmed by single crystal X-ray analysis. MS (ESI) 361.0 [M+H]+. $^1$H NMR (400 MHz, CDCl$_3$) δ ppm 7.80 (d, J=2.2 Hz, 1H), 7.58 (dd, J=8.4, 2.4 Hz, 1H), 7.31 (d, J=8.3 Hz, 1H), 6.21 (s, 1H), 4.33 (d, J=6.8 Hz, 2H), 3.19 (t, J=6.9 Hz, 1H), 1.57-1.69 (m, 1H), 0.93-1.04 (m, 2H), 0.74-0.82 (m, 2H).

Example 312 was prepared from Example 312b using procedures similar to those described in Example 62, Example 310. MS (ESI) 648.0 [M+H]+. $^1$H NMR (400 MHz, MeOH-d$_4$) δ ppm 8.25 (t, J=1.8 Hz, 1H), 8.01-8.07 (m, 4H), 7.76-7.81 (m, 2H), 7.50-7.52 (m, 2H), 7.22 (d, J=8.0 Hz, 2H), 6.12 (s, 1H), 3.20 (s, 3H), 2.45 (s, 3H), 1.52-1.56 (m, 1H), 0.87-0.92 (m, 2H), 0.61-0.65 (m, 2H).

Example 313

(4'-(3-(1,1-difluoroethyl)-1H-pyrazol-1-yl)-3-fluoro-3'-(2-methyl-4-(4-(trifluoromethoxy)phenyl)oxazol-5-yl)-5-(methylsulfonyl)-[1,1'-biphenyl]-4-yl)methanol

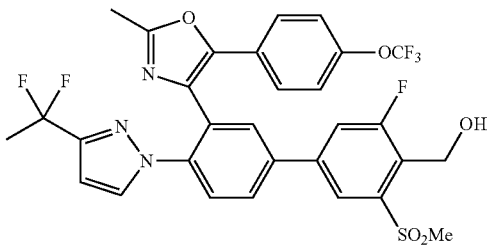 [SMILES: Cc1nc(-c2cc(-c3cc(F)c(CO)c(S(C)(=O)=O)c3)ccc2-n2ccc(C(C)(F)F)n2)c(-c2ccc(OC(F)(F)F)cc2)o1]

Example 313a

Preparation of (1-(4-bromo-2-(2-methyl-4-(4-(trifluoromethoxy)phenyl)oxazol-5-yl)phenyl)-1H-pyrazol-3-yl) methanol

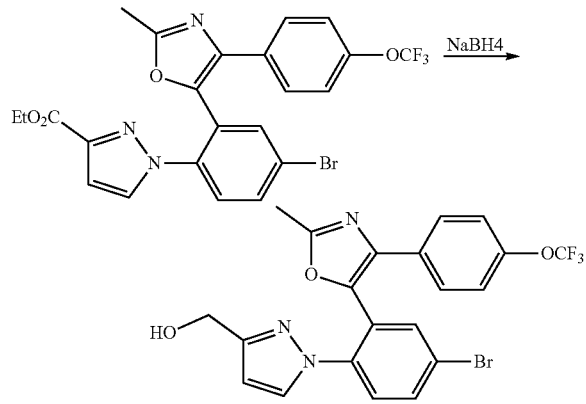

Example 336c (0.35 g, 0.65 mmol) was taken in up EtOH (30 mL) under nitrogen atmosphere in a reaction vessel. The vessel was cooled to 0° C. and sodium borohydride (0.494 g, 13.0 mmol) was added in portions. The reaction mixture was stirred at rt for 60 h. The solvent was removed under a vacuum. A 10% NaHCO₃ solution (50 mL) and EtOAc were added to the residue, and the layers were separated. The water was extracted with EtOAc (2×50 mL). The combined organic extracts were washed with water, brine, dried over Na₂SO₄ and concentrated to give crude product. The crude product was purified by silica gel chromatography (12 g silica column) eluting with 40-60% EtOAc in hexane to give the title compound (0.25 g, 0.506 mmol). MS (ESI) 496.0 [M+H]+. ¹H NMR (400 MHz, CDCl₃) δ ppm 7.73 (s, 1H), 7.68 (dd, J=2.4, 8.8 Hz, 1H), 7.52 (d, J=8.8 Hz, 1H), 7.38 (m, 2H), 7.15 (d, J=2.4 Hz, 2H), 7.06 (dd, J=0.8, 8.8 Hz, 2H), 6.11 (d, J=2.4 Hz, 1H), 4.53 (d, J=6 Hz, 2H), 2.50 (s, 3H), 1.71 (t, J=6 Hz, 1H).

The intermediate Example 313a was used to make compounds of the invention by further modifications as described in the patent (e.g. Example 1j) and standard chemical transformations known to those skilled in the art.

Example 313b

Preparation of 1-(4-bromo-2-(2-methyl-4-(4-(trifluoromethoxy)phenyl)oxazol-5-yl)phenyl)-1H-pyrazole-3-carbaldehyde

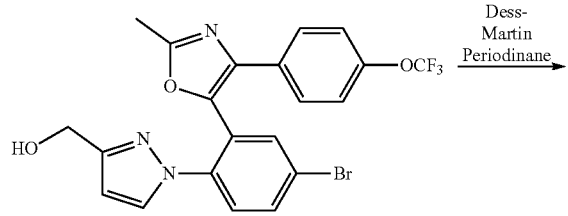

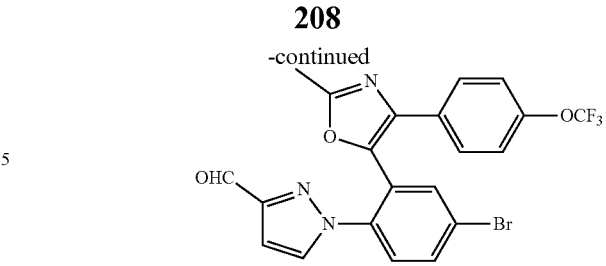

Example 313a (0.45 g, 0.91 mmol) was taken in DCM (50 mL) under nitrogen atmosphere in a reaction vessel. The vessel was cooled to 0° C. and Dess-Martin Periodinane (0.579 g, 1.37 mmol) was added. The reaction mixture was stirred at rt for 2 h, after which time TLC indicated that the starting material had been consumed. The mixture was filtered over celite and the filtrate was concentrated to give crude product. The crude product was purified by CombiFlash® column chromatography (40 g silica column) eluting with 10-30% EtOAc in hexane to give the title compound (0.43 g, 0.87 mmol). MS (ESI) 494.0 [M+H]+. ¹H NMR (400 MHz, CD₃OD) δ ppm 9.70 (s, 1H), 7.95 (d, J=2.4 Hz, 1H), 7.88 (dd, J=2.4, 8.8 Hz, 1H), 7.63 (m, 2H), 7.35 (m, 2H), 7.14 (d, J=8 Hz, 2H), 6.63 (d, J=2.8 Hz, 1H), 2.53 (s, 3H).

Example 313c

Preparation of 1-(1-(4-bromo-2-(2-methyl-4-(4-(trifluoromethoxy)phenyl)oxazol-5-yl)phenyl)-1H-pyrazol-3-yl)ethanol

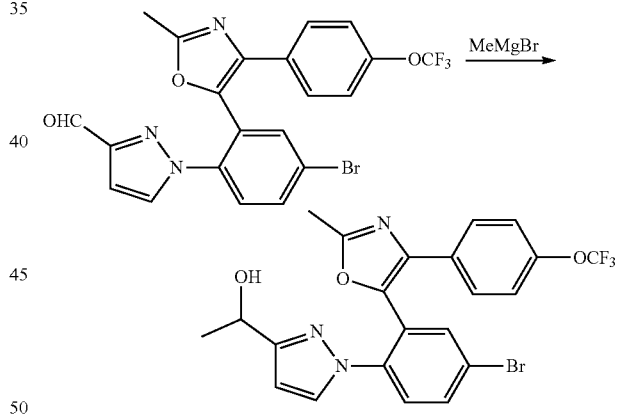

Example 313b (0.3 g, 0.6 mmol) was taken in THF (25 mL) in a reaction vessel under nitrogen atmosphere. The reaction vessel was cooled to 0° C., and MeMgBr was added (3.0 M solution in diethyl ether) (1.62 mL, 4.88 mmol) dropwise. The reaction mixture was stirred at 0° C. for 2 h. The reaction mixture was quenched with saturated NH₄Cl solution (20 mL) and extracted with EtOAc (2×50 mL). The combined organic extracts were washed with water, brine, dried over Na₂SO₄ and concentrated to give the title compound (0.3 g, 0.6 mmol). MS (ESI) 508.0 [M+H]+. ¹H NMR (400 MHz, CD₃OD) δ ppm 7.79-7.82 (m, 2H), 7.54 (dd, J=1.6, 7.2 Hz, 1H), 7.40-7.43 (m, 3H), 7.16 (dd, J=1, 8.8 Hz, 2H), 6.21 (d, J=2.4 Hz, 1H), 4.70 (q, J=6.4 Hz, 1H), 2.51 (s, 3H), 1.33 (d, J=6.4 Hz, 3H).

The intermediate Example 313c was used to make compounds of the invention by further modifications as described in the patent (e.g. Example 1j) and standard chemical transformations known to those skilled in the art.

Example 313d

Preparation of 1-(1-(4-bromo-2-(2-methyl-4-(4-(trifluoromethoxy)phenyl)oxazol-5-yl)phenyl)-1H-pyrazol-3-yl)ethanone

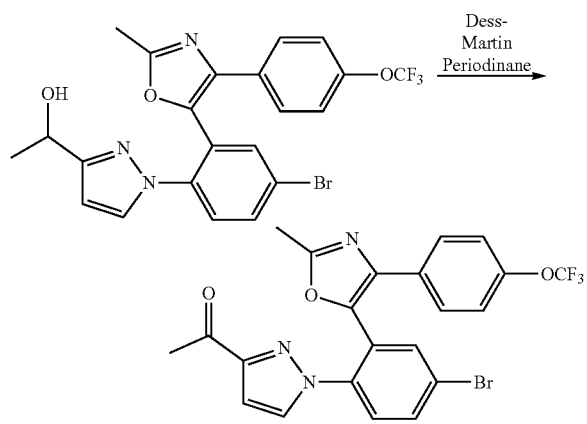

Example 313c (0.2 g, 0.4 mmol) was taken in DCM (25 mL) in a reaction vessel under nitrogen atmosphere. The reaction vessel was cooled to 0° C. and Dess-MartinPeriodinane (0.23 g, 0.55 mmol) was added. The reaction mixture was stirred at RT for 2 h. The reaction mixture was filtered thru celite and the filtrate was concentrated to give the crude product. The crude product was purified by CombiFlash® column chromatography (12 g silica column) eluting with 10-30% EtOAc in hexane to give the title compound (0.16 g, 0.32 mmol). MS (ESI) 506.0, 507.7 [M+H]+. $^1$H NMR (400 MHz, CD$_3$OD) δ ppm 7.90 (d, J=2.4 Hz, 1H), 7.84 (dd, J=2.4, 8.8 Hz, 1H), 7.58-7.60 (m, 2H), 7.33 (m, 2H), 7.11 (dd, J=1, 9 Hz, 2H), 6.56 (d, J=2.4 Hz, 1H), 2.49 (s, 3H), 2.31 (s, 3H).

Example 313e

Preparation of 5-(5-bromo-2-(3-(2-methyl-1,3-dithiolan-2-yl)-1H-pyrazol-1-yl)phenyl)-2-methyl-4-(4-(trifluoromethoxy)phenyl)oxazole

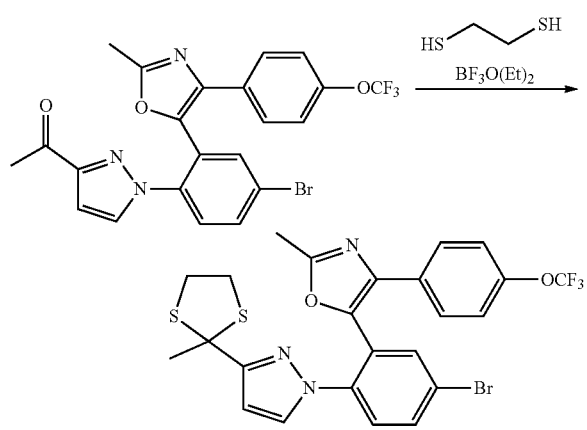

Example 313d (0.2 g, 0.4 mmol) was taken up in DCE (15 mL) in a reaction vessel under nitrogen atmosphere. Ethane-1,2-dithiol (0.066 mL, 0.79 mmol) was added followed by drop wise addition of boron trifluoride etherate (0.20 mL, 1.6 mmol). The reaction mixture was stirred at 70° C. for 2 h. The reaction mixture was quenched with 10% aq. NaHCO$_3$ solution and the mixture was extracted with DCM (2×50 mL). The combined organic extracts were washed with water, brine, dried over Na$_2$SO$_4$ and concentrated to give the title compound (0.22 g, 0.32 mmol). MS (ESI) 582.4, 584.3 [M+H]+. $^1$H NMR (400 MHz, CD$_3$OD) δ ppm 7.79-7.81 (m, 2H), 7.54 (dd, J=1, 8.0 Hz, 1H), 7.43-7.48 (m, 3H), 7.18 (dd, J=1, 8.8 Hz, 2H), 6.35 (d, J=3 Hz, 1H), 3.43 (s, 4H), 2.50 (s, 3H), 1.93 (s, 3H).

Example 313f

Preparation of 5-(5-bromo-2-(3-(1,1-difluoroethyl)-1H-pyrazol-1-yl)phenyl)-2-methyl-4-(4-(trifluoromethoxy)phenyl)oxazole

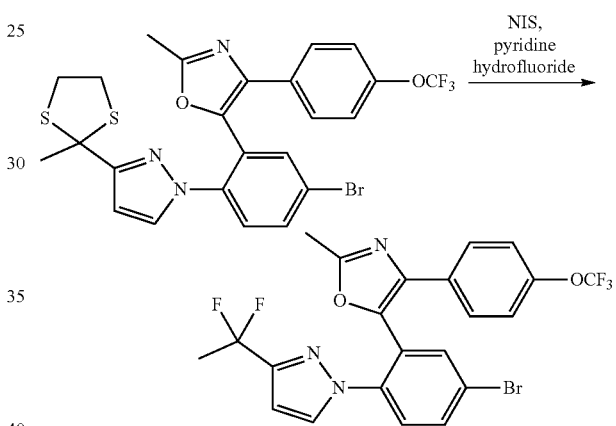

N-Iodosuccinimide (0.220 g, 0.979 mmol) was taken up in DCE (5 mL) in a reaction vessel under nitrogen atmosphere. The reaction vessel was cooled to −78° C. and pyridine hydrofluoride (70% Hydrogenfluoride, 30% pyridine, 0.141 mL, 1.14 mmol) was added drop wise. The reaction mixture was stirred at −78° C. for 15 min. A solution of Example 313e (0.19 g, 0.33 mmol) in DCE (10 mL) was added dropwise. The reaction mixture was stirred at −78° C. for 10 min, and then warmed up to 10° C. over 30 min. The reaction mixture was quenched with 10% aq. NaHCO$_3$ solution, the organics were separated and the aqueous layer was extracted with EtOAc (2×50 mL). The combined organic extracts were washed with water and brine, dried over Na$_2$SO$_4$ and concentrated to give crude product. The crude product was purified by CombiFlash® column chromatography (12 g silica column) eluting with 10-20% EtOAc in hexane to give the title compound (0.065 g, 0.092 mmol). MS (ESI) 528.0 [M+H]+. $^1$H NMR (400 MHz, CD$_3$OD) δ ppm 7.84 (m, 2H), 7.57-7.60 (m, 2H), 7.38-7.43 (m, 2H), 7.16 (m, 2H), 6.35 (d, J=2 Hz, 1H), 2.50 (s, 3H), 1.78 (t, J=18.4 Hz, 3H).

Example 313 was prepared from Example 313f using procedures similar to Example 1j, except dioxane/water was used as solvent and K$_3$PO$_4$ was used as base. MS (ESI) 652.2 [M+H]+. $^1$H NMR (400 MHz, CD$_3$OD) δ ppm 8.21 (d, J=1.2 Hz, 1H), 8.03-8.05 (m, 2H), 7.89 (dd, J=1.8 Hz, 10.6 Hz, 1H), 7.79-7.81 (m, 1H), 7.65 (d, J=2.4 Hz, 1H), 7.43-7.47 (m, 2H), 7.17 (dd, J=0.8 Hz, J=8.8 Hz, 2H), 6.39 (d, J=2.4 Hz, 1H), 5.14 (d, J=2.0 Hz, 2H), 3.40 (s, 3H), 2.53 (s, 3H), 1.76-1.85 (t, J=18.2 Hz, 3H). $^{19}$F NMR: −59.41, −86.16 and −115.54 ppm.

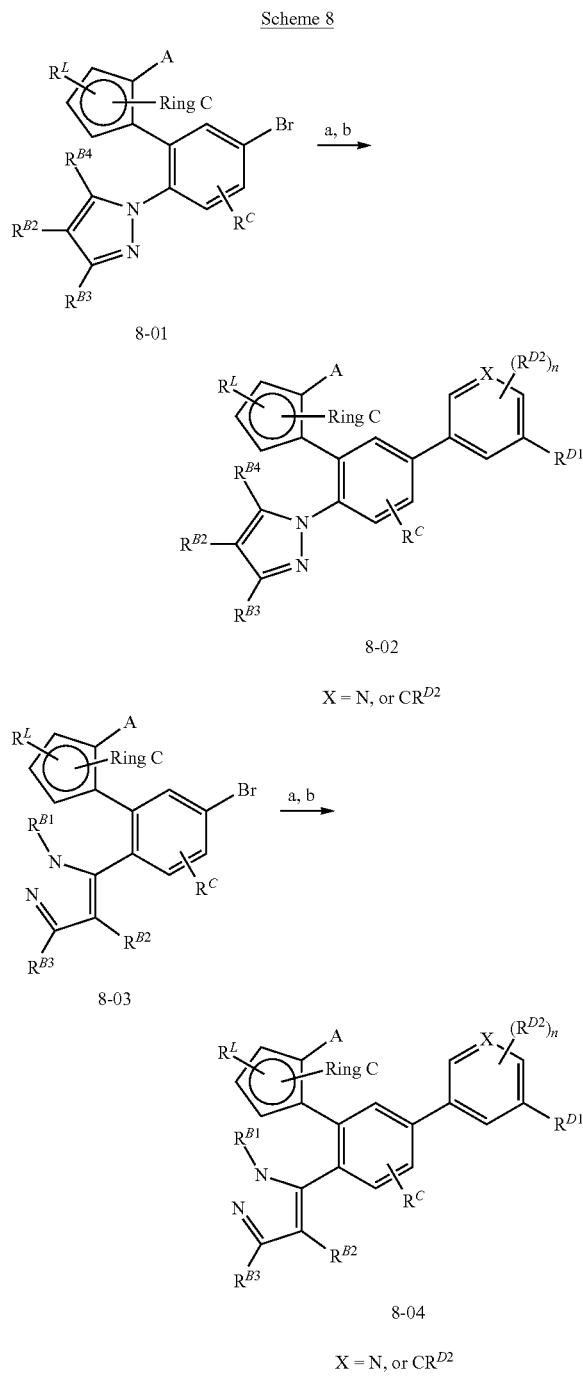

Scheme 8

8-01

8-02

X = N, or CR$^{D2}$ 8-03

8-04

X = N, or CR$^{D2}$ (a) bis(pinacolato)diboron, PdCl$_2$(dppf), dppf, KOAc, DMF, 100° C.
(b) phenyl or pyridyl bromide, K$_2$CO$_3$, PdCl$_2$(dppf), dioxane, H$_2$O, 80° C.

Compounds of the invention, can also be prepared by reacting the bromides 8-01 and 8-03 with bis(pinacolato) diboron with appropriate palladium coupling conditions, such as PdCl$_2$(dppf) with a base such as KOAc in DMF to form the boronate intermediates. These boronates could be purified or used directly in palladium coupling with a substituted phenyl or pyridyl bromide to yield 8-02 and 8-03. In Scheme 8 one pyridine isomer is exemplified, but similar chemistry can be used to form other pyridine analogs of the invention.

Example 314

(5-(4-(4-chloro-3-(trifluoromethyl)-1H-pyrazol-1-yl)-3-(2-methyl-4-(4-(trifluoromethoxy)phenyl)oxazol-5-yl)phenyl)-3-(methylsulfonyl)pyridin-2-yl) methanol 5-(5-bromo-2-(4-chloro-3-(trifluoromethyl)-1H-pyrazol-1-yl)phenyl)-2-methyl-4-(4-(trifluoromethoxy)phenyl)oxazole was prepared by methods described in the invention such as Example 309.

To the yellow solution of 5-(5-bromo-2-(4-chloro-3-(trifluoromethyl)-1H-pyrazol-1-yl)phenyl)-2-methyl-4-(4-(trifluoromethoxy)phenyl)oxazole (200 mg, 0.35 mmol) in DMF (4 mL) was added bis(pinacolato)diboron (134 mg, 0.529 mmol) and potassium acetate (104 mg, 1.06 mmol). The mixture was purged with nitrogen for 10 min and then DPPF (11 mg, 0.021 mmol) and PdCl$_2$(dppf) (15 mg, 0.021 mmol) were added. The mixture was again purged with nitrogen for 5 min. The pressure tube was closed and heated at 100° C. overnight. The reaction mixture was quenched with ice cold water (10 mL) and extracted with EtOAc (3×15 mL). The combined EtOAc layers were washed with water (1×15 mL) and brine (1×15 mL), dried by Na$_2$SO$_4$, filtered and concentrated to get a brown gummy crude product containing 5-(2-(4-chloro-3-(trifluoromethyl)-1H-pyrazol-1-yl)-5-(4,4,5,5-tetramethyl-1,3,2-dioxaborolan-2-yl)phenyl)-2-methyl-4-(4-(trifluoromethoxy)phenyl)oxazole (410 mg, MS (ESI) 614.2 [M+1]) that was taken forward without any further purification.

To a solution of the crude material (200 mg, 0.326 mmol) in dioxane (5 mL) was added (5-bromo-3-(methylsulfonyl) pyridin-2-yl)methanol (87 mg, 0.33 mmol), K$_2$CO$_3$ (135 mg, 0.978 mmol) and water (1.5 mL). The mixture was purged with nitrogen for 10 min, and then PdCl$_2$(dppf) (7.15 mg, 9.78 μmol) was added. The reaction pressure tube was again purged nitrogen for 5 min, and the vessel was sealed and heated at 80° C. overnight. The vessel was cooled to rt, and the mixture was diluted with EtOAc (30 mL), and washed with water (1×20 mL). The aqueous layer was extracted with EtOAc (2×25 mL). The combined organic layers were washed with brine (1×30 mL), dried by Na$_2$SO$_4$, filtered and concentrated to get a brown gummy solid, which was purified by silica gel (40 g silica column) column chromatography (50:50; EtOAc:Hexane) followed by reverse phase purification to afford 5.5 mgs of a white solid.

MS (ESI) 672.8 [M+H]. $^1$H NMR (400 MHz, CD$_3$OD-d$_4$) δ ppm 9.19 (d, J=2.0 Hz, 1H), 8.69 (d, J=2.0 Hz, 1H) 8.21 (d, J=2.0 Hz, 1H) 8.07-8.12 (m, 1H) 7.91 (s, 1H) 7.81 (d, J=8.5 Hz, 1H) 7.35-7.41 (m, 2H) 7.18 (dd, J=9.0, 1.0 Hz, 2H) 5.18 (s, 2H) 3.40 (s, 3H) 2.59 (s, 3H).

Example 315

(4'-(3-cyclopropyl-1H-pyrazol-1-yl)-3-fluoro-3'-(2-methyl-4-(4-(trifluoromethoxy)phenyl)oxazol-5-yl)-5-(methylsulfonyl)-[1,1'-biphenyl]-4-yl)methanol

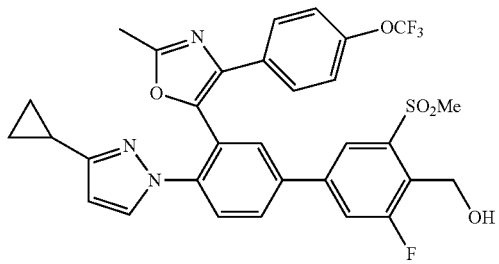 [SMILES: Cc1nc(-c2ccc(OC(F)(F)F)cc2)c(-c2cc(-c3cc(F)c(CO)c(S(C)(=O)=O)c3)ccc2-n2ccc(C3CC3)n2)o1]

Example 315a

Preparation of 5-bromo-2-(3-cyclopropyl-1H-pyrazol-1-yl)benzonitrile

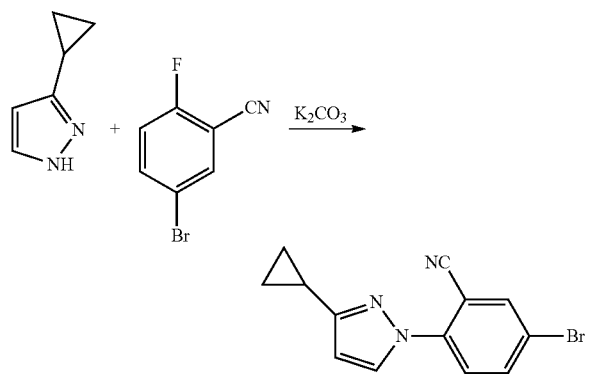

In a 50 mL round-bottomed flask was added 3-cyclopropyl-1H-pyrazole (2.0 g, 18 mmol), K$_2$CO$_3$ (5.1 g, 37 mmol) and 5-bromo-2-fluorobenzonitrile (3.7 g, 18 mmol) in DMF (15 mL) to give a yellow suspension. Then reaction mixture was stirred at rt for overnight under nitrogen atmosphere. The excess DMF was distilled from the mixture at reduced pressure, and the residue was diluted with water (50 mL). The aq layer was extracted with EtOAc (3×50 mL). The combined organic layers were washed with brine (1×25 mL). The organic solution was dried over Na$_2$SO$_4$, filtered and concentrated at reduced pressure to give crude product. The crude material was added to a silica gel column and was eluted with 2%-10% of ethyl acetate-petether to afford a white color solid (3.7 g, 12 mmol). $^1$H NMR (400 MHz, CD$_3$OD) δ ppm 8.05 (d, J=2 Hz, 1H), 7.84 (d, J=2 Hz, 1H), 7.76 (dd, J=2, 8.8 Hz, 1H), 7.70 (d, J=8.8 Hz, 1H), 6.22 (d, J=2 Hz, 1H), 2.00 (m, 1H), 1.00 (m, 2H), 0.86 (m, 2H).

Example 315b

Preparation of 5-bromo-2-(3-cyclopropyl-1H-pyrazol-1-yl)benzaldehyde

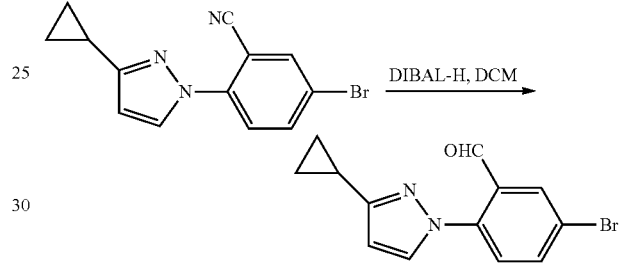

In a 250 mL round-bottomed flask was added 5-bromo-2-(3-cyclopropyl-1H-pyrazol-1-yl)benzonitrile (2.5 g, 8.7 mmol) in DCM (150 mL) to give a yellow solution. DIBAL-H (17.3 mL, 17.3 mmol) was added dropwise for 20 min at −40° C. and under nitrogen atmosphere. The reaction mixture was stirred for 1 hr at −40° C. The reaction mixture was quenched with sat. NH$_4$Cl solution (40 mL), and DCM (200 mL) was added. The mixture was stirred for 30 min at rt. The reaction mixture was filtered through a celite bed and the celite bed was washed with DCM (100 mL). The combined organic layers were dried over Na$_2$SO$_4$, filtered and concentrated at reduced pressure to afford the crude product. The crude product was added to a silica gel column and was eluted with 2%-20% of EtOAc and pet ether to afford the title compound (600 mg, 2.06 mmol). $^1$H NMR (400 MHz, CDCl$_3$) δ ppm 10.08 (s, 1H), 8.09 (d, J=2 Hz, 1H), 7.73 (dd, J=2, 8.4 Hz, 1H), 7.66 (d, J=2 Hz, 1H), 7.34 (d, J=8.4 Hz, 1H), 6.23 (d, J=2 Hz, 1H), 1.99 (m, 1H), 0.98 (m, 2H), 0.82 (m, 2H).

Example 315 was prepared from Example 315b using procedures similar to Example 308 and 309. MS (ESI) 628.0 [M+H]+. $^1$H NMR (400 MHz, CD$_3$OD-d$_4$) δ ppm 8.21 (1H, d, J=1.1 Hz), 7.97-8.04 (2H, m), 7.88 (1H, dd, J=10.54, 1.88 Hz), 7.69-7.77 (1H, m), 7.32-7.47 (3H, m), 7.16 (2H, dd, J=8.94, 0.97 Hz), 5.90 (1H, d, J=2.51 Hz), 5.14 (2H, d, J=1.95 Hz), 3.40 (3H, s), 2.56 (3H, s), 1.80 (1H, s), 0.83-0.93 (2H, m), 0.53-0.63 (2H, m).

The following compounds were made in a manner similar to that described in the previous experimental procedures:

| Ex # | Structure | Name | Characterization Data |
|---|---|---|---|
| 316 | 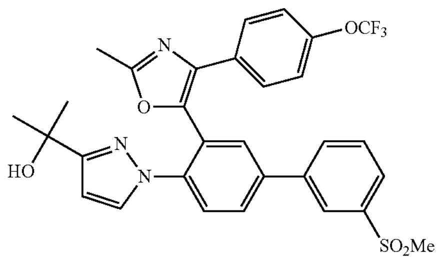 [SMILES: Cc1nc(-c2ccc(OC(F)(F)F)cc2)c(-c2cc(-c3cccc(S(C)(=O)=O)c3)ccc2-n2ccc(C(C)(C)O)n2)o1] | 2-(1-(3-(2-methyl-4-(4-(trifluoromethoxy)phenyl)oxazol-5-yl)-3'-(methylsulfonyl)biphenyl-4-yl)-1H-pyrazol-3-yl)propan-2-ol | MS (ESI) 598.2 [M + H]+. |
| 317 | 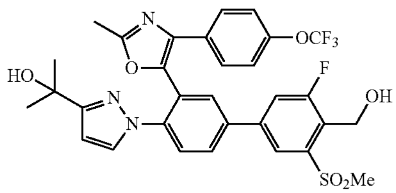 [SMILES: Cc1nc(-c2ccc(OC(F)(F)F)cc2)c(-c2cc(-c3cc(F)c(CO)c(S(C)(=O)=O)c3)ccc2-n2ccc(C(C)(C)O)n2)o1] | 2-(1-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1H-pyrazol-3-yl)propan-2-ol | MS (ESI) 646.2 [M + H]+. |
| 318 | 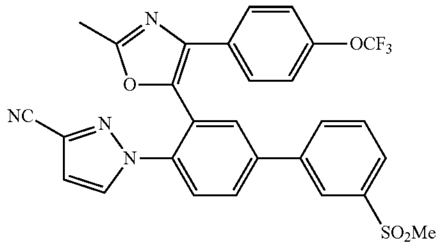 [SMILES: Cc1nc(-c2ccc(OC(F)(F)F)cc2)c(-c2cc(-c3cccc(S(C)(=O)=O)c3)ccc2-n2ccc(C#N)n2)o1] | 1-(3-(2-methyl-4-(4-(trifluoromethoxy)phenyl)oxazol-5-yl)-3'-(methylsulfonyl)biphenyl-4-yl)-1H-pyrazole-3-carbonitrile | MS (ESI) 565.2 [M + H]+. |
| 319 | 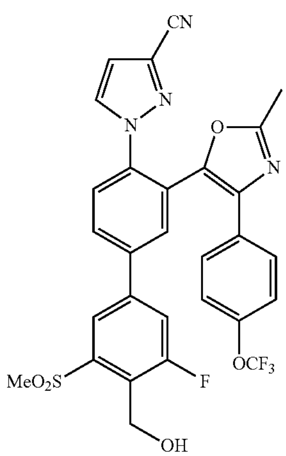 [SMILES: Cc1nc(-c2ccc(OC(F)(F)F)cc2)c(-c2cc(-c3cc(F)c(CO)c(S(C)(=O)=O)c3)ccc2-n2ccc(C#N)n2)o1] | 1-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1H-pyrazole-3-carbonitrile | MS (ESI) 613.0 [M + H]+ $^1$H NMR (400 MHz, CD$_3$OD) δ ppm 8.20-8.19 (d, J = 1.2 Hz, 1H), 8.10-8.09 (m, 1H), 8.06-8.04 (dd, J = 8.4 Hz, 2.0 Hz, 1H), 7.94-7.91 (dd, J = 10.4 Hz, 2.0 Hz, 1H), 7.82-7.79 (m, 2H), 7.42 (d, J = 8.4 Hz, 2H), 7.19 (d, J = 8.4 Hz, 2H), 6.74 (d, J = 2.4 Hz, 1H), 5.14 (d, J = 2.0 Hz, 2H), 3.40 (s, 3H), 2.55 (s, 3H). |
| 320 | 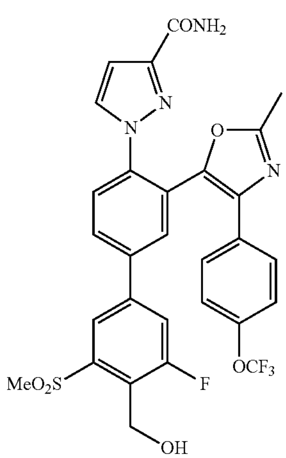 [SMILES: Cc1nc(-c2ccc(OC(F)(F)F)cc2)c(-c2cc(-c3cc(F)c(CO)c(S(C)(=O)=O)c3)ccc2-n2ccc(C(N)=O)n2)o1] | 1-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1H-pyrazole-3-carboxamide | MS (ESI) 631.4 [M + H]+. |

-continued

| Ex # | Structure | Name | Characterization Data |
|---|---|---|---|
| 321 | 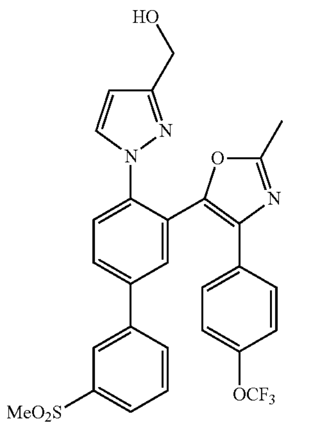 [SMILES: Cc1nc(-c2ccc(OC(F)(F)F)cc2)c(-c2cc(-c3cccc(S(C)(=O)=O)c3)ccc2-n2ccc(CO)n2)o1] | (1-(3-(2-methyl-4-(4-(trifluoromethoxy)phenyl)oxazol-5-yl)-3'-(methylsulfonyl)biphenyl-4-yl)-1H-pyrazol-3-yl)methanol | MS (ESI) 570.2 [M + H]+. |
| 322 | 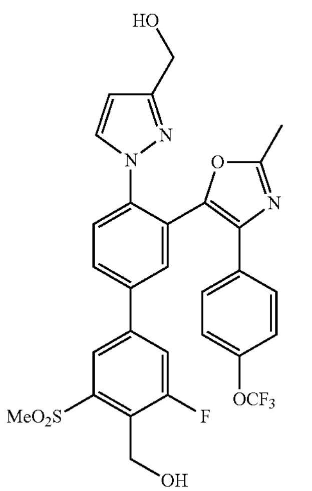 [SMILES: Cc1nc(-c2ccc(OC(F)(F)F)cc2)c(-c2cc(-c3cc(F)c(CO)c(S(C)(=O)=O)c3)ccc2-n2ccc(CO)n2)o1] | (3-fluoro-4'-(3-(hydroxymethyl)-1H-pyrazol-1-yl)-3'-(2-methyl-4-(4-(trifluoromethoxy)phenyl)oxazol-5-yl)-5-(methylsulfonyl)biphenyl-4-yl)methanol | MS (ESI) 618.0 [M + H]+. |
| 323 | 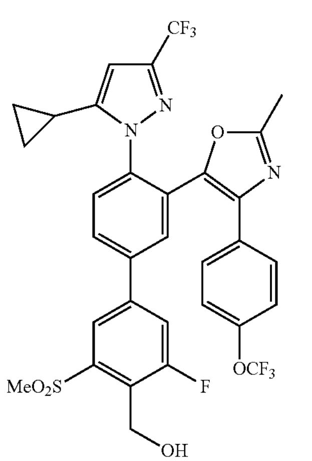 [SMILES: Cc1nc(-c2ccc(OC(F)(F)F)cc2)c(-c2cc(-c3cc(F)c(CO)c(S(C)(=O)=O)c3)ccc2-n2nc(C(F)(F)F)cc2C2CC2)o1] | (4'-(5-cyclopropyl-3-(trifluoromethyl)-1H-pyrazol-1-yl)-3-fluoro-3'-(2-methyl-4-(4-(trifluoromethoxy)phenyl)oxazol-5-yl)-5-(methylsulfonyl)biphenyl-4-yl)methanol | MS (ESI) 696.0 [M + H]+. |

-continued

| Ex # | Structure | Name | Characterization Data |
|---|---|---|---|
| 324 | 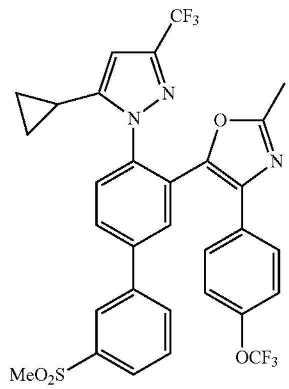 [SMILES: Cc1nc(-c2ccc(OC(F)(F)F)cc2)c(-c2cc(-c3cccc(S(C)(=O)=O)c3)ccc2-n2nc(C(F)(F)F)cc2C2CC2)o1] | 5-(4-(5-cyclopropyl-3-(trifluoromethyl)-1H-pyrazol-1-yl)-3'-(methylsulfonyl)biphenyl-3-yl)-2-methyl-4-(4-(trifluoromethoxy)phenyl)oxazole | MS (ESI) 648.0 [M + H]+. |
| 325 | 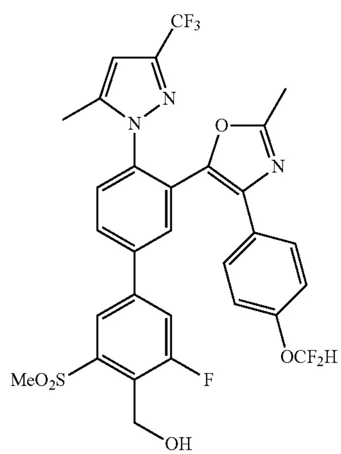 | (3'-(4-(4-(difluoromethoxy)phenyl)-2-methyloxazol-5-yl)-3-fluoro-4'-(5-methyl-3-(trifluoromethyl)-1H-pyrazol-1-yl)-5-(methylsulfonyl)biphenyl-4-yl)methanol | MS (ESI) 652.0 [M + H]+. |
| 326 | 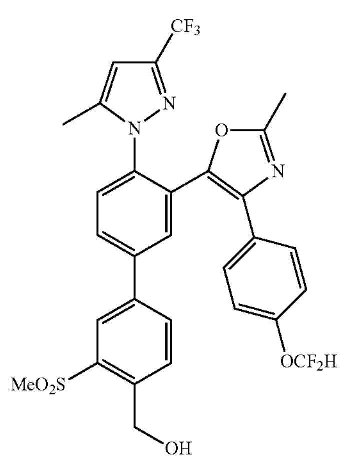 | (3'-(4-(4-(difluoromethoxy)phenyl)-2-methyloxazol-5-yl)-4'-(5-methyl-3-(trifluoromethyl)-1H-pyrazol-1-yl)-3-(methylsulfonyl)biphenyl-4-yl)methanol | MS (ESI) 634.0 [M + H]+. |

| Ex # | Structure | Name | Characterization Data |
|---|---|---|---|
| 327 | 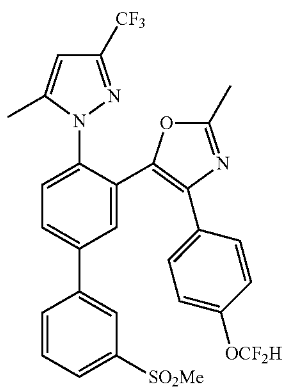 | 4-(4-(difluoromethoxy)phenyl)-2-methyl-5-(4-(5-methyl-3-(trifluoromethyl)-1H-pyrazol-1-yl)-3'-(methylsulfonyl)biphenyl-3-yl)oxazole | MS (ESI) 604.0 [M + H]+. |
| 328 | 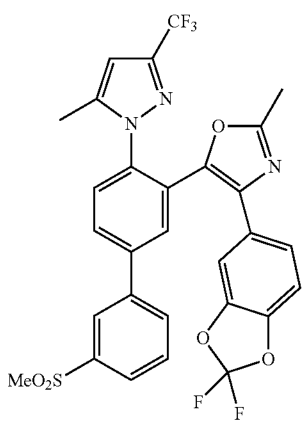 [SMILES: Cc1nc(-c2ccc3c(c2)OC(F)(F)O3)c(-c2cc(-c3cccc(S(C)(=O)=O)c3)ccc2-n2nc(C(F)(F)F)cc2C)o1] | 4-(2,2-difluorobenzo[d][1,3]dioxol-5-yl)-2-methyl-5-(4-(5-methyl-3-(trifluoromethyl)-1H-pyrazol-1-yl)-3'-(methylsulfonyl)biphenyl-3-yl)oxazole | MS (ESI) 618.0 [M + H]+. |
| 329 | 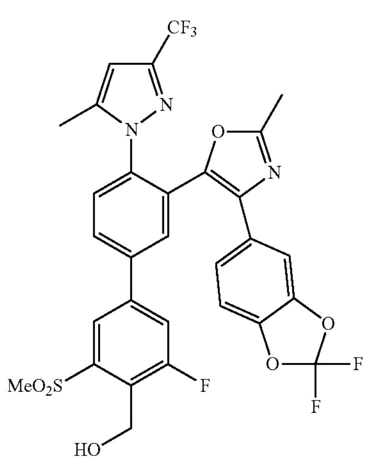 [SMILES: Cc1nc(-c2ccc3c(c2)OC(F)(F)O3)c(-c2cc(-c3cc(F)c(CO)c(S(C)(=O)=O)c3)ccc2-n2nc(C(F)(F)F)cc2C)o1] | (3'-(4-(2,2-difluorobenzo[d][1,3]dioxol-5-yl)-2-methyloxazol-5-yl)-3-fluoro-4'-(5-methyl-3-(trifluoromethyl)-1H-pyrazol-1-yl)-5-(methylsulfonyl)biphenyl-4-yl)methanol | MS (ESI) 666.0 [M + H]+. |

-continued

| Ex # | Structure | Name | Characterization Data |
|---|---|---|---|
| 330 | 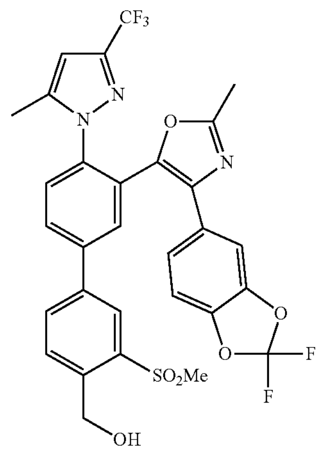 [SMILES: Cc1nc(-c2ccc3c(c2)OC(F)(F)O3)c(-c2cc(-c3ccc(CO)c(S(C)(=O)=O)c3)ccc2-n2nc(C(F)(F)F)cc2C)o1] | (3'-(4-(2,2-difluorobenzo[d][1,3]dioxol-5-yl)-2-methyloxazol-5-yl)-4'-(5-methyl-3-(trifluoromethyl)-1H-pyrazol-1-yl)-3-(methylsulfonyl)biphenyl-4-yl)methanol | MS (ESI) 648.0 [M + H]+. |
| 331 | 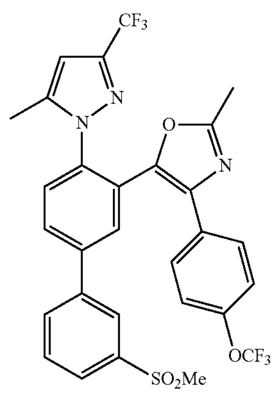 [SMILES: Cc1nc(-c2ccc(OC(F)(F)F)cc2)c(-c2cc(-c3cccc(S(C)(=O)=O)c3)ccc2-n2nc(C(F)(F)F)cc2C)o1] | 2-methyl-5-(4-(5-methyl-3-(trifluoromethyl)-1H-pyrazol-1-yl)-3'-(methylsulfonyl)biphenyl-3-yl)-4-(4-(trifluoromethoxy)phenyl)oxazole | MS (ESI) 622.0 [M + H]+. |
| 332 | 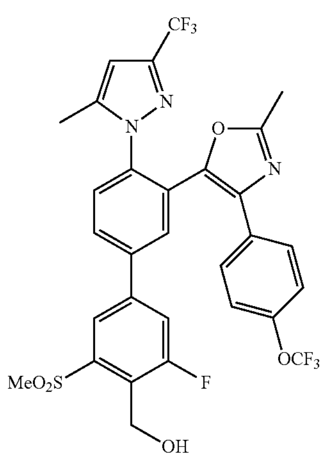 [SMILES: Cc1nc(-c2ccc(OC(F)(F)F)cc2)c(-c2cc(-c3cc(F)c(CO)c(S(C)(=O)=O)c3)ccc2-n2nc(C(F)(F)F)cc2C)o1] | (3-fluoro-4'-(5-methyl-3-(trifluoromethyl)-1H-pyrazol-1-yl)-3'-(2-methyl-4-(4-(trifluoromethoxy)phenyl)oxazol-5-yl)-5-(methylsulfonyl)biphenyl-4-yl)methanol | MS (ESI) 670.0 [M + H]+. <br> $^1$H NMR (400 MHz, METHANOL-d$_4$) δ ppm 8.19 (s, 1H), 8.08 (d, J = 2.0 Hz, 1H), 8.05-8.02 (dd, J = 8.2 Hz, 2.2 Hz, 1H), 7.87-7.84 (dd, J = 10.4 Hz, 1.6 Hz, 1H), 7.73-7.71 (d, J = 8.0 Hz, 1H), 7.50-7.48 (m, 2H), 7.24-7.22 (d, J = 8.0 Hz, 2H), 6.35 (s, 1H), 5.14-5.13 (d, J = 1.6 Hz, 2H), 3.39 (s, 3H), 2.45 (s, 3H), 2.07 (s, 3H) |

| Ex # | Structure | Name | Characterization Data |
|---|---|---|---|
| 333 | 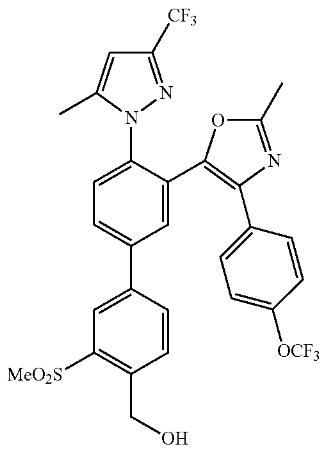 [SMILES: Cc1nc(-c2ccc(OC(F)(F)F)cc2)c(-c2cc(-c3ccc(CO)c(S(C)(=O)=O)c3)ccc2-n2nc(C(F)(F)F)cc2C)o1] | (4'-(5-methyl-3-(trifluoromethyl)-1H-pyrazol-1-yl)-3'-(2-methyl-4-(4-(trifluoromethoxy)phenyl)oxazol-5-yl)-3-(methylsulfonyl)biphenyl-4-yl)methanol | MS (ESI) 652.0 [M + H]+. $^1$H NMR (400 MHz, METHANOL-$d_4$) δ ppm 8.29 (d, J = 2.0 Hz, 1H), 8.05-8.00 (m, 3H), 7.91-7.89 (m, 1H), 7.72-7.70 (d, J = 8.0 Hz, 1H), 7.51-7.49 (m, 2H), 7.25-7.23 (d, J = 8.4 Hz, 2H), 6.36 (s, 1H), 5.10 (s, 2H), 3.28 (s, 3H), 2.44 (s, 3H), 2.08 (s, 3H) |
| 334 | 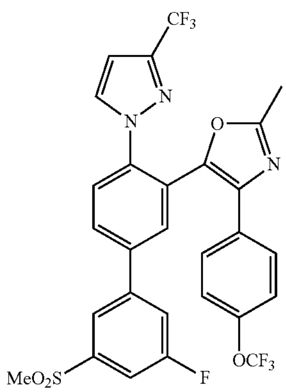 [SMILES: Cc1nc(-c2ccc(OC(F)(F)F)cc2)c(-c2cc(-c3cc(F)cc(S(C)(=O)=O)c3)ccc2-n2ccc(C(F)(F)F)n2)o1] | 5-(3'-fluoro-5'-(methylsulfonyl)-4-(3-(trifluoromethyl)-1H-pyrazol-1-yl)biphenyl-3-yl)-2-methyl-4-(4-(trifluoromethoxy)phenyl)oxazole | MS (ESI) 626.0 [M + H]+. |
| 335 | 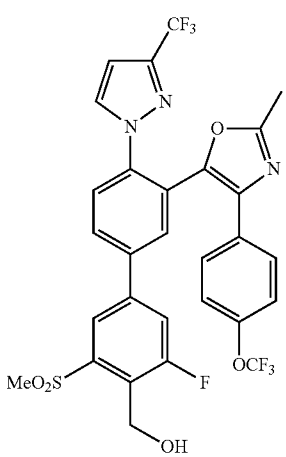 [SMILES: Cc1nc(-c2ccc(OC(F)(F)F)cc2)c(-c2cc(-c3cc(F)c(CO)c(S(C)(=O)=O)c3)ccc2-n2ccc(C(F)(F)F)n2)o1] | (3-fluoro-3'-(2-methyl-4-(4-(trifluoromethoxy)phenyl)oxazol-5-yl)-5-(methylsulfonyl)-4'-(3-(trifluoromethyl)-1H-pyrazol-1-yl)biphenyl-4-yl)methanol | MS (ESI) 656.0 [M + H]+. $^1$H NMR (400 MHz, METHANOL-$d_4$) δ ppm 8.22 (s, 1H), 8.10-8.09 (d, J = 2.0 Hz, 1H), 8.06-8.04 (dd, J = 8.4 Hz, 2.0 Hz, 1H), 7.92-7.89 (dd, J = 10.4 Hz, 1.6 Hz, 1H), 7.82-7.80 (m, 1H), 7.74 (d, J = 1.6 Hz, 1H), 7.43-7.40 (m, 2H), 7.18-7.16 (d, J = 8.0 Hz, 2H), 6.51 (d, J = 2.4 Hz, 1H), 5.15-5.14 (d, J = 1.6 Hz, 2H), 3.40 (s, 3H), 2.54 (s, 3H) |

| Ex # | Structure | Name | Characterization Data |
|---|---|---|---|
| 336 | 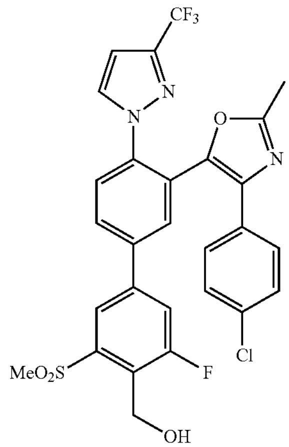 [SMILES: Cc1nc(-c2ccc(Cl)cc2)c(-c2cc(-c3cc(F)c(CO)c(S(C)(=O)=O)c3)ccc2-n2ccc(C(F)(F)F)n2)o1] | (3'-(4-(4-chlorophenyl)-2-methyloxazol-5-yl)-3-fluoro-5-(methylsulfonyl)-4'-(3-(trifluoromethyl)-1H-pyrazol-1-yl)biphenyl-4-yl)methanol | MS (ESI) 606.0 [M + H]+. |
| 337 | 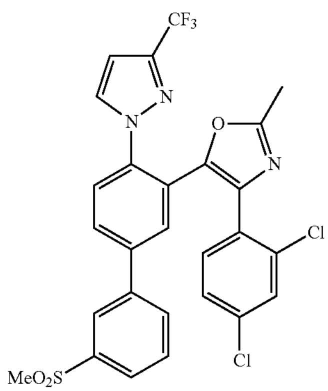 [SMILES: Cc1nc(-c2ccc(Cl)cc2Cl)c(-c2cc(-c3cccc(S(C)(=O)=O)c3)ccc2-n2ccc(C(F)(F)F)n2)o1] | 4-(2,4-dichlorophenyl)-2-methyl-5-(3'-(methylsulfonyl)-4-(3-(trifluoromethyl)-1H-pyrazol-1-yl)biphenyl-3-yl)oxazole | MS (ESI) 592.0 [M + H]+. $^1$H NMR (400 MHz, METHANOL-d$_4$) δ ppm 8.30-8.28 (t, J = 1.2 Hz, 1H), 8.11-8.08 (m, 1H), 8.05-8.03 (m, 2H), 7.95-7.93 (m, 1H), 7.82-7.78 (m, 1H), 7.64-7.62 (m, 2H), 7.43 (d, J = 2.0 Hz, 1H), 7.26-7.24 (m, 1H), 7.16-7.14 (m, 1H), 6.54-6.53 (d, J = 2.8 Hz, 1H), 3.23 (s, 3H), 2.61 (s, 3H) |
| 338 | 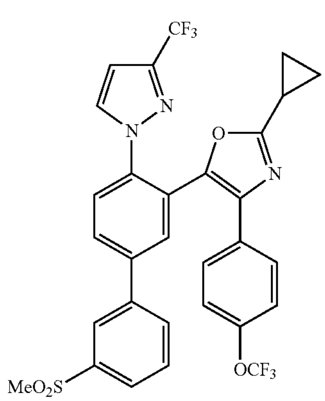 [SMILES: CS(=O)(=O)c1cccc(-c2ccc(-n3ccc(C(F)(F)F)n3)c(-c3oc(C4CC4)nc3-c3ccc(OC(F)(F)F)cc3)c2)c1] | 2-cyclopropyl-5-(3'-(methylsulfonyl)-4-(3-(trifluoromethyl)-1H-pyrazol-1-yl)biphenyl-3-yl)-4-(4-(trifluoromethoxy)phenyl)oxazole | MS (ESI) 634.2 [M + H]+ |

-continued

| Ex # | Structure | Name | Characterization Data |
|---|---|---|---|
| 339 | 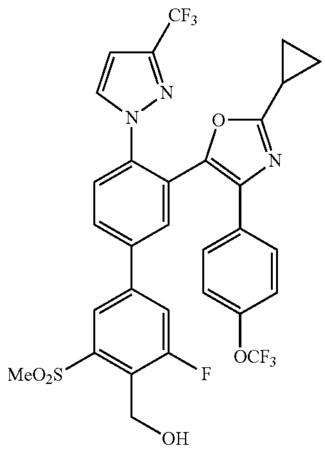 [SMILES: CS(=O)(=O)c1cc(-c2ccc(-n3ccc(C(F)(F)F)n3)c(-c3oc(C4CC4)nc3-c3ccc(OC(F)(F)F)cc3)c2)cc(F)c1CO] | (3'-(2-cyclopropyl-4-(4-(trifluoromethoxy)phenyl)oxazol-5-yl)-3-fluoro-5-(methylsulfonyl)-4'-(3-(trifluoromethyl)-1H-pyrazol-1-yl)biphenyl-4-yl)methanol | MS (ESI) 682.2 [M + H]+. $^1$H NMR (400 MHz, METHANOL-d$_4$) δ ppm 8.17 (s, 1H), 8.03-8.00 (m, 2H), 7.85-7.77 (m, 3H), 7.50-7.48 (m, 2H), 7.20-7.18 (dd, J = 8.8 Hz, 0.8 Hz, 2H), 6.59 (d, J = 2.4 Hz, 1H), 5.13 (d, J = 2.0 Hz, 2H), 3.38 (s, 3H), 2.17-2.10 (m, 1H), 1.14-1.04 (m, 4H) |
| 340 | 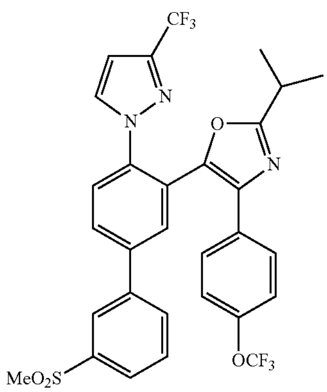 [SMILES: CC(C)c1nc(-c2ccc(OC(F)(F)F)cc2)c(-c2cc(-c3cccc(S(C)(=O)=O)c3)ccc2-n2ccc(C(F)(F)F)n2)o1] | 2-isopropyl-5-(3'-(methylsulfonyl)-4-(3-(trifluoromethyl)-1H-pyrazol-1-yl)biphenyl-3-yl)-4-(4-(trifluoromethoxy)phenyl)oxazole | MS (ESI) 636.2 [M + H]+. |
| 341 | 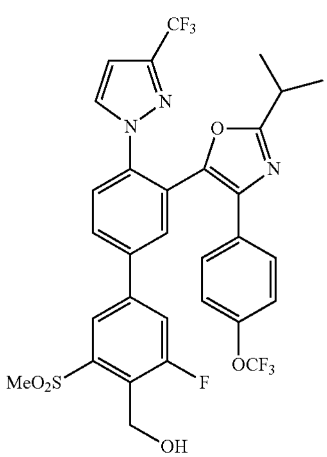 [SMILES: CC(C)c1nc(-c2ccc(OC(F)(F)F)cc2)c(-c2cc(-c3cc(F)c(CO)c(S(C)(=O)=O)c3)ccc2-n2ccc(C(F)(F)F)n2)o1] | (3-fluoro-3'-(2-isopropyl-4-(4-(trifluoromethoxy)phenyl)oxazol-5-yl)-5-(methylsulfonyl)-4'-(3-(trifluoromethyl)-1H-pyrazol-1-yl)biphenyl-4-yl)methanol | MS (ESI) 684.2 [M + H]+. $^1$H NMR (400 MHz, METHANOL-d$_4$) δ ppm 8.17 (d, J = 1.2 Hz, 1H), 8.05-8.00 (m, 2H), 7.85-7.79 (m, 3H), 7.55-7.53 (m, 2H), 7.22-7.20 (dd, J = 8.8 Hz, 0.8 Hz, 2H), 6.61-6.60 (d, J = 2.8 Hz, 1H), 5.13 (d, J = 1.6 Hz, 2H), 3.38 (s, 3H), 3.14-3.10 (m, 1H), 1.35-1.33 (d, J = 7.2 Hz, 6H) |

-continued

| Ex # | Structure | Name | Characterization Data |
|---|---|---|---|
| 342 | 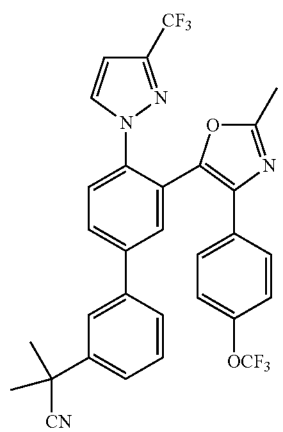 [SMILES: Cc1nc(-c2ccc(OC(F)(F)F)cc2)c(-c2cc(-c3cccc(C(C)(C)C#N)c3)ccc2-n2ccc(C(F)(F)F)n2)o1] | 2-methyl-2-(3'-(2-methyl-4-(4-(trifluoromethoxy)phenyl)oxazol-5-yl)-4'-(3-(trifluoromethyl)-1H-pyrazol-1-yl)biphenyl-3-yl)propanenitrile | MS (ESI) 597.2 [M + H]+. |
| 343 | 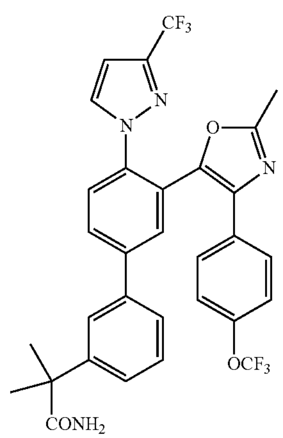 [SMILES: Cc1nc(-c2ccc(OC(F)(F)F)cc2)c(-c2cc(-c3cccc(C(C)(C)C(N)=O)c3)ccc2-n2ccc(C(F)(F)F)n2)o1] | 2-methyl-2-(3'-(2-methyl-4-(4-(trifluoromethoxy)phenyl)oxazol-5-yl)-4'-(3-(trifluoromethyl)-1H-pyrazol-1-yl)biphenyl-3-yl)propanamide | MS (ESI) 615.2 [M + H]+. |
| 344 | 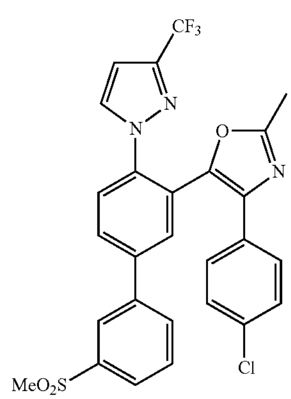 [SMILES: Cc1nc(-c2ccc(Cl)cc2)c(-c2cc(-c3cccc(S(C)(=O)=O)c3)ccc2-n2ccc(C(F)(F)F)n2)o1] | 4-(4-chlorophenyl)-2-methyl-5-(3'-(methylsulfonyl)-4-(3-(trifluoromethyl)-1H-pyrazol-1-yl)biphenyl-3-yl)oxazole | MS (ESI) 558.2 [M + H]+. |

-continued

| Ex # | Structure | Name | Characterization Data |
|---|---|---|---|
| 345 | 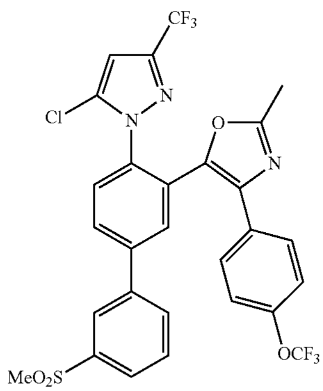 [SMILES: Cc1nc(-c2ccc(OC(F)(F)F)cc2)c(-c2cc(-c3cccc(S(C)(=O)=O)c3)ccc2-n2nc(C(F)(F)F)cc2Cl)o1] | 5-(4-(5-chloro-3-(trifluoromethyl)-1H-pyrazol-1-yl)-3'-(methylsulfonyl)biphenyl-3-yl)-2-methyl-4-(4-(trifluoromethoxy)phenyl)oxazole | MS (ESI) 642.0 [M + H]+. |
| 346 | 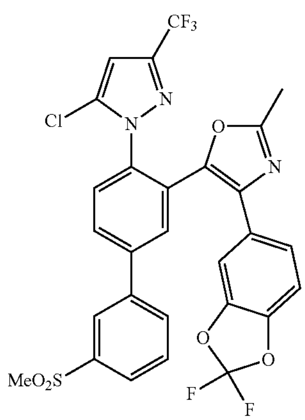 [SMILES: Cc1nc(-c2ccc3c(c2)OC(F)(F)O3)c(-c2cc(-c3cccc(S(C)(=O)=O)c3)ccc2-n2nc(C(F)(F)F)cc2Cl)o1] | 5-(4-(5-chloro-3-(trifluoromethyl)-1H-pyrazol-1-yl)-3'-(methylsulfonyl)biphenyl-3-yl)-4-(2,2-difluorobenzo[d][1,3]dioxol-5-yl)-2-methyloxazole | MS (ESI) 638.0 [M + H]+. |
| 347 | 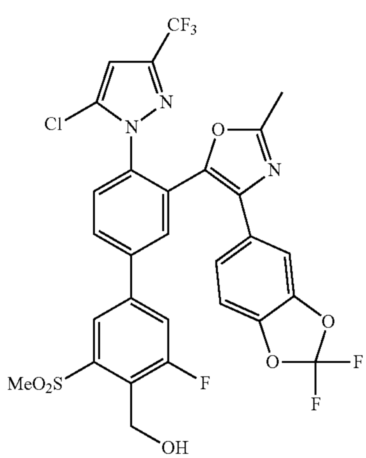 [SMILES: Cc1nc(-c2ccc3c(c2)OC(F)(F)O3)c(-c2cc(-c3cc(F)c(CO)c(S(C)(=O)=O)c3)ccc2-n2nc(C(F)(F)F)cc2Cl)o1] | (4'-(5-chloro-3-(trifluoromethyl)-1H-pyrazol-1-yl)-3'-(4-(2,2-difluorobenzo[d][1,3]dioxol-5-yl)-2-methyloxazol-5-yl)-3-fluoro-5-(methylsulfonyl)biphenyl-4-yl)methanol | MS (ESI) 686.5 [M + H]+. |

| Ex # | Structure | Name | Characterization Data |
|---|---|---|---|
| 348 | 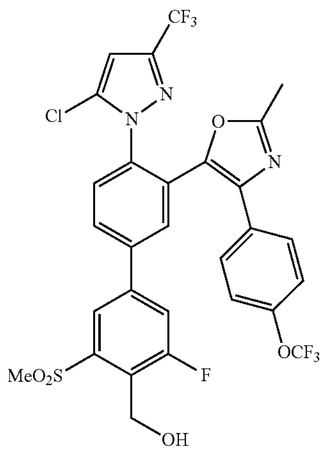 [SMILES: Cc1nc(-c2ccc(OC(F)(F)F)cc2)c(-c2cc(-c3cc(F)c(CO)c(S(C)(=O)=O)c3)ccc2-n2nc(C(F)(F)F)cc2Cl)o1] | (4'-(5-chloro-3-(trifluoromethyl)-1H-pyrazol-1-yl)-3-fluoro-3'-(2-methyl-4-(4-(trifluoromethoxy)phenyl)oxazol-5-yl)-5-(methylsulfonyl)biphenyl-4-yl)methanol | MS (ESI) 690.0 [M + H]+. <br> $^1$H NMR (400 MHz, CDCl$_3$) δ ppm 8.13 (s, 1 H) 7.90 (d, J = 2.00 Hz, 1 H) 7.80 (dd, J = 8.25, 2.00 Hz, 1 H) 7.66 (d, J = 8.26 Hz, 1 H) 7.59 (dd, J = 10.01, 1.75 Hz, 1 H) 7.42-7.46 (m, 2 H) 7.14 (s, 2 H) 6.37 (s, 1 H) 5.10 (s, 2 H) 3.27-3.30 (m, 3 H) 2.47 (s, 3 H). |
| 349 | 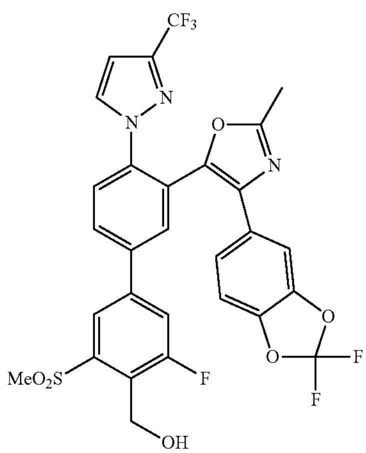 [SMILES: Cc1nc(-c2ccc3c(c2)OC(F)(F)O3)c(-c2cc(-c3cc(F)c(CO)c(S(C)(=O)=O)c3)ccc2-n2ccc(C(F)(F)F)n2)o1] | (3'-(4-(2,2-difluorobenzo[d][1,3]dioxol-5-yl)-2-methyloxazol-5-yl)-3-fluoro-5-(methylsulfonyl)-4'-(3-(trifluoromethyl)-1H-pyrazol-1-yl)biphenyl-4-yl)methanol | MS (ESI) 652.0 [M + H]+. |
| 350 | 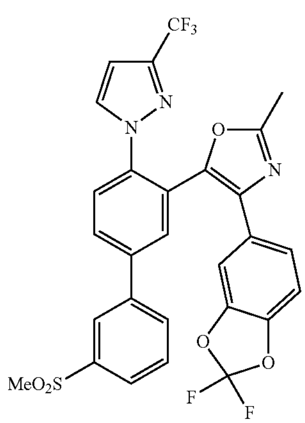 [SMILES: Cc1nc(-c2ccc3c(c2)OC(F)(F)O3)c(-c2cc(-c3cccc(S(C)(=O)=O)c3)ccc2-n2ccc(C(F)(F)F)n2)o1] | 4-(2,2-difluorobenzo[d][1,3]dioxol-5-yl)-2-methyl-5-(3'-(methylsulfonyl)-4-(3-(trifluoromethyl)-1H-pyrazol-1-yl)biphenyl-3-yl)oxazole | MS (ESI) 604.0 [M + H]+. |

| Ex # | Structure | Name | Characterization Data |
|---|---|---|---|
| 351 | 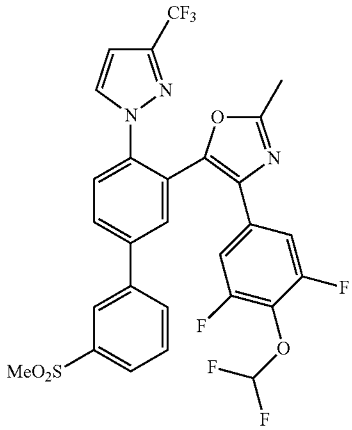 [SMILES: Cc1nc(-c2cc(F)c(OC(F)F)c(F)c2)c(-c2cc(-c3cccc(S(C)(=O)=O)c3)ccc2-n2ccc(C(F)(F)F)n2)o1] | 4-(4-(difluoromethoxy)-3,5-difluorophenyl)-2-methyl-5-(3'-(methylsulfonyl)-4-(3-(trifluoromethyl)-1H-pyrazol-1-yl)biphenyl-3-yl)oxazole | MS (ESI) 626.0 [M + H]+. $^1$H NMR (400 MHz, CDCl$_3$) δ ppm 8.20 (1 H, t, J = 1.75 Hz) 8.01 (1 H, d, J = 7.75 Hz) 7.81-7.94 (3 H, m) 7.65-7.80 (2 H, m) 7.38 (1 H, d, J = 1.50 Hz) 6.95-7.06 (2 H, m) 6.30-6.76 (2 H, m) 3.13 (3 H, s) 2.52 (3 H, s) |
| 352 | 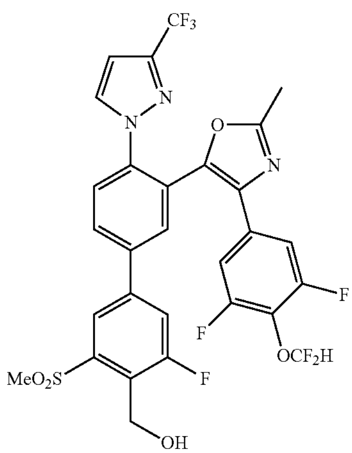 | (3'-(4-(4-(difluoromethoxy)-3,5-difluorophenyl)-2-methyloxazol-5-yl)-3-fluoro-5-(methylsulfonyl)-4'-(3-(trifluoromethyl)-1H-pyrazol-1-yl)biphenyl-4-yl)methanol | MS (ESI) 674.0 [M + H]+. |
| 353 | 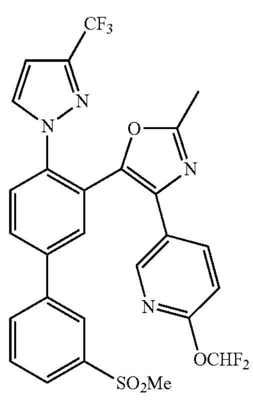 [SMILES: Cc1nc(-c2ccc(OC(F)F)nc2)c(-c2cc(-c3cccc(S(C)(=O)=O)c3)ccc2-n2ccc(C(F)(F)F)n2)o1] | 4-(6-(difluoromethoxy)pyridin-3-yl)-2-methyl-5-(3'-(methylsulfonyl)-4-(3-(trifluoromethyl)-1H-pyrazol-1-yl)biphenyl-3-yl)oxazole | MS (ESI) 591.1 [M + H]+. |

| Ex # | Structure | Name | Characterization Data |
|---|---|---|---|
| 354 | 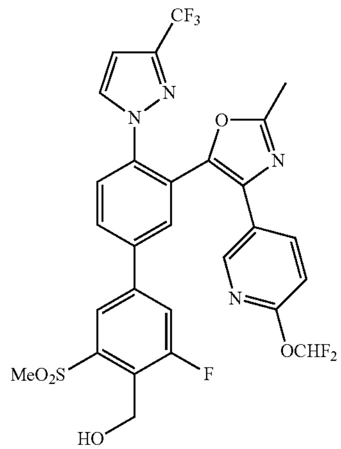 [SMILES: Cc1nc(-c2ccc(OC(F)F)nc2)c(-c2cc(-c3cc(F)c(CO)c(S(C)(=O)=O)c3)ccc2-n2ccc(C(F)(F)F)n2)o1] | (3'-(4-(6-(difluoromethoxy)pyridin-3-yl)-2-methyloxazol-5-yl)-3-fluoro-5-(methylsulfonyl)-4'-(3-(trifluoromethyl)-1H-pyrazol-1-yl)biphenyl-4-yl)methanol | MS (ESI) 639.1 [M + H]+. |
| 355 | 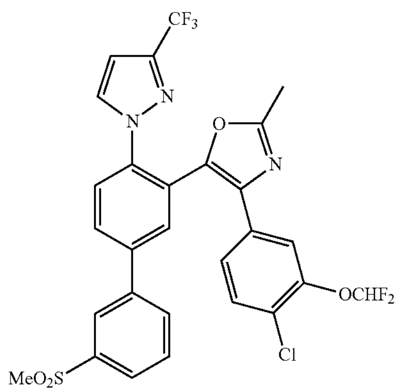 [SMILES: Cc1nc(-c2ccc(Cl)c(OC(F)F)c2)c(-c2cc(-c3cccc(S(C)(=O)=O)c3)ccc2-n2ccc(C(F)(F)F)n2)o1] | 4-(4-chloro-3-(difluoromethoxy)phenyl)-2-methyl-5-(3'-(methylsulfonyl)-4-(3-(trifluoromethyl)-1H-pyrazol-1-yl)biphenyl-3-yl)oxazole | MS (ESI) 624.0 [M + H]+. |
| 356 | 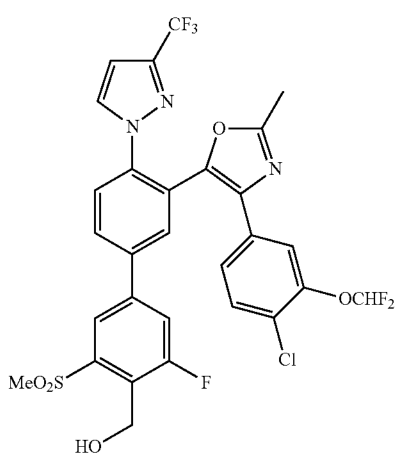 [SMILES: Cc1nc(-c2ccc(Cl)c(OC(F)F)c2)c(-c2cc(-c3cc(F)c(CO)c(S(C)(=O)=O)c3)ccc2-n2ccc(C(F)(F)F)n2)o1] | (3'-(4-(4-chloro-3-(difluoromethoxy)phenyl)-2-methyloxazol-5-yl)-3-fluoro-5-(methylsulfonyl)-4'-(3-(trifluoromethyl)-1H-pyrazol-1-yl)biphenyl-4-yl)methanol | MS (ESI) 672.0 [M + H]+. |

-continued

| Ex # | Structure | Name | Characterization Data |
|---|---|---|---|
| 357 | 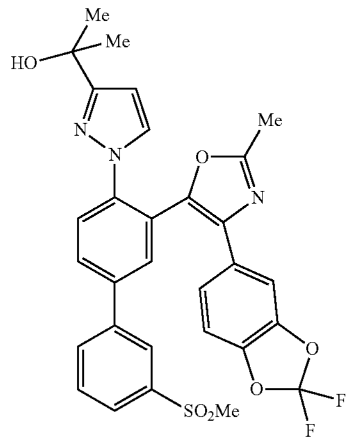 [SMILES: Cc1nc(-c2ccc3c(c2)OC(F)(F)O3)c(-c2cc(-c3cccc(S(C)(=O)=O)c3)ccc2-n2ccc(C(C)(C)O)n2)o1] | 2-(1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazol-3-yl)propan-2-ol | MS (ESI) 594.0 [M + H]+. |
| 358 | 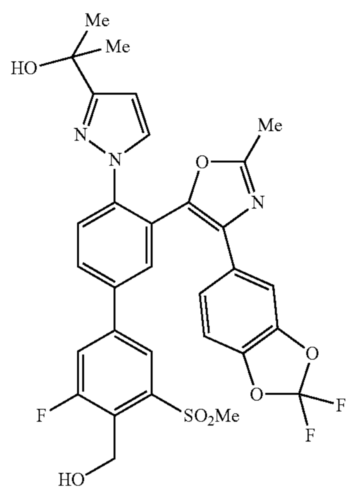 [SMILES: Cc1nc(-c2ccc3c(c2)OC(F)(F)O3)c(-c2cc(-c3cc(F)c(CO)c(S(C)(=O)=O)c3)ccc2-n2ccc(C(C)(C)O)n2)o1] | 2-(1-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1H-pyrazol-3-yl)propan-2-ol | MS (ESI) 642.0 [M + H]+. |
| 359 | 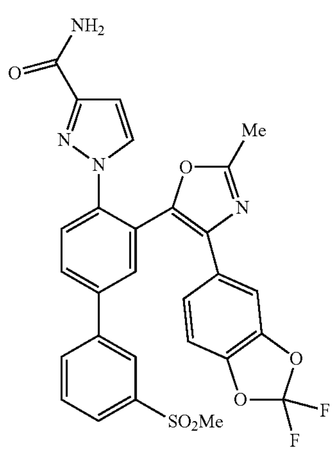 [SMILES: Cc1nc(-c2ccc3c(c2)OC(F)(F)O3)c(-c2cc(-c3cccc(S(C)(=O)=O)c3)ccc2-n2ccc(C(N)=O)n2)o1] | 1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazole-3-carboxamide | MS (ESI) 579.0 [M + H]+. |

| Ex # | Structure | Name | Characterization Data |
|---|---|---|---|
| 360 | 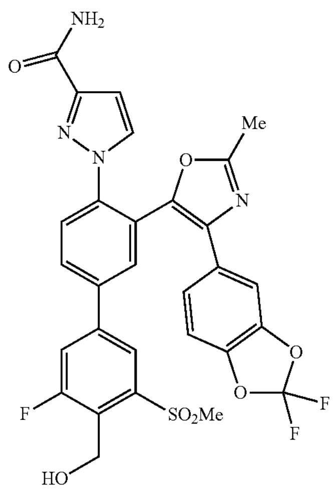 [SMILES: Cc1nc(-c2ccc3c(c2)OC(F)(F)O3)c(-c2cc(-c3cc(F)c(CO)c(S(C)(=O)=O)c3)ccc2-n2ccc(C(N)=O)n2)o1] | 1-(3-(4-(2,2-difluorobenzo[d][1,3]dioxol-5-yl)-2-methyloxazol-5-yl)-3-fluoro-4'-(hydroxymethyl)-5'-(methylsulfonyl)-[1,1'-biphenyl]-4-yl)-1H-pyrazole-3-carboxamide | MS (ESI) 627.0 [M + H]+. |
| 361 | 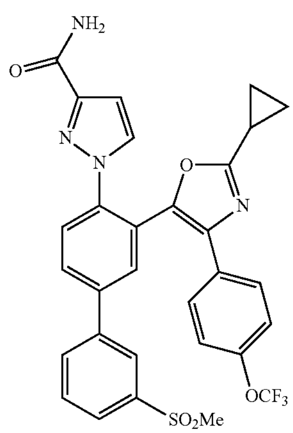 [SMILES: CS(=O)(=O)c1cccc(-c2ccc(-n3ccc(C(N)=O)n3)c(-c3oc(C4CC4)nc3-c3ccc(OC(F)(F)F)cc3)c2)c1] | 1-(3-(2-cyclopropyl-4-(4-(trifluoromethoxy)phenyl)oxazol-5-yl)-3'-(methylsulfonyl)-[1,1'-biphenyl]-4-yl)-1H-pyrazole-3-carboxamide | MS (ESI) 609.0 [M + H]+. |
| 362 | 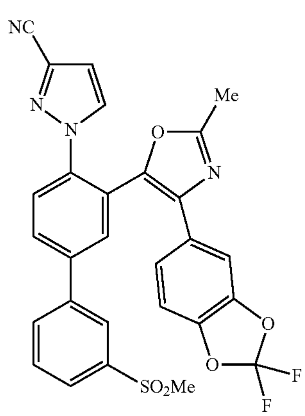 [SMILES: Cc1nc(-c2ccc3c(c2)OC(F)(F)O3)c(-c2cc(-c3cccc(S(C)(=O)=O)c3)ccc2-n2ccc(C#N)n2)o1] | 1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazole-3-carbonitrile | MS (ESI) 561.0 [M + H]+. |

-continued

| Ex # | Structure | Name | Characterization Data |
|---|---|---|---|
| 363 | 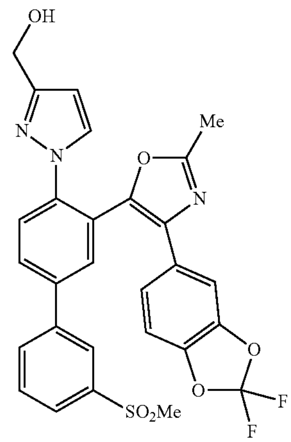 [SMILES: Cc1nc(-c2ccc3c(c2)OC(F)(F)O3)c(-c2cc(-c3cccc(S(C)(=O)=O)c3)ccc2-n2ccc(CO)n2)o1] | (1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazol-3-yl)methanol | MS (ESI) 566.2 [M + H]+. |
| 364 | 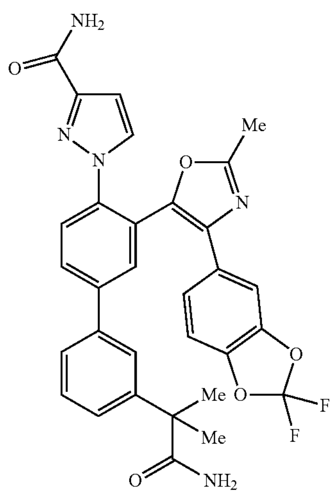 [SMILES: Cc1nc(-c2ccc3c(c2)OC(F)(F)O3)c(-c2cc(-c3cccc(C(C)(C)C(N)=O)c3)ccc2-n2ccc(C(N)=O)n2)o1] | 1-(3'-(1-amino-2-methyl-1-oxopropan-2-yl)-3-(4-(2,2-difluorobenzo[d][1,3]dioxol-5-yl)-2-methyloxazol-5-yl)-[1,1'-biphenyl]-4-yl)-1H-pyrazole-3-carboxamide | MS (ESI) 586.2 [M + H]+. $^1$H NMR (400 MHz, DMSO-d$_6$) δ ppm 8.02-7.99 (dd, J = 8.4 Hz, 2.0 Hz, 1H), 7.96-7.95 (d, J = 2.0 Hz, 1H), 7.86-7.84 (d, J = 8.4 Hz, 1H), 7.75 (d, J = 2.4 Hz, 1H), 7.63-7.60 (m, 2H), 7.48-7.38 (m, 2H), 7.31-7.26 (m, 3H), 7.17-7.15 (m, 2H), 6.96 (bs, 1H), 6.92 (bs, 1H), 6.60 (d, J = 2.4 Hz, 1H), 2.45 (s, 3H), 1.49 (s, 6H) |
| 365 | 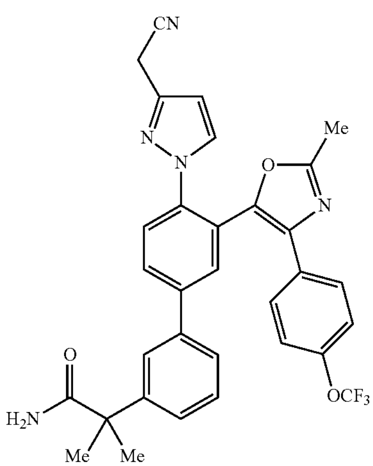 [SMILES: Cc1nc(-c2ccc(OC(F)(F)F)cc2)c(-c2cc(-c3cccc(C(C)(C)C(N)=O)c3)ccc2-n2ccc(CC#N)n2)o1] | 2-(4'-(3-(cyanomethyl)-1H-pyrazol-1-yl)-3'-(2-methyl-4-(4-(trifluoromethoxy)phenyl)oxazol-5-yl)-[1,1'-biphenyl]-3-yl)-2-methylpropanamide | MS (ESI) 586.2 [M + H]+. |

| Ex # | Structure | Name | Characterization Data |
|---|---|---|---|
| 366 | 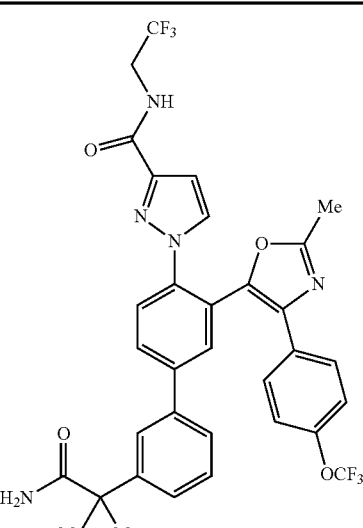 | 1-(3'-(1-amino-2-methyl-1-oxopropan-2-yl)-3-(2-methyl-4-(4-(trifluoromethoxy)phenyl)oxazol-5-yl)-[1,1'-biphenyl]-4-yl)-N-(2,2,2-(trifluoroethyl)-1H-pyrazole-3-carboxamide | MS (ESI) 672.2 [M + H]+. |
| 367 | 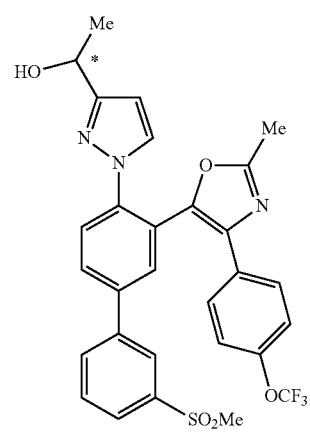 [SMILES: Cc1nc(-c2ccc(OC(F)(F)F)cc2)c(-c2cc(-c3cccc(S(C)(=O)=O)c3)ccc2-n2ccc(C(C)O)n2)o1] | 1-(1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)ethanol | MS (ESI) 584.2 [M + H]+. Specific optical rotation: [α]25D = −2.00 (c 0.1, MeOH) $^1$H NMR (400 MHz, METHANOL-$d_4$) δ ppm 8.26 (1 H, t, J = 1.76 Hz) 7.96-8.08 (4 H, m) 7.72-7.82 (2 H, m) 7.40-7.53 (3 H, m) 7.18 (2 H, dd, J = 8.91, 0.88 Hz) 6.26 (1 H, d, J = 2.51 Hz) 4.75 (1 H, d, J = 6.53 Hz) 3.21 (3 H, s) 2.54 (3 H, s) 1.37 (3 H, d, J = 6.53 Hz) |
| 368 | 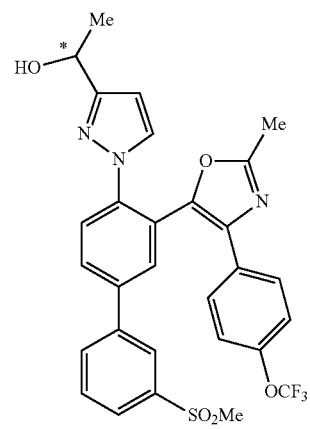 [SMILES: Cc1nc(-c2ccc(OC(F)(F)F)cc2)c(-c2cc(-c3cccc(S(C)(=O)=O)c3)ccc2-n2ccc(C(C)O)n2)o1] | 1-(1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)ethanol | MS (ESI) 584.2 [M + H]+. Specific optical rotation: [α]25D = +2.00 (c 0.1, MeOH) $^1$H NMR (400 MHz, METHANOL-$d_4$) δ ppm 8.26 (1 H, t, J = 1.63 Hz) 7.96-8.09 (4 H, m) 7.71-7.83 (2 H, m) 7.42-7.54 (3 H, m) 7.18 ((2 H, dd, J = 8.91, 0.88 Hz) 6.26 (1 H, d, J = 2.26 Hz) 4.75 (1 H, d, J = 6.53 Hz) 3.21 (3 H, s) 2.54 (3 H, s) 1.38 (3 H, d, J = 6.53 Hz) |

| Ex # | Structure | Name | Characterization Data |
|------|-----------|------|----------------------|
| 369 | 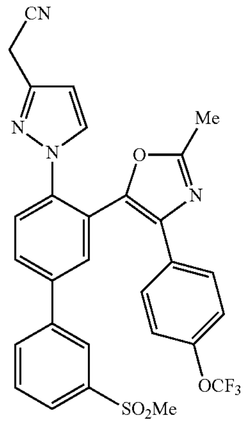 [SMILES: Cc1nc(-c2ccc(OC(F)(F)F)cc2)c(-c2cc(-c3cccc(S(C)(=O)=O)c3)ccc2-n2ccc(CC#N)n2)o1] | 2-(1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)acetonitrile | MS (ESI) 579.2 [M + H]+. |
| 370 | 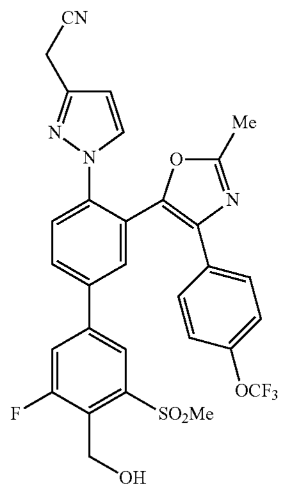 [SMILES: Cc1nc(-c2ccc(OC(F)(F)F)cc2)c(-c2cc(-c3cc(F)c(CO)c(S(C)(=O)=O)c3)ccc2-n2ccc(CC#N)n2)o1] | 2-(1-(3'-fluoro-4'-(hydroxymethyl)-3-(2-methyl-4-(4-(trifluoromethoxy)phenyl)oxazol-5-yl)-5-(methylsulfonyl)-[1,1'-biphenyl]-4-yl)-1H-pyrazol-3-yl)acetonitrile | MS (ESI) 627.2 [M + H]+. $^1$H NMR (400 MHz, METHANOL-$d_6$) δ ppm 8.21 (1 H, d, J = 1.26 Hz) 7.97-8.09 (2 H, m) 7.82-7.94 (1 H, m) 7.76 (1 H, d, J = 8.28 Hz) 7.58 (1 H, d, J = 2.51 Hz) 7.40-7.49 (2 H, m) 7.18 (2 H, d, J = 8.03 Hz) 6.24 (1 H, d, J = 2.51 Hz) 5.14 (2 H, d, J = 2.01 Hz) 3.76 (2 H, s) 3.40 (3 H, s) 2.56 (3 H, s) |
| 371 | 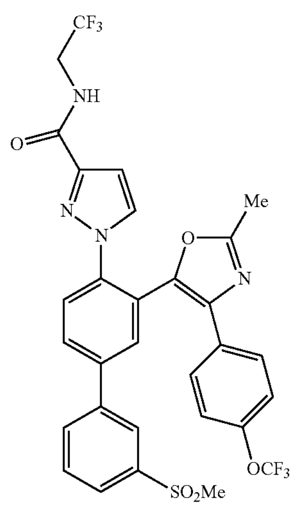 [SMILES: Cc1nc(-c2ccc(OC(F)(F)F)cc2)c(-c2cc(-c3cccc(S(C)(=O)=O)c3)ccc2-n2ccc(C(=O)NCC(F)(F)F)n2)o1] | 1-(3-(2-methyl-4-(4-(trifluoromethoxy)phenyl)oxazol-5-yl)-3'-(methylsulfonyl)-[1,1'-biphenyl]-4-yl)-N-(2,2,2-trifluoroethyl)-1H-pyrazole-3-carboxamide | MS (ESI) 665.2 [M + H]+. |

-continued

| Ex # | Structure | Name | Characterization Data |
|---|---|---|---|
| 372 | 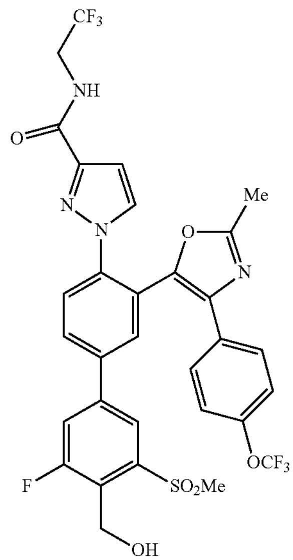 [SMILES: Cc1nc(-c2ccc(OC(F)(F)F)cc2)c(-c2cc(-c3cc(F)c(CO)c(S(C)(=O)=O)c3)ccc2-n2ccc(C(=O)NCC(F)(F)F)n2)o1] | 1-(3'-fluoro-4'-(hydroxymethyl)-3-(2-methyl-4-(4-(trifluoromethoxy)phenyl)oxazol-5-yl)-5-(methylsulfonyl)-[1,1'-biphenyl]-4-yl)-N-(2,2,2-trifluoroethyl)-1H-pyrazole-3-carboxamide | MS (ESI) 713.2 [M + H]+. |
| 373 | 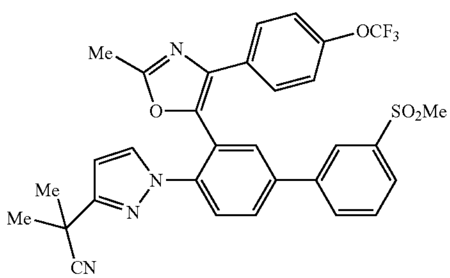 [SMILES: Cc1nc(-c2ccc(OC(F)(F)F)cc2)c(-c2cc(-c3cccc(S(C)(=O)=O)c3)ccc2-n2ccc(C(C)(C)C#N)n2)o1] | 2-methyl-2-(1-(3-(2-methyl-4-(4-(trifluoromethoxy)phenyl)oxazol-5-yl)-3'-methylsulfonyl)-[1,1'-biphenyl]-4-yl)-1H-pyrazol-3-yl)propanenitrile | MS (ESI) 607.2 [M + H]+. |
| 374 | 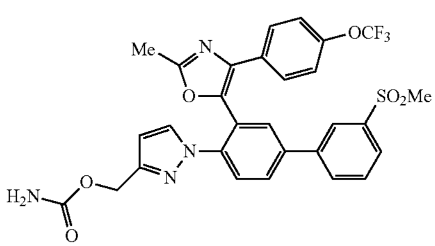 [SMILES: Cc1nc(-c2ccc(OC(F)(F)F)cc2)c(-c2cc(-c3cccc(S(C)(=O)=O)c3)ccc2-n2ccc(COC(N)=O)n2)o1] | (1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)methyl carbamate | MS (ESI) 613.0 [M + H]+. |

| Ex # | Structure | Name | Characterization Data |
|---|---|---|---|
| 375 | 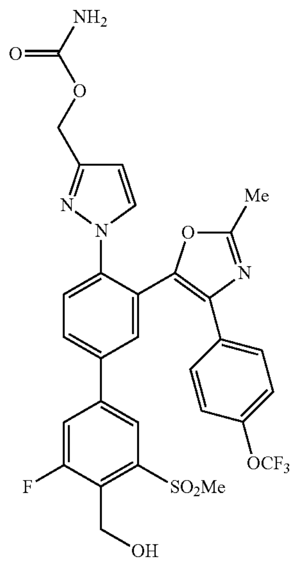 [SMILES: Cc1nc(-c2ccc(OC(F)(F)F)cc2)c(-c2cc(-c3cc(F)c(CO)c(S(C)(=O)=O)c3)ccc2-n2ccc(COC(N)=O)n2)o1] | (1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazol-3-yl)methyl carbamate | MS (ESI) 661.0 [M + H]+. |
| 376 | 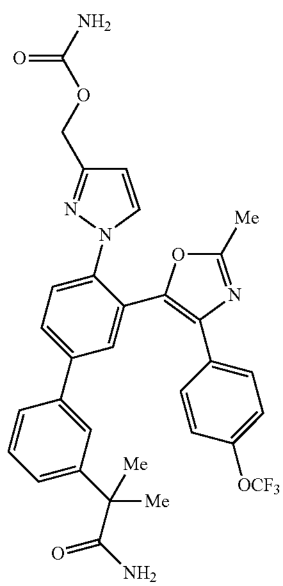 [SMILES: Cc1nc(-c2ccc(OC(F)(F)F)cc2)c(-c2cc(-c3cccc(C(C)(C)C(N)=O)c3)ccc2-n2ccc(COC(N)=O)n2)o1] | (1-(3'-(1-amino-2-methyl-1-oxopropan-2-yl)-3-(2-methyl-4-(4-(trifluoromethoxy)phenyl)oxazol-5-yl)-[1,1'-biphenyl]-4-yl)-1H-pyrazol-3-yl)methyl carbamate | MS (ESI) 620.0 [M + H]+. |
| 377 | 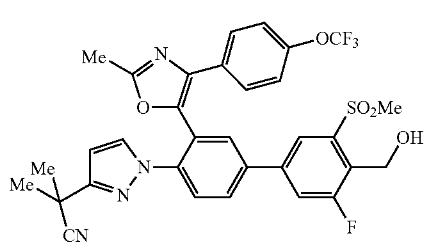 [SMILES: Cc1nc(-c2ccc(OC(F)(F)F)cc2)c(-c2cc(-c3cc(F)c(CO)c(S(C)(=O)=O)c3)ccc2-n2ccc(C(C)(C)C#N)n2)o1] | 2-(1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazol-3-yl)-2-methylpropanenitrile | MS (ESI) 655.2 [M + H]+. |

| Ex # | Structure | Name | Characterization Data |
|---|---|---|---|
| 378 | 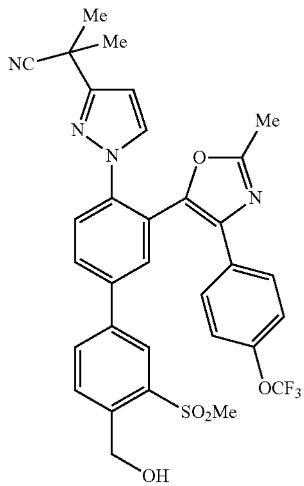 [SMILES: Cc1nc(-c2ccc(OC(F)(F)F)cc2)c(-c2cc(-c3ccc(CO)c(S(C)(=O)=O)c3)ccc2-n2ccc(C(C)(C)C#N)n2)o1] | 2-(1-(4'-(hydroxymethyl)-3-(2-methyl-4-(4-(trifluoromethoxy)phenyl)oxazol-5-yl)-3'-(methylsulfonyl)-[1,1'-biphenyl]-4-yl)-1H-pyrazol-3-yl)-2-methylpropanenitrile | MS (ESI) 637.2 [M + H]+. |
| 379 | 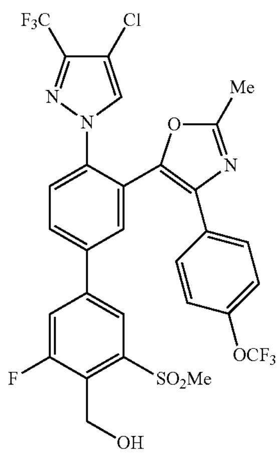 [SMILES: Cc1nc(-c2ccc(OC(F)(F)F)cc2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3-fluoro-3'-(2-methyl-4-(4-(trifluoromethoxy)phenyl)oxazol-5-yl)-5-(methylsulfonyl)-[1,1'-biphenyl]-4-yl)methanol | MS (ESI) 690.0 [M + H]+. <sup>1</sup>H NMR (400 MHz, CDCl<sub>3</sub>) δ ppm 8.16 (1 H, s) 7.90 (1 H, d, J = 2.25 Hz) 7.77-7.83 (1 H, m) 7.71 (1 H, d, J = 8.50 Hz) 7.64 (1 H, dd, J = 10.01, 1.75 Hz) 7.33-7.39 (2 H, m) 7.28 (1 H, d, J = 1.00 Hz) 7.10 (2 H, d, J = 8.00 Hz) 5.10 (2 H, dd, J = 7.00, 1.75 Hz) 3.30 (3 H, s) 2.85 (1 H, t, J = 7.00 Hz) 2.57 (3 H, s) |
| 380 | 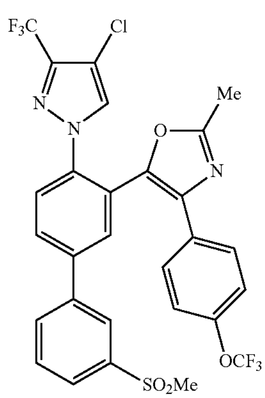 [SMILES: Cc1nc(-c2ccc(OC(F)(F)F)cc2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-2-methyl-4-(4-(trifluoromethoxy)phenyl)oxazole | MS (ESI) 642.0 [M + H]+. <sup>1</sup>H NMR (400 MHz, METHANOL-d<sub>4</sub>) δ ppm 8.30 (s, 1 H) 8.13 (s, 1 H) 8.02-8.11 (m, 3 H) 7.92 (s, 1 H) 7.75-7.83 (m, 2 H) 7.38 (d, J = 9.03 Hz, 2 H) 7.18 (d, J = 8.78 Hz, 2 H) 3.23 (s, 3 H) 2.58 (s, 3 H) |

-continued

| Ex # | Structure | Name | Characterization Data |
|---|---|---|---|
| 381 | 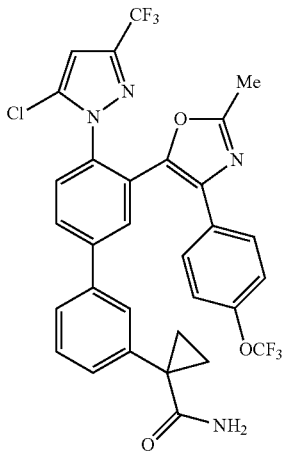 [SMILES: Cc1nc(-c2ccc(OC(F)(F)F)cc2)c(-c2cc(-c3cccc(C4(C(N)=O)CC4)c3)ccc2-n2nc(C(F)(F)F)cc2Cl)o1] | 1-(4'-(5-chloro-3-(trifluoromethyl)-1H-pyrazol-1-yl)-3'-(2-methyl-4-(4-(trifluoromethoxy)phenyl)oxazol-5-yl)-[1,1'-biphenyl]-3-yl)cyclopropanecarboxamide | MS (ESI) 647.2 [M + H]+. |
| 382 | 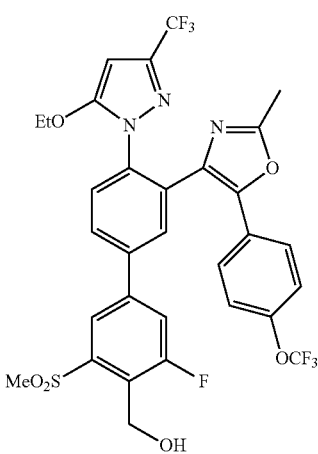 [SMILES: CCOc1cc(C(F)(F)F)nn1-c1ccc(-c2cc(F)c(CO)c(S(C)(=O)=O)c2)cc1-c1nc(C)oc1-c1ccc(OC(F)(F)F)cc1] | (4'-(5-ethoxy-3-(trifluoromethyl)-1H-pyrazol-1-yl)-3-fluoro-3'-(2-methyl-5-(4-(trifluoromethoxy)phenyl)oxazol-4-yl)-5-(methylsulfonyl)biphenyl-4-yl)methanol | MS (ESI) 700.0 [M + H]+. |
| 383 | 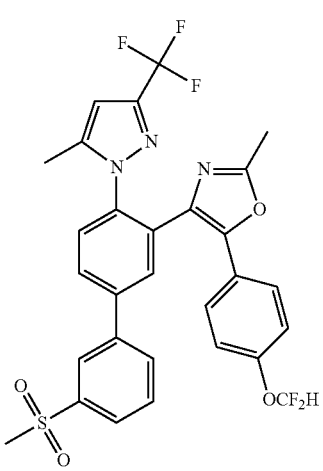 | 5-(4-(difluoromethoxy)phenyl)-2-methyl-4-(4-(5-methyl-3-(trifluoromethyl)-1H-pyrazol-1-yl)-3'-(methylsulfonyl)biphenyl-3-yl)oxazole | MS (ESI) 604.0 [M + H]+. |

-continued

| Ex # | Structure | Name | Characterization Data |
|---|---|---|---|
| 384 | 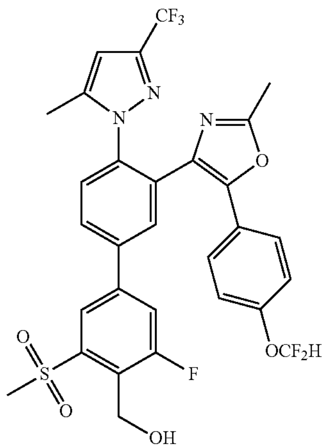 | (3'-(5-(4-(difluoromethoxy)phenyl)-2-methyloxazol-4-yl)-3-fluoro-4'-(5-methyl-3-(trifluoromethyl)-1H-pyrazol-1-yl)-5-(methylsulfonyl)biphenyl-4-yl)methanol | MS (ESI) 652.0 [M + H]+. |
| 385 | 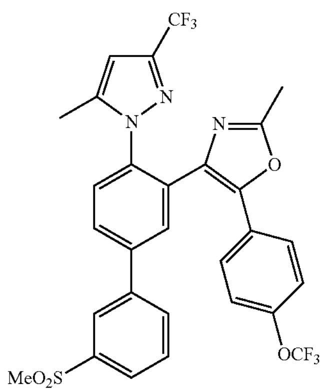 [SMILES: Cc1nc(-c2cc(-c3cccc(S(C)(=O)=O)c3)ccc2-n2nc(C(F)(F)F)cc2C)c(-c2ccc(OC(F)(F)F)cc2)o1] | 2-methyl-4-(4-(5-methyl-3-(trifluoromethyl)-1H-pyrazol-1-yl)-3'-(methylsulfonyl)biphenyl-3-yl)-5-(4-(trifluoromethoxy)phenyl)oxazole | MS (ESI) 622.2 [M + H]+. $^1$H NMR (400 MHz, METHANOL-$d_4$) δ ppm 8.26 (t, J = 1.8 Hz, 1H), 8.08-8.02 (m, 4H), 7.80-7.76 (t, J = 8.0 Hz, 1H), 7.73-7.71 (d, J = 7.8 Hz, 1H), 7.52-7.49 (m, 2H), 7.25-7.23 (d, J = 8.0 Hz, 2H), 6.36 (s, 1H), 3.21 (s, 3H), 2.45 (s, 3H), 2.08 (s, 3H) |
| 386 | 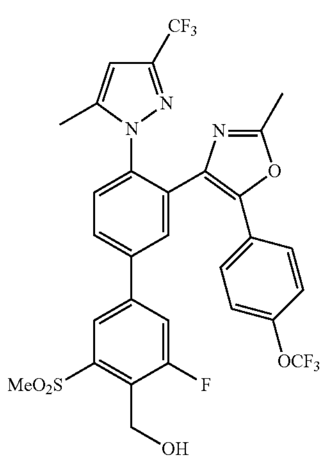 [SMILES: Cc1nc(-c2cc(-c3cc(F)c(CO)c(S(C)(=O)=O)c3)ccc2-n2nc(C(F)(F)F)cc2C)c(-c2ccc(OC(F)(F)F)cc2)o1] | (3-fluoro-4'-(5-methyl-3-(trifluoromethyl)-1H-pyrazol-1-yl)-3'-(2-methyl-5-(4-(trifluoromethoxy)phenyl)oxazol-4-yl)-5-(methylsulfonyl)biphenyl-4-yl)methanol | MS (ESI) 670.2 [M + H]+.\ $^1$H NMR (400 MHz, METHANOL-$d_4$) δ ppm 8.19 (s, 1H), 8.08 (d, J = 2.0 Hz, 1H), 8.05-8.02 (dd, J = 8.4 Hz, 2.0 Hz, 1H), 7.91-7.85 (m, 1H), 7.73-7.71 (d, J = 8.4 Hz, 1H), 7.50-7.48 (d, J = 8.4 Hz, 2H), 7.24-7.22 (m, 2H), 6.35 (s, 1H), 5.14 (d, J = 1.6 Hz, 2H), 3.39 (s, 3H), 2.45 (s, 3H), 2.07 (s, 3H) |

| Ex # | Structure | Name | Characterization Data |
|---|---|---|---|
| 387 | 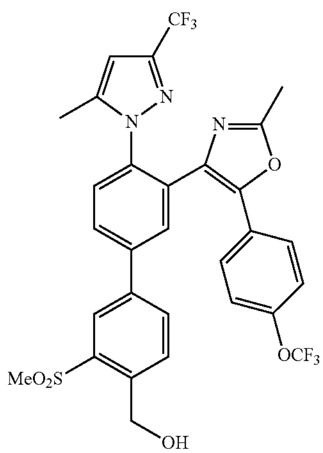 [SMILES: Cc1nc(-c2cc(-c3ccc(CO)c(S(C)(=O)=O)c3)ccc2-n2nc(C(F)(F)F)cc2C)c(-c2ccc(OC(F)(F)F)cc2)o1] | (4'-(5-methyl-3-(trifluoromethyl)-1H-pyrazol-1-yl)-3'-(2-methyl-5-(4-(trifluoromethoxy)phenyl)oxazol-4-yl)-3-(methylsulfonyl)biphenyl-4-yl)methanol | MS (ESI) 652.0 [M + H]+. |
| 388 | 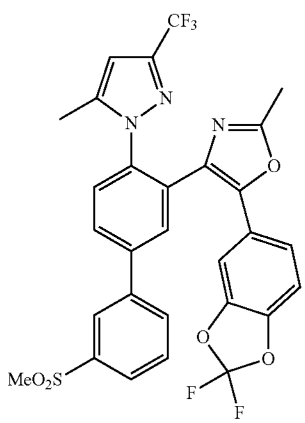 [SMILES: Cc1nc(-c2cc(-c3cccc(S(C)(=O)=O)c3)ccc2-n2nc(C(F)(F)F)cc2C)c(-c2ccc3c(c2)OC(F)(F)O3)o1] | 5-(2,2-difluorobenzo[d][1,3]dioxol-5-yl)-2-methyl-4-(4-(5-methyl-3-(trifluoromethyl)-1H-pyrazol-1-yl)-3'-(methylsulfonyl)biphenyl-3-yl)oxazole | MS (ESI) 618.0 [M + H]+. $^1$H NMR (400 MHz, METHANOL-d$_4$) δ ppm 8.26-8.25 (t, J = 1.8 Hz, 1H), 8.10-8.13 (m, 4H), 7.82-7.78 (t, J = 7.8 Hz, 1H), 7.72-7.70 (d, J = 8.4 Hz, 1H), 7.19-7.17 (m, 2H), 7.14-7.11 (m 1H), 6.38 (s, 1H), 3.21 (s, 3H), 2.47 (s, 3H), 2.06 (s, 3H) |
| 389 | 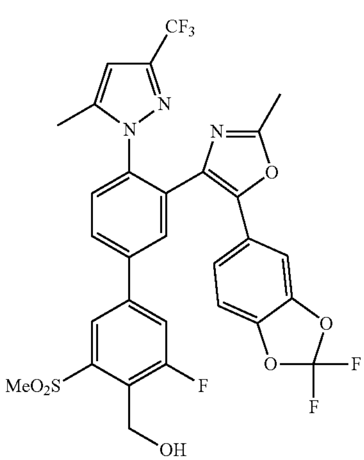 [SMILES: Cc1nc(-c2cc(-c3cc(F)c(CO)c(S(C)(=O)=O)c3)ccc2-n2nc(C(F)(F)F)cc2C)c(-c2ccc3c(c2)OC(F)(F)O3)o1] | (3'-(5-(2,2-difluorobenzo[d][1,3]dioxol-5-yl)-2-methyloxazol-4-yl)-3-fluoro-4'-(5-methyl-3-(trifluoromethyl)-1H-pyrazol-1-yl)-5-(methylsulfonyl)biphenyl-4-yl)methanol | MS (ESI) 666.0 [M + H]+. $^1$H NMR (400 MHz, METHANOL-d$_4$) δ ppm 8.18 (d, J = 1.2 Hz, 1H), 8.10-8.09 (d, J = 2.0 Hz, 1H), 8.06-8.03 (m, 1H), 7.93-7.90 (dd, J = 10.4 Hz, 2.0 Hz, 1H), 7.72-7.70 (d, J = 8.4 Hz, 1H), 7.19-7.17 (m, 2H), 7.14-7.11 (m, 1H), 6.38 (s, 1H), 5.15-5.14 (d, J = 2.0 Hz, 2H), 3.39 (s, 3H), 2.47 (s, 3H), 2.06 (s, 3H) |

| Ex # | Structure | Name | Characterization Data |
|---|---|---|---|
| 390 | 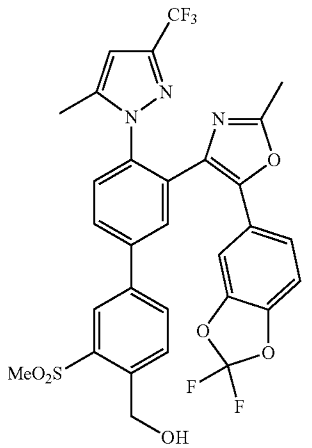 [SMILES: Cc1nc(-c2cc(-c3ccc(CO)c(S(C)(=O)=O)c3)ccc2-n2nc(C(F)(F)F)cc2C)c(-c2ccc3c(c2)OC(F)(F)O3)o1] | (3'-(5-(2,2-difluorobenzo[d][1,3]dioxol-5-yl)-2-methyloxazol-4-yl)-4'-(5-methyl-3-(trifluoromethyl)-1H-pyrazol-1-yl)-3-(methylsulfonyl)biphenyl-4-yl)methanol | MS (ESI) 648.0 [M + H]+. $^1$H NMR (400 MHz, METHANOL-d$_4$) δ ppm 8.28-8.27 (d, J = 2.0 Hz, 1H), 8.08-8.02 (m, 3H), 7.93-7.91 (d, J = 8.0 Hz, 1H), 7.71-7.69 (d, J = 8.0 Hz, 1H), 7.20-7.18 (m, 2H), 7.14-7.12 (m, 1H), 6.39 (s, 1H), 5.11 (s, 2H), 3.33 (s, 3H), 2.46 (s, 3H), 2.07 (s, 3H) |
| 391 | 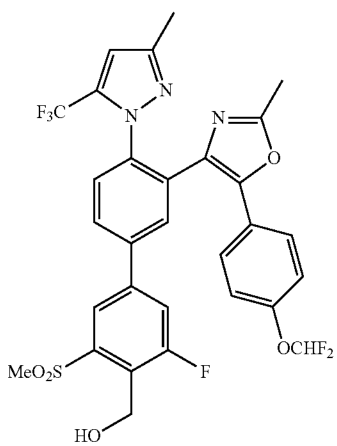 [SMILES: Cc1cc(C(F)(F)F)n(-c2ccc(-c3cc(F)c(CO)c(S(C)(=O)=O)c3)cc2-c2nc(C)oc2-c2ccc(OC(F)F)cc2)n1] | (3'-(5-(4-(difluoromethoxy)phenyl)-2-methyloxazol-4-yl)-3-fluoro-4'-(3-methyl-5-(trifluoromethyl)-1H-pyrazol-1-yl)-5-(methylsulfonyl)biphenyl-4-yl)methanol | MS (ESI) 652.0 [M + H]+. $^1$H NMR (400 MHz, METHANOL-d$_4$) δ ppm 8.11 (d, J = 1.2 Hz, 1H), 8.03-8.00 (m, 2H), 7.88-7.85 (dd, J = 10.4 Hz, 1.6 Hz, 1H), 7.74-7.72 (m, 1H), 7.50-7.46 (m, 2H), 7.13-7.11 (m, 2H), 7.07-6.70 (m, 1H), 6.42 (s, 1H), 5.13 (d, J = 1.6 Hz, 2H), 3.38 (s, 3H), 2.41 (s, 3H), 2.11 (s, 3H) |
| 392 | 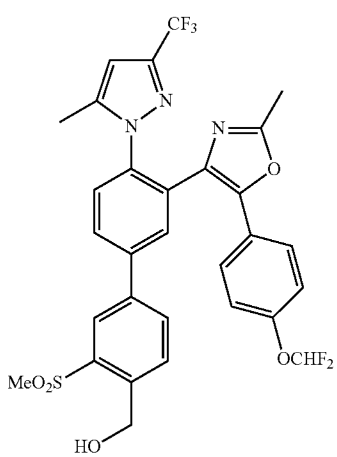 [SMILES: Cc1nc(-c2cc(-c3ccc(CO)c(S(C)(=O)=O)c3)ccc2-n2nc(C(F)(F)F)cc2C)c(-c2ccc(OC(F)F)cc2)o1] | (3'-(5-(4-(difluoromethoxy)phenyl)-2-methyloxazol-4-yl)-4'-(5-methyl-3-(trifluoromethyl)-1H-pyrazol-1-yl)-3-(methylsulfonyl)biphenyl-4-yl)methanol | MS (ESI) 634.0 [M + H]+. |

| Ex # | Structure | Name | Characterization Data |
|---|---|---|---|
| 393 | 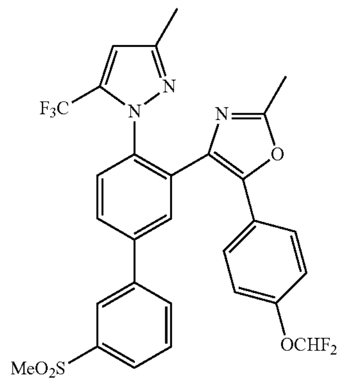 [SMILES: Cc1cc(C(F)(F)F)n(-c2ccc(-c3cccc(S(C)(=O)=O)c3)cc2-c2nc(C)oc2-c2ccc(OC(F)F)cc2)n1] | 5-(4-(difluoromethoxy)phenyl)-2-methyl-4-(4-(3-methyl-5-(trifluoromethyl)-1H-pyrazol-1-yl)-3'-(methylsulfonyl)biphenyl-3-yl)oxazole | MS (ESI) 604.0 [M + H]+. |
| 394 | 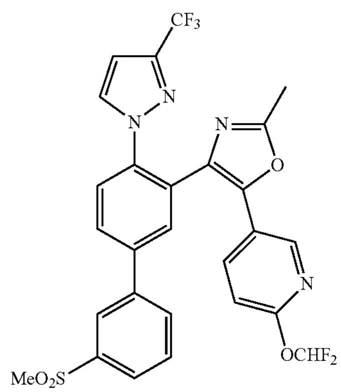 [SMILES: Cc1nc(-c2cc(-c3cccc(S(C)(=O)=O)c3)ccc2-n2ccc(C(F)(F)F)n2)c(-c2ccc(OC(F)F)nc2)o1] | 5-(6-(difluoromethoxy)pyridin-3-yl)-2-methyl-4-(3'-(methylsulfonyl)-4-(3-(trifluoromethyl)-1H-pyrazol-1-yl)biphenyl-3-yl)oxazole | MS (ESI) 591.0 [M + H]+. |
| 395 | 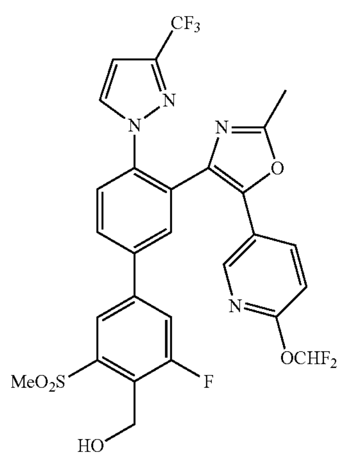 [SMILES: Cc1nc(-c2cc(-c3cc(F)c(CO)c(S(C)(=O)=O)c3)ccc2-n2ccc(C(F)(F)F)n2)c(-c2ccc(OC(F)F)nc2)o1] | (3'-(5-(6-(difluoromethoxy)pyridin-3-yl)-2-methyloxazol-4-yl)-3-fluoro-5-(methylsulfonyl)-4'-(3-(trifluoromethyl)-1H-pyrazol-1-yl)biphenyl-4-yl)methanol | MS (ESI) 639.0 [M + H]+. $^1$H NMR (400 MHz, CDCl$_3$) δ ppm 8.14 (1 H, s) 8.11 (1 H, d, J = 2.00 Hz) 7.89 (1 H, d, J = 2.25 Hz) 7.79-7.84 (1 H, m) 7.63-7.77 (3 H, m) 7.35 (1 H, d, J = 1.50 Hz) 7.16-7.58 (1 H, m) 6.79 (1 H, d, J = 8.76 Hz) 6.42 (1 H, s) 5.11 (2 H, s) 3.30 (3 H, s) 2.56 (3 H, s) |

-continued

| Ex # | Structure | Name | Characterization Data |
|---|---|---|---|
| 396 | 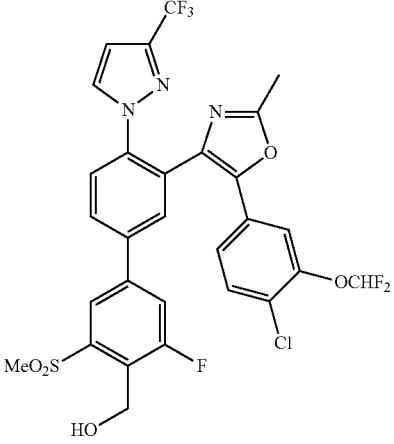 [SMILES: Cc1nc(-c2cc(-c3cc(F)c(CO)c(S(C)(=O)=O)c3)ccc2-n2ccc(C(F)(F)F)n2)c(-c2ccc(Cl)c(OC(F)F)c2)o1] | (3'-(5-(4-chloro-3-(difluoromethoxy)phenyl)-2-methyloxazol-4-yl)-3-fluoro-5-(methylsulfonyl)-4'-(3-(trifluoromethyl)-1H-pyrazol-1-yl)biphenyl-4-yl)methanol | MS (ESI) 672.0 [M + H]+. |
| 397 | 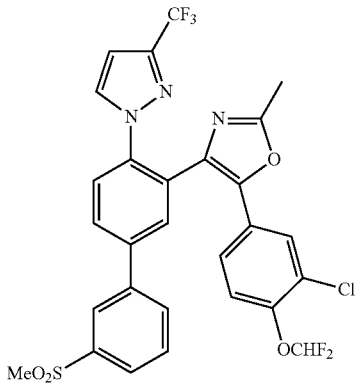 [SMILES: Cc1nc(-c2cc(-c3cccc(S(C)(=O)=O)c3)ccc2-n2ccc(C(F)(F)F)n2)c(-c2ccc(OC(F)F)c(Cl)c2)o1] | 5-(3-chloro-4-(difluoromethoxy)phenyl)-2-methyl-4-(3'-(methylsulfonyl)-4-(3-(trifluoromethyl)-1H-pyrazol-1-yl)biphenyl-3-yl)oxazole | MS (ESI) 624.0 [M + H]+. |
| 398 | 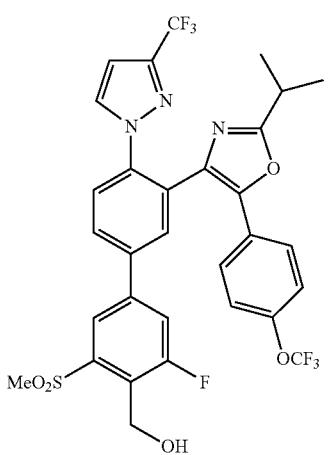 [SMILES: CC(C)c1nc(-c2cc(-c3cc(F)c(CO)c(S(C)(=O)=O)c3)ccc2-n2ccc(C(F)(F)F)n2)c(-c2ccc(OC(F)(F)F)cc2)o1] | (3-fluoro-3'-(2-isopropyl-5-(4-(trifluoromethoxy)phenyl)oxazol-4-yl)-5-(methylsulfonyl)-4'-(3-(trifluoromethyl)-1H-pyrazol-1-yl)biphenyl-4-yl)methanol | MS (ESI) 684.2 [M + H]+. |

-continued

| Ex # | Structure | Name | Characterization Data |
|---|---|---|---|
| 399 | 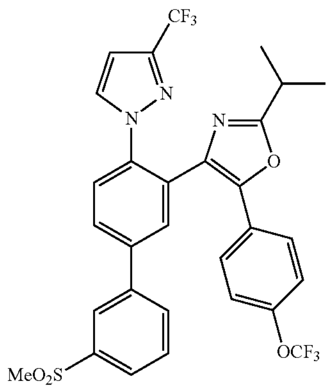 [SMILES: CC(C)c1nc(-c2cc(-c3cccc(S(C)(=O)=O)c3)ccc2-n2ccc(C(F)(F)F)n2)c(-c2ccc(OC(F)(F)F)cc2)o1] | 2-isopropyl-4-(3'-(methylsulfonyl)-4-(3-(trifluoromethyl)-1H-pyrazol-1-yl)biphenyl-3-yl)-5-(4-(trifluoromethoxy)phenyl)oxazole | MS (ESI) 636.2 [M + H]+. |
| 400 | 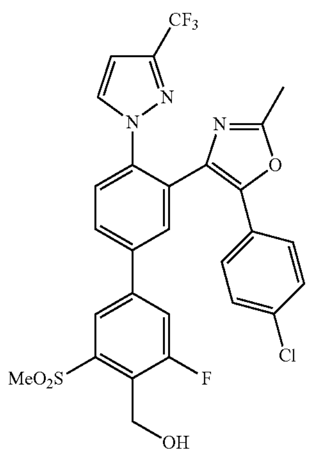 [SMILES: Cc1nc(-c2cc(-c3cc(F)c(CO)c(S(C)(=O)=O)c3)ccc2-n2ccc(C(F)(F)F)n2)c(-c2ccc(Cl)cc2)o1] | (3'-(5-(4-chlorophenyl)-2-methyloxazol-4-yl)-3-fluoro-5-(methylsulfonyl)-4'-(3-(trifluoromethyl)-1H-pyrazol-1-yl)biphenyl-4-yl)methanol | MS (ESI) 606.2 [M + H]+. $^1$H NMR (400 MHz, METHANOL-d$_4$) δ ppm 8.20 (d, J = 1.2 Hz, 1H), 8.06-8.02 (m, 2H), 7.91-7.88 (dd, J = 10.6 Hz, 1.8 Hz, 1H), 7.82-7.79 (d, J = 8.4 Hz, 1H), 7.75-7.74 (m, 1H), 7.33-7.24 (m, 4H), 6.55-6.54 (d, J = 2.8 Hz, 1H), 5.14 (d, J = 2.0 Hz, 2H), 3.40 (s, 3H), 2.52 (s, 3H) |
| 401 | 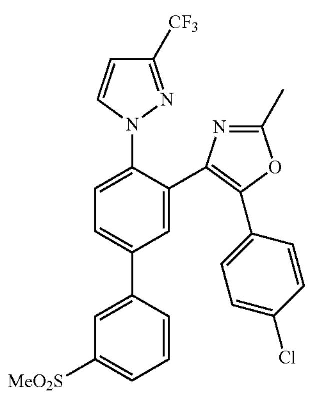 [SMILES: Cc1nc(-c2cc(-c3cccc(S(C)(=O)=O)c3)ccc2-n2ccc(C(F)(F)F)n2)c(-c2ccc(Cl)cc2)o1] | 5-(4-chlorophenyl)-2-methyl-4-(3'-(methylsulfonyl)-4-(3-(trifluoromethyl)-1H-pyrazol-1-yl)biphenyl-3-yl)oxazole | MS (ESI) 558.2 [M + H]+. |

| Ex # | Structure | Name | Characterization Data |
|---|---|---|---|
| 402 | 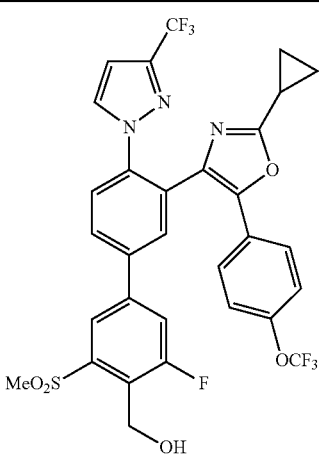 | (3'-(2-cyclopropyl-5-(4-(trifluoromethoxy)phenyl)oxazol-4-yl)-3-fluoro-5-(methylsulfonyl)-4'-(3-(trifluoromethyl)-1H-pyrazol-1-yl)biphenyl-4-yl)methanol | MS (ESI) 682.2 [M + H]+. $^1$H NMR (400 MHz, METHANOL-$d_4$) δ ppm 8.17 (s, 1H), 8.03-8.00 (m, 2H), 7.85-7.77 (m, 3H), 7.50-7.48 (m, 2H), 7.20-7.18 (dd, J = 8.8 Hz, 0.8 Hz, 2H), 6.59 (d, J = 2.4 Hz, 1H), 5.13 (d, J = 2.0 Hz, 2H), 3.38 (s, 3H), 2.17-2.10 (m, 1H), 1.14-1.04 (m, 4H) |
| 403 | 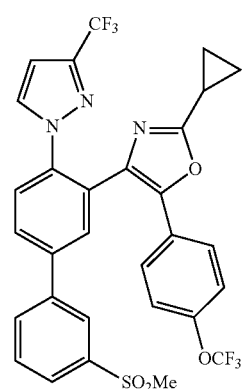 | 2-cyclopropyl-4-(3'-(methylsulfonyl)-4-(3-(trifluoromethyl)-1H-pyrazol-1-yl)biphenyl-3-yl)-5-(4-(trifluoromethoxy)phenyl)oxazole | MS (ESI) 634.2 [M + H]+. |
| 404 | 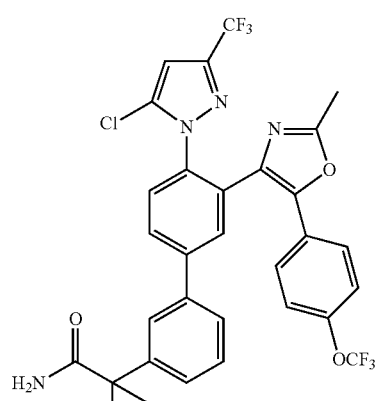 | 2-(4'-(5-chloro-3-(trifluoromethyl)-1H-pyrazol-1-yl)-3'-(2-methyl-5-(4-(trifluoromethoxy)phenyl)oxazol-4-yl)biphenyl-3-yl)-2-methylpropanamide | MS (ESI) 649.2 [M + H]+. $^1$H NMR (400 MHz, CDCl$_3$) δ ppm 7.84 (d, J = 2.00 Hz, 1 H) 7.76 (dd, J = 8.25, 2.00 Hz, 1 H) 7.57-7.62 (m, 2 H) 7.45-7.52 (m, 5 H) 7.14 (d, J = 8.26 Hz, 2 H) 6.40 (s, 1 H) 2.44 (s, 3 H) 1.54 (s, 6 H) |

-continued

| Ex # | Structure | Name | Characterization Data |
|---|---|---|---|
| 405 | 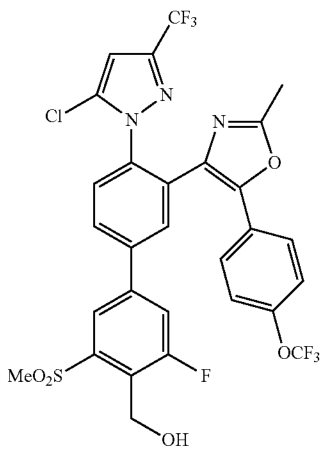 [SMILES: Cc1nc(-c2cc(-c3cc(F)c(CO)c(S(C)(=O)=O)c3)ccc2-n2nc(C(F)(F)F)cc2Cl)c(-c2ccc(OC(F)(F)F)cc2)o1] | (4'-(5-chloro-3-(trifluoromethyl)-1H-pyrazol-1-yl)-3-fluoro-3'-(2-methyl-5-(4-(trifluoromethoxy)phenyl)oxazol-4-yl)-5-(methylsulfonyl)biphenyl-4-yl)methanol | MS (ESI) 690.0 [M + H]+. |
| 406 | 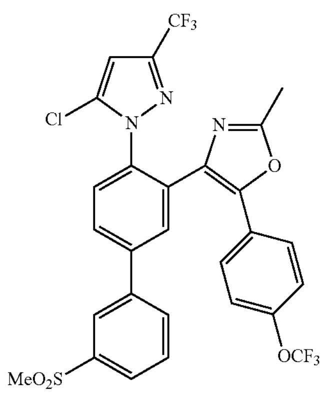 [SMILES: Cc1nc(-c2cc(-c3cccc(S(C)(=O)=O)c3)ccc2-n2nc(C(F)(F)F)cc2Cl)c(-c2ccc(OC(F)(F)F)cc2)o1] | 4-(4-(5-chloro-3-(trifluoromethyl)-1H-pyrazol-1-yl)-3'-(methylsulfonyl)biphenyl-3-yl)-2-methyl-5-(4-(trifluoromethoxy)phenyl)oxazole | MS (ESI) 642.0 [M + H]+. |
| 407 | 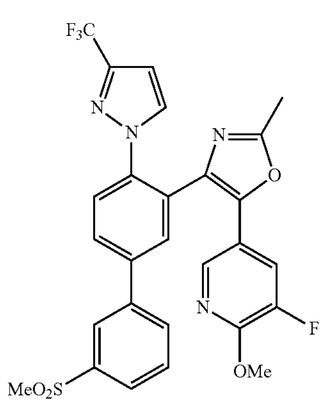 [SMILES: COc1ncc(-c2oc(C)nc2-c2cc(-c3cccc(S(C)(=O)=O)c3)ccc2-n2ccc(C(F)(F)F)n2)cc1F] | 5-(5-fluoro-6-methoxypyridin-3-yl)-2-methyl-4-(3'-(methylsulfonyl)-4-(3-(trifluoromethyl)-1H-pyrazol-1-yl)biphenyl-3-yl)oxazole | MS (ESI) 573.2 [M + H]+. |

-continued

| Ex # | Structure | Name | Characterization Data |
|---|---|---|---|
| 408 | 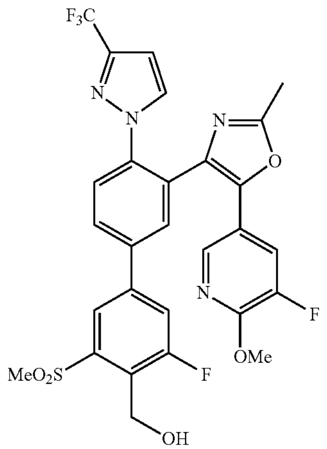 [SMILES: COc1ncc(-c2oc(C)nc2-c2cc(-c3cc(F)c(CO)c(S(C)(=O)=O)c3)ccc2-n2ccc(C(F)(F)F)n2)cc1F] | (3-fluoro-3'-(5-(5-fluoro-6-methoxypyridin-3-yl)-2-methyloxazol-4-yl)-5-(methylsulfonyl)-4'-(3-(trifluoromethyl)-1H-pyrazol-1-yl)biphenyl-4-yl)methanol | MS (ESI) 621.2 [M + H]+. $^1$H NMR (400 MHz, CDCl$_3$) δ ppm 8.15 (1 H, d, J = 1.00 Hz), 7.88 (1 H, d, J = 2.00 Hz), 7.73-7.85 (3 H, m), 7.66 (1 H, dd, J = 10.01, 1.75 Hz), 7.31-7.41 (2 H, m), 6.43 (1 H, d, J = 2.25 Hz), 5.10 (2 H, d, J = 1.50 Hz), 3.99 (3 H, s), 3.30 (3 H, s), 2.55 (3 H, s) |
| 409 | 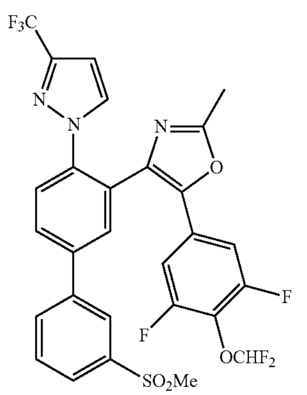 [SMILES: Cc1nc(-c2cc(-c3cccc(S(C)(=O)=O)c3)ccc2-n2ccc(C(F)(F)F)n2)c(-c2cc(F)c(OC(F)F)c(F)c2)o1] | 5-(4-(difluoromethoxy)-3,5-difluorophenyl)-2-methyl-4-(3'-(methylsulfonyl)-4-(3-(trifluoromethyl)-1H-pyrazol-1-yl)biphenyl-3-yl)oxazole | MS (ESI) 626.0 [M + H]+. |
| 410 | 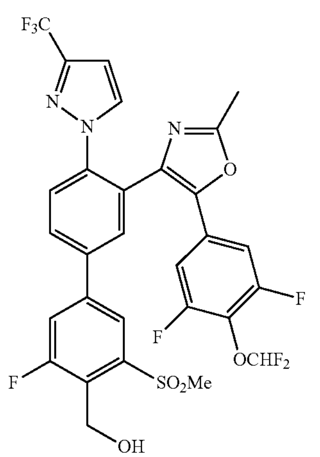 [SMILES: Cc1nc(-c2cc(-c3cc(F)c(CO)c(S(C)(=O)=O)c3)ccc2-n2ccc(C(F)(F)F)n2)c(-c2cc(F)c(OC(F)F)c(F)c2)o1] | (3'-(5-(4-(difluoromethoxy)-3,5-difluorophenyl)-2-methyloxazol-4-yl)-3-fluoro-5-(methylsulfonyl)-4'-(3-(trifluoromethyl)-1H-pyrazol-1-yl)biphenyl-4-yl)methanol | MS (ESI) 674.1 [M + H]+. |

-continued

| Ex # | Structure | Name | Characterization Data |
|---|---|---|---|
| 411 | 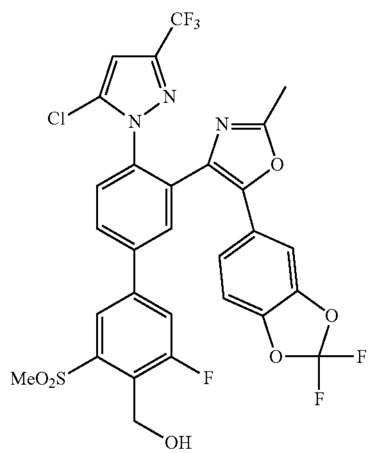 [SMILES: Cc1nc(-c2cc(-c3cc(F)c(CO)c(S(C)(=O)=O)c3)ccc2-n2nc(C(F)(F)F)cc2Cl)c(-c2ccc3c(c2)OC(F)(F)O3)o1] | (4'-(5-chloro-3-(trifluoromethyl)-1H-pyrazol-1-yl)-3'-(5-(2,2-difluorobenzo[d][1,3]dioxol-5-yl)-2-methyloxazol-4-yl)-3-fluoro-5-(methylsulfonyl)biphenyl-4-yl)methanol | MS (ESI) 686.0 [M + H]+. |
| 412 | 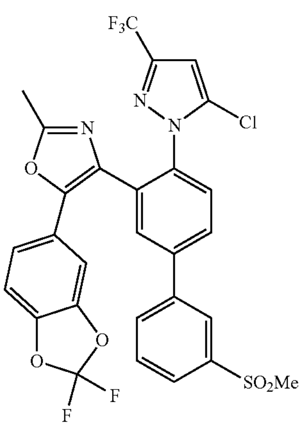 [SMILES: Cc1nc(-c2cc(-c3cccc(S(C)(=O)=O)c3)ccc2-n2nc(C(F)(F)F)cc2Cl)c(-c2ccc3c(c2)OC(F)(F)O3)o1] | 4-(4-(5-chloro-3-(trifluoromethyl)-1H-pyrazol-1-yl)-3'-(methylsulfonyl)biphenyl-3-yl)-5-(2,2-difluorobenzo[d][1,3]dioxol-5-yl)-2-methyloxazole | MS (ESI) 638.0 [M + H]+. <br> $^1$H NMR (400 MHz, METHANOL-d$_4$) δ ppm 8.28 (t, J = 1.63 Hz, 1 H) 8.14 (d, J = 2.01 Hz, 1 H) 8.11 (dd, J = 7.78, 1.76 Hz, 1 H) 8.06 (dd, J = 8.41, 2.13 Hz, 2 H) 7.81 (t, J = 7.91 Hz, 1 H) 7.75 (d, J = 8.28 Hz, 1 H) 7.10-7.16 (m, 3 H) 6.68 (s, 1 H) 3.22 (s, 3 H) 2.51 (s, 3 H) |
| 413 | 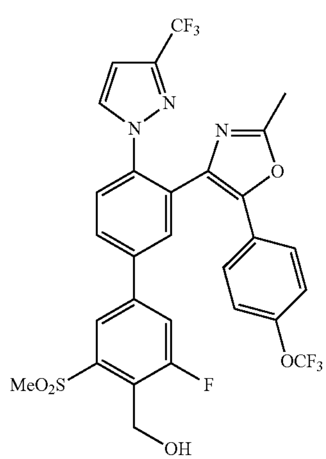 [SMILES: Cc1nc(-c2cc(-c3cc(F)c(CO)c(S(C)(=O)=O)c3)ccc2-n2ccc(C(F)(F)F)n2)c(-c2ccc(OC(F)(F)F)cc2)o1] | (3-fluoro-3'-(2-methyl-5-(4-(trifluoromethoxy)phenyl)oxazol-4-yl)-5-(methylsulfonyl)-4'-(3-(trifluoromethyl)-1H-pyrazol-1-yl)biphenyl-4-yl)methanol | MS (ESI) 656.0 [M + H]+. <br> $^1$H NMR (400 MHz, METHANOL-d$_4$) δ ppm 8.22 (s, 1H), 8.10-8.09 (d, J = 2.0 Hz, 1H), 8.06-8.04 (dd, J = 8.4 Hz, 2.0 Hz, 1H), 7.92-7.89 (dd, J = 10.4 Hz, 1.6 Hz, 1H), 7.82-7.80 (m, 1H), 7.74 (d, J = 1.6 Hz, 1H), 7.43-7.40 (m, 2H), 7.18-7.16 (d, J = 8.0 Hz, 2H), 6.51 (d, J = 2.4 Hz, 1H), 5.15-5.14 (d, J = 1.6 Hz, 2H), 3.40 (s, 3H), 2.54 (s, 3H) |

-continued

| Ex # | Structure | Name | Characterization Data |
|---|---|---|---|
| 414 | 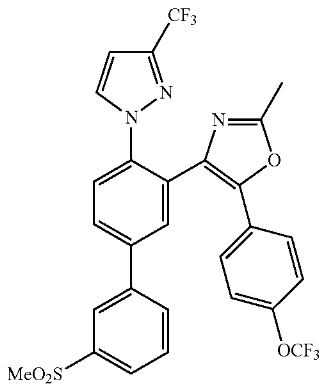 [SMILES: Cc1nc(-c2cc(-c3cccc(S(C)(=O)=O)c3)ccc2-n2ccc(C(F)(F)F)n2)c(-c2ccc(OC(F)(F)F)cc2)o1] | 2-methyl-4-(3'-(methylsulfonyl)-4-(3-(trifluoromethyl)-1H-pyrazol-1-yl)biphenyl-3-yl)-5-(4-(trifluoromethoxy)phenyl)oxazole | MS (ESI) 608.0 [M + H]+. |
| 415 | 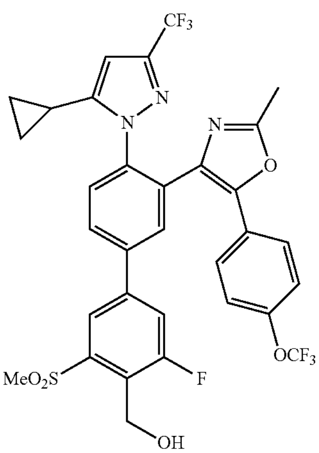 [SMILES: Cc1nc(-c2cc(-c3cc(F)c(CO)c(S(C)(=O)=O)c3)ccc2-n2nc(C(F)(F)F)cc2C2CC2)c(-c2ccc(OC(F)(F)F)cc2)o1] | (4'-(5-cyclopropyl-3-(trifluoromethyl)-1H-pyrazol-1-yl)-3-fluoro-3'-(2-methyl-5-(4-(trifluoromethoxy)phenyl)oxazol-4-yl)-5-(methylsulfonyl)biphenyl-4-yl)methanol | MS (ESI) 696.0 [M + H]+. |
| 416 | 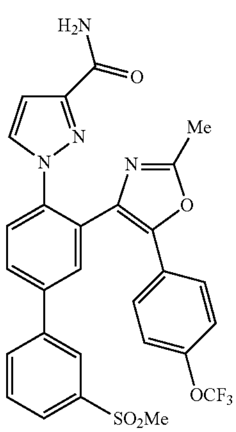 [SMILES: Cc1nc(-c2cc(-c3cccc(S(C)(=O)=O)c3)ccc2-n2ccc(C(N)=O)n2)c(-c2ccc(OC(F)(F)F)cc2)o1] | 1-(3-(2-methyl-5-(4-(trifluoromethoxy)phenyl)oxazol-4-yl)-3'-methylsulfonyl)-[1,1'-biphenyl]-4-yl)-1H-pyrazole-3-carboxamide | MS (ESI) 583.0 [M + H]+. |

-continued

| Ex # | Structure | Name | Characterization Data |
|---|---|---|---|
| 417 | 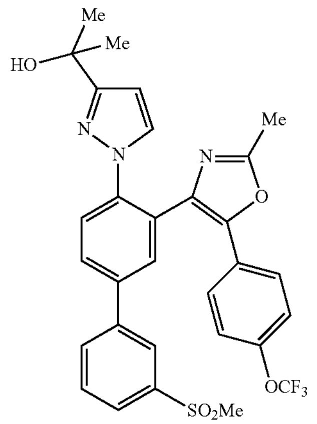 [SMILES: Cc1nc(-c2cc(-c3cccc(S(C)(=O)=O)c3)ccc2-n2ccc(C(C)(C)O)n2)c(-c2ccc(OC(F)(F)F)cc2)o1] | 2-(1-(3-(2-methyl-5-(4-(trifluoromethoxy) phenyl)oxazol-4-yl)-3'-(methylsulfonyl)-[1,1'-biphenyl]-4-yl)-1H-pyrazol-3-yl)propan-2-ol | MS (ESI) 598.2 [M + H]+. |
| 418 | 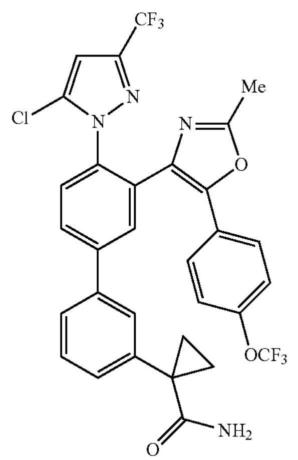 [SMILES: Cc1nc(-c2cc(-c3cccc(C4(C(N)=O)CC4)c3)ccc2-n2nc(C(F)(F)F)cc2Cl)c(-c2ccc(OC(F)(F)F)cc2)o1] | 1-(4'-(5-chloro-3-(trifluoromethyl)-1H-pyrazol-1-yl)-3'-(2-methyl-5-(4-(trifluoromethoxy) phenyl)oxazol-4-yl)-[1,1'-biphenyl]-3-yl) cyclopropanecarboxamide | MS (ESI) 647.2 [M + H]+. |
| 419 | 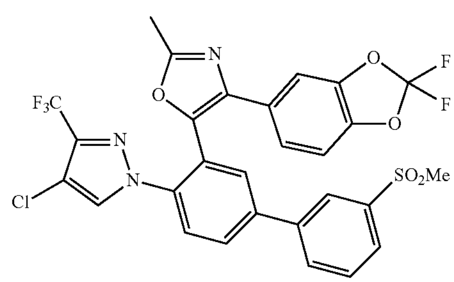 [SMILES: Cc1nc(-c2ccc3c(c2)OC(F)(F)O3)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(2,2-difluorobenzo[d][1,3]dioxol-5-yl)-2-methyloxazole | MS (ESI) 638 [M + H]+. $^{1}$H NMR (400 MHz, METHANOL-d$_{4}$) δ ppm 8.31 (m, 1 H) 8.10-8.16 (m, 2 H) 8.02-8.08 (m, 2 H) 7.91 (d, J = 0.75 Hz, 1 H) 7.74-7.84 (m, 2 H) 7.02-7.09 (m, 3 H) 3.23 (s, 3 H) 2.59 (s, 3 H). |
| 420 | 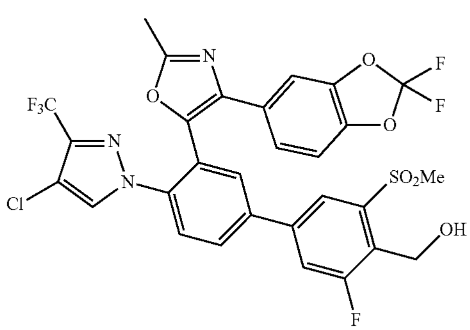 [SMILES: Cc1nc(-c2ccc3c(c2)OC(F)(F)O3)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(2,2-difluorobenzo[d][1,3]dioxol-5-yl)-2-methyloxazol-5-yl)-3-fluoro-5-(methylsulfonyl)-[1,1'-biphenyl]-4-yl) methanol | MS (ESI) 686 [M + H]+. $^{1}$H NMR (400 MHz, METHANOL-d$_{4}$) δ ppm 8.24 (d, J = 1.07 Hz, 1 H), 8.15 (s, 1 H), 8.04 (dd, J = 8.41, 2.20 Hz, 1 H), 7.91-7.99 (m, 2 H), 7.77 (d, J = 8.41 Hz, 1 H), 7.02-7.09 (m, 3 H), 5.16 (s, 2 H), 3.41 (s, 3 H), 2.59 (s, 3 H). |

| Ex # | Structure | Name | Characterization Data |
|---|---|---|---|
| 421 | 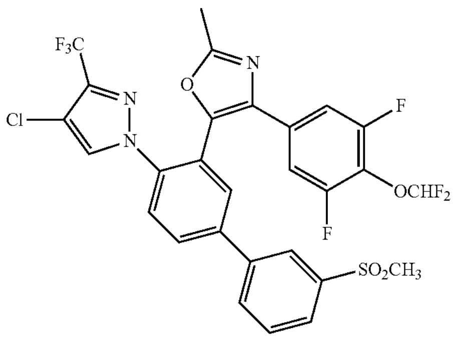 [SMILES: Cc1nc(-c2cc(F)c(OC(F)F)c(F)c2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-methylsulfonyl)-[1,1'-biphenyl]-3-yl)-4-(4-(difluoromethoxy)-3,5-difluorophenyl)-2-methyloxazole | MS (ESI) 660 [M + H]+. $^1$H NMR (400 MHz, METHANOL-d$_4$) δ ppm 8.30 (s, 1 H), 8.02-8.16 (m, 5 H), 7.79 (m, 2H), 6.63-7.05 (m, 3 H), 3.23 (s, 3 H), 2.57 (s, 3 H). |
| 422 | 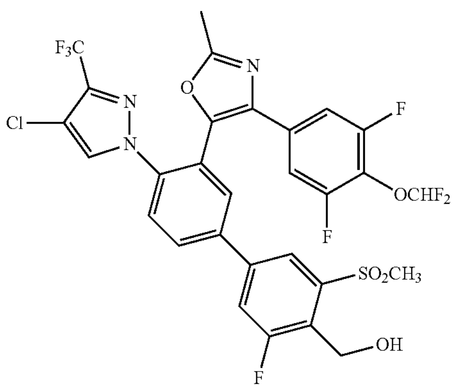 [SMILES: Cc1nc(-c2cc(F)c(OC(F)F)c(F)c2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(4-(difluoromethoxy)-3,5-difluorophenyl)-2-methyloxazol-5-yl)-3-fluoro-5-(methylsulfonyl)-[1,1'-biphenyl]-4-yl)methanol | MS (ESI) 708 [M + H]+. |
| 423 | 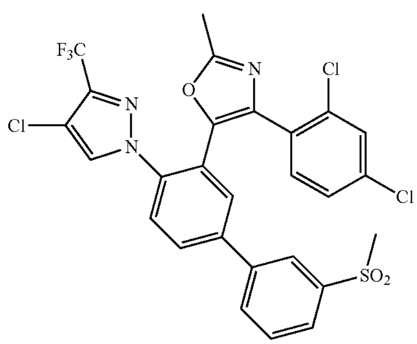 [SMILES: Cc1nc(-c2ccc(Cl)cc2Cl)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(2,4-dichlorophenyl)-2-methyloxazole | MS (ESI) 626 [M + H]+. |
| 424 | 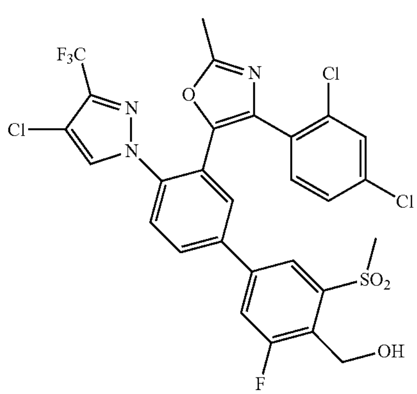 [SMILES: Cc1nc(-c2ccc(Cl)cc2Cl)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(2,4-dichlorophenyl)-2-methyloxazol-5-yl)-3-fluoro-5-(methylsulfonyl)-[1,1'-biphenyl]-4-yl)methanol | MS (ESI) 674 [M + H]+. $^1$H NMR (400 MHz, METHANOL-d$_4$) δ ppm 8.18 (s, 1 H), 8.04 (d, J = 2.20 Hz, 1 H), 7.89-7.99 (m, 3 H), 7.66 (d, J = 8.41 Hz, 1 H), 7.44 (d, J = 2.07 Hz, 1 H), 7.28-7.32 (m, 1 H), 7.20-7.24 (m, 1 H), 5.15 (d, J = 1.88 Hz, 2 H), 3.41 (s, 3 H), 2.60 (s, 3 H). |

| Ex # | Structure | Name | Characterization Data |
|---|---|---|---|
| 425 | 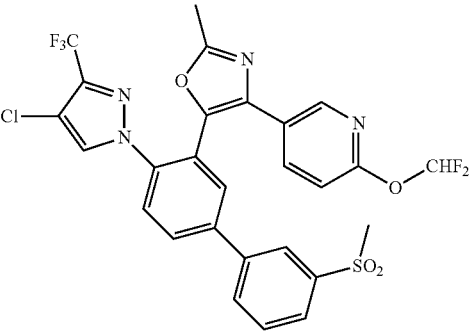 [SMILES: Cc1nc(-c2ccc(OC(F)F)nc2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-methylsulfonyl)-[1,1'-biphenyl]-3-yl)-4-(6-(difluoromethoxy)pyridin-3-yl)-2-methyloxazole | MS (ESI) 624.5 [M + H]+. $^1$H NMR (400 MHz, METHANOL-$d_4$) δ ppm 8.28 (m, 1H), 7.99-8.14 (m, 6H), 7.73-7.84 (m, 3H), 7.51 (t, J = 73 Hz, 1H), 6.90 (dd, J = 8.6, 0.7 Hz, 1H), 3.22 (s, 3 H), 2.58 (s, 3 H). |
| 426 | 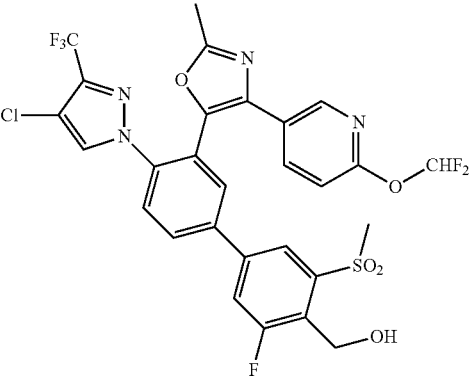 [SMILES: Cc1nc(-c2ccc(OC(F)F)nc2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(6-(difluoromethoxy)pyridin-3-yl)-2-methyloxazol-5-yl)-3-fluoro-5-(methylsulfonyl)-[1,1'-biphenyl]-4-yl)methanol | MS (ESI) 673 [M + H]+. $^1$H NMR (400 MHz, CD$_3$OD) δ ppm 8.22 (s, 1H) 8.14 (d, J = 2 Hz, 1H), 8.12 (d, J = 2 Hz, 1H) 8.04 (dd, J = 2, 8.4 Hz, 1H), 8.01 (d, J = 1 Hz, 1H), 7.96 (dd, J = 10.5, 2.0 Hz, 1H) 7.79 (d, J = 8.4 Hz, 1H), 7.75 (dd, J = 2.4, 8.4 Hz, 1H), 7.52 (t, J = 73 Hz, 1H), 6.91 (dd, J = 8.6, 0.7 Hz, 1 H), 5.15 (d, J = 2.0 Hz, 2 H) 3.41 (s, 3 H) 2.58 (s, 3 H). |
| 427 | 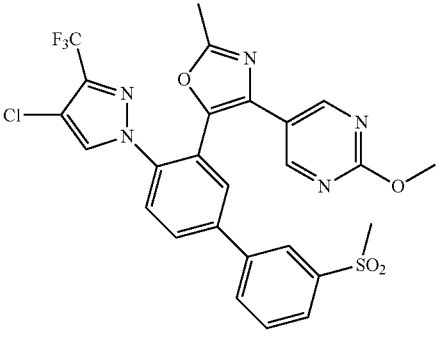 [SMILES: COc1ncc(-c2nc(C)oc2-c2cc(-c3cccc(S(C)(=O)=O)c3)ccc2-n2cc(Cl)c(C(F)(F)F)n2)cn1] | 5-(4-(4-chloro-3-(trifluoromethyl)-1H-pyrazol-1-yl)-3'-(methylsulfonyl)-[1,1'-biphenyl]-3-yl)-4-(2-methoxypyrimidin-5-yl)-2-methyloxazole | MS (ESI) 589.5 [M + H]+. $^1$H NMR (400 MHz, CD$_3$OD) δ ppm 8.46 (s, 2H), 8.30 (m, 1H), 8.16 (d, J = 2 Hz, 1H), 8.12 (m, 1H), 8.05-8.08 (m, 3H), 7.79-7.84 (m, 2H), 4.03 (s, 3H), 3.23 (s, 3H), 2.59 (s, 3H). |
| 428 | 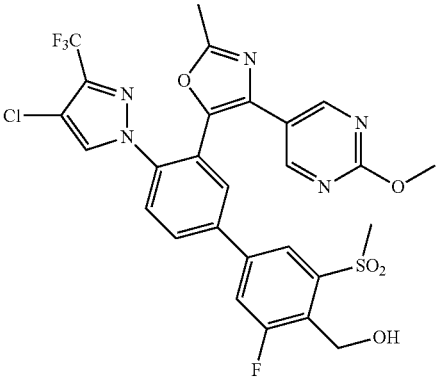 [SMILES: COc1ncc(-c2nc(C)oc2-c2cc(-c3cc(F)c(CO)c(S(C)(=O)=O)c3)ccc2-n2cc(Cl)c(C(F)(F)F)n2)cn1] | (4'-(4-chloro-3-(trifluoromethyl)-1H-pyrazol-1-yl)-3-fluoro-3'-(4-(2-methoxypyrimidin-5-yl)-2-methyloxazol-5-yl)-5-(methylsulfonyl)-[1,1'-biphenyl]-4-yl)methanol | MS (ESI) 637.9 [M + H]+. $^1$H NMR (400 MHz, CD$_3$OD) δ ppm 8.45 (s, 2H), 8.23 (d, J = 1 Hz, 1H), 8.17 (d, J = 2 Hz, 1H), 8.05-8.08 (m, 2H), 7.97 (dd, J = 2, 10 Hz, 1H), 7.80 (d, J = 8.4 Hz, 1H), 5.15 (d, J = 2 Hz, 2H), 4.03 (s, 3H), 3.42 (s, 3H), 2.59 (s, 3H).. |

-continued

| Ex # | Structure | Name | Characterization Data |
|---|---|---|---|
| 429 | 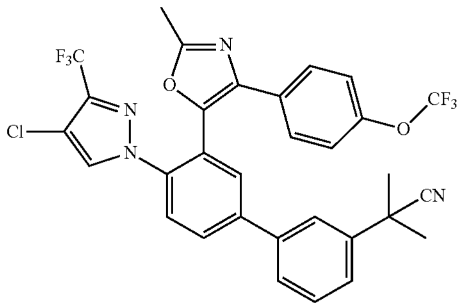 [SMILES: Cc1nc(-c2ccc(OC(F)(F)F)cc2)c(-c2cc(-c3cccc(C(C)(C)C#N)c3)ccc2-n2cc(Cl)c(C(F)(F)F)n2)o1] | 2-(4'-(4-chloro-3-(trifluoromethyl)-1H-pyrazol-1-yl)-3'-(2-methyl-4-(4-(trifluoromethoxy)phenyl)oxazol-5-yl)-[1,1'-biphenyl]-3-yl)-2-methylpropanenitrile | MS (ESI) 631 [M + H]+. $^1$H NMR (400 MHz, CD$_3$OD-d$_4$) δ ppm 8.02 (d, J = 1.94 Hz, 1 H) 7.95-7.99 (m, 1 H) 7.90 (d, J = 0.88 Hz, 1 H) 7.82 (m, 1 H) 7.56-7.76 (m, 4 H) 7.39-7.43 (m, 2 H) 7.20 (dd, J = 8.91, 0.94 Hz, 2 H) 2.55-2.58 (m, 3 H) 1.82 (s, 6 H). |
| 430 | 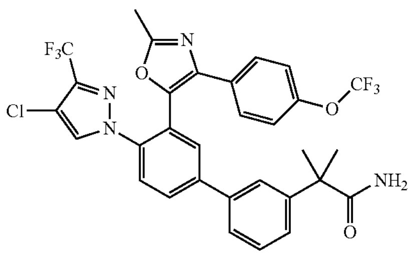 [SMILES: Cc1nc(-c2ccc(OC(F)(F)F)cc2)c(-c2cc(-c3cccc(C(C)(C)C(N)=O)c3)ccc2-n2cc(Cl)c(C(F)(F)F)n2)o1] | 2-(4'-(4-chloro-3-(trifluoromethyl)-1H-pyrazol-1-yl)-3'-(2-methyl-4-(4-(trifluoromethoxy)phenyl)oxazol-5-yl)-[1,1'-biphenyl]-3-yl)-2-methylpropanamide | MS (ESI) 649 [M + H]+. $^1$H NMR (400 MHz, METHANOL-d$_4$) δ ppm 8.00 (d, J = 1.94 Hz, 1 H) 7.94 (dd, J = 8.35, 2.13 Hz, 1 H) 7.89 (d, J = 0.88 Hz, 1 H) 7.72 (d, J = 8.47 Hz, 2 H) 7.56-7.61 (m, 1 H) 7.49-7.51 (m, 2 H) 7.38-7.42 (m, 2 H) 7.19 (m, 2 H) 2.56 (s, 3 H) 1.63 (s, 6 H). |
| 431 | 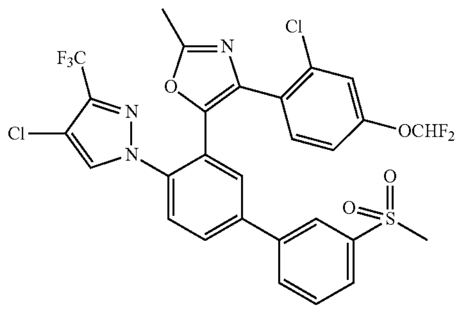 [SMILES: Cc1nc(-c2ccc(OC(F)F)cc2Cl)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-methylsulfonyl)-[1,1'-biphenyl]-3-yl)-4-(2-chloro-4-(difluoromethoxy)phenyl)-2-methyloxazole | MS (ESI) 658 [M + H]+. $^1$H NMR (400 MHz, METHANOL-d$_4$) δ ppm 8.18 (m, 1H), 8.03-8.07 (m, 2H), 7.91-7.99 (m, 3H), 7.80 (m, 1H), 7.67 (d, J = 8.2, Hz, 1H), 7.30 (d, J = 8.6 Hz, 1H), 7.21 (d, J = 2.4 Hz, 1H), 7.08 (dd, J = 2.4, 8.4 Hz, 1H), 6.94 (t, J = 73 Hz, 1H), 3.22 (s, 3 H), 2.58 (s, 3 H) |
| 432 | 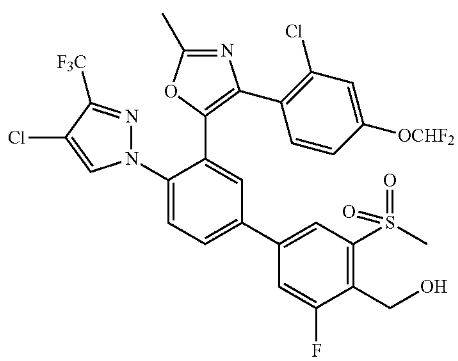 [SMILES: Cc1nc(-c2ccc(OC(F)F)cc2Cl)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(2-chloro-4-(difluoromethoxy)phenyl)-2-methyloxazol-5-yl)-3-fluoro-5-(methylsulfonyl)-[1,1'-biphenyl]-4-yl)methanol | MS (ESI) 706 [M + H]+. $^1$H NMR (400 MHz, CD$_3$OD) δ ppm 8.12 (d, J = 1.1 Hz, 1H), 7.95-8.00 (m, 3H), 7.87-7.92 (m, 1H), 7.67 (d, J = 8.7 Hz, 1H), 7.30 (d, J = 8.8 Hz, 1H), 7.21 (d, J = 2.4 Hz, 1H), 7.08 (dd, J = 2.4, 8.8 Hz, 1H), 6.94 (t, J = 73 Hz, 1H), 5.15 (d, J = 1.9 Hz, 2 H), 3.40 (s, 3 H), 2.57 (s, 3 H). |
| 433 | 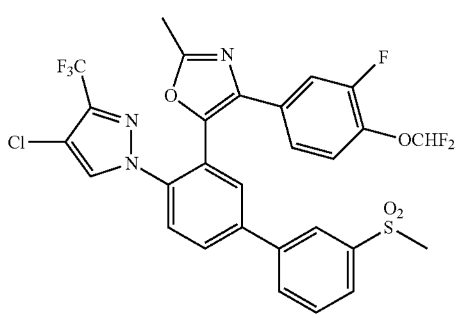 [SMILES: Cc1nc(-c2ccc(OC(F)F)c(F)c2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-methylsulfonyl)-[1,1'-biphenyl]-3-yl)-4-(4-(difluoromethoxy)-3-fluorophenyl)-2-methyloxazole | MS (ESI) 642 [M + H]+. |

| Ex # | Structure | Name | Characterization Data |
|---|---|---|---|
| 434 | 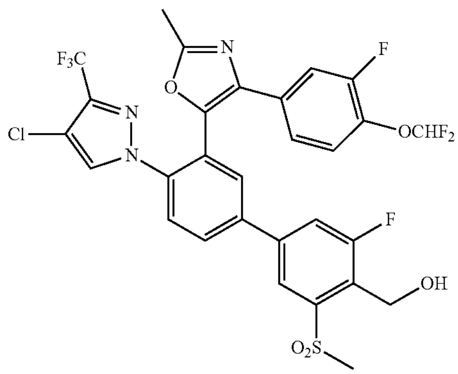 [SMILES: Cc1nc(-c2ccc(OC(F)F)c(F)c2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(4-(difluoromethoxy)-3-fluorophenyl)-2-methyloxazol-5-yl)-3-fluoro-5-(methylsulfonyl)-[1,1'-biphenyl]-4-yl)methanol | MS (ESI) 690 [M + H]+. |
| 435 | 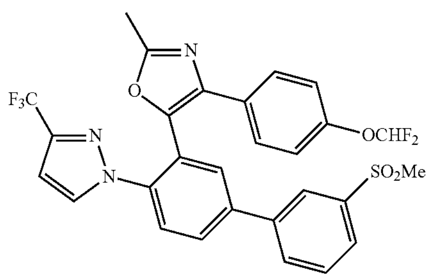 [SMILES: Cc1nc(-c2ccc(OC(F)F)cc2)c(-c2cc(-c3cccc(S(C)(=O)=O)c3)ccc2-n2ccc(C(F)(F)F)n2)o1] | 4-(4-(difluoromethoxy)phenyl)-2-methyl-5-(3'-(methylsulfonyl)-4-(3-(trifluoromethyl)-1H-pyrazol-1-yl)-[1,1'-biphenyl]-3-yl)oxazole | MS (ESI) 590.0 [M + H]+. |
| 436 | 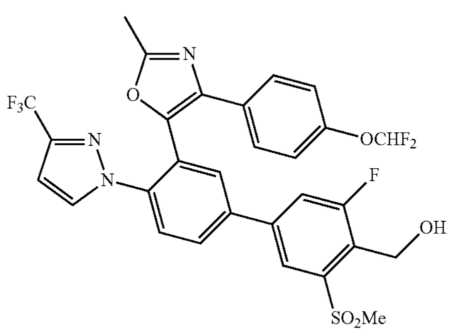 [SMILES: Cc1nc(-c2ccc(OC(F)F)cc2)c(-c2cc(-c3cc(F)c(CO)c(S(C)(=O)=O)c3)ccc2-n2ccc(C(F)(F)F)n2)o1] | (3'-(4-(4-(difluoromethoxy)phenyl)-2-methyloxazol-5-yl)-3-fluoro-5-(methylsulfonyl)-4'-(3-(trifluoromethyl)-1H-pyrazol-1-yl)-[1,1'-biphenyl]-4-yl)methanol | MS (ESI) 638.0 [M + H]+. |
| 437 | 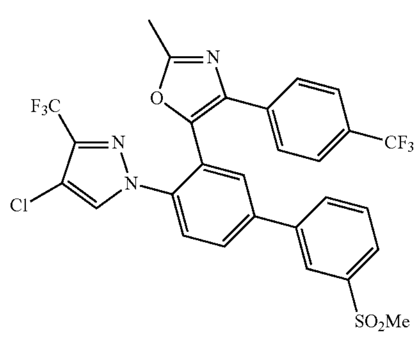 [SMILES: Cc1nc(-c2ccc(C(F)(F)F)cc2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-2-methyl-4-(4-(trifluoromethyl)phenyl)oxazole | MS (ESI) 626.0 [M + H]+. <br>1H NMR (400 MHz, METHANOL-d4) δ ppm 8.31 (1 H, t, J = 1.66 Hz), 8.16 (1 H, d, J = 2.07 Hz), 8.10-8.13 (1 H, m), 8.03-8.08 (2 H, m), 7.90 (1 H, d, J = 0.88 Hz), 7.79-7.85 (1 H, m), 7.77 (1 H, d, J = 8.35 Hz), 7.54 (2 H, d, J = 8.16 Hz), 7.47 (2 H, d, J = 8.09 Hz), 3.23 (3 H, s), 2.60 (3 H, s). |

| Ex # | Structure | Name | Characterization Data |
|---|---|---|---|
| 438 | 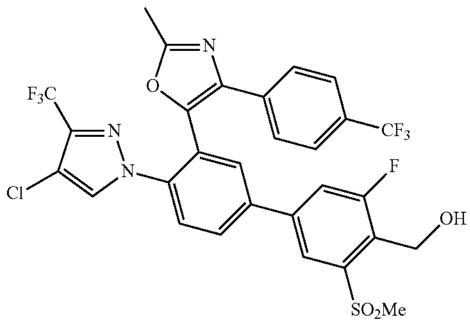 [SMILES: Cc1nc(-c2ccc(C(F)(F)F)cc2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3-fluoro-3'-(2-methyl-4-(4-(trifluoromethyl)phenyl)oxazol-5-yl)-5-(methylsulfonyl)-[1,1'-biphenyl]-4-yl)methanol | MS (ESI) 674.0 [M + H]+. $^1$H NMR (400 MHz, METHANOL-d$_4$) δ ppm 8.25 (1 H, d, J = 1.07 Hz) 8.17 (1 H, d, J = 2.07 Hz) 8.06 (1 H, dd, J = 8.41, 2.20 Hz) 7.95 (1 H, dd, J = 10.45, 1.85 Hz) 7.91 (1 H, d, J = 0.88 Hz) 7.78 (1 H, d, J = 8.47 Hz) 7.56 (2 H, d, J = 8.16 Hz) 7.46 (2 H, d, J = 8.09 Hz) 5.16 (2 H, d, J = 1.88 Hz) 3.41 (3 H, s) 2.61 (3 H, s); |
| 439 | 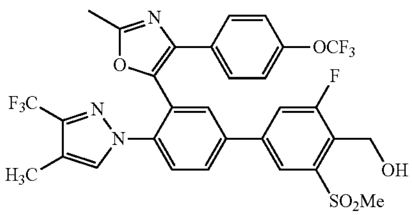 [SMILES: Cc1nc(-c2ccc(OC(F)(F)F)cc2)c(-c2cc(-c3cc(F)c(CO)c(S(C)(=O)=O)c3)ccc2-n2cc(C)c(C(F)(F)F)n2)o1] | (3-fluoro-4'-(4-methyl-3-(trifluoromethyl)-1H-pyrazol-1-yl)-3'-(2-methyl-4-(4-(trifluoromethoxy)phenyl)oxazol-5-yl)-5-(methylsulfonyl)-[1,1'-biphenyl]-4-yl)methanol | MS (ESI) 670.2 [M + H]+. $^1$H NMR (400 MHz, CDCl$_3$-d) δ ppm 8.17 (1 H, d, J = 1.1 Hz) 7.89 (1 H, d, J = 2.0 Hz) 7.76-7.83 (1 H, m) 7.69-7.76 (1 H, m) 7.65 (1 H, dd, J = 10.0. 1.9 Hz) 7.32-7.41 (2 H, m) 7.02-7.14 (3 H, m) 5.11 (2H, dd, J = 7.1, 1.7 Hz) 3.31 (3 H, s) 2.88 (1 H, t, J = 7.1 Hz) 2.57 (3 H, s) 1.98 (3 H, s) |
| 440 | 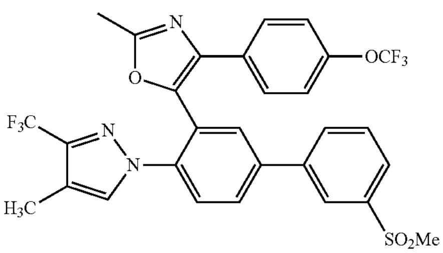 [SMILES: Cc1nc(-c2ccc(OC(F)(F)F)cc2)c(-c2cc(-c3cccc(S(C)(=O)=O)c3)ccc2-n2cc(C)c(C(F)(F)F)n2)o1] | 2-methyl-5-(4-(4-methyl-3-(trifluoromethyl)-1H-pyrazol-1-yl)-3'-methylsulfonyl)-[1,1'-biphenyl]-3-yl)-4-(4-(trifluoromethoxy)phenyl)oxazole | MS (ESI) 622.2 [M + H]+. $^1$H NMR (400 MHz, CHLOROFORM-d) δ ppm 8.22 (1H, m), 7.96-8.05 (1H, m), 7.86-7.93 (2H, m), 7.77-7.84 (1H, m), 7.66-7.75 (2H, m), 7.33-7.43 (2H, m), 7.02-7.12 (3H, m), 3.13 (3H, s), 2.57 (3H, s), 1.99 (3H, s). |
| 441 | 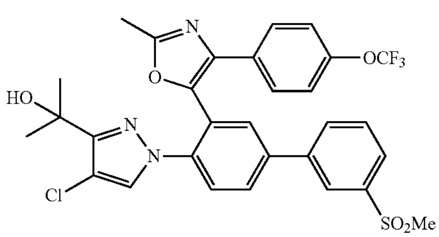 [SMILES: Cc1nc(-c2ccc(OC(F)(F)F)cc2)c(-c2cc(-c3cccc(S(C)(=O)=O)c3)ccc2-n2cc(Cl)c(C(C)(C)O)n2)o1] | 2-(4-chloro-1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)propan-2-ol | MS (ESI) 632.2 [M + H]+. $^1$H NMR (400 MHz, methanol-d$_4$) δ ppm 1.47 (s, 6H), 2.56 (s, 3H), 3.21 (s, 3H), 7.18 (dd, J = 0.8, 8.8 Hz, 2H), 7.46-7.48 (m, 2H), 7.65 (s, 1H), 7.75-7.79 (m, 2H), 8.00-8.06 (m, 4H), 8.26 (m, 1H). |
| 442 | 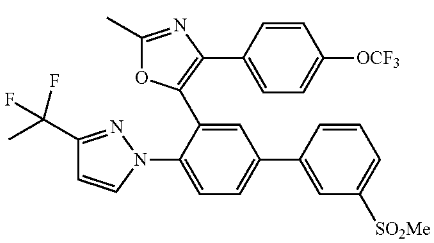 [SMILES: Cc1nc(-c2ccc(OC(F)(F)F)cc2)c(-c2cc(-c3cccc(S(C)(=O)=O)c3)ccc2-n2ccc(C(C)(F)F)n2)o1] | 5-(4-(3-(1,1-difluoroethyl)-1H-pyrazol-1-yl)-3'-(methylsulfonyl)-[1,1'-biphenyl]-3-yl)-2-methyl-4-(4-(trifluoromethoxy)phenyl)oxazole | MS (ESI) 604.2 [M + H]+. $^1$H NMR (400 MHz, CD$_3$OD-d$_4$) δ ppm 1.76-1.86 (t, J = 18.4 Hz, 3H), 2.52 (s, 3H), 3.21 (s, 3H), 6.39 (d, J = 2.4 Hz, 1H), 7.17 (dd, J = 0.8 Hz, 8.8 Hz, 2H), 7.45-7.47 (m, 2H), 7.65 (d, J = 2.4 Hz, 1H), 7.76-7.81 (m, 2H), 8.02-8.07 (m, 4H), 8.28 (m, 1H). |

| Ex # | Structure | Name | Characterization Data |
|---|---|---|---|
| 443 | 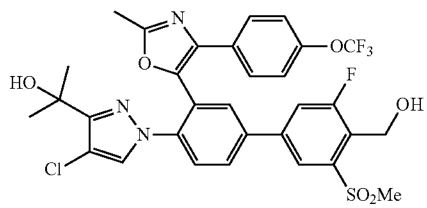 [SMILES: Cc1nc(-c2ccc(OC(F)(F)F)cc2)c(-c2cc(-c3cc(F)c(CO)c(S(C)(=O)=O)c3)ccc2-n2cc(Cl)c(C(C)(C)O)n2)o1] | 2-(4-chloro-1-(3'-fluoro-4'-(hydroxymethyl)-3-(2-methyl-4-(4-(trifluoromethoxy)phenyl)oxazol-5-yl)-5-(methylsulfonyl)-[1,1'-biphenyl]-4-yl)-1H-pyrazol-3-yl)propan-2-ol | MS (ESI) 680.0 [M + H]+. $^1$H NMR (400 MHz, CD$_3$OD-d$_4$) δ ppm 1.46 (s, 6H), 2.56 (s, 3H), 3.39 (s, 3H), 5.14 (d, J = 1.6 Hz, 2H), 7.18 (d, J = 8.0 Hz, 2H), 7.45-7.47 (m, 2H), 7.66 (s, 1H), 7.76-7.82 (m, 1H), 7.87 (dd, J = 1.8, 10.6 Hz, 1H), 8.01 (m, 2H), 8.20 (d, J = 1.2 Hz, 1H). |
| 444 | 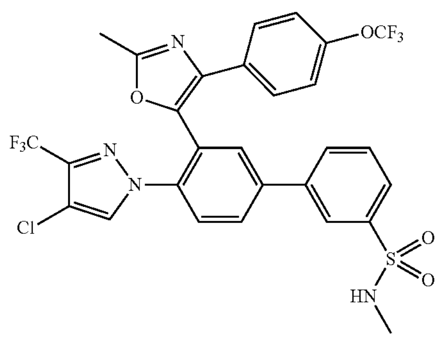 [SMILES: CNS(=O)(=O)c1cccc(-c2ccc(-n3cc(Cl)c(C(F)(F)F)n3)c(-c3oc(C)nc3-c3ccc(OC(F)(F)F)cc3)c2)c1] | 4'-(4-chloro-3-(trifluoromethyl)-1H-pyrazol-1-yl)-N-methyl-3'-(2-methyl-4-(4-(trifluoromethoxy)phenyl)oxazol-5-yl)-[1,1'-biphenyl]-3-sulfonamide | MS (ESI) 657.2 [M + H]+. $^1$H NMR (400 MHz, CDCl$_3$-d) δ ppm 8.13 (m, H) 7.89-7.94 (m, 2H) 7.78-7.83 (m, 2H) 7.63-7.71 (m, 2H) 7.35-7.40 (m, 2H) 7.29 (d, J = 1.0 Hz, 1H) 7.07-7.14 (m, 2H) 4.36 (q, J = 5.5 Hz, 1H) 2.73 (d, J = 5.5 Hz, 3H) 1.54 (s, 3H). |
| 445 | 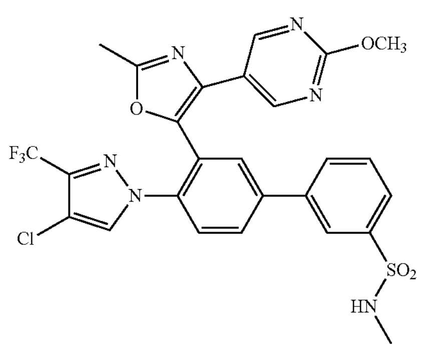 [SMILES: CNS(=O)(=O)c1cccc(-c2ccc(-n3cc(Cl)c(C(F)(F)F)n3)c(-c3oc(C)nc3-c3cnc(OC)nc3)c2)c1] | 4'-(4-chloro-3-(trifluoromethyl)-1H-pyrazol-1-yl)-3'-(4-(2-methoxypyrimidin-5-yl)-2-methyloxazol-5-yl)-N-methyl-[1,1'-biphenyl]-3-sulfonamide | MS (ESI) 605.0 [M + H]+. $^1$H NMR (400 MHz, CDCl$_3$-d) δ ppm 8.51- (s, 2H), 8.07 (m, 1 H), 7.89-7.94 (m, 2H), 7.80-7.84 (m, 2 H), 7.65-7.71 (m, 2 H), 7.43 (d, J = 0.88 Hz, 1 H), 4.44 (q, J = 5.4 Hz, 1 H), 4.03 (s, 3H), 2.73 (d, J = 5.3 Hz, 3 H), 2.56 (s, 3 H). |
| 446 | 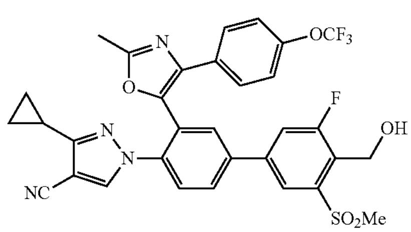 [SMILES: Cc1nc(-c2ccc(OC(F)(F)F)cc2)c(-c2cc(-c3cc(F)c(CO)c(S(C)(=O)=O)c3)ccc2-n2cc(C#N)c(C3CC3)n2)o1] | 3-cyclopropyl-1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazole-4-carbonitrile | MS (ESI) 653.2 [M + H]+. $^1$H NMR (400 MHz, METHANOL-d$_4$) δ ppm 8.23 (1 H, d, J = 1.1 Hz) 8.14 (1 H, s) 8.10 (1 H, s) 8.03 (1 H, dd, J = 8.4, 2.2 Hz) 7.92 (1 H, dd, J = 10.4, 1.8 Hz) 7.74 (1 H, d, J = 8.4 Hz) 7.35-7.44 (2 H, m) 7.16-7.26 (2 H, m) 5.15 (2 H, d, J = 1.9 Hz) 3.41 (3 H, s) 2.59 (3 H, s) 1.80-1.90 (1 H, m) 0.92-1.04 (2 H, m) 0.68-0.79 (2 H, m) |

-continued

| Ex # | Structure | Name | Characterization Data |
|---|---|---|---|
| 447 | 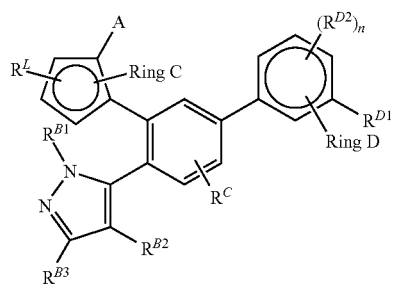 | 3-cyclopropyl-1-(3-(2-methyl-4-(4-(trifluoromethoxy)phenyl)oxazol-5-yl)-3'-(methylsulfonyl)-[1,1'-biphenyl]-4-yl)-1H-pyrazole-4-carbonitrile | MS (ESI) 606.0 [M + H]+. $^1$H NMR (400 MHz, METHANOL-$d_4$) δ ppm 8.29 (1H, m) 8.13 (1 H, s) 7.98-8.11 (4 H, m) 7.77-7.83 (1 H, m) 7.73 (1 H, d, J = 8.4 Hz) 7.36-7.44 (2 H, m) 7.17-7.24 (2 H, m) 3.23 (3 H, s) 2.59 (3 H, s) 1.80-1.90 (1 H, m) 0.95-1.03 (2 H, m) 0.71-0.78 (2 H, m) |
| 448 | 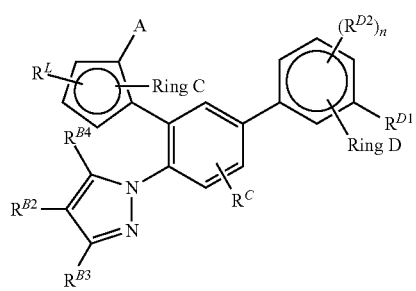 | 3-cyclopropyl-1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazole-4-carboxamide | MS (ESI) 671.2 [M + H]+. $^1$H NMR (400 MHz, METHANOL-$d_4$) δ ppm 8.21 (1H, d, J = 1.2 Hz), 7.96-8.06 (3H, m), 7.89 (1H, dd, J = 10.4, 1.8 Hz), 7.74 (1H, dd, J = 8.1, 0.6 Hz), 7.39-7.46 (2H, m), 7.17 (2H, dd, J = 8.9, 0.9 Hz), 5.14 (2H, d, J = 1.8 Hz), 3.40 (3H, s), 2.56 (3H, s), 2.40 (1H, m), 0.83-0.91 (2H, m), 0.61-0.70 (2 H, m) |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of the formula I or II,

I

II or a pharmaceutically acceptable salt or solvate thereof, wherein

Ring C is selected from oxazolyl and triazolyl;

Ring D is selected from phenyl and pyridyl;

A is phenyl or a 5 or 6 membered heteroaryl, wherein the phenyl is optionally fused to a 5 or 6 membered heterocyclyl or 5 or 6 membered heteroaryl, wherein A is optionally substituted with 1, 2, or 3 $R^A$ groups, wherein each $R^A$ is independently $R^{A1}$, —$C_1$-$C_6$alkyl-$R^{A1}$, $C_1$-$C_6$alkyl, $C_1$-$C_6$ haloalkyl, $C_2$-$C_6$alkenyl, $C_2$-$C_6$alkynyl, $C_3$-$C_8$cycloalkyl, pyrrolidinone, or pyrrolidinyl, wherein the cycloalkyl is optionally substituted with 1, 2, 3, or 4 groups that are independently $R^{A1}$, $C_1$-$C_6$alkyl, or —$C_1$-$C_6$alkyl-$R^{A1}$, wherein each $R^{A1}$ is independently halogen, cyano, nitro, —OR, —$NR_2$, —SR, —C(O)R, or —C(O)OR;

alternatively, two $R^A$'s on adjacent carbons can join to form a —O—$CH_2$—O—, —O—$CH_2$—$CH_2$—, —O—$CH_2$—$CH_2$—O—, —$CH_2$—$CH_2$—$CH_2$—, or —O—$CF_2$—O—;

$R^{B1}$ is hydrogen, $C_{1-3}$alkyl, halo, cyclopropyl, or $C_{1-3}$haloalkyl;

$R^{B2}$ is hydrogen, halo, —CN, —C(O)$NR_2$, or $C_{1-3}$alkyl;

$R^{B3}$ is $C_{1-6}$alkyl, $C_{1-6}$haloalkyl, or $C_{3-6}$cycloalkyl, each of which is substituted with 0-1 $R^{B5}$; hydrogen; cyano; —C(O)—R; —C(O)$NR_2$; —NHC(O)R; —NHSO$_2$R; or a 5-membered ring heteroaryl, wherein the heteroaryl ring consists of carbon atoms and 1, 2, or 3 heteroatoms independently selected from the group consisting of N, S, and O and is substituted with 0-1 R;

$R^{B4}$ is H, halogen, $C_{1-3}$alkyl, $C_{1-3}$haloalkyl, —$C_3$-$C_6$cycloalkyl, or —O—$C_{1-3}$alkyl;

$R^{B5}$ is cyano, —O—R, —C(O)$NR_2$, —C(O)OR, —$NR_2$, —OC(O)—$NH_2$, —S(O)$_2NR_2$, or a 5-membered ring heteroaryl, wherein the heteroaryl ring consists of carbon atoms and 1, 2, or 3 heteroatoms independently selected from the group consisting of N, S, and O;

$R^C$ is hydrogen, halogen, cyano, or nitro;

n is 0, 1, 2, 3, or 4; and each $R^{D1}$ and $R^{D2}$ are independently $R^{D3}$, $C_1$-$C_6$alkyl, —$C_1$-$C_6$alkyl-$R^{D3}$, $C_1$-$C_6$haloalkyl, $C_2$-$C_6$alkenyl, $C_2$-$C_6$alkynyl, or $C_3$-$C_8$cycloalkyl, wherein the cycloalkyl is each optionally substituted with 1, 2, 3, or 4 groups that are independently $R^{D3}$, $C_1$-$C_6$alkyl, $C_3$-$C_6$cycloalkyl, or —$C_1$-$C_6$alkyl-$R^{D3}$, wherein each $R^{D3}$ is independently halogen, cyano, —OR, —$NR_2$, —SR, —C(O)R, —C(O)OR, —C(O)$NR_2$, —S(O)R, —S(O)$_2$R, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)$_2$R, —N(R)S(O)$_2$OR, —N(R)S(O)$_2NR_2$, or —S(O)$_2$N(R)C(O)$NR_2$; and $R^L$ is hydrogen, $C_1$-$C_6$alkyl, $C_3$-$C_6$cycloalkyl, $C_1$-$C_6$haloalkyl, —C(O)R, —C(O)OR, —C(O)$NR_2$, —S(O)R, —S(O)$_2$R, —S(O)OR, —S(O)$_2$OR, —S(O)$NR_2$, or —S(O)$_2NR_2$;

wherein each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl, or —$C_1$-$C_6$alkyl-$C_{3-6}$cycloalkyl; or for any —C(O)$NR_2$ or —$NR_2$, alternatively, the two Rs along with the N to which they attach may form morpholinyl, pyrrolidinyl, or piperdinyl; and wherein each $R^2$ is independently cyano, —$OR^3$, —C(O)$NH_2$, —$N(R^3)_2$, —$N(R^3)S(O)_2R^3$, —$N(R^3)S(O)_2OR^3$, or —$N(R^3)S(O)_2N(R^3)_2$, wherein each $R^3$ is independently hydrogen, $C_1$-$C_6$alkyl, $C_3$-$C_6$cycloalkyl, or $C_1$-$C_6$haloalkyl.

2. The compound of formula I or II,

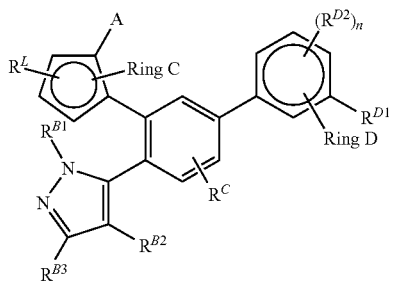

I

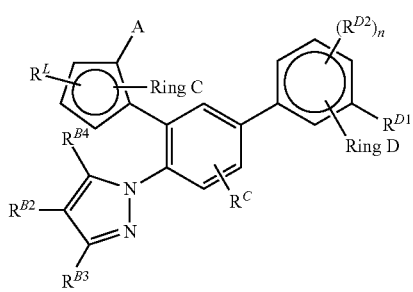

II or a pharmaceutically acceptable salt or solvate thereof, wherein

Ring C is selected from oxazolyl and triazolyl;

Ring D is selected from phenyl and pyridyl;

A is phenyl, pyridinyl or pyrimidinyl, wherein A is optionally substituted with 1, 2, or 3 $R^A$ groups, wherein each $R^A$ is independently halogen, —CN, $C_{1-6}$alkyl, $C_{1-6}$haloalkyl, $C_3$-$C_6$cycloalkyl, —O—$C_{1-6}$haloalkyl, —O—$C_{1-6}$alkyl, —CO—$C_{1-6}$alkyl, —O—$C_{3-6}$cycloalkyl, pyrrolidinone, pyrrolidinyl, —C(O)O—$C_{1-6}$alkyl, or —$NR_2$; or alternatively, two adjacent $R^A$'s join to form —O—$CH_2$—O— or —O—$CF_2$—O—;

$R^{B1}$ is $C_{1-3}$alkyl, $C_{1-3}$haloalkyl, or cyclopropyl;

$R^{B2}$ is H, halogen, —CN, —C(O)$NR_2$, or —$C_{1-3}$-alkyl;

$R^{B3}$ is $C_{1-6}$alkyl, $C_{1-6}$haloalkyl, or $C_{3-6}$cycloalkyl, each of which is substituted with 0-1 $R^{B5}$; hydrogen; cyano; —C(O)—R; —C(O)$NR_2$; —NHC(O)R; —$NHSO_2R$; or a 5-membered ring heteroaryl, wherein the heteroaryl ring consists of carbon atoms and 1, 2, or 3 heteroatoms independently selected from the group consisting of N, S, and O and is substituted with 0-1 R;

$R^{B4}$ is H, halogen, $C_{1-3}$alkyl, $C_{1-3}$haloalkyl, cyclopropyl, or —O—$C_{1-3}$alkyl;

$R^{B5}$ is cyano, —O—R, —C(O)$NR_2$, —C(O)OR, —$NR_2$, —OC(O)—$NH_2$, or a 5-membered ring heteroaryl, wherein the heteroaryl ring consists of carbon atoms and 1, 2, or 3 heteroatoms selected from the group consisting of N, S, and O;

each R is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_3$-$C_6$cycloalkyl, or —$C_1$-$C_6$alkyl-$C_{3-6}$cycloalkyl; or for any —C(O)$NR_2$ or —$NR_2$, alternatively, the two Rs along with the N to which they attach may form morpholinyl, pyrrolidinyl, or piperdinyl;

each $R^2$ is independently —OH, —C(O)$NH_2$, or cyano, n is 0, 1, 2, 3, or 4; and $R^{D1}$ is —S(O)$_2$—$C_{1-3}$alkyl, —S(O)$_2N(R^3)_2$, —C(CH$_3$)$_2$—C(O)$NH_2$, —C(CH$_3$)$_2$—CN, or -cyclopropyl-C(O)$NH^2$;

each $R^{D2}$ is independently halogen or —$CH_2OH$;

$R^3$ is H, $C_{1-3}$alkyl, cyclopropyl, or $C_{1-3}$haloalkyl;

$R^C$ is hydrogen or halogen; and $R^L$ is absent, hydrogen, $C_1$-$C_6$alkyl, $C_3$-$C_6$cycloalkyl, or $C_1$-$C_6$haloalkyl.

3. The compound of claim 1, or a pharmaceutically acceptable salt or solvate thereof, wherein $R^{B1}$ is —$C_{1-3}$-alkyl, —$C_{1-3}$-haloalkyl, or cyclopropyl;

$R^{B2}$ is H, halogen, CN, or methyl;

$R^{B3}$ is $C_{1-6}$alkyl, $C_{1-6}$haloalkyl, $C_{3-8}$cycloalkyl, each of which is substituted with 0-1 $R^{B5}$; cyano, —C(O)$NR_2$, —NHC(O)R, or —$NHSO_2R$; and $R^{B4}$ is H, halogen, methyl, —$CF_3$, cyclopropyl, or —O—$C_{1-3}$alkyl.

4. The compound of claim 1, or a pharmaceutically acceptable salt or solvate thereof, wherein $R^{B5}$ is cyano, —O—R, —C(O)$NR_2$, —C(O)OR, or —OC(O)—$NH_2$; and each R is independently, hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_3$-$C_6$cycloalkyl, or —$C_1$-$C_6$alkyl-$C_{3-6}$cycloalkyl, or for —C(O)$NR_2$, alternatively, two Rs along with the N to which they attach may form morpholinyl, pyrrolidinyl, or piperdinyl.

5. The compound of claim 1, or a pharmaceutically acceptable salt or solvate thereof, wherein A is phenyl or pyridinyl, wherein A is optionally substituted with 1, 2, or 3 $R^A$ groups.

6. The compound of claim 1, or a pharmaceutically acceptable salt or solvate thereof, wherein A is phenyl optionally substituted with 1, 2, or 3 $R^A$ groups.

7. The compound of claim 1, or a pharmaceutically acceptable salt or solvate thereof, wherein
Ring C is selected from oxazolyl, and
$R^L$ is hydrogen or methyl.

8. The compound of claim 1, or a pharmaceutically acceptable salt or solvate thereof, wherein
Ring C is selected from triazolyl, and
$R^L$ is hydrogen.

9. The compound of claim 1, or a pharmaceutically acceptable salt or solvate thereof, wherein
Ring D is selected from phenyl.

10. The compound of claim 1, or a pharmaceutically acceptable salt or solvate thereof, wherein
each $R^{D1}$ is $—S(O)_2$-methyl, $—S(O)_2N(R^3)_2$, $—C(CH_3)_2—C(O)NH_2$, -cyclopropyl-$C(O)NH_2$;
$R^3$ is H or $C_{1-3}$alkyl.

11. A compound selected from Examples 1-448 listed below, or a pharmaceutically acceptable salt or solvate thereof:

| Ex # | Structure | Name |
|---|---|---|
| 1 | 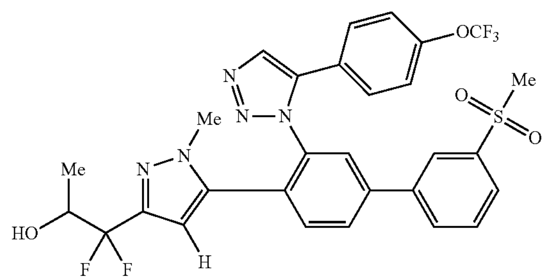 [SMILES: CC(O)C(F)(F)c1cc(-c2ccc(-c3cccc(S(C)(=O)=O)c3)cc2-n2nncc2-c2ccc(OC(F)(F)F)cc2)n(C)n1] | 1,1-difluoro-1-(1-methyl-5-(3'-(methylsulfonyl)-3-(5-(4-trifluoromethoxy)phenyl)-1H-1,2,3-triazol-1-yl)biphenyl-4-yl)-1H-pyrazol-3-yl)propan-2-ol |
| 2 | 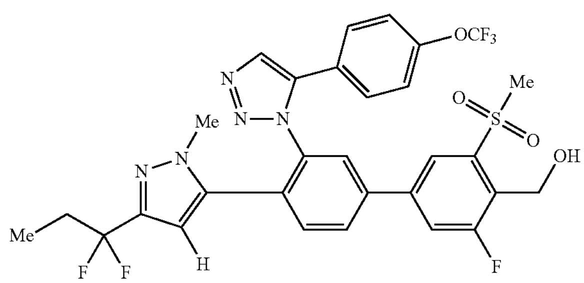 [SMILES: CCC(F)(F)c1cc(-c2ccc(-c3cc(F)c(CO)c(S(C)(=O)=O)c3)cc2-n2nncc2-c2ccc(OC(F)(F)F)cc2)n(C)n1] | (4'-(3-(1,1-difluoropropyl)-1-methyl-1H-pyrazol-5-yl)-3-fluoro-5-(methylsulfonyl)-3'-(5-(4-(trifluoromethoxy)phenyl)-1H-1,2,3-triazol-1-yl)biphenyl-4-yl)-1H-pyrazol |
| 3 | 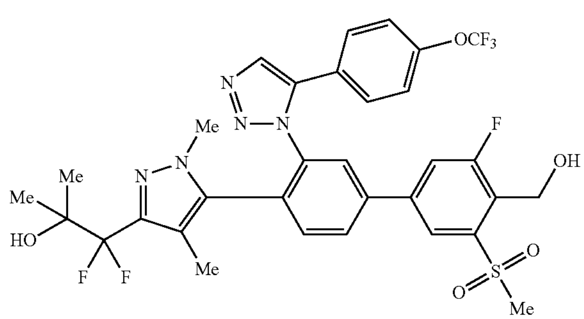 [SMILES: Cc1c(C(F)(F)C(C)(C)O)nn(C)c1-c1ccc(-c2cc(F)c(CO)c(S(C)(=O)=O)c2)cc1-n1nncc1-c1ccc(OC(F)(F)F)cc1] | 1,1-difluoro-1-(5-(3'-fluoro-4'-(hydroxymethyl)-5'-(methylsulfonyl)-3-(5-(4-(trifluoromethoxy)phenyl)-1H-1,2,3-triazol-1-yl)biphenyl-4-yl)-1-methyl-IH-pyrazol-3-yl)-2-methylpropan-2-ol |
| 4 | 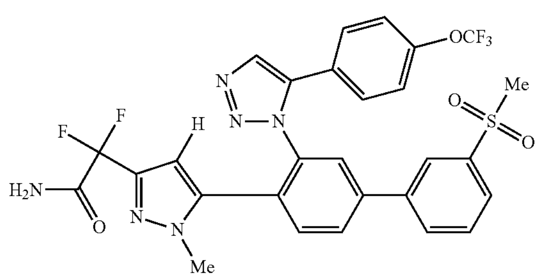 [SMILES: Cn1nc(C(F)(F)C(N)=O)cc1-c1ccc(-c2cccc(S(C)(=O)=O)c2)cc1-n1nncc1-c1ccc(OC(F)(F)F)cc1] | 2,2-difluoro-2-(1-methyl-5-(3'-(methylsulfonyl)-3-(5-(4-trifluoromethoxy)phenyl)-1H-1,2,3-triazol-1-yl)biphenyl-4-yl)-1H-pyrazol-3-yl)acetamide |

-continued

| Ex # | Structure | Name |
|---|---|---|
| 5 | 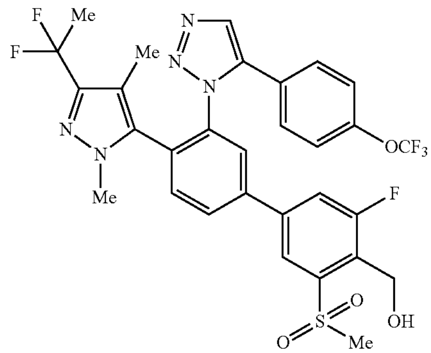 [SMILES: Cc1c(C(C)(F)F)nn(C)c1-c1ccc(-c2cc(F)c(CO)c(S(C)(=O)=O)c2)cc1-n1nncc1-c1ccc(OC(F)(F)F)cc1] | ((4'-(3-(1,1-difluoroethyl)-1,4-dimethyl-1H-pyrazol-5-yl)-3-fluoro-5-(methylsulfonyl)-3'-(5-(4-trifluoromethoxy)phenyl)-1H-1,2,3-triazol-1-yl)biphenyl-4-yl)methanol |
| 6 | 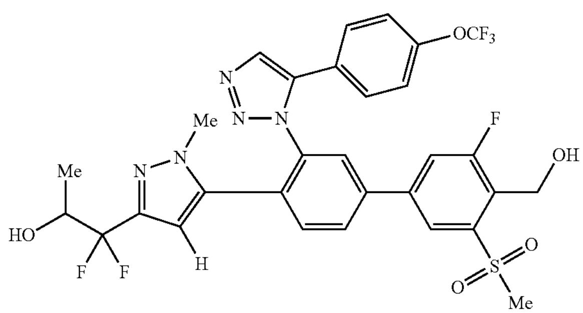 [SMILES: CC(O)C(F)(F)c1cc(-c2ccc(-c3cc(F)c(CO)c(S(C)(=O)=O)c3)cc2-n2nncc2-c2ccc(OC(F)(F)F)cc2)n(C)n1] | 1,1-difluoro-1-(5-(3'-fluoro-4'-(hydroxymethyl)-5'-(methylsulfonyl)-3-(5-(4-(trifluoromethoxy)phenyl)-1H-1,2,3-triazol-1-yl)biphenyl-4-yl)-1-methyl-1H-pyrazol-3-yl)propan-2-ol |
| 7 | 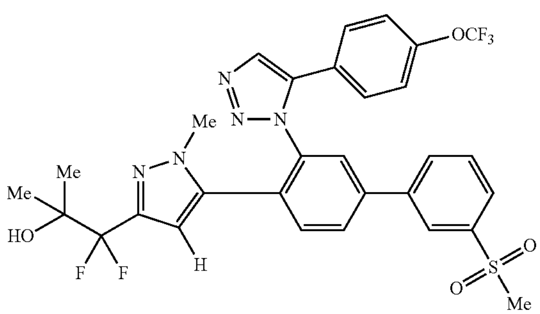 [SMILES: Cn1nc(C(F)(F)C(C)(C)O)cc1-c1ccc(-c2cccc(S(C)(=O)=O)c2)cc1-n1nncc1-c1ccc(OC(F)(F)F)cc1] | 1,1-difluoro-2-methyl-1-(1-methyl-5-3'-(methylsulfonyl)-3-(5-(4-(trifluoromethoxy)phenyl)-1H-1,2,3-triazol-1-yl)biphenyl-4-yl)-1H-pyrazol-3-yl)propan-2-ol |
| 8 | 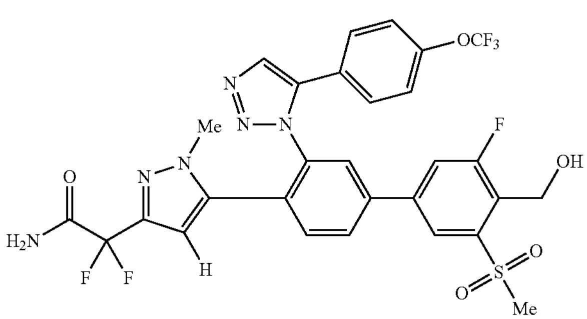 [SMILES: Cn1nc(C(F)(F)C(N)=O)cc1-c1ccc(-c2cc(F)c(CO)c(S(C)(=O)=O)c2)cc1-n1nncc1-c1ccc(OC(F)(F)F)cc1] | 2,2-difluoro-2-(5-(3'-fluoro-4'-(hydroxymethyl)-5'-(methylsulfonyl)-3-(5-(4-(trifluoromethoxy)phenyl)-1H-1,2,3-triazol-1-yl)biphenyl-4-yl)-1-methyl-1H-pyrazol-3-yl)acetamide |

-continued

| Ex # | Structure | Name |
|---|---|---|
| 9 | 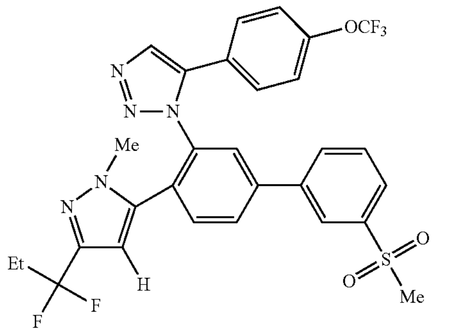 [SMILES: CCC(F)(F)c1cc(-c2ccc(-c3cccc(S(C)(=O)=O)c3)cc2-n2nncc2-c2ccc(OC(F)(F)F)cc2)n(C)n1] | 1-(4-(3-(1,1-difluoropropyl)-1-methyl-1H-pyrazol-5-yl)-3'-methylsulfonyl)biphenyl-3-yl)-5-(4-(trifluoromethoxy)phenyl)-1H-1,2,3-triazole |
| 10 | 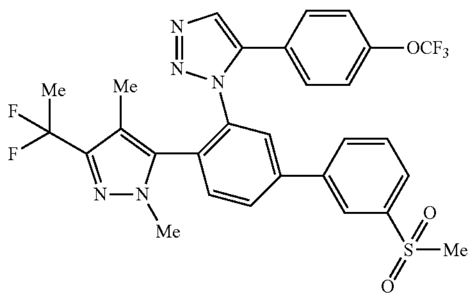 [SMILES: Cc1c(C(C)(F)F)nn(C)c1-c1ccc(-c2cccc(S(C)(=O)=O)c2)cc1-n1nncc1-c1ccc(OC(F)(F)F)cc1] | 1-(4-(3-(1,1-difluoroethyl)-1,4-dimethyl-1H-pyrazol-5-yl)-3'-(methylsulfonyl)biphenyl-3-yl)-5-(4-trifluoromethoxy)phenyl)-1H-1,2,3-triazole |
| 11 | 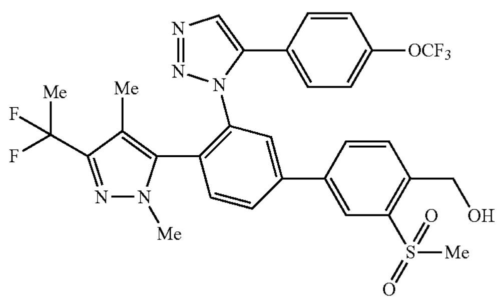 [SMILES: Cc1c(C(C)(F)F)nn(C)c1-c1ccc(-c2ccc(CO)c(S(C)(=O)=O)c2)cc1-n1nncc1-c1ccc(OC(F)(F)F)cc1] | (4'-(3-(1,1-difluoroethyl)-1,4-dimethyl-1H-pyrazol-5-yl)-3-(methylsulfonyl)-3'-(5-(4-(trifluoromethoxy)phenyl)-1H-1,2,3-triazol-1-yl)biphenyl-4-yl)methanol |
| 12 | 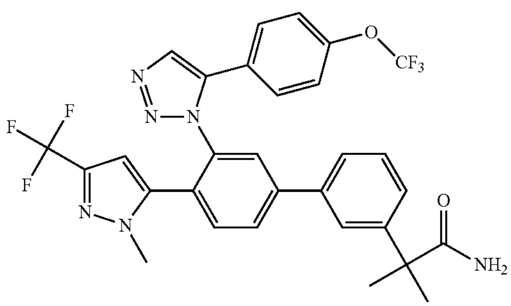 [SMILES: Cn1nc(C(F)(F)F)cc1-c1ccc(-c2cccc(C(C)(C)C(N)=O)c2)cc1-n1nncc1-c1ccc(OC(F)(F)F)cc1] | 2-methyl-2-{4'-[1-methyl-3-(trifluoromethyl)-1H-pyrazol-5-yl]-3'-(5-{4-[(trifluoromethyl)oxy]phenyl}1H-1,2,3-triazol-1-yl)biphenyl-3-yl}propanamide |
| 13 | 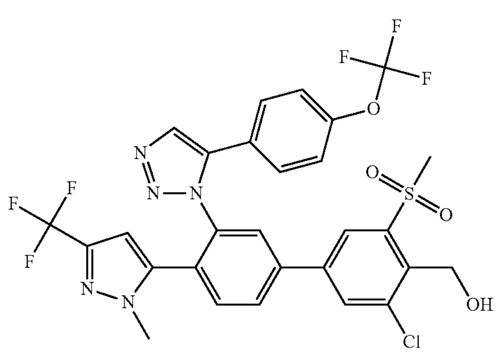 | [3-chloro-5-(methylsulfonyl)-4'-[1-methyl-3-(trifluoromethyl)-1H-pyrazol-5-yl]-3'-(5-{4-[(trifluoromethyl)oxy]phenyl}-1H-1,2,3-triazol-1-yl)biphenyl-4-yl]methanol |

| Ex # | Structure | Name |
|---|---|---|
| 14 | 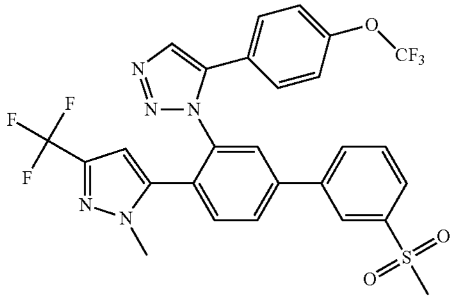 [SMILES: Cn1nc(C(F)(F)F)cc1-c1ccc(-c2cccc(S(C)(=O)=O)c2)cc1-n1nncc1-c1ccc(OC(F)(F)F)cc1] | 1-{3'-(methylsulfonyl)-4-[1-methyl-3-(trifluoromethyl)-1H-pyrazol-5-yl]biphenyl-3-yl}-5-{4-[(trifluoromethyl)oxy]phenyl}-1H-1,2,3-triazole |
| 15 | 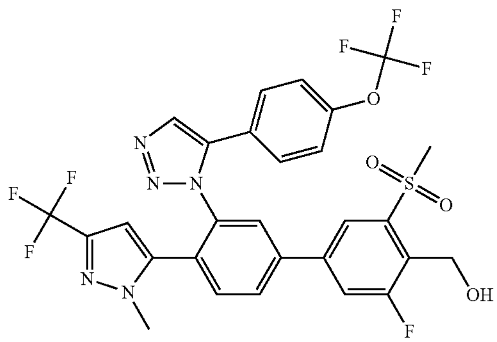 [SMILES: Cn1nc(C(F)(F)F)cc1-c1ccc(-c2cc(F)c(CO)c(S(C)(=O)=O)c2)cc1-n1nncc1-c1ccc(OC(F)(F)F)cc1] | (3-fluoro-4'-(1-methyl-3-(trifluoromethyl)-1H-pyrazol-5-yl)-5-methylsulfonyl)-3'-(5-(4-(trifluoromethoxy)phenyl)-1H-1,2,3-triazol-1-yl)biphenyl-4-yl)methanol |
| 16 | 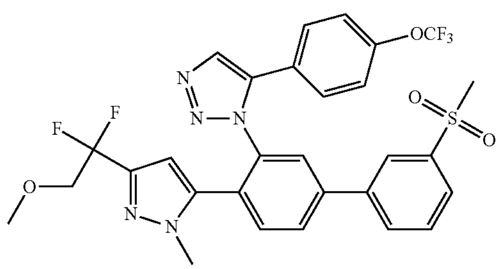 [SMILES: COCC(F)(F)c1cc(-c2ccc(-c3cccc(S(C)(=O)=O)c3)cc2-n2nncc2-c2ccc(OC(F)(F)F)cc2)n(C)n1] | 1-[4-{3-[1,1-difluoro-2-(methyloxy)ethyl]-1-methyl-1H-pyrazol-5-yl}3'-(methylsulfonyl)biphenyl-3-yl]-5-{4-[(trifluoromethyl)oxy]phenyl}-1H-1,2,3-triazole |
| 17 | 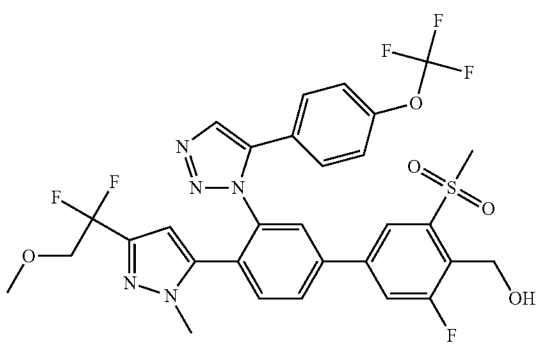 [SMILES: COCC(F)(F)c1cc(-c2ccc(-c3cc(F)c(CO)c(S(C)(=O)=O)c3)cc2-n2nncc2-c2ccc(OC(F)(F)F)cc2)n(C)n1] | [4'-{3-[1,1-difluoro-2-methyloxy)ethyl]-1-methyl-1H-pyrazol-5-yl}-3-fluoro-5-(methylsulfonyl)-3'-(5-{4-[(trifluoromethyl)oxy]phenyl}-1H-1,2,3-triazol-1-yl)biphenyl-4-yl]methanol |
| 18 | 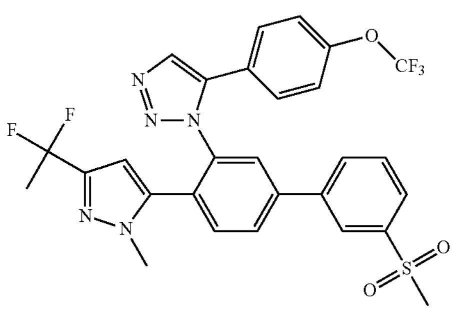 | 1-{4-[3-(1,1-difluoroethyl)-1-methyl-1H-pyrazol-5-yl]-3'-(methylsulfonyl)bipheny-3-yl}-5-{4-[(trifluoromethyl)oxy]phenyl}-1H-1,2,3-triazole |

| Ex # | Structure | Name |
|---|---|---|
| 19 | 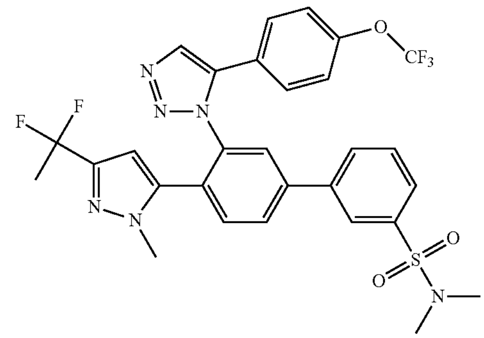 [SMILES: CN(C)S(=O)(=O)c1cccc(-c2ccc(-c3cc(C(C)(F)F)nn3C)c(-n3nncc3-c3ccc(OC(F)(F)F)cc3)c2)c1] | 4'-[3-(1,1-difluoroethyl)-1-methyl-1H-pyrazol-5-yl]-N,N-dimethyl-3'-(5-{4-[(trifluoromethyl)oxy]phenyl}-1H-1,2,3-triazol-1-yl)biphenyl-3-sulfonamide |
| 20 | 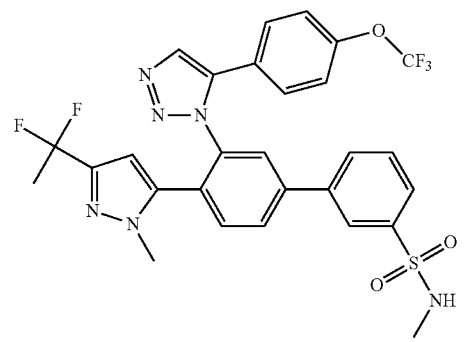 [SMILES: CNS(=O)(=O)c1cccc(-c2ccc(-c3cc(C(C)(F)F)nn3C)c(-n3nncc3-c3ccc(OC(F)(F)F)cc3)c2)c1] | 4'-[3-(1,1-difluoroethyl)-1-methyl-1H-pyrazol-5-yl]-N-methyl-3'-(5-{4-[(trifluoromethyl)oxy]phenyl}-1H-1,2,3-triazol-1-yl)biphenyl-3-sulfonamide |
| 21 | 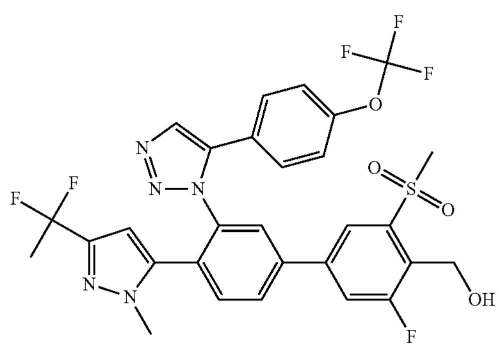 [SMILES: Cn1nc(C(C)(F)F)cc1-c1ccc(-c2cc(F)c(CO)c(S(C)(=O)=O)c2)cc1-n1nncc1-c1ccc(OC(F)(F)F)cc1] | {4'-[3-(1,1-difluoroethyl)-1-methyl-1H-pyrazol-5-yl]-3-fluoro-5-methylsulfonyl)-3'-(5-{4-trifluoromethyl)oxy]phenyl}-1H-1,2,3-triazol-1-yl)biphenyl-4-yl}methanol |
| 22 | 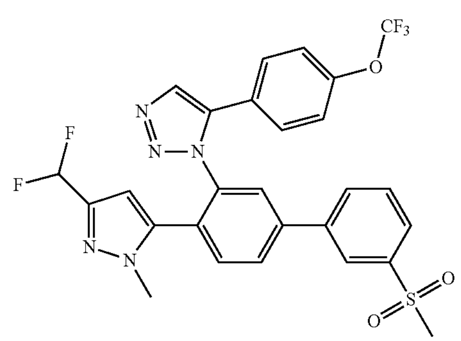 [SMILES: Cn1nc(C(F)F)cc1-c1ccc(-c2cccc(S(C)(=O)=O)c2)cc1-n1nncc1-c1ccc(OC(F)(F)F)cc1] | 1-{4-[3-(difluoromethyl)-1-methyl-1H-pyrazol-5-yl-3'-(methylsulfonyl)biphenyl-3-yl}-5-{4-[(trifluoromethyl)oxy]phenyl}-1H-1,2,3-triazole |

| Ex # | Structure | Name |
|---|---|---|
| 23 | 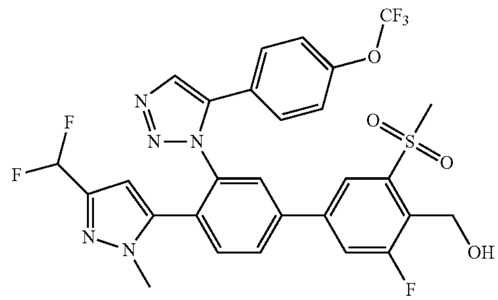 [SMILES: Cn1nc(C(F)F)cc1-c1ccc(-c2cc(F)c(CO)c(S(C)(=O)=O)c2)cc1-n1nncc1-c1ccc(OC(F)(F)F)cc1] | {4'-[3-(difluoromethyl)-1-methyl-1H-pyrazol-5-yl]-3-fluoro-5-methylsulfonyl)-3'-(5-{4-[(trifluoromethyl)oxy]phenyl}-1H-1,2,3-triazol-1-yl)biphenyl-4-yl}methanol |
| 24 | 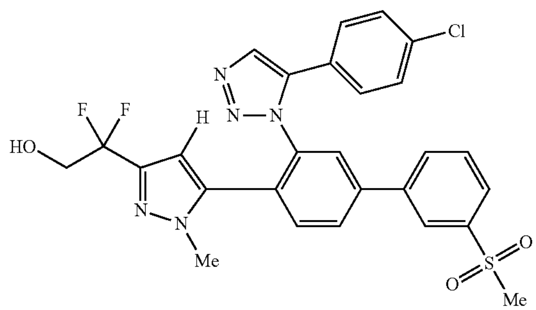 [SMILES: Cn1nc(C(F)(F)CO)cc1-c1ccc(-c2cccc(S(C)(=O)=O)c2)cc1-n1nncc1-c1ccc(Cl)cc1] | 2-(5-(3-(5-(4-chlorophenyl)-1H-1,2,3-triazol-1-yl)-3'-(methylsulfonyl)-[1,1'-biphenyl]-4-yl)-1-methyl-1H-pyrazol-3-yl)-2,2-difluoroethanol |
| 25 | 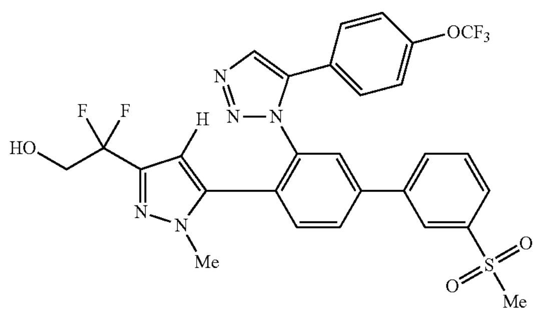 [SMILES: Cn1nc(C(F)(F)CO)cc1-c1ccc(-c2cccc(S(C)(=O)=O)c2)cc1-n1nncc1-c1ccc(OC(F)(F)F)cc1] | 2,2-difluoro-2-(1-methyl-5-(3'-(methylsulfonyl)-3-(5-(4-(trifluoromethoxy)phenyl)-1H-1,2,3-triazol-1-yl)-1,1'-biphenyl]-4-yl)-1H-pyrazol-3-yl)ethanol |
| 26 | 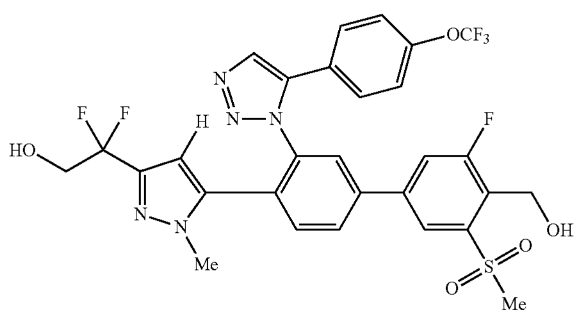 [SMILES: Cn1nc(C(F)(F)CO)cc1-c1ccc(-c2cc(F)c(CO)c(S(C)(=O)=O)c2)cc1-n1nncc1-c1ccc(OC(F)(F)F)cc1] | 2,2-difluoro-2-(5-(3'-fluoro-4'-(hydroxymethyl)-5'-(methylsulfonyl)-3-(5-(4-(trifluoromethoxy)phenyl)-1H-1,2,3-triazol-1-yl)-[1,1'-biphenyl]-4-yl)-1-methyl-1H-pyrazol-3-yl)ethanol |
| 27 | 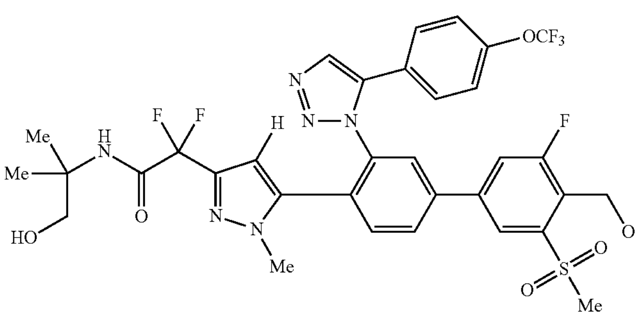 [SMILES: Cn1nc(C(F)(F)C(=O)NC(C)(C)CO)cc1-c1ccc(-c2cc(F)c(CO)c(S(C)(=O)=O)c2)cc1-n1nncc1-c1ccc(OC(F)(F)F)cc1] | 2,2-difluoro-2-(5-(3'-fluoro-4'-(hydroxymethyl)-5'-(methylsulfonyl)-3-(5-(4-(trifluoromethoxy)phenyl)-1H-1,2,3-triazol-1-yl)-[1,1'-biphenyl]-4-yl)-1-methyl-1H-pyrazol-3-yl)-N-(1-hydroxy-2-methylpropan-2-yl)acetamide |

-continued

| Ex # | Structure | Name |
|---|---|---|
| 28 | 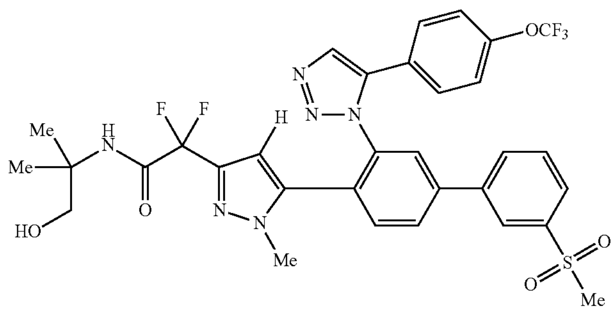 [SMILES: Cn1nc(C(F)(F)C(=O)NC(C)(C)CO)cc1-c1ccc(-c2cccc(S(C)(=O)=O)c2)cc1-n1nncc1-c1ccc(OC(F)(F)F)cc1] | 2,2-difluoro-N-(1-hydroxy-2-(methylsulfonyl)-3-(5-(4-trifluoromethoxy)phenyl)-1H-1,2,3-triazol-1-yl)-[1,1'-biphenyl]-4-yl)-1H-pyrazol-3-yl)acetamide |
| 29 | 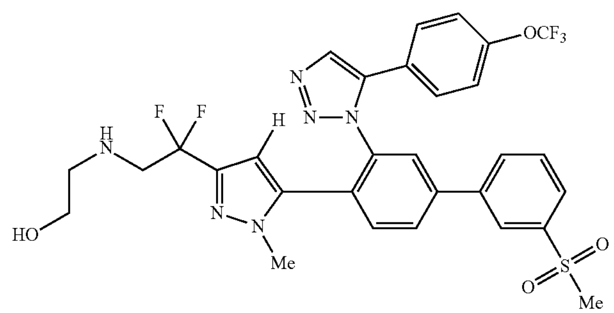 [SMILES: Cn1nc(C(F)(F)CNCCO)cc1-c1ccc(-c2cccc(S(C)(=O)=O)c2)cc1-n1nncc1-c1ccc(OC(F)(F)F)cc1] | 2-((2,2-difluoro-2-(1-methyl-5-(3'-(methylsulfonyl)-3-(5-(4-trifluoromethoxy)phenyl)-1H-1,2,3-triazol-1-yl)-[1,1'-biphenyl]-4-yl)-1H-pyrazol-3-yl)ethyl)amino)ethanol |
| 30 | 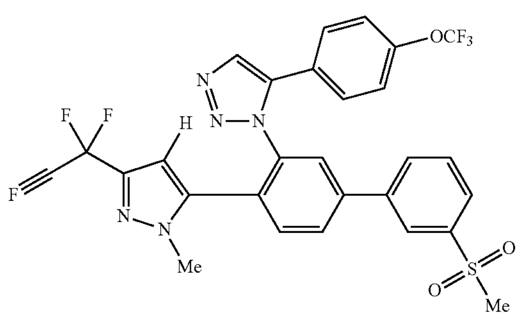 | 2,2-difluoro-2-(1-methyl-5-(3'-(methylsulfonyl)-3-(5-(4-trifluoromethoxy)phenyl)-1H-1,2,3-triazol-1-yl)-[1,1'-biphenyl]-4-yl)-1H-pyrazol-3-yl)acetonitrile |
| 31 | 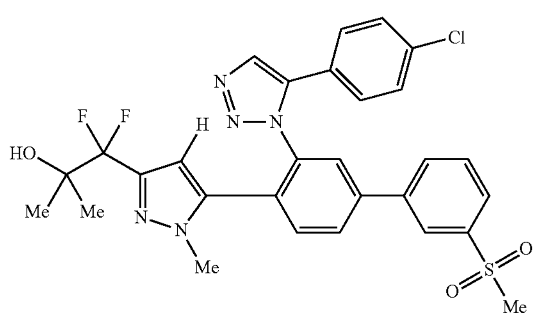 [SMILES: Cn1nc(C(F)(F)C(C)(C)O)cc1-c1ccc(-c2cccc(S(C)(=O)=O)c2)cc1-n1nncc1-c1ccc(Cl)cc1] | 1-(5-(3-(5-(4-chlorophenyl)-1H-1,2,3-triazol-1-yl)-3'-(methylsulfonyl)-[1,1'-biphenyl]-4-yl)-1-methyl-1H-pyrazol-3-yl)-1,1-difluoro-2-methylpropan-2-ol |
| 32 | 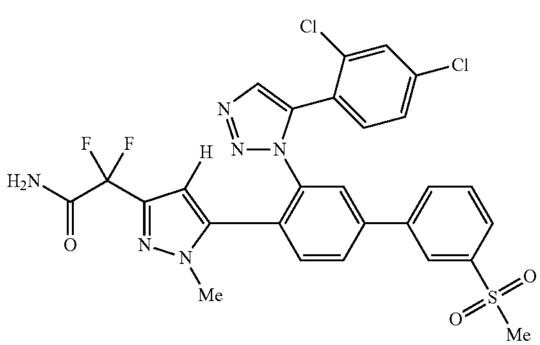 [SMILES: Cn1nc(C(F)(F)C(N)=O)cc1-c1ccc(-c2cccc(S(C)(=O)=O)c2)cc1-n1nncc1-c1ccc(Cl)cc1Cl] | 2-(5-(3-(5-(2,4-dichlorophenyl)-1H-1,2,3-triazol-1-yl)-3'-(methylsulfonyl)-[1,1'-biphenyl]-4-yl)-1-methyl-1H-pyrazol-3-yl)-2,2-difluoroacetamide |

-continued

| Ex # | Structure | Name |
|---|---|---|
| 33 | 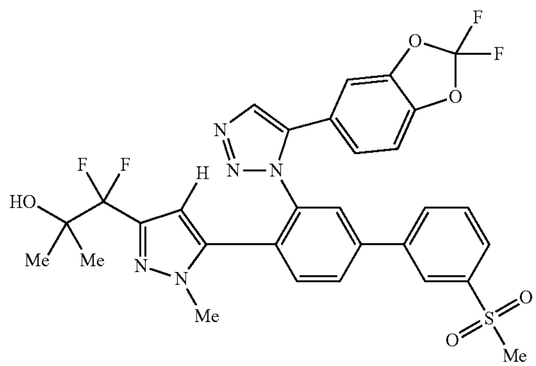 [SMILES: Cn1nc(C(F)(F)C(C)(C)O)cc1-c1ccc(-c2cccc(S(C)(=O)=O)c2)cc1-n1nncc1-c1ccc2c(c1)OC(F)(F)O2] | 1-(5-(3-(5-(2,2-difluorobenzo[d][1,3]dioxol-5-yl)-1H-1,2,3-triazol-1-yl)-3'-(methylsulfonyl)-[1,1'-biphenyl]-4-yl)-1-methyl-1H-pyrazol-3-yl)-1,1-difluoro-2-methylpropan-2-ol |
| 34 | 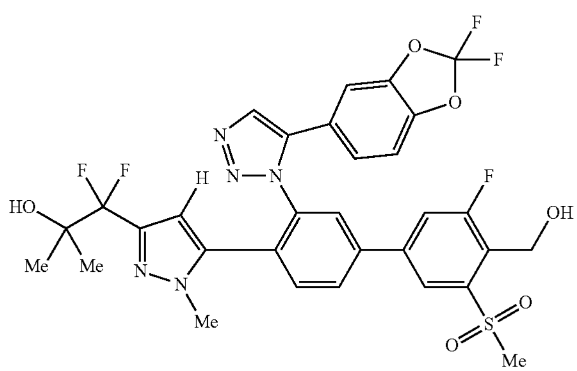 [SMILES: Cn1nc(C(F)(F)C(C)(C)O)cc1-c1ccc(-c2cc(F)c(CO)c(S(C)(=O)=O)c2)cc1-n1nncc1-c1ccc2c(c1)OC(F)(F)O2] | 1-(5-(3-(5-(2,2-difluorobenzo[d][1,3]dioxol-5-yl)-1H-1,2,3-triazol-1-yl)-3'-fluoro-4'-(hydroxymethyl)-5'-(methylsulfonyl)-[1,1'-biphenyl]-4-yl)-1-methyl-1H-pyrazol-3-yl)-1,1-difluoro-2-methylpropan-2-ol |
| 35 | 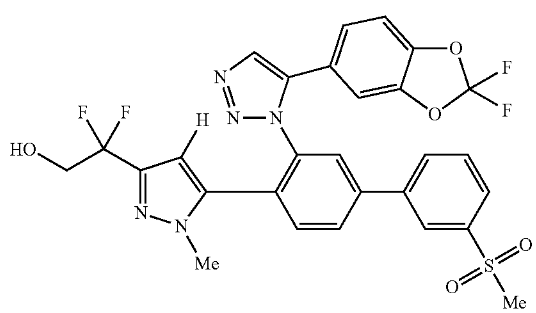 [SMILES: Cn1nc(C(F)(F)CO)cc1-c1ccc(-c2cccc(S(C)(=O)=O)c2)cc1-n1nncc1-c1ccc2c(c1)OC(F)(F)O2] | 2-(5-(3-(5-(2,2-difluorobenzo[d][1,3]dioxol-5-yl)-1H-1,2,3-triazol-1-yl)-3'-(methylsulfonyl)-[1,1'-biphenyl]-4-yl)-1-methyl-1H-pyrazol-3-yl)-2,2-difluoroethanol |
| 36 | 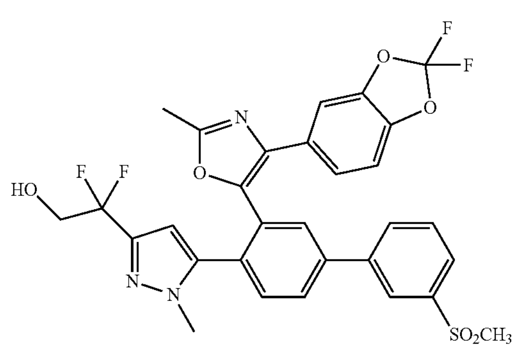 [SMILES: Cc1nc(-c2ccc3c(c2)OC(F)(F)O3)c(-c2cc(-c3cccc(S(C)(=O)=O)c3)ccc2-c2cc(C(F)(F)CO)nn2C)o1] | 2-(5-(3-(5-(2,2-difluorobenzo[d][1,3]dioxol-5-yl)-1H-(hydroxymethyl)-5'-(methylsulfonyl)-[1,1'-biphenyl]-4-yl)-1-methyl-1H-pyrazol-3-yl)-2,2-difluoroethanol |

-continued

| Ex # | Structure | Name |
|---|---|---|
| 37 | 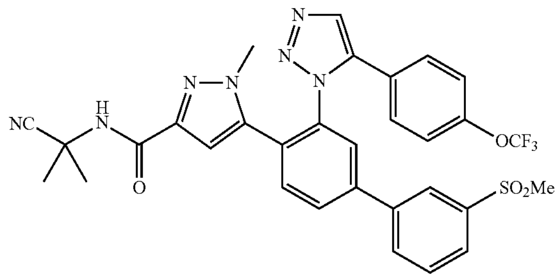 [SMILES: Cn1nc(C(=O)NC(C)(C)C#N)cc1-c1ccc(-c2cccc(S(C)(=O)=O)c2)cc1-n1nncc1-c1ccc(OC(F)(F)F)cc1] | N-(1-cyano-1-methylethyl)-1-methyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide |
| 38 | 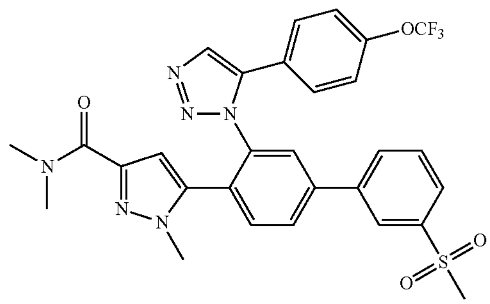 [SMILES: CN(C)C(=O)c1cc(-c2ccc(-c3cccc(S(C)(=O)=O)c3)cc2-n2nncc2-c2ccc(OC(F)(F)F)cc2)n(C)n1] | N,N,1-trimethyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide |
| 39 | 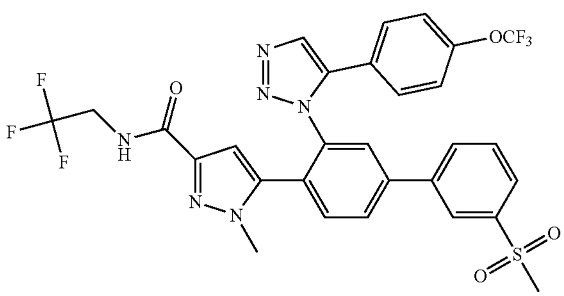 [SMILES: Cn1nc(C(=O)NCC(F)(F)F)cc1-c1ccc(-c2cccc(S(C)(=O)=O)c2)cc1-n1nncc1-c1ccc(OC(F)(F)F)cc1] | 1-methyl-5-[3'-(methylsulfonyl)-3-(5-{4-[(trifluoromethyl)oxy]phenyl}-1H-1,2,3-triazol-1-yl)biphenyl-4-yl]-N-(2,2,2-trifluoroethyl)-1H-pyrazole-3-carboxamide |
| 40 | 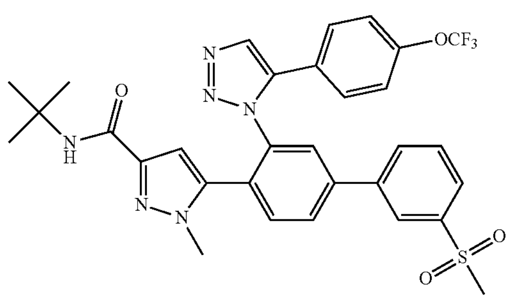 [SMILES: Cn1nc(C(=O)NC(C)(C)C)cc1-c1ccc(-c2cccc(S(C)(=O)=O)c2)cc1-n1nncc1-c1ccc(OC(F)(F)F)cc1] | N-(1,1-dimethylethyl)-1-methyl-5-[3'-(methylsulfonyl)-3-(5-{4-[(trifluoromethyl)oxy]phenyl}-1H-1,2,3-triazol-1-yl)biphenyl-4-yl]-1H-pyrazole-3-carboxamide |
| 45 | 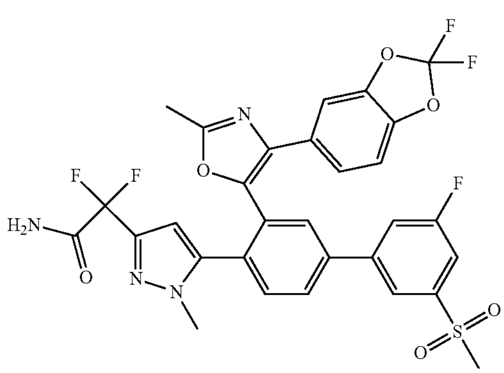 [SMILES: Cc1nc(-c2ccc3c(c2)OC(F)(F)O3)c(-c2cc(-c3cc(F)cc(S(C)(=O)=O)c3)ccc2-c2cc(C(F)(F)C(N)=O)nn2C)o1] | 2-(5-(3-(4-(2,2-difluorobenzo[d][1,3]dioxol-5-yl)-2-methyloxazol-5-yl)-3'-fluoro-5'-methylsulfonyl)biphenyl-4-yl)-1-methyl-1H-pyrazol-3-yl)-2,2-difluoroacetamide |

| Ex # | Structure | Name |
|---|---|---|
| 46 | 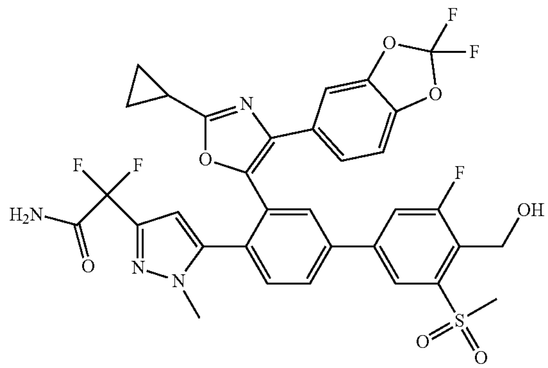 [SMILES: Cn1nc(C(F)(F)C(N)=O)cc1-c1ccc(-c2cc(F)c(CO)c(S(C)(=O)=O)c2)cc1-c1oc(C2CC2)nc1-c1ccc2c(c1)OC(F)(F)O2] | 2-(5-(3-(2-cyclopropyl-4-(2,2-difluorobenzo[d][1,3]dioxol-5-yl)oxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide |
| 47 | 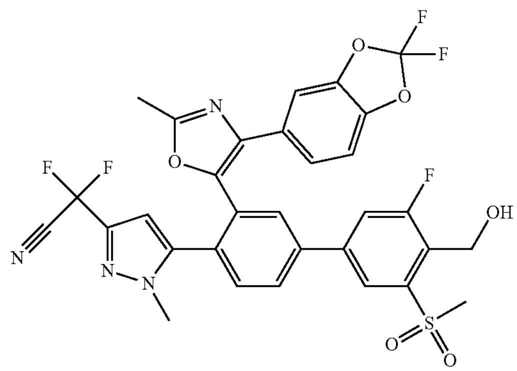 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C#N)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-methylsulfonyl)biphenyl-4-yl)-1-methyl-1H-pyrazol-3-yl)-2,2-difluoroacetonitrile |
| 48 | 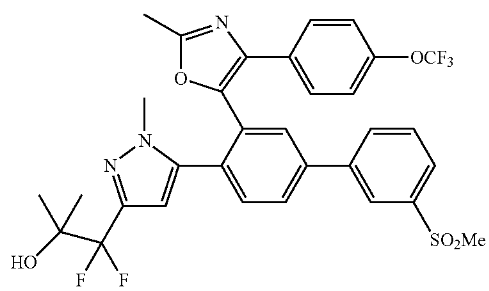 [SMILES: Cc1nc(-c2ccc(OC(F)(F)F)cc2)c(-c2cc(-c3cccc(S(C)(=O)=O)c3)ccc2-c2cc(C(F)(F)C(C)(C)O)nn2C)o1] | 1,1-difluoro-2-methyl-1-(1-methyl-5-(3-(2-methyl-4-(4-(trifluoromethoxy)phenyl)oxazol-5-yl)-3'-(methylsulfonyl)biphenyl-4-yl)-1H-pyrazol-3-yl)propan-2-ol |
| 49 | 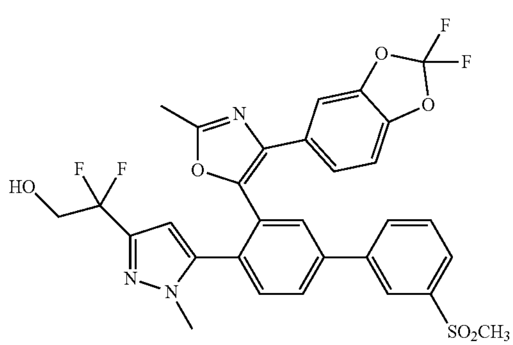 [SMILES: Cc1nc(-c2ccc3c(c2)OC(F)(F)O3)c(-c2cc(-c3cccc(S(C)(=O)=O)c3)ccc2-c2cc(C(F)(F)CO)nn2C)o1] | 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2,2-difluoroethanol |

| Ex # | Structure | Name |
| --- | --- | --- |
| 50 | 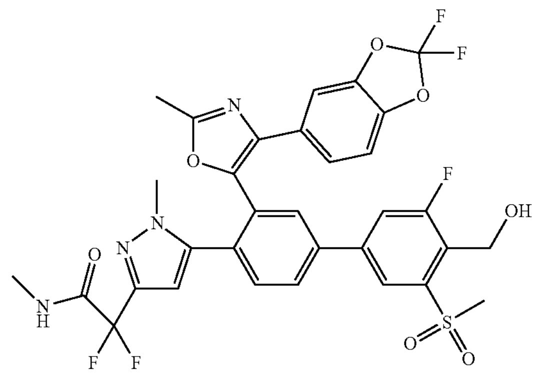 [SMILES: CNC(=O)C(F)(F)c1cc(-c2ccc(-c3cc(F)c(CO)c(S(C)(=O)=O)c3)cc2-c2oc(C)nc2-c2ccc3c(c2)OC(F)(F)O3)n(C)n1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide |
| 51 | 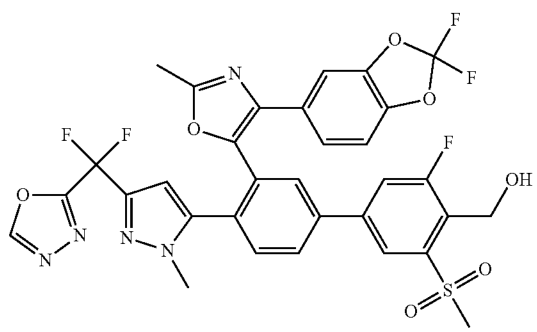 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)c3nnco3)nn2C)o1] | (4'(3-(difluoro(1,3,4-oxadiazol-2-yl)methyl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol |
| 52 | 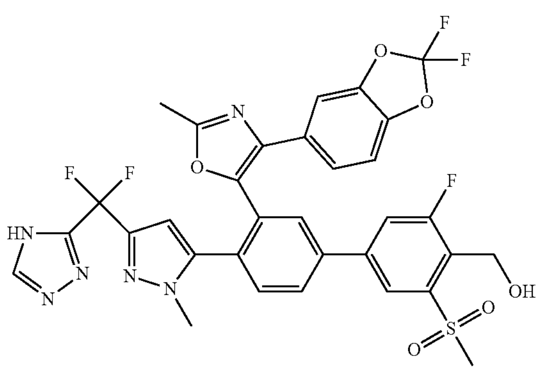 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)c3nnc[nH]3)nn2C)o1] | (4'-(3-(difluoro(4H-1,2,4-triazol-3-yl)methyl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol |
| 53 | 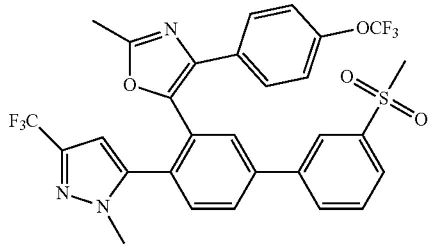 [SMILES: Cc1nc(-c2ccc(OC(F)(F)F)cc2)c(-c2cc(-c3cccc(S(C)(=O)=O)c3)ccc2-c2cc(C(F)(F)F)nn2C)o1] | 2-methyl-5-(4-(1-methyl-3-(trifluoromethyl)-1H-pyrazol-5-yl)-3'-(methylsulfonyl)biphenyl-3-yl)-4-(4-(trifluoromethoxy)phenyl)Oxazole |

-continued

| Ex # | Structure | Name |
|---|---|---|
| 54 | 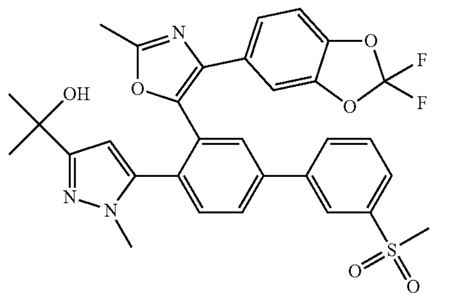 [SMILES: Cc1nc(-c2ccc3c(c2)OC(F)(F)O3)c(-c2cc(-c3cccc(S(C)(=O)=O)c3)ccc2-c2cc(C(C)(C)O)nn2C)o1] | 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)propan-2-ol |
| 55 | 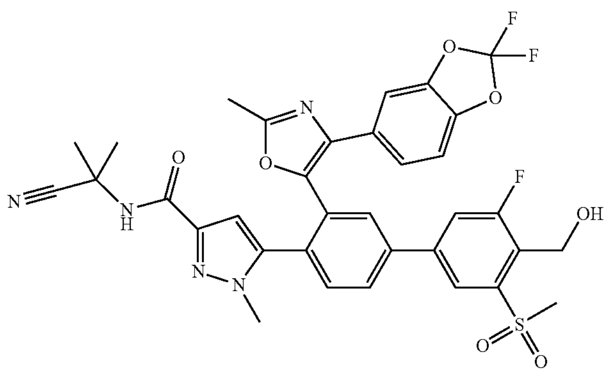 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NC(C)(C)C#N)nn2C)o1] | N-(2-cyanopropan-2-yl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazole-3-carboxamide |
| 56 | 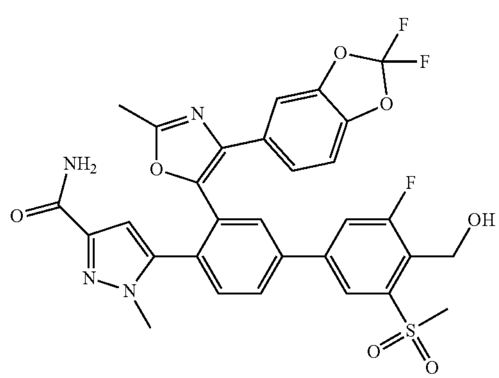 [SMILES: Cc1nc(-c2ccc3c(c2)OC(F)(F)O3)c(-c2cc(-c3cc(F)c(CO)c(S(C)(=O)=O)c3)ccc2-c2cc(C(N)=O)nn2C)o1] | 5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazole-3-carboxamide |
| 57 | 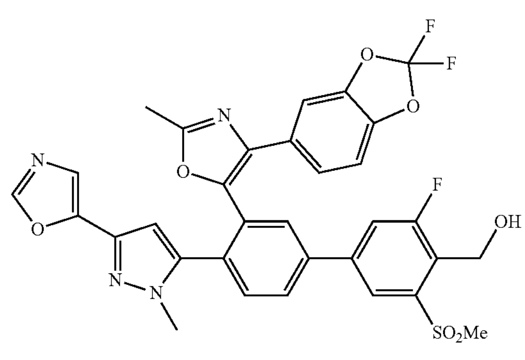 [SMILES: Cc1nc(-c2ccc3c(c2)OC(F)(F)O3)c(-c2cc(-c3cc(F)c(CO)c(S(C)(=O)=O)c3)ccc2-c2cc(-c3cnco3)nn2C)o1] | (3'-(4-(42,2-difluorobenzo[d][1,3]dioxol-5-yl)-2-methyloxazol-5-yl)-3-fluoro-4'-(1-methyl-3-(oxazol-5-yl)-1H-pyrazol-5-yl)-5-(methylsulfonyl)-[1,1'-biphenyl]-4-yl)methanol |

| Ex # | Structure | Name |
|---|---|---|
| 58 | 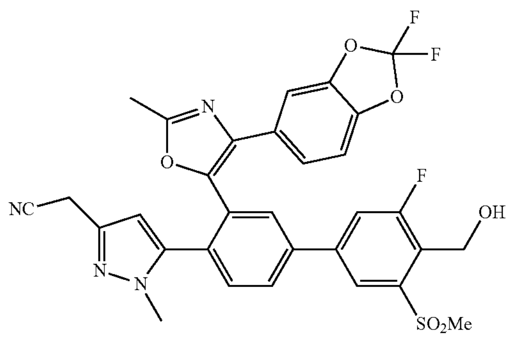 [SMILES: Cc1nc(-c2ccc3c(c2)OC(F)(F)O3)c(-c2cc(-c3cc(F)c(CO)c(S(C)(=O)=O)c3)ccc2-c2cc(CC#N)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)acetonitrile |
| 59 | 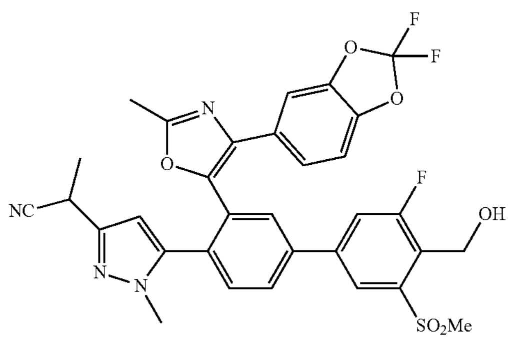 [SMILES: Cc1nc(-c2ccc3c(c2)OC(F)(F)O3)c(-c2cc(-c3cc(F)c(CO)c(S(C)(=O)=O)c3)ccc2-c2cc(C(C)C#N)nn2C)o1] | (S)-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)propanenitrile |
| 60 | 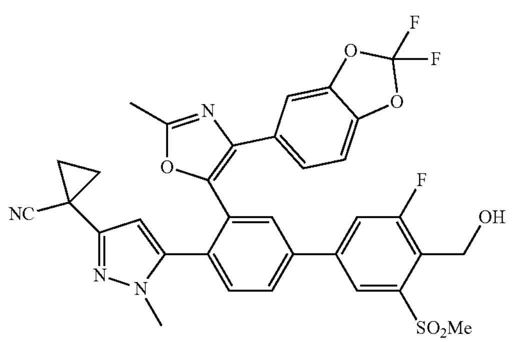 [SMILES: Cc1nc(-c2ccc3c(c2)OC(F)(F)O3)c(-c2cc(-c3cc(F)c(CO)c(S(C)(=O)=O)c3)ccc2-c2cc(C3(C#N)CC3)nn2C)o1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)cyclopropanecarbonitrile |
| 61 | 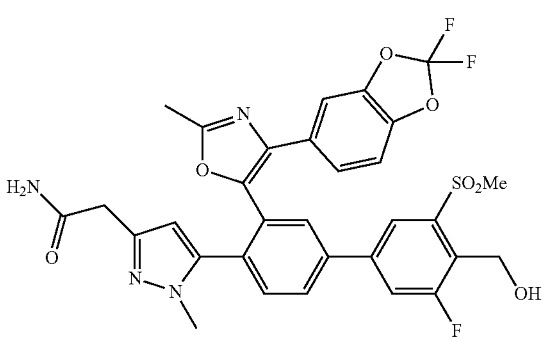 [SMILES: Cc1nc(-c2ccc3c(c2)OC(F)(F)O3)c(-c2cc(-c3cc(F)c(CO)c(S(C)(=O)=O)c3)ccc2-c2cc(CC(N)=O)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)acetamide |

| Ex # | Structure | Name |
|---|---|---|
| 62 | 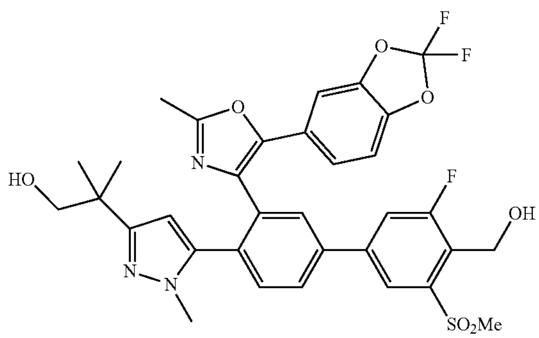 [SMILES: Cc1nc(-c2cc(-c3cc(F)c(CO)c(S(C)(=O)=O)c3)ccc2-c2cc(C(C)(C)CO)nn2C)c(-c2ccc3c(c2)OC(F)(F)O3)o1] | 2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2-methylpropan-1-ol |
| 63 | 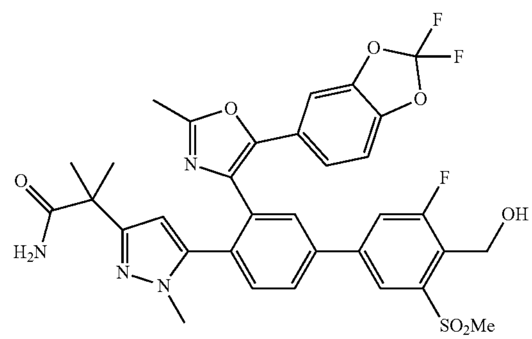 [SMILES: Cc1nc(-c2cc(-c3cc(F)c(CO)c(S(C)(=O)=O)c3)ccc2-c2cc(C(C)(C)C(N)=O)nn2C)c(-c2ccc3c(c2)OC(F)(F)O3)o1] | 2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2-methylpropanamide |
| 64 | 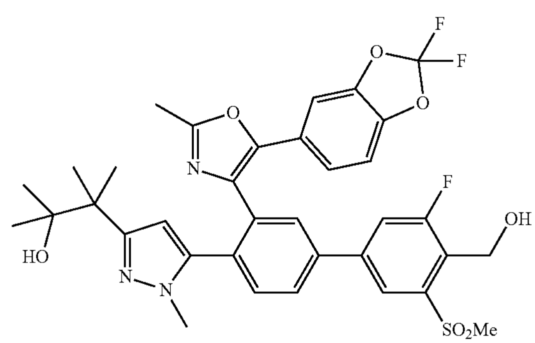 [SMILES: Cc1nc(-c2cc(-c3cc(F)c(CO)c(S(C)(=O)=O)c3)ccc2-c2cc(C(C)(C)C(C)(C)O)nn2C)c(-c2ccc3c(c2)OC(F)(F)O3)o1] | 3-(5-(3-(5-(2,2-difluorobenzo[d][1,3]dioxol-5-yl)-2-methyloxazol-4-yl)-3'-fluoro-4'-(hydroxymethyl)-5'-methylsulfonyl)biphenyl-4-yl)-1-methyl-1H-pyrazol-3-yl)-2,3-dimethylbutan-2-ol |
| 65 | 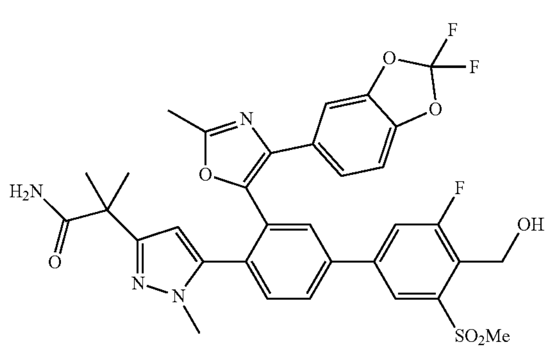 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C(N)=O)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-methylsulfonyl)biphenyl-4-yl)-1-methyl-1H-pyrazol-3-yl)-2-methylpropanamide |

-continued

| Ex # | Structure | Name |
|---|---|---|
| 66 | 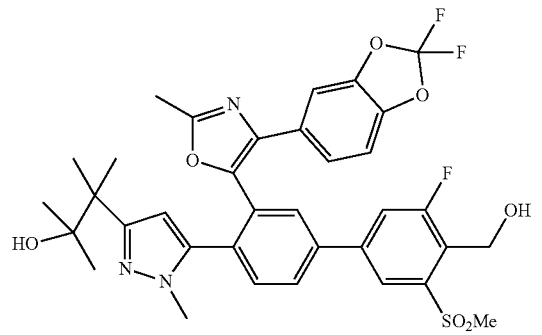 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C(C)(C)O)nn2C)o1] | 3-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,3-dimethylbutan-2-ol |
| 67 | 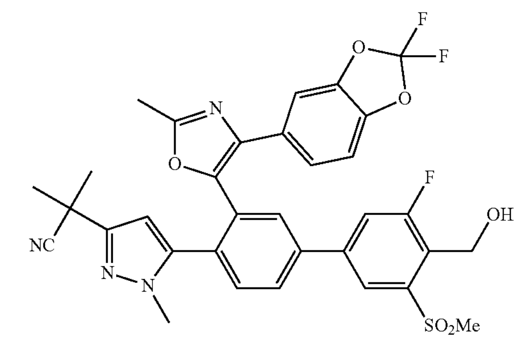 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C#N)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2-methylpropanenitrile |
| 68 | 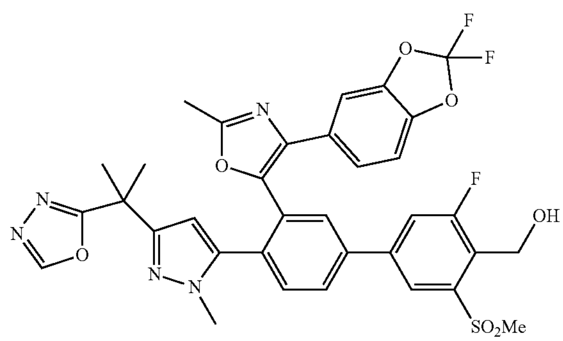 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)c3nnco3)nn2C)o1] | (4'-(3-(2-(1,3,4-oxadiazol-2-yl)propan-2-yl)-1-methyl-1H-pyrazol-5-yl)-3'-(4-(2,2-difluorobenzo[d][1,3]dioxol-5-yl)-2-methyloxazol-5-yl)-3-fluoro-5-(methylsulfonyl)biphenyl-4-yl)methanol |
| 69 | 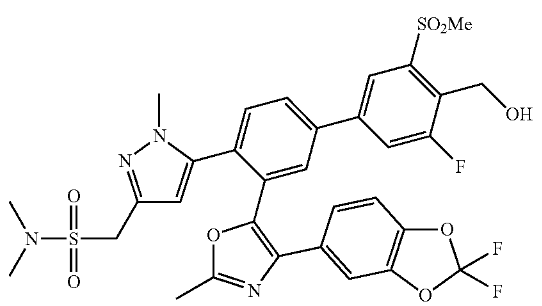 [SMILES: Cc1nc(-c2ccc3c(c2)OC(F)(F)O3)c(-c2cc(-c3cc(F)c(CO)c(S(C)(=O)=O)c3)ccc2-c2cc(CS(=O)(=O)N(C)C)nn2C)o1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-N,N-dimethylmethanesulfonamide |
| 70 | 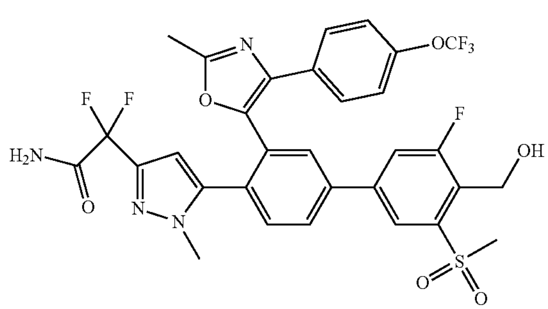 [SMILES: Cc1nc(-c2ccc(OC(F)(F)F)cc2)c(-c2cc(-c3cc(F)c(CO)c(S(C)(=O)=O)c3)ccc2-c2cc(C(F)(F)C(N)=O)nn2C)o1] | 2,2-difluoro-2-(5-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1-methyl-1H-pyrazol-3-yl)acetamide |

| Ex # | Structure | Name |
|---|---|---|
| 71 | 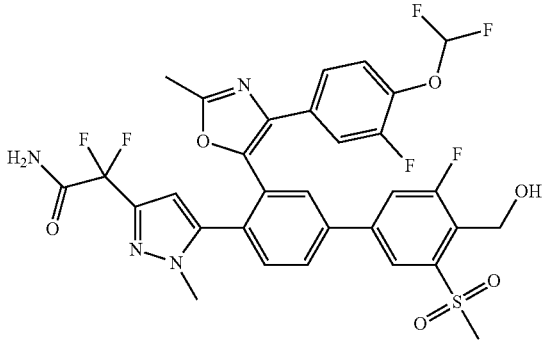 [SMILES: Cc1nc(-c2ccc(OC(F)F)c(F)c2)c(-c2cc(-c3cc(F)c(CO)c(S(C)(=O)=O)c3)ccc2-c2cc(C(F)(F)C(N)=O)nn2C)o1] | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide |
| 72 | 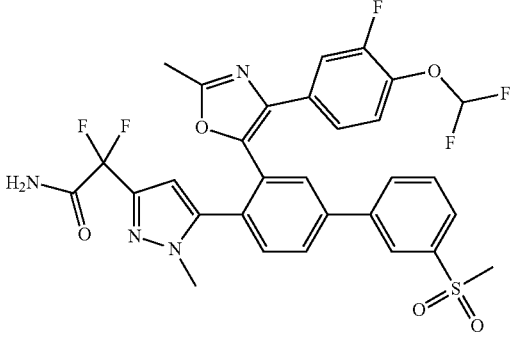 [SMILES: Cc1nc(-c2ccc(OC(F)F)c(F)c2)c(-c2cc(-c3cccc(S(C)(=O)=O)c3)ccc2-c2cc(C(F)(F)C(N)=O)nn2C)o1] | 2-(5-(3-(4-(4-(difluoromethoxy)-3-fluorophenyl)-2-methyloxazol-5-yl)-3'-methylsulfonyl)biphenyl-4-yl)-1-methyl-1H-pyrazol-3-yl)-2,2-difluoroacetamide |
| 73 | 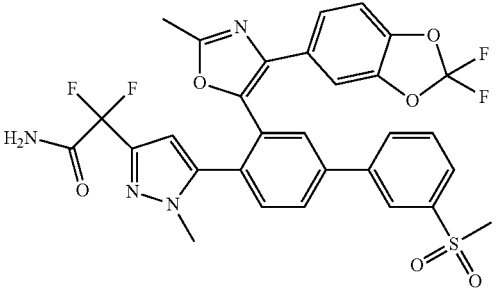 [SMILES: Cc1nc(-c2ccc3c(c2)OC(F)(F)O3)c(-c2cc(-c3cccc(S(C)(=O)=O)c3)ccc2-c2cc(C(F)(F)C(N)=O)nn2C)o1] | 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2,2-difluoroacetamide |
| 74 | 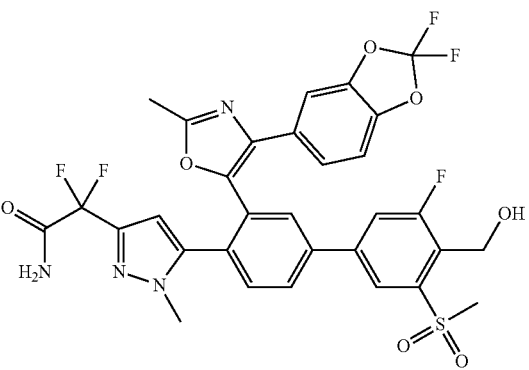 | 2-(5-(3-(4-(2,2-difluorobenzo[d][1,3]dioxol-5-yl)-2-methyloxazol-5-yl)-3'-fluoro-4'-(hydroxymethyl)-5'-methylsulfonyl)biphenyl-4-yl)-1-methyl-1H-pyrazol-3-yl)-2,2-difluoroacetamide |

| Ex # | Structure | Name |
|---|---|---|
| 75 | 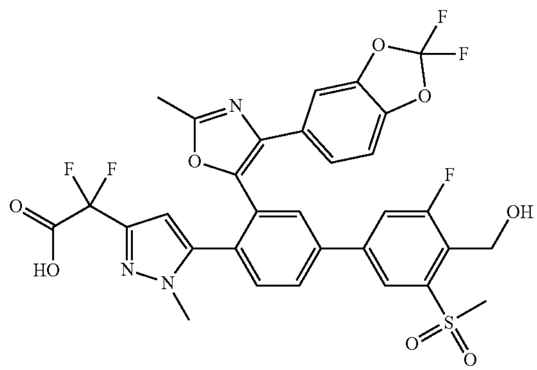 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)O)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroaceticacid |
| 76 | 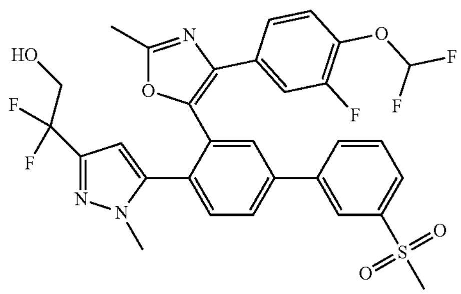 [SMILES: Cc1nc(-c2ccc(OC(F)F)c(F)c2)c(-c2cc(-c3cccc(S(C)(=O)=O)c3)ccc2-c2cc(C(F)(F)CO)nn2C)o1] | 2-(5-(3-(4-(4-(difluoromethoxy)-3-fluorophenyl)-2-methyloxazol-5-yl)-3'-(methylsulfonyl)biphenyl-4-yl)-1-methyl-1H-pyrazol-3-yl)-2,2-difluoroethanol |
| 77 | 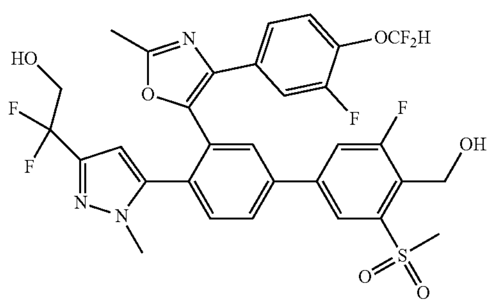 | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroethanol |
| 78 | 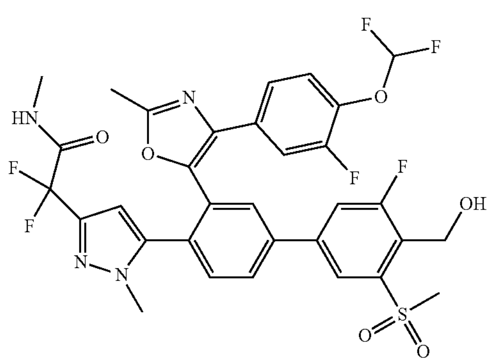 [SMILES: CNC(=O)C(F)(F)c1cc(-c2ccc(-c3cc(F)c(CO)c(S(C)(=O)=O)c3)cc2-c2oc(C)nc2-c2ccc(OC(F)F)c(F)c2)n(C)n1] | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide |

-continued

| Ex # | Structure | Name |
|---|---|---|
| 79 | 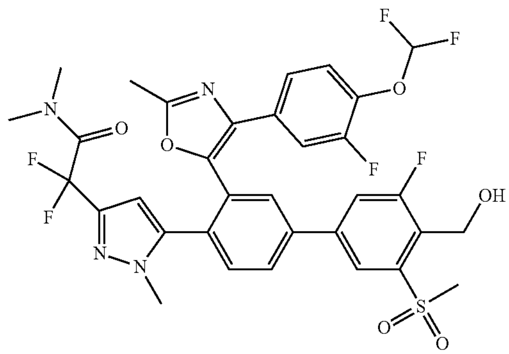 [SMILES: Cc1nc(-c2ccc(OC(F)F)c(F)c2)c(-c2cc(-c3cc(F)c(CO)c(S(C)(=O)=O)c3)ccc2-c2cc(C(F)(F)C(=O)N(C)C)nn2C)o1] | 2-(5-(3-(4-(4-(difluoromethoxy)-3-fluorophenyl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N,N-dimethylacetamide |
| 80 | 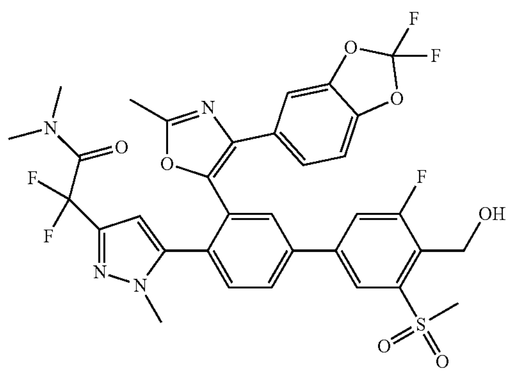 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)N(C)C)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N,N-dimethylacetamide |
| 81 | 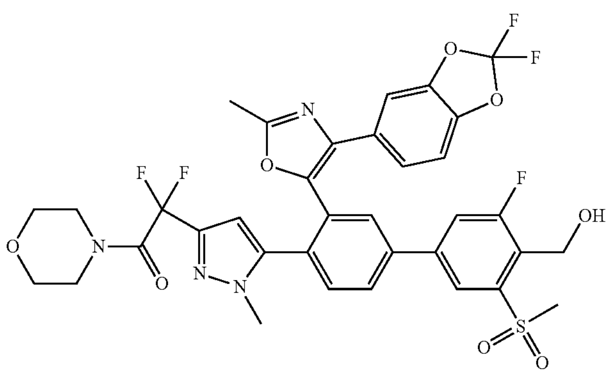 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)N3CCOCC3)nn2C)o1] | 2-(5-(3-(4-(2,2-difluorobenzo[d][1,3]dioxol-5-yl)-2-methyloxazol-5-yl)-3'-fluoro-4'-OH(hydroxymethyl)-5'-methylsulfonyl)biphenyl-4-yl)-1-methyl-1H-pyrazol-3-yl)-2,2-difluoro-1-morpholinoethanone |
| 82 | 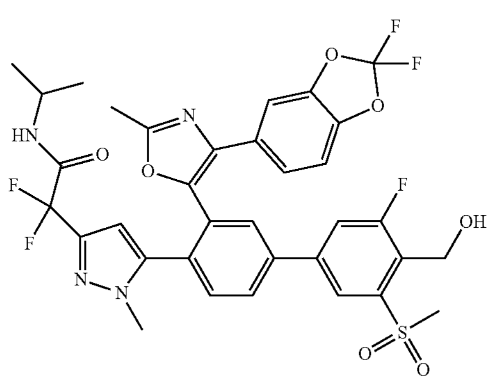 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NC(C)C)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-isopropylacetamide |

-continued

| Ex # | Structure | Name |
|---|---|---|
| 83 | 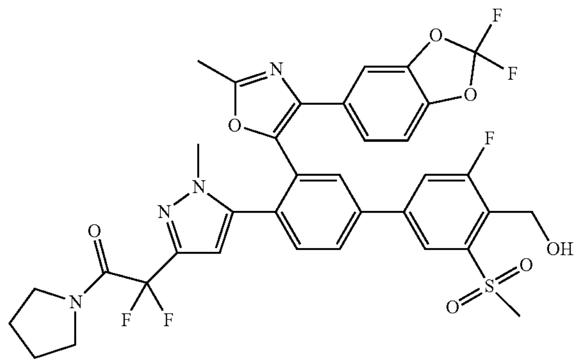 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)N3CCCC3)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoro-1-(pyrrolidin-1-yl)ethanone |
| 84 | 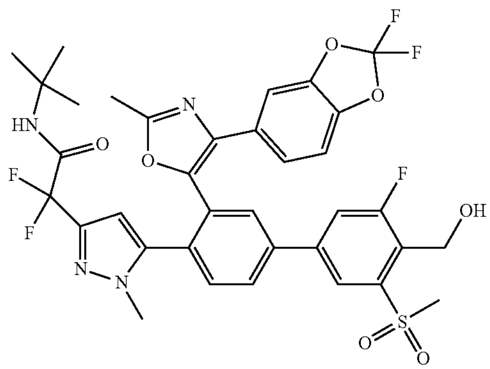 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NC(C)(C)C)nn2C)o1] | N-tert-butyl-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide |
| 85 | 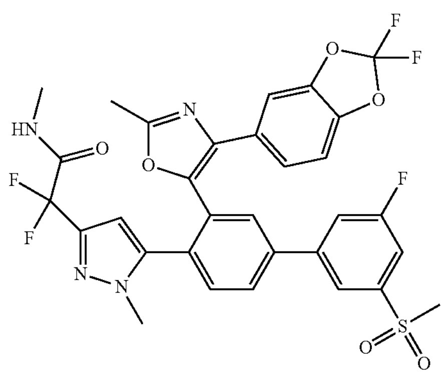 [SMILES: CNC(=O)C(F)(F)c1cc(-c2ccc(-c3cc(F)cc(S(C)(=O)=O)c3)cc2-c2oc(C)nc2-c2ccc3c(c2)OC(F)(F)O3)n(C)n1] | 2-(5-(3-(4-(2,2-difluorobenzo[d][1,3]dioxol-5-yl)-2-methyloxazol-5-yl)-3'-fluoro-5'-(methylsulfonyl)biphenyl-4-yl)-1-methyl-1H-pyrazol-3-yl)-2,2-difluoro-N-methylacetamide |
| 86 | 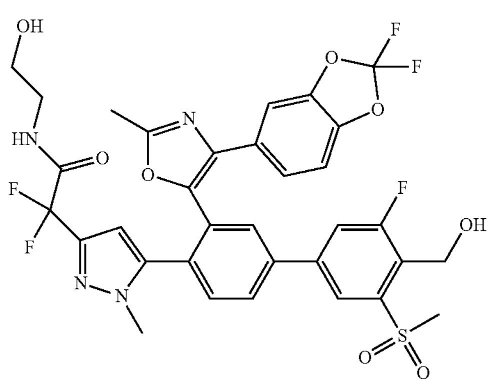 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCCO)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-(2-hydroxyethyl)acetamide |

| Ex # | Structure | Name |
|---|---|---|
| 87 | 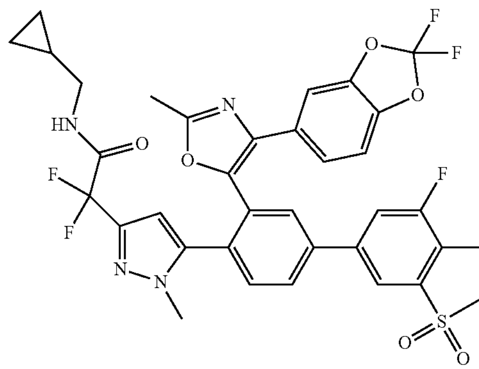 | N-(cyclopropylmethyl)-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide |
| 88 | 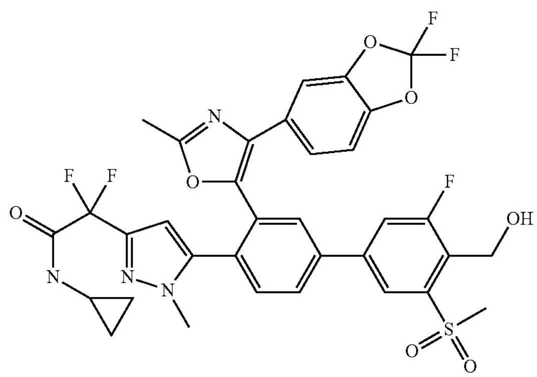 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NC3CC3)nn2C)o1] | N-cyclopropyl-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide |
| 89 | 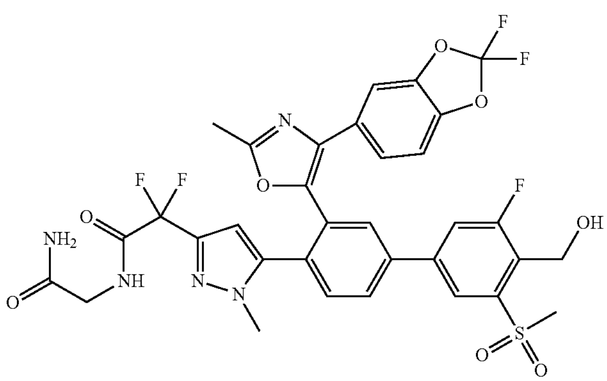 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCC(N)=O)nn2C)o1] | N-(2-amino-2-oxoethyl)-2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoroacetamide |
| 90 | 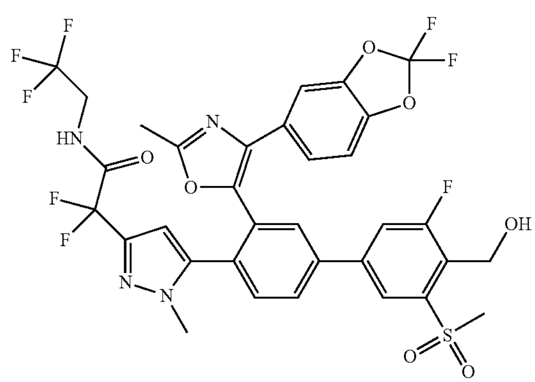 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)C(=O)NCC(F)(F)F)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2,2-difluoro-N-(2,2,2-trifluoroethyl)acetamide |

| Ex # | Structure | Name |
|---|---|---|
| 91 | 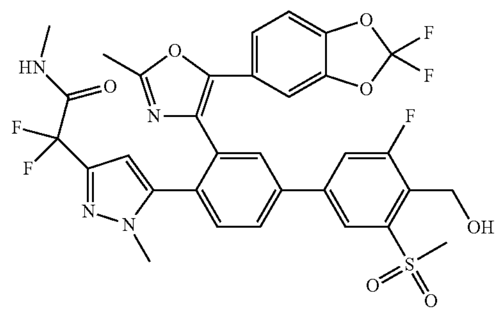 [SMILES: CNC(=O)C(F)(F)c1cc(-c2ccc(-c3cc(F)c(CO)c(S(C)(=O)=O)c3)cc2-c2nc(C)oc2-c2ccc3c(c2)OC(F)(F)O3)n(C)n1] | 2-(5-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-1-methyl-1H-pyrazol-3-yl)-2,2-difluoro-N-methylacetamide |
| 92 | 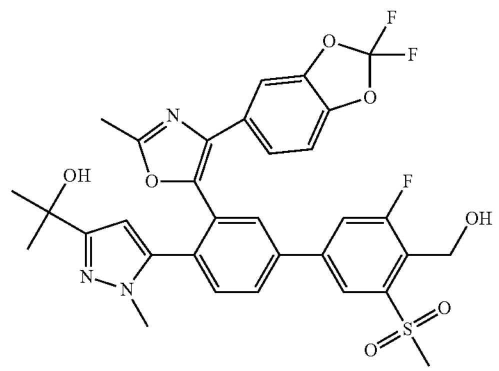 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)O)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)propan-2-ol |
| 93 | 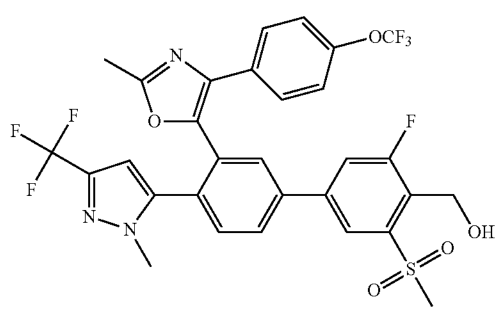 [SMILES: Cc1nc(-c2ccc(OC(F)(F)F)cc2)c(-c2cc(-c3cc(F)c(CO)c(S(C)(=O)=O)c3)ccc2-c2cc(C(F)(F)F)nn2C)o1] | (3-fluoro-4'-(1-methyl-3-1-(trifluoromethyl)-1H-pyrazol-5-yl)-3'-(2-methyl-4-(4-(trifluoromethoxy)phenyl)oxazol-5-yl)-5-(methylsulfonyl)biphenyl-4-yl)methanol |
| 94 | 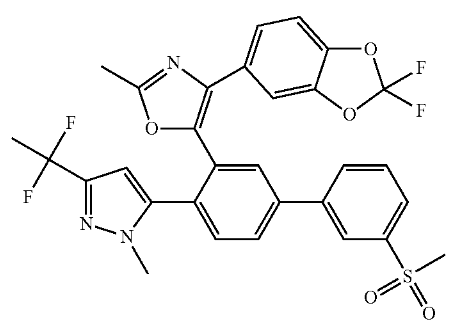 [SMILES: Cc1nc(-c2ccc3c(c2)OC(F)(F)O3)c(-c2cc(-c3cccc(S(C)(=O)=O)c3)ccc2-c2cc(C(C)(F)F)nn2C)o1] | 4-(2,2-difluorobenzo[d][1,3]dioxol-5-yl)-5-(4-(3-(1,1-difluoroethyl)-1-methyl-1H-pyrazol-5-yl)-3'-(methylsulfonyl)biphenyl-3-yl)-2-methyloxazole |

-continued

| Ex # | Structure | Name |
|---|---|---|
| 95 | 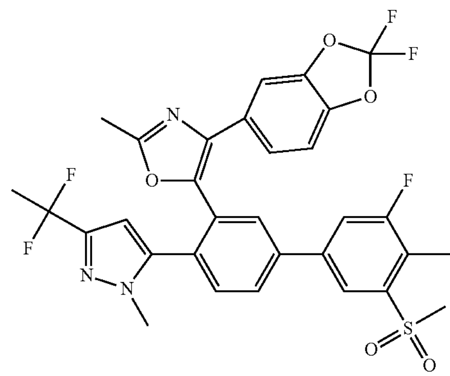 | (3'-(4-(2,2-difluorobenzo[d][1,3]dioxol-5-yl)-2-methyloxazol-5-yl)-4'-(3-(1,1-difluoroethyl)-1-methyl-1H-pyrazol-5-yl)-3-fluoro-5-(methylsulfonyl)biphenyl-4-yl)methanol |
| 96 | 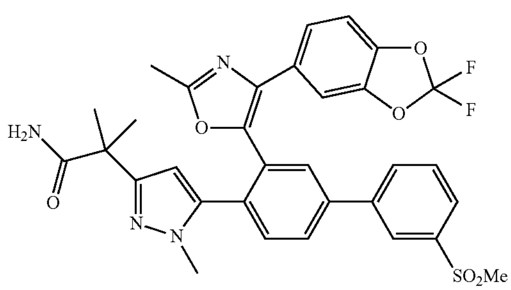 [SMILES: Cc1nc(-c2ccc3c(c2)OC(F)(F)O3)c(-c2cc(-c3cccc(S(C)(=O)=O)c3)ccc2-c2cc(C(C)(C)C(N)=O)nn2C)o1] | 2-(5-(3-(4-(2,2-difluorobenzo[d][1,3]dioxol-5-yl)-2-methyloxazol-5-yl)-3'-(methylsulfonyl)biphenyl-4-yl)-1-methyl-1H-pyrazol-3-yl)-2-methylpropanamide |
| 97 | 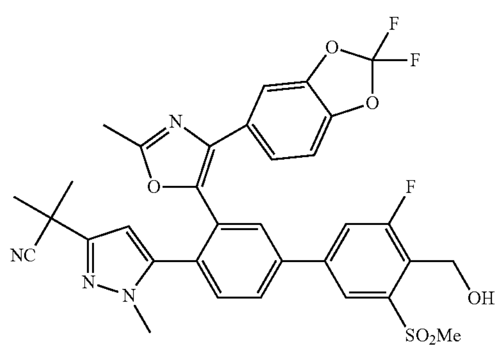 [SMILES: Cc1nc(-c2ccc3c(c2)OC(F)(F)O3)c(-c2cc(-c3cc(F)c(CO)c(S(C)(=O)=O)c3)ccc2-c2cc(C(C)(C)C#N)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)biphenyl-4-yl)-1-methyl-1H-pyrazol-3-yl)-2-methylpropanenitrile |
| 98 | 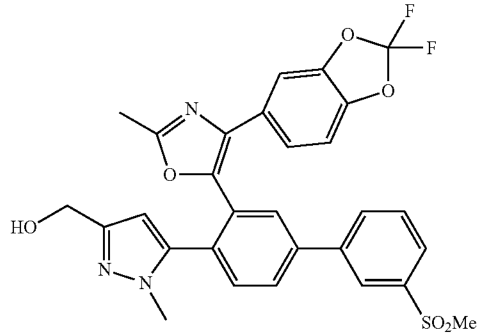 [SMILES: Cc1nc(-c2ccc3c(c2)OC(F)(F)O3)c(-c2cc(-c3cccc(S(C)(=O)=O)c3)ccc2-c2cc(CO)nn2C)o1] | (5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)methanol |

-continued

| Ex # | Structure | Name |
|---|---|---|
| 99 | 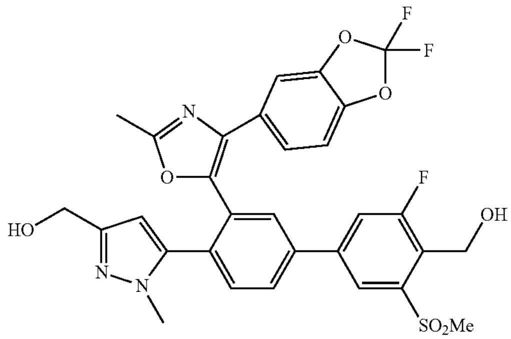 [SMILES: Cc1nc(-c2ccc3c(c2)OC(F)(F)O3)c(-c2cc(-c3cc(F)c(CO)c(S(C)(=O)=O)c3)ccc2-c2cc(CO)nn2C)o1] | (5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)methanol |
| 100 | 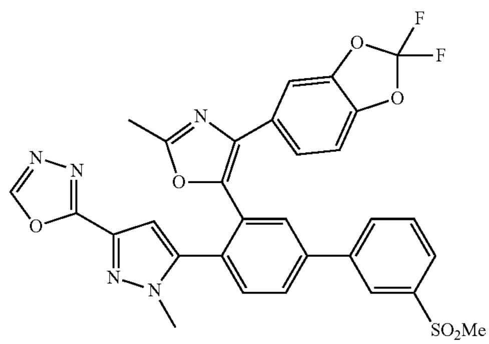 [SMILES: Cc1nc(-c2ccc3c(c2)OC(F)(F)O3)c(-c2cc(-c3cccc(S(C)(=O)=O)c3)ccc2-c2cc(-c3nnco3)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)-1,3,4-oxadiazole |
| 101 | 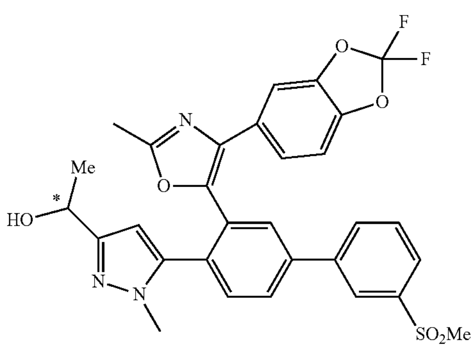 [SMILES: Cc1nc(-c2ccc3c(c2)OC(F)(F)O3)c(-c2cc(-c3cccc(S(C)(=O)=O)c3)ccc2-c2cc(C(C)O)nn2C)o1] | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethanol |
| 102 | 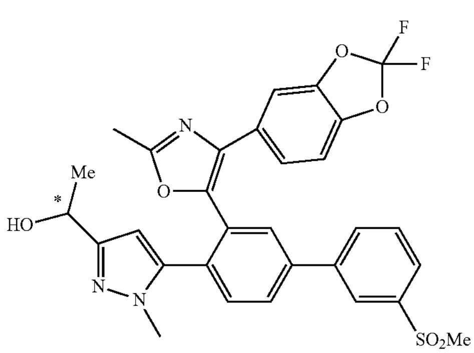 [SMILES: Cc1nc(-c2ccc3c(c2)OC(F)(F)O3)c(-c2cc(-c3cccc(S(C)(=O)=O)c3)ccc2-c2cc(C(C)O)nn2C)o1] | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethanol |

| Ex # | Structure | Name |
| --- | --- | --- |
| 103 | 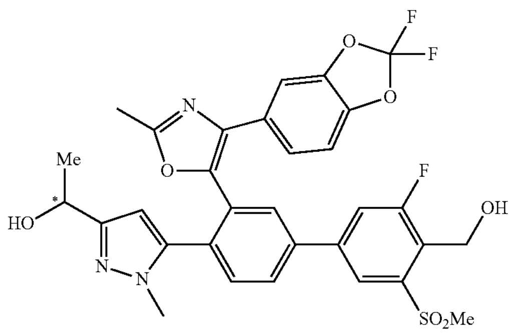 | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethanol |
| 104 | 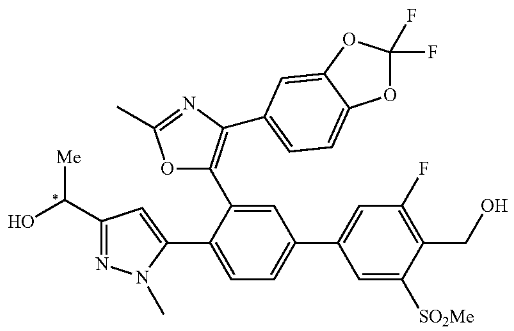 | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethanol |
| 105 | 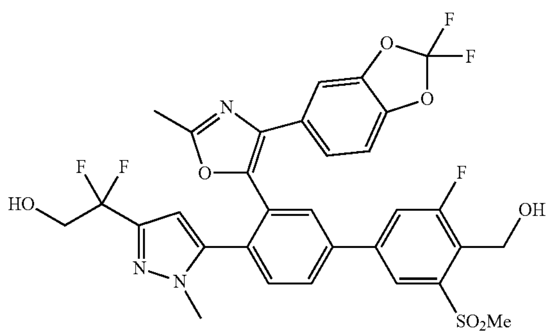 [SMILES: Cc1nc(-c2ccc3c(c2)OC(F)(F)O3)c(-c2cc(-c3cc(F)c(CO)c(S(C)(=O)=O)c3)ccc2-c2cc(C(F)(F)CO)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2,2-difluoroethanol |
| 106 | 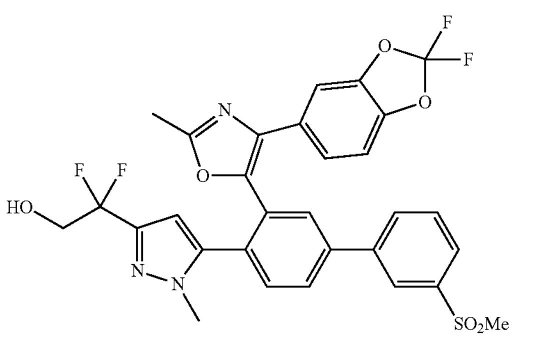 [SMILES: Cc1nc(-c2ccc3c(c2)OC(F)(F)O3)c(-c2cc(-c3cccc(S(C)(=O)=O)c3)ccc2-c2cc(C(F)(F)CO)nn2C)o1] | 2-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)-2,2-difluoroethanol |

| Ex # | Structure | Name |
|---|---|---|
| 107 | 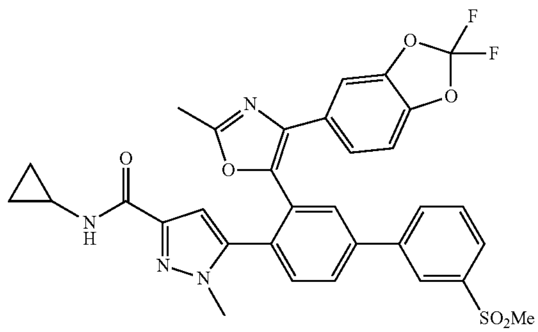 [SMILES: Cc1nc(-c2ccc3c(c2)OC(F)(F)O3)c(-c2cc(-c3cccc(S(C)(=O)=O)c3)ccc2-c2cc(C(=O)NC3CC3)nn2C)o1] | N-cyclopropyl-5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carboxamide |
| 108 | 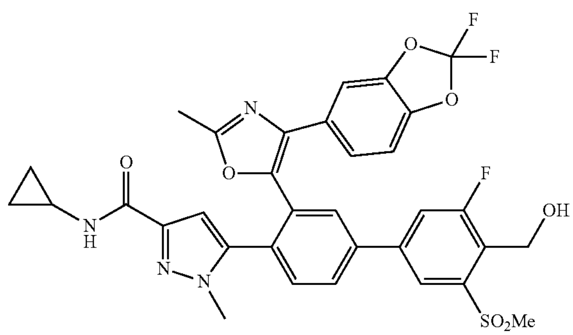 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NC3CC3)nn2C)o1] | N-cyclopropyl-5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carboxamide |
| 109 | 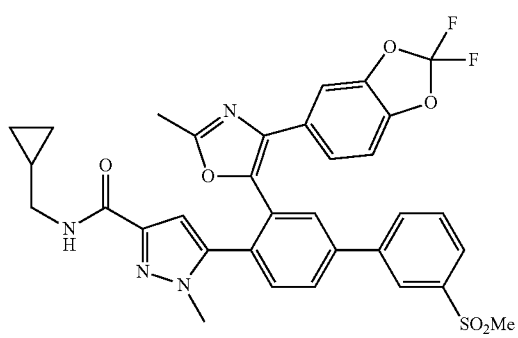 [SMILES: Cc1nc(-c2ccc3c(c2)OC(F)(F)O3)c(-c2cc(-c3cccc(S(C)(=O)=O)c3)ccc2-c2cc(C(=O)NCC3CC3)nn2C)o1] | N-(cyclopropylmethyl)-5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carboxamide |
| 110 | 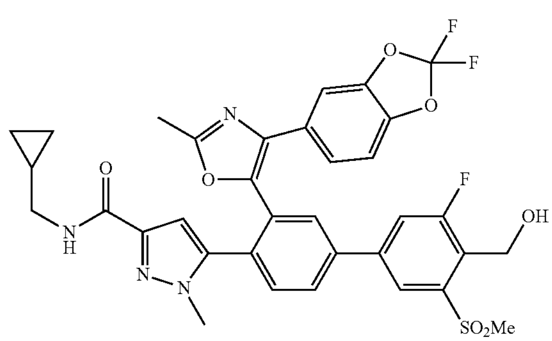 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NCC3CC3)nn2C)o1] | N-(cyclopropylmethyl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carboxamide |

-continued

| Ex # | Structure | Name |
|---|---|---|
| 111 | 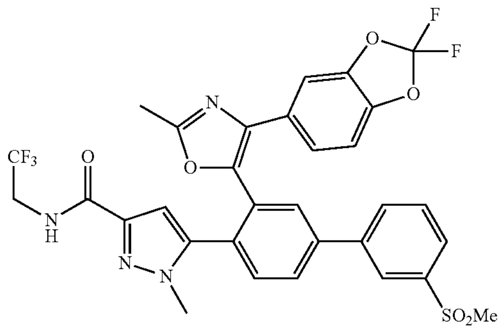 [SMILES: Cc1nc(-c2ccc3c(c2)OC(F)(F)O3)c(-c2cc(-c3cccc(S(C)(=O)=O)c3)ccc2-c2cc(C(=O)NCC(F)(F)F)nn2C)o1] | 5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-N-(2,2,2-trifluoroethyl)-1H-pyrazole-3-carboxamide |
| 112 | 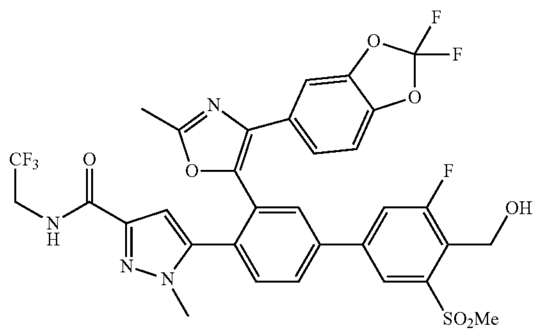 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NCC(F)(F)F)nn2C)o1] | 5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-N-(2,2,2-trifluoroethyl)-1H-pyrazole-3-carboxamide |
| 113 | 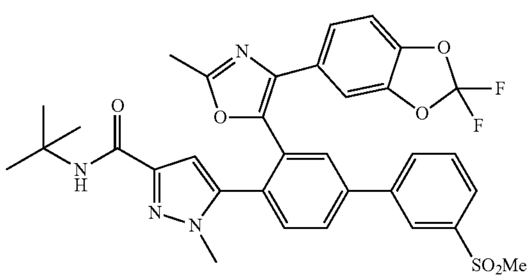 [SMILES: Cc1nc(-c2ccc3c(c2)OC(F)(F)O3)c(-c2cc(-c3cccc(S(C)(=O)=O)c3)ccc2-c2cc(C(=O)NC(C)(C)C)nn2C)o1] | N-(tert-butyl)-5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carboxamide |
| 114 | 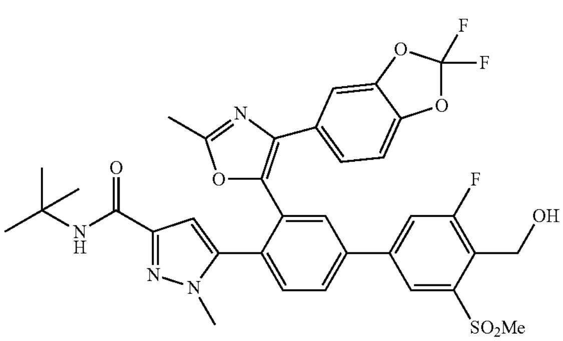 [SMILES: Cc1nc(-c2ccc3c(c2)OC(F)(F)O3)c(-c2cc(-c3cc(F)c(CO)c(S(C)(=O)=O)c3)ccc2-c2cc(C(=O)NC(C)(C)C)nn2C)o1] | N-(tert-butyl)-5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carboxamide |

| Ex # | Structure | Name |
|---|---|---|
| 115 | 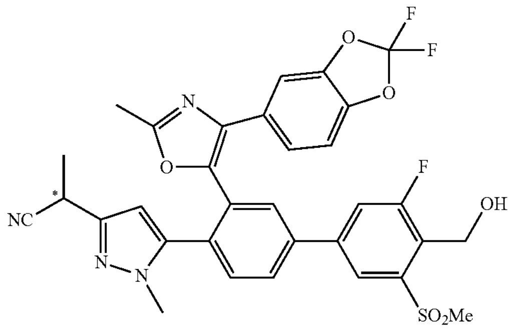 [SMILES: Cc1nc(-c2ccc3c(c2)OC(F)(F)O3)c(-c2cc(-c3cc(F)c(CO)c(S(C)(=O)=O)c3)ccc2-c2cc(C(C)C#N)nn2C)o1] | 2-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)propanenitrile |
| 116 | 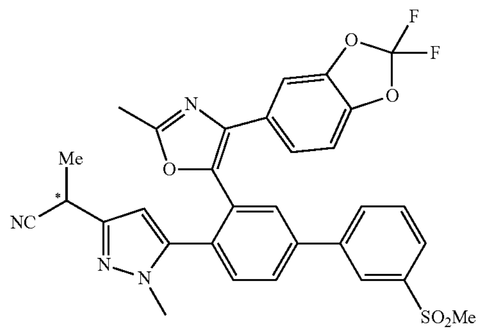 [SMILES: Cc1nc(-c2ccc3c(c2)OC(F)(F)O3)c(-c2cc(-c3cccc(S(C)(=O)=O)c3)ccc2-c2cc(C(C)C#N)nn2C)o1] | 2-(5-(3-(4-(2,2-difluorobenzo[d][1,3]dioxol-5-yl)-2-methyloxazol-5-yl)-3'-methylsulfonyl)[1,1'-biphenyl]-4-yl)-1-methyl-1H-pyrazol-3-yl)propanenitrile |
| 117 | 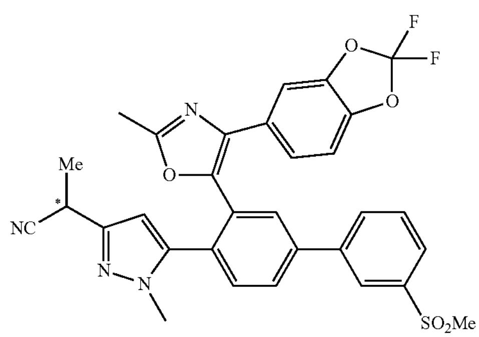 [SMILES: Cc1nc(-c2ccc3c(c2)OC(F)(F)O3)c(-c2cc(-c3cccc(S(C)(=O)=O)c3)ccc2-c2cc(C(C)C#N)nn2C)o1] | 2-(5-(3-(4-(2,2-difluorobenzo[d][1,3]dioxol-5-yl)-2-methyloxazol-5-yl)-3'-(methylsulfonyl)[1,1'-biphenyl]-4-yl)-1-methyl-1H-pyrazol-3-yl)propanenitrile |
| 118 | 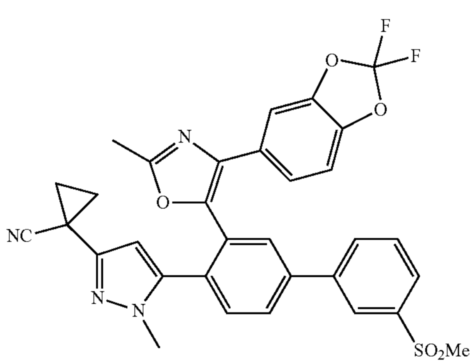 [SMILES: Cc1nc(-c2ccc3c(c2)OC(F)(F)O3)c(-c2cc(-c3cccc(S(C)(=O)=O)c3)ccc2-c2cc(C3(C#N)CC3)nn2C)o1] | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)cyclopropanecarbonitrile |

| Ex # | Structure | Name |
|---|---|---|
| 119 | 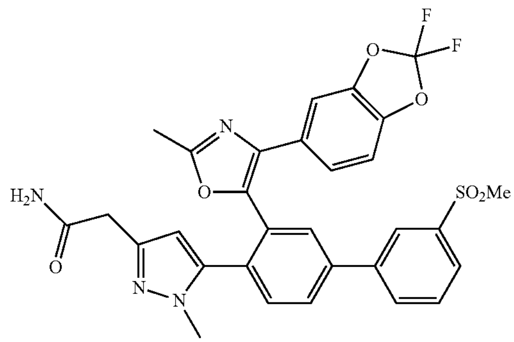 [SMILES: Cc1nc(-c2ccc3c(c2)OC(F)(F)O3)c(-c2cc(-c3cccc(S(C)(=O)=O)c3)ccc2-c2cc(CC(N)=O)nn2C)o1] | 2-(5-(3-(4-(2,2-difluorobenzo[d][1,3]dioxol-5-yl)-2-methyloxazol-5-yl)-3'-(methylsulfonyl)41,1'-biphenyl]-4-yl)-1-methyl-1H-pyrazol-3-yl)acetamide |
| 120 | 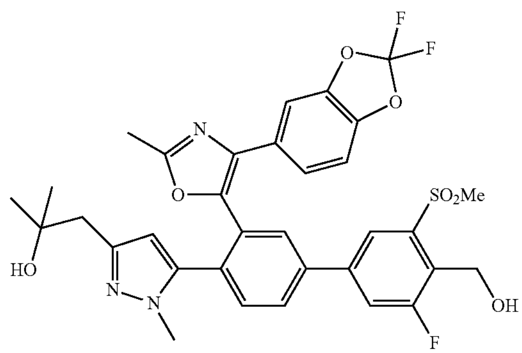 [SMILES: Cc1nc(-c2ccc3c(c2)OC(F)(F)O3)c(-c2cc(-c3cc(F)c(CO)c(S(C)(=O)=O)c3)ccc2-c2cc(CC(C)(C)O)nn2C)o1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)-2-methylpropan-2-ol |
| 121 | 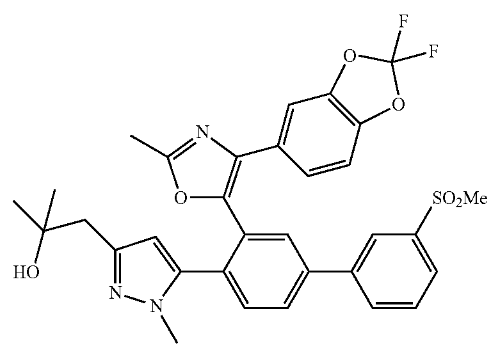 [SMILES: Cc1nc(-c2ccc3c(c2)OC(F)(F)O3)c(-c2cc(-c3cccc(S(C)(=O)=O)c3)ccc2-c2cc(CC(C)(C)O)nn2C)o1] | 1-(5-(3-(4-(2,2-difluorobenzo[d][1,3]dioxol-5-yl)-2-methyloxazol-5-yl)-3'-(methylsulfonyl)41,1'-biphenyl]-4-yl)-1-methyl-1H-pyrazol-3-yl)-2-methylpropan-2-ol |
| 122 | 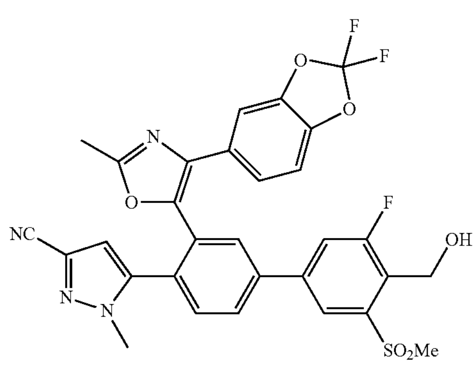 [SMILES: Cc1nc(-c2ccc3c(c2)OC(F)(F)O3)c(-c2cc(-c3cc(F)c(CO)c(S(C)(=O)=O)c3)ccc2-c2cc(C#N)nn2C)o1] | 5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazole-3-carbonitrile |

| Ex # | Structure | Name |
|---|---|---|
| 123 | 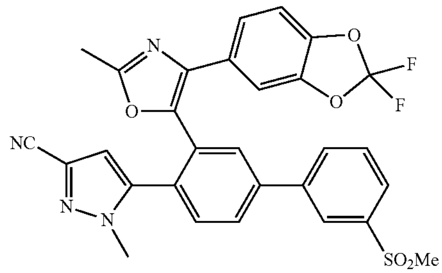 [SMILES: Cc1nc(-c2ccc3c(c2)OC(F)(F)O3)c(-c2cc(-c3cccc(S(C)(=O)=O)c3)ccc2-c2cc(C#N)nn2C)o1] | 5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazole-3-carbonitrile |
| 124 | 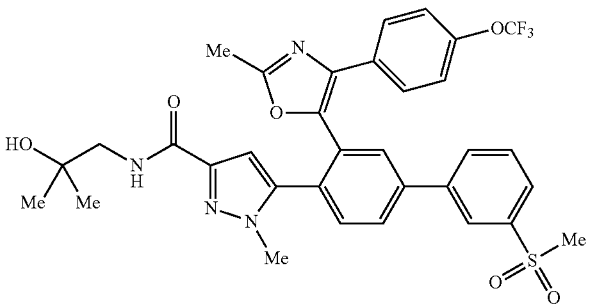 [SMILES: Cc1nc(-c2ccc(OC(F)(F)F)cc2)c(-c2cc(-c3cccc(S(C)(=O)=O)c3)ccc2-c2cc(C(=O)NCC(C)(C)O)nn2C)o1] | N-(2-hydroxy-2-methylpropyl)-1-methyl-5-(3-(2-methyl-4-(4-(trifluoromethoxy)phenyl)oxazol-5-yl)-3'-(methylsulfonyl)-[1,1'-biphenyl]-4-yl)-1H-pyrazole-3-carboxamide |
| 125 | 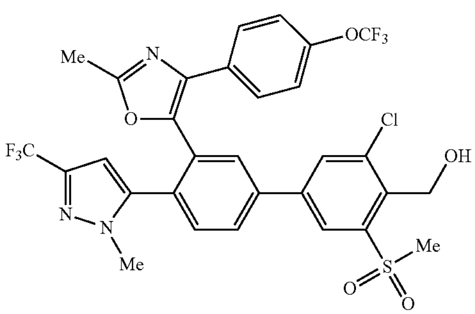 [SMILES: Cc1nc(-c2ccc(OC(F)(F)F)cc2)c(-c2cc(-c3cc(Cl)c(CO)c(S(C)(=O)=O)c3)ccc2-c2cc(C(F)(F)F)nn2C)o1] | (3-chloro-4'-(1-methyl-3-(trifluoromethyl)-1H-pyrazol-5-yl)-3'-(2-methyl-4-(4-(trifluoromethoxy)phenyl)oxazol-5-yl)-5-(methylsulfonyl)-[1,1'-biphenyl]-4-yl)methanol |
| 126 | 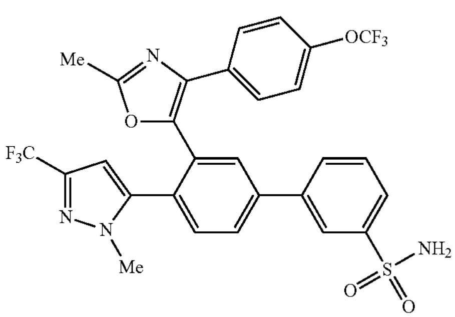 [SMILES: Cc1nc(-c2ccc(OC(F)(F)F)cc2)c(-c2cc(-c3cccc(S(N)(=O)=O)c3)ccc2-c2cc(C(F)(F)F)nn2C)o1] | 4'-(1-methyl-3-(trifluoromethyl)-1H-pyrazol-5-yl)-3'-(2-methyl-4-(4-(trifluoromethoxy)phenyl)oxazol-5-yl)-[1,1'-biphenyl]-3-sulfonamide |
| 127 | 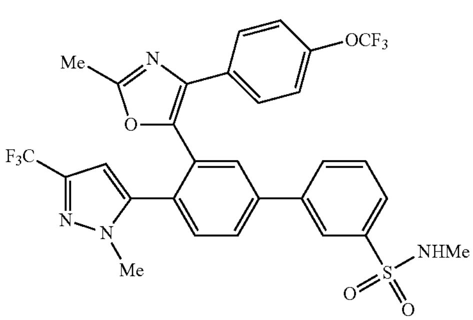 [SMILES: CNS(=O)(=O)c1cccc(-c2ccc(-c3cc(C(F)(F)F)nn3C)c(-c3oc(C)nc3-c3ccc(OC(F)(F)F)cc3)c2)c1] | N-methyl-4'-(1-methyl-3-(trifluoromethyl)-1H-pyrazol-5-yl)-3'-(2-methyl-4-(4-(trifluoromethoxy)phenyl)oxazol-5-yl)-[1,1'-biphenyl]-3-sulfonamide |

| Ex # | Structure | Name |
|---|---|---|
| 128 | 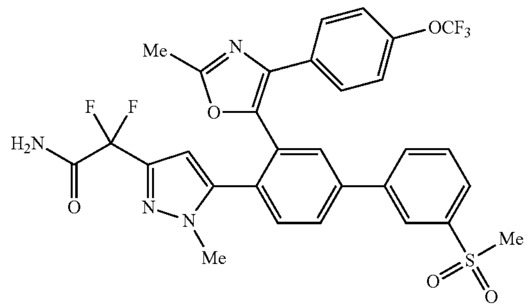 [SMILES: Cc1nc(-c2ccc(OC(F)(F)F)cc2)c(-c2cc(-c3cccc(S(C)(=O)=O)c3)ccc2-c2cc(C(F)(F)C(N)=O)nn2C)o1] | 2,2-difluoro-2-(1-methyl-5-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)acetamide |
| 129 | 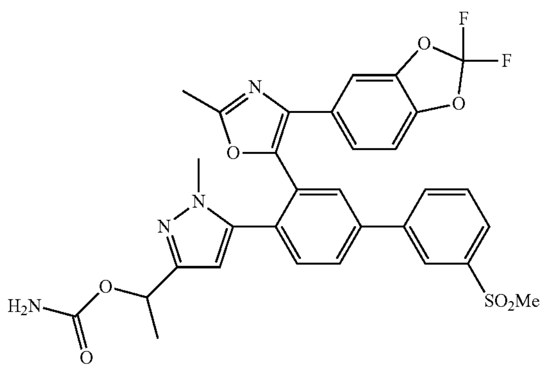 | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethylcarbamate |
| 130 | 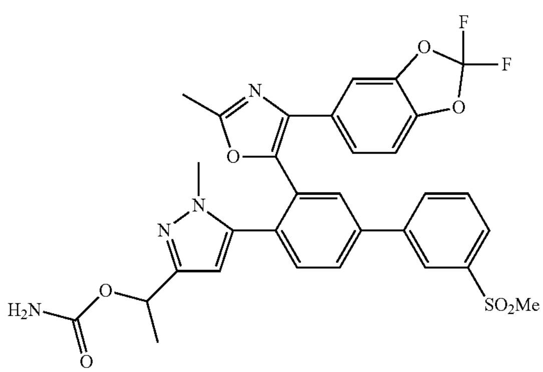 | 1-(5-(3-(4-(2,2-difluorobenzo[d][1,3]dioxol-5-yl)-2-methyloxazol-5-yl)-3'-(methylsulfonyl)-[1,1'-biphenyl]-4-yl)-1-methyl-1H-pyrazol-3-yl)ethylcarbamate |
| 131 | 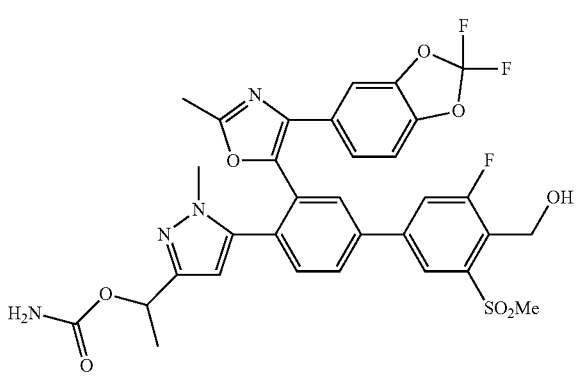 | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethylcarbamate |

-continued

| Ex # | Structure | Name |
|---|---|---|
| 132 | 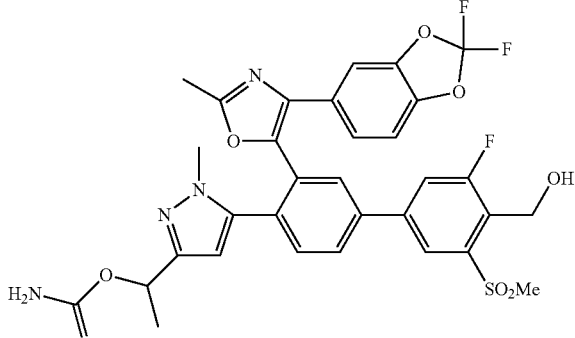<br>chiral | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethylcarbamate |
| 133 | 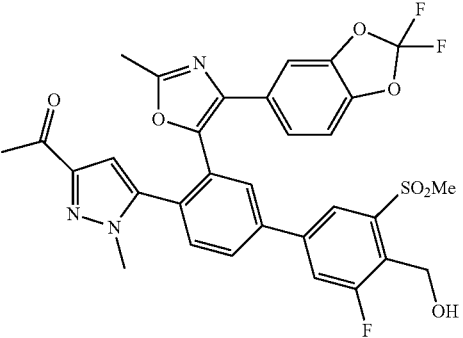 [SMILES: CC(=O)c1cc(-c2ccc(-c3cc(F)c(CO)c(S(C)(=O)=O)c3)cc2-c2oc(C)nc2-c2ccc3c(c2)OC(F)(F)O3)n(C)n1] | 1-(5-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1-methyl-1H-pyrazol-3-yl)ethanone |
| 300 | 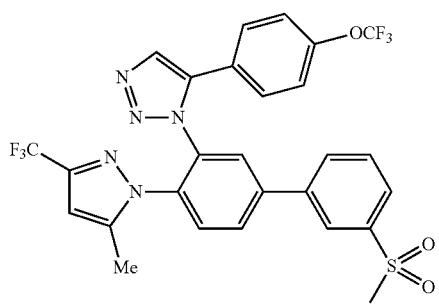 [SMILES: Cc1cc(C(F)(F)F)nn1-c1ccc(-c2cccc(S(C)(=O)=O)c2)cc1-n1nncc1-c1ccc(OC(F)(F)F)cc1] | 1-{3'-(methylsulfonyl)-4-[5-methyl-3-(trifluoromethyl)-1H-pyrazol-1-yl]biphenyl-3-yl}-5-{4-[(trifluoromethyl)oxy]phenyl}-1H-1,2,3-triazole |
| 301 | 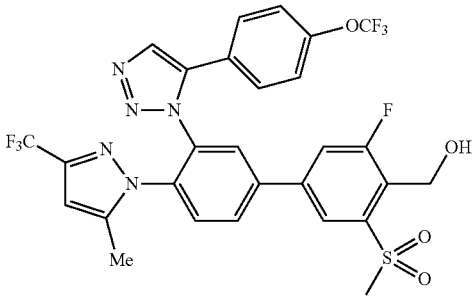 [SMILES: Cc1cc(C(F)(F)F)nn1-c1ccc(-c2cc(F)c(CO)c(S(C)(=O)=O)c2)cc1-n1nncc1-c1ccc(OC(F)(F)F)cc1] | [3-fluoro-5-(methylsulfonyl)-4'45-methyl-3-(trifluoromethyl)-1H-pyrazol-1-yl]-3'-(5-{4-[(trifluoromethyl)oxy]phenyl}-1H-1,2,3-triazol-1-yl)biphenyl-4-yl]methanol |

-continued

| Ex # | Structure | Name |
|---|---|---|
| 302 | 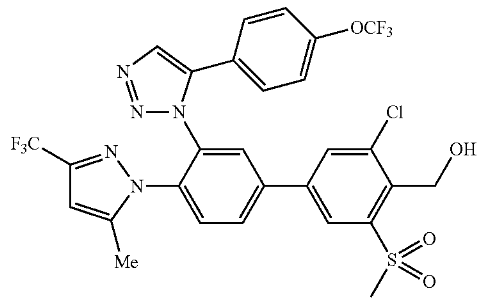 [SMILES: Cc1cc(C(F)(F)F)nn1-c1ccc(-c2cc(Cl)c(CO)c(S(C)(=O)=O)c2)cc1-n1nncc1-c1ccc(OC(F)(F)F)cc1] | [3-chloro-5-(methylsulfonyl)-4'-[5-methyl-3-(trifluoromethyl)-1H-pyrazol-1-yl]-3'-(5-{4-[(trifluoromethyl)oxy]phenyl}-1H-1,2,3-triazol-1-yl)biphenyl-4-yl]methanol |
| 303 | 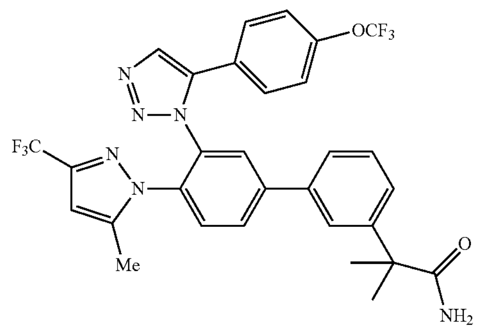 [SMILES: Cc1cc(C(F)(F)F)nn1-c1ccc(-c2cccc(C(C)(C)C(N)=O)c2)cc1-n1nncc1-c1ccc(OC(F)(F)F)cc1] | 2-methyl-2-{4'-[5-methyl-3-(trifluoromethyl)-1H-pyrazol-1-yl]-3'-(5-{4-[(trifluoromethyl)oxy]phenyl}-1H-1,2,3-triazol-1-yl)biphenyl-3-yl}propanamide |
| 304 | 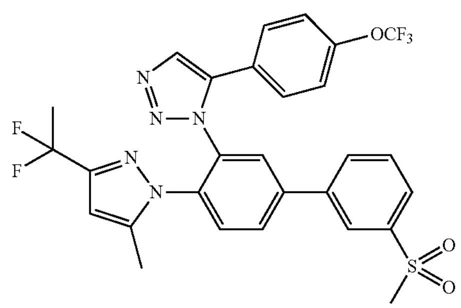 [SMILES: Cc1cc(C(C)(F)F)nn1-c1ccc(-c2cccc(S(C)(=O)=O)c2)cc1-n1nncc1-c1ccc(OC(F)(F)F)cc1] | 1-{4-[3-(1,1-difluoroethyl)-5-methyl-1H-pyrazol-1-yl]-3'-(methylsulfonyl)biphenyl-3-yl}-5-{4-[(trifluoromethyl)oxy]phenyl}-1H-1,2,3-triazole |
| 305 | 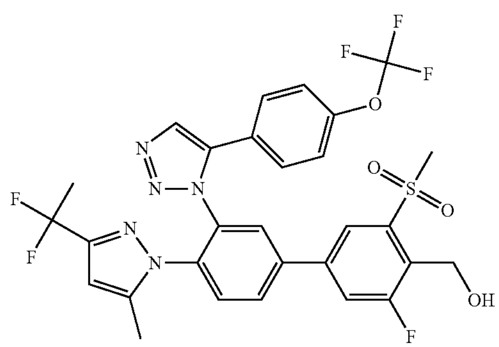 [SMILES: Cc1cc(C(C)(F)F)nn1-c1ccc(-c2cc(F)c(CO)c(S(C)(=O)=O)c2)cc1-n1nncc1-c1ccc(OC(F)(F)F)cc1] | {4'-3-(1,1-difluoroethyl)-5-methyl-1H-pyrazol-1-yl]-3-fluoro-5-(methylsulfonyl)-3'-(5-{4-[(trifluoromethyl)oxy]phenyl}-1H-1,2,3-triazol-1-yl)biphenyl-4-}methanol |
| 306 | 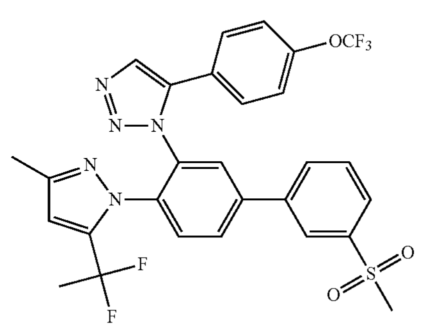 [SMILES: Cc1cc(C(C)(F)F)n(-c2ccc(-c3cccc(S(C)(=O)=O)c3)cc2-n2nncc2-c2ccc(OC(F)(F)F)cc2)n1] | 1-{4-[5-(1,1-difluoroethyl)-3-methyl-1H-pyrazol-1-yl]-3'-(methylsulfonyl)biphenyl-3-yl}-5-{4-[(trifluoromethyl)oxy]phenyl}-1H-1,2,3-triazole |

| Ex # | Structure | Name |
|---|---|---|
| 307 | 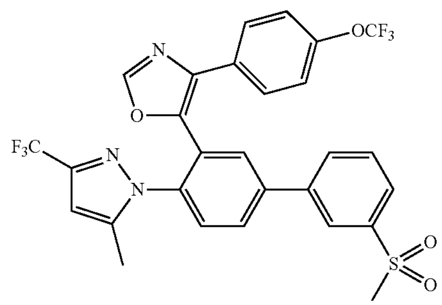 [SMILES: Cc1cc(C(F)(F)F)nn1-c1ccc(-c2cccc(S(C)(=O)=O)c2)cc1-c1ocnc1-c1ccc(OC(F)(F)F)cc1] | 5-{3'-(methylsulfonyl)-4-[5-methyl-3-(trifluoromethyl)-1H-pyrazol-1-yl]biphenyl-3-yl}-4-{4-[(trifluoromethyl)oxy]phenyl}-1,3-oxazole |
| 308 | 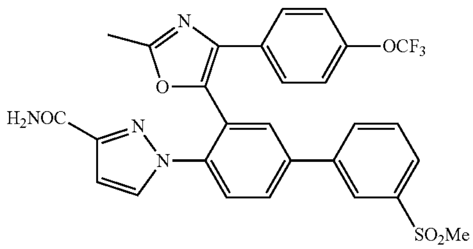 [SMILES: Cc1nc(-c2ccc(OC(F)(F)F)cc2)c(-c2cc(-c3cccc(S(C)(=O)=O)c3)ccc2-n2ccc(C(N)=O)n2)o1] | 1-(3-(2-methyl-4-(4-(trifluoromethoxy)phenyl)oxazol-5-yl)-3'-(methylsulfonyl)biphenyl-4-yl)-1H-pyrazole-3-carboxamide |
| 309 | 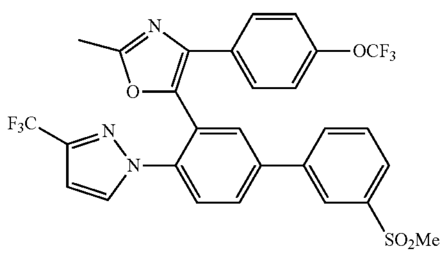 [SMILES: Cc1nc(-c2ccc(OC(F)(F)F)cc2)c(-c2cc(-c3cccc(S(C)(=O)=O)c3)ccc2-n2ccc(C(F)(F)F)n2)o1] | 2-methyl-5-(3'-(methylsulfonyl)-4-(3-(trifluoromethyl)-1H-pyrazol-1-yl)-[1,1'-biphenyl]-3-yl)-4-(4-(trifluoromethoxy)phenyl)oxazole |
| 310 | 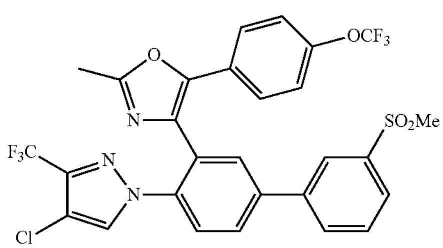 [SMILES: Cc1nc(-c2cc(-c3cccc(S(C)(=O)=O)c3)ccc2-n2cc(Cl)c(C(F)(F)F)n2)c(-c2ccc(OC(F)(F)F)cc2)o1] | 4-(4-(4-chloro-3-(trifluoromethyl)-1H-pyrazol-1-yl)-3'-(methylsulfonyl)-1-1,1'-biphenyl]-3-yl)-2-methyl-5-(4-(trifluoromethoxy)phenyl)oxazole |
| 311 | 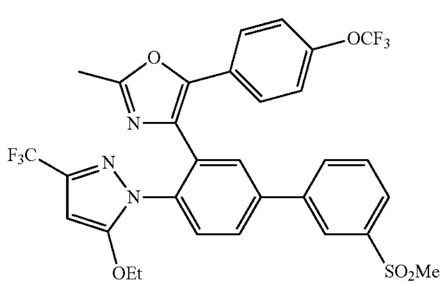 [SMILES: CCOc1cc(C(F)(F)F)nn1-c1ccc(-c2cccc(S(C)(=O)=O)c2)cc1-c1nc(C)oc1-c1ccc(OC(F)(F)F)cc1] | 4-(4-(5-ethoxy-3-(trifluoromethyl)-1H-pyrazol-1-yl)-3'-(methylsulfonyl)biphenyl-3-yl)-2-(trifluoromethoxy)phenyl)oxazole |

-continued

| Ex # | Structure | Name |
|---|---|---|
| 312 | 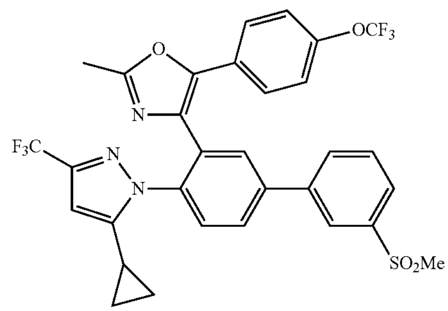 [SMILES: Cc1nc(-c2cc(-c3cccc(S(C)(=O)=O)c3)ccc2-n2nc(C(F)(F)F)cc2C2CC2)c(-c2ccc(OC(F)(F)F)cc2)o1] | 4-(4-(5-cyclopropyl-3-(trifluoromethyl)-1H-pyrazol-1-yl)-3'-(methylsulfonyl)biphenyl-3-yl)-2-methyl-5-(4-(trifluoromethoxy)phenyl)oxazole |
| 313 | 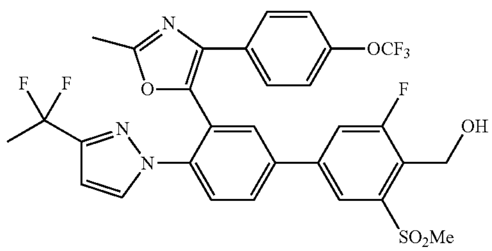 [SMILES: Cc1nc(-c2ccc(OC(F)(F)F)cc2)c(-c2cc(-c3cc(F)c(CO)c(S(C)(=O)=O)c3)ccc2-n2ccc(C(C)(F)F)n2)o1] | (4'-(3-(1,1-difluoroethyl)-1H-pyrazol-1-yl)-3-fluoro-3'-(2-methyl-4-(4-(trifluoromethoxy)phenyl)oxazol-5-yl)-5-(methylsulfonyl)-[1,1'-biphenyl]-4-yl)methanol |
| 314 | 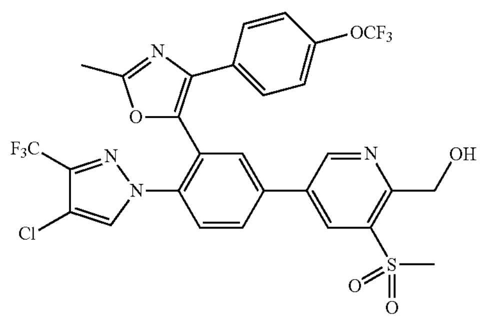 [SMILES: Cc1nc(-c2ccc(OC(F)(F)F)cc2)c(-c2cc(-c3cnc(CO)c(S(C)(=O)=O)c3)ccc2-n2cc(Cl)c(C(F)(F)F)n2)o1] | (5-(4-(4-chloro-3-(trifluoromethyl)-1H-pyrazol-1-yl)-3-(2-methyl-4-(4-(trifluoromethoxy)phenyl)oxazol-5-yl)phenyl)-3-(methylsulfonyl)pyridin-2-yl)methanol |
| 315 | 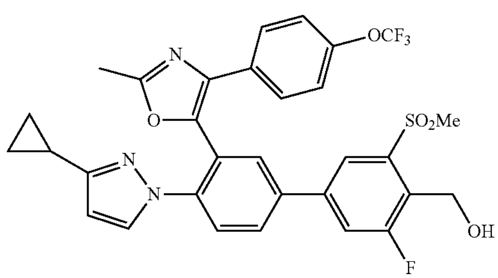 [SMILES: Cc1nc(-c2ccc(OC(F)(F)F)cc2)c(-c2cc(-c3cc(F)c(CO)c(S(C)(=O)=O)c3)ccc2-n2ccc(C3CC3)n2)o1] | (4'-(3-cyclopropyl-1H-pyrazol-1-yl)-3-fluoro-3'-(2-methyl-4-(4-(trifluoromethoxy)phenyl)oxazol-5-yl)-5-(methylsulfonyl)-[1,1'-biphenyl]-4-yl)methanol |
| 316 | 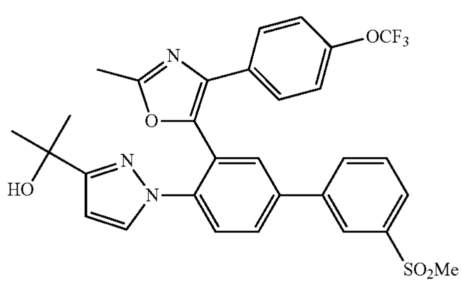 [SMILES: Cc1nc(-c2ccc(OC(F)(F)F)cc2)c(-c2cc(-c3cccc(S(C)(=O)=O)c3)ccc2-n2ccc(C(C)(C)O)n2)o1] | 2-(1-(3-(2-methyl-4-(4-(trifluoromethoxy)phenyl)oxazol-5-yl)-3'-(methylsulfonyl)biphenyl-4-yl)-1H-pyrazol-3-yl)propan-2-ol |

-continued

| Ex # | Structure | Name |
|---|---|---|
| 317 | 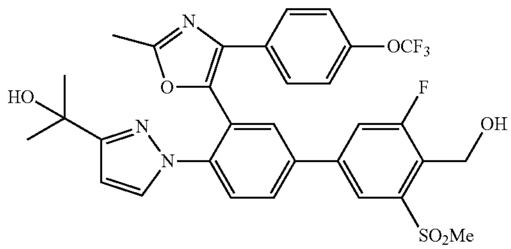 [SMILES: Cc1nc(-c2ccc(OC(F)(F)F)cc2)c(-c2cc(-c3cc(F)c(CO)c(S(C)(=O)=O)c3)ccc2-n2ccc(C(C)(C)O)n2)o1] | 2-(1-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1H-pyrazol-3-yl)propan-2-ol |
| 318 | 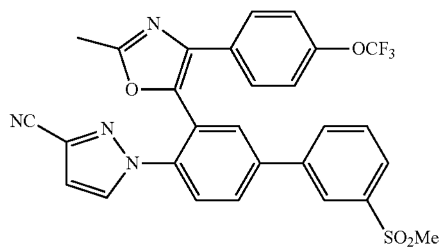 [SMILES: Cc1nc(-c2ccc(OC(F)(F)F)cc2)c(-c2cc(-c3cccc(S(C)(=O)=O)c3)ccc2-n2ccc(C#N)n2)o1] | 1-(3-(2-methyl-4-(4-(trifluoromethoxy)phenyl)oxazol-5-yl)-3'-(methylsulfonyl)biphenyl-4-yl)-1H-H-pyrazole-3-carbonitrile |
| 319 | 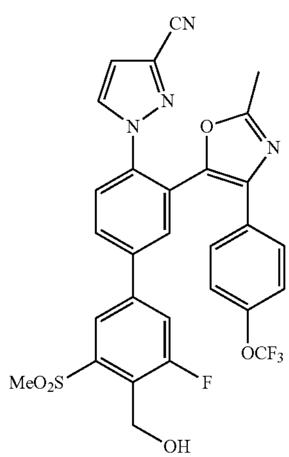 [SMILES: Cc1nc(-c2ccc(OC(F)(F)F)cc2)c(-c2cc(-c3cc(F)c(CO)c(S(C)(=O)=O)c3)ccc2-n2ccc(C#N)n2)o1] | 1-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1H-pyrazole-3-carbonitrile |
| 320 | 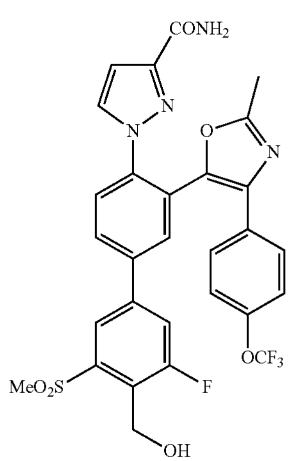 [SMILES: Cc1nc(-c2ccc(OC(F)(F)F)cc2)c(-c2cc(-c3cc(F)c(CO)c(S(C)(=O)=O)c3)ccc2-n2ccc(C(N)=O)n2)o1] | 1-(3'-fluoro-4'-(hydroxymethyl)-3-(2-methyl-4-(4-(trifluoromethoxy)phenyl)oxazol-5-yl)-5'-(methylsulfonyl)biphenyl-4-yl)-1H-pyrazole-3-carboxamide |

| Ex # | Structure | Name |
|---|---|---|
| 321 | 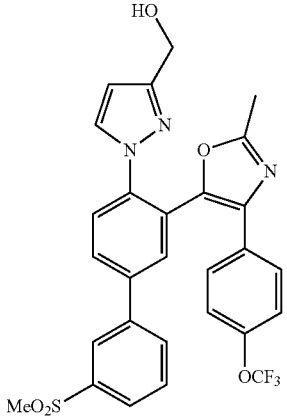 [SMILES: Cc1nc(-c2ccc(OC(F)(F)F)cc2)c(-c2cc(-c3cccc(S(C)(=O)=O)c3)ccc2-n2ccc(CO)n2)o1] | (1-(3-(2-methyl-4-(4-(trifluoromethoxy)phenyl)oxazol-5-yl)-3'-(methylsulfonyl)biphenyl-4-yl)-1H-pyrazol-3-yl)methanol |
| 322 | 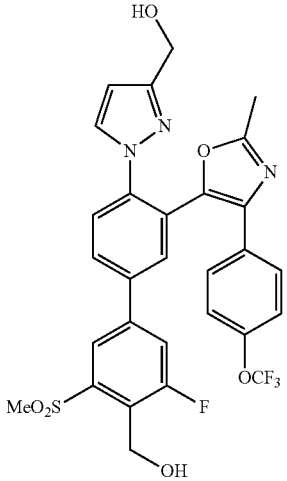 [SMILES: Cc1nc(-c2ccc(OC(F)(F)F)cc2)c(-c2cc(-c3cc(F)c(CO)c(S(C)(=O)=O)c3)ccc2-n2ccc(CO)n2)o1] | (3-fluoro-4'-(3-(hydroxymethyl)-1H-pyrazol-1-yl)-3'-(2-methyl-4-(4-(trifluoromethoxy)phenyl)oxazol-5-yl)-5-(methylsulfonyl)biphenyl-4-yl)methanol |
| 323 | 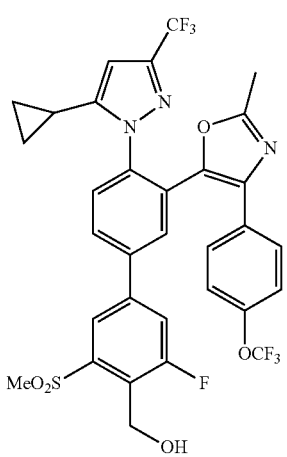 [SMILES: Cc1nc(-c2ccc(OC(F)(F)F)cc2)c(-c2cc(-c3cc(F)c(CO)c(S(C)(=O)=O)c3)ccc2-n2nc(C(F)(F)F)cc2C2CC2)o1] | (4'-(5-cyclopropyl-3-(trifluoromethyl)-1H-pyrazol-1-yl)-3-fluoro-3'-(2-methyl-4-(4-(trifluoromethoxy)phenyl)oxazol-5-yl)-5-(methylsulfonyl)biphenyl-4-yl)methanol |

| Ex # | Structure | Name |
|---|---|---|
| 324 | 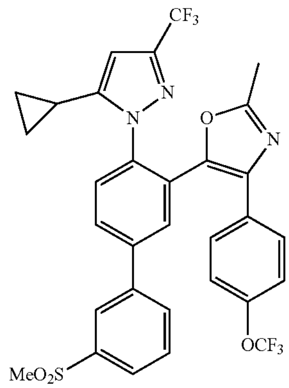 [SMILES: Cc1nc(-c2ccc(OC(F)(F)F)cc2)c(-c2cc(-c3cccc(S(C)(=O)=O)c3)ccc2-n2nc(C(F)(F)F)cc2C2CC2)o1] | 5-(4-(5-cyclopropyl-3-(trifluoromethyl)-1H-pyrazol-1-yl)-3'-(methylsulfonyl)biphenyl-3-yl)-2-methyl-4-(4-(trifluoromethoxy)phenyl)oxazole |
| 325 | 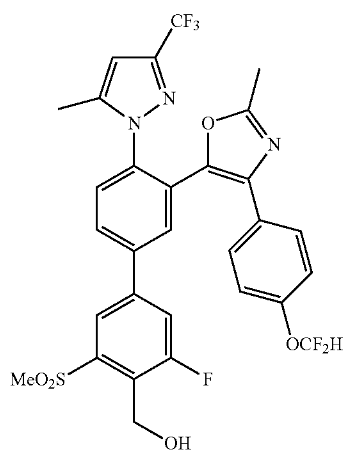 | (3'-(4-(4-(difluoromethoxy)phenyl)-2-methyloxazol-5-yl)-3-fluoro-4'-(5-methyl-3-(trifluoromethyl)-1H-pyrazol-1-yl)-5-(methylsulfonyl)biphenyl-4-yl)methanol |
| 326 | 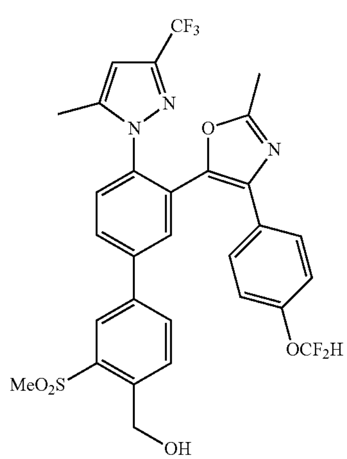 | (3'-(4-(4-(difluoromethoxy)phenyl)-2-methyloxazol-5-yl)-4'-(5-methyl-3-(trifluoromethyl)-1H-pyrazol-1-yl)-3-(methylsulfonyl)biphenyl-4-yl)methanol |

| Ex # | Structure | Name |
|---|---|---|
| 327 | 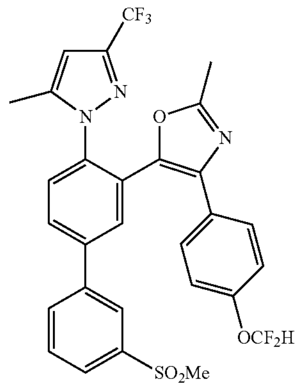 | 4(4-(difluoromethoxy)phenyl)-2-methyl-5-(4-(5-methyl-3-(trifluoromethyl)-1H-pyrazol-1-yl)-3'-methylsulfonyl)biphenyl-3-yl)oxazole |
| 328 | 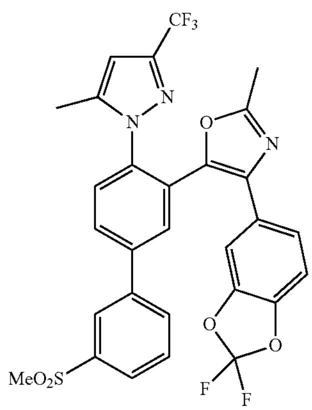 [SMILES: Cc1nc(-c2ccc3c(c2)OC(F)(F)O3)c(-c2cc(-c3cccc(S(C)(=O)=O)c3)ccc2-n2nc(C(F)(F)F)cc2C)o1] | 4-(2,2-difluorobenzo[d][1,3]dioxol-5-yl)-2-methyl-5-(4-(5-methyl-3-(trifluoromethyl)-1H-pyrazol-1-yl)-3'-(methylsulfonyl)biphenyl-3-yl)oxazole |
| 329 | 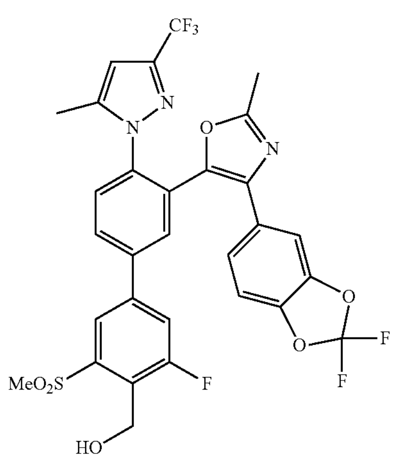 [SMILES: Cc1nc(-c2ccc3c(c2)OC(F)(F)O3)c(-c2cc(-c3cc(F)c(CO)c(S(C)(=O)=O)c3)ccc2-n2nc(C(F)(F)F)cc2C)o1] | (3'-(4-(2,2-difluorobenzo[d][1,3]dioxol-5-yl)-2-methyloxazol-5-yl)-3-fluoro-4'-(5-methyl-3-(trifluoromethyl)-1H-pyrazol-1-yl)-5-(methylsulfonyl)biphenyl-4-yl)methanol |

| Ex # | Structure | Name |
|---|---|---|
| 330 | 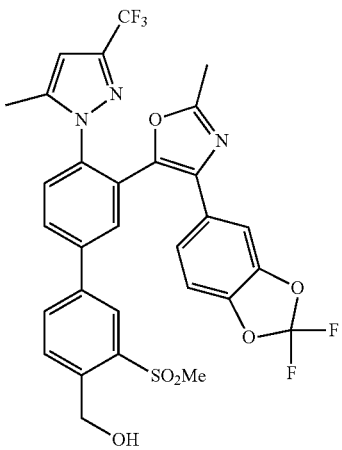 [SMILES: Cc1nc(-c2ccc3c(c2)OC(F)(F)O3)c(-c2cc(-c3ccc(CO)c(S(C)(=O)=O)c3)ccc2-n2nc(C(F)(F)F)cc2C)o1] | difluorobenzo[d][1,3]dioxol-5-yl)-2-methyloxazol-5-yl)-4'(5-methyl-3-(trifluoromethyl)-1H-pyrazol-1-yl)-3-(methylsulfonyl)biphenyl-4-yl)methanol |
| 331 | 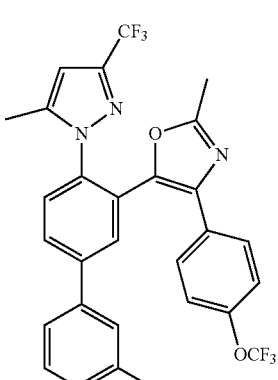 | 2-methyl-5-(4-(5-methyl-3-(trifluoromethyl)-1H-pyrazol-1-yl)-3'-(methylsulfonyl)biphenyl-3-yl)-4-(4-(trifluoromethoxy)phenyl)oxazole |
| 332 | 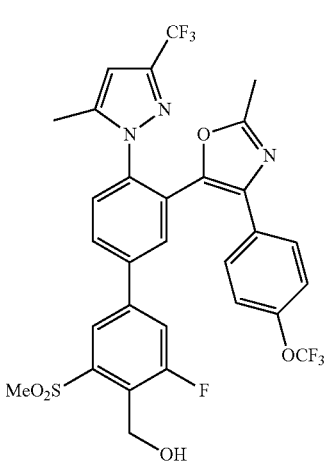 [SMILES: Cc1nc(-c2ccc(OC(F)(F)F)cc2)c(-c2cc(-c3cc(F)c(CO)c(S(C)(=O)=O)c3)ccc2-n2nc(C(F)(F)F)cc2C)o1] | (3-fluoro-4'-(5-methyl-3-(trifluoromethyl)-1H-pyrazol-1-yl)-3'-(2-methyl-4-(4-(trifluoromethoxy)phenyl)oxazol-5-yl)-5-(methylsulfonyl)biphenyl-4-yl)methanol |

-continued

| Ex # | Structure | Name |
|---|---|---|
| 333 | 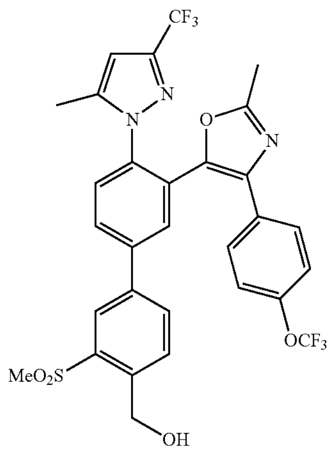 [SMILES: Cc1nc(-c2ccc(OC(F)(F)F)cc2)c(-c2cc(-c3ccc(CO)c(S(C)(=O)=O)c3)ccc2-n2nc(C(F)(F)F)cc2C)o1] | (4'-(5-methyl-3-(trifluoromethyl)-1H-pyrazol-1-yl)-3'-(2-methyl-4-(4-(trifluoromethoxy)phenyl)oxazol-5-yl)-3-(methylsulfonyl)biphenyl-4-yl)methanol |
| 334 | 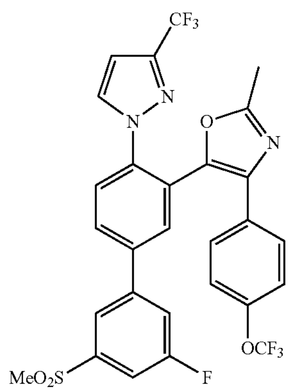 [SMILES: Cc1nc(-c2ccc(OC(F)(F)F)cc2)c(-c2cc(-c3cc(F)cc(S(C)(=O)=O)c3)ccc2-n2ccc(C(F)(F)F)n2)o1] | 5-(3'-fluoro-5'-(methylsulfonyl)-4-(3-(trifluoromethyl)-1H-pyrazol-1-yl)biphenyl-3-yl)-2-methyl-4-(4-(trifluoromethoxy)phenyl)oxazole |
| 335 | 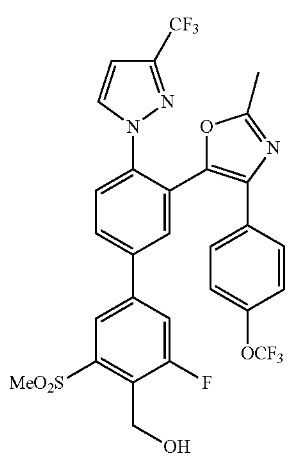 [SMILES: Cc1nc(-c2ccc(OC(F)(F)F)cc2)c(-c2cc(-c3cc(F)c(CO)c(S(C)(=O)=O)c3)ccc2-n2ccc(C(F)(F)F)n2)o1] | (3-fluoro-3'-(2-methyl-4-(4-(trifluoromethoxy)phenyl)oxazol-5-yl)-5-(methylsulfonyl)-4'-(3-(trifluoromethyl)-1H-pyrazol-1-yl)biphenyl-4-yl)methanol |

| Ex # | Structure | Name |
|---|---|---|
| 336 | 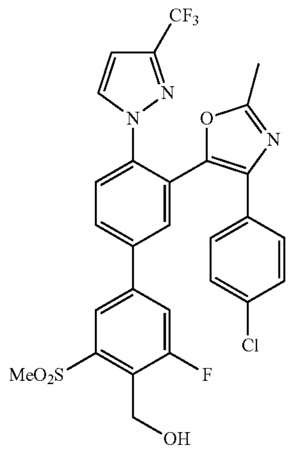 [SMILES: Cc1nc(-c2ccc(Cl)cc2)c(-c2cc(-c3cc(F)c(CO)c(S(C)(=O)=O)c3)ccc2-n2ccc(C(F)(F)F)n2)o1] | (3'-(4-(4-chlorophenyl)-2-methyloxazol-5-yl)-3-fluoro-5-(methylsulfonyl)-4'-(3-(trifluoromethyl)-1H-pyrazol-1-yl)biphenyl-4-yl)methanol |
| 337 | 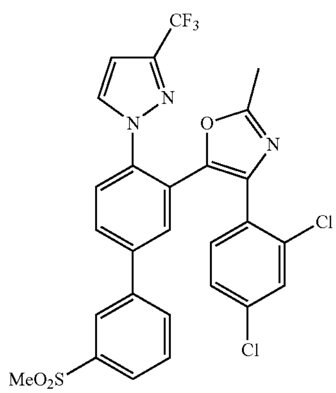 [SMILES: Cc1nc(-c2ccc(Cl)cc2Cl)c(-c2cc(-c3cccc(S(C)(=O)=O)c3)ccc2-n2ccc(C(F)(F)F)n2)o1] | 4-(2,4-dichlorophenyl)-2-methyl-5-(3'-(methylsulfonyl)-4-(3-(trifluoromethyl)-1H-pyrazol-1-yl)biphenyl-3-yl)oxazole |
| 338 | 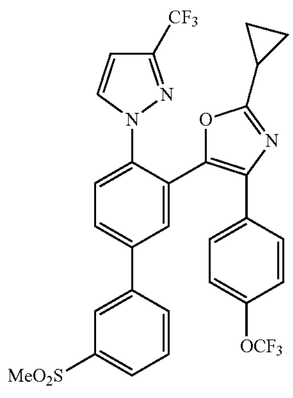 [SMILES: CS(=O)(=O)c1cccc(-c2ccc(-n3ccc(C(F)(F)F)n3)c(-c3oc(C4CC4)nc3-c3ccc(OC(F)(F)F)cc3)c2)c1] | 2-cyclopropyl-5-(3'-(methylsulfonyl)-4-(3-(trifluoromethyl)-1H-pyrazol-1-yl)biphenyl-3-yl)-4-(4-(trifluoromethoxy)phenyl)oxazole |

| Ex # | Structure | Name |
|---|---|---|
| 339 | 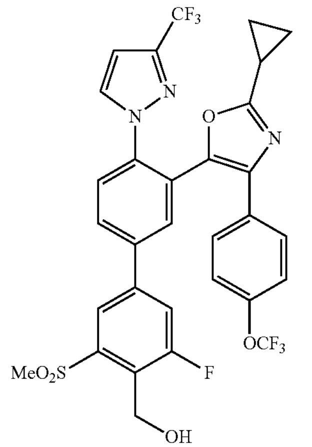 [SMILES: CS(=O)(=O)c1cc(-c2ccc(-n3ccc(C(F)(F)F)n3)c(-c3oc(C4CC4)nc3-c3ccc(OC(F)(F)F)cc3)c2)cc(F)c1CO] | (3'-(2-cyclopropyl-4-(4-(trifluoromethoxy)phenyl)oxazol-5-yl)-3-fluoro-5-(methylsulfonyl)-4'-(3-(trifluoromethyl)-1H-pyrazol-1-yl)biphenyl-4-yl)methanol |
| 340 | 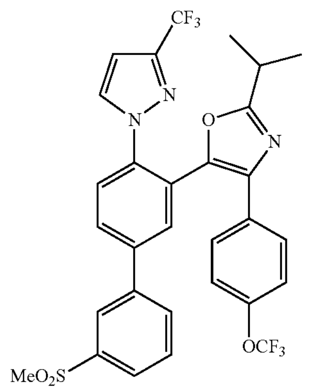 [SMILES: CC(C)c1nc(-c2ccc(OC(F)(F)F)cc2)c(-c2cc(-c3cccc(S(C)(=O)=O)c3)ccc2-n2ccc(C(F)(F)F)n2)o1] | 2-isopropyl-5-(3'-(methylsulfonyl)-4-(3-(trifluoromethyl)-1H-pyrazol-1-yl)biphenyl-3-yl)-4-(4-(trifluoromethoxy)phenyl)oxazole |
| 341 | 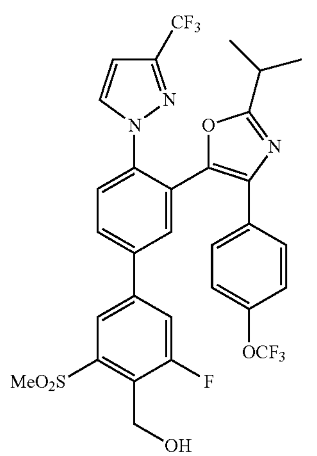 [SMILES: CC(C)c1nc(-c2ccc(OC(F)(F)F)cc2)c(-c2cc(-c3cc(F)c(CO)c(S(C)(=O)=O)c3)ccc2-n2ccc(C(F)(F)F)n2)o1] | (3-fluoro-3'-(2-isopropyl-4-(4-(trifluoromethoxy)phenyl)oxazol-5-yl)-5-(methylsulfonyl)-4'-(3-(trifluoromethyl)-1H-pyrazol-1-yl)biphenyl-4-yl)methanol |

| Ex # | Structure | Name |
|---|---|---|
| 342 | 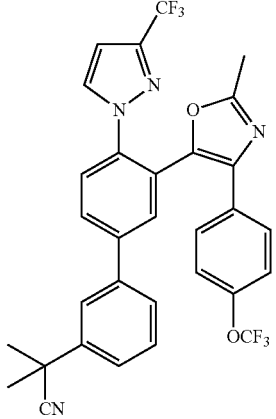 [SMILES: Cc1nc(-c2ccc(OC(F)(F)F)cc2)c(-c2cc(-c3cccc(C(C)(C)C#N)c3)ccc2-n2ccc(C(F)(F)F)n2)o1] | 2-methyl-2-(3'-(2-methyl-4-(4-(trifluoromethoxy)phenyl)oxazol-5-yl)-4'-(3-(trifluoromethyl)-1H-pyrazol-1-yl)biphenyl-3-yl)propanenitrile |
| 343 | 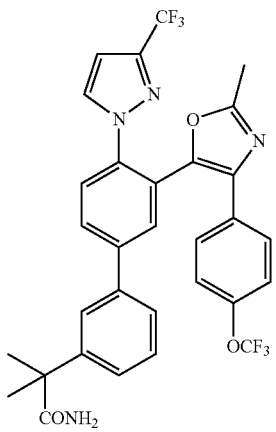 [SMILES: Cc1nc(-c2ccc(OC(F)(F)F)cc2)c(-c2cc(-c3cccc(C(C)(C)C(N)=O)c3)ccc2-n2ccc(C(F)(F)F)n2)o1] | 2-methyl-2-(3'-(2-methyl-4-(4-(trifluoromethoxy)phenyl)oxazol-5-yl)-4'-(3-(trifluoromethyl)-1H-pyrazol-1-yl)biphenyl-3-yl)propanamide |
| 344 | 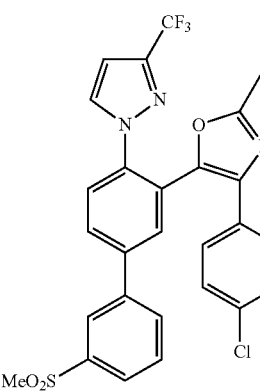 | 4-(4-chlorophenyl)-2-methyl-5-(3'-(methylsulfonyl)-4-(3-(trifluoromethyl)-1H-pyrazol-1-yl)biphenyl-3-yl)oxazole |

| Ex # | Structure | Name |
|---|---|---|
| 345 | 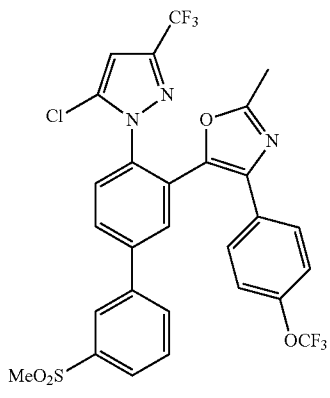 [SMILES: Cc1nc(-c2ccc(OC(F)(F)F)cc2)c(-c2cc(-c3cccc(S(C)(=O)=O)c3)ccc2-n2nc(C(F)(F)F)cc2Cl)o1] | 5-(4-(5-chloro-3-(trifluoromethyl)-1H-pyrazol-1-yl)-3'-(methylsulfonyl)biphenyl-3-yl)-2-methyl-4-(4-(trifluoromethoxy)phenyl)oxazole |
| 346 | 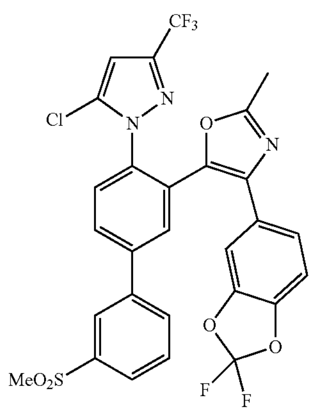 [SMILES: Cc1nc(-c2ccc3c(c2)OC(F)(F)O3)c(-c2cc(-c3cccc(S(C)(=O)=O)c3)ccc2-n2nc(C(F)(F)F)cc2Cl)o1] | 5-(4-(5-chloro-3-(trifluoromethyl)-1H-pyrazol-1-yl)-3'-(methylsulfonyl)biphenyl-3-yl)-4-(2,2-difluorobenzo[d][1,3]dioxol-5-yl)-2-methyloxazole |
| 347 | 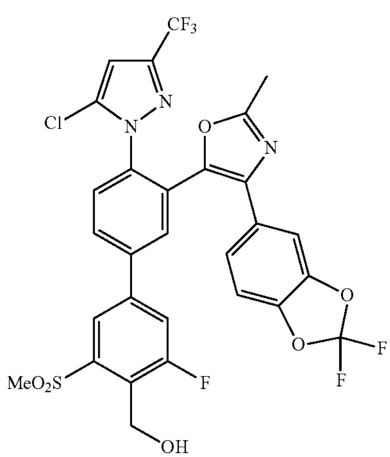 [SMILES: Cc1nc(-c2ccc3c(c2)OC(F)(F)O3)c(-c2cc(-c3cc(F)c(CO)c(S(C)(=O)=O)c3)ccc2-n2nc(C(F)(F)F)cc2Cl)o1] | (4'-(5-chloro-3-(trifluoromethyl)-1H-pyrazol-1-yl)-3'-(4-(2,2-(4-difluorobenzo[d][1,3]dioxol-5-yl)-2-methyloxazol-5-yl)-3-fluoro-5-(methylsulfonyl)biphenyl-4-yl)methanol |

| Ex # | Structure | Name |
|---|---|---|
| 348 | 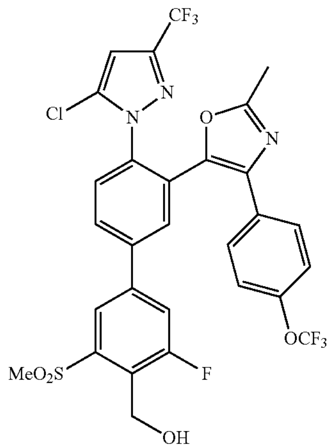 [SMILES: Cc1nc(-c2ccc(OC(F)(F)F)cc2)c(-c2cc(-c3cc(F)c(CO)c(S(C)(=O)=O)c3)ccc2-n2nc(C(F)(F)F)cc2Cl)o1] | 4'45-chloro-3-(trifluoromethyl)-1H-pyrazol-1-yl)-3-fluoro-3'42-methyl-4-(4-(trifluoromethoxy)phenyl)oxazol-5-yl)-5-(methylsulfonyl)biphenyl-4-yl)methanol |
| 349 | 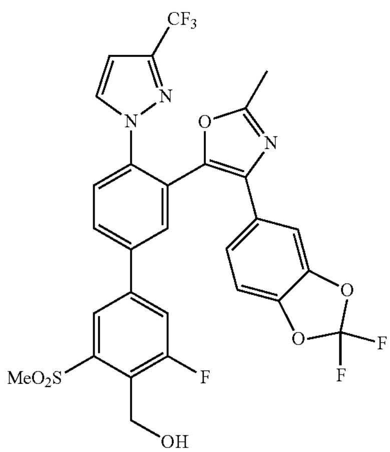 [SMILES: Cc1nc(-c2ccc3c(c2)OC(F)(F)O3)c(-c2cc(-c3cc(F)c(CO)c(S(C)(=O)=O)c3)ccc2-n2ccc(C(F)(F)F)n2)o1] | (3'(4-(2,2-difluorobenzo[d][1,3]dioxol-5-yl)-2-methyloxazol-5-yl)-3-fluoro-5-(methylsulfonyl)-4'-(3-(trifluoromethyl)-1H-pyrazol-1-yl)biphenyl-4-yl)methanol |
| 350 | 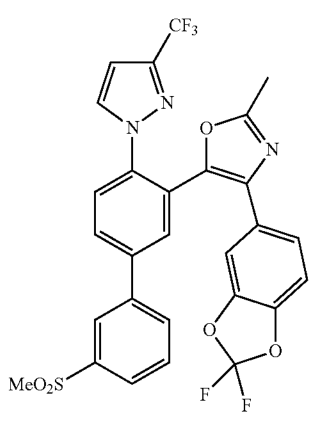 [SMILES: Cc1nc(-c2ccc3c(c2)OC(F)(F)O3)c(-c2cc(-c3cccc(S(C)(=O)=O)c3)ccc2-n2ccc(C(F)(F)F)n2)o1] | 4-(2,2-difluorobenzo[d][1,3]dioxol-5-yl)-2-methyl-5-(3'-(methylsulfonyl)-4-(3-(trifluoromethyl)-1H-pyrazol-1-yl)biphenyl-3-yl)oxazole |

-continued

| Ex # | Structure | Name |
|---|---|---|
| 351 | 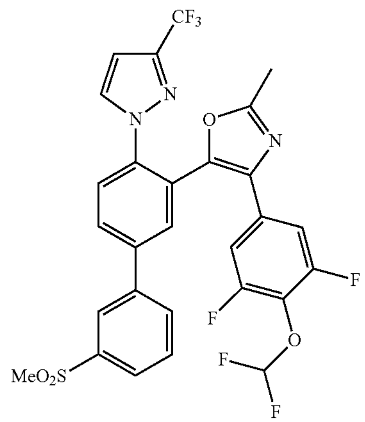 [SMILES: Cc1nc(-c2cc(F)c(OC(F)F)c(F)c2)c(-c2cc(-c3cccc(S(C)(=O)=O)c3)ccc2-n2ccc(C(F)(F)F)n2)o1] | 4-(4-(difluoromethoxy)-3,5-difluorophenyl)-2-methyl-5-(3'-(methylsulfonyl)-4-(3-(trifluoromethyl)-1H-pyrazol-1-yl)biphenyl-3-yl)oxazole |
| 352 | 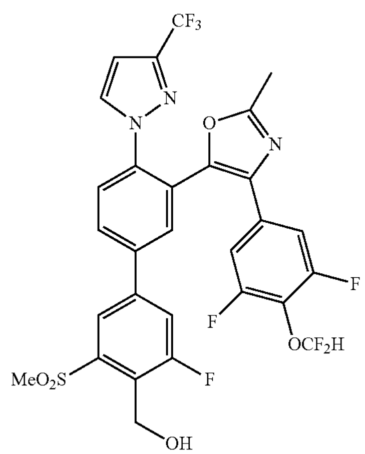 | (3'-(4-(4-(difluoromethoxy)-3,5-difluorophenyl)-2-methyloxazol-5-yl)-3-fluoro-5-(methylsulfonyl)-4'-(3-(trifluoromethyl)-1H-pyrazol-1-yl)biphenyl-4-yl)methanol |
| 353 | 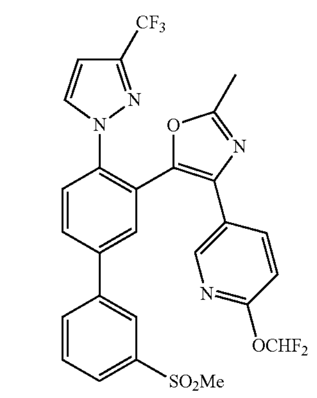 [SMILES: Cc1nc(-c2ccc(OC(F)F)nc2)c(-c2cc(-c3cccc(S(C)(=O)=O)c3)ccc2-n2ccc(C(F)(F)F)n2)o1] | 4-(6-(difluoromethoxy)pyridin-3-yl)-2-methyl-5-(3'-(methylsulfonyl)-4-(3-(trifluoromethyl)-1H-pyrazol-1-yl)biphenyl-3-yl)oxazole |

-continued

| Ex # | Structure | Name |
|---|---|---|
| 354 | 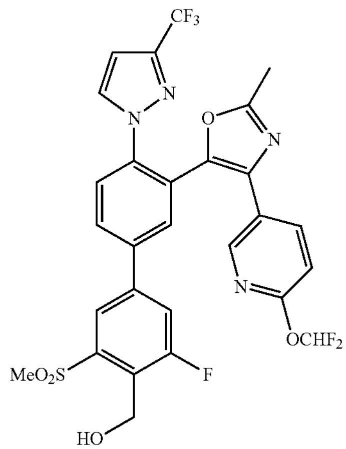 [SMILES: Cc1nc(-c2ccc(OC(F)F)nc2)c(-c2cc(-c3cc(F)c(CO)c(S(C)(=O)=O)c3)ccc2-n2ccc(C(F)(F)F)n2)o1] | (3'-(4-(6-(difluoromethoxy)pyridin-3-yl)-2-methyloxazol-5-yl)-3-fluoro-5-(methylsulfonyl)-4'-(3-(trifluoromethyl)-1H-pyrazol-1-yl)biphenyl-4-yl)methanol |
| 355 | 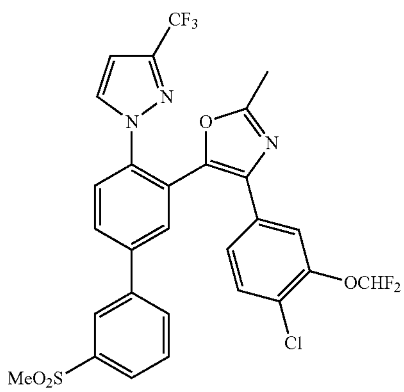 [SMILES: Cc1nc(-c2ccc(Cl)c(OC(F)F)c2)c(-c2cc(-c3cccc(S(C)(=O)=O)c3)ccc2-n2ccc(C(F)(F)F)n2)o1] | 4-(4-chloro-3-(difluoromethoxy)phenyl)-2-methyl-5-(3'-(methylsulfonyl)-4-(3-(trifluoromethyl)-1H-pyrazol-1-yl)biphenyl-3-yl)oxazole |
| 356 | 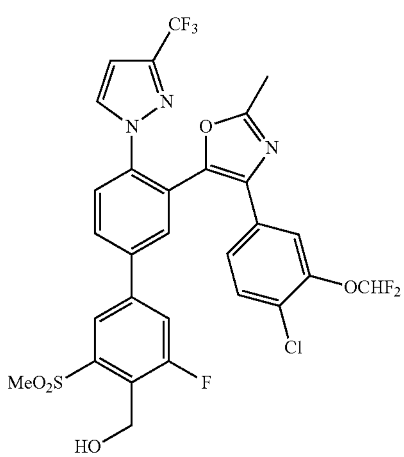 [SMILES: Cc1nc(-c2ccc(Cl)c(OC(F)F)c2)c(-c2cc(-c3cc(F)c(CO)c(S(C)(=O)=O)c3)ccc2-n2ccc(C(F)(F)F)n2)o1] | (3'-(4-(4-chloro-3-(difluoromethoxy)phenyl)-2-methyloxazol-5-yl)-3-fluoro-5-(methylsulfonyl)-4'-(3-(trifluoromethyl)-1H-pyrazol-1-yl)biphenyl-4-yl)methanol |

-continued

| Ex # | Structure | Name |
|---|---|---|
| 357 | 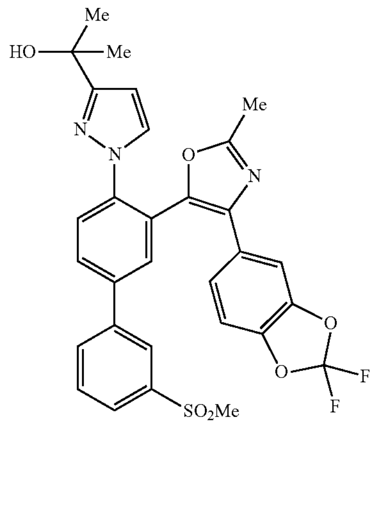 [SMILES: Cc1nc(-c2ccc3c(c2)OC(F)(F)O3)c(-c2cc(-c3cccc(S(C)(=O)=O)c3)ccc2-n2ccc(C(C)(C)O)n2)o1] | 2-(1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazol-3-yl)propan-2-ol |
| 358 | 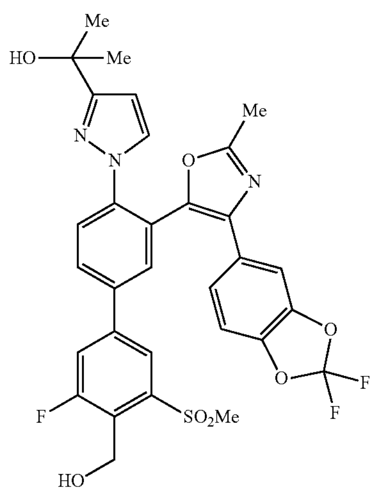 [SMILES: Cc1nc(-c2ccc3c(c2)OC(F)(F)O3)c(-c2cc(-c3cc(F)c(CO)c(S(C)(=O)=O)c3)ccc2-n2ccc(C(C)(C)O)n2)o1] | 2-(1-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1H-pyrazol-3-yl)propan-2-ol |
| 359 | 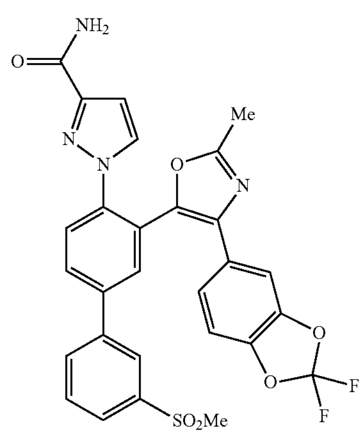 [SMILES: Cc1nc(-c2ccc3c(c2)OC(F)(F)O3)c(-c2cc(-c3cccc(S(C)(=O)=O)c3)ccc2-n2ccc(C(N)=O)n2)o1] | 1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazole-3-carboxamide |

-continued

| Ex # | Structure | Name |
|---|---|---|
| 360 | 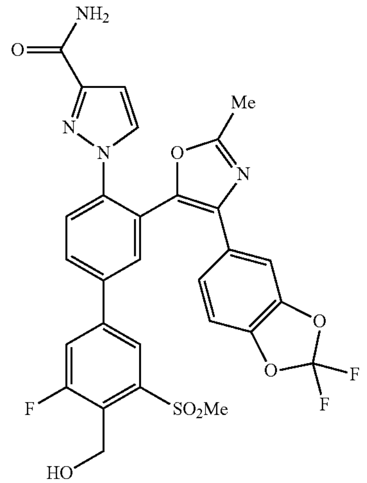 [SMILES: Cc1nc(-c2ccc3c(c2)OC(F)(F)O3)c(-c2cc(-c3cc(F)c(CO)c(S(C)(=O)=O)c3)ccc2-n2ccc(C(N)=O)n2)o1] | 1-(3-(4-(2,2-difluorobenzo[d][1,3]dioxol-5-yl)-2-methyloxazol-5-yl)-3'-fluoro-4'-(hydroxymethyl)-5'-(methylsulfonyl)-[1,1'-biphenyl]-4-yl)-1H-pyrazole-3-carboxamide |
| 361 | 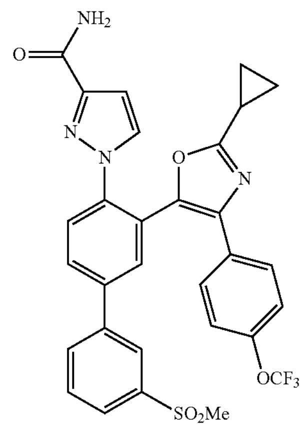 [SMILES: CS(=O)(=O)c1cccc(-c2ccc(-n3ccc(C(N)=O)n3)c(-c3oc(C4CC4)nc3-c3ccc(OC(F)(F)F)cc3)c2)c1] | 1-(3-(2-cyclopropyl-4-(4-(trifluoromethoxy)phenyl)oxazol-5-yl)-3'-(methylsulfonyl)[1,1'-biphenyl]-4-yl)-1H-pyrazole-3-carboxamide |
| 362 | 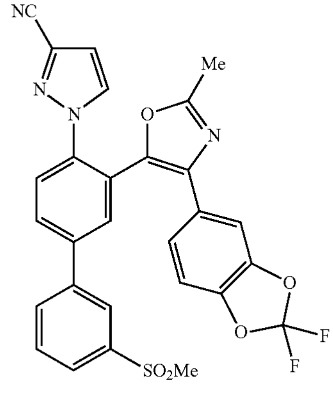 [SMILES: Cc1nc(-c2ccc3c(c2)OC(F)(F)O3)c(-c2cc(-c3cccc(S(C)(=O)=O)c3)ccc2-n2ccc(C#N)n2)o1] | 1-(3-(4-(2,2-difluorobenzo[d][1,3]dioxol-5-yl)-2-methyloxazol-5-yl)-3'-(methylsulfonyl)-[1,1'-biphenyl]-4-yl)-1H-pyrazole-3-carbonitrile |

| Ex # | Structure | Name |
|---|---|---|
| 363 | 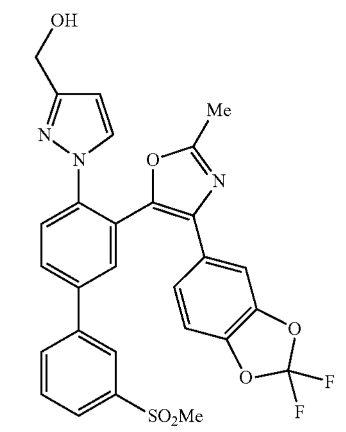 [SMILES: Cc1nc(-c2ccc3c(c2)OC(F)(F)O3)c(-c2cc(-c3cccc(S(C)(=O)=O)c3)ccc2-n2ccc(CO)n2)o1] | (1-(3-(4-(2,2-difluorobenzo[d][1,3]dioxol-5-yl)-2-methyloxazol-5-yl)-3'-(methylsu1fonyl)-[1,1'-biphenyl]-4-yl)-1H-pyrazol-3-yl)methanol |
| 364 | 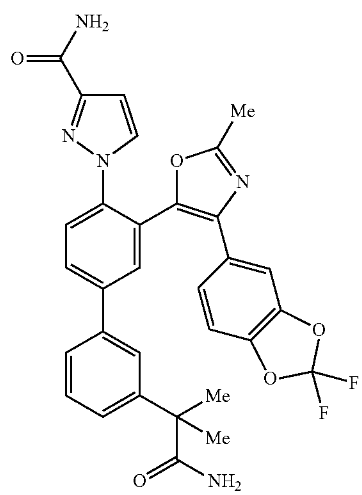 [SMILES: Cc1nc(-c2ccc3c(c2)OC(F)(F)O3)c(-c2cc(-c3cccc(C(C)(C)C(N)=O)c3)ccc2-n2ccc(C(N)=O)n2)o1] | 1-(3'-(1-amino-2-methyl-1-oxopropan-difluorobenzo[d][1,3]dioxol-5-yl)-2-methyloxazol-5-yl)-[1,1'-biphenyl]-4-yl)-1H-pyrazole-3-carboxamide |
| 365 | 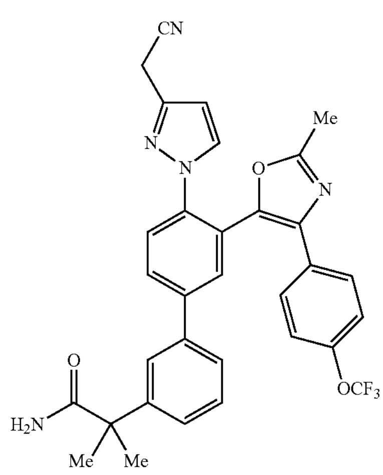 [SMILES: Cc1nc(-c2ccc(OC(F)(F)F)cc2)c(-c2cc(-c3cccc(C(C)(C)C(N)=O)c3)ccc2-n2ccc(CC#N)n2)o1] | 2-(4'-(3-(cyanomethyl)-1H-pyrazol-1-yl)-3'-(2-methyl-4-(4-(trifluoromethoxy)phenyl)oxazol-5-yl)-[1,1'-biphenyl]-3-yl)-2-methylpropanamide |

-continued
| Ex # | Structure | Name |
|---|---|---|
| 366 | 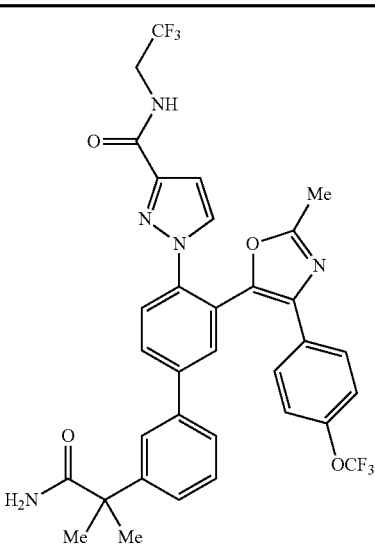 | 1-(3'-(1-amino-2-methyl-1-oxopropan-2-yl)-3-(2-methyl-4-(4-(trifluoromethoxy)phenyl)oxazol-5-yl)-[1,1'-biphenyl]-4-yl)-N-(2,2,2-trifluoroethyl)-1H-pyrazole-3-carboxamide |
| 367 | 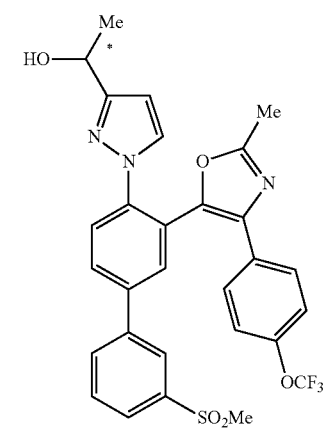 [SMILES: Cc1nc(-c2ccc(OC(F)(F)F)cc2)c(-c2cc(-c3cccc(S(C)(=O)=O)c3)ccc2-n2ccc(C(C)O)n2)o1] | 1-(1-(3-(2-methyl-4-(4-(trifluoromethoxy)phenyl)oxazol-5-yl)-3'-(methylsulfonyl)[1,1'-biphenyl]-4-yl)-1H-pyrazol-3-yl)ethanol |
| 368 | 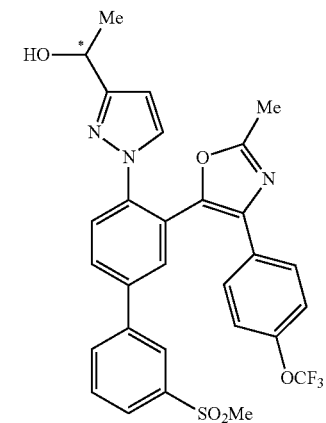 [SMILES: Cc1nc(-c2ccc(OC(F)(F)F)cc2)c(-c2cc(-c3cccc(S(C)(=O)=O)c3)ccc2-n2ccc(C(C)O)n2)o1] | 1-(1-(3-(2-methyl-4-(4-(trifluoromethoxy)phenyl)oxazol-5-yl)-3'-(methylsulfonyl)[1,1'-biphenyl]-4-yl)-1H-pyrazol-3-yl)ethanol |

-continued

| Ex # | Structure | Name |
|---|---|---|
| 369 | 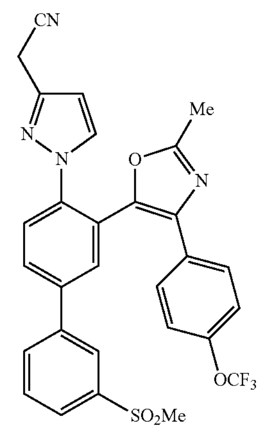 [SMILES: Cc1nc(-c2ccc(OC(F)(F)F)cc2)c(-c2cc(-c3cccc(S(C)(=O)=O)c3)ccc2-n2ccc(CC#N)n2)o1] | 2-(1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)acetonitrile |
| 370 | 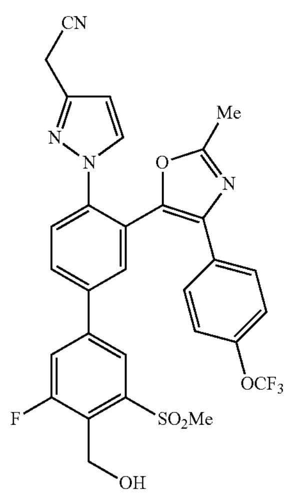 [SMILES: Cc1nc(-c2ccc(OC(F)(F)F)cc2)c(-c2cc(-c3cc(F)c(CO)c(S(C)(=O)=O)c3)ccc2-n2ccc(CC#N)n2)o1] | 2-(1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazol-3-yl)acetonitrile |
| 371 | 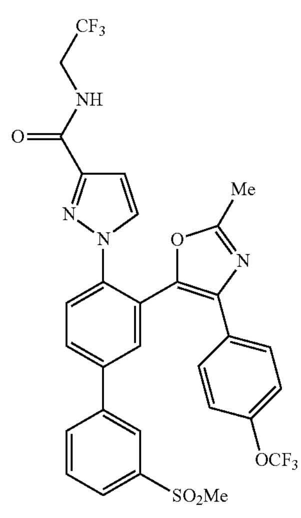 [SMILES: Cc1nc(-c2ccc(OC(F)(F)F)cc2)c(-c2cc(-c3cccc(S(C)(=O)=O)c3)ccc2-n2ccc(C(=O)NCC(F)(F)F)n2)o1] | 1-(3-(2-methyl-4-(4-(trifluoromethoxy)phenyl)oxazol-5-yl)-3'-(methylsulfonyl)-[1,1'-biphenyl]-4-yl)-N-(2,2,2-trifluoroethyl)-1H-pyrazole-3-carboxamide |

-continued

| Ex # | Structure | Name |
|---|---|---|
| 372 | 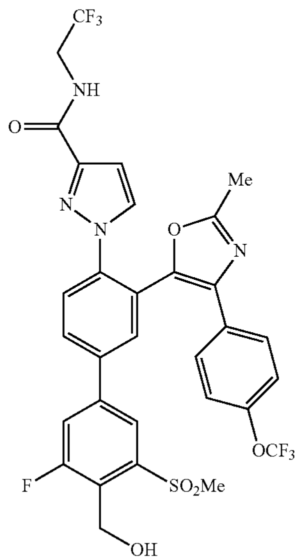 [SMILES: Cc1nc(-c2ccc(OC(F)(F)F)cc2)c(-c2cc(-c3cc(F)c(CO)c(S(C)(=O)=O)c3)ccc2-n2ccc(C(=O)NCC(F)(F)F)n2)o1] | 1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-N-(2,2,2-trifluoroethyl)-1H-pyrazole-3-carboxamide |
| 373 | 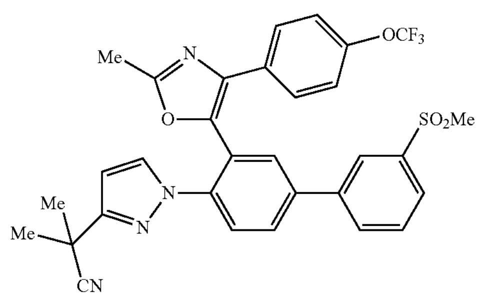 [SMILES: Cc1nc(-c2ccc(OC(F)(F)F)cc2)c(-c2cc(-c3cccc(S(C)(=O)=O)c3)ccc2-n2ccc(C(C)(C)C#N)n2)o1] | 2-methyl-2-(1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)propanenitrile |
| 374 | 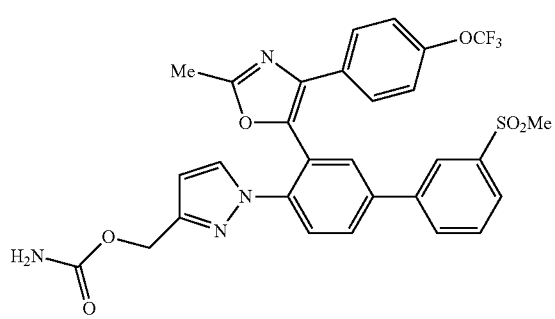 [SMILES: Cc1nc(-c2ccc(OC(F)(F)F)cc2)c(-c2cc(-c3cccc(S(C)(=O)=O)c3)ccc2-n2ccc(COC(N)=O)n2)o1] | (1-(3-(2-methyl-4-(4-(trifluoromethoxy)phenyl)oxazol-5-yl)-3'-(methylsulfonyl)-[1,1'-biphenyl]-4-yl)-1H-pyrazol-3-yl)methylcarbamate |

-continued

| Ex # | Structure | Name |
|---|---|---|
| 375 | 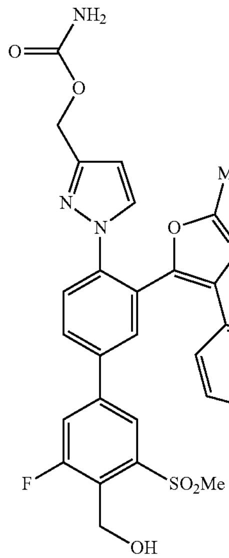 | (1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazol-3-yl)methylcarbamate |
| 376 | 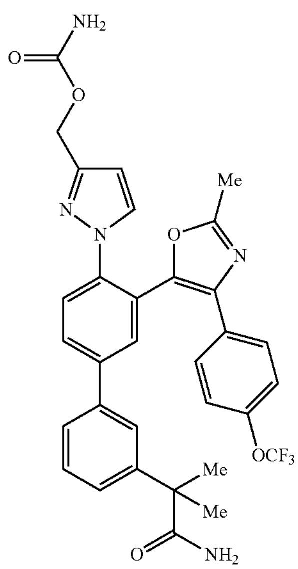 [SMILES: Cc1nc(-c2ccc(OC(F)(F)F)cc2)c(-c2cc(-c3cccc(C(C)(C)C(N)=O)c3)ccc2-n2ccc(COC(N)=O)n2)o1] | (1-(3'-(1-amino-2-methyl-1-oxopropan-2-yl)-3-(2-methyl-4-(4-(trifluoromethoxy)phenyl)oxazol-5-yl)-[1,1'-biphenyl]-4-yl)-1H-pyrazol-3-yl)methylcarbamate |
| 377 | 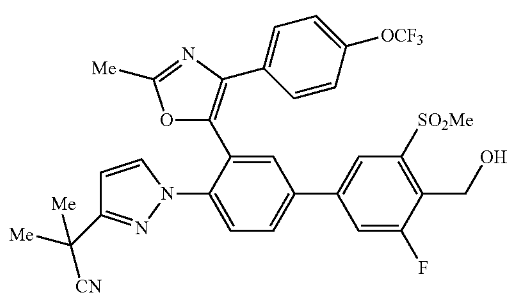 [SMILES: Cc1nc(-c2ccc(OC(F)(F)F)cc2)c(-c2cc(-c3cc(F)c(CO)c(S(C)(=O)=O)c3)ccc2-n2ccc(C(C)(C)C#N)n2)o1] | 2-(1-(3'-fluoro-4'-(hydroxymethyl)-3-2-methyl-4-(4-(trifluoromethoxy)phenyl)oxazol-5-yl)-5'-(methylsulfonyl)-[1,1'-biphenyl]-4-yl)-1H-pyrazol-3-yl)-2-methylpropanenitrile |

-continued

| Ex # | Structure | Name |
|---|---|---|
| 378 | 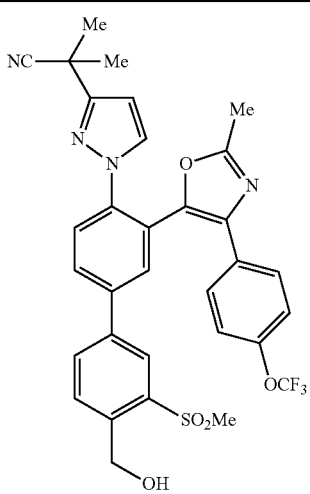 | 2-(1-(4'-(hydroxymethyl)-3-(2-methyl-4-(4-(trifluoromethoxy)phenyl)oxazol-5-yl)-3'-(methylsulfonyl)-[1,1'-biphenyl]-4-yl)-1H-pyrazol-3-yl)-2-methylpropanenitrile |
| 379 | 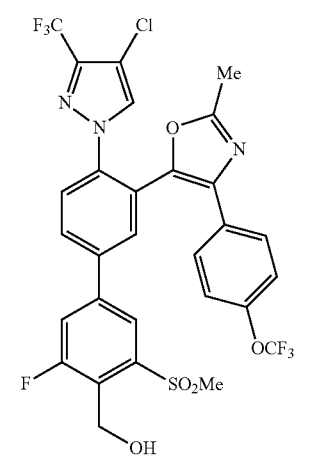 [SMILES: Cc1nc(-c2ccc(OC(F)(F)F)cc2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3-fluoro-3'-(2-methyl-4-(4-(trifluoromethoxy)phenyl)oxazol-5-yl)-5-(methylsulfonyl)-[1,1'-biphenyl]-4-yl)methanol |
| 380 | 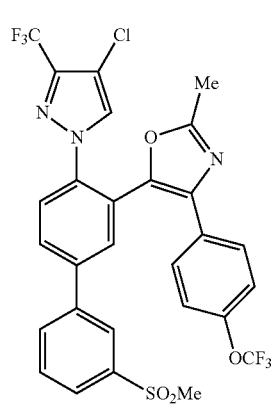 [SMILES: Cc1nc(-c2ccc(OC(F)(F)F)cc2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-2-methyl-4-(4-(trifluoromethoxy)phenyl)oxazole |

-continued

| Ex # | Structure | Name |
|---|---|---|
| 381 | 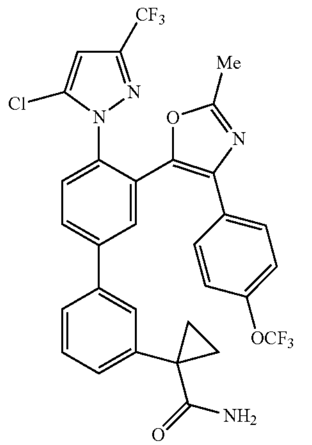 [SMILES: Cc1nc(-c2ccc(OC(F)(F)F)cc2)c(-c2cc(-c3cccc(C4(C(N)=O)CC4)c3)ccc2-n2nc(C(F)(F)F)cc2Cl)o1] | 1-(4'-(5-chloro-3-(trifluoromethyl)-1H-pyrazol-1-yl)-3'-(2-methyl-4-(4-(trifluoromethoxy)phenyl)oxazol-5-yl)-[1,1'-biphenyl]-3-yl)cyclopropanecarboxamide |
| 382 | 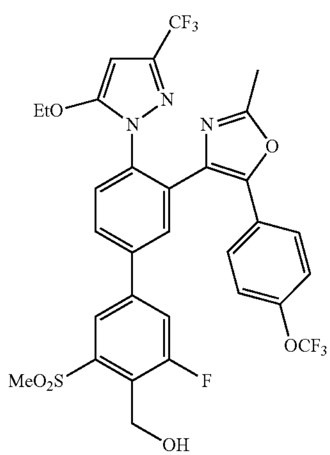 [SMILES: CCOc1cc(C(F)(F)F)nn1-c1ccc(-c2cc(F)c(CO)c(S(C)(=O)=O)c2)cc1-c1nc(C)oc1-c1ccc(OC(F)(F)F)cc1] | (4'-(5-ethoxy-3-(trifluoromethyl)-1H-pyrazol-1-yl)-3-fluoro-3'-(2-methyl-5-(4-(trifluoromethoxy)phenyl)oxazol-4-yl)-5-(methylsulfonyl)biphenyl-4-yl)methanol |
| 383 | 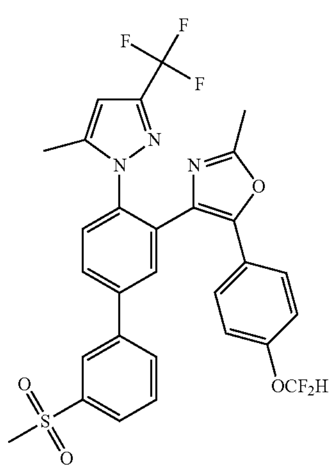 | 5-(4-(difluoromethoxy)phenyl)-2-methyl-4-(4-(5-methyl-3-(trifluoromethyl)-1H-pyrazol-1-yl)-3'-(methylsulfonyl)biphenyl-3-yl)oxazole |

-continued

| Ex # | Structure | Name |
|---|---|---|
| 384 | 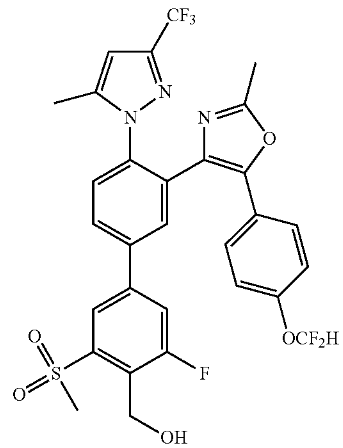 | (3'-(5-(4-(difluoromethoxy)phenyl)-2-methyloxazol-4-yl)-3-fluoro-4'-(5-methyl-3-(trifluoromethyl)-1H-pyrazol-1-yl)-5-(methylsulfonyl)biphenyl-4-yl)methanol |
| 385 | 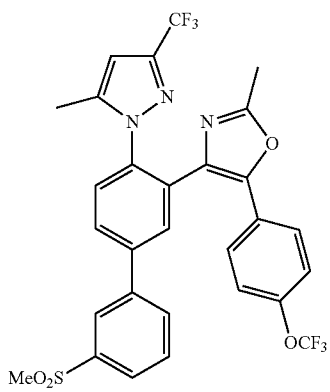 [SMILES: Cc1nc(-c2cc(-c3cccc(S(C)(=O)=O)c3)ccc2-n2nc(C(F)(F)F)cc2C)c(-c2ccc(OC(F)(F)F)cc2)o1] | 2-methyl-4-(4-(5-methyl-3-(trifluoromethyl)-1H-pyrazol-1-yl)-3'-(methylsulfonyl)biphenyl-3-yl)-5-(4-(trifluoromethoxy)phenyl)oxazole |
| 386 | 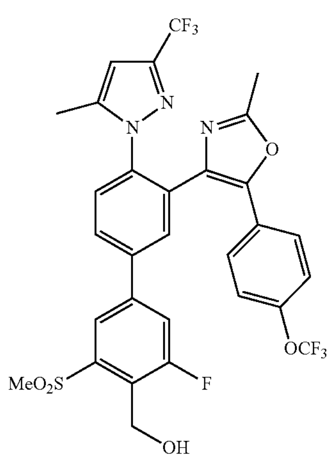 [SMILES: Cc1nc(-c2cc(-c3cc(F)c(CO)c(S(C)(=O)=O)c3)ccc2-n2nc(C(F)(F)F)cc2C)c(-c2ccc(OC(F)(F)F)cc2)o1] | (3-fluoro-4'-(5-methyl-3-(trifluoromethyl)-1H-pyrazol-1-yl)-3'-(2-methyl-5-(4-(trifluoromethoxy)phenyl)oxazol-4-yl)-5-(methylsulfonyl)biphenyl-4-yl)methanol |

-continued

| Ex # | Structure | Name |
|---|---|---|
| 387 | 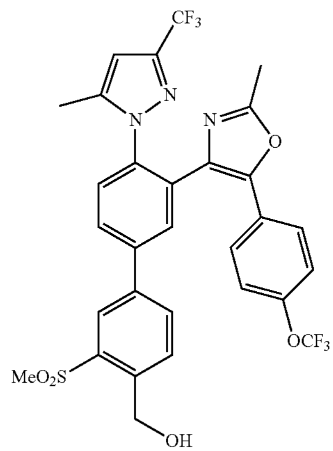 [SMILES: Cc1nc(-c2cc(-c3ccc(CO)c(S(C)(=O)=O)c3)ccc2-n2nc(C(F)(F)F)cc2C)c(-c2ccc(OC(F)(F)F)cc2)o1] | (4'-(5-methyl-3-(trifluoromethyl)-1H-pyrazol-1-yl)-3'-(2-methyl-5-(4-(trifluoromethoxy)phenyl)oxazol-4-yl)-3-(methylsulfonyl)biphenyl-4-yl)methanol |
| 388 | 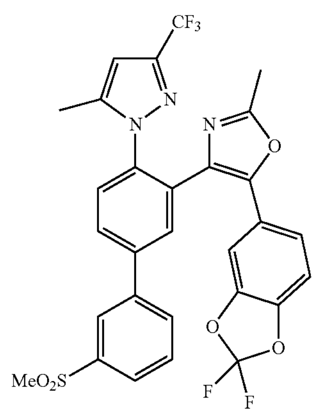 [SMILES: Cc1nc(-c2cc(-c3cccc(S(C)(=O)=O)c3)ccc2-n2nc(C(F)(F)F)cc2C)c(-c2ccc3c(c2)OC(F)(F)O3)o1] | 5-(2,2-difluorobenzo[d][1,3]dioxol-5-yl)-2-methyl-4-(4-(5-methyl-3-(trifluoromethyl)-1H-pyrazol-1-yl)-3'-(methylsulfonyl)biphenyl-3-yl)oxazole |
| 389 | 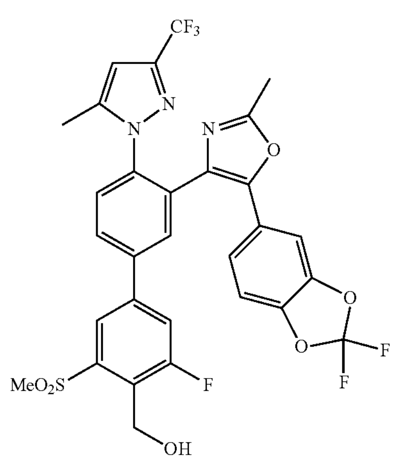 [SMILES: Cc1nc(-c2cc(-c3cc(F)c(CO)c(S(C)(=O)=O)c3)ccc2-n2nc(C(F)(F)F)cc2C)c(-c2ccc3c(c2)OC(F)(F)O3)o1] | difluorobenzo[d][1,3]dioxol-5-yl)-2-methyloxazol-4-yl)-3-fluoro-4'-(5-methyl-3-(trifluoromethyl)-1H-pyrazol-1-yl)-5-(methylsulfonyl)biphenyl-4-yl)methanol |

| Ex # | Structure | Name |
|---|---|---|
| 390 | 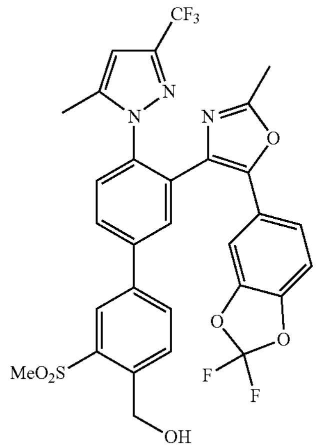 [SMILES: Cc1nc(-c2cc(-c3ccc(CO)c(S(C)(=O)=O)c3)ccc2-n2nc(C(F)(F)F)cc2C)c(-c2ccc3c(c2)OC(F)(F)O3)o1] | (3'-(5-(2,2-difluorobenzo[d][1,3]dioxol-5-yl)-2-methyloxazol-4-yl)-4'-(5-methyl-3-(trifluoromethyl)-1H-pyrazol-1-yl)-3-(methylsulfonyl)biphenyl-4-yl)methanol |
| 391 | 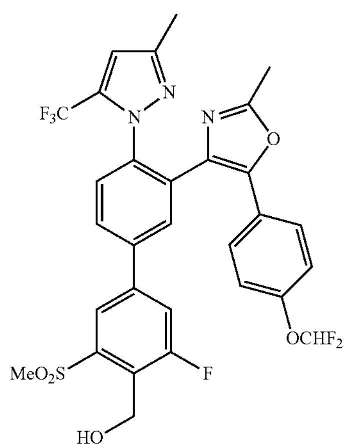 [SMILES: Cc1cc(C(F)(F)F)n(-c2ccc(-c3cc(F)c(CO)c(S(C)(=O)=O)c3)cc2-c2nc(C)oc2-c2ccc(OC(F)F)cc2)n1] | (3'-(5-(4-(difluoromethoxy)phenyl)-2-methyloxazol-4-yl)-3-fluoro-4'-(3-methyl-5-(trifluoromethyl)-1H-pyrazol-1-yl)-5-(methylsulfonyl)biphenyl-4-yl)methanol |
| 392 | 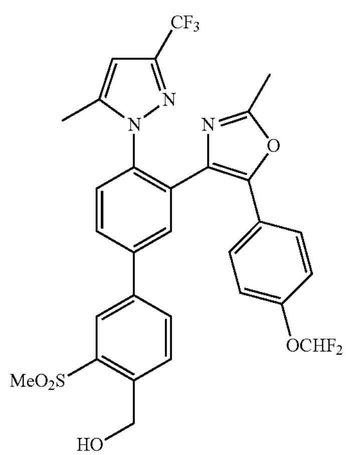 [SMILES: Cc1nc(-c2cc(-c3ccc(CO)c(S(C)(=O)=O)c3)ccc2-n2nc(C(F)(F)F)cc2C)c(-c2ccc(OC(F)F)cc2)o1] | (3'-(5-(4-(difluoromethoxy)phenyl)-2-methyloxazol-4-yl)-4'-(5-methyl-3-(trifluoromethyl)-1H-pyrazol-1-yl)-3-methylsulfonyl)biphenyl-4-yl)methanol |

| Ex # | Structure | Name |
|---|---|---|
| 393 | 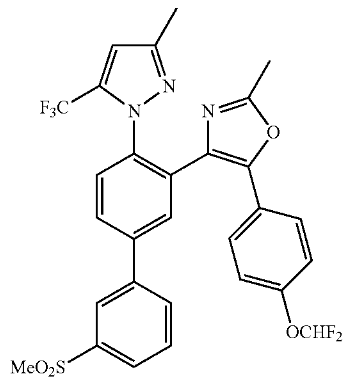 [SMILES: Cc1cc(C(F)(F)F)n(-c2ccc(-c3cccc(S(C)(=O)=O)c3)cc2-c2nc(C)oc2-c2ccc(OC(F)F)cc2)n1] | 5-(4-(difluoromethoxy)phenyl)-2-methyl-4-(4-(3-methyl-5-(trifluoromethyl)-1H-pyrazol-1-yl)-3'-(methylsulfonyl)biphenyl-3-yl)oxazole |
| 394 | 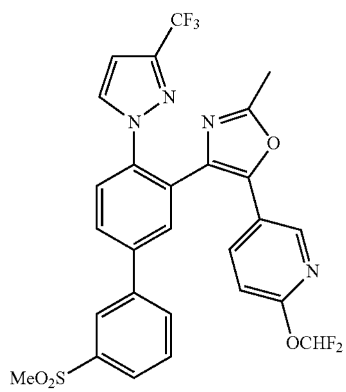 [SMILES: Cc1nc(-c2cc(-c3cccc(S(C)(=O)=O)c3)ccc2-n2ccc(C(F)(F)F)n2)c(-c2ccc(OC(F)F)nc2)o1] | 5-(6-(difluoromethoxy)pyridin-3-yl)-2-methyl-4-(3'-(methylsulfonyl)-4-(3-(trifluoromethyl)-1H-pyrazol-1-yl)biphenyl-3-yl)oxazole |
| 395 | 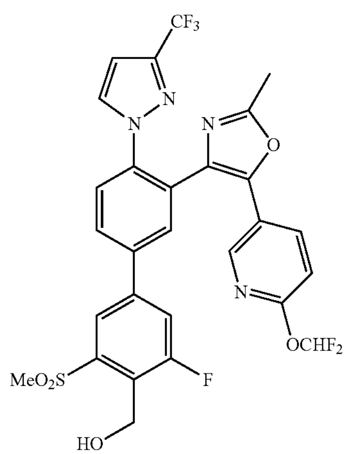 [SMILES: Cc1nc(-c2cc(-c3cc(F)c(CO)c(S(C)(=O)=O)c3)ccc2-n2ccc(C(F)(F)F)n2)c(-c2ccc(OC(F)F)nc2)o1] | (3'-(5-(6-(difluoromethoxy)pyridin-3-yl)-2-methyloxazol-4-yl)-3-fluoro-5-(methylsulfonyl)-4'-(3-(trifluoromethyl)-1H-pyrazol-1-yl)biphenyl-4-yl)methanol |

-continued

| Ex # | Structure | Name |
|---|---|---|
| 396 | 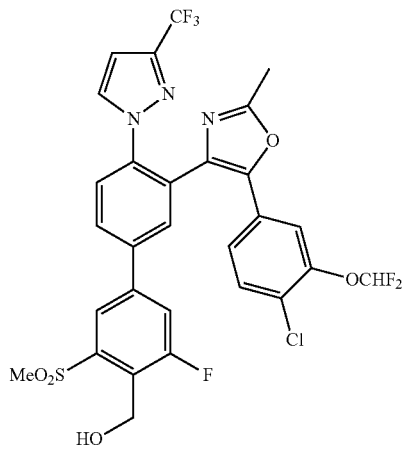 [SMILES: Cc1nc(-c2cc(-c3cc(F)c(CO)c(S(C)(=O)=O)c3)ccc2-n2ccc(C(F)(F)F)n2)c(-c2ccc(Cl)c(OC(F)F)c2)o1] | (3'-(5-(4-chloro-3-(difluoromethoxy)phenyl)-2-methyloxazol-4-yl)-3-fluoro-5-(methylsulfonyl)-4'-(3-(trifluoromethyl)-1H-pyrazol-1-yl)biphenyl-4-yl)methanol |
| 397 | 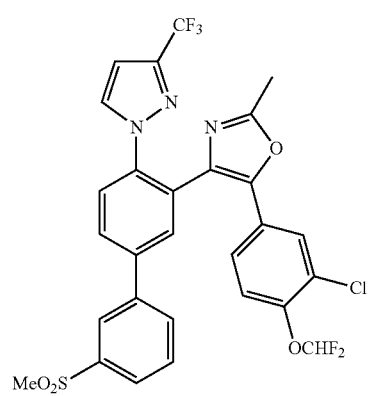 [SMILES: Cc1nc(-c2cc(-c3cccc(S(C)(=O)=O)c3)ccc2-n2ccc(C(F)(F)F)n2)c(-c2ccc(OC(F)F)c(Cl)c2)o1] | 5-(3-chloro-4-(difluoromethoxy)phenyl)-2-methyl-4-(3'-(methylsulfonyl)-4-(3-(trifluoromethyl)-1H-pyrazol-1-yl)biphenyl-3-yl)oxazole |
| 398 | 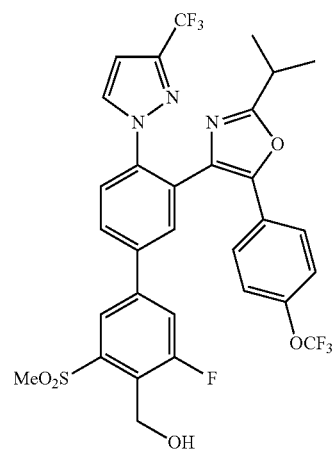 [SMILES: CC(C)c1nc(-c2cc(-c3cc(F)c(CO)c(S(C)(=O)=O)c3)ccc2-n2ccc(C(F)(F)F)n2)c(-c2ccc(OC(F)(F)F)cc2)o1] | (3-fluoro-3'-(2-isopropyl-5-(4-(trifluoromethoxy)phenyl)oxazol-4-yl)-5-(methylsulfonyl)-4'-(3-(trifluoromethyl)-1H-pyrazol-1-yl)biphenyl-4-yl)methanol |

-continued
| Ex # | Structure | Name |
|---|---|---|
| 399 | 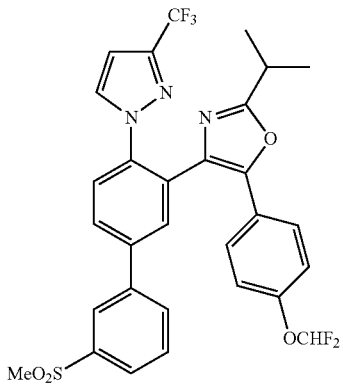 [SMILES: CC(C)c1nc(-c2cc(-c3cccc(S(C)(=O)=O)c3)ccc2-n2ccc(C(F)(F)F)n2)c(-c2ccc(OC(F)F)cc2)o1] | 2-isopropyl-4-(3'-(methylsulfonyl)-4-(3-(trifluoromethyl)-1H-pyrazol-1-yl)biphenyl-3-yl)-5-(4-(trifluoromethoxy)phenyl)oxazole |
| 400 | 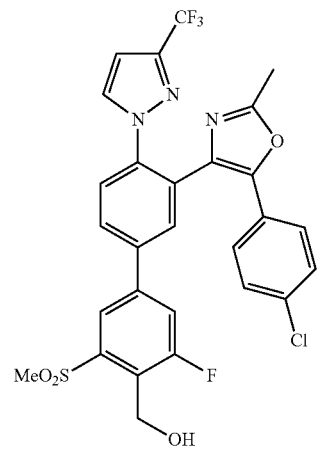 [SMILES: Cc1nc(-c2cc(-c3cc(F)c(CO)c(S(C)(=O)=O)c3)ccc2-n2ccc(C(F)(F)F)n2)c(-c2ccc(Cl)cc2)o1] | (3'-(5-(4-chlorophenyl)-2-methyloxazol-4-yl)-3-fluoro-5-(methylsulfonyl)-4'-(3-(trifluoromethyl)-1H-pyrazol-1-yl)biphenyl-4-yl)methanol |
| 401 | 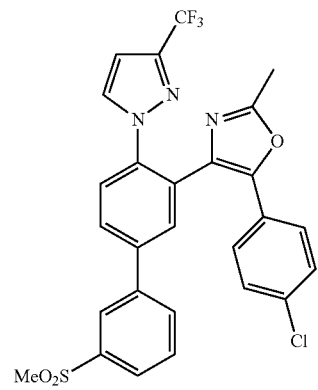 [SMILES: Cc1nc(-c2cc(-c3cccc(S(C)(=O)=O)c3)ccc2-n2ccc(C(F)(F)F)n2)c(-c2ccc(Cl)cc2)o1] | 5-(4-chlorophenyl)-2-methyl-4-(3'-(methylsulfonyl)-4-(3-(trifluoromethyl)-1H-pyrazol-1-yl)biphenyl-3-yl)oxazole |

| Ex # | Structure | Name |
|---|---|---|
| 402 | 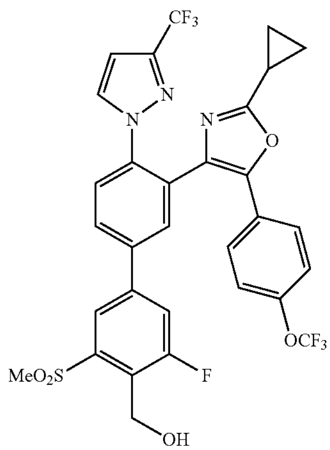 [SMILES: CS(=O)(=O)c1cc(-c2ccc(-n3ccc(C(F)(F)F)n3)c(-c3nc(C4CC4)oc3-c3ccc(OC(F)(F)F)cc3)c2)cc(F)c1CO] | (3'-(2-cyclopropyl-5-(4-(trifluoromethoxy)phenyl)oxazol-4-yl)-3-fluoro-5-(methylsulfonyl)-4'-(3-(trifluoromethyl)-1H-pyrazol-1-yl)biphenyl-4-yl)methanol |
| 403 | 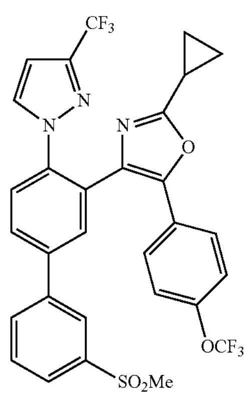 [SMILES: CS(=O)(=O)c1cccc(-c2ccc(-n3ccc(C(F)(F)F)n3)c(-c3nc(C4CC4)oc3-c3ccc(OC(F)(F)F)cc3)c2)c1] | 2-cyclopropyl-4-(3'-(methylsulfonyl)-4-(3-(trifluoromethyl)-1H-pyrazol-1-yl)biphenyl-3-yl)-5-(4-(trifluoromethoxy)phenyl)oxazole |
| 404 | 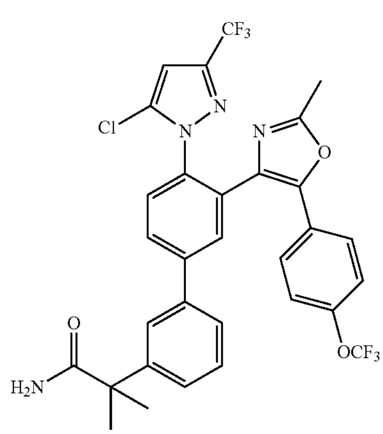 [SMILES: Cc1nc(-c2cc(-c3cccc(C(C)(C)C(N)=O)c3)ccc2-n2nc(C(F)(F)F)cc2Cl)c(-c2ccc(OC(F)(F)F)cc2)o1] | 2-(4'-(5-chloro-3-(trifluoromethyl)-1H-pyrazol-1-yl)-3'-(2-methyl-5-(4-(trifluoromethoxy)phenyl)oxazol-4-yl)biphenyl-3-yl)-2-methylpropanamide |

-continued

| Ex # | Structure | Name |
|---|---|---|
| 405 | 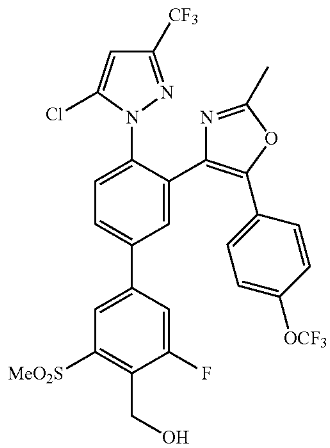 [SMILES: Cc1nc(-c2cc(-c3cc(F)c(CO)c(S(C)(=O)=O)c3)ccc2-n2nc(C(F)(F)F)cc2Cl)c(-c2ccc(OC(F)(F)F)cc2)o1] | (4'-(5-chloro-3-(trifluoromethyl)-1H-pyrazol-1-yl)-3-fluoro-3'-(2-methyl-5-(4-(trifluoromethoxy)phenyl)oxazol-4-yl)-5-(methylsulfonyl)biphenyl-4-yl)methanol |
| 406 | 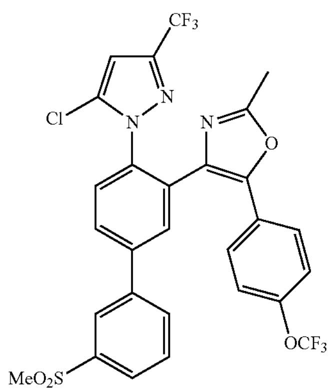 [SMILES: Cc1nc(-c2cc(-c3cccc(S(C)(=O)=O)c3)ccc2-n2nc(C(F)(F)F)cc2Cl)c(-c2ccc(OC(F)(F)F)cc2)o1] | 4-(4-(5-chloro-3-(trifluoromethyl)-1H-pyrazol-1-yl)-3'-(methylsulfonyl)biphenyl-3-yl)-2-methyl-5-(4-(trifluoromethoxy)phenyl)oxazole |
| 407 | 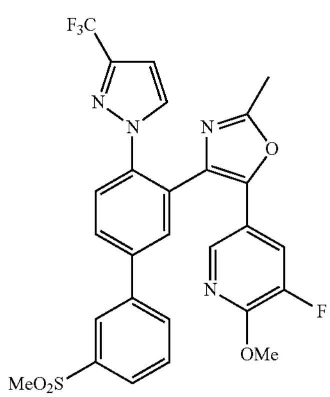 [SMILES: COc1ncc(-c2oc(C)nc2-c2cc(-c3cccc(S(C)(=O)=O)c3)ccc2-n2ccc(C(F)(F)F)n2)cc1F] | 5-(5-fluoro-6-methoxypyridin-3-yl)-2-methyl-4-(3'-(methylsulfonyl)-4-(3-(trifluoromethyl)-1H-pyrazol-1-yl)biphenyl-3-yl)oxazole |

-continued

| Ex # | Structure | Name |
|---|---|---|
| 408 | 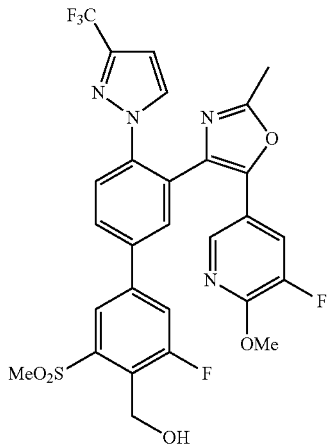 [SMILES: COc1ncc(-c2oc(C)nc2-c2cc(-c3cc(F)c(CO)c(S(C)(=O)=O)c3)ccc2-n2ccc(C(F)(F)F)n2)cc1F] | (3-fluoro-3'-(5-(5-fluoro-6-methoxypyridin-3-yl)-2-methyloxazol-4-yl)-5-(methylsulfonyl)-4'-(3-(trifluoromethyl)-1H-pyrazol-1-yl)biphenyl-4-yl)methanol |
| 409 | 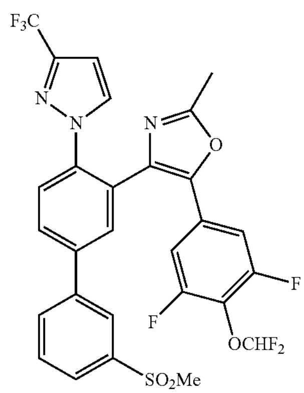 [SMILES: Cc1nc(-c2cc(-c3cccc(S(C)(=O)=O)c3)ccc2-n2ccc(C(F)(F)F)n2)c(-c2cc(F)c(OC(F)F)c(F)c2)o1] | 5-(4-(difluoromethoxy)-3,5-difluorophenyl)-2-methyl-4-(3'-(methylsulfonyl)-4-(3-(trifluoromethyl)-1H-pyrazol-1-yl)biphenyl-3-yl)oxazole |
| 410 | 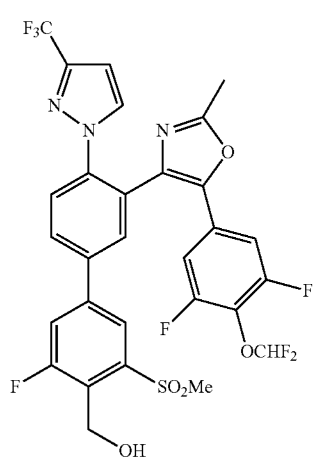 [SMILES: Cc1nc(-c2cc(-c3cc(F)c(CO)c(S(C)(=O)=O)c3)ccc2-n2ccc(C(F)(F)F)n2)c(-c2cc(F)c(OC(F)F)c(F)c2)o1] | (3'-(5-(4-(difluoromethoxy)-3,5-difluorophenyl)-2-methyloxazol-4-yl)-3-fluoro-5-(methylsulfonyl)-4'-(3-(trifluoromethyl)-1H-pyrazol-1-yl)biphenyl-4-yl)methanol |

-continued

| Ex # | Structure | Name |
|---|---|---|
| 411 | 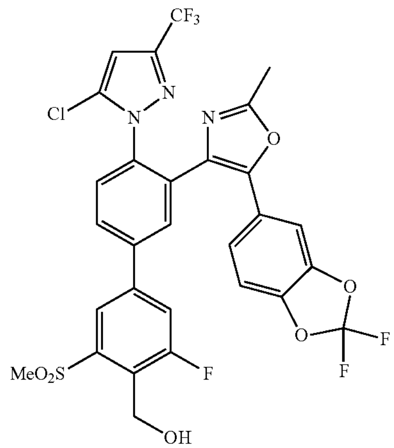 | (4'-(5-chloro-3-(trifluoromethyl)-1H-pyrazol-1-yl)-3'-(5-(2,2-difluorobenzo[d][1,3]dioxol-5-yl)-2-methyloxazol-4-yl)-3-fluoro-5-(methylsulfonyl)biphenyl-4-yl)methanol |
| 412 | 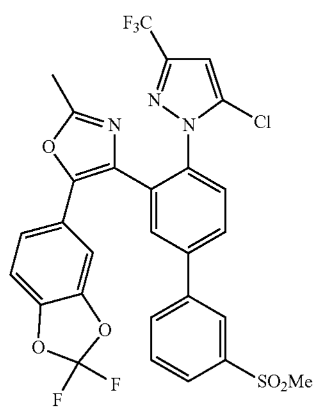 [SMILES: Cc1nc(-c2cc(-c3cccc(S(C)(=O)=O)c3)ccc2-n2nc(C(F)(F)F)cc2Cl)c(-c2ccc3c(c2)OC(F)(F)O3)o1] | 4-(4-(5-chloro-3-(trifluoromethyl)-1H-pyrazol-1-yl)-3'-(methylsulfonyl)biphenyl-3-yl)-5-(2,2-difluorobenzo[d][1,3]dioxol-5-yl)-2-methyloxazole |
| 413 | 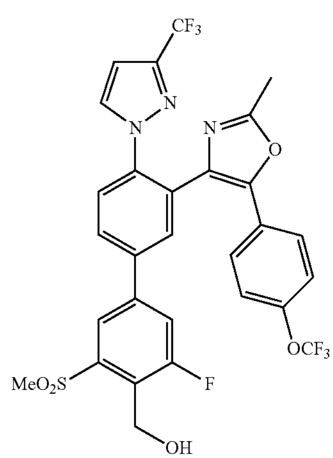 [SMILES: Cc1nc(-c2cc(-c3cc(F)c(CO)c(S(C)(=O)=O)c3)ccc2-n2ccc(C(F)(F)F)n2)c(-c2ccc(OC(F)(F)F)cc2)o1] | (3-fluoro-3'-(2-methyl-5-(4-trifluoromethoxy)phenyl)oxazol-4-yl)-5-(methylsulfonyl)-4'-(3-(trifluoromethyl)-1H-pyrazol-1-yl)biphenyl-4-yl)methanol |

| Ex # | Structure | Name |
|---|---|---|
| 414 | 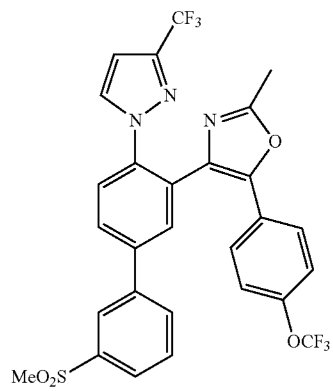 [SMILES: Cc1nc(-c2cc(-c3cccc(S(C)(=O)=O)c3)ccc2-n2ccc(C(F)(F)F)n2)c(-c2ccc(OC(F)(F)F)cc2)o1] | 2-methyl-4-(3'-(methylsulfonyl)-4-(3-(trifluoromethyl)-1H-pyrazol-1-yl)biphenyl-3-yl)-5-(4-(trifluoromethoxy)phenyl)oxazole |
| 415 | 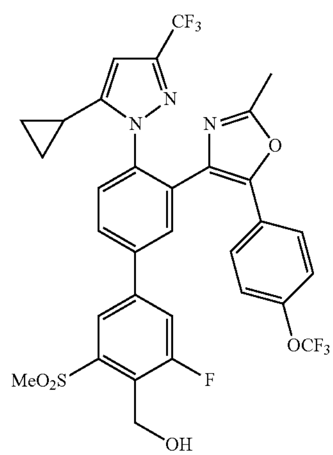 [SMILES: Cc1nc(-c2cc(-c3cc(F)c(CO)c(S(C)(=O)=O)c3)ccc2-n2nc(C(F)(F)F)cc2C2CC2)c(-c2ccc(OC(F)(F)F)cc2)o1] | (4'-(5-cyclopropyl-3-(trifluoromethyl)-1H-pyrazol-1-yl)-3-fluoro-3'-(2-methyl-5-(4-(trifluoromethoxy)phenyl)oxazol-4-yl)-5-(methylsulfonyl)biphenyl-4-yl)methanol |
| 416 | 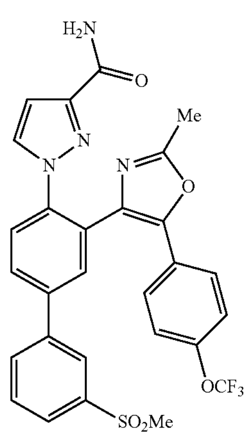 [SMILES: Cc1nc(-c2cc(-c3cccc(S(C)(=O)=O)c3)ccc2-n2ccc(C(N)=O)n2)c(-c2ccc(OC(F)(F)F)cc2)o1] | 1-(3-(2-methyl-5-(4-(trifluoromethoxy)phenyl)oxazol-4-yl)-3'-(methylsulfonyl)-[1,1'-biphenyl]-4-yl)-1H-pyrazole-3-carboxamide |

-continued

| Ex # | Structure | Name |
|---|---|---|
| 417 | 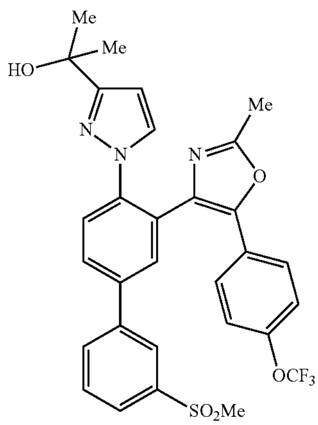 [SMILES: Cc1nc(-c2cc(-c3cccc(S(C)(=O)=O)c3)ccc2-n2ccc(C(C)(C)O)n2)c(-c2ccc(OC(F)(F)F)cc2)o1] | 2-(1-(3-(2-methyl-5-(4-(trifluoromethoxy)phenyl)oxazol-4-yl)-3'-(methylsulfonyl)41,1'-biphenyl]-4-yl)-1H-pyrazol-3-yl)propan-2-ol |
| 418 | 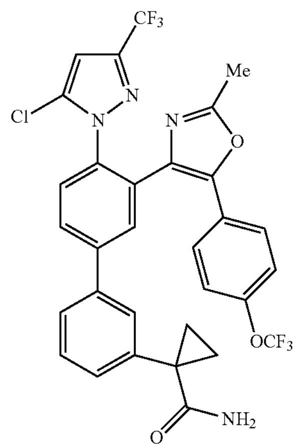 [SMILES: Cc1nc(-c2cc(-c3cccc(C4(C(N)=O)CC4)c3)ccc2-n2nc(C(F)(F)F)cc2Cl)c(-c2ccc(OC(F)(F)F)cc2)o1] | 1-(4'-(5-chloro-3-(trifluoromethyl)-1H-pyrazol-1-yl)-3'-(2-methyl-5-(4-(trifluoromethoxy)phenyl)oxazol-4-yl)-[1,1'-biphenyl]-3-yl)cyclopropanecarboxamide |
| 419 | 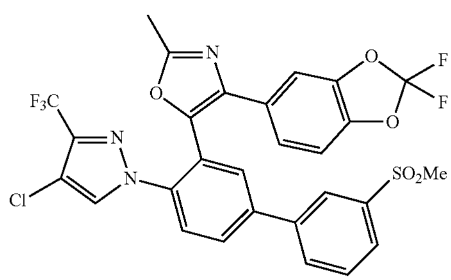 [SMILES: Cc1nc(-c2ccc3c(c2)OC(F)(F)O3)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(2,2-difluorobenzo[d][1,3]dioxol-5-yl)-2-methyloxazole |
| 420 | 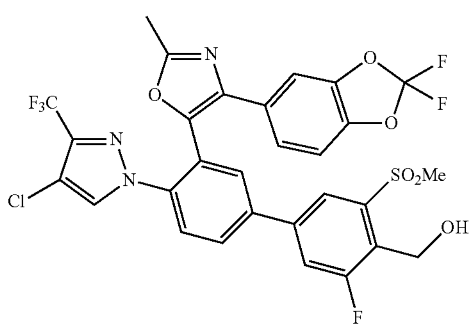 [SMILES: Cc1nc(-c2ccc3c(c2)OC(F)(F)O3)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(2,2-difluorobenzo[d][1,3]dioxol-5-yl)-2-methyloxazol-5-yl)-3-fluoro-5-(methylsulfonyl)-[1,1'-biphenyl]-4-yl)methanol |

-continued

| Ex # | Structure | Name |
|---|---|---|
| 421 | 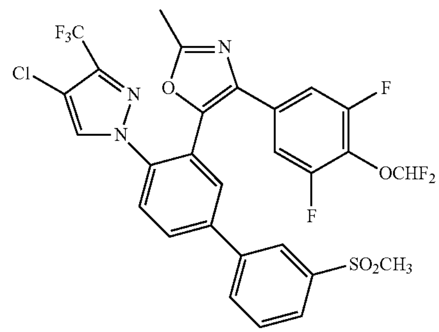 [SMILES: Cc1nc(-c2cc(F)c(OC(F)F)c(F)c2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(4-(difluoromethoxy)-3,5-difluorophenyl)-2-methyloxazole |
| 422 | 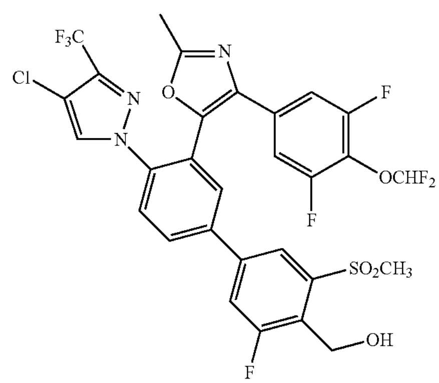 [SMILES: Cc1nc(-c2cc(F)c(OC(F)F)c(F)c2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'(4-(difluoromethoxy)-3,5-difluorophenyl)-2-methyloxazol-5-yl)-3-fluoro-5-(methylsulfonyl)-[1,1'-biphenyl]-4-yl)methanol |
| 423 | 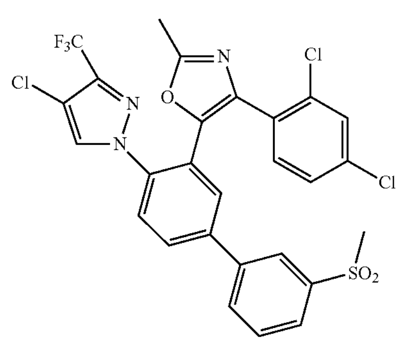 [SMILES: Cc1nc(-c2ccc(Cl)cc2Cl)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(2,4-dichlorophenyl)-2-methyloxazole |
| 424 | 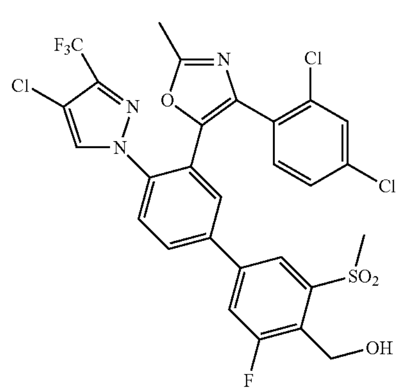 [SMILES: Cc1nc(-c2ccc(Cl)cc2Cl)c(-c2cc(-c3cc(F)c(CO)c(S(C)(=O)=O)c3)ccc2-n2cc(Cl)c(C(F)(F)F)n2)o1] | (4'-(4-chloro-3-trifluoromethyl)-1H-pyrazol-1-yl)-3'-(4-(2,4-dichlorophenyl)-2-methyloxazol-5-yl)-3-fluoro-5-(methylsulfonyl)-[1,1'-biphenyl]-4-yl)methanol |

| Ex # | Structure | Name |
|---|---|---|
| 425 | 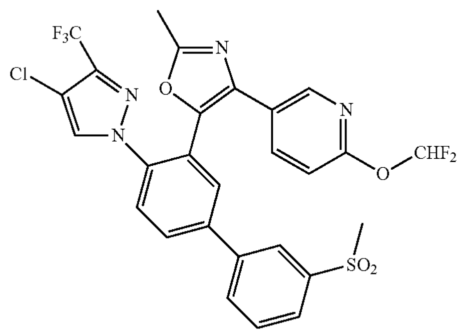 [SMILES: Cc1nc(-c2ccc(OC(F)F)nc2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(6-(difluoromethoxy)pyridin-3-yl)-2-methyloxazole |
| 426 | 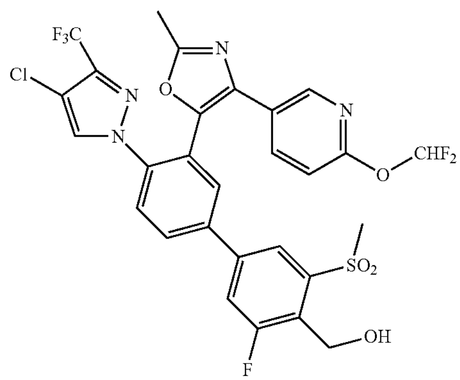 [SMILES: Cc1nc(-c2ccc(OC(F)F)nc2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(6-(difluoromethoxy)pyridin-3-yl)-2-methyloxazol-5-yl)-3-fluoro-5-(methylsulfonyl)-[1,1'-biphenyl]-4-yl)methanol |
| 427 | 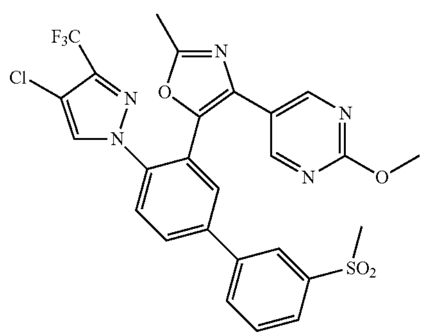 [SMILES: COc1ncc(-c2nc(C)oc2-c2cc(-c3cccc(S(C)(=O)=O)c3)ccc2-n2cc(Cl)c(C(F)(F)F)n2)cn1] | 5-(4-(4-chloro-3-(trifluoromethyl)-1H-pyrazol-1-yl)-3'-(methylsulfonyl)-[1,1'-biphenyl]-3-yl)-4-(2-methoxypyrimidin-5-yl)-2-methyloxazole |
| 428 | 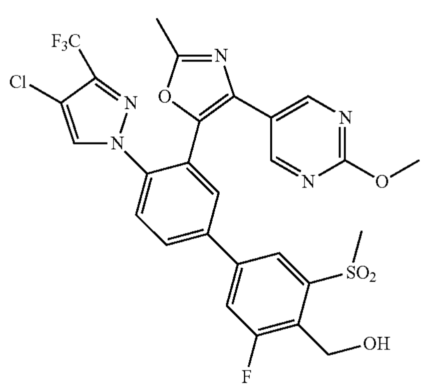 [SMILES: COc1ncc(-c2nc(C)oc2-c2cc(-c3cc(F)c(CO)c(S(C)(=O)=O)c3)ccc2-n2cc(Cl)c(C(F)(F)F)n2)cn1] | (4'-(4-chloro-3-(trifluoromethyl)-1H-pyrazol-1-yl)-3-fluoro-3'-(4-(2-methoxypyrimidin-5-yl)-2-methyloxazol-5-yl)-5-(methylsulfonyl)-[1,1'-biphenyl]-4-yl)methanol |

-continued

| Ex # | Structure | Name |
|---|---|---|
| 429 | 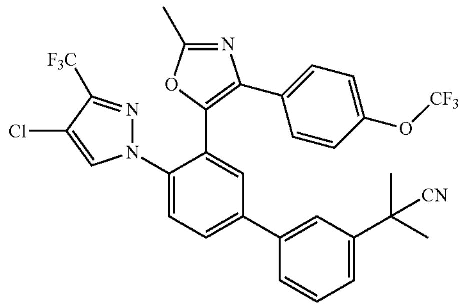 [SMILES: Cc1nc(-c2ccc(OC(F)(F)F)cc2)c(-c2cc(-c3cccc(C(C)(C)C#N)c3)ccc2-n2cc(Cl)c(C(F)(F)F)n2)o1] | 2-(4'-(4-chloro-3-(trifluoromethyl)-1H-pyrazol-1-yl)-3'-(2-methyl-4-(4-(trifluoromethoxy)phenyl)oxazol-5-yl)-[1,1'-biphenyl]-3-yl)-2-methylpropanenitrile |
| 430 | 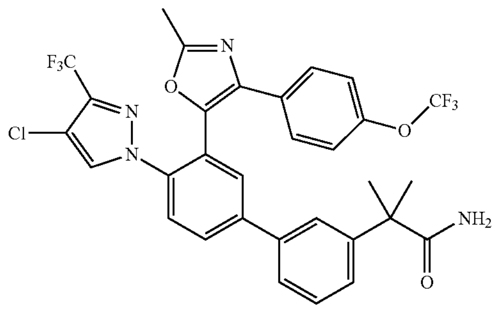 [SMILES: Cc1nc(-c2ccc(OC(F)(F)F)cc2)c(-c2cc(-c3cccc(C(C)(C)C(N)=O)c3)ccc2-n2cc(Cl)c(C(F)(F)F)n2)o1] | 2-(4'-(4-chloro-3-(trifluoromethyl)-1H-pyrazol-1-yl)-3'-(2-methyl-4-(4-(trifluoromethoxy)phenyl)oxazol-5-yl)-[1,1'-biphenyl]-3-yl)-2-methylpropanamide |
| 431 | 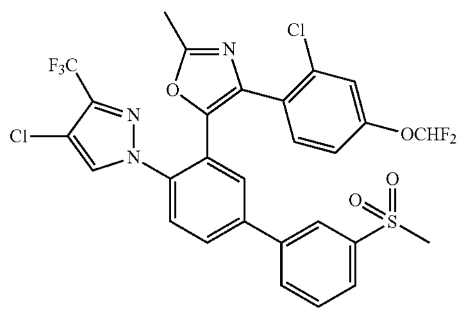 [SMILES: Cc1nc(-c2ccc(OC(F)F)cc2Cl)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(2-chloro-4-(difluoromethoxy)phenyl)-2-methyloxazole |
| 432 | 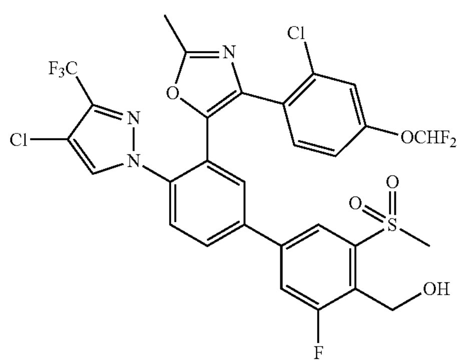 [SMILES: Cc1nc(-c2ccc(OC(F)F)cc2Cl)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(2-chloro-4-(difluoromethoxy)phenyl)-2-methyloxazol-5-yl)-3-fluoro-5-(methylsulfonyl)-[1,1'-biphenyl]-4-yl)methanol |
| 433 | 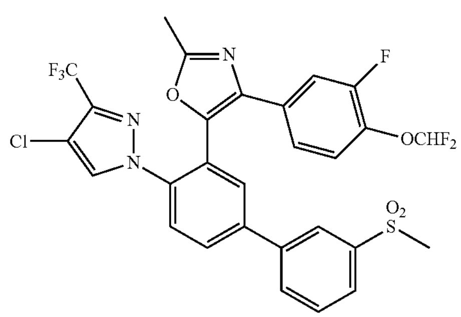 [SMILES: Cc1nc(-c2ccc(OC(F)F)c(F)c2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-4-(4-(difluoromethoxy)-3-fluorophenyl)-2-methyloxazole |

-continued

| Ex # | Structure | Name |
|---|---|---|
| 434 | 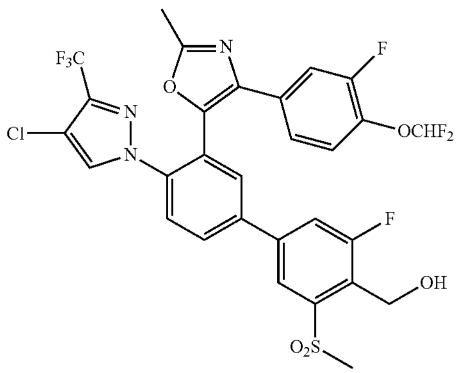 [SMILES: Cc1nc(-c2ccc(OC(F)F)c(F)c2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3'-(4-(difluoromethoxy)-3-fluorophenyl)-2-methyloxazol-5-yl)-3-fluoro-5-(methylsulfonyl)-[1,1'-biphenyl]-4-yl)methanol |
| 435 | 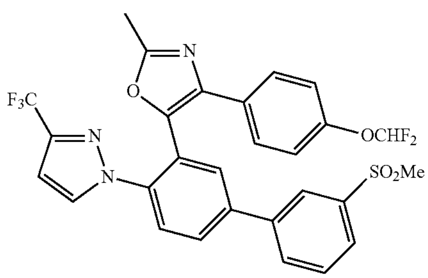 [SMILES: Cc1nc(-c2ccc(OC(F)F)cc2)c(-c2cc(-c3cccc(S(C)(=O)=O)c3)ccc2-n2ccc(C(F)(F)F)n2)o1] | 4-(4-(difluoromethoxy)phenyl)-2-methyl-5-(3'-(methylsulfonyl)-4-(3-(trifluoromethyl)-1H-pyrazol-1-yl)-[1,1'-biphenyl]-3-yl)oxazole |
| 436 | 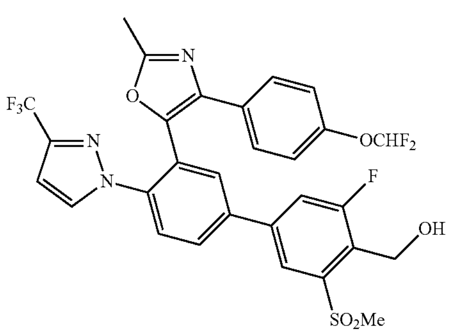 [SMILES: Cc1nc(-c2ccc(OC(F)F)cc2)c(-c2cc(-c3cc(F)c(CO)c(S(C)(=O)=O)c3)ccc2-n2ccc(C(F)(F)F)n2)o1] | (3'-(4-(4-(difluoromethoxy)phenyl)-2-methyloxazol-5-yl)-3-fluoro-5-(methylsulfonyl)-4'-(3-(trifluoromethyl)-1H-pyrazol-1-yl)-[1,1'-biphenyl]-4-yl)methanol |
| 437 | 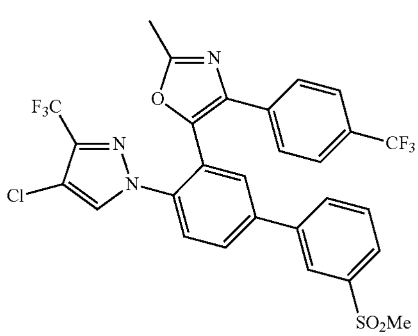 [SMILES: Cc1nc(-c2ccc(C(F)(F)F)cc2)c(-c2cc(-c3cccc(S(C)(=O)=O)c3)ccc2-n2cc(Cl)c(C(F)(F)F)n2)o1] | 5-(4-(4-chloro-3-(trifluoromethyl)-1H-pyrazol-1-yl)-3'-(methylsulfonyl)-[1,1'-biphenyl]-3-yl)-2-methyl-4-(4-(trifluoromethyl)phenyl)oxazole |

| Ex # | Structure | Name |
|---|---|---|
| 438 | 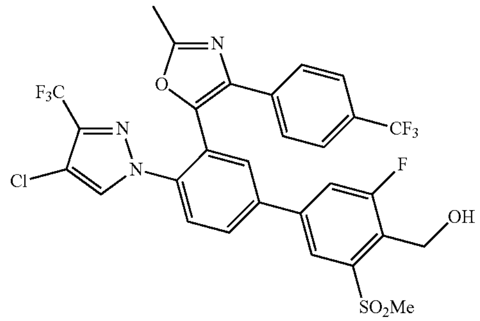 [SMILES: Cc1nc(-c2ccc(C(F)(F)F)cc2)c(-c2cc(-c3cc(F)c(CO)c(S(C)(=O)=O)c3)ccc2-n2cc(Cl)c(C(F)(F)F)n2)o1] | (4'-(4-chloro-3-(trifluoromethyl)-1H-pyrazol-1-yl)-3-fluoro-3'-(2-methyl-4-(4-(trifluoromethyl)phenyl)oxazol-5-yl)-5-(methylsulfonyl)-[1,1'-biphenyl]-4-yl)methanol |
| 439 | 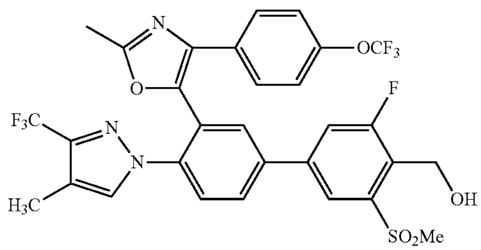 [SMILES: Cc1nc(-c2ccc(OC(F)(F)F)cc2)c(-c2cc(-c3cc(F)c(CO)c(S(C)(=O)=O)c3)ccc2-n2cc(C)c(C(F)(F)F)n2)o1] | (3-fluoro-4'-(4-methyl-3-(trifluoromethyl)-1H-pyrazol-1-yl)-3'-(2-methyl-4-(4-(trifluoromethoxy)phenyl)oxazol-5-yl)-5-(methylsulfonyl)-[1,1'-biphenyl]-4-yl)methanol |
| 440 | 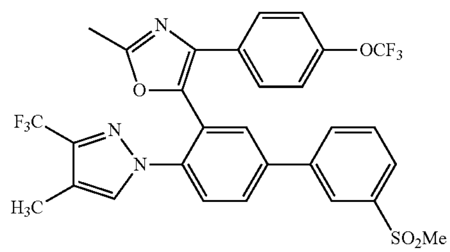 [SMILES: Cc1nc(-c2ccc(OC(F)(F)F)cc2)c(-c2cc(-c3cccc(S(C)(=O)=O)c3)ccc2-n2cc(C)c(C(F)(F)F)n2)o1] | 2-methyl-5-(4-(4-methyl-3-(trifluoromethyl)-1H-pyrazol-1-yl)-3'-(methylsulfonyl)-[1,1'-biphenyl]-3-yl)-4-(4-(trifluoromethoxy)phenyl)oxazole |
| 441 | 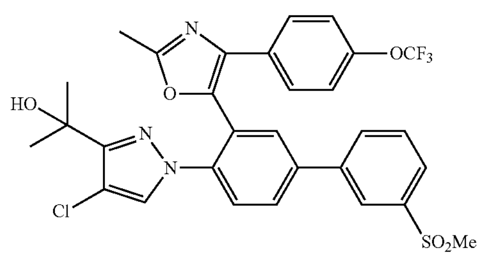 [SMILES: Cc1nc(-c2ccc(OC(F)(F)F)cc2)c(-c2cc(-c3cccc(S(C)(=O)=O)c3)ccc2-n2cc(Cl)c(C(C)(C)O)n2)o1] | 2-(4-chloro-1-(3-(2-methyl-4-(4-(trifluoromethoxy)phenyl)oxazol-5-yl)-3'-(methylsulfonyl)41,1'-biphenyl]-4-yl)-1H-pyrazol-3-yl)propan-2-ol |
| 442 | 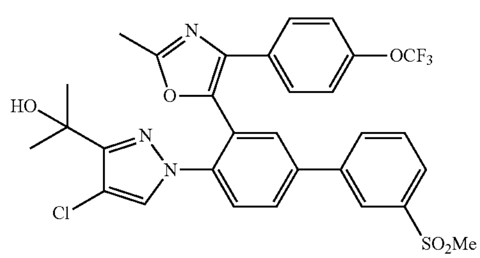 [SMILES: Cc1nc(-c2ccc(OC(F)(F)F)cc2)c(-c2cc(-c3cccc(S(C)(=O)=O)c3)ccc2-n2cc(Cl)c(C(C)(C)O)n2)o1] | 5-(4-(3-(1,1-difluoroethyl)-1H-pyrazol-1-yl)-3'-(methylsulfonyl)-[1,1'-biphenyl]-3-yl)-2-methyl-4-(4-(trifluoromethoxy)phenyl)oxazole |
| 443 | 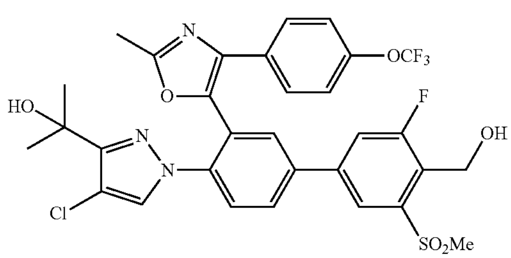 [SMILES: Cc1nc(-c2ccc(OC(F)(F)F)cc2)c(-c2cc(-c3cc(F)c(CO)c(S(C)(=O)=O)c3)ccc2-n2cc(Cl)c(C(C)(C)O)n2)o1] | 2-(4-chloro-1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazol-3-yl)propan-2-ol |

| Ex # | Structure | Name |
|---|---|---|
| 444 | 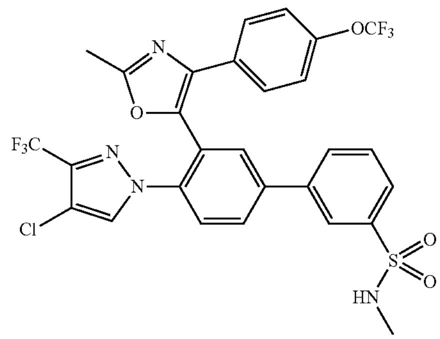 [SMILES: CNS(=O)(=O)c1cccc(-c2ccc(-n3cc(Cl)c(C(F)(F)F)n3)c(-c3oc(C)nc3-c3ccc(OC(F)(F)F)cc3)c2)c1] | 4'-(4-chloro-3-(trifluoromethyl)-1H-pyrazol-1-yl)-N-methyl-3'-(2-methyl-4-(4-(trifluoromethoxy)phenyl)oxazol-5-yl)-[1,1'-biphenyl]-3-sulfonamide |
| 445 | 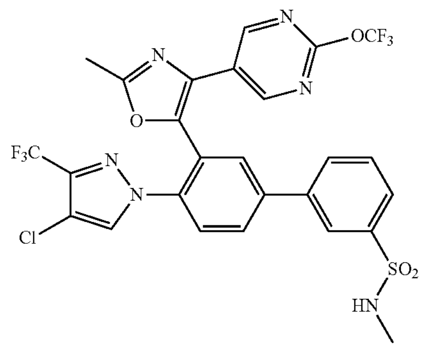 [SMILES: CNS(=O)(=O)c1cccc(-c2ccc(-n3cc(Cl)c(C(F)(F)F)n3)c(-c3oc(C)nc3-c3cnc(OC(F)(F)F)nc3)c2)c1] | 4'-(4-chloro-3-(trifluoromethyl)-1H-pyrazol-1-yl)-3'-(4-(2-methoxypyrimidin-5-yl)-2-methyloxazol-5-yl)-N-methyl-[1,1'-biphenyl]-3-sulfonamide |
| 446 | 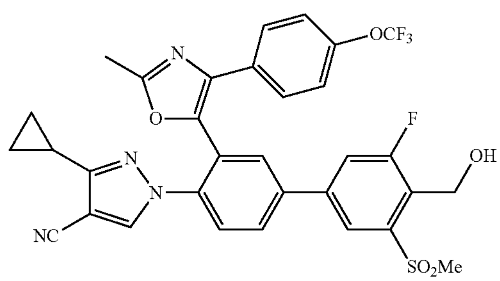 [SMILES: Cc1nc(-c2ccc(OC(F)(F)F)cc2)c(-c2cc(-c3cc(F)c(CO)c(S(C)(=O)=O)c3)ccc2-n2cc(C#N)c(C3CC3)n2)o1] | 3-cyclopropyl-1-(3'-fluoro-4'-(hydroxymethyl)-3-(2-methyl-4-(4-(trifluoromethoxy)phenyl)oxazol-5-yl)-5'-(methylsulfonyl)-[1,1'-biphenyl]-4-yl)-1H-pyrazole-4-carbonitrile |
| 447 | 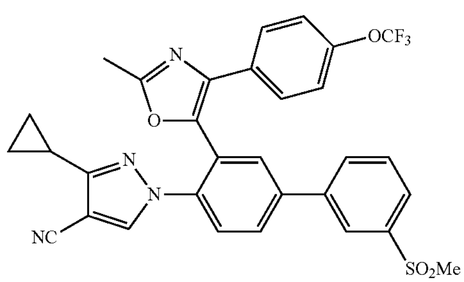 [SMILES: Cc1nc(-c2ccc(OC(F)(F)F)cc2)c(-c2cc(-c3cccc(S(C)(=O)=O)c3)ccc2-n2cc(C#N)c(C3CC3)n2)o1] | 3-cyclopropyl-1-(3-(2-methyl-4-(4-(trifluoromethoxy)phenyl)oxazol-5-yl)-3'-(methylsulfonyl)41,1'-biphenyl]-4-yl)-1H-pyrazole-4-carbonitrile |
| 448 | 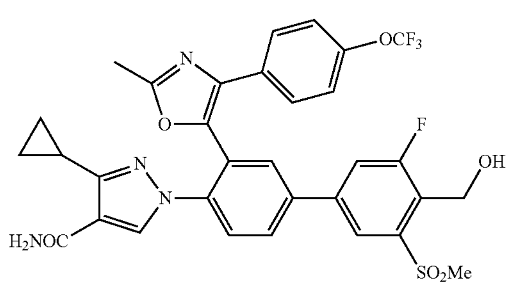 [SMILES: Cc1nc(-c2ccc(OC(F)(F)F)cc2)c(-c2cc(-c3cc(F)c(CO)c(S(C)(=O)=O)c3)ccc2-n2cc(C(N)=O)c(C3CC3)n2)o1] | 3-cyclopropyl-1-(3'-fluoro-4'-(hydroxymethyl)-3-(2-methyl-4-(4-(trifluoromethoxy)phenyl)oxazol-5-yl)-5'-(methylsulfonyl)41,1'-biphenyl]-4-yl)-1H-pyrazole-4-carboxamide. |

12. A composition comprising a compound of claim 1, or a pharmaceutically acceptable salt or solvate thereof, and one or more pharmaceutically acceptable carriers.

13. A method of therapeutically treating a disease or disorder, comprising administering to a subject in need thereof a therapeutically effective amount of a compound of claim 1, or a pharmaceutically acceptable salt or solvate thereof, wherein the disease or disorder is atherosclerosis or diabetes.

14. The method of claim 13, wherein the disease or disorder is atherosclerosis.

15. The method of claim 13, wherein the disease or disorder is diabetes.

16. A composition comprising a compound of claim 11, or a pharmaceutically acceptable salt or solvate thereof, and one or more pharmaceutically acceptable carriers.

17. A method of therapeutically treating a disease or disorder, comprising administering to a subject in need thereof a therapeutically effective amount of a compound of claim 11, or a pharmaceutically acceptable salt or solvate thereof, wherein the disease or disorder is atherosclerosis or diabetes.

18. The method of claim 17, wherein the disease or disorder is atherosclerosis.

19. The method of claim 17, wherein the disease or disorder is diabetes.

* * * * *